US007998950B2

(12) United States Patent
Aktoudianakis et al.

(10) Patent No.: US 7,998,950 B2
(45) Date of Patent: Aug. 16, 2011

(54) ANTIVIRAL COMPOUNDS

(75) Inventors: Evangelos Aktoudianakis, San Mateo, CA (US); Azim Alan Celebi, Burlingame, CA (US); Zhimin Du, Foster City, CA (US); Salman Y. Jabri, Irvine, CA (US); Haolun Jin, Foster City, CA (US); Choung U. Kim, San Carlos, CA (US); Jiayao Li, Foster City, CA (US); Samuel E. Metobo, Newark, CA (US); Michael R. Mish, La Honda, CA (US); Barton W. Phillips, San Mateo, CA (US); Joseph H. Saugier, Livermore, CA (US); Zheng-Yu Yang, Palo Alto, CA (US); Catalin Sebastian Zonte, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 12/509,250

(22) Filed: Jul. 24, 2009

(65) Prior Publication Data

US 2010/0022508 A1 Jan. 28, 2010

Related U.S. Application Data

(60) Provisional application No. 61/083,855, filed on Jul. 25, 2008, provisional application No. 61/147,681, filed on Jan. 27, 2009, provisional application No. 61/220,110, filed on Jun. 24, 2009.

(51) Int. Cl.
*A61K 31/55* (2006.01)
*A61K 31/5365* (2006.01)
*A61K 31/495* (2006.01)
*A61K 31/436* (2006.01)
*C07D 265/28* (2006.01)
*C07D 471/12* (2006.01)
*C07D 498/12* (2006.01)

(52) U.S. Cl. ............... 514/211.1; 514/220; 514/230.2; 514/250; 514/293; 544/101; 544/346; 546/84; 540/548

(58) Field of Classification Search .......... 514/211.1, 514/220, 230.2, 250, 293; 544/101, 346; 546/84; 540/548
See application file for complete search history.

(56) References Cited

FOREIGN PATENT DOCUMENTS

| WO | WO-2006/072636 A2 | 7/2006 |
| WO | WO-2007/019101 A2 | 2/2007 |
| WO | WO-2008/128953 A1 | 10/2008 |
| WO | WO-2009/000745 A1 | 12/2008 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10), (2004) 2394-2404.*
Xu et al. (2000) "Anti-HIV Agents 45[1] and Antitumor Agents 205.[2] Two New Sesquiterpenes, Leitneridanins A and B, and the Cytotoxic and Anti-HIV Principles from *Leitneria floridana*"J. Nat. Prod. 63:1712-1715.
International Search Report and The Written Opinion for International Application No. PCT/US2009/051741, filed Jul. 24, 2009.

* cited by examiner

*Primary Examiner* — Rebecca Anderson
*Assistant Examiner* — Samantha Shterengarts

(57) ABSTRACT

The invention is related to anti-viral compounds, compositions containing such compounds, and therapeutic methods that include the administration of such compounds, as well as to processes and intermediates useful for preparing such compounds.

17 Claims, No Drawings

ANTIVIRAL COMPOUNDS

PRIORITY OF INVENTION

This application claims priority under 35 U.S.C. §119(e) to U.S. Provisional Patent Application No. 61/083,855, filed 25 Jul. 2008; U.S. Provisional Patent Application No. 61/147,681, filed on 27 Jan. 2009; and to U.S. Provisional Patent Application No. 61/220,110, filed on 24 Jun. 2009. The entire content of each of these provisional patent applications is hereby incorporated herein by reference.

FIELD OF THE INVENTION

The invention relates generally to compounds with HIV inhibitory activity.

BACKGROUND OF THE INVENTION

Human immunodeficiency virus (HIV) is a retrovirus that can lead to acquired immunodeficiency syndrome (AIDS), a condition in humans in which the immune system is weakened, leading to life-threatening opportunistic infections. Although drugs having anti-HIV activity are in wide use and have shown effectiveness, toxicity and other side effects have limited their usefulness. Inhibitors of HIV are useful to limit the establishment and progression of infection by HIV as well as in diagnostic assays for HIV.

There is a need for new HIV therapeutic agents.

SUMMARY OF THE INVENTION

In one embodiment the invention provides compounds of formula I:

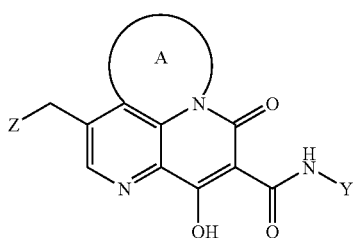

I or a pharmaceutically acceptable salt or prodrug thereof, wherein:

A is a 5 membered to 8 membered, optionally substituted, heterocyclic ring;

Z is a substituted phenyl; and

Y is selected from the group consisting of optionally substituted alkoxycarbonyl, carboxy, optionally substituted alkyl, optionally substituted heteroalkyl, optionally substituted alkoxy, alkoxyalkyl, nitro, hydroxy, hydroxyalkyl, optionally substituted alkenyl, optionally substituted alkynyl, alkylsulfonyl, alkyloxysulfonyl, optionally substituted amino, optionally substituted aminosulfonyl, alkylthio, alkylthioalkyl, haloalkyl, haloalkoxy, haloalkoxyalkyl, cycloalkyl, cycloalkenyl, oxo, thioxo, alkylenedioxy, alkylene, alkenylene, nitroso, amidino, guanidine, cyano, optionally substituted carbamoyl, optionally substituted carbamoylalkyl, optionally substituted sulfanoyl, sulfoamino, sulfo, formyl, alkylcarbonyl, alkylcarbonyloxy, hydrazino, morpholino, phosphono, phosphinico, optionally substituted aryl, optionally substituted heteroaryl, optionally substituted heterocycle, optionally substituted aralkyl, optionally substituted heteroaralkyl, optionally substituted aryloxy, optionally substituted heteroaryloxy, optionally substituted heterocycleoxy, optionally substituted arylthio, optionally substituted heteroarylthio, optionally substituted aralkyloxy, optionally substituted heteroaralkyloxy, optionally substituted aralkylthio, optionally substituted heteroaralkylthio, optionally substituted aryloxyalkyl, optionally substituted heteroaryloxyalkyl, optionally substituted arylthioalkyl, optionally substituted heteroarylthioalkyl, optionally substituted arylsulfonyl, optionally substituted heteroarylsulfonyl, optionally substituted aralkylsulfonyl, optionally substituted heteroaralkylsulfonyl, optionally substituted alkylcarbonyl alkyl, optionally substituted arylcarbonyl alkyl, alkylsulfonyloxy, sulfamoyloxy and optionally substituted arylcarbonyl.

In some embodiments the substituent attached to the phenyl of a compound of Formula I is selected from the group consisting of X, R, —O⁻, =O, —OR, —SR, —S⁻, —NR$_2$, —N⁺R$_3$, =NR, —CX$_3$, —CN, —OCN, —SCN, —N=C=O, —NCS, —NO, —NO$_2$, =N$_2$, —N$_3$, —NHC(=O)R, —C(=O)R, —C(=O)NRR—S(—O)$_2$—, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —P(=O)(O⁻)$_2$, —OS(=O)$_2$OR, —S(=O)$_2$NR, —S(=O)R, —OP(=O)(OR)$_2$, —P(=O)(OR)$_2$, —P(=O)(O⁻)$_2$, —P(=O)(OH)$_2$, —P(O)(OR)(O⁻), —C(=O)R, —C(=O)X, —C(S)R, —C(O)OR, —C(O)O⁻, —C(S)OR, —C(O)SR, —C(S)SR, —C(O)NRR, —C(S)NRR, —C(=NR)NRR, where each X is independently selected from the group consisting of F, Cl, Br, and I, and each R is independently selected from the group consisting of H, alkyl, heteroalkyl, aryl, and arylalkyl.

The compounds of formula I inhibit the activity of an integrase protein which is encoded by the HIV genome and which is required for the integration of the HIV genome into the genome of a target cell, such as a macrophage or CD4⁺ T cell. Thus, the compounds of the present invention are useful, for example, for inhibiting HIV infection of susceptible human cells.

The present invention also provides a pharmaceutical composition comprising a compound of formula I, or a pharmaceutically acceptable salt or prodrug thereof, and at least one pharmaceutically acceptable carrier.

The present invention also provides for a method of treating disorders associated with HIV, said method comprising administering to an individual a pharmaceutical composition which comprises a therapeutically effective amount of a compound of formula I, or a pharmaceutically acceptable salt or prodrug thereof.

The present invention also provides a method of inhibiting HIV, comprising administering to a mammal afflicted with a condition associated with HIV activity, a therapeutically effective amount of a compound of formula I, or a pharmaceutically acceptable salt or prodrug thereof, effective to inhibit HIV.

The present invention also provides a compound of formula I, or a pharmaceutically acceptable salt or prodrug thereof, for use in medical therapy (preferably for use in inhibiting HIV or treating a condition associated with HIV activity), as well as the use of a compound of formula I, or a pharmaceutically acceptable salt or prodrug thereof, for the manufacture of a medicament useful for inhibiting HIV or the treatment of a condition associated with HIV activity in a mammal.

The present invention also provides synthetic processes and novel intermediates disclosed herein which are useful for preparing compounds of the invention. Some of the compounds of the invention are useful to prepare other compounds of the invention.

In another aspect the invention provides a method of inhibiting HIV activity in a sample comprising treating the sample with a compound of formula I, or a pharmaceutically acceptable salt or prodrug thereof.

In one embodiment the invention provides a compound having improved inhibitory or pharmacokinetic properties, including enhanced activity against development of viral resistance, improved oral bioavailability, greater potency or extended effective half-life in viva. Certain compounds of the invention may have fewer side effects, less complicated dosing schedules, or be orally active.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the embodiments.

Definitions and Abbreviations

Abbreviations and Acronyms

A list of abbreviations commonly used in the field of organic chemistry appears in The ACS Style Guide (third edition) and in the Guidelines for Authors for the *Journal of Organic Chemistry*. The chemical elements are identified herein in accordance with the Periodic Table of the Elements, CAS version, Handbook of Chemistry and Physics, 67th Ed., 1986-87.

More specifically, and by way of non-limiting example, when the following abbreviations are used herein, they have the following meanings:

| | |
|---|---|
| $^1$H-NMR | proton nuclear magnetic resonance spectroscopy |
| $^{31}$P-NMR | phophorus-31 nuclear magnetic resonance spectroscopy |
| $^{19}$F-NMR | fluorine-19 nuclear magnetic resonance spectroscopy |
| AcOH | acetic acid |
| Ac$_2$O | acetic anhydride |
| abs | absolute |
| aq | aqueous |
| ap | approximate |
| atm | atmosphere |
| br | broad |
| Bu | butyl |
| ACN | acetonitrile |
| Ac$_2$O | acetic anhydride |
| AcOH | acetic acid |
| Celite ® | brand of diatomaceous earth from Celite Corp. |
| CD$_3$CN | acetonitrile-d$_3$ |
| CD$_3$OD | methanol-d$_4$ |
| d | doublet |
| DCE | dichloroethane |
| DCM | dichloromethane |
| dd | double doublet |
| DIBAL | diisobutylaluminum hydride |
| DIEA | diisopropylethyl amine |
| DMF | N,N-dimethylformamide |
| DMSO | dimethylsulfoxide |
| DMSO-d$_6$ | dimethyldsulfoxide-d$_6$ |
| DPPA | diphenylphosphoryl azide |
| equiv | equivalent(s) |
| Et$_3$N | triethylamine |

-continued

| | |
|---|---|
| Et$_2$O | diethyl ether |
| EtOAc | ethyl acetate |
| EtOH | ethanol |
| FBS | fetal bovine serum |
| g | gram(s) |
| h | hour(s) |
| HCl | hydrogen chloride |
| HPLC | high performance liquid chromatography |
| Hz | hertz |
| ISCO ® | Brand of Medium Pressure Chromatography from ISCO inc. |
| IPA | isopropanol |
| J | NMR coupling constant |
| L | liter(s) |
| LAH | lithium aluminium hydride |
| LCMS | liquid chromatography-mass spectrometry |
| LHMDS | lithium hexamethyldisilazide |
| L-Selectride | lithium tri-sec-butylborohydride |
| M | molar |
| Me | methyl |
| MeCN | acetonitrile |
| MeOH | methanol |
| mg | milligram(s) |
| MHz | megahertz |
| min | minute(s) |
| mL | milliliter |
| mmol | millimole |
| MPLC | medium pressure liquid chromatography |
| MS | mass spectrometry |
| Ms | methanesulfonyl |
| N | normal |
| NaHMDS | sodium hexamethyldisilazide |
| NBS | N-bromosuccinimide |
| nM | nanomolar |
| Pd—C | palladium on carbon |
| Pr | propyl |
| py—BOP | benzotriazol-1-yl-oxytripyrrolidineophosponium hexafluorophosphate |
| q | quartet |
| Ra—Ni | Raney-Nickel |
| R$_f$ | TLC retention factor |
| Rochelle's | potassium sodium tartrate salt |
| RP | Reverse phase |
| RT | retention time |
| rt | room temperature |
| s | singlet |
| t | triplet |
| t-BuOH | tert-butanol |
| TEA | triethylamine |
| TFA | trifluoroacetic acid |
| THF | tetrahydrofuran |
| TLC | thin layer chromatography |
| Ts | p-toluenesulfonyl |
| v/v | volume-to-volume proportion |
| v/v/v | volume-to-volume-to-volume proportion |
| μL | microliter |
| μm | micrometer |

Definitions

Whenever a compound described herein is substituted with more than one of the same designated group, e.g., "$R^1$", "$R^2$", or "$R^3$", then it will be understood that the groups may be the same or different, i.e., each group is independently selected.

"Alkyl" is a hydrocarbon containing normal, secondary, tertiary or cyclic carbon atoms. Examples are methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), cyclopropyl, 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, cyclopropylmethyl, and spiro cyclic groups such as spirocyclopropyl and spirocyclobutyl.

"Alkenyl" is a hydrocarbon containing normal, secondary, tertiary or cyclic carbon atoms with at least one site of unsaturation, i.e. a carbon-carbon, sp$^2$ double bond. Examples include, but are not limited to, ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$).

"Alkynlyl" is a hydrocarbon containing normal, secondary, tertiary or cyclic carbon atoms with at least one site of unsaturation, i.e. a carbon-carbon, sp triple bond. Examples include, but are not limited to, acetylenic (—C≡CH) and propargyl (—CH$_2$C≡CH).

"Alkylene" refers to a saturated, branched or straight chain or cyclic hydrocarbon radical having two monovalent radical centers derived by the removal of two hydrogen atoms from the same or two different carbon atoms of a parent alkane. Typical alkylene radicals include, but are not limited to, methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

"Alkenylene" refers to a saturated, branched or straight chain or cyclic hydrocarbon radical having two monovalent radical centers derived by the removal of two hydrogen atoms from the same or two different carbon atoms of a parent alkane, and which contains at least one double bond.

The term "cycloalkenyl" means a C$_3$-C$_{10}$ cyclic non-aromatic hydrocarbonyl group and includes, for example, cyclopropenyl (e.g., 1-cyclopropenyl), cyclobutenyl (e.g., 1-cyclobutenyl), cyclopentenyl (e.g., 1-cyclopenten-1-yl, 2-cyclopenten-1-yl or 3-cyclopenten-1-yl), cyclohexenyl (e.g., 1-cyclohexen-1-yl, 2-cyclohexen-1-yl or 3-cyclohexen-1-yl), cycloheptenyl (e.g., 1-cycloheptenyl) or cyclooctenyl (e.g., 1-cyclooctenyl).

The term "heteroalkyl" means a stable straight or branched chain hydrocarbon radical including at least one carbon atom and at least one heteroatom selected from the group consisting of O, N, P, and S, and wherein the nitrogen, phosphorus, and sulfur atoms may optionally be oxidized and the nitrogen heteroatom may optionally be quaternized. The heteroatom(s) O, N, P and S may be placed at any interior position of the heteroalkyl group or at the position at which the heteroalkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$, —CH=CH—N(CH$_3$)—CH$_3$, O—CH$_3$, —O—CH$_2$—CH$_3$, and —CN. Heteroatoms may be consecutive, such as, for example, —CH$_2$—NH—OCH$_3$. Similarly, the term "heteroalkylene" means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or —SO2R'.

The terms "cycloalkyl" and "heterocycloalkyl" refer to cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means a polyunsaturated, aromatic, hydrocarbon substituent which can be a single ring or multiple rings (such as from 1 to 3 rings) which are fused together or linked covalently (e.g., phenyl, 1-naphthyl, 2-naphthyl, 1-antolyl, 2-antolyl, 9-antolyl, 1-phenantolyl, 2-phenantolyl, 3-phenantolyl, 4-phenantolyl or 9-phenantolyl).

The term "heteroaryl" refers to aryl groups (or rings) that contain at least one heteroatom (in at least one ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom-n.

Non-limiting examples of heteroaryl groups include furyl (e.g., 2-furyl or 3-furyl), thienyl (e.g., 2-thienyl or 3-thienyl), pyrrolyl (e.g., 1-pyrrolyl, 2-pyrrolyl or 3-pyrrolyl), imidazolyl (e.g., 1-imidazolyl, 2-imidazolyl or 4-imidazolyl), pyrazolyl (e.g., 1-pyrazolyl, 3-pyrazolyl or 4-pyrazolyl), triazolyl (e.g., 1,2,4-triazol-1-yl, 1,2,4-triazolyl-3-yl or 1,2,4-triazol-4-yl), tetrazolyl (e.g., 1-tetrazolyl, 2-tetrazolyl or 5-tetrazolyl), oxazolyl (e.g., 2-oxazolyl, 4-oxazolyl or 5-oxazolyl), isoxazolyl (e.g., 3-isoxazolyl, 4-isoxazolyl or 5-isoxazolyl), thiazolyl (e.g., 2-thiazolyl, 4-thiazolyl or 5-thiazolyl), thiadiazolyl, isothiazolyl (e.g., 3-isothiazolyl, 4-isothiazolyl or 5-isothiazolyl), pyridyl (e.g., 2-pyridyl, 3-pyridyl or 4-pyridyl), pyridazinyl (e.g., 3-pyridazinyl or 4-pyridazinyl), pyrimidinyl (e.g., 2-pyrimidinyl, 4-pyrimidinyl or 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl or 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl or 7-benzo[b]thienyl), benzimidazolyl (e.g., 1-benzoimidazolyl, 2-benzoimidazolyl, 4-benzoimidazolyl or 5-benzoimidazolyl), dibenzofuryl, benzoxazolyl, quinoxalyl (e.g., 2-quinoxalinyl, 5-quinoxalinyl or 6-quinoxalinyl), cinnolinyl (e.g., 3-cinnolinyl, 4-cinnolinyl, 5-cinnolinyl, 6-cinnolinyl, 7-cinnolinyl or 8-cinnolinyl), quinazolyl (e.g., 2-quinazolinyl, 4-quinazolinyl, 5-quinazolinyl, 6-quinazolinyl, 7-quinazolinyl or 8-quinazolinyl), quinolyl (e.g., 2-quinolyl, 3-quinolyl, 4-quinolyl, 5-quinolyl, 6-quinolyl, 7-quinolyl or 8-quinolyl), phthalazinyl (e.g., 1-phthalazinyl, 5-phthalazinyl or 6-phthalazinyl), isoquinolyl (e.g., 1-isoquinolyl, 3-isoquinolyl, 4-isoquinolyl, 5-isoquinolyl, 6-isoquinolyl, 7-isoquinolyl or 8-isoquinolyl), puryl, pteridinyl (e.g., 2-pteridinyl, 4-pteridinyl, 6-pteridinyl or 7-pteridinyl), carbazolyl, phenantridinyl, acridinyl (e.g., 1-acridinyl, 2-acridinyl, 3-acridinyl, 4-acridinyl or 9-acridinyl), indolyl (e.g., 1-indolyl, 2-indolyl, 3-indolyl, 4-indolyl, 5-indolyl, 6-indolyl or 7-indolyl), isoindolyl, phenazinyl (e.g., 1-phenazinyl or 2-phenazinyl) and phenothiazinyl (e.g., 1-phenothiazinyl, 2-phenothiazinyl, 3-phenothiazinyl or 4-phenothiazinyl).

The term "Halo" includes F, Cl, Br and I.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

The term "substituted" in reference to a chemical group such as alkyl, alkylene, aryl, arylalkyl, alkoxy, heteroaryl, etc. (e.g., "substituted alkyl", "substituted heterocyclic ring") means at least one hydrogen atom is/are independently replaced with a non-hydrogen substituent. Typical substituents include, but are not limited to, X, R, —O⁻, ═O, —OR, —SR, —S⁻, —NR₂, —N⁺R₃, ═NR, —CX₃, —CN, —OCN, —SCN, —N═C═O, —NCS, —NO, —NO₂, ═N₂, —N₃, —NHC(═O)R, —C(═O)R, —C(═O)NRR—S(═O)₂—, —S(═O)₂OH, —S(═O)₂R, —OS(═O)₂OR, —S(═O)₂NR, —S(═O)R, —OP(═O)(OR)₂, —P(═O)(OR)₂, —P(═O)(O⁻)₂, —P(═O)(OH)₂, —P(O)(OR)(O⁻), —C(═O)R, —C(═O)X, —C(S)R, —C(O)OR, —C(O)O⁻, —C(S)OR, —C(O)SR, —C(S)SR, —C(O)NRR, —C(S)NRR, —C(═NR)NRR, where each X is independently a halogen (F, Cl, Br, or I); and each R is independently H, alkyl, aryl, arylalkyl, or a protecting group or prodrug moiety.

Other examples of substituents include, for example, alkyl (e.g., methyl, ethyl, isopropyl), benzyl, carbonyl, carboxamide, carbamoylalkyl (e.g., carbamoylmethyl), a ketone, a mono- or di-alkylcarbamoylalkyl (e.g., dimethylcarbamoylethyl), hydroxyalkyl, heterocyclealkyl (e.g., morpholinoethyl, tetrahydropyranylethyl), an alkoxycarbonylalkyl (e.g., ethoxycarbonylmethyl, ethoxycarbonylethyl), a mono- or dialkylaminoalkyl (e.g., dimethylaminoethyl), an alkoxyalkyl (e.g., methoxyethyl, ethoxymethyl, ethoxyethyl, 1-propoxyethyl, etc.), an acyl (e.g., formyl, an optionally substituted alkylcarbonyl (e.g., acetyl, propironyl, butyryl, isobutyryl, valelyl, isovalelyl, pivaloyl, hexanoyl, octanoyl, methoxyethylcarbonyl, 2,2,2-trifluoroethylcarbonyl, ethoxycarbonyl, methylcarbonyl), an alkoxyalkylcarbonyl (e.g., methoxyethylcarbonyl), an alkylcarbamoylalkylcarbonyl (e.g., methylcarbamoylethylcarbonyl), an alkoxycarbonylacetyl), an optionally substituted arylcarbonyl (e.g., benzoyl, toluoyl), an optionally substituted aralkyl (e.g., benzyl, 4-F-benzyl, etc.), hydroxy, an optionally substituted alkylsulfonyl (e.g., methanesulfonyl, ethanesulfonyl, isopropylsulfonyl, 2,2,2-trifluoroethanesulfonyl, benzylsulfonyl, methoxyethylsulfonyl, etc.), an arylsulfonyl optionally substituted by an alkyl or a halogen (e.g., benzenesulfonyl, toluenesulfonyl, 4-fluorobenzenesulfonyl), a cycloalkyl (e.g., cyclopropyl), an aryl optionally substituted by an alkyl (e.g., phenyl, trityl, etc.), an alkylaminosulfonyl (e.g., methylaminosulfonyl, dimethylaminosulfonyl, etc.), an alkylaminocarbonyl (e.g., dimethylaminocarbonyl, etc.), an alkoxycarbonyl (e.g., ethoxycarbonyl, etc.), a cycloalkylcarbonyl (e.g., cyclopropylcarbonyl, cyclohexylcarbonyl, etc.), an optionally substituted sulfamoyl (e.g., sulfamoyl, methylsulfamoyl, dimethylsulfamoyl, etc.), an alkylcarbonylamino (e.g., methylcarbonylamino), a heterocycle (e.g., morpholino, tetrahydropyranyl), an optionally substituted amino (e.g., mono- or dialkylamino(e.g., dimethylamino), formylamino).

Unless otherwise indicated, when the term "substituted" is used in conjunction with groups such as arylalkyl, which have two or more moieties capable of substitution, the substituents can be attached to the aryl moiety, the alkyl moiety, or both.

The term "optionally substituted" in reference to a particular chemical moiety (e.g., an optionally substituted aryl group) refers to a moiety having 0, 1, 2, or more substituents.

The term ≈≈≈means that a bond is a single or double bond. In a non-limiting example,

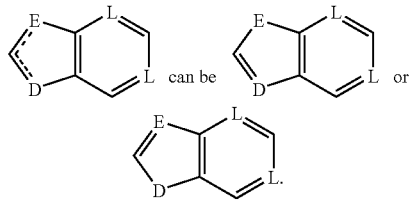

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

"Heterocycle" or "heterocyclyl" as used herein (e.g., a heterocyclic ring) means an organic ring which contains at least one atom other than carbon (e.g., a six membered ring that contains five carbon atoms and one nitrogen atom or one oxygen atom or one sulfur atom). The non-carbon atom(s) is/are typically oxygen and/or nitrogen and/or sulfur. The term heterocycle includes, by way of example and not limitation, those heterocycles described in Paquette, Leo A.; *Principles of Modern Heterocyclic Chemistry* (W.A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. The terms "heterocycle" or "heterocyclyl" includes saturated rings (i.e., heterocycloalkyls), partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

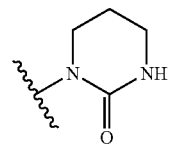

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

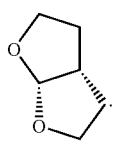

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. The invention includes all stereoisomers of the compounds described herein.

Examples of groups falling within the scope of the term "alkoxy" include methoxy, ethoxy, n-propoxy, isopropoxy, n-butoxy, isobutoxy, and tert-butoxy.

Examples of groups falling within the scope of the term "alkoxycarbonyl" include methoxycarbonyl, ethoxycarbonyl, n-propoxycarbonyl, isopropoxycarbonyl, n-butoxycarbonyl, isobutoxycarbonyl and tert-butoxycarbonyl.

Examples of groups falling within the scope of the term "alkoxyalkyl" include methoxymethyl, ethoxymethyl, n-propoxmethyl, isopropoxymethyl, n-butoxymethyl, isobutoxymethyl, tert-butoxymethyl, methoxyethyl, ethoxyethyl, n-propoxyethyl, isopropoxyethyl, n-butoxyethyl, isobutoxyethyl and tert-butoxyethyl.

Examples of groups falling within the scope of the term "alkylsulfonyl" include methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, neopentylsulfonyl, tert-pentylsulfonyl, n-hexylsulfonyl, isohexylsulfonyl, n-heptylsulfonyl, n-octylsulfonyl, n-nonylsulfonyl and n-decylsulfonyl.

Examples of groups falling within the scope of the term "alkylthio" include methylthio, ethylthio, n-propylthio, isopropylthio, n-butylthio, isobutylthio, sec-butylthio, tert-butylthio, n-pentylthio, isopentylthio, neopentylthio, tert-pentylthio, n-hexylthio, isohexylthio, n-heptylthio, n-octylthio, n-nonylthio and n-decylthio.

Examples of groups falling within the scope of the term "alkylthioalkyl" include methylthiomethyl, ethylthiomethyl, n-propylthiomethyl, isopropylthiomethyl, n-butylthiomethyl, isobutylthiomethyl, sec-butylthiomethyl, tert-butylthiomethyl, n-pentylthiomethyl, isopentylthiomethyl, neopentylthiomethyl, tert-pentylthiomethyl, n-hexylthiomethyl, isohexylthiomethyl, n-heptylthiomethyl, n-octylthiomethyl, n-nonylthiomethyl, n-decylthiomethyl, methylthioethyl, ethylthioethyl, n-propylthioethyl, isopropylthioethyl, n-butylthioethyl, isobutylthioethyl, sec-butylthioethyl, tert-butylthioethyl, n-pentylthioethyl, isopentylthioethyl, neopentylthioethyl, tert-pentylthioethyl, n-hexylthioethyl, isohexylthioethyl, n-heptylthioethyl, n-octylthioethyl, n-nonylthioethyl and n-decylthioethyl.

Examples of groups falling within the scope of the term "haloalkyl" include trifluoromethyl, chloromethyl, dichloromethyl, 1,1-dichloroethyl and 2,2,2-trichloroethyl.

Examples of groups falling within the scope of the term "haloalkoxy" include trifluoromethoxy, chloromethoxy, dichloromethoxy, 1,1-dichloroethoxy and 2,2,2-trichloroethoxy.

Examples of groups falling within the scope of the term "haloalkoxyalkyl" include trifluoromethoxymethyl, chloromethoxymethyl, dichloromethoxymethyl, 1,1-dichloroethoxymethyl, 2,2,2-trichloroethoxymethyl, trifluoromethoxyethyl, chloromethoxyethyl, dichloromethoxyethyl, 1,1-dichloroethoxyethyl and 2,2,2-trichloroethoxyethyl.

Examples of groups falling within the scope of the term "acyl" include acetyl, propionyl, butyryl, isobutyryl, valeryl, isovaleryl, pivaloyl, hexanoyl, octanoyl, lauroyl, and benzoyl.

Examples of groups falling within the scope of the term "alkylcarbonyl" include acetyl, propionyl, butyryl, isobutyryl, valeryl, isovaleryl, pivaloyl, hexanoyl, octanoyl and lauroyl.

Examples of groups falling within the scope of the term "alkylcarbonyloxy" include acetyloxy, propionyloxy, butyryloxy, isobutyryloxy, valeryloxy, isovaleryloxy, pivaloyloxy, hexanoyloxy, octanoyloxy and lauroyloxy.

Examples of groups falling within the scope of the term "aralkyl" include benzyl, diphenylmethyl, triphenylmethyl, phenethyl, 1-naphthylmethyl and 2-naphthylmethyl.

Examples of groups falling within the scope of the term "heteroaralkyl" include furylmethyl, thienylmethyl, pyrrolylmethyl, imidazolylmethyl, pyrazolylmethyl, triazolylmethyl, tetrazolylmethyl, oxazolylmethyl, isoxazolylmethyl, thiazolylmethyl, thiadiazolylmethyl, isothiazolylmethyl, pyridylmethyl, pyridazinylmethyl, pyrimidinylmethyl, furazanylmethyl, pyrazinylmethyl, oxadiazolylmethyl, benzofurylmethyl, benzothienylmethyl, benzimidazolylmethyl, dibenzofurylmethyl, benzooxazolylmethyl, quinoxalylmethyl, cinnolinylmethyl, quinazolylmethyl, quinolylmethyl, phthalazinylmethyl, isoquinolylmethyl, puriylmethyl, pteridinylmethyl, carbazolylmethyl, phenantridinylmethyl, acridinylmethyl, indolylmethyl, isoindolylmethyl, phenazinylmethyl, phenothiazinylmethyl, furylethyl, thienylethyl, pyrrolylethyl, imidazolylethyl, pyrazolylethyl, triazolylethyl, tetrazolylethyl, oxazolylethyl, isoxazolylethyl, thiazolylethyl, thiadiazolylethyl, isothiazolylethyl, pyridylethyl, pyridazinylethyl, pyrimidinylethyl, furazanylethyl, pyrazinylethyl, oxadiazolylethyl, benzofurylethyl, benzothienylethyl, benzimidazolylethyl, dibenzo furylethyl, benzooxazolylethyl, uinoxalylethyl, cinnolinylethyl, quinazolylethyl, quinolylethyl, phthalazinylethyl, isoquinolylethyl, puriylethyl, pteridinylethyl, carbazolylethyl, phenantridinylethyl, acridinylethyl, indolylethyl, isoindolylethyl, phenazinylethyl and phenothiazinylethyl.

Compounds of the Invention

In one aspect the present invention provides compounds of Formula I, or a pharmaceutically acceptable prodrug or salt thereof:

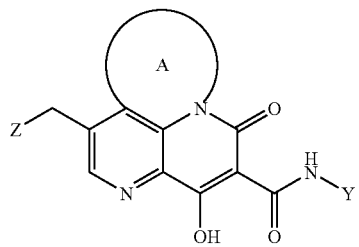

I wherein:
A is a 5 membered to 8 membered, optionally substituted, heterocyclic ring;
Z is a substituted phenyl; and
Y is selected from the group consisting of optionally substituted alkoxycarbonyl, carboxy, optionally substituted alkyl, optionally substituted heteroalkyl, optionally substituted alkoxy, alkoxyalkyl, nitro, hydroxy, hydroxyalkyl, optionally substituted alkenyl, optionally substituted alkynyl, alkylsulfonyl, alkyloxysulfonyl, optionally substituted amino, optionally substituted aminosulfonyl, alkylthio, alkylthioalkyl, haloalkyl, haloalkoxy, haloalkoxyalkyl, cycloalkyl, cycloalkenyl, oxo, thioxo, alkylenedioxy, alkylene, alkenylene, nitroso, amidino, guanidine, cyano, optionally substituted carbamoyl, optionally substituted carbamoylalkyl, optionally substituted sulfamoyl, sulfoamino, sulfo, formyl, alkylcarbonyl, alkylcarbonyloxy, hydrazino, morpholino, phosphono, phosphinico, optionally substituted aryl, optionally substituted heteroaryl, optionally substituted heterocycle, optionally substituted aralkyl, optionally substituted heteroaralkyl, optionally substituted aryloxy, optionally substituted heteroaryloxy, optionally substituted heterocycleoxy, optionally substituted arylthio, optionally substituted heteroarylthio, optionally substituted aralkyloxy, optionally substituted heteroaralkyloxy, optionally substituted aralkylthio, optionally substituted heteroaralkylthio, optionally substituted aryloxyalkyl, optionally substituted heteroaryloxyalkyl, optionally substituted arylthioalkyl, optionally substituted heteroarylthioalkyl, optionally substituted arylsulfonyl, optionally substituted heteroarylsulfonyl, optionally substituted aralkylsulfonyl, optionally substituted heteroaralkylsulfonyl, optionally substituted alkylcarbonyl alkyl, optionally substituted arylcarbonyl alkyl, alkylsulfonyloxy, sulfamoyloxy and optionally substituted arylcarbonyl.

In some embodiments the substituent attached to the phenyl of a compound of Formula I is selected from the group consisting of X, R, —O⁻, =O, —OR, —SR, —S⁻, —NR$_2$, —N⁺R$_3$, =NR, —CX$_3$, —CN, —OCN, —SCN, —N=C=O, —NCS, —NO, —NO$_2$, =N$_2$, —N$_3$, —NHC(=O)R, —C(=O)R, —C(=O)NRR—S(=O)$_2$—, —S(=O)$_2$OH, —S(=O)$_2$R, —OS(=O)$_2$OR, —S(=O)$_2$R, —S(=O)R, —OP(=O)(OR)$_2$, —P(=O)(OR)$_2$, —P(=O)(O⁻)$_2$, —P(=O)(OH)$_2$, —P(O)(OR)(O⁻), —C(=O)R, —C(=O)X, —C(S)R, —C(O)OR, —C(O)O⁻, —C(S)OR, —C(O)SR, —C(S)SR, —C(O)NRR, —C(S)NRR, —C(=NR)NRR, where each X is independently selected from the group consisting of F, Cl, Br, and I, and each R is independently selected from the group consisting of H, alkyl, heteroalkyl, aryl, and arylalkyl.

The compounds of Formula I each include a ring designated as "A" (referred to as the "A ring"). The A ring is a 5, 6, 7 or 8 membered heterocyclic ring.

Representative examples of 5 membered A lings are:

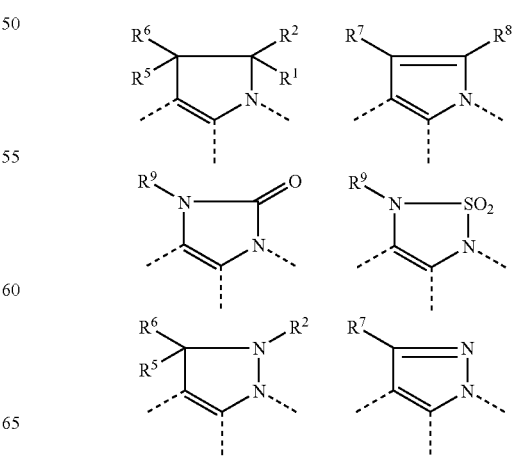

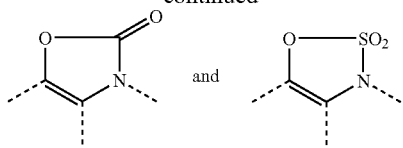 and
Representative examples of 6 membered A rings are:
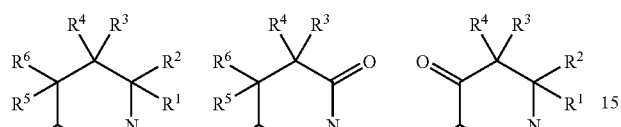

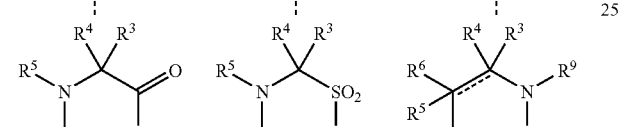
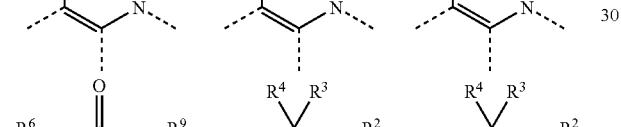

and
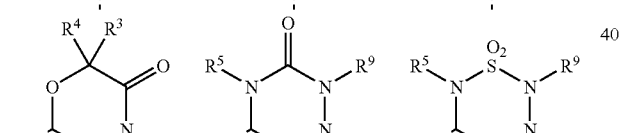
wherein, n is 0, 1, or 2.
Representative examples of 7 membered A rings are:
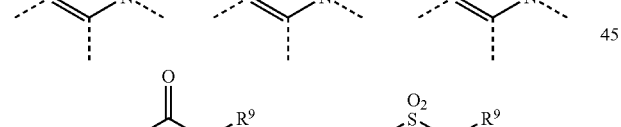
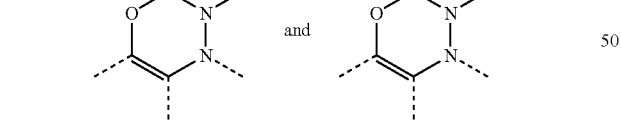
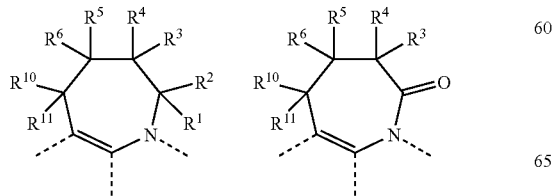
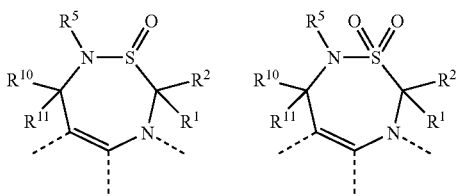

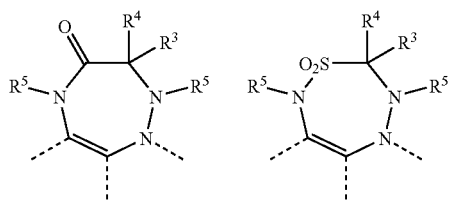
and
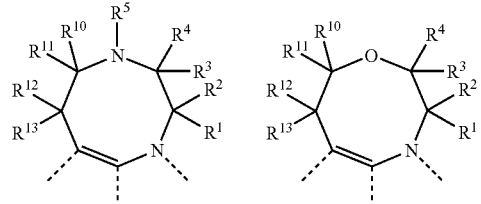

wherein, n is 0, 1, or 2.

Representative examples of 8 membered A rings are:

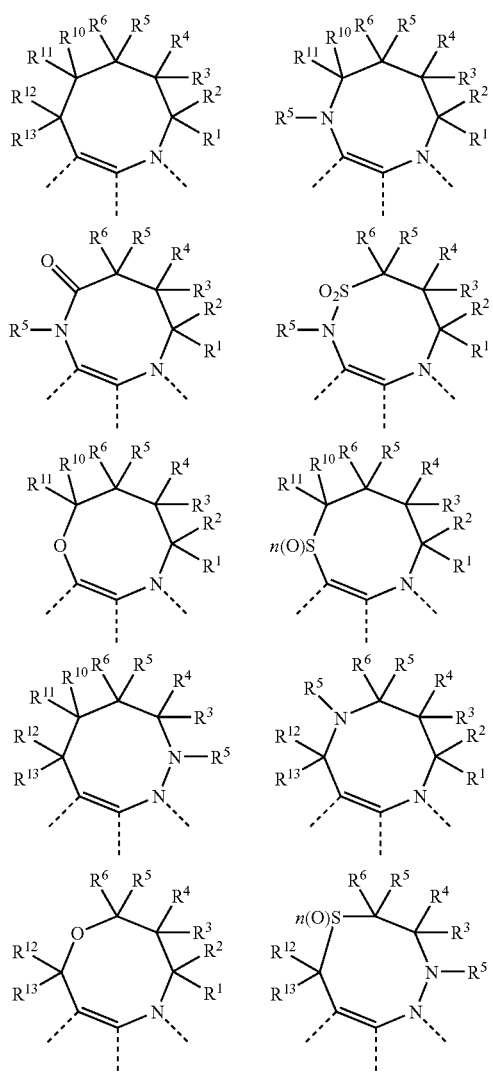

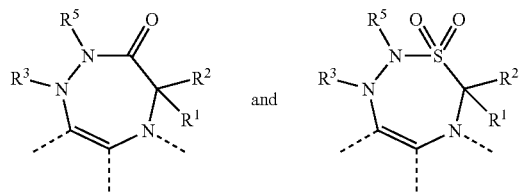
and
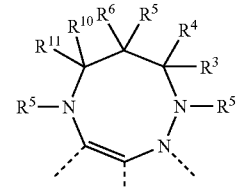

wherein, n is 0, 1, or 2.

In the context of the foregoing, representative, A rings, $R^1$, $R^2$, $R^3$, $R^4$, $R^5$, $R^6$, $R^7$, $R^8$, $R^9$, $R^{10}$, $R^{11}$, $R^{12}$, and $R^{13}$ are each independently selected from the group consisting of X, R, —O⁻, =O, —OR, —SR, —S⁻, —NR₂, —N⁺R₃, =NR, —CX₃, —CN, —OCN, —SCN, —N=C=O, —NCS, —NO, —NO₂, =N₂, —N₃, —NHC(=O)R, —C(=O)R, —C(=O)NRR—S(=O)₂—, —S(=O)₂OH, —S(=O)₂R, —OS(=O)₂OR, —S(=O)₂NR, —S(=O)R, —OP(=O)(OR)₂, —P(=O)(OR)₂, —P(=O)(O⁻)₂, —P(=O)(OH)₂, —P(O)(OR)(O⁻), —C(=O)R, —C(=O)X, —C(S)R, —C(O)OR, —C(O)O⁻, —C(S)OR, —C(O)SR, —C(S)SR, —C(O)NRR, —C(S)NRR, and —C(=NR)NRR, where (a) each X is independently selected from the group consisting of F, Cl, Br, and I;

(b) each R is independently selected from the group consisting of H, alkyl, heteroalkyl, aryl, and arylalkyl;

(c) any two members of the group consisting of $R^1$, $R^2$, $R^3$, $R^4$, $R^5$, $R^6$, $R^7$, $R^8$, $R^9$, $R^{10}$, $R^{11}$, $R^{12}$, and $R^{13}$ can together form a spiro ring, provided that said two members are attached to the same carbon atom in the same A ring; and (d) any two members of the group consisting of $R^1$, $R^2$, $R^3$, $R^4$, $R^5$, $R^6$, $R^7$, $R^8$, $R^9$, $R^{10}$, $R^{11}$, $R^{12}$, and $R^{13}$ can together form a fused ring, provided that said two members are attached to adjacent carbon or nitrogen atoms in the same A ring.

Each of the foregoing, representative, A rings show bonds, denoted by a broken line (━ ━ ━), that are attached to the A ring structure. These bonds are part of the core, bicyclic, naphthyridone scaffold and their inclusion in the drawing of the A ring structure shows how the A ring is attached to the core, bicyclic, naphthyridone scaffold. For example, the A ring of compound 12 (shown in Example 1) has a structure denoted by

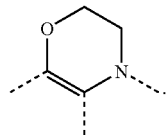

Representative compounds of the present invention that fall within the scope of Formula I are described in the Examples herein.

Further, by way of non-limiting example, structure 1A is an example of a compound of the present invention wherein the A ring is substituted with a spiro group:

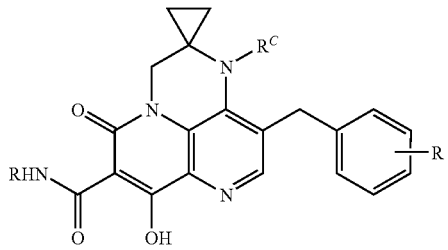

1A

Again by way of non-limiting example, structure 1B is an example of a compound of the present invention wherein the A ring is substituted with a ring that is fused to the A ring:

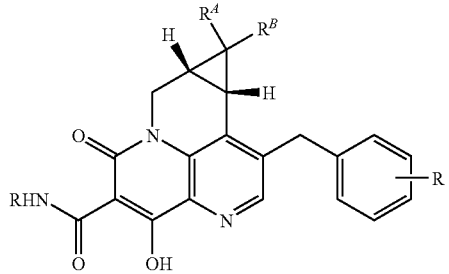

1B

In another aspect, some compounds of the present invention have a structure of Formula II:

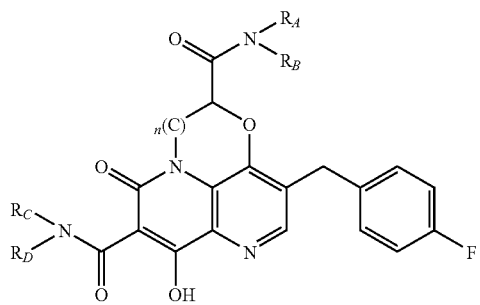

II wherein, n is selected from 0, 1, 2 and 3;

$R_A$ and $R_B$ are each independently selected from H and optionally substituted $C_1$-$C_8$ alkyl, and $R_A$ and $R_B$ can be linked, together with the N to which they are each attached, to form a heterocycle; and $R_C$ and $R_D$ are each independently selected from H, optionally substituted $C_1$-$C_8$ alkyl, optionally substituted heterocyclyl alkyl, optionally substituted amine, optionally substituted aryloxy, and optionally substituted alkoxy.

In another aspect, some compounds of the present invention have a structure of Formula III:

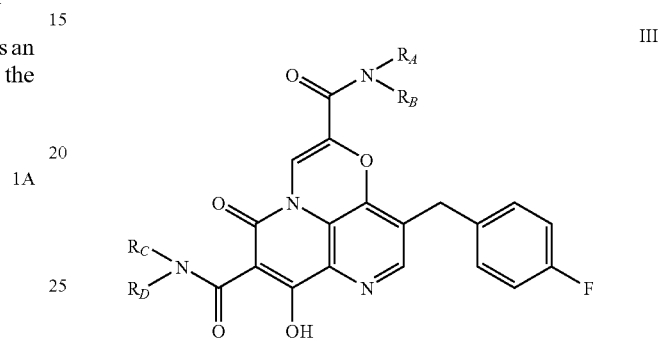

III wherein, n is selected from 0, 1, 2 and 3;

$R_A$ and $R_B$ are each independently selected from H and optionally substituted $C_1$-$C_8$ alkyl, and $R_A$ and $R_B$ can be linked, together with the N to which they are each attached, to form a heterocycle; and $R_C$ and $R_D$ are each independently selected from H, optionally substituted $C_1$-$C_8$ alkyl, optionally substituted heterocyclyl alkyl, optionally substituted amine, optionally substituted aryloxy, and optionally substituted alkoxy.

In another aspect, some compounds of the present invention have a structure of Formula IV:

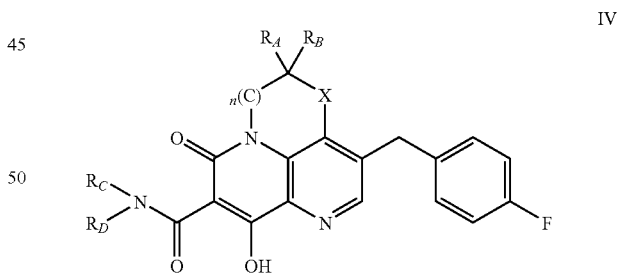

IV wherein:

n is selected from 0, 1, 2 and 3;

X is selected from C, O and $NR_E$, wherein $R_E$ is selected from H, optionally substituted alkoxy and optionally substituted $C_1$-$C_8$ alkyl;

$R_A$ and $R_B$ are each independently selected from H and optionally substituted $C_1$-$C_8$ alkyl; and $R_C$ and $R_D$ are each independently selected from H, optionally substituted $C_1$-$C_8$ alkyl, optionally substituted heterocyclyl alkyl, optionally substituted amine, optionally substituted aryloxy, and optionally substituted alkoxy.

In another aspect, some compounds of the present invention have a structure of Formula V:

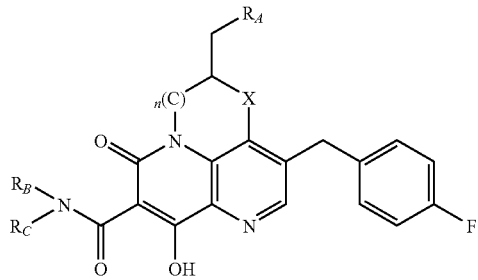

wherein:

n is selected from 0, 1, 2 and 3;

X is selected from C, O and $NR_E$, wherein $R_E$ is selected from H, optionally substituted alkoxy and optionally substituted $C_1$-$C_8$ alkyl;

$R_A$ is independently selected from H, optionally substituted alkoxy and optionally substituted $C_1$-$C_8$ alkyl; and $R_B$ and $R_C$ are each independently selected from H, optionally substituted $C_1$-$C_8$ alkyl, optionally substituted heterocyclyl alkyl, optionally substituted amine, optionally substituted aryloxy, and optionally substituted alkoxy.

In another aspect, some compounds of the present invention have a structure of Formula VI:

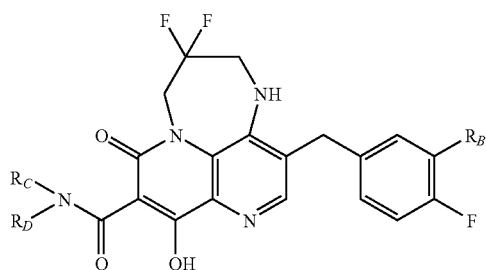

wherein:

$R_B$ is independently selected from H, alkoxy and optionally substituted $C_1$-$C_8$ alkyl; and $R_C$ and $R_D$ are each independently selected from H, optionally substituted $C_1$-$C_8$ alkyl, optionally substituted heterocyclyl alkyl, optionally substituted amine, optionally substituted aryloxy, and optionally substituted alkoxy.

Prodrugs

The present invention includes prodrugs of the compounds of Formula I. The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Prodrug moiety" refers to a labile functional group which separates from the active inhibitory compound during metabolism, either systemically or inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2OC(=O)R^9$ and acyloxymethyl carbonates —$CH_2OC(=O)OR^9$ where $R^9$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2OC(=O)C(CH_3)_3$. An exemplary acyloxymethyl carbonate prodrug moiety is pivaloyloxymethylcarbonate (POC) —$CH_2OC(=O)OC(CH_3)_3$.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to a phosphate have also been described (Khamnei and Torrence, (1996) *J. Med. Chem.* 39:4109-4115). Benzyl esters are reported to generate parent phosphonic acids. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate phosphoric acid and a quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958).

Protecting Groups

In the context of the present invention, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. Although only one delocalized resonance structure may be depicted, all such forms are contemplated within the scope of the invention.

Salts and Hydrates

Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, citric, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of an hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will typically be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived from a physiologically acceptable acid or base, are within the scope of the present invention.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Methods of Inhibition of HIV

Another aspect of the invention relates to methods of inhibiting the activity of HIV comprising the step of treating a sample suspected of containing HIV with a compound or composition of the invention.

Compounds of the invention may act as inhibitors of HIV, as intermediates for such inhibitors or have other utilities as described below. The inhibitors will generally bind to one or more locations on the HIV integrase protein. Compounds may bind with varying degrees of reversibility. Those compounds binding substantially irreversibly are useful as probes for identifying the presence of HIV. Accordingly, the invention relates to methods of detecting HIV in a sample suspected of containing HIV comprising the steps of: treating a sample suspected of containing HIV with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino. In one embodiment the invention provides a compound of formula (I) that comprises or that is bound or linked to one or more detectable labels. Within the context of the invention samples suspected of containing HIV include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing HIV. Samples can be contained in any medium including water and organic solvent/water mixtures. Samples include living organisms such as humans, and man made materials such as cell cultures.

The treating step of the invention comprises adding the compound of the invention to the sample or it comprises adding a precursor of the composition to the sample. The addition step comprises any method of administration as described above.

If desired, the activity of HIV after application of the compound can be observed by any method including direct and indirect methods of detecting HIV activity. Quantitative, qualitative, and semiquantitative methods of determining HIV activity are all contemplated. Typically one of the screening methods described above are applied, however, any other method such as observation of the physiological properties of a living organism are also applicable.

The compounds of this invention are useful in the treatment or prophylaxis of conditions associated with HIV in man.

However, in screening compounds capable of inhibiting HIV it should be kept in mind that the results of enzyme assays may not always correlate with cell culture assays. Thus, a cell based assay should typically be the primary screening tool.

In another aspect, the present invention provides methods of treating AIDS and/or treating disorders associated with AIDS. The methods of this aspect of the invention each include the step of administering to a human being infected with HIV a pharmaceutical composition which includes a therapeutically effective amount of a compound of the present invention. The therapeutically effective amount of the compound of the present invention reduces the rate of replication of HIV, in some instances completely inhibiting the replication of HIV in the infected person. Compounds of the present invention are typically administered in the form of pharmaceutical formulations as described herein in the section entitled "Pharmaceutical Formulations".

Screens for HIV Inhibitors

Compounds of the invention are screened for inhibitory activity against HIV by any of the conventional techniques for evaluating enzyme activity. Within the context of the invention, typically compounds are first screened for inhibition of HIV in vitro and compounds showing inhibitory activity are then screened for activity in vivo. Compounds having in vitro Ki (inhibitory constants) of less then about $5 \times 10^{-6}$ M, typically less than about $1 \times 10^{-7}$ M and preferably less than about $5 \times 10^{-8}$ M are preferred for in vivo use.

Representative examples of assays useful for measuring the anti-HIV activity of compounds of the present invention include the assays and methods described in the following publications which are each incorporated herein by reference: Wolfe, et al *J. Virol.* (1996) 70:1424-1432; Hazuda, et al *Nucleic Acids Res.* (1994) 22:1121-22; Haazuda, et al *J. Virol.* (1997) 71:7005-7011; Hazuda, et al *Drug Design and Discovery* (1997) 15:17-24; and Hazuda, et al *Science* (2000) 287:646-650.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation.

These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents ale exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of conditions associated with HIV activity.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

A compound of the invention may be employed in combination with other therapeutic agents for the treatment or prophylaxis of AIDS and/or one or more other diseases present in a human subject suffering from AIDS (e.g., bacterial and/or fungal infections, other viral infections such as hepatitis B or hepatitis C, or cancers such as Kaposi's sarcoma). The additional therapeutic agent(s) may be coformulated with one or more compounds of the invention (e.g., coformulated in a tablet).

Examples of such additional therapeutic agents include agents that are effective for the treatment or prophylaxis of viral, parasitic or bacterial infections, or associated conditions, or for treatment of tumors or related conditions, include 3'-azido-3'-deoxythymidine (zidovudine, AZT), 2'-deoxy-3'-thiacytidine (3TC), 2',3'-dideoxy-2',3'-didehydroadenosine (D4A), 2',3'-dideoxy-2',3'-didehydrothymidine (D4T), carbovir (carbocyclic 2',3'-dideoxy-2',3'-didehydroguanosine), 3'-azido-2',3'-dideoxyuridine, 5-fluorothymidine, (E)-5-(2-bromovinyl)-2'-deoxyuridine (BVDU), 2-chlorodeoxyadenosine, 2-deoxycoformycin, 5-fluorouracil, 5-fluorouridine, 5-fluoro-2'-deoxyuridine, 5-trifluoromethyl-2'-deoxyuridine, 6-azauridine, 5-fluoroorotic acid, methotrexate, triacetyluridine, 1-(2'-deoxy-2'-fluoro-1-β-arabinosyl)-5-iodocytidine (FIAC), tetrabydro-imidazo(4,5,1-jk)-(1,4)-benzodiazepin-2 (1H)-thione (TIBO), 2'-nor-cyclicGMP, 6-methoxypurine arabinoside (ara-M), 6-methoxypurine arabinoside 2'-O-valerate; cytosine arabinoside (ara-C), 2',3'-dideoxynucleosides such as 2',3'-dideoxycytidine (ddC), 2',3'-dideoxyadenosine (ddA) and 2',3'-dideoxyinosine (ddI); acyclic nucleosides such as acyclovir, penciclovir, famciclovir, ganciclovir, HPMPC, PMEA, PMEG, PMPA, PMPDAP, FPMPA, HPMPA, HPMPDAP, (2R,5R)-9→tetrahydro-5-(phosphonomethoxy)-2-furanyladenine, (2R, SR)-1→tetrahydro-5-(phosphonomethoxy)-2-furanylthymine; other antivirals including ribavirin (adenine arabinoside), 2-thio-6-azauridine, tubercidin, aurintricarboxylic acid, 3-deazaneoplanocin, neoplanocin, rimantidine, adamantine, and foscarnet (trisodiuam phosphonoformate); antibacterial agents including bactericidal fluoroquinolones (ciprofloxacin, pefloxacin and the like); aminoglycoside bactericidal antibiotics (streptomycin, gentamicin, amicacin and the like); β-lactamase inhibitors (cephalosporins, penicillins and the like); other antibacterials including tetracycline, isoniazid, rifampin, cefoperazone, claithromycin and azithromycin, antiparasite or antifungal agents including pentamidine (1,5-bis(4'-aminophenoxy)pentane), 9-deaza-inosine, sulfamethoxazole, sulfadiazine, quinapyramine, quinine, fluconazole, ketoconazole, itraconazole, Amphoteiscin B, 5-fluorocytosine, clotrimazole, hexadecylphosphocholine and nystatin; renal excretion inhibitors such as probenicid; nucleoside transport inhibitors such as dipyridamole, dilazep and nitrobenzylthioinosine, immunomodulators such as FTK506, cyclosporin A, thymosin α-1; cytokines including TNF and TGF-β; interferons including IFN-α, IFN-β, and IFN-γ; interleukins including various interleukins, macrophage/granulocyte colony stimulating factors including CM-CSF, G-CSF, M-CSF, cytokine antagonists including anti-TNF antibodies, anti-interleukin antibodies, soluble interleukin receptors, protein kinase C inhibitors and the like.

Examples of suitable active therapeutic agents or ingredients which can be combined with one or more compounds of the invention, and which have activity against HIV, include 1) HIV protease inhibitors, e.g., amprenavir, atazanavir, fosamprenaviri indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, RO0334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifivirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vieriviroc, INCB9471, PRO-140, INCB15050, PF-232798, CCR5mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon, 12) ribavirin analogs, e.g., rebetol, copegus, levovirin, VX-497, and viramidine (taribavirin) 13) NS5a inhibitors, e.g., A-831 and A-689, 14) NS5b polymerase inhibitors, e.g., NM-283, valopicitabine, R1626, PSI-6130 (R1656), HIV-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) non-nucleoside inhibitors of HIV, e.g., benzimidazole derivatives, benzo-1,2,4-thiadiazine derivatives, and phenylalanine derivatives, 19) other drugs for treating HIV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811, 19) pharmacokinetic enhancers (molecules that enhance the bioavailability of another drug by inhibiting the metabolism of the other drug which is typically coadministered with the pharmacokinetic enhancer), e.g., BAS-100, PF-4194477, TMC-41629, roxythromycin and SPI452, 20) RNAse H inhibitors, e.g., ODN-93 and ODN-112, 21) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS1119, ALG889, and PA-1050040.

Again by way of example, the following list discloses exemplary HIV antivirals, with their corresponding U.S. patent numbers that can be combined with one or more of the compounds of the present invention.

Exemplary HIV Antivirals and Patent Numbers

Ziagen (Abacavir sulfate, U.S. Pat. No. 5,034,394)
Epzicom (Ahbacavir sulfate/lamivudine, U.S. Pat. No. 5,034, 394)
Hepsera (Adefovir dipivoxil, U.S. Pat. No. 4,724,233)
Agenerase (Amprenavir, U.S. Pat. No. 5,646,180)
Reyataz (Atazanavir sulfate, U.S. Pat. No. 5,849,911)
Rescriptor (Delavirdine mesilate, U.S. Pat. No. 5,563,142)
Hivid (Dideoxycytidine; Zalcitabine, U.S. Pat. No. 5,028, 595)
Videx (Dideoxyinosine; Didanosine, U.S. Pat. No. 4,861, 759)
Sustiva (Efavirenz, U.S. Pat. No. 5,519,021)
Emtriva (Emtricitabine, U.S. Pat. No. 6,642,245)
Lexiva (Fosamprenavir calcium, U.S. Pat. No. 6,436,989)
Virudin; Triapten; Foscavir (Foscarnet sodium, U.S. Pat. No. 6,476,009)
Crixivan (Indinavir sulfate, U.S. Pat. No. 5,413,999)
Epivir (Lamivudine, U.S. Pat. No. 5,047,407)
Combivir (Lamivudine/Zidovudine, U.S. Pat. No. 4,724,232)
Aluviran (Lopinavir)
Kaletra (Lopinavir/ritonavir, U.S. Pat. No. 5,541,206)
Viracept (Nelfilnavir mesilate, U.S. Pat. No. 5,484,926)
Viramune (Nevirapine, U.S. Pat. No. 5,366,972)
Norvir (Ritonavir, U.S. Pat. No. 5,541,206)
Invirase; Fortovase (Saquinavir mesilate, U.S. Pat. No. 5,196, 438)
Zerit (Stavudine, U.S. Pat. No. 4,978,655)
Truvada (Tenofovir disoproxil fumarate/emtricitabine, U.S. Pat. No. 5,210,085)
Aptivus (Tipranavir)
Retrovir (Zidovudine; Azidothymidine, U.S. Pat. No. 4,724, 232)

In yet another embodiment, the present invention provides a combination pharmaceutical agent comprising:

a) a first pharmaceutical composition comprising a compound of the present invention, or a pharmaceutically acceptable salt, solvate, or ester thereof, and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HIV, and other drugs for treating HIV, and combinations thereof.

Exemplary Methods of Making the Compounds of the Invention.

The invention also relates to methods of making the compositions of the invention. The compositions are prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., *Advanced Organic Chemistry, Third Edition*, (John Wiley & Sons, New York, 1985), *Comprehensive Organic Synthesis. Selectivity, Strategy & Efficiency in Modern Organic Chemistry. In 9 Volumes*, Barry M. Trost, Editor-in-Chief (Pergamon Press, New York, 1993 printing).

A number of exemplary methods for the preparation of the compositions of the invention are provided below. These methods are intended to illustrate the nature of such preparations and are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the examples (hereafter "exemplary schemes") leads to various analogs of the specific exemplary materials produce. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (*Stereochemistry of Carbon Compounds*, (1962) by E. L. Eliel, McGraw Hill; Lochmuller, C. H., (1975) *J. Chromatogr.*, 113(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall. New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

Synthetic Schemes

Compounds of the present invention of Formula I can be prepared, for example, according to the following reaction schemes.

Using these representative synthetic schemes, the preparation of compounds of the invention begins with the preparation of bromides of formula 1-10, which serve as versatile intermediates in the formation of ring A. Preparation of compound 1-7 is reported in WO2005/077050A2, which is incorporated herein by reference in its entirety. Heck reaction of allyl alcohol with iodides of formula 1-1 generates aldehydes of formula 1-2. Methylenation under modified Mannich conditions provides enals of formula 1-3. Condensation with an aminoester of formula 1-5 under acidic conditions provides pyridines of formula 1-6. Selective formation of the monoester 1-8 can be effected via hydrolysis to diacid 1-7, subsequent formation of a corresponding cyclic anhydride with a reagent such as acetic anhydride and regioselective ring opening with an alcohol such as i-PrOH in the presence of a Lewis acid, preferably magnesium (II) perchlorate. Treatment with DPPA in aqueous t-BuOH provides anilines of formula 1-9. Finally, bis-bromination with a reagent such as NBS provides bromides of formula 1-10. The substituent $R_1$ in Scheme 1 can be, for example, para fluoro.

Scheme 1

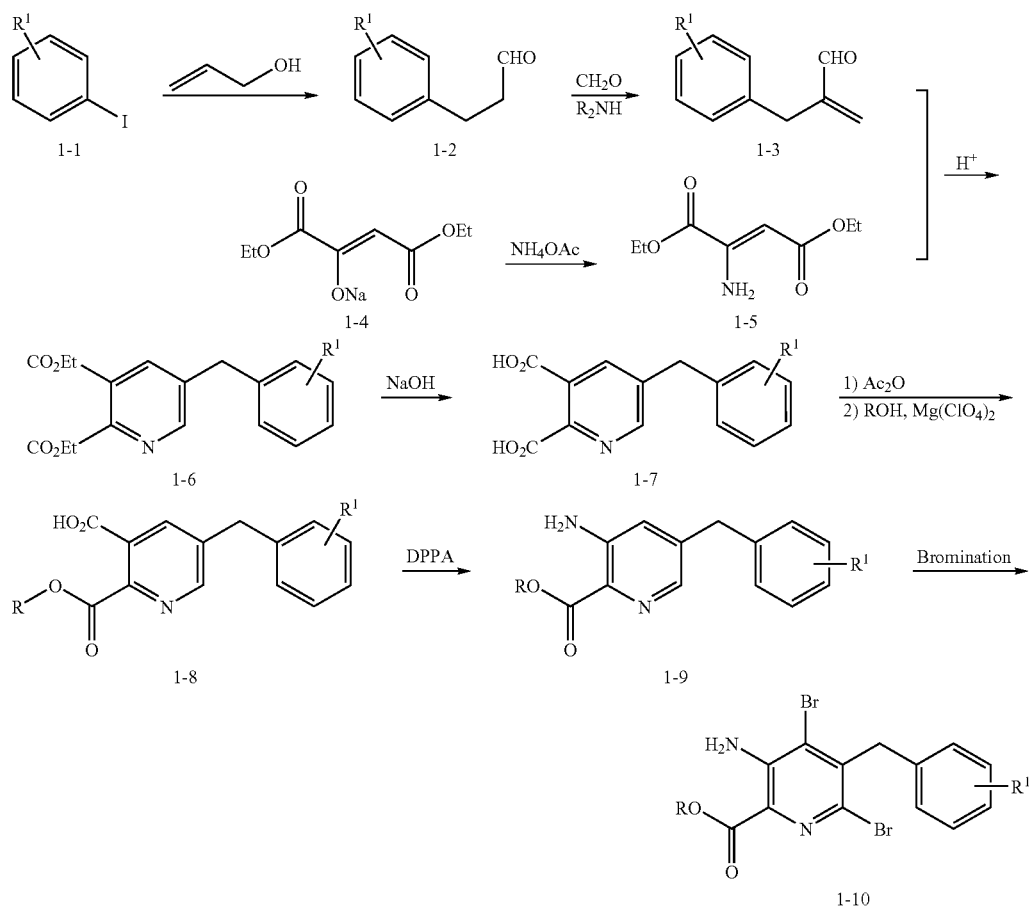

Alternatively, intermediates of formula 1-9 are prepared according to scheme 2. The known compound 2-1 (disclosed in WO 2007/136714), is converted to 2-2 using the same procedures used to convert 1-7 to 1-9 in Scheme 1. 3-Bromo intermediate 2-2 is coupled with a suitably substituted benzyl zinc bromide with palladium (II) as a catalyst in an appropriate Negishi coupling condition to afford 2-3. The Boc protection group is removed under acidic conditions to provide intermediates of formula 1-9.

Scheme 2

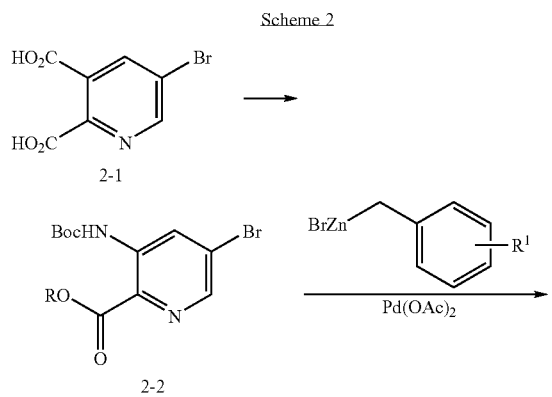

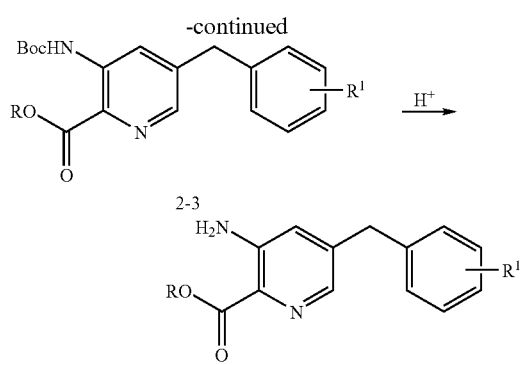

Compounds of formula 1-A are readily prepared by the methods outlined in Scheme 3. Reaction of a suitably protected bromo-aniline of formula 3-1 with an electrophile of structure 3-2 (where X is a suitable leaving group), in the presence of a suitable base, such as NaHMDS or the like, provide compound 3-3. Hydrolysis of the ester functionality, and if necessary, removal of the protecting groups (by methods known in the prior art) provides the intermediate 3-4. Subsequent treatment of compound 3-4 with an appropriate base, such as NaHMDS or the like, provides the cyclyzed product 3-5 via a nucleophilic aromatic substitution. Esterification, followed by amide formation with the malonyl-Cl derivative 3-7 provides compounds of formula 3-8. Cyclization in the presence of a base, preferably NaOEt, provides heterocycles of formula 3-9. Conversion to compounds of formula I-A can be effected by treatment with an appropriate primary amine. In Scheme 3, PG is a protecting group. The substituent R in Scheme 3 can be, for example, para fluoro. The substituent $R_2$ in Scheme 3 can be, for example, substituted heteroalkyl. The substituent $R_3$ in Scheme 3 can be, for example, $C_1$ to $C_5$ alkyl or $C_1$ to $C_5$ heteroalkyl.

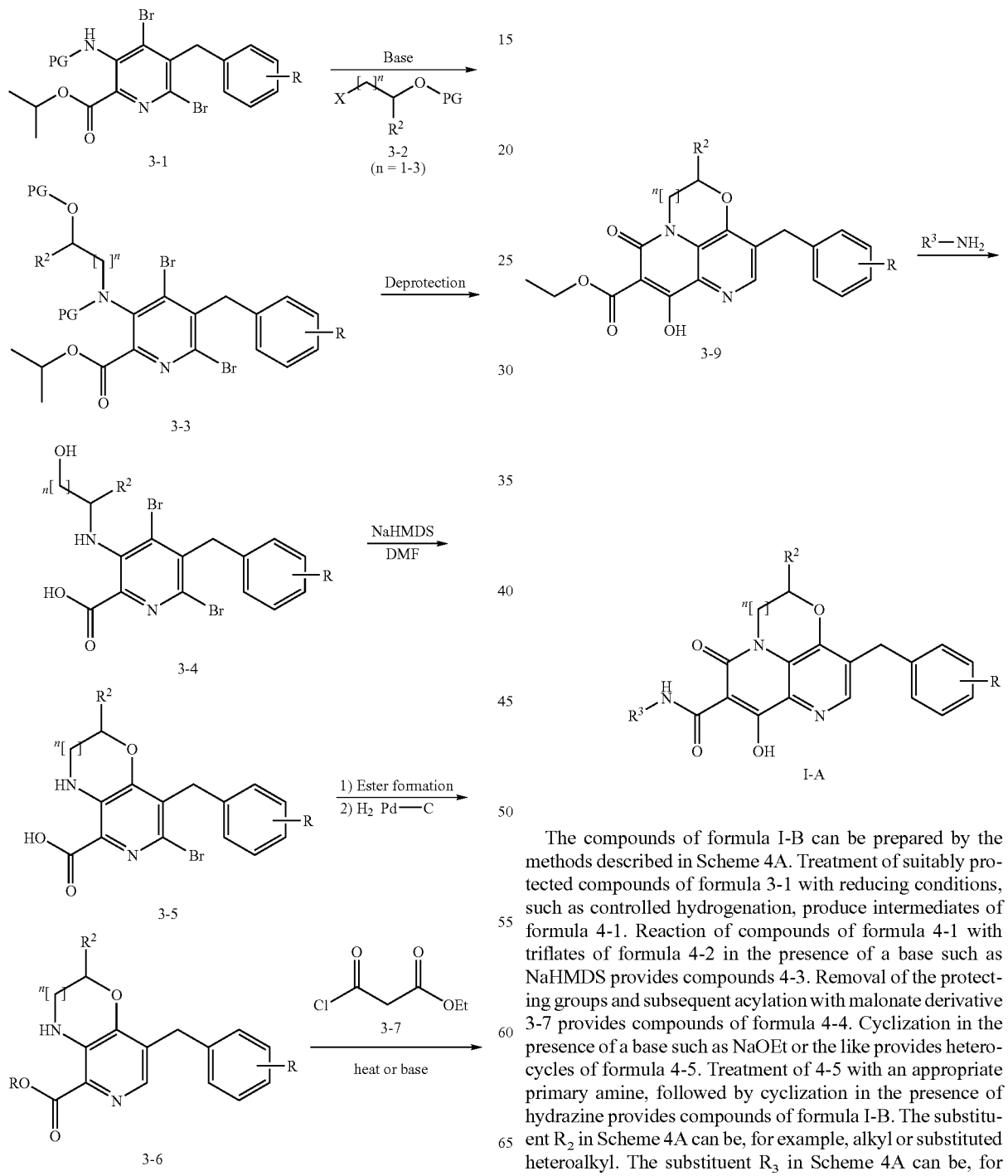

The compounds of formula I-B can be prepared by the methods described in Scheme 4A. Treatment of suitably protected compounds of formula 3-1 with reducing conditions, such as controlled hydrogenation, produce intermediates of formula 4-1. Reaction of compounds of formula 4-1 with triflates of formula 4-2 in the presence of a base such as NaHMDS provides compounds 4-3. Removal of the protecting groups and subsequent acylation with malonate derivative 3-7 provides compounds of formula 4-4. Cyclization in the presence of a base such as NaOEt or the like provides heterocycles of formula 4-5. Treatment of 4-5 with an appropriate primary amine, followed by cyclization in the presence of hydrazine provides compounds of formula I-B. The substituent $R_2$ in Scheme 4A can be, for example, alkyl or substituted heteroalkyl. The substituent $R_3$ in Scheme 4A can be, for example, alkyl.

Scheme 4A
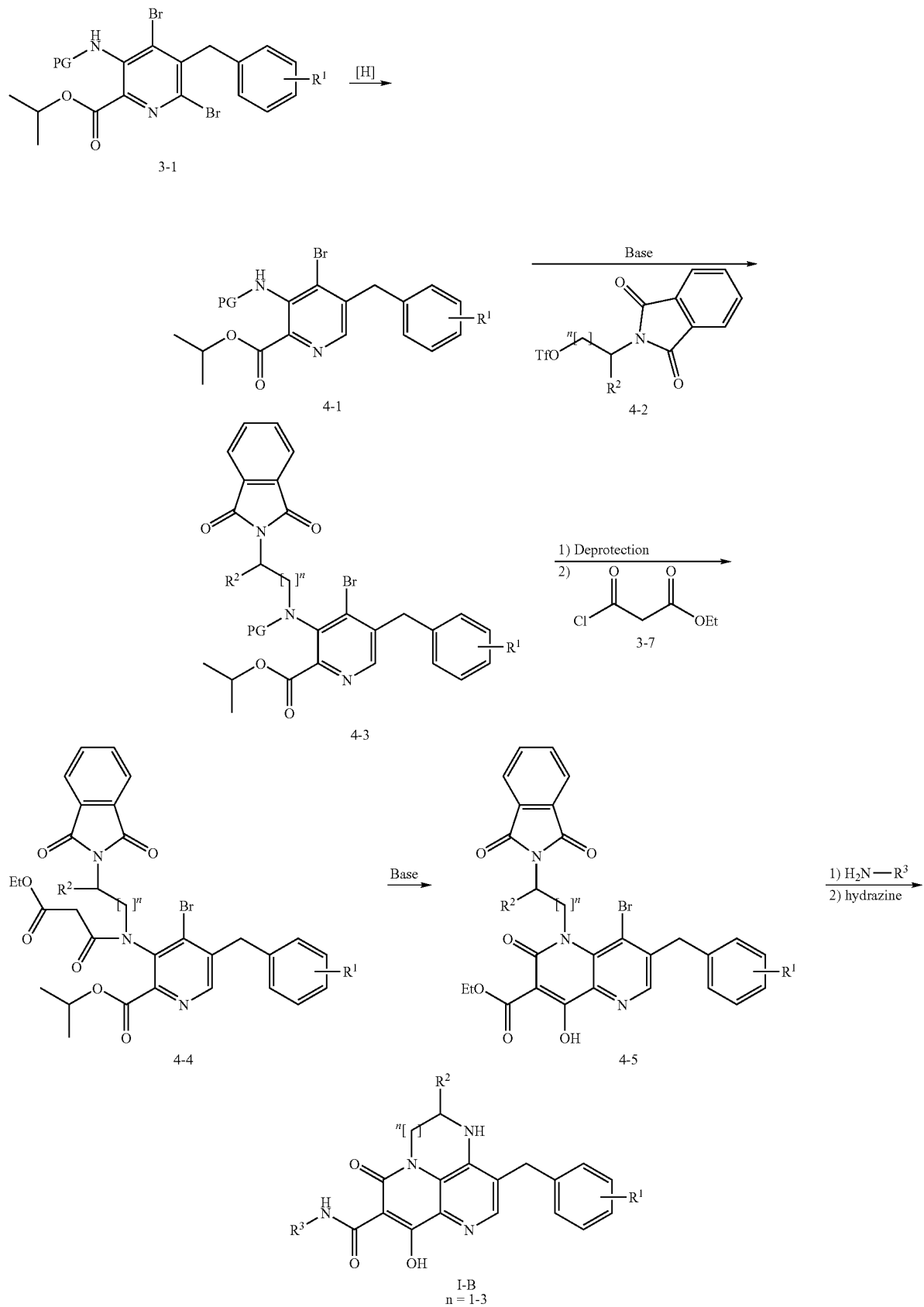

The compounds of formula I-B' can be prepared by the methods described in Scheme 4B. Treatment of suitably protected compounds of formula 3-1 (as shown in Scheme 4A) with reducing conditions, such as controlled hydrogenation, produce intermediates of formula 4-1B. Reaction of compounds of formula 4-1B with triflates of formula 4-2B in the presence of a base such as NaHMDS provides compounds 4-3B. Removal of the protecting groups and subsequent acylation with malonate derivative 3-7 provides compounds of formula 4-4B. Cyclization in the presence of a base such as NaOEt or the like provides heterocycles of formula 4-5B. Treatment of 4-5B with an appropriate primary amine, followed by cyclization in the presence of hydrazine provides compounds of formula I-B'. The substituent R$_3$ in Scheme 4B can be, for example, alkyl.

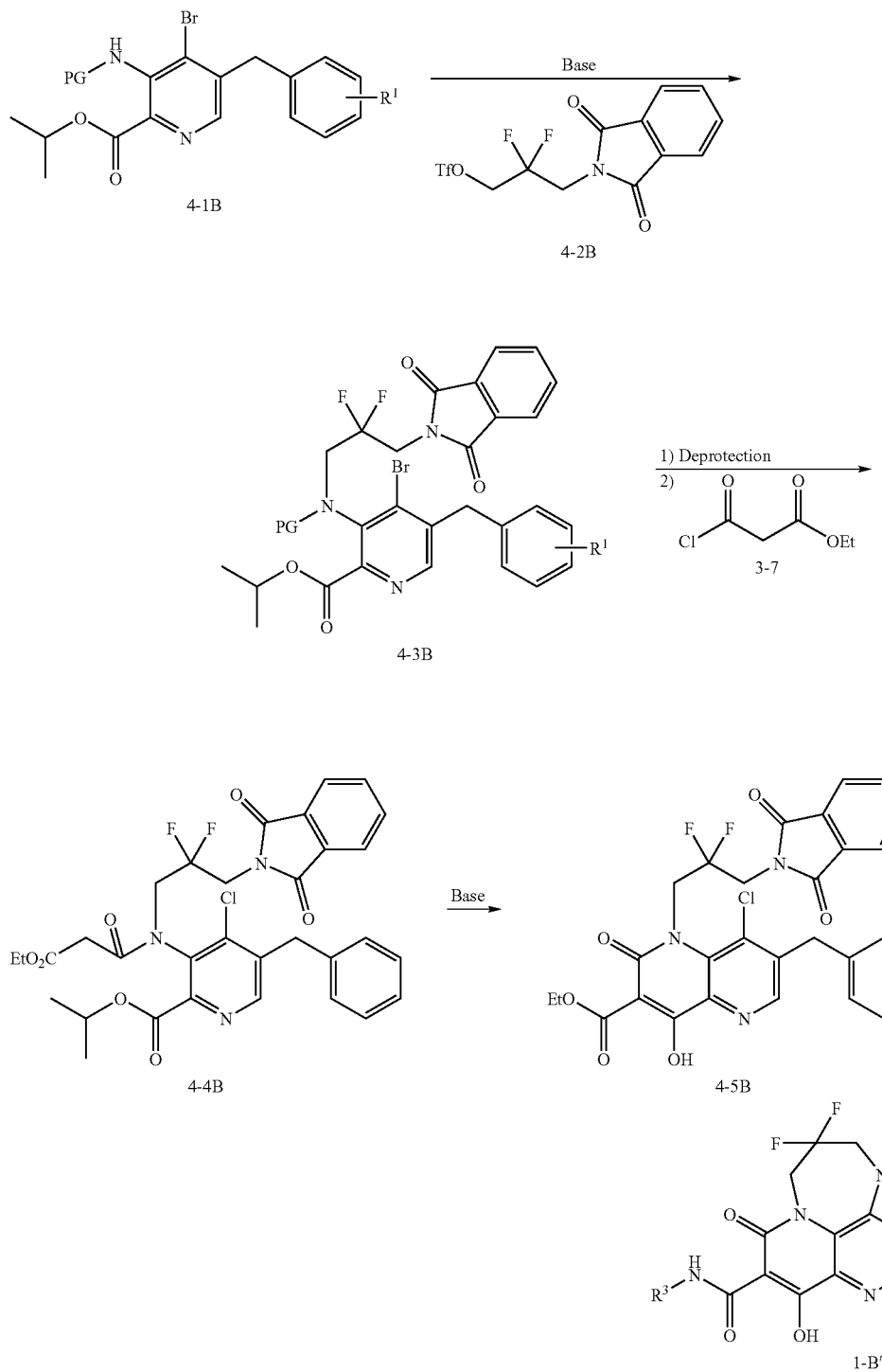

Scheme 5 describes preparation of compounds of formula I-C, beginning with suitably protected bromides of formula 4-1. Heck reaction with allyl alcohol provides aminals of formula 5-1. Reduction with a hydride source such as triethylsilane in the presence of trifluoroacetic acid (TFA) provides compounds of formula 5-2. Removal of any protecting groups, followed by condensation with malonyl derivate 3-7 provides compounds of formula 5-3. Treatment with a base such as NaOEt provides cyclized heterocycles of formula 5-4. Compounds of formula I-C are produced by treatment of 4-5 with an appropriate primary amine. The substituent R in Scheme 5 can be, for example, para fluoro. The substituent $R_3$ in Scheme 5 can be, for example, alkyl.

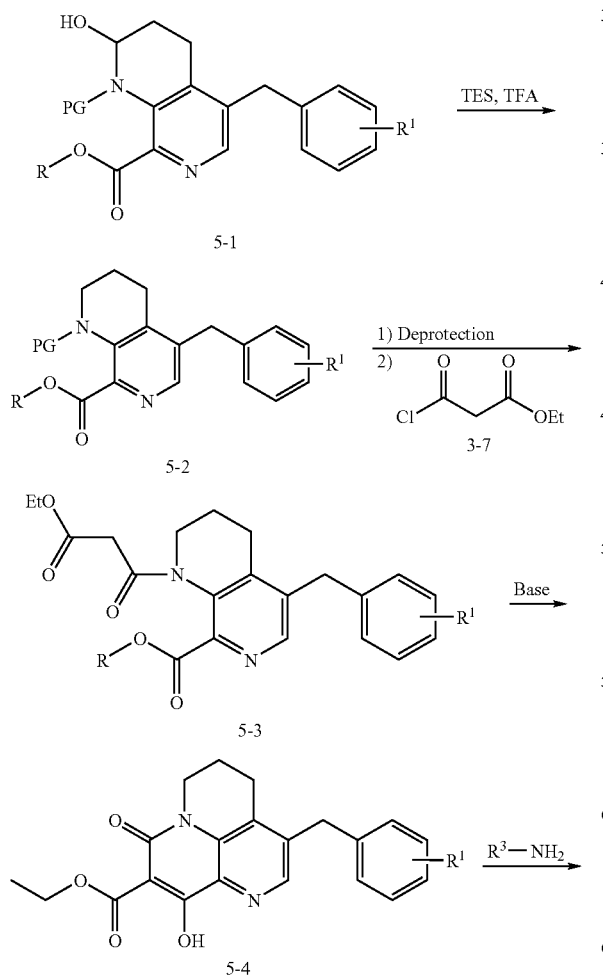

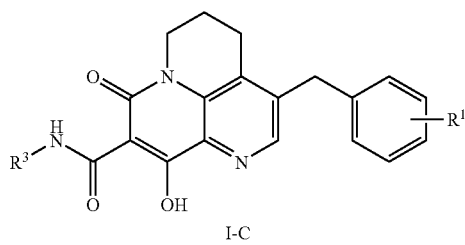

The compounds of formula I-D are prepared according to reaction sequences shown in Scheme 6. Thus, alkylation of a suitably protected aniline of formula 4-1 with an allyl halide such as 2-methyl-bromopropene in the presence of a base such as NaHMDS provides compounds of formula 6-1. Cyclization under reducing Heck conditions provides substituted indulines of formula 6-2. Removal of the protecting group and acylation with malonate derivative 3-7 provides compounds of formula 6-3. Cyclization in the presence of a base such as NaOEt provides tricyclic heterocycles of formula 6-4. Subsequent treatment with an appropriate primary amine provides compounds of formula I-D. The substituent R in Scheme 6 can be, for example, para fluoro. The substituent $R_2$ in Scheme 6 can be, for example, alkyl or substituted heteroalkyl. The substituent $R_3$ in Scheme 6 can be, for example, alkyl.

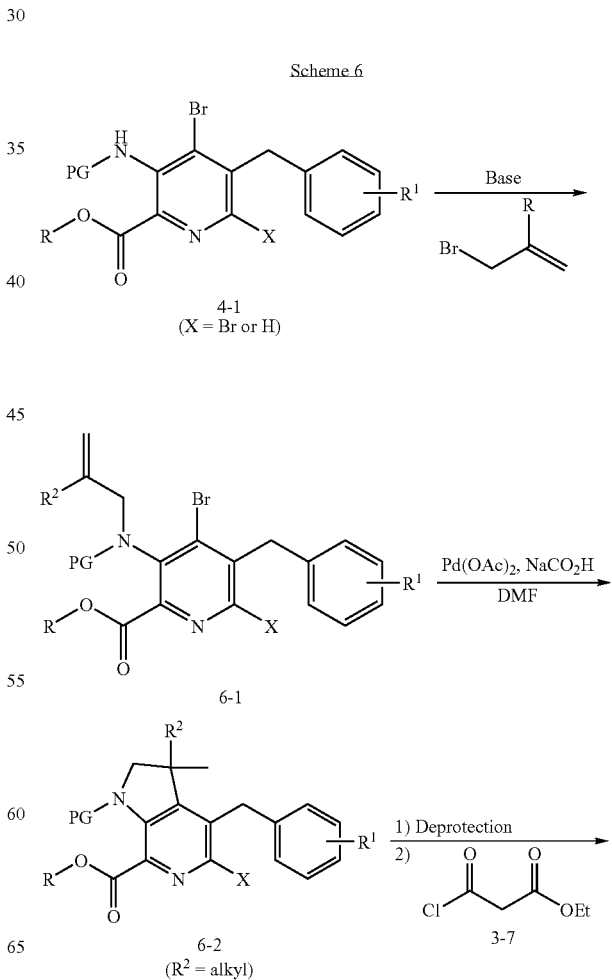

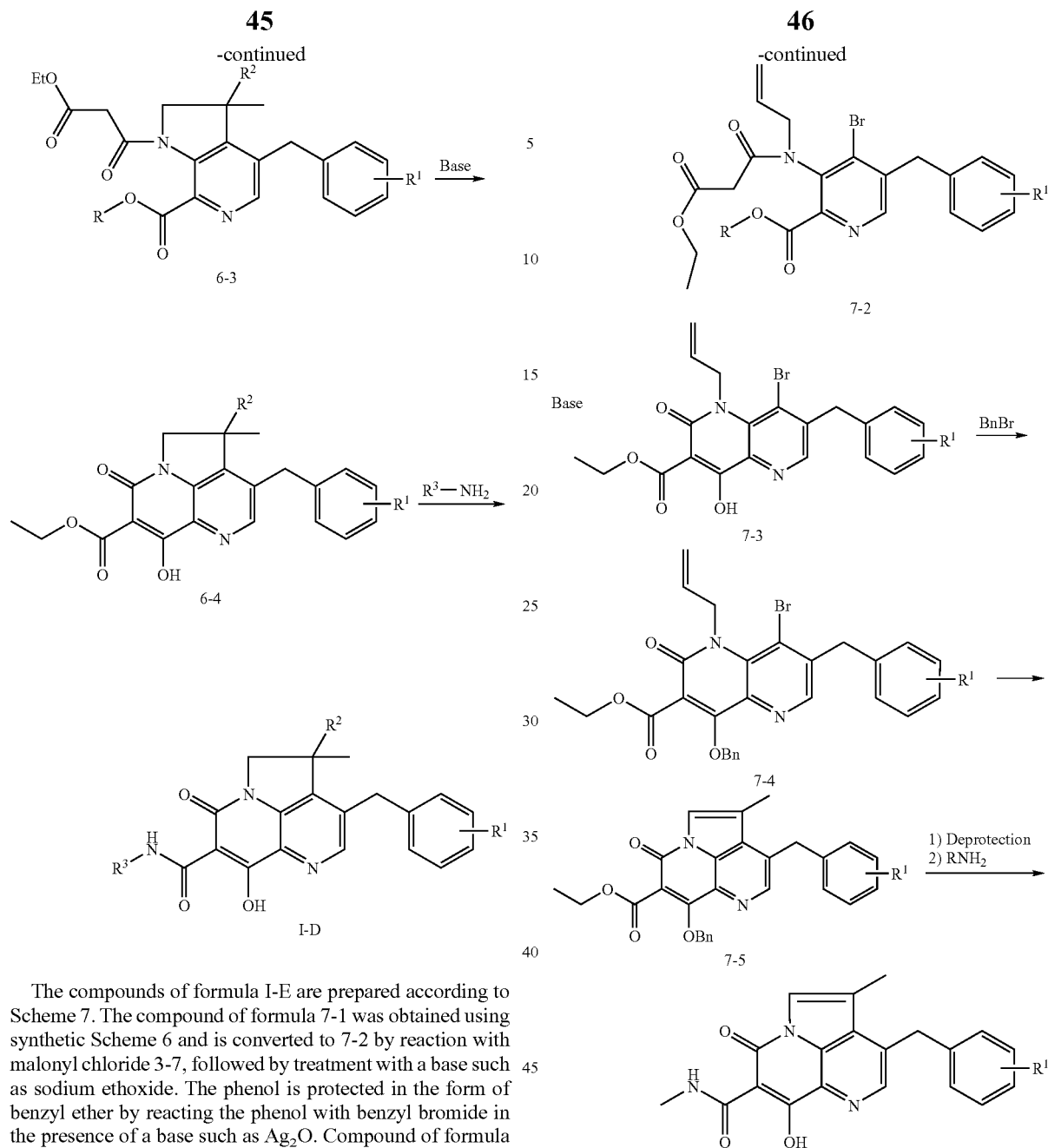

The compounds of formula I-E are prepared according to Scheme 7. The compound of formula 7-1 was obtained using synthetic Scheme 6 and is converted to 7-2 by reaction with malonyl chloride 3-7, followed by treatment with a base such as sodium ethoxide. The phenol is protected in the form of benzyl ether by reacting the phenol with benzyl bromide in the presence of a base such as Ag$_2$O. Compound of formula 7-4 is treated with Pd(AcO)$_2$, under a Heck reaction condition to form a compound of formula 7-5. Removal of the benzyl protection group on 7-5, followed by reaction between the ester and appropriate amines produces the compound of formula I-E.

Scheme 7

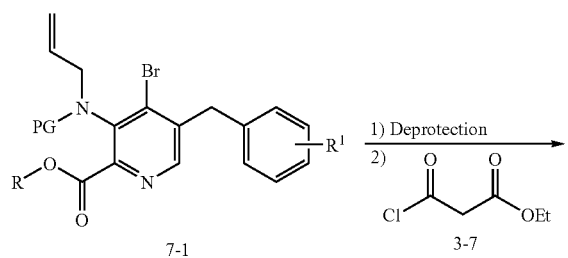

The compounds of formula I-F are prepared according to Scheme 8. Compound of formula 7-1, obtained using synthetic Schemes 1 or 2, is converted to 8-2 by reaction with malonyl chloride 3-7, followed by treatment with a base such as sodium ethoxide. The phenol is protected in the form of benzyl ether by reacting the phenol with benzyl bromide in the presence of a base, such as Cs$_2$CO$_3$. The nitrogen is aminated using known reagent 8-3 to afford 8-4. Michael addition of the amino group to 2-methylene-malonic acid dialkyl ester gives intermediates of formula 8-5. Cyclization is accomplished by treating 8-5 with a base. Removal of the two carboxylate moieties according to a procedure disclosed in the art (*J. Org. Chem.*, 60, 3928-3930) followed by reaction between ester 8-7 and appropriate amines afford the compound of formula I-F.

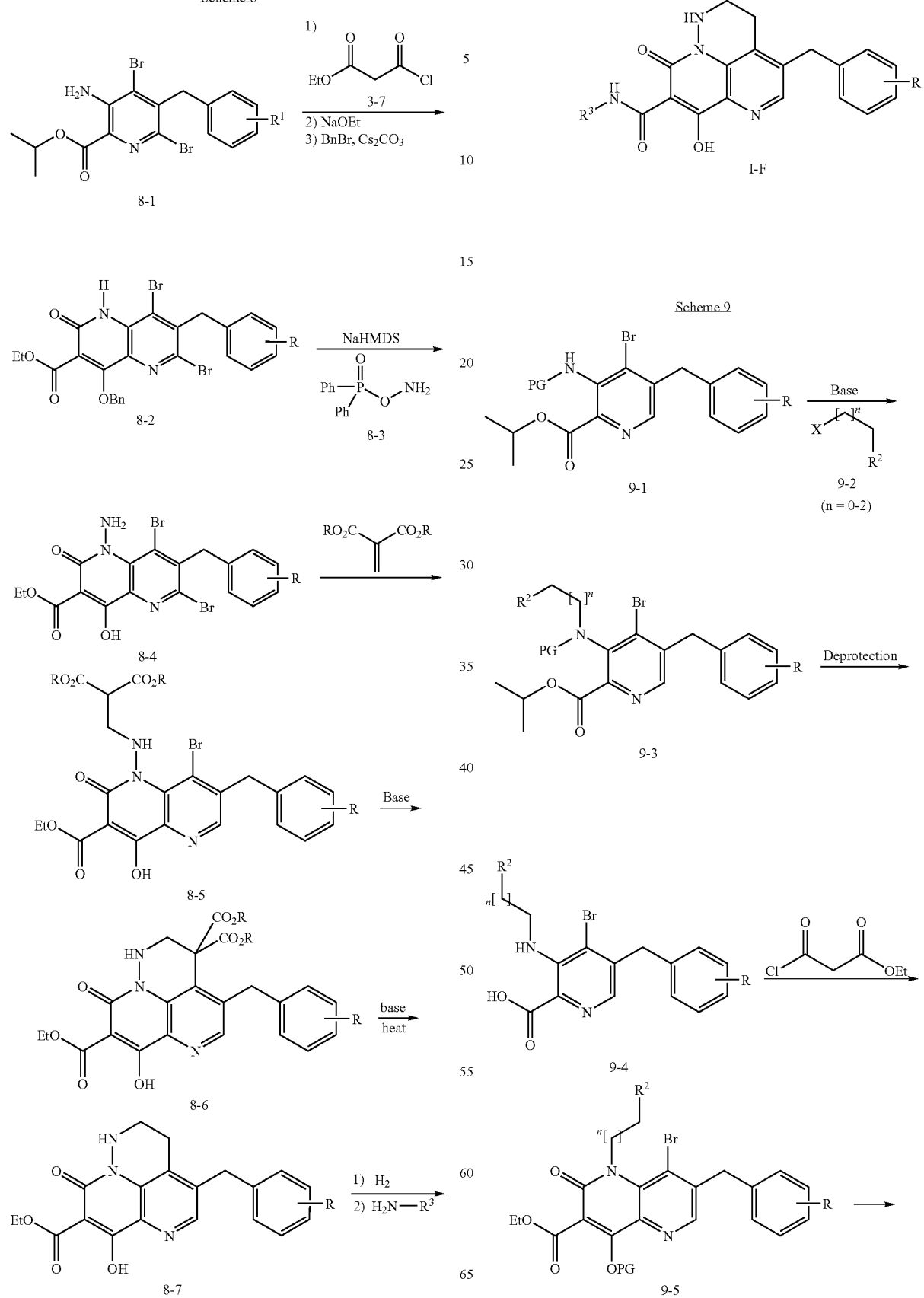

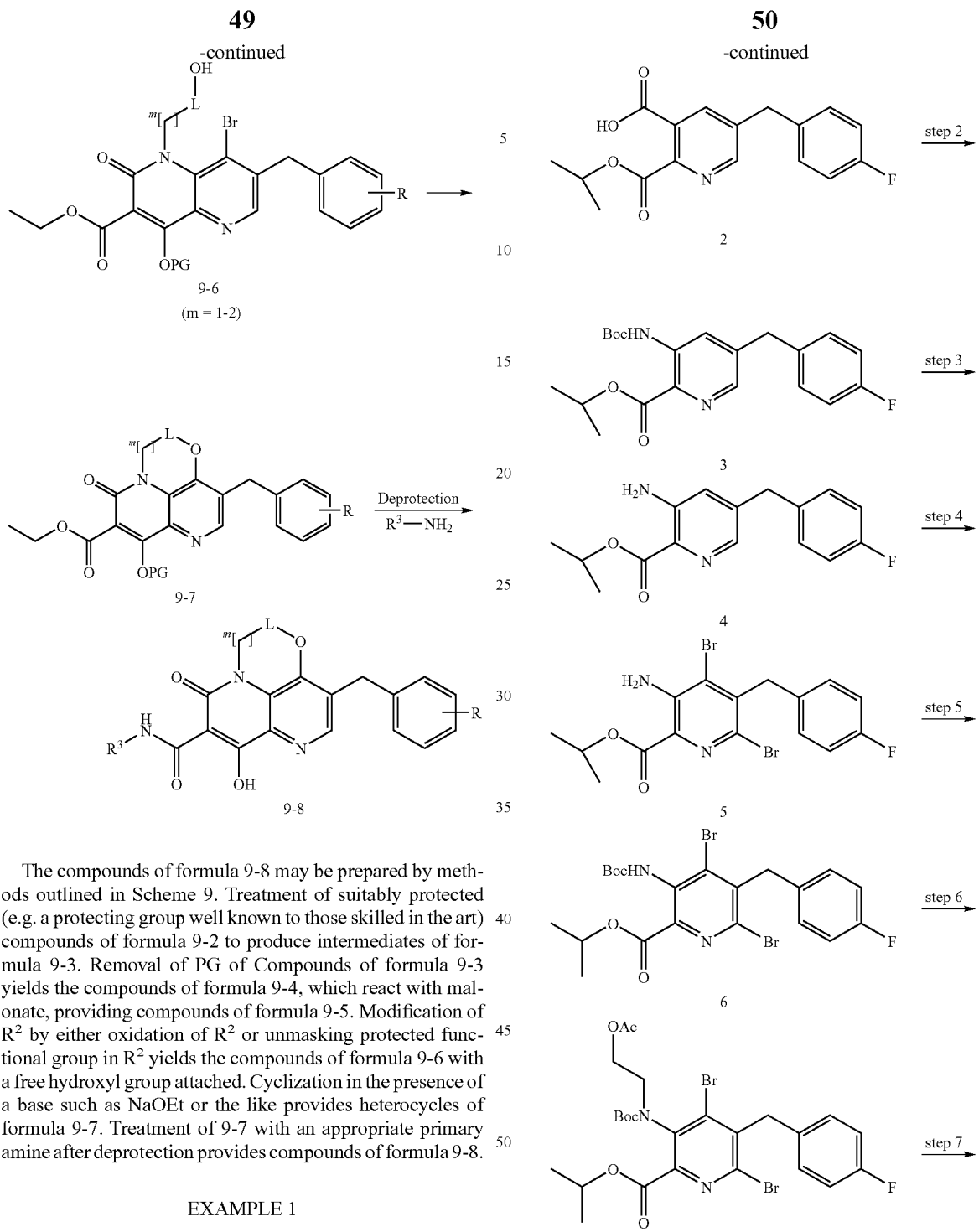

The compounds of formula 9-8 may be prepared by methods outlined in Scheme 9. Treatment of suitably protected (e.g. a protecting group well known to those skilled in the art) compounds of formula 9-2 to produce intermediates of formula 9-3. Removal of PG of Compounds of formula 9-3 yields the compounds of formula 9-4, which react with malonate, providing compounds of formula 9-5. Modification of $R^2$ by either oxidation of $R^2$ or unmasking protected functional group in $R^2$ yields the compounds of formula 9-6 with a free hydroxyl group attached. Cyclization in the presence of a base such as NaOEt or the like provides heterocycles of formula 9-7. Treatment of 9-7 with an appropriate primary amine after deprotection provides compounds of formula 9-8.

EXAMPLE 1

Preparation of Compound 12

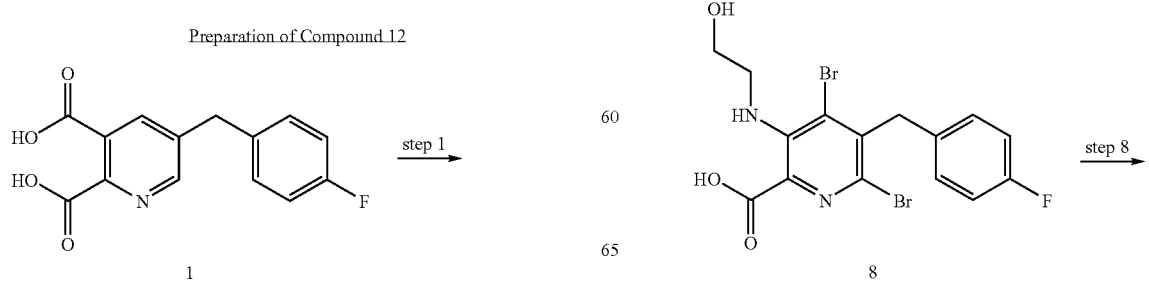

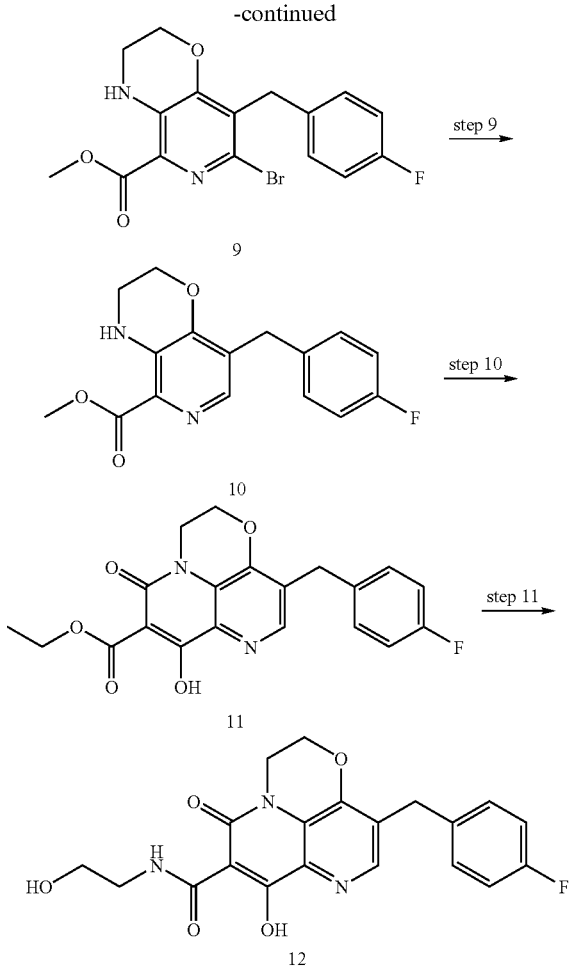

Step 1

A 5-L 3-neck rbf fitted with an overhead stirrer, a thermocouple, a J-CHEM-type temperature controller and a heating mantle was charged with diacid 1 (228 g, 829 mmol) and a large stir bar. This material was suspended in acetic anhydride (1.1 L) and heated to 120° C. for 30 minutes. An aliquot of the now homogeneous solution was quenched in MeOH and monitored by LCMS to verify complete formation of the anhydride. The flask was cooled to room temperature, the contents transferred to a 3-L rbf and concentrated by rotary evaporation. A separate 3-neck-5 L rbf fitted with a thermocouple and an overhead stirring apparatus was charged with 1-L IPA and 750 mL THF. The mixture was cooled to below 0° C. in an ice-acetone bath and treated portion-wise with magnesium(II) perchlorate (254 g, 1.13 mmol) over 15 min. A considerable exotherm was observed, with the internal temperature rising to 33° C. during the addition. Once the internal temperature had returned to 0° C., the crude anhydride was added as a solution in 500 mL THF. The reaction was allowed to warm to room temperature (rt) and stir for a total of 18 h. The supernatant was decanted into 2×3-L rbf and most of the solvent removed by rotary evaporation. The black residues were taken up in 1.5-L of EtOAc and returned to the 5-L rbf with the solids. With vigorous stirring, the mixture was treated with 6N HCL (200 mL), water (500 mL) and brine (500 mL). The organic layer was separated and extracted with 0.5 N NaHCO$_3$ (3×1 L). The relatively colorless aqueous layers were combined and washed with 50% EtOAc in hexane, then diluted with 1 L EtOAc and acidified with 6N HCl. After stirring for 15 min, the layers were separated and the aqueous washed with 350 mL EtOAc (2×). The organic layers were combined, washed with brine and concentrated in vacuo. The solid product was triturated in a mixture of ether and hexanes. Filtration provided the desired product (135 g, 51% yield) as a tan powder. Concentration of the filtrate provided a second batch of the desired product 2 (56 g, 21% yield) as a waxy solid. $^1$H NMR (CDCl$_3$) δ 8.66 (s, 1H), 8.03 (s, 1H), 7.13 to 7.10 (m, 2H), 7.02 to 6.97 (m, 2H), 5.31 (heptet, J=6 Hz, 1H) 4.03 (s, 3H), 1.35 (d, J=6 Hz, 6H); LCMS RT=2.15 min, MS [M−H]=317.89.

Step 2

A 5-L 3-neck rbf fitted with an overhead stirrer, a thermocouple, a J-CHEM-type temperature controller and a heating mantle was charged with Intermediate 2 (100 g, 315 mmol) and 1000 mL of t-BuOH. The reaction mixture was evacuated and back-filled with N$_2$, followed by addition of TEA (132 mL, 946 mmol) and DPPA (102 mL, 473 mmol). The reaction mixture was then heated to 65° C. for 2 h. The reaction mixture was cooled to room temperature and quenched with 500 g of ice. The reaction mixture was diluted with 50% EtOAc in hexanes and 150 g of citric acid in 1-L of water. The layers were separated and the organic layer was washed with sat. sodium bicarbonate, dried with sodium sulfate and concentrated in vacuo to provide the desired product 3 as a brown solid. This material was used unpurified in the next reaction. An analytical sample was purified by column chromatography (ISCO, 0 to 50% EtOAc in hexanes). $^1$H NMR (CDCl$_3$) δ; LCMS RT=2.71 min; MS [M−H]=388.96.

Step 3

Intermediate 3 (ca. 122 g, 0.315 mmol) was taken up in 500 mL DCM and 250 mL TFA. After 6 h stirring, the solvents were removed in vacuo and the residue partitioned between 1-L EtOAc and 10% sodium citrate solution. The organic layer was separated, washed with brine and dried with sodium sulfate. The solution was concentrated in vacuo, and the solid triturated with ether to provide the desired product 4 (72.1 g, 79% yield-2 steps) as a tan powder. $^1$H-NMR (DMSO-d$_6$) d 7.95 (s, 1H), 7.11 to 7.08 (m, 2H), 6.72 (s, 1H), 5.28 (hept, J=6 Hz, 1H), 3.87 (s, 3H), 1.40 (d, J=6 Hz, 6H); MS [M+H]+= 288.96 LCMS RT=2.16 min.

Step 4

A 2-L 1-neck rbf was charged with Intermediate 4 (52.1 g, 180 mmol), 300 mL DMF and NBS (96 g, 540 mmol) and the reaction left to stir overnight in the dark. Excess solvent was then removed in vacuo, and the residue partitioned between EtOAc (1 L) and 1N sodium carbonate. A precipitate formed during this procedure, and both layers were filtered to provide the desired product 5 (25.7 g, 32% yield) as a tan solid. The organic layer of the filtrate was separated, washed with 2.5% LiCl and dried with sodium sulfate. After removal of the solvent in vacuo, the residue was triturated with ether to provide a second batch of the desired product 5 (50.1 g, 62% yield) as an orange solid. $^1$H-NMR (DMSO-d$_6$) d 7.13 to 7.09 (m, 2H), 6.96 to 6.93 (m, 2H), 6.43 (bs, 2H), 5.23 (hept, J=7 Hz, 1H); 4.34 (s, 2H), 1.42 (d, J=6 Hz, 6H); MS [M+H]+= 446.8 LCMS RT=2.73 min.

Step 5

A solution of Intermediate 5 (10.19 g, 22.9 mmol) in 100 mL DMF was treated with di-tert-butyl-di-carbonate (10.97 g, 50.3 mmol), DIEA (12 mL, 69 mmol) and DMAP (281 mg, 2.3 mmol) and the reaction mixture left to stir overnight at room temperature. The reaction was diluted with 1-L EtOAc and 1-L of pH 3 citrate buffer. The organic layer was separated, washed with 10% sodium citrate and brine and concentrated in vacuo to provide a dark oil. Purification by silica gel chromatography (ISCO™, 0 to 50% EtOAc in hexanes) provided the bis-Roc intermediate (10.5 g, 71% yield) as a yellow crystalline solid. An analytical sample was recrystallized from EtOAc-hexanes as white, cotton-like crystals. $^1$H-NMR (DMSO) d 7.06 to 7.03 (m, 2H), 6.95 to 6.93 (m, 2H), 5.26 (hept, J=6 Hz, 2H), 4.45 (s, 2H), 1.35 (d, J=6 Hz, 6H), 1.33 (s, 18h); MS [M+H]=668.8 LCMS RT=2.81 min.

A solution of Bis-Boc intermediate (1.74 g, 2.69 mmol) in 1,2-Dichloroethane [DCE] (50 mL), was added Trifluoroacetic acid (1 mL, 2%). The reaction was stirred at room temperature for 5 hours. Upon completion, the reaction was diluted with 50 mL EtOAc and quenched with a 10% sodium citrate solution. The layers were separated, and the aqueous layer was extracted with ethyl acetate (2×). The combined organic layer was washed with brine (2×), then dried (over Na$_2$SO$_4$), filtered and concentrated in vacuo. The crude residue was triturated with ether to afford the desired product 6 (1.42 g, 97% yield) as a tan powder: MS [M+H]=546.7; LCMS RT=2.73 min.

Step 6

A solution of 6 (6.47 g, 11.85 mmol) in 100 mL of DMF stirred at −16° C. was treated drop-wise with NaHMDS/1M THF over approximately 6 min. After stirring for 10 min at −16° C. to −14° C. 2-bromoethyl acetate was added dropwise to the reaction over a period of 5 min. The reaction was stirred at low temperature for 10 min post addition before warming to ambient and subsequently heating at 80° C. for 2 h. Monitoring by LCMS indicated that the reaction was complete. After cooling to ambient it was evaporated at 50° C. in-vacuo partitioning between 400 mL of ethyl acetate and 500 mL of 5% aqueous citric acid. The phases were separated and the aqueous phase was extracted with 300 mL of ethyl acetate. The pooled organic phases were washed with 500 mL of water and 300 mL of brine before drying with Na$_2$SO$_4$, filtering, evaporation in-vacuo at 30° C. and treatment with high vacuum to afford 7.58 g of 7, trace M+1=634.70, major fragment ion M+1−C$_4$H$_8$=576.73.

Step 7

Compound 7 from the preceding step was dissolved in 25 mL of dichloromethane and treated with 25 mL of TFA. Monitoring of the reaction by HPLC indicated that it was complete after stifling overnight. Following evaporation in-vacuo at 30° C. the residue was portioned between ethyl acetate and saturated aqueous NaHCO$_3$. The separated aqueous phase was extracted with ethyl acetate and the pooled organic phases were washed with water and twice with brine before drying (Na$_2$SO$_4$), being filtered, evaporated in vacuo at 30° C. and treated with high vacuum. Purification of the initially obtained product (6.25 g) was accomplished by preparative flash chromatography (silica gel 60, ethyl acetate/hexane gradient) affording 4.34 g of intermediate (M+1=532.80).

An aqueous solution of K$_2$CO$_3$ (5.9 g, 30 mL water) was added to intermediate obtained above (4.34 g, 8.15 mmol) dissolved in 150 mL of methanol. The reaction was stirred for 4 min before adding a trace of additional water to generate a homogeneous reaction. Analysis of the reaction by HPLC/LCMS indicated completion after 88 min. The reaction was evaporated in-vacuo at 30° C. to a thick slurry which was partitioned between ethyl acetate and water after the aqueous phase was acidified using approximately 4N HCl. The phases were separated and the aqueous phase was extracted twice with ethyl acetate before the combined organic phases were washed with water and brine. Drying (Na$_2$SO$_4$), filtration and evaporation in-vacuo at 30° C. followed by high vacuum treatment afforded 3.46 g of 8, (M+1, M+3, M+5=446.80, 448.76, 450.77, 1:2:1).

Step 8

Sodium hexamethyldisilylazide (1M/THF, 1.2 mL) was added dropwise to a 0° C. solution of 8 (234 mg, 0.522 mmol) in 4 mL of DMF. The homogeneous solution was removed from the ice bath and heated at 100° C. for 14 min. Evaluation of the reaction indicated, iv remained and an additional 0.6 mL of NaHMDS/THF was added to the reaction after it had cooled to ambient temperature. After stirring in a 100° C. bath for 15 min the reaction was complete. When cool the reaction was diluted into ethyl acetate and 10% aqueous citric acid (pH=~5). The combined organic fractions from the initial phase separation and two subsequent ethyl acetate extractions were washed twice with water and once with brine, dried (Na$_2$SO$_4$), filtered, evaporated in vacuo at 30° C. and high vacuum to afford 179.7 mg of cyclized intermediate, (M+3=368.98), which was used in the next step without farther characterization.

A solution of crude acid (2.64 g, 7.2 mmol) obtained from a reaction similar to the preceding reaction in 150 mL of THF/MeOH 2:1 was treated with TMS diazomethane (2M/Hex, 12 mL, 24 mmol). LCMS was used to monitor the reaction for completion. When the reaction was complete the excess TMS diazomethane was decomposed by the cautious addition of a solution of acetic acid in THF. Evaporation in-vacuo at 30° C., partitioning between ethyl acetate and water, washing of the organic phase with water and brine, drying (Na$_2$SO$_4$), filtration, and evaporation in-vacuo at 30° C. afforded crude product. Purification was accomplished via preparative flash chromatography (silica gel 60, ethyl acetate/hexane gradient) to afford 1.23 g of 9, M+1=380.05.

Step 9

A mixture of Intermediate 9 (101 mg, 0.22 mmol), sodium acetate (60 mg, 1 mmol) and 10 mg 10% Pd—C in 1 mL MeOH and 1 mL EtOAc was stirred vigorously under a hydrogen atmosphere for 1 h. The reaction was diluted with EtOAc and filtered thru a plug of Celite. The filtrate was concentrated in vacuo and the residue purified by silica gel chromatography (ISCO™, 0 to 80% EtOAc in hexanes) to afford the desired product 10 (75 mg, 91% yield) as a yellowish powder: MS [M+H]=303.3; LCMS RT=1.89.

Step 10

A solution of Intermediate 10 (75 mg, 0.20 mmol) and ethyl malonyl monochloride (125 μL, 0.4 mmol) in 5 mL DCE was heated at 75° C. for 2 h. The reaction was diluted with 20 mL EtOAc and 20 mL of pH 6 citrate buffer. The organic layer was separated, brine and concentrated in vacuo to provide an oily residue. Purification by silica gel chromatography (ISCO™, 0 to 100% EtOAc in hexanes) provided the malonyl intermediate (54 mg, 65% yield) as a yellow oil. This material was taken up in 2 mL EtOH and cooled to 0° C. This mixture was treated with 21% NaOEt in EtOH (100 μL, 0.26 mmol) and allowed to stir for 5 min. The reaction was diluted with 10 mL EtOAc and 10 mL pH 3.0 citrate buffer. The organic layer was separated, dried with sodium sulfate and concentrated in vacuo. This residue was triturated with Et$_2$O to provide the desired product 11 (38.7 mg, 78% Yield): MS [M+H]=385.0; LCMS RT=: 1.99.

Step 11

A solution of Intermediate 11 (38.7 mg, 0.1 mmol) and 110 μL ethanolamine in 1.5 mL DMF was heated at 125° C. for 5 min in a microwave reactor. The reaction mixture was diluted with 15 mL DMF and concentrated in vacuo. The residue was crystallized from Et$_2$O; MeOH (2:1) to provide the desired product 12 (22.6 mg, 57% yield) as a tan powder. $^{0,1}$H-NMR (DMSO-d$_6$) d 10.33 (t, 1H), 8.34 (s, 1H), 7.29 to 7.25 (m, 2H), 7.12 to 7.07 (m, 2H), 4.82 (t, 1), 4.48 (t, 2H), 4.11 (app. t, 2H), 3.53 (app. q, 2H), 3.42 (m, 2H); MS [M+H]$_+$=400.21 LCMS RT=2.15 min.

EXAMPLE 2

Preparation of Compound 13

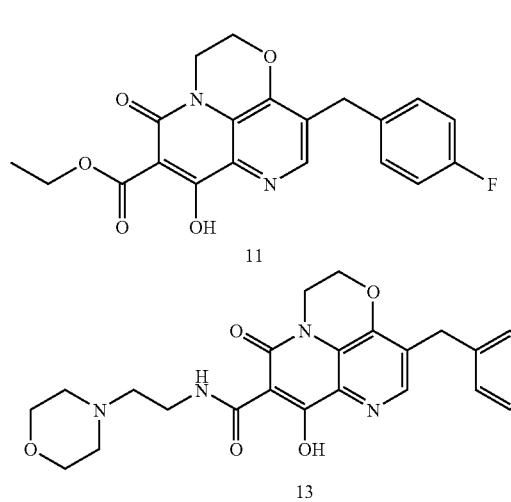

Compound 13 was prepared in the same manner as step 11 in Example 1.

$^{0.1}$H-NMR (CH$_3$OH-d$_4$) d 8.39 (s, 1H), 7.31 (m, 2H), 7.04 (m, 2H), 4.62 (t, J=4.9 Hz, 2H), 4.28 (t, J=4.9 Hz, 2H), 3.67 (t, J=6 Hz, 2H), 2.91 (bs, 4H), 2.82 (t, J=6H) $^{19}$F NMR (376 MHz, CH$_3$OH-d$_4$) d −72.81 (s, TFA), −114 (h); MS [M+H]$^+$= 469.13.

EXAMPLE 3

Preparation of Compound 14

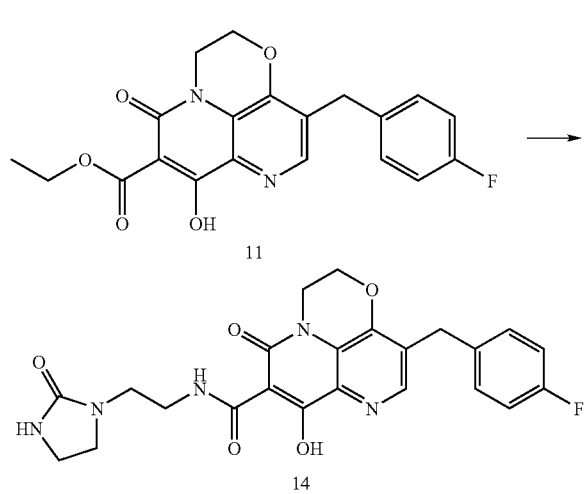

Compound 14 was prepared in the same manner as step 11 in Example 1. $^{0.1}$H-NMR (CH$_3$OH-d$_4$) d 8.38 (s, 1H), 7.31 (m, 2H), 7.03 (m, 2H), 4.59 (t, J=4.9 Hz, 2H), 4.28 (t, J=4.9 Hz, 2H), 4.12 (s, 2H), 3.91-3.96 (cm, 6H), 3.63 (t, J=6.2 Hz, 2H), 3.52 (bs, 4H), $^{19}$F NMR (376 MHz, CH$_3$CH-d$_4$) d-72.81 (s, TFA), −114 (m); MS [M+H]$^+$=468.11.

EXAMPLE 4

Preparation of Compound 15

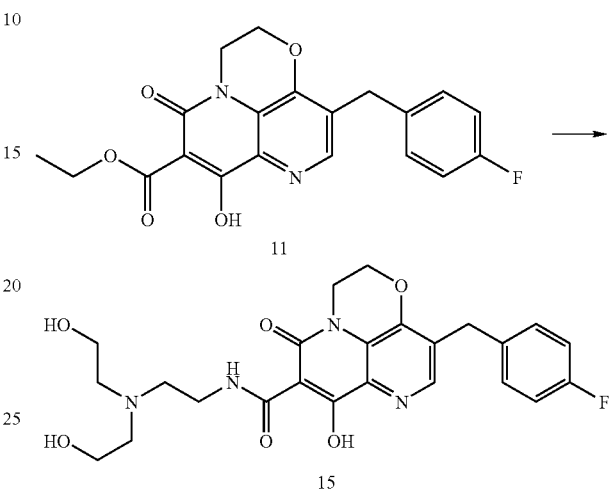

Compound 15 was prepared in the same manner as step 11 in Example 1. $^{0.1}$H-NMR (CH$_3$OH-d$_4$) d 8.38 (s, 1H), 7.31 (m, 2H), 7.03 (m, 2H), 4.59 (t, J=4.9 Hz, 2H), 4.28 (t, J=4.9 Hz, 2H), 4.12 (s, 2H), 3.91-3.96 (cm, 6H), 3.63 (t, J=6.2 Hz, 2H), 3.52 (bs, 4H). $^{19}$F NMR (376 MHz, CH$_3$OH-d$_4$) d −72.69 (s, TFA), −114.10 (m); MS [M+H]$^+$=487.12.

EXAMPLE 5

Preparation of Compound 16

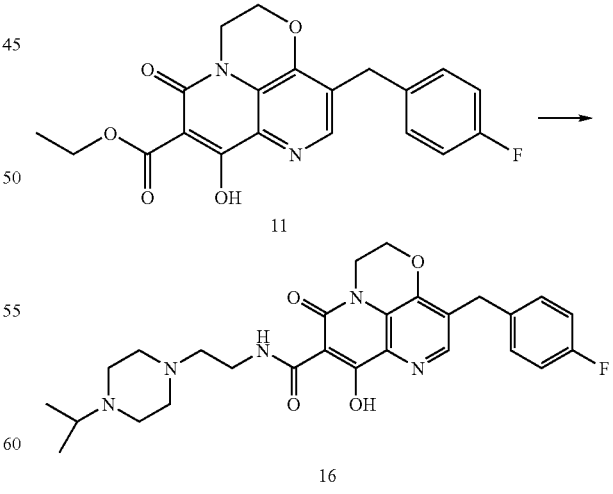

Compound 16 was prepared in the same manner as step 11 in Example 1. $^{0.1}$H-NMR (CH$_3$OH-d$_4$) d 8.39 (s, 1H), 7.31 (m, 2H), 7.04 (m, 2H), 4.62 (t, J=4.9 Hz, 2H), 4.28 (t, J=4.9 Hz, 2H), 4.13 (s, 3H), 3.66 (t, S=6 Hz, 2H), 3.55 (h, J=6.6 Hz, 1H), 2.80 (t, J=6 Hz, 2H), 1.39 (d, J=6.3 Hz, J=6H). $^{19}$F NMR (376 MHz, CH$_3$OH-d$_4$) d −72.81 (s, TFA), −114 (m); MS [M+H]$^+$=510.18.

EXAMPLE 6

Preparation of Compound 17

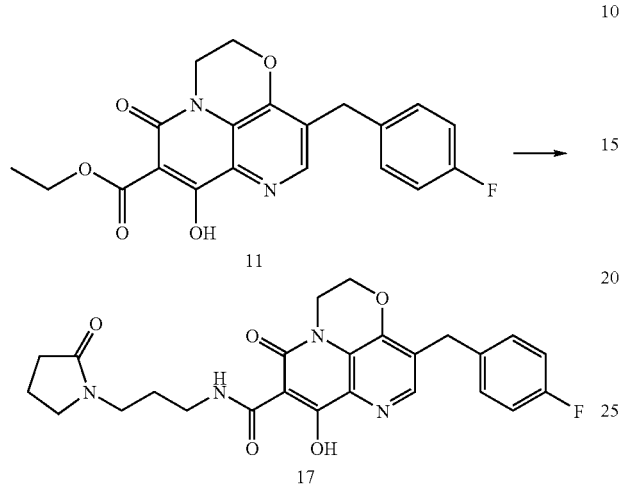

Compound 17 was prepared in the same manner as step 11 in Example 1. $^{0.1}$H-NMR (CH$_3$OH d$_4$) d 8.39 (s, 1H), 7.31 (m, 2H), 7.04 (m, 2H), 4.62 (t, J=4.9 Hz, 2H), 4.28 (t, J=4.9 Hz, 2H), 4.13 (s, 3H), 3.66 (t, J=6 Hz, 2H), 3.55 (h, J=6.6 Hz, 1H), 2.80 (t, J=6 Hz, 2H), 1.39 (d, J=6.3 Hz, J=6H). $^{19}$F NMR (376 MHz, CH$_3$OH-d$_4$) d −72.81 (s, TFA), −114 (m); MS [M+H]$^+$= 510.18.

EXAMPLE 7

Preparation of Compound 18

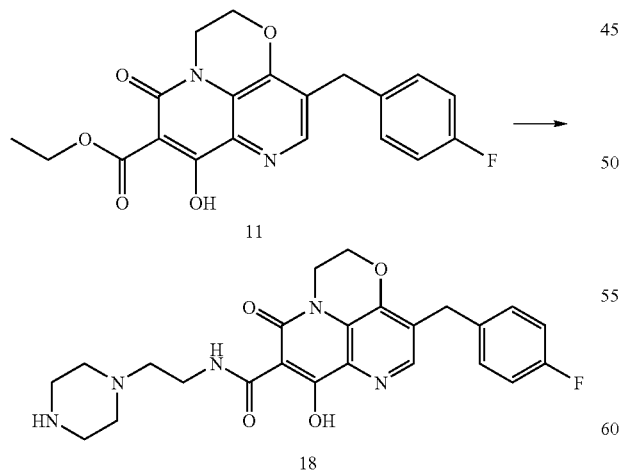

Compound 18 was prepared in the same manner as step 11 in Example 1. $^{0.1}$H-NMR (CH$_3$OH-d$_4$) d 8.39 (s, 1H), 7.31 (m, 2H), 7.04 (m, 2H), 4.62 (t, J=4.9 Hz, 2H), 4.28 (t, J=4.9 Hz, 2H), 4.13 (s, 2H), 3.67 (t, J=6 Hz, 2H), 2.91 (bm, 4H), 2.82 (t, J=6.1 Hz, 2H). $^{19}$F NMR (376 MHz, CH$_3$OH-d$_4$) d −72.81 (s, TFA), −114 (m); MS [M+H]$^+$=468.16.

EXAMPLE 8

Preparation of Compound 24

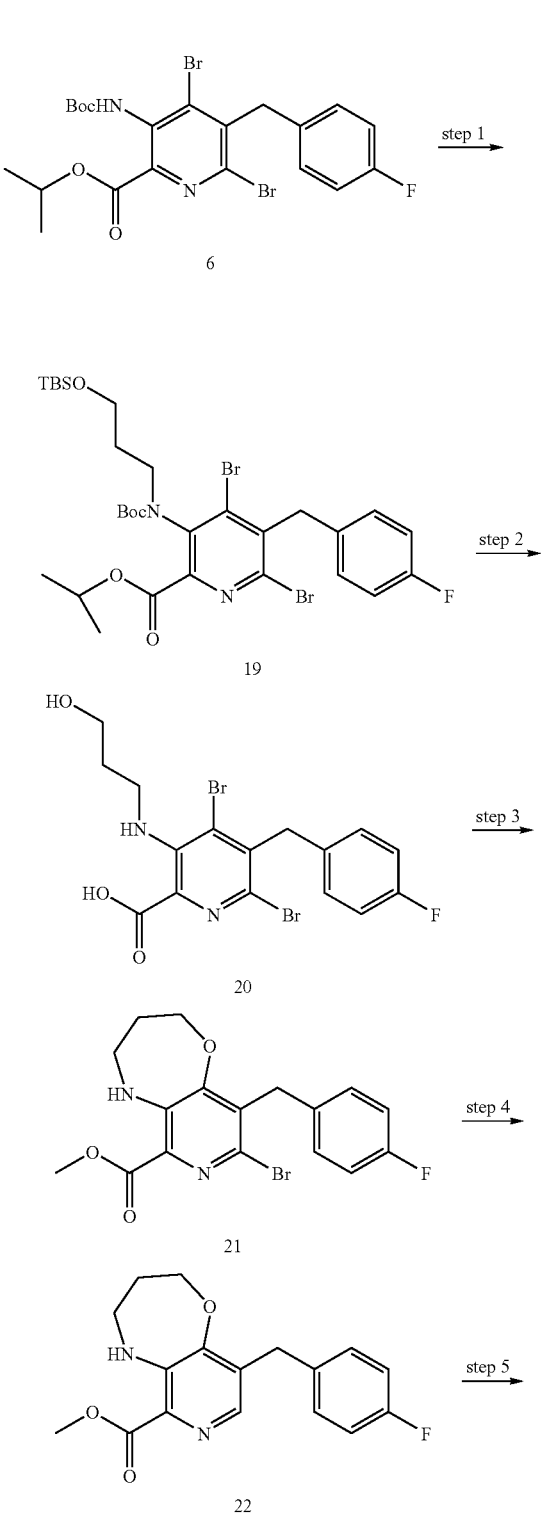

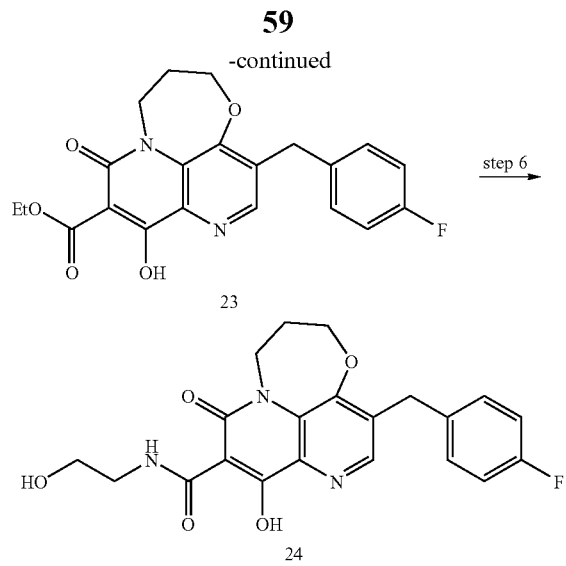

Step 4

Intermediate 22 was prepared using the same procedure as for compound 10 in step 9, example 1. MS [M+H]=317.1 LCMS RT=2.12 min.

Step 5

Intermediate 23 was prepared using the same procedure as for compound 11 in step 10, example 1. MS [M+H]=398.9 LCMS RT=2.16 min.

Step 6

Compound 24 of this example was prepared from 23 using the same procedure used for compound 12, Example 1. $^1$H-NMR (DMSO-$d_6$) d 10.35 (t, 1H), 8.41 (s, 1H), 7.227 to 7.22 (m, 2H), 7.03 to 7.09 (m, 2H), 4.88 (t, 1H), 4.33 (app. t, 2H), 4.25 (app. t, 2H), 3.51 (app. q, 2H), 3.42 (app. q, 2H), 2.16 (m, 2H); MS [M+H]+=414.04 LCMS RT=2.14 min.

EXAMPLE 9

Preparation of Compound 30

Step 1

A solution of Intermediate 6 (318 mg, 0.58 mmol) in 7 mL DMF was cooled to −10° C. in an ice-acetone bath and treated with NaHMDS (1 M, 0.73 mL, 0.73 mmol). After 1 minutes stirring, 3-bromopropoxy-tert-butyldimethylsilane (338 µL, 1.46 mmol) was added, and the reaction heated to 80° C. for 30 min. The reaction was diluted with EtOAc and pH 3 citrate buffer. The organic layer was separated, washed with brine, dried with sodium sulfate and concentrated in vacuo. Purification by silica gel chromatography (ISCO™, 0 to 70% EtOAc in hexanes) provided the desired product 19 (397 mg, 94% yield) as a yellow oil. MS [M+H]=718.6; LCMS RT=4.41 min.

Step 2

A solution of Intermediate 19 (397 mg, 0.55 mmol) in 10 mL DCM was treated with 10 mL TFA and allowed to stir for 2 h. The reaction was concentrated in vacuo and the residue partitioned between EtOAc and 10% sodium citrate solution. The organic layer was separated, washed with brine, dried with sodium sulfate and concentrated in vacuo. The residue was triturated with ether to provide the desired product (205 mg, 74% yield) as a tan solid. MS [M+H]=504.8 LCMS RT=2.49 min.

A solution of the intermediate obtained above (205 mg, 0.41 mmol) in 10 mL MeOH was treated with 1 mL of 2 N $K_2CO_3$ solution and 1 mL water. The mixture was stirred at room temperature for 30 min. The reaction was diluted with 150 mL EtOAc, acidified with 0.7 mL 6N HCl and diluted again with 5 mL brine. The organic layer was dried with sodium sulfate and concentrated in vacuo to provide the desired product 20 (157 mg, 83% yield) as a brown solid. MS [M+H]=462.7; LCMS RT=2.19 min.

Step 3

A solution of Intermediate 20 (340 mg, 0.737 mmol) in 20 mL DMF was treated with NaHMDS (1N, 1.98 mL, 1.98 mmol) and heated to 100° C. After 2 h the reaction mixture was cooled to 0° C. and treated with MeI (450 µL, 7.37 mmol) and 4 Å MS and allowed to stir at room temperature for 16 h. The reaction was diluted with ethyl acetate and pH 5 buffer. The organic layer was washed with 2.5% LiCl (2×), dried with sodium sulfate and concentrated in vacuo. Purification by silica gel chromatography (ISCO™, 0 to 80% EtOAc in hexanes) provided the desired product 21 (108 mg, 67% yield) as a yellow crystalline solid. MS [M+H]=395.1, 397.0 LCMS RT=2.59 min.

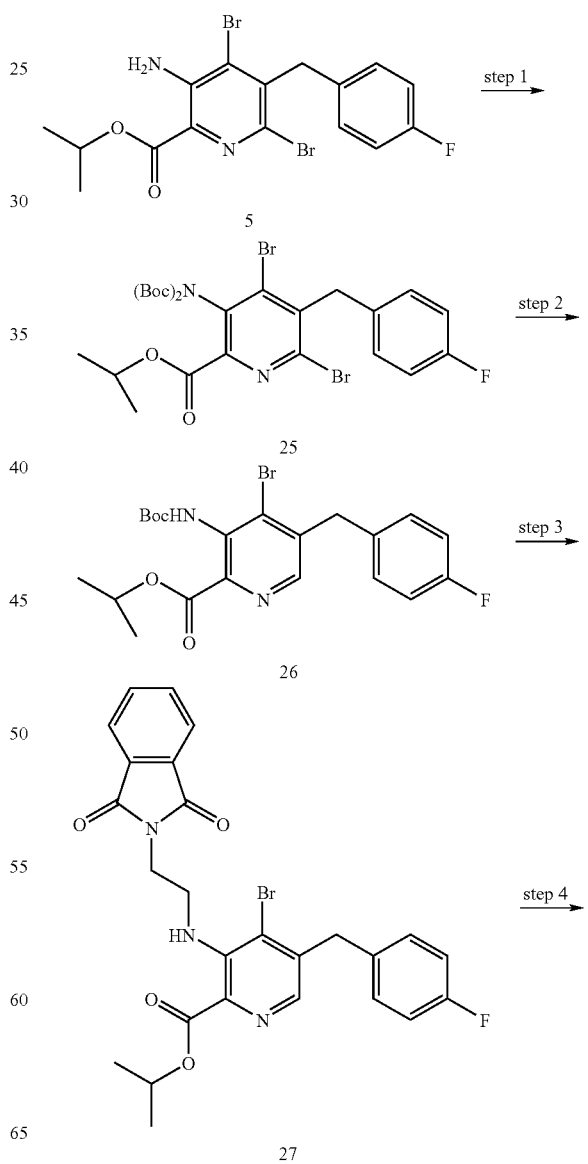

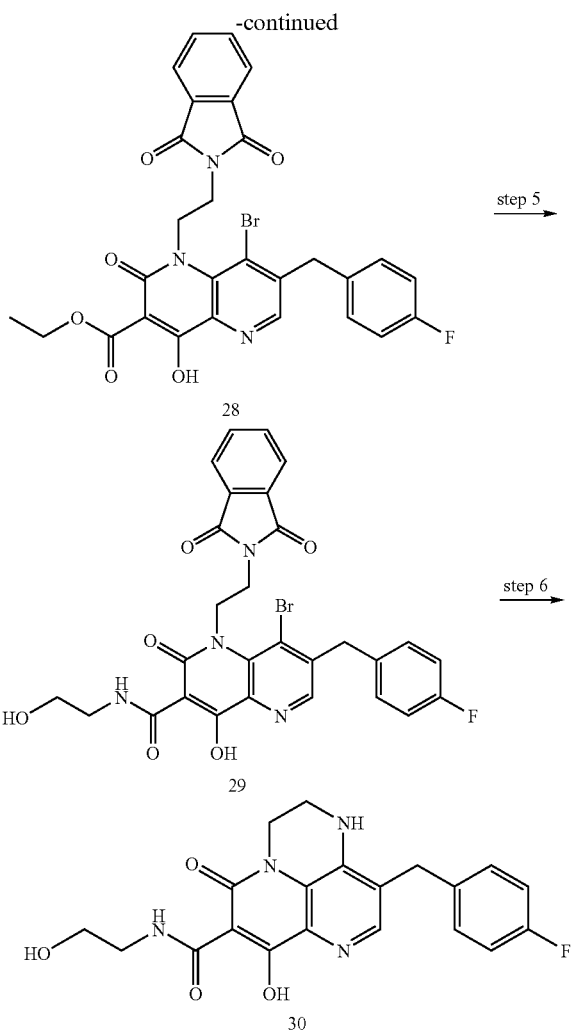

Step 1

Compound 5 was converted to the Bis-Boc intermediate as described in step 5, example 1. A solution of bis-Boc intermediate (9.61 g, 14.86 mmol) in DMF (74 mL) was purged with argon (3×), and sequentially treated with Pd(PPh$_3$)$_4$ (860 mg, 0.743 mmol, 0.05 equivalents; Strem) and sodium formate (1.06 g, 15.62 mmol). The reaction was stirred at 80° C. for 1 hour. The reaction [monitored by TLC, LC or LC/MS] was sluggish, so another 0.05 equivalents of Pd(PPh$_3$)$_4$ was added and the reaction was stirred at 80° C. for 3 hours [in subsequent runs, 0.10 equivalents of Pd(PPh$_3$)$_4$ have been added from the start instead]. At this point, the reaction was cooled to room temperature, then diluted with ethyl acetate and quenched with a saturated NH$_4$Cl solution. The layers were separated, and the aqueous layer was extracted with ethyl acetate (2×). The combined organic layer was washed with aqueous LiCl (5%), and brine, then dried (over Na$_2$SO$_4$), filtered and concentrated in vacuo. The crude residue was recrystallized in ethyl acetate to afford the desired product 25 (8.454 g, quant) as a yellowish powder: $^1$H-NMR (CDCl$_3$-d$_6$) 8.45 (s, 1H), 7.09 (m, 2H), 6.97 (m, 2H), 5.31 (sept, J=6.6 Hz, 1H), 4.20 (s, 2H), 1.38 (d, J=63 Hz, 6H), 1.34 (s, 18H); MS [M+H]+ 567, 569 (fragment: 1:1); LCMS RT=2.74 [product, 25], 2.91 [starting material, Bis-Boc 5].

Step 2

To a solution of Intermediate 25 (8.45 g, 14.86 mmol) in 1,2-Dichloroethane [DCE] (149 mL), was added Trifluoroacetic acid (3 mL, 2%). The reaction was stirred at room temperature for 4-5 hours. The reaction was monitored [by TLC, LC or LC/MS] to completion [if sluggish, the 3 mL of TFA is added again]. Upon completion, the reaction was diluted with ethyl acetate and quenched with a 10% sodium citrate solution. The layers were separated, and the aqueous layer was extracted with methyl acetate (2×). The combined organic layer was washed with brine (2×), then dried (over Na$_2$SO$_4$), filtered and concentrated in vacuo. The crude residue was recrystallized in ethyl acetate to afford the desired product 26 (7 g, quant) as a yellowish powder: $^1$H NMR (DMSO) 8.20 (s, 1H), 7.41 (bs, 1H), 7.11 (m, 2H), 6.96 (m, 2H), 5.26 (sept, J=6.4 Hz, 1H), 4.12 (s, 2H), 1.47 (s, 9H), 1.38 (d, J=6.0 Hz, 6H); MS [M+H]=467, 469 (fragment: 1:1)); LCMS RT=: 2.51 [product, 26], 2.62 [starting material, 25].

Step 3

To a solution of mono-Boc 26 (1.5 g, 3.21 mmol) dissolved in DMF (20 mL), cooled in a ice-water bath, was added Sodium bis(trimethylsilyl)amide (NaHMDS) (3.2 mL, 3.20 mmol, 1M THF) and stirred for 5 minutes under nitrogen atmosphere. Trifluoro-methanesulfonic acid 2-(1,3-dioxo-1,3-dihydro-isoindol-2-yl)-ethyl ester [well precedent synthesis from the commercially available N-(2-Hydroxyethyl)-phthalimide] (1.04 g, 3.22 mmol) was added and the reaction was allowed to stir for 1 hour in the ice-water bath. The reaction was quenched with saturated NH$_4$Cl and diluted with ethyl acetate. The organic layer was washed with H$_2$O, aqueous LiCl, and brine, then dried (over Na$_2$SO$_4$), filtered and concentrated in vacuo. The crude residue was purified by chromatography on silica gel (1/4—ethyl acetate/hexane) to afford the desired Boc protected 27 (1.31 g, 65%): $^1$H NMR (CDCl$_3$) 8.34, 8.28 (s, rotamers, 1H) 7.79 (m, 2H), 7.68 (m, 2H), 7.07 (m, 2H), 6.98 (m, 2H), 5.28 (m, 1H), 4.2-3.5 (m, 6H), 1.35 (m, 6H), 1.60, 1.28 (s, rotamers, 9H); MS [M+H]= 640, 642 (fragment 1:1).

To a solution of intermediate obtained above (2.61 g, 4.08 mmol) in Dichloromethane (40 mL), was added Trifluoroacetic acid (10 mL, 25%). The reaction was stirred at room temperature for 2 hours then heated at 55° C. for 4 hours. Upon completion, the reaction was diluted with ethyl acetate and quenched with a 10% sodium citrate solution. The layers were separated, and the aqueous layer was extracted with ethyl acetate (2×). The combined organic layer was washed with brine (2×), then dried (over Na$_2$SO$_4$), filtered and concentrated in vacuo to afford the desired product 27 (2.2 g, quant) with no further purification: $^1$H NMR (CDCl$_3$) 7.94 (s, 1H), 7.81 (dd, Ja=2.4 Hz, Jb=3.2 Hz, 2H), 7.705 (dd, Ja=2.4 Hz, Jb=3.2 Hz, 2H), 7.09 (dd, Ja3.2 Hz, Jb=5.2 Hz, 2H), 6.94 (dd, J=8.8 Hz, 2H), 5.17 (sept, J=6.4 Hz, 1H), 4.05 (s, 1H), 3.91 (t, J=6.0 Hz, 2H), 3.69 (t, J=6.0 Hz, 2H), 1.36 (d, J=6.4 Hz, 6H); MS [M+H]=540, 542 (fragment 1:1).

Step 4

To a solution of intermediate 27 (2.18 g, 4.04 mmol) in 1,2-Dichloroethane [DCE] (40 mL), was added Ethyl 3-chloro-3-oxo-propionate (0.562 mL, 4.45 mmol) and 2,6-lutidine (1.4 mL, 12.1 mmol). The reaction was stirred at room temperature for 30 minutes. At which point, the reaction was diluted with ethyl acetate and quenched with a 10% citric acid solution. The layers were separated, and the aqueous layer was extracted with ethyl acetate (2×). The combined organic layer was washed with brine (2×), then dried (over Na$_2$SO$_4$), filtered and concentrated in vacuo. The crude residue was purified by chromatography on silica gel (2/3—ethyl acetate/hexane) to afford the desired intermediate (1.87 g, +0.470 g of starting material 27, 90% brsm) without further characterization: MS [M+H]=654, 656 (fragment 1:1).

To a solution of intermediate obtained above (1.87 g, 2.86 mmol) in ethanol (28.6 mL) was added sodium ethoxide [21 wt % solution in ethanol] (1.28 mL, 3.44 mmol). The reaction was stirred at room temperature for 2 hours. Another portion of sodium ethoxide (0.400 mL) was added to drive the ring closure to completion. At which point, the reaction was concentrated in vacuo then dissolved in ethyl acetate and quenched with a 10% citric acid solution. The layers were separated, and the aqueous layer was extracted with ethyl acetate (2×). The combined organic layer was washed with brine (2×), then dried (over $Na_2SO_4$), filtered and concentrated in vacuo to afford a mixture of desired product and product with the phthalimide protecting group partially (halfway) hydrolyzed. The crude mixture was subsequently redissolved in Tetrahydrofuran [THF] (28 mL) then treated with 1,1'-Carbonyldiimidazole [CDI] (325 mg, 2.00 mmol). The re-protection reaction was stirred at room temperature for 1 hour. Upon completion, the reaction mixture was diluted with ethyl acetate and quenched with a 10% citric acid solution. The layers were separated, and the aqueous layer was extracted with ethyl acetate (2×). The combined organic layer was washed with brine (2×), then dried (over $Na_2SO_4$), filtered and concentrated in vacuo. The solid material was triturated with Diethylether to afford the desired product 28 (1.29 g, 70%): $^1$H NMR (CD$_3$OD) 8.07 (s, 1H), 7.65 (m, 4H), 7.02 (m, 2H), 6.94 (m, 2H), 5.09 (t, 2H), 4.17 (q, J=7.6 Hz, 2H), 4.13 (s, 2H), 3.83 (t, J=5.2 Hz, 2H), 1.44 (t, J=6.8 Hz, 3H); [M+H]=594, 594 (fragment 1:1).

Step 5

To a solution of intermediate 28 (50 mg, 0.084 mmol) in DMF (1.0 mL) was added 2-ethanolamine (0.020 mL). The reaction was heated in an oil bath at 100° C. for 15 minutes. Upon completion, the reaction was diluted with ethyl acetate and quenched with a 10% citric acid solution. The layers were separated, and the aqueous layer was extracted with ethyl acetate (2×). The combined organic layer was washed with brine (2×), then dried (over $Na_2SO_4$), filtered and concentrated in vacuo to afford the desired product 29 (17 mg, 47%) with no further purification or characterization: MS [M+H]= 609, 611 (fragment 1:1).

Step 6

To a solution of intermediate 29 (50 mg, 0.080 mmol) in DMF (1.0 mL), was added hydrazine [anhydrous] (0.025 mL). The reaction was heated in an oil bath at 75° C. for 30 minutes. Upon completion, the reaction was purified directly by reversed phase HPLC [Phenomenex Synergi Polar RP Axia packed column] (eluting with 0.1% formic acid) to afford the desired product 30 (20 mg, 60%): 400 MHz $^1$H NMR (CD$_3$OD) δ (ppm) 7.87 (s, 1H), 7.144 (dd, J=2.8 Hz, J=5.6 Hz, 2H), 6.93 (dd, J=8.8 Hz, 2H), 4.093 (t, J=5.6 Hz, 2H), 3.884 (s, 2H), 3.634 (t, J=5.6 Hz, 2H), 3.47 (m, 4H); $^{19}$F NMR (CD$_3$OD) δ (ppm) −118.04; MS: 399 (M+1)

EXAMPLE 10

Preparation of Compound 32

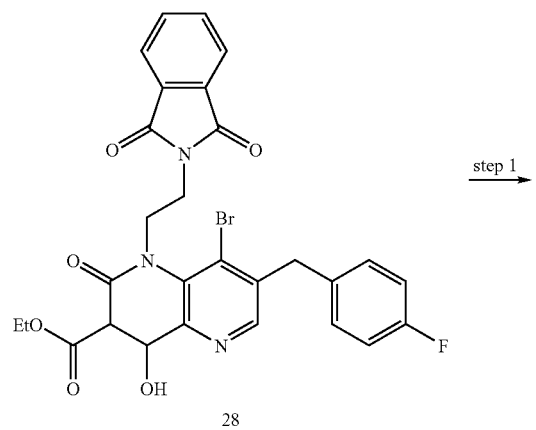

28

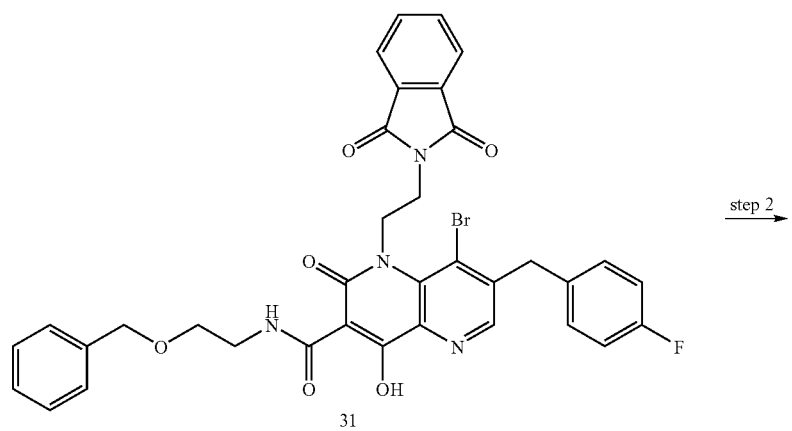

31

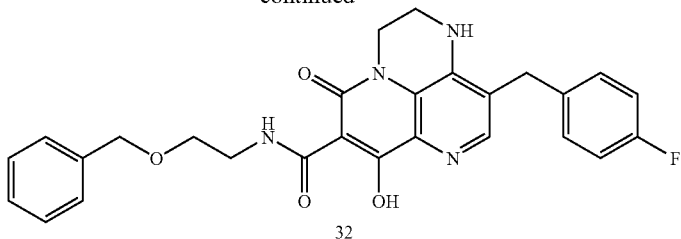

Step 1

The compound was made in a similar fashion as compound 29 in Example 9, to afford the desired product 31 (50 mg, 85% from 50 mg of 28) with no further purification or characterization: MS [M+H]=699, 701 (fragment 1:1).

Step 2

Compound 32 was made in a similar fashion as compound 30 in Example 9, to afford the desired product S24 (12 mg, 69% from 25 mg of S23) as the TFA salt: 400 MHz $^1$H NMR (CD$_3$OD) δ (ppm) 7.79 (s, 1H), 7.36 (m, 2H), 7.25 (m, 5H), 7.08 (dd, J=8.4 Hz, 2H), 4.57 (s, 2H), 4.26 (t, J=5.6 Hz, 2H), 4.02 (s, 2H), 3.634 (t, J=5.6 Hz, 2H), 3.7 (m, 4H); $^{19}$F NMR (CD$_3$OD) δ (ppm) −77.46, −117.94; MS: 489 (M+1).

EXAMPLE 11

Preparation of Compound 33

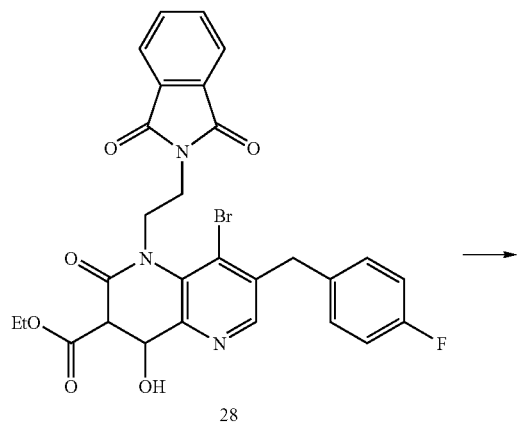

In a one-pot procedure, to a solution of intermediate 28 (50 mg, 0.084 mmol) in DMF (1.0 mL) was added 2-methoxy-ethylamine (0.025 mL). The reaction was heated in a microwave reactor at 120° C. for 25 minutes total heating time. Upon completion, hydrazine [anhydrous] (0.025 mL) was added to the mixture. The reaction was heated in an oil bath at 100° C. for 5 minutes. At which point, the reaction was purified directly by reversed phase HPLC [Phenomenex Gemini Axia packed column] (eluting with 0.1% TFA) to afford the desired product 33 (33 mg, 74%); 400 MHz $^1$H NMR (CD$_3$OD) δ (ppm) 7.81 (s, 1H), 7.29 (m, 2H), 7.1 (m, 2H), 4.26 (t, J=5.6 Hz, 2H), 4.04 (s, 2H), 3.79 (t, J=5.2 Hz, 2H), 3.68 (m, J=5.6 Hz, 2H), 3.595 (t, J=5.6 Hz, 2H), 3.4 (s, 3H); $^{19}$F NMR (CD$_3$OD) δ (ppm) −77.15, −117.55; MS: 413 (M+1).

EXAMPLE 12

Preparation of Compound 34

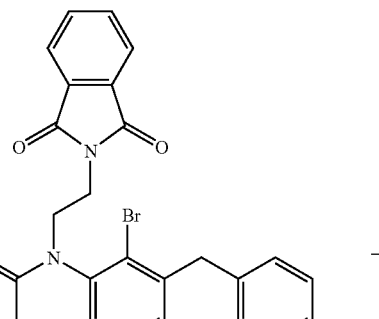

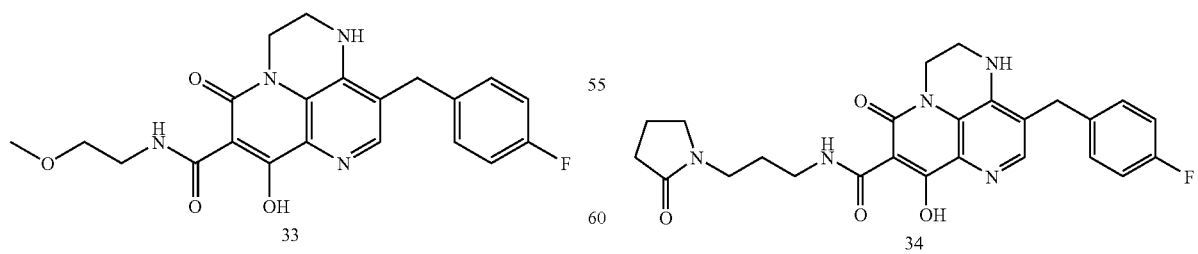

Compound 34 was made in a similar fashion as compound 33 (7 mg, 28% from 25 mg of 28) as the TFA salt: 400 MHz $^1$H NMR (CD$_3$OD) δ (ppm) 7.72 (s, 1H), 7.20 (m, 2H), 7.0 (m, 2H), 4.17 (t, J=5.2 Hz, 2H), 3.94 (s, 2H), 3.79 (t, J=6.8 Hz, 2H), 2.30 (m, J=7.6 Hz, 2H), 3.31 (t, J=5.6 Hz, 2H), 1.97 (m, 2H), 1.813 (m, 2H); $^{19}$F NMR (CD$_3$OD) δ (ppm) −77.16, −117.55; MS: 480 (M+1).

EXAMPLE 13

Preparation of Compound 35

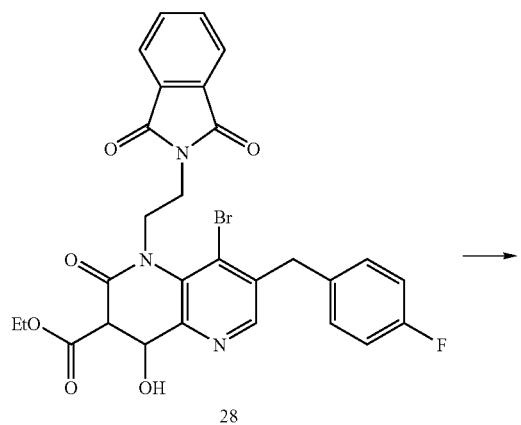

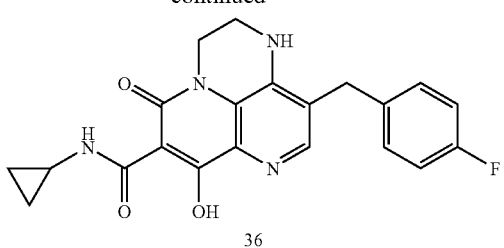

Compound 35 was made in a similar fashion as compound 33 (13 mg, 53% from 25 mg of 28) as the TFA salt: 400 MHz $^1$H NMR (CD$_3$OD) δ (ppm) 7.74 (s, 1H), 7.2 (m, 2H), 7.01 (m, 2H), 4.18 (m, 2H), 3.95 (s, 2H), 3.95-3.8 (m, 10H), 3.5-3.2 (m, 4H); $^{19}$F NMR (CD$_3$OD) δ (ppm) −77.11, −117.50; MS: 468 (M+1).

EXAMPLE 14

Preparation of Compound 36

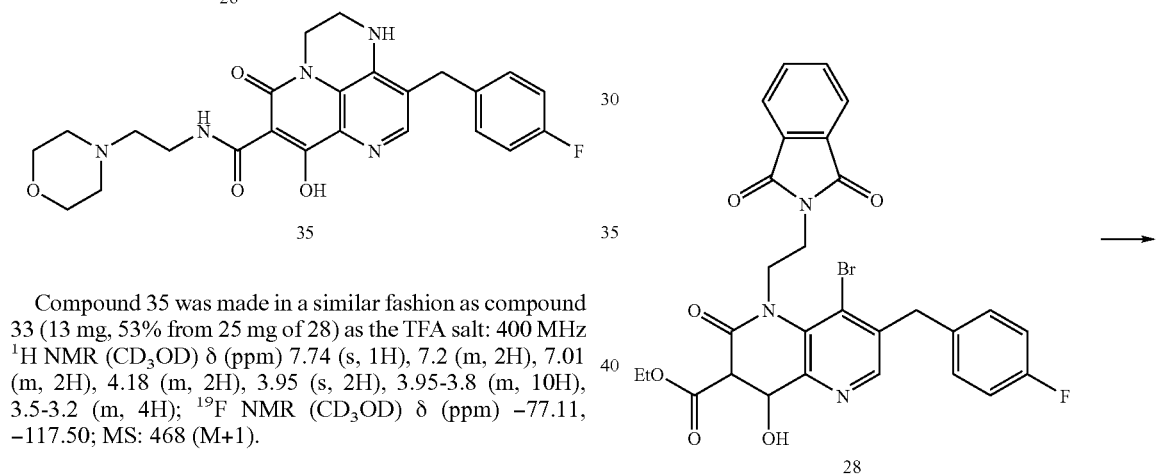

Compound 36 was made in a similar fashion as compound 33 (17 mg, 80% from 25 mg of 28) as the TFA salt. 400 MHz $^1$H NMR (CD$_3$OD) δ (ppm) 7.81 (s, 1H), 7.29 (m, 2H), 7.11 (m, 2H), 4.24 (t, J=5.6 Hz, 2H), 4.04 (s, 2H), 3.78 (t, J=5.2 Hz, 2H), 3.68 (m, J=6.4 Hz, 2H), 3.02 (m, 1H), 0.95 (m, 2H), 0.73 (m, 2H); $^{19}$F NMR (CD$_3$OD) δ (ppm) −77.18, −117.54; MS: 395 (M+1).

EXAMPLE 15

Preparation of Compound 37

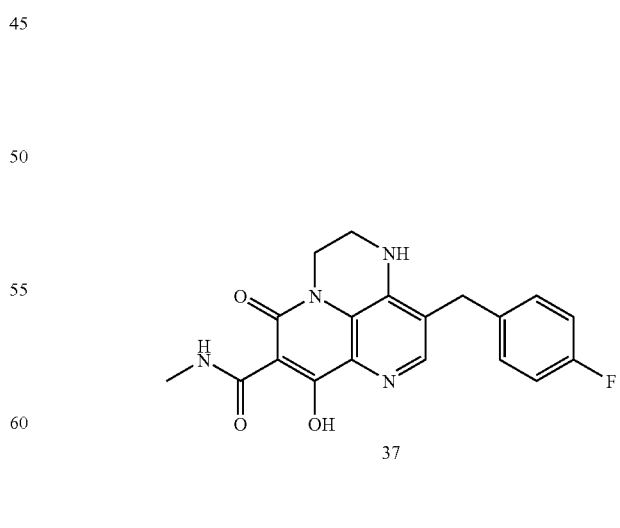

Compound 37 was made in a similar fashion as compound 33 (11 mg, 54% from 25 mg of 28) as the TFA salt: 400 MHz $^1$H NMR (CD$_3$OD) δ (ppm) 7.83 (s, 1H), 7.32 (m, 2H), 7.12

(m, 2H), 4.28 (m, 2H), 4.06 (s, 2H), 3.80 (m, 2H), 3.077 (s, 3H); $^{19}$F NMR (CD$_3$OD) δ (ppm) −72.45, −112.97; MS: 369 (M+1).

EXAMPLE 16

Preparation of Compound 38

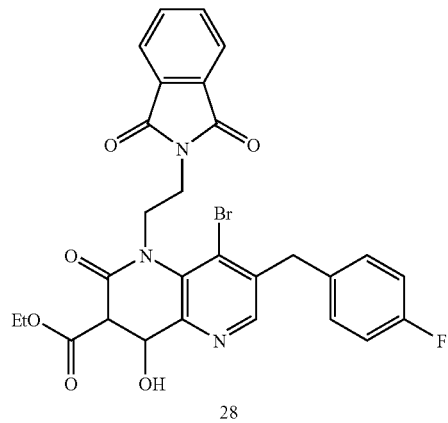

Compound 38 was made in a similar fashion as compound 33 (16 mg, 70% from 25 mg of 28) as the TFA salt: 400 MHz $^1$H NMR (CD$_3$OD) δ (ppm) 7.81 (s, 1H), 7.29 (m, 2H), 7.10 (m, 2H), 4.26 (m, 2H), 4.04 (s, 2H), 3.78 (m, 2H), 3.65 (m, 4H), 3.56 (q. J=6.8 Hz, 2H), 1.21 (t, J=6.8 Hz, 3H); $^{19}$F NMR (CD$_3$OD) δ (ppm) −77.05, −117.56; MS: 427 (M+1).

EXAMPLE 17

Preparation of Compound 39

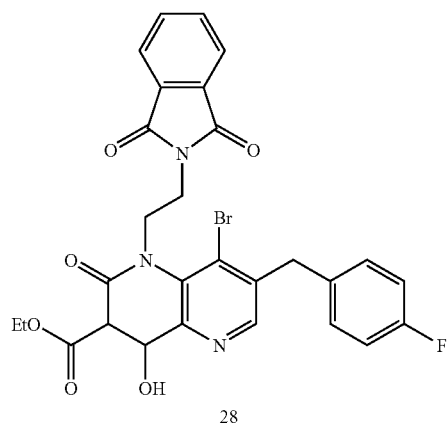

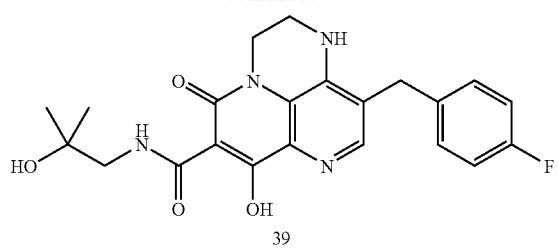

Compound 39 was made in a similar fashion as compound 33 (19 mg, 84% from 25 mg of 28) as the TFA salt: 400 MHz $^1$H NMR (CD$_3$OD) δ (ppm) 7.81 (s, 1H), 7.30 (m, 2H), 7.10 (m, 2H), 4.265 (m, 2H), 4.05 (s, 2H), 3.79 (m, 2H), 3.49 (s, 2H), 1.27 (s, 6H); $^{19}$F NMR (CD$_3$OD) δ (ppm) −77.22, −117.54; MS: 427 (M+1).

EXAMPLE 18

Preparation of Compound 43

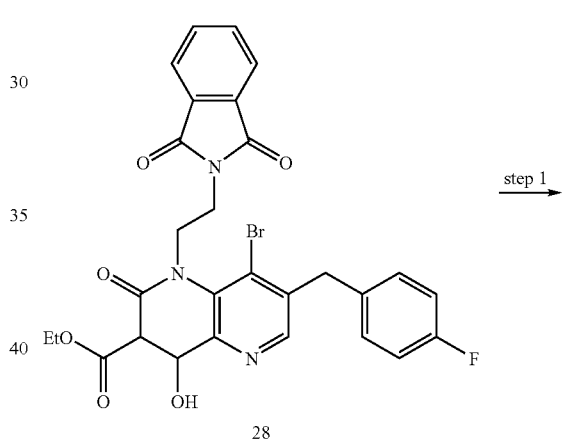

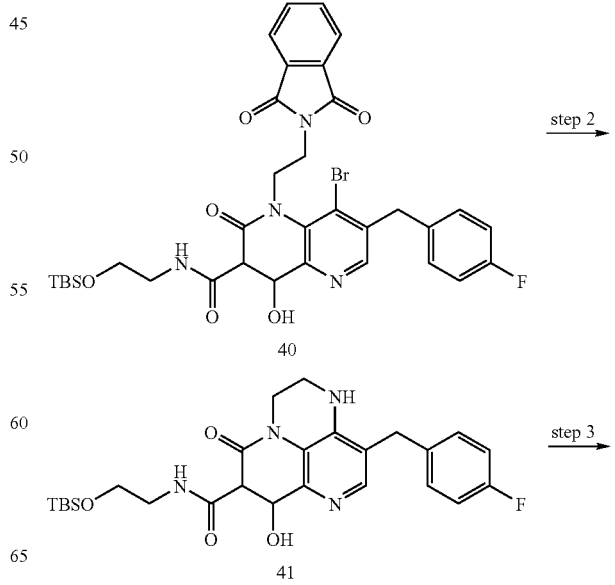

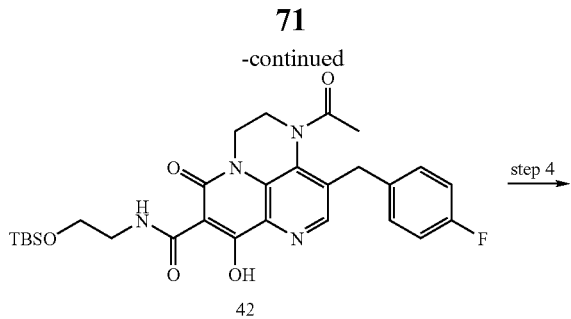

42

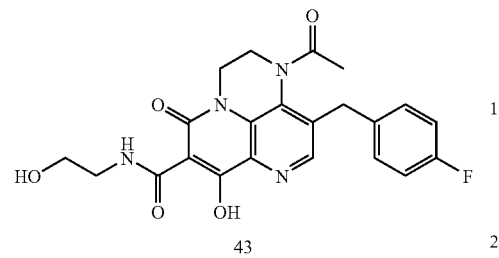

43

Step 1

Compound 40 was made in a similar fashion as compound 29 in Example 9 (450 mg, crude from 300 mg of 28) after trituration in 1:1 hexanes:diethyl ether with no further characterization: MS [M+H]=723, 725 (fragment 1:1).

Step 2

Compound 41 was made in a similar fashion as compound 30, example 9. However, upon completion, the reaction was diluted with ethyl acetate and quenched with a 10% citric acid solution. The layers were separated, and the aqueous layer was extracted with ethyl acetate (2×). The combined organic layer was washed with brine (2×), then dried (over $Na_2SO_4$), filtered and concentrated in vacuo. The solid material was triturated in diethyl ether to afford the desired product 41 (203 mg, 78% from 300 mg of 28): 400 MHz $^1$H NMR (CDCl$_3$) δ (ppm) 8.22 (s, 1H), 7.05 (m, 2H), 6.92 (m, 2H), 7.08 (dd, J=8.4 Hz, 2H), 4.35 (bs, 1H), 4.14 (t, J=5.2 Hz, 2H) 3.89 (s, 2H), 3.74 (t, J=5.2 Hz, 2H), 3.7-3.3 (m, 4H), 0.84 (s, 9H), 0.014 (s, 6H), 3.7 (m, 4H); MS: 594 (M+1).

Step 3

To a solution of intermediate 41 (65 mg, 0.127 mmol) dissolved in DMF (1.27 mL), cooled in a ice-water bath, was added Sodium bis(trimethylsilyl)amide (NaHMDS) (0.443 mL, 0.443 mmol, 1M THF) and stirred for 5 minutes under nitrogen atmosphere. Acetyl chloride (0.045 mL, 0.634 mmol) was added and the reaction was allowed to stir for 1 hour in the ice-water bath. Another addition of NaHMDS followed by AcCl was performed. At which point, the reaction was quenched with 10% citric acid solution and diluted with ethyl acetate. The organic layer was washed with H$_2$O, aqueous LiCl, and brine, then dried (over Na$_2$SO$_4$), filtered and concentrated in vacuo to afford the desired product 42 (70 mg, crude) with no further purification or characterization: MS: 555 (M+1).

To a solution of intermediate 42 (70 mg, crude, 0.127 mmol) in 1,2-Dichloroethane (1 mL), was added Trifluoroacetic acid (20 mL, 20%). The reaction was stirred at room temperature overnight. Upon completion, the reaction was concentrated in vacuo then azeotroped with toluene/THF several times. The crude residue was treated with ammonia (7N in methanol) for 30 minutes [to cleave a small amount of bis-acetylated product] before being concentrated in vacuo and then purified directly by reversed phase HPLC [Phenomenex Synergi Polar RP Axia packed column] (eluting with 0.1% formic acid) to afford the desired product 43 (5 mg, 10%; 2 steps): 400 MHz $^1$H NMR (CD$_3$OD) δ (ppm) 8.26 (s, 1H), 7.04 (m, 2H), 6.94 (m, 2H), 4.51 (m, 1H), 4.32 (m, 1H), 3.96 (m, 2H), 3.64 (t, J=5.2 Hz, 2H), 3.61 (m, 1H), 3.48 (t, J=5.2 Hz, 2H), 3.27 (m, 1H), 2.14 (s, 3H); $^{19}$F NMR (CD$_3$OD) δ (ppm) −118.30; MS: 441 (M+1).

EXAMPLE 19

Preparation of Compound 45

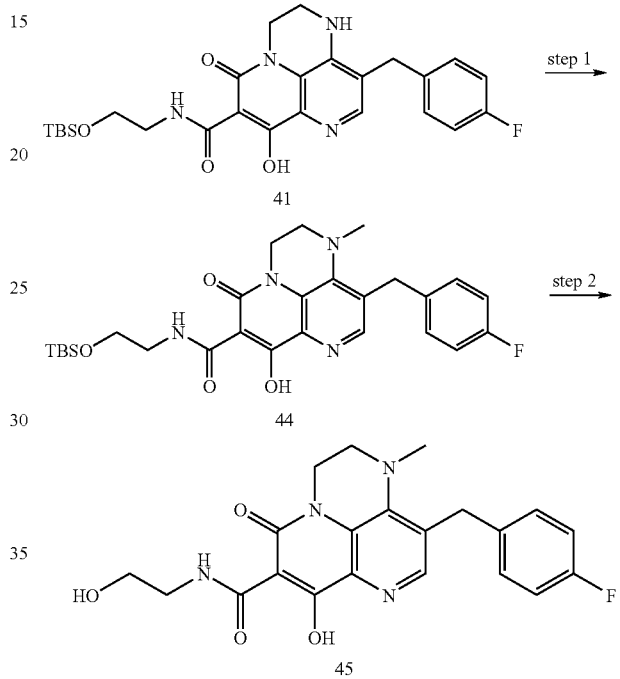

Step 1

To a solution of intermediate 41 (75 mg, 0.146 mmol) dissolved in THF (1.5 mL), cooled to −78° C., was added n-Butyllithium (0.192 mL, 0.482 mmol, 2.5M THF) dropwise and stirred for 5 minutes under argon atmosphere. Iodomethane (0.010 mL, 0.161 mmol) was added and the reaction was allowed to stir for 15 minutes in the dry ice-acetone bath. At which point, the reaction, which had gone to 1/3 completion, was warmed to 0° C. then quenched with acetic acid (0.01 mL in 10 mL of ethyl acetate) then poured into water. The organic layer was washed with H$_2$O, and brine, then dried (over Na$_2$SO$_4$), filtered and concentrated in vacuo to afford the desired product 42 (70 mg, crude) with no further purification or purification: MS: 527 (M+1).

To a solution of intermediate 42 (70 mg, crude, 0.14 mmol) in 1,2-Dichloroethane (1 mL), was added Trifluoroacetic acid (20 mL, 20%). The reaction was stirred at room temperature overnight. Upon completion, the reaction was concentrated in vacuo then azeotroped with toluene/THF several times. The crude residue was purified directly by reversed phase HPLC [Phenomenex Gemini Axia packed column] (eluting with 0.1% TFA) to afford the desired product 43 (16 mg, 27%; 2 steps): 400 MHz $^1$H NMR (CD$_3$OD) δ (ppm) 7.95 (s, 1H), 7.19 (m, 2H), 7.07 (m, 2H), 4.37 (m, 2H), 4.22 (m, 2H), 3.72

(m, 4H), 3.60 (m, 2H), 3H); $^{19}$F NMR (CD$_3$OD) δ (ppm) −77.14, −117.83; MS: 413 (M+1).

EXAMPLE 20

Preparation of Compound 49

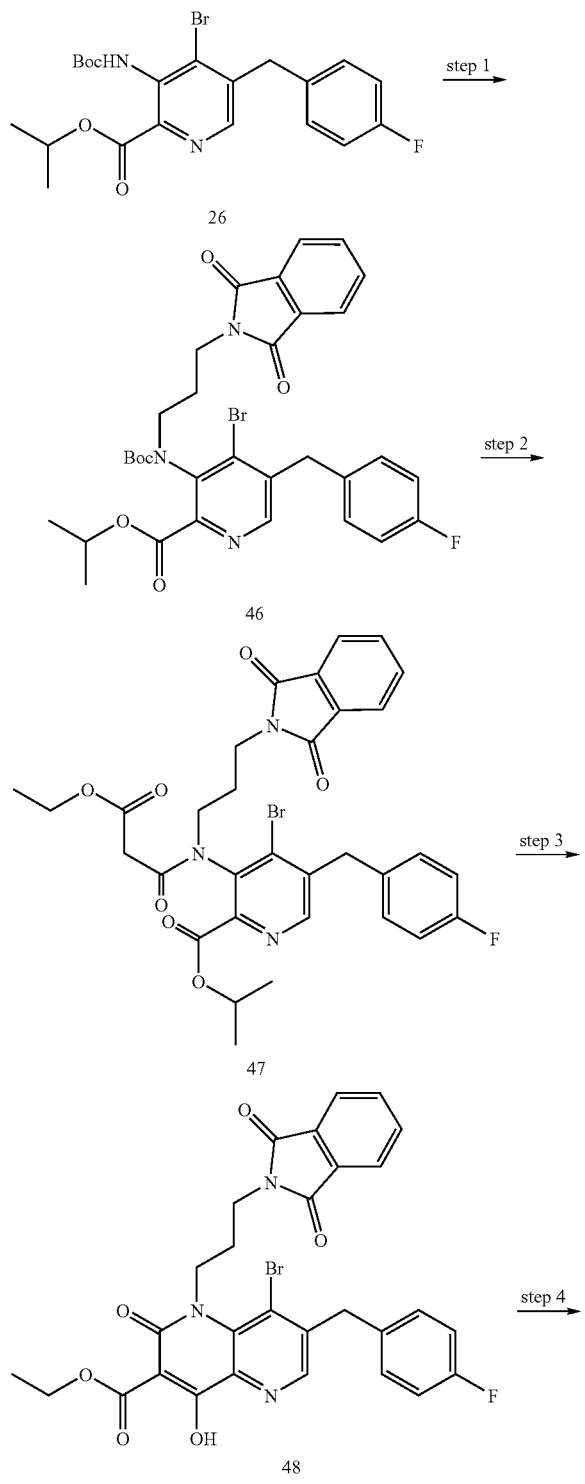

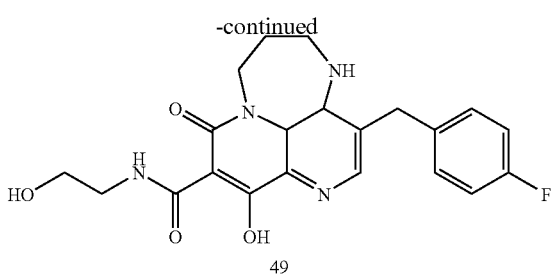

Step 1

A DMF (20 mL) solution of compounds 26, as described in Example 9, (5 g, 3.21 mmol) was cooled in a ice-water bath, and treated with sodium bis(trimethylsilyl)amide (NaHMDS, 3.86 mL, 3.86 mmol, 1M THF) and stirred for 5 minutes under nitrogen atmosphere. Commercially available N-(3-bromopropyl)phthalimide (1.04 g, 3.86 mmol) was added and the reaction was stirred overnight at room temperature. The reaction was quenched with saturated NH$_4$Cl (aq) and diluted with ethyl acetate. The organic layer was washed with H$_2$O, aqueous LiCl, and brine, then dried (over Na$_2$SO$_4$), filtered and concentrated in vacuo. The crude residue was purified by preparative flash chromatography (silica gel, ethyl acetate/hexane, 1:4) to afford the desired product, 46 (1.5 g, 72%): $^1$H NMR (CDCl$_3$) 8.34, 8.28 (s, rotamers, 1H) 7.79 (m, 2H), 7.68 (m, 2H), 7.07 (m, 2H), 6.98 (m, 2H), 5.28 (m, 1H), 4.2-3.2 (m, 6H), 2.0 (m, 2H), 1.35 (m, 6H), 1.5, 1.25 (s, rotamers, 9H); MS [M+H]=654, 656 (fragment 1:1).

Step 2

Trifluoroacetic acid (4.5 ml) was added to a solution of intermediate 46 (1.5 g, 2.30 mmol) in dichloromethane (23 mL). The reaction was stirred at room temperature for 1 hour then heated at 55° C. for 5 hours. Upon completion, the reaction was cooled to room temperature then diluted with ethyl acetate and cautiously (gas evolution!) quenched with saturated NaHCO$_3$. The phases were separated, and the aqueous layer was extracted with ethyl acetate (2×). The combined organic layers were washed with brine (2×), dried (Na$_2$SO$_4$), filtered and concentrated in vacuo to afford the desired product de-Boc intermediate (1.3 g, quant.) with no further purification: $^1$H NMR (CDCl$_3$) 7.93 (s, 1H), 7.83 (dd, Ja=2.4 Hz, Jb=3.2 Hz, 2H), 7.71 (dd, Ja=2.4 Hz, Jb=3.2 Hz, 2H), 7.12 (dd, Ja=3.2 Hz, Jb=5.6 Hz, 2H), 6.96 (dd, J=8.8 Hz, 2H), 5.288 (sept, J=6.0 Hz, 1H), 4.08 (s, 1H), 3.79 (t, J=6.8 Hz, 2H), 3.375 (t, J=7.2 Hz, 2H), 1.992 (m, 2H), 1.41 (d, J=6.0 Hz, 6H); MS [M+H]=554, 556 (fragment 1:1).

A solution of de-Boc intermediate (1.3 g, 2.35 mmol) in 1,2-dichloroethane (DCE, 23 mL), was treated with ethyl 3-chloro-3-oxo-propionate (0.310 mL, 2.47 mmol) and 2,6-lutidine (0.82 mL, 7.05 mmol). The reaction was stirred at room temperature. After 30 minutes additional ethyl 3-chloro-3-oxo-propionate (0.125 mL, 1.0 mmol) and 2,6-lutidine (0.30 mL, 2.58 mmol) were added to the reaction. When complete, the reaction was diluted with ethyl acetate and quenched with a 10% citric acid (aq.) solution. The phases were separated, and the aqueous layer was extracted with ethyl acetate (2×). The combined organic layers were washed with brine (2×), dried (Na$_2$SO$_4$), filtered and concentrated in vacuo. The crude residue was purified by preparative flash chromatography (silica gel, ethyl acetate/hexane) to afford the desired product 47 (1.87 g) MS [M+H]=668, 670 (fragment 1:1).

Step 3

A solution of 47 (1.45 g, 2.17 mmol) in 17.5 mL of ethanol) was treated dropwise with 0.9 mL of NaOEt/EtOH (21% wt/wt, 2.68 M, 2.4 mmol) and monitored by LCMS. When reaction progress has stopped then it was charged with 25 mL of aqueous citric acid (10% wt/vol) before evaporating in vacuo at 30° C. to remove ethanol. After further dilution with 25 mL of water and an additional 25 mL of 10% aqueous citric acid the product was extracted with ethyl acetate (1×100 mL, 2×~50 mL). Combined organic extracts were washed with water and brine (2×), dried (Na$_2$SO$_4$), filtered, and evaporated in vacuo at 30° C., followed by high vacuum treatment. The product 48 was used as obtained without further characterization. (M+1=609.81).

Step 4

Microwave treatment (150° C., 900 sec) of 48 (86.5 mg, 142.2 μM) and ethanolamine (85 μL, 86.3 mg, 1.41 mmol) in 1 mL of DMF afforded crude 49. After dilution of the reaction mixture with 1 ml water/TFA (0.1% v/v) purification was accomplished via preparative HPLC to afford 45.8 mg of 49 (as a TFA salt). $^1$H NMR (400 MHz, CH$_3$OH d$_4$) d 7.77 (s, 1H), 7.35 (m, 2H), 7.111 (m, 2H), 4.38 (t, J=6.45 Hz, 2H), 4.06 (s, 2H), 3.75 (m, 2H), 3.68 (t, J=6.75 Hz, 2H), 3.63 (m, 2H), 2.17 (q, J=5 Hz, 2H), $^{19}$F NMR (376 MHz, CH$_3$OH d$_4$) d −72.39 (s, TFA), −112.93 (m), M+1=413.07.

EXAMPLE 21

Preparation of Compound 50

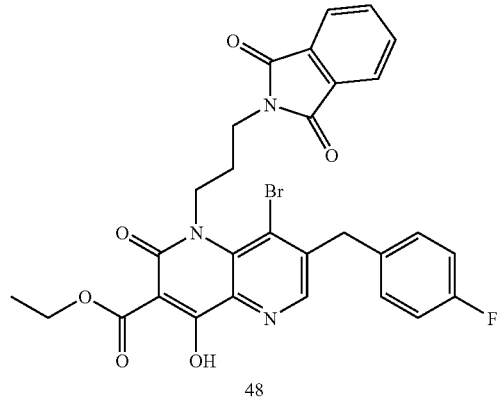

Compound 50 was prepared from 48 and cyclopropylamine in the same manner as Example 11. $^1$H NMR (400 MHz, CH$_3$OH d$_4$) d 7.74 (s, 1H), 7.28 (m, 2H), 7.09 (m, 2H), 4.34 (t, J=6.4 Hz, 2H), 4.03 (s, 2H), 3.66 (t, J=6.6 Hz, 2H), 3.00 (m, 1H), 2.67 (s, H), 0.92 (m, 2H), 0.71 (m, 2H), 19F NMR (376 MHz, CH3OH d4) d −77.087 (s, TFA), −117.469 (m), M+1=409.10.

EXAMPLE 22

Preparation of Compound 51

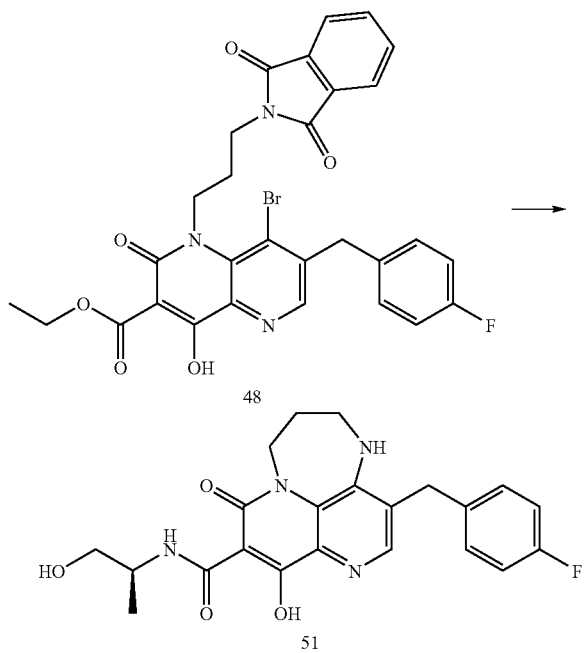

Compound 51 was prepared from 48 and s-2-Amino-propan-1-ol in the same manner as in Example 11. $^1$H NMR (400 MHz, CH$_3$OH d$_4$) d 7.75 (s, 1H), 7.14 (m, 2H), 6.94 (m, 2H), 4.24 (t, J=6.35 Hz, 2H), 4.07 (m 1H), 3.90 (s, 2H), 3.40-3.54 (m, 4H), 1.97 (q, J=6.6 Hz, 2H) 1.15 (d, J=5.8 Hz, 3H), $^{19}$F (376 MHz, CH$_3$OH d$_4$) d −77.40 (s, TFA), −118.17 (m), M+1=427.09.

EXAMPLE 23

Preparation of Compound 52

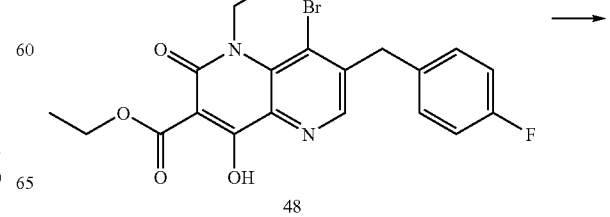

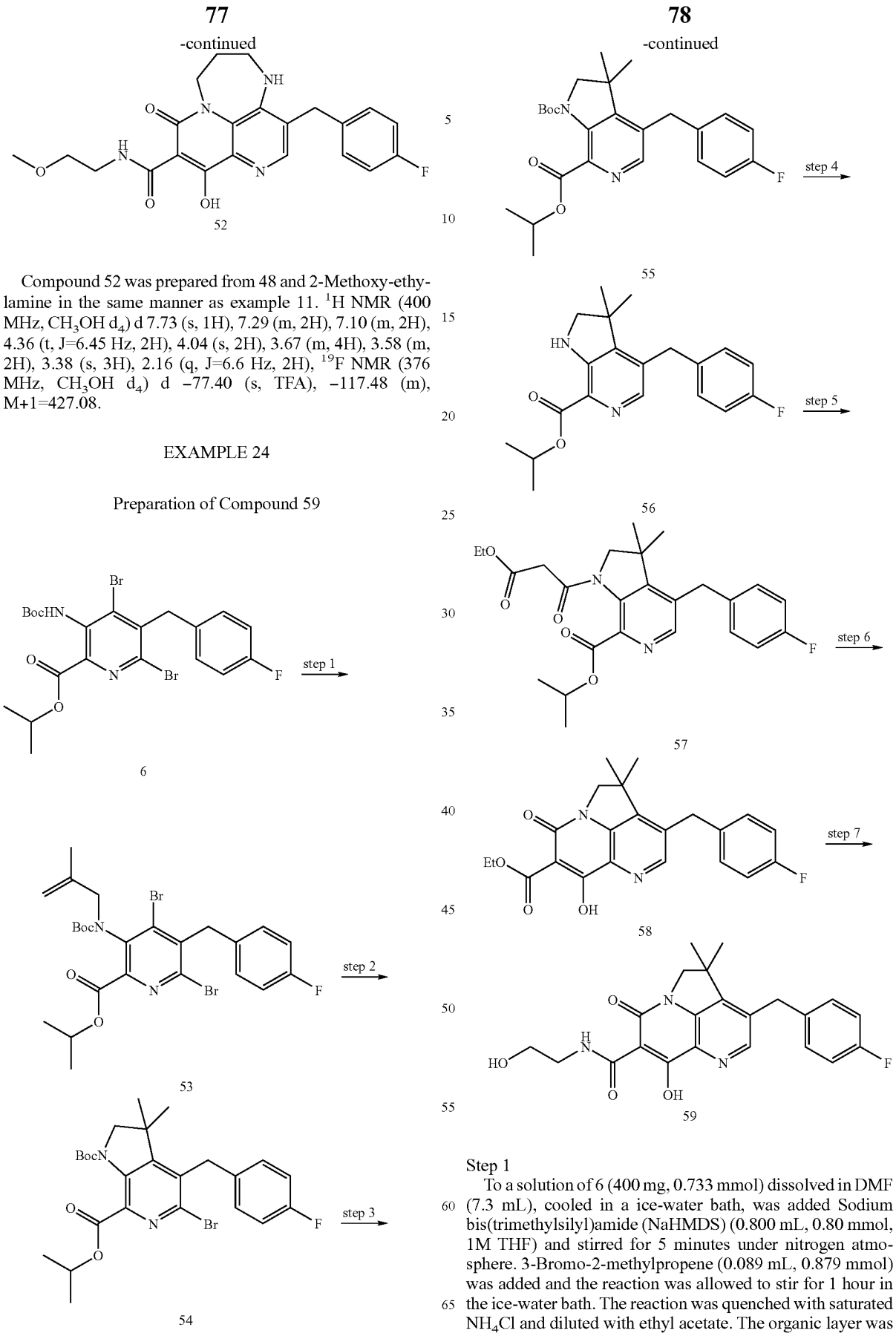

Compound 52 was prepared from 48 and 2-Methoxy-ethylamine in the same manner as example 11. $^1$H NMR (400 MHz, CH$_3$OH d$_4$) d 7.73 (s, 1H), 7.29 (m, 2H), 7.10 (m, 2H), 4.36 (t, J=6.45 Hz, 2H), 4.04 (s, 2H), 3.67 (m, 4H), 3.58 (m, 2H), 3.38 (s, 3H), 2.16 (q, J=6.6 Hz, 2H), $^{19}$F NMR (376 MHz, CH$_3$OH d$_4$) d −77.40 (s, TFA), −117.48 (m), M+1=427.08.

EXAMPLE 24

Preparation of Compound 59

Step 1

To a solution of 6 (400 mg, 0.733 mmol) dissolved in DMF (7.3 mL), cooled in a ice-water bath, was added Sodium bis(trimethylsilyl)amide (NaHMDS) (0.800 mL, 0.80 mmol, 1M THF) and stirred for 5 minutes under nitrogen atmosphere. 3-Bromo-2-methylpropene (0.089 mL, 0.879 mmol) was added and the reaction was allowed to stir for 1 hour in the ice-water bath. The reaction was quenched with saturated NH$_4$Cl and diluted with ethyl acetate. The organic layer was washed with H$_2$O aqueous LiCl, and brine, then dried (over Na₂SO₄), filtered and concentrated in vacuo. The crude residue was purified by chromatography on silica gel (1/4—ethyl acetate/hexane) to afford the desired product 53 (400 mg, 90%): ¹H NMR (CDCl₃) 7.04 (m, 2H), 6.92 (m, 2H), 5.25 (sept, J=6.4 Hz, 1H), 4.738 (s, 1H), 4.587 (s, 1H), 4.44 (s, 2H), 4.0 (dd, 2H), 1.91 (s, 3H), 1.35 (d, J=6.4 Hz, 6H), 1.325 (s, 9H); MS [M+H]=597:599:601 (fragment 1:2:1).

Step 2

Following the procedure exemplified in Tet. *Lett* 48 (2007) 2307-2310, to a solution of 53 (337 mg, 0.564 mmol) dissolved in DMF (5.6 mL) was added Palladium acetate [Pd (OAc)₂] (12.6 mg, 0.0564 mmol), sodium acetate (116 mg, 1.41 mmol), sodium formate (46 mg, 0.676 mmol) and tetraethylammonium chloride (124 mg, 0.676 mmol) and purged several times with vacuum and argon. The reaction was heated to 80° C. and stirred for 1.5 hours under argon atmosphere. At which point, the reaction was cooled to room temperature then quenched with saturated NH₄Cl and diluted with ethyl acetate. The organic layer was washed with H₂O, aqueous LiCl, and brine, then dried (over Na₂SO₄), filtered and concentrated in vacuo. The crude residue was purified by chromatography on silica gel (1/4—ethyl acetate/hexane) to afford the desired product 54 (80 mg, 27%): ¹H NMR (CDCl₃) 6.95 (m, 4H), 5.21 (sept, J=6.4 Hz, 1H), 4.22 (s, 2H), 3.77 (s, 2H), 1.48 (s, 9H), 1.39 (d, J=6.4 Hz, 6H), 1.23 (s, 6H); MS [M+H]=519, 521, 523 (fragment 1:2:1).

Step 3

To a solution of bicycle intermediate 54 (65 mg, 0.125 mmol) dissolved in MeOH:EtOAc (1.25 mL:0.625 mL) was added sodium acetate (12.5 mg, 0.15 mmol) and Palladium (10 wt % on carbon) [Pd/C] (13 mg). The reaction was run under hydrogen gas (using a balloon), purging several times with vacuum, at room temperature for 1 hour. At which point the reaction was degassed, and filtered to remove Palladium, then diluted with ethyl acetate and quenched with water. The organic layer was washed with brine, then dried (over Na₂SO₄), filtered and concentrated in vacuo to afford the desired product 55 (60 mg, quant): ¹H NMR (CDCl₃) 8.04 (s, 1H), 7.01 (m, 2H), 6.96 (m, 2H), 5.24 (sept, J=6.4 Hz, 1H), 4.07 (s, 2H), 3.77 (s, 2H), 1.48 (s, 9H), 1.39 (d, J=6.4 Hz, 6H), 1.26 (s, 6H); MS [M+H]=443.

Step 4

To a solution of intermediate 55 (60 mg, 0.15 mmol) in 1,2-Dichloroethane [DCE] (1.25 mL), was added Trifluoroacetic acid (0.40 mL). The reaction was stirred at room temperature for 1.5 hours. Upon completion, the reaction was diluted with ethyl acetate and quenched with a 10% sodium citrate solution. The layers were separated, and the aqueous layer was extracted with ethyl acetate (2×). The combined organic layer was washed with brine (2×), then dried (over Na₂SO₄), filtered and concentrated in vacuo to afford the desired product 56 (55 mg, quant): ¹H NMR (CDCl₃) 7.72 (s, 1H), 7.04 (m, 2H), 6.94 (m, 2H), 5.28 (sept, J=6.4 Hz, 1H), 4.03 (s, 2H), 3.43 (s, 2H), 1.4 (d, J=6.0 Hz, 6H), 1.32 (s, 6H); MS [M+H]=343.

Step 5

To a solution of intermediate 56 (55 mg, 0.15 mmol) in 1,2-Dichloroethane [DCE] (0.50 mL), was added Ethyl 3-chloro-3-oxo-propionate (0.023 mL, 0.185 mmol). The reaction was stirred at 80° C. for 1 hour. Upon completion, the reaction was cooled to room temperature then directly purified by chromatography on silica gel (1/1—ethyl acetate/hexane) to afford the desired product 57 (64 mg, 90%): ¹H NMR (CDCl₃) 8.13 (s, 1H), 7.00 (m, 2H), 6.96 (m, 2H), 5.25 (sept, J=6.4 Hz, 1H), 4.18 (q, J=7.2 Hz, 2H), 4.1 (s, 2H), 3.875 (s, 2H), 3.537 (s, 2H), 1.4 (d, J=6.4 Hz, 6H), 1.32 (s, 6H), 1.24 (t, J=7.2 Hz, 3H); MS [M+H]=457.

Step 6

To a solution of intermediate 57 (64 mg, 0.14 mmol) in ethanol (1.4 mL) was added sodium ethoxide [21 wt % solution in ethanol] (0.105 mL, 0.28 mmol). The reaction was stirred at room temperature for 2 hours. Upon completion, the reaction was concentrated in vacuo then dissolved in ethyl acetate and quenched with saturated NH₄Cl. The layers were separated, and the aqueous layer (acidified to pH=2 with 1N HCl) was extracted with ethyl acetate (2×). The combined organic layer was washed with brine (2×), then dried (over Na₂SO₄), filtered and concentrated in vacuo to afford the desired product 58 (53 mg, quant): ¹H NMR (CDCl₃) 8.28 (s, 1H), 7.04 (m, 2H), 6.99 (m, 2H), 4.5 (q, J=7.2 Hz, 2H), 4.18 (s, 2H), 4.08 (s, 2H), 1.47 (m, 9H); MS [M+H]=397.

Step 7

To a solution of intermediate 58 (25 mg, 0.063 mmol) in DMF (0.70 mL) was added 2-ethanolamine (0.017 mL). The reaction heated in a microwave reactor at 150° C. for 15 minutes. Upon completion, the reaction was purified directly by reversed phase HPLC [Phenomenex Gemini Axia packed column] (eluting with 0.1% TFA) to afford the desired product 59 (26 mg, 78%): 400 MHz ¹H NMR (CDCl₃) δppm) 10.38 (bs, 1H), 8.275 (s, 1H), 7.00 (dd, J=2.8 Hz, J=6.0 Hz, 2H), 6.935 (dd, J=8.4 Hz, 2H), 4.148 (s, 2H), 4.055 (s, 2H), 3.794 (t, J=5.2 Hz, 2H), 3.6 (m, 2H), 1.44 (s, 6H); ¹⁹F NMR (CDCl₃) δppm) −115.99; MS: 412 (M+1).

EXAMPLE 25

Preparation of Compound 60

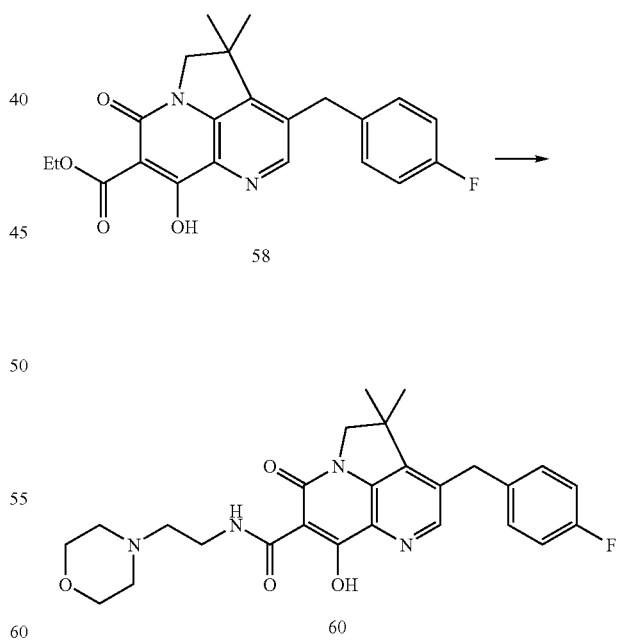

Compound 60 was made in a similar fashion as compound 59 (13 mg, 67% from 12 mg of 58) as the TFA salt: 400 MHz ¹H NMR (CDCl₃) δppm) 1̃.51 (bs, 1H), 8.34 (s, 1H), 7.03 (dd, J=5.2 Hz, J=9.2 Hz, 2H), 6.98 (dd, J=8.8 Hz, 2H), 4.195 (s, 2H), 4.088 (s, 2H), 3.95 (m, 4H), 3.89 (m, 2H), 3.732 (m, 2H), 3.35 (m, 2H), 2.9 (m, 2H), 1.48 (s, 6H); $^{19}$F NMR (CDCl$_3$) δppm) −76.251, −115.90; MS: 481 (M+1).

EXAMPLE 26

Preparation of Compound 65

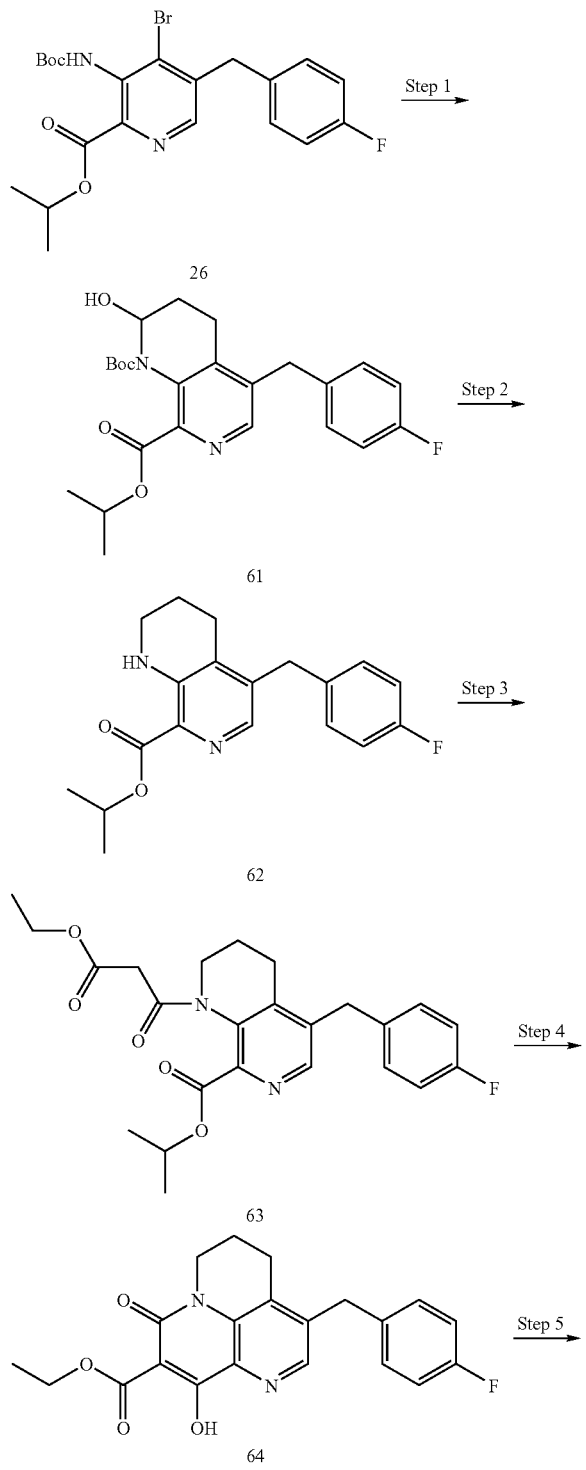

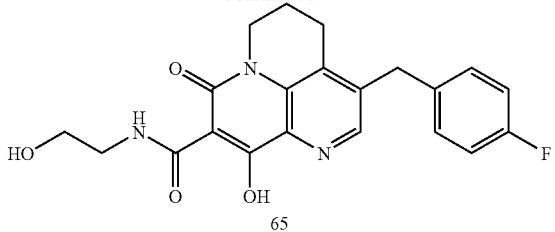

Step 1

To a solution of 26 (150 mg, 0.322 mmol) dissolved in DMA (3.2 mL) was added Palladium acetate [Pd(OAc)$_2$] (22 mg, 0.097 mmol), tri-(o-tolyl)phosphine (59 mg, 0.193 mmol), tetrabutylammonium bromide (104 mg, 0.32 mmol), allyl alcohol (0.110 mL, 1.6 mmol) and N,N-diisopropylethylamine (0.170 mL, 0.97 mmol) then purged several times with vacuum and argon. The reaction was heated to 100° C. and stirred for 2 hours under argon atmosphere. At which point, the reaction was cooled to room temperature then quenched with saturated NH$_4$Cl and diluted with ethyl acetate. The organic layer was washed with H$_2$O, aqueous LiCl, and brine, then dried (over Na$_2$SO$_4$), filtered and concentrated in in vacuo. The crude residue was purified by chromatography on silica gel (1/1—ethyl acetate/hexane) to afford the desired aminal product 61 (160 mg, impure): MS [M+H]=445.

Step 2

To a solution of intermediate 61 (50 mg, 0.113 mmol) in Dichloromethane (1.13 mL), was added Triethylsilane (0.364 mL, 2.25 mmol) and Trifluoroacetic acid (0.170 mL, 2.25 mmol). The reaction was stirred at room temperature for 4 hours. Upon completion, the reaction was diluted with ethyl acetate and quenched with a 10% sodium citrate solution. The layers were separated, and the aqueous layer was extracted with ethyl acetate (2×). The combined organic layer was washed with brine (2×), then dried (over Na$_2$SO$_4$), filtered and concentrated in vacuo to afford the desired product 62 (30 mg, 81%): $^1$H NMR (CDCl$_3$) 7.88 (bs, 1H), 7.78 (s, 1H), 7.02 (m, 2H), 6.92 (m, 2H), 5.25 (sept, J=6.4 Hz, 1H), 3.85 (s, 2H), 3.35 (m, 2H), 2.56 (t, J=6.8 Hz, 2H), 1.84 (m, 2H), 1.4 (d, J=6.4 Hz, 6H); MS [M+H]=329.

Step 3

To a solution of intermediate 62 (30 mg, 0.091 mmol) in 1,2-Dichloroethane [DCE] (0.30 mL), was added Ethyl 3-chloro-3-oxo-propionate (0.017 mL, 0.137 mmol). The reaction was stirred at 80° C. for 1 hour. Upon completion, the reaction was cooled to room temperature then directly purified by chromatography on silica gel (1/4—ethyl acetate/hexane) to afford the desired product 63 (34 mg, 84%) without further characterization: MS [M+H]=442.

Step 4

To a solution of intermediate 63 (34 mg, 0.091 mmol) in ethanol (1 mL) was added sodium ethoxide [21 wt % solution in ethanol] (0.050 mL, 0.137 mmol). The reaction was stirred at room temperature for 2 hours. Upon completion, the reaction was concentrated in vacuo then dissolved in ethyl acetate and quenched with a 10% citric acid solution. The layers were separated, and the aqueous layer was extracted with ethyl acetate (2×). The combined organic layer was washed with brine (2×), then dried (over Na$_2$SO$_4$), filtered and concentrated in vacuo to afford the desired product 64 (53 mg, quant): $^1$H NMR (CD$_3$OD) 8.43 (s, 1H), 7.24 (m, 2H), 7.08 (m, 2H), 4.47 (q, J=6.8 Hz, 2H), 4.23 (s, 2H), 4.13 (m, 2H), 2.95 (m, 2H), 2.11 (m, 2H), 1.44 (t, J=6.8 Hz, 3H); MS [M+H]=383.

Step 5

To a solution of intermediate 64 (35 mg, 0.091 mmol) in DMF (0.70 mL) was added 2-ethanolamine (0.050 mL). The reaction heated in a microwave reactor at 150° C. for 10 minutes. Upon completion, the reaction was diluted with ethyl acetate and quenched with a 10% citric acid solution. The layers were separated, and the aqueous layer was extracted with ethyl acetate (2×). The combined organic layer was washed with brine (2×), then dried (over $Na_2SO_4$), filtered and concentrated in vacuo. The crude material was recrystallized in ethyl acetate:hexane:methanol (1:4:0.5) to afford the desired product 65 (17 mg, 47%): 400 MHz $^1$H NMR (CD$_3$OD) δppm) 8.365 (s, 1H), 7.17 (dd, J=5.2 Hz, 2H), 7.01 (dd, J=8.4 Hz, 2H), 4.166 (s, 2H), 4.089 (t, J=5.6 Hz, 2H), 3.714 (t, J=5.2 Hz, 2H), 3.551 (t, J=4.8 Hz, 2H), 2.899 (t, J=6 Hz, 2H), 2.058 (m, 2H); $^{19}$F NMR (CD$_3$OD) δppm) −119.03; MS: 400 (M+1).

EXAMPLE 27

Preparation of Compound 72

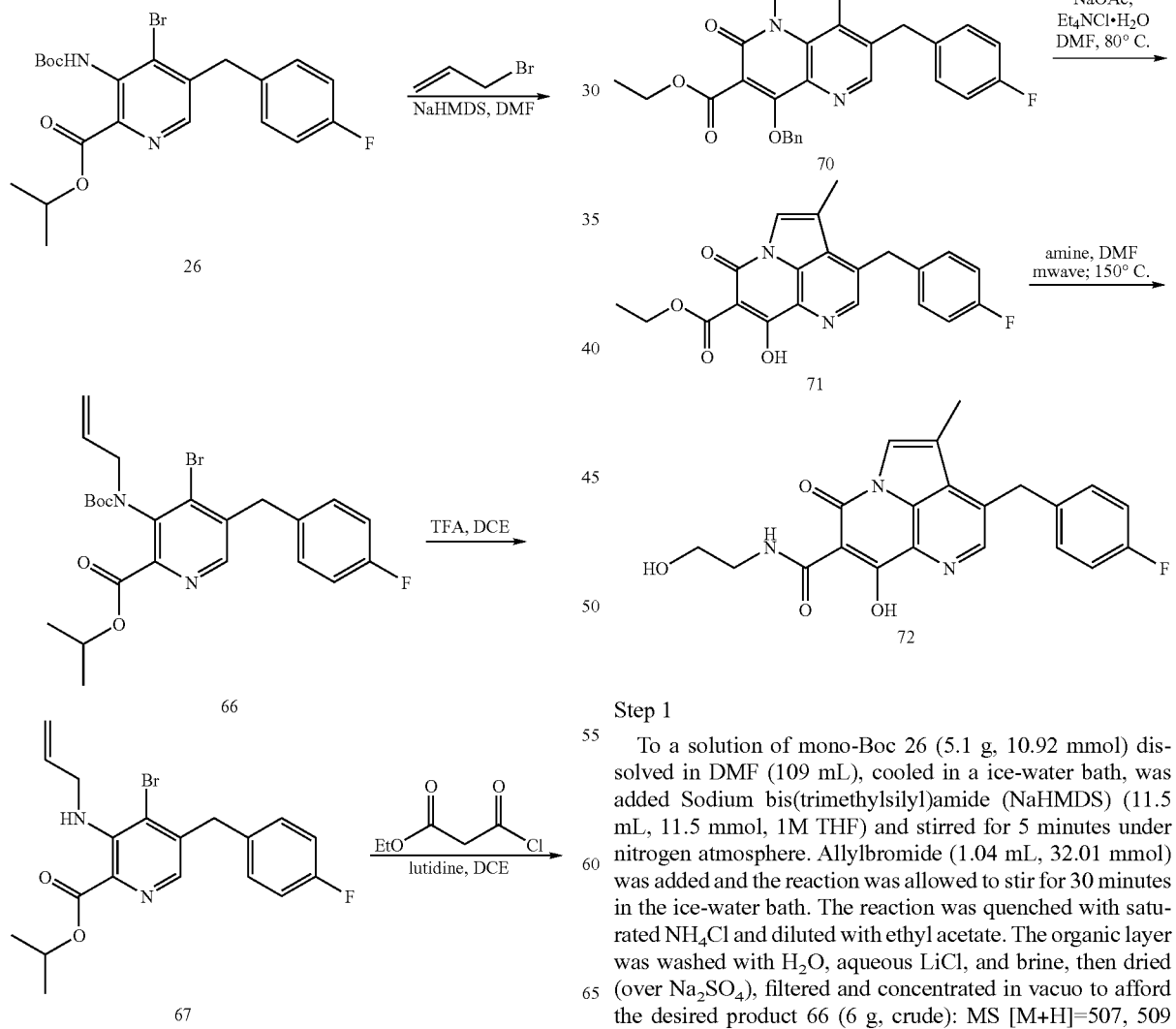

Step 1

To a solution of mono-Boc 26 (5.1 g, 10.92 mmol) dissolved in DMF (109 mL), cooled in a ice-water bath, was added Sodium bis(trimethylsilyl)amide (NaHMDS) (11.5 mL, 11.5 mmol, 1M THF) and stirred for 5 minutes under nitrogen atmosphere. Allylbromide (1.04 mL, 32.01 mmol) was added and the reaction was allowed to stir for 30 minutes in the ice-water bath. The reaction was quenched with saturated NH$_4$Cl and diluted with ethyl acetate. The organic layer was washed with H$_2$O, aqueous LiCl, and brine, then dried (over Na$_2$SO$_4$), filtered and concentrated in vacuo to afford the desired product 66 (6 g, crude): MS [M+H]=507, 509 (fragment 1:1).

Step 2

To a solution of intermediate 66 (6 g, 10.92 mmol) in 1,2-Dichloroethane (100 mL), was added Trifluoroacetic acid (20 mL, 20%). The reaction was stirred at room temperature overnight then heated at 55° C. for 2 hours. Upon completion, the reaction was diluted with ethyl acetate and quenched with a 10% sodium citrate solution. The layers were separated, and the aqueous layer was extracted with ethyl acetate (2×). The combined organic layer was washed with brine (2×), then dried (over $Na_2SO_4$), filtered and concentrated in vacuo to afford the desired product 67 (4.57 g, quant) with no further purification: $^1$H NMR (CDCl$_3$) 8.03 (s, 1H), 7.13 (m, 2H), 7.00 (m, 2H), 5.9 (m, 1H), 5.29 (m, 2H), 4.19 (s, 2H), 4.12 (d, 2H), 1.39 (d, J=6.4 Hz, 6H); MS [M+H]=407, 409 (fragment 1:1).

Step 3

To a solution of intermediate 67 (4.57 g, 10.92 mmol) in 1,2-Dichloroethane [DCE] (100 mL), was added Ethyl 3-chloro-3-oxo-propionate (1.44 mL, 11.5 mmol) and 2,6-lutidine (3.8 mL, 32976 mmol). The reaction was stirred at room temperature for 30 minutes. At which point, the reaction was diluted with ethyl acetate and quenched with a 10% citric acid solution. The layers were separated, and the aqueous layer was extracted with ethyl acetate (2×). The combined organic layer was washed with brine (2×), then dried (over $Na_2SO_4$), filtered and concentrated in vacuo to afford the desired product 68 (6.6 g, crude) without further purification or characterization: MS [M+H]=521, 523 (fragment 1:1).

Step 4

To a solution of intermediate 68 (6.6 g, 10.92 mmol) in ethanol (100 mL) was added sodium ethoxide [21 wt % solution in ethanol] (4.9 mL, 13.1 mmol). The reaction was stirred at room temperature for 2 hours. At which point, the reaction was concentrated in vacuo then dissolved in ethyl acetate and quenched with a 10% citric acid solution. The layers were separated, and the aqueous layer was extracted with ethyl acetate (2×). The combined organic layer was washed with brine (2×), then dried (over $Na_2SO_4$), filtered and concentrated in vacuo to afford the desired product 69 (6.0 g, crude) without further purification or characterization: MS [M+H]=461, 463 (fragment 1:1).

Step 5

To a solution of intermediate 69 (4 g, 8.695 mmol) in Dichloromethane (66 mL), was added Benzyl bromide (2.07 mL 17.4 mmol) and silver (I) oxide (4 g, 17.4 mmol). The reaction was stirred at room temperature for 4 hours. Upon completion, the reaction was filtered through a pad of celite then concentrated in vacuo. The crude residue was directly purified by chromatography on silica gel (1/4—ethyl acetate/hexane) to afford the desired product 70 (2.83 g, 70% over 5 steps): $^1$H NMR (CDCl$_3$) 8.29 (s, 1H), 7.45 (m, 2H), 7.3 (m, 3H), 7.1 (m, 2H), 7.0 (m, 2H), 5.8 (m, 1H), 5.55 (s, 2H), 5.2 (m, 2H), 5.1 (m, 2H), 4.33 (q, J=7.2 Hz, 2H), 4.23 (s, 2H), 3.83 (t, J=5.2 Hz, 2H), 1.27 (t, J=6.8 Hz, 3H); MS [M+H]= 551, 553 (fragment 1:1).

Step 6

To a solution of intermediate 70 (100 mg, 0.182 mmol) dissolved in DMF (1.8 mL) was added Palladium acetate [Pd(OAc)$_2$] (0.4 mg, 0.00182 mmol), sodium acetate (37 mg, 0.455 mmol), sodium formate (15 mg, 0.218 mmol) and tetraethylammonium chloride hydrate (40 mg, 0.218 mmol) and purged several times with vacuum and argon. The reaction was heated to 80° C. and stirred overnight under argon atmosphere. At which point, the reaction was cooled to room temperature then quenched with saturated NH$_4$Cl and diluted with ethyl acetate. The organic layer was washed with H$_2$O, aqueous LiCl, and brine, then dried (over Na$_2$SO$_4$), filtered and concentrated in vacuo to afford the desired product 71 (65 mg, crude) with no further purification or characterization: MS [M+H]=381, 383 (fragment 1:1).

Step 7

To a solution of intermediate 71 (62 mg, crude) in DMF (1.0 mL) was added 2-ethanolamine (0.035 mL). The reaction heated in a microwave reactor at 150° C. for 15 minutes. Upon completion, the reaction was purified directly by reversed phase HPLC [Phenomenex Gemini Axia packed column] (eluting with 0.1% Formic acid) to afford the desired product 72 (14 mg, 20%): 400 MHz $^1$H NMR (CD$_3$OD) δ (ppm) 8.433 (s, 1H), 7.798 (s, 1H), 7.15 (m, 2H), 7.01 (m, 2H), 4.509 (s, 2H), 3.744 (t, J=5.6 Hz, 2H), 3.595 (t, J=5.6 Hz, 2H), 2.33 (s, 3H); $^{19}$F NMR (CDCl$_3$) δ (ppm) −118.512; MS: 396 (M+1).

EXAMPLE 28

Preparation of Compound 79

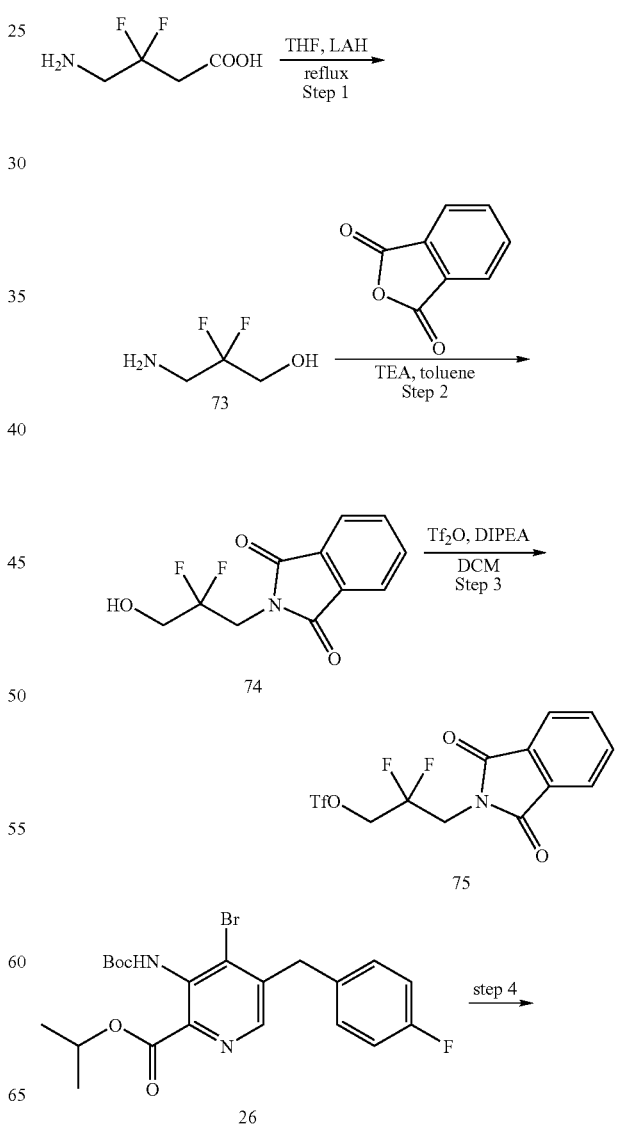

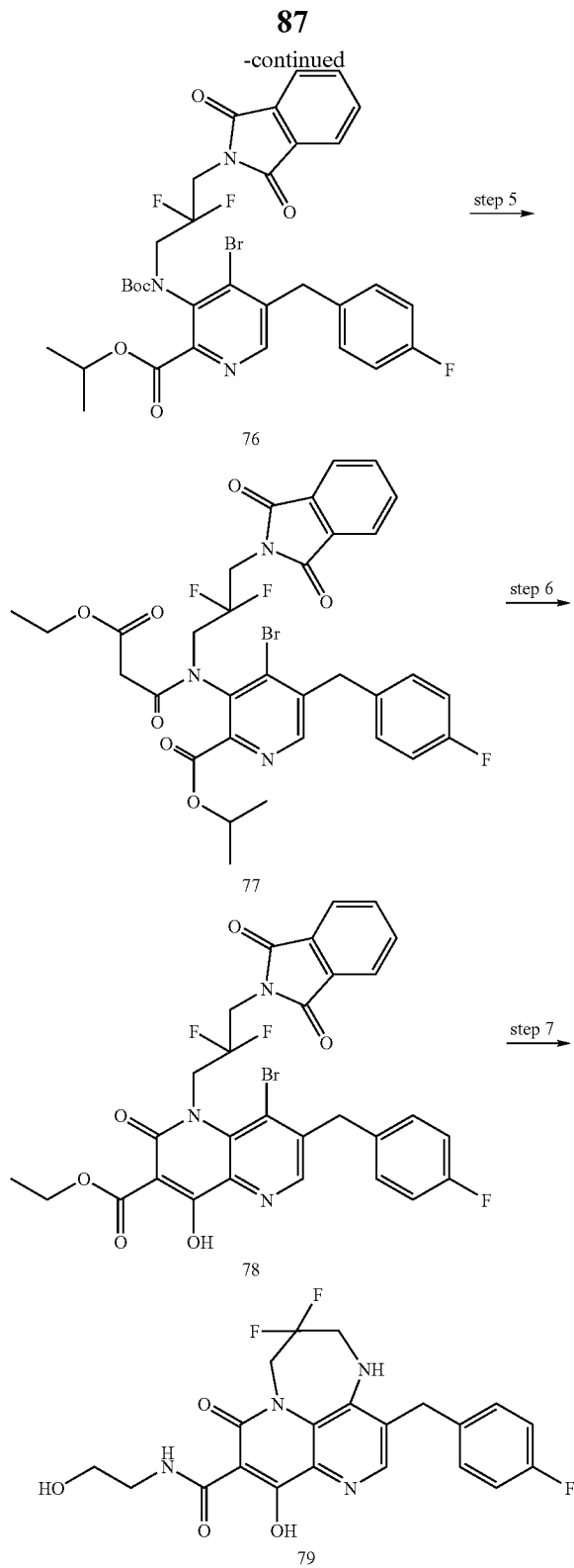

MgSO$_4$. After removal of the solvent in vacuo, 525 mg of the desired compound 73 was obtained.

To the crude compound 73 in 100 mL of toluene, was added TEA (552 mg, 5.46 mmol) and phthalic anhydrite (740 mg, 5 mmol). After azeotroping for 3 h, the toluene was removed in vacuo and the residue was purified by preparative flash chromatography (silica gel, ethyl acetate/hexane, 1:4) to afford the desired product 74 (358 mg): $^1$H NMR (CDCl$_3$); 7.92 (2H, m), 7.8 (2H, m), 4.21 (2H, t), 3.74 (2H, m) 3.23 (1H, br; OH) MS [M+H]=241.89

Step 3 & Step 4

Into the solution of compound 74 (300 mg, 1.24 mmol) in 10 ml of DCM, was added DIPEA (241 mg, 1.87 mmol) and trifluoromethanesulfonic anhydrite (525 mg, 1.87 mmol) at 0° C. After stirring 2 h at room temperature, the reaction mixture was diluted with ethyl ether (150 ml), washed with saturated aq. NaHCO$_3$ and brine, dried over Na$_2$SO$_4$, filtered and concentrated in vacuo to yield the desired product 75, which was used without further purification.

A DMF (15 mL) solution of compound 26 (from the preparation of example 9) (520 mg, 1.1 mmol) was cooled in a ice-water bath, and treated with sodium bis(trimethylsilyl)amide (NaHMDS, 1.3 mL, 1.3 mmol, 1M THF) and stirred for 5 minutes under a nitrogen atmosphere. A solution of compound 75 in 5 mL of DMF solution was added and the reaction was stirred overnight at room temperature. The reaction was quenched with saturated NH$_4$Cl (aq) and diluted with ethyl acetate. The organic layer was washed with H$_2$O, aqueous LiCl, and brine, then dried (over Na$_2$SO$_4$), filtered and concentrated in vacuo. The crude residue was purified by preparative flash chromatography (silica gel, ethyl acetate/hexane, 1:1) to afford the desired product 76 (530 mg):

$^1$H NMR (CDCl$_3$): 8.35 (1H, s), 7.84 (2H, m), 7.73 (2H, m), 7.07 (2H, m), 6.95 (2H, m), 5.38 (2H, m), 4.35 (2H, m), 4.2 (2H, m), 3.55 (1H, m), 1.37 (16H, m), 1.3 (9H, s). MS [M+H]=691.73.

Step 5

Trifluoroacetic acid (2 ml) was added to a solution of intermediate 76 (530 mg, 0.767 mmol) in dichloromethane (10 mL). The reaction was stirred at room temperature for 1 hour then heated at 55° C. for 5 hours. Upon completion, the reaction was cooled to room temperature then diluted with ethyl acetate and cautiously (gas evolution) quenched with saturated NaHCO$_3$. The phases were separated, and the aqueous layer was extracted with ethyl acetate (2×). The combined organic layers were washed with brine (2×), dried (Na$_2$SO$_4$), filtered and concentrated in vacuo to afford the desired des-Boc intermediate (quant.) which was used without further purification: MS [M+H]=589.93

A solution of de-protected intermediate (0.767 mmol) in 1,2-dichloroethane (DCE, 23 mL), was treated with ethyl 3-chloro-3-oxo-propionate (0.116 mL, 0.92 mmol) and 2,6-lutidine (0.212 mL, 1.2 mmol). The reaction was stirred at room temperature. After 30 minutes additional ethyl 3-chloro-3-oxo-propionate (0.125 mL, 1.0 mmol) and 2,6-lutidine (0.30 mL, 2.58 mmol) were added to the reaction. Then reflux for 2 h. The reaction mixture was diluted with ethyl acetate and washed with a 10% citric acid (aq.) solution. The two layers were separated, and the aqueous layer was extracted with ethyl acetate (2×). The combined organic layers were washed with brine (2×), dried (Na$_2$SO$_4$), filtered and concentrated in vacuo. The crude residue was purified by preparative flash chromatography (silica gel, ethyl acetate/hexane) to afford the desired product 77 (316 mg)

Step 1 & Step 2

Into the solution of 2,2-difluoro-3-aminopropionic acid (2 g, 14.4 mmol) in 40 mL of THF, was added 2N LAH solution in THF at 0° C. The mixture was heated to reflux for 3 h. After cooling to 0° C., 1.75 mL of 5N KOH water solution was added and the mixture was filtered. The solid was washed with 40 ml of THF. The combined filtrates were dried with ¹H NMR (CDCl₃): 8.38 (1H, s), 7.72 (2H, m), 7.12 (2H, m), 7.01 (2H, m), 5.45 (1H, m), 4.35 (2H, m), 4.16 (2H, m), 4.14 (2H, m), 3.37 (2H, d), 3.07 (2H, d), 1.4 (3H, d), 1.36 (3H, d), 1.21 (3H, t). MS [M+H]=705.9.

Step 6

A solution of 77 (118 mg, 0.167 mmol) in 10 mL of ethanol was treated dropwise with 0.065 mL of NaOEt/EtOH (21% wt/wt, 0.2 mmol) and the reaction monitored by LCMS. Once reaction progress ceased, the reaction mixture was treated with 25 mL of aqueous citric acid (10% wt/vol) before evaporating in vacuo at 30° C. to remove ethanol. After further dilution with 25 mL of water and an additional 25 mL of 10% aqueous citric acid the product was extracted with ethyl acetate (1×100 mL, 2×~50 mL). Combined organic extracts were washed with water and brine (2×), dried (Na₂SO₄), filtered, and evaporated in vacuo at 30° C., followed by high vacuum treatment providing the desired product 78. The desired product 78 was used as obtained without further characterization.

MS [M+H]=643.85.

Step 7

A solution of compound 78 (0.167 mmol) in 3 mL DMF was treated with ethanolamine (6 mg, 1 mmol) and subjected to microwave treatment (150° C., 900 sec). After dilution of the reaction mixture with 1 mL water/TFA (0.1% v/v) purification was accomplished via preparative HPLC to afford 67.6 mg of desired product 79 (as a TFA salt).

¹H NMR (MeOD): 7.86 (1H, s), 7.26 (2H, m), 7.1 (2H, m), 4.72 (2H, t), 4.06 (1H, s), 3.91 (2H, t), 3.73 (2H, t), 3.62 (2H, t), MS [M+H]=449.12.

EXAMPLE 29

Preparation of Compound A9

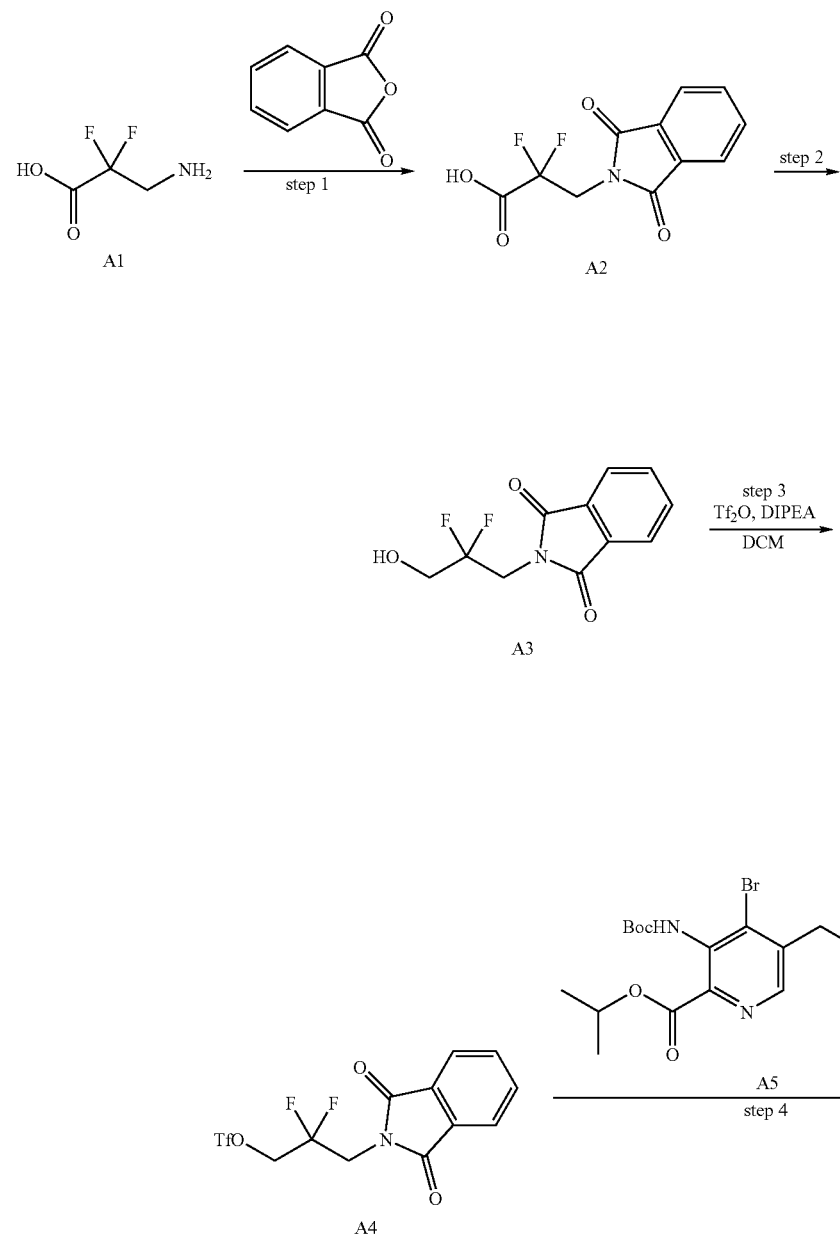

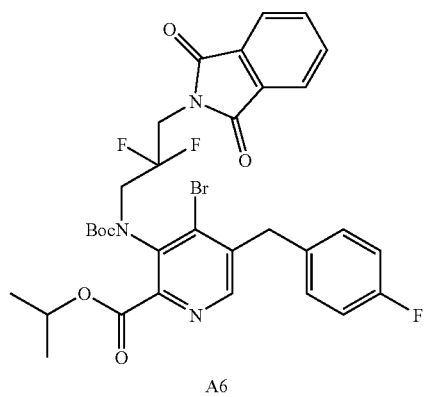

A6

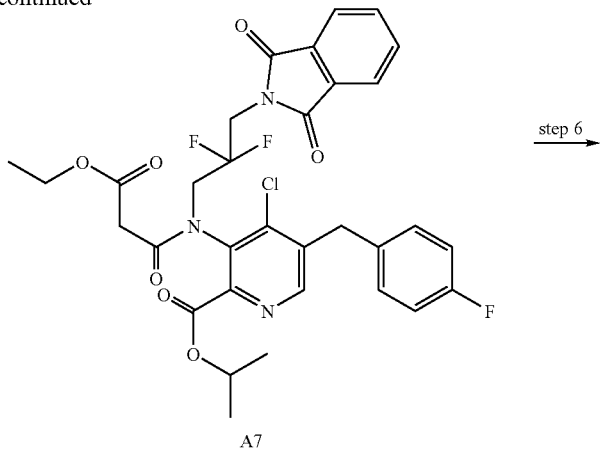

A7

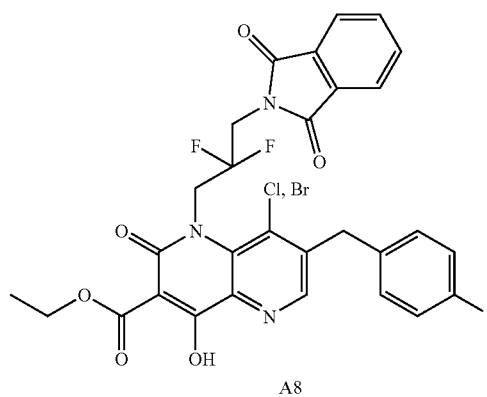

A8

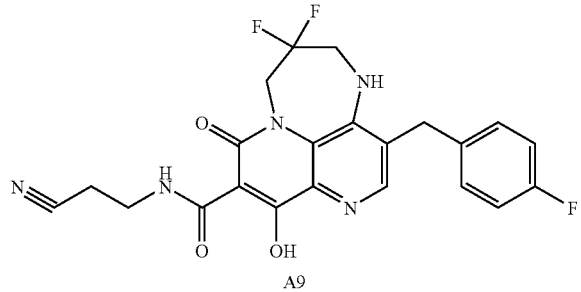

A9

Step 1

A suspension of 2,2-difluoro-3-aminopropionic acid A1 (7.08 g, 56.6 mmol) in 250 ml of toluene was treated with phthalic anhydride (8.80 g, 59.4 mmol) and triethylamine (20 mL, 14.35 g, 14.4 mmol) and refluxed with water removed by a Dean-Stark trap, drained 5 times at intervals. After cooling to ambient temperature the solvent was removed in vacuo at 30° C. The residue obtained was partitioned between ethyl acetate and ~2N HCl (aq) with the aqueous phase extracted a second time with ethyl acetate. Evaporation at 30° C. (in vacuo) of the combined organic phases that had been washed with ~2N HCl, brine and dried ($Na_2SO_4$) afforded 3-(1,3-Dioxo-1,3-dihydro-isoindol-2-yl)-2,2-difluoro-propionic acid (13.74 g) A2.

$^1$H NMR (400 MHz, $CDCl_3$) d 7.91 (m, 2H), 7.87 (m, 2H), 4.21 (t, J=14.9 Hz, 2H),

Step 2

Under argon atmosphere 3-(1,3-Dioxo-1,3-dihydro-isoindol-2-yl)-2,2-difluoro-propionic acid, A2 (13.74 g, 53.85 mmol), dissolved in THF (200 mL) was treated with borane-methylsulfide complex (6.3 mL, 5.04 g, 66.6 mmol). After stirring overnight an additional portion of borane-methylsulfide complex (6.0 mL, 4.80 g, 63.43 mmol) was added. When the reaction was complete it was cautiously diluted with water and extracted with ethyl acetate (2×). An ethyl acetate solution prepared from the residue obtained by evaporation of the initial ethyl acetate extractions at 30° C. in vacuo was washed with water, brine (2×), dried ($Na_2SO_4$), filtered, and evaporated in vacuo at 30° C. Crude A3 was sonicated in ethyl acetate, and filtered to give pure 2-(2,2-Difluoro-3-hydroxy-propyl)-isoindole-1,3-dione, A3 (7.45 g). Flash chromatography of the liquor residue (Yamazen, 5 L silica gel cartridge, ethyl acetate/hexane gradient) afforded additional pure 2-(2,2-Difluoro-3-hydroxy-propyl)-isoindole-1,3-dione, A3 (1.39 g).

$^1$H NMR (400 MHz, $CDCl_3$) d 7.90 (m, 2H), 7.77 (m, 2H), 4.18 (t, J=12.3 Hz, 2H), 3.72 (t, J=12.1 Hz, 2H).

Step 3

Into the solution of compound A3 (300 mg, 1.24 mmol) in 10 ml of DCM, were added DIPEA (241 mg, 1.87 mmol) and trifluoromethanesulfonic anhydrite (525 mg, 1.87 mmol) at 0° C. After stirring 2 h at room temperature, the reaction mixture was diluted with ethyl ether (150 ml), washed with saturated aq. $NaHCO_3$ and brine, dried over $Na_2SO_4$, filtered and concentrated in vacuo to yield crude A4. Compound A4 was used without purification.

Step 4

A DMF (15 mL) solution of A5 (520 mg, 1.1 mmol) was cooled in a ice-water bath, and treated with sodium bis(trimethylsilyl)amide (NaHMDS, 1.3 mL, 1.3 mmol, 1M THF) and stirred for 5 minutes under nitrogen atmosphere. Compound A4 in 5 ml of DMF solution was added and the reaction was stirred overnight at room temperature. The reaction was quenched with saturated $NH_4Cl$ (aq) and diluted with ethyl acetate. The organic layer was washed with $H_2O$, aqueous LiCl, and brine, then dried (over $Na_2SO_4$), filtered and concentrated in vacuo. The crude residue was purified by preparative flash chromatography (silica gel, ethyl acetate/hexane, 1:1) to afford the desired product A6 (530 mg):

$^1$H NMR ($CDCl_3$): 8.35 (1H, s), 7.84 (2H, m), 7.73 (2H, m), 7.07 (2H, m), 6.95 (2H, m), 5.38 (2H, m), 4.35 (2H, m), 4.2 (2H, m), 3.55 (1H, m), 1.37 (6H, m), 1.3 (9H, s).

MS [M+H]=691.73.

Step 5

A solution of A6 (16.42 g, 23.8 mmol) in 1,2-dichloroethane (200 mL) was treated with trifluoroacetic acid (50 mL) and stirred overnight before heating for several hours in an oil bath (100° C.). When cool, the reaction mixture was evaporated in vacuo at 30° C. before partitioning between ethyl acetate and saturated NaHCO$_3$ (aq.) and extracting the aqueous phase with two additional portions of ethyl acetate. Combined organic phases were washed with water, brine (2×), dried (Na$_2$SO$_4$), filtered, and evaporated in vacuo at 30° C. followed by high vacuum treatment to afford deprotected product (13.13 g).

MS [M+H]=590.09, 591.94 Br79/81

A solution of crude product obtained above (13.13 g, 22.24 mmol) in 1,2-dichloroethane (200 mL) was treated with ethyl 3-chloro-3-oxopropionate (5.02 g, 33.34 mmol) and heated in an oil bath for about 3.5 h. Evaluation of reaction progress indicated a significant portion of the bromine in the substrate and product had been exchanged for chlorine. As the acylation reaction was incomplete additional portions of ethyl 3-chloro-3-oxopropionate (1.79 g, 11.91 mmol; 0.59 g, 3.97 mmol) were added at intervals and heating was continued for 2 and 1 hr after the respective additions. Evaporation of the cooled reaction mixture at 30° C. in vacuo afforded a syrup that was partitioned between ethyl acetate and water. The organic phases were pooled after a second extraction with ethyl acetate, washed with water, brine, dried (Na$_2$SO$_4$), filtered, and evaporated in vacuo at 30° C. followed by high vacuum treatment to afford 18.77 g of A7 which was used as obtained.

MS [M+H]=660.28, 662.12 Cl 35/37; 704.96, 706.87 Br 79/81

Step 6

A solution of A7 (18.77 g, est. 22.24 mmol) in 250 mL of ethanol was treated dropwise with 20 mL of NaOEt/EtOH (21% wt/wt, 53.6 mmol) and allowed to stir at ambient temperature overnight. An additional 5 mL portion of NaOEt/EtOH (21% wt/wt, 13.4 mmol) was added to the reaction which was allowed to stir for 3 h at ambient temperature followed by heating in an oil bath (70° C.) for one hour to complete the cyclization reaction. When cool, the reaction was evaporated in vacuo at 30° C. before portioning between ethyl acetate and 4N HCl (aq.), washed with water, brine and dried (Na$_2$SO$_4$), filtered, evaporated in vacuo at 30° C. The residue obtained was dissolved in THF (200 mL) and treated with carbonyl diimidazole (3.97 g, 24.5 mmol) and stirred overnight. After evaporation in vacuo at 30° C., the residue was partitioned between ethyl acetate and 4N HCl (aq.) using water and methylene chloride as necessary to solublize the matrix in a reasonable volume. A mixture of ethyl acetate/methylene chloride (usable as an upper phase vs. the aqueous phase) was used to extract the acidic aqueous phase. The combined organic extracts were washed with water, and brine (2×), dried (Na$_2$SO$_4$), filtered, evaporated in vacuo at 30° C., followed by high vacuum treatment to afford A8 (14.0 g) which was used as obtained without further purification.

MS [M+H]=600.06, 601.95 Cl 35/37; 643.85, 645.79 Br 79/81.

Step 7

Microwave treatment (120° C., 2×1200 sec) of A8 (313.1, 0.52 mmol) and 3-aminopropionitrile (100 µL) in 2.5 mL of DMF was followed by the addition of hydrazine (0.1 mL, 102 mg, 3.2 mmol) and additional microwave treatment (120° C., 1200 sec) afforded crude A9. Isolation and purification were accomplished via preparative HPLC to afford 151 mg of A9 (as a TFA salt).

$^1$H NMR (400 MHz, CH$_3$OH d$_4$) d 7.87 (s, 1H), 7.28 (m, 2H), 7.10 (m, 2H), 4.74 (t, J=12 Hz, 2H), 4.07 (s, 2H), 3.93 (t, J=12.5 Hz, 2H), 3.78 (t, J=6.6 Hz, 2H), 2.84 (t, J=6.6 Hz, 2H)

$^{19}$F NMR (376 MHz, CH$_3$OH d$_4$) d −77.296 (s, TFA), −107.771.746 (m), −117.391 (m) MS [M+1]=458.07.

EXAMPLE 30

Preparation of Compound A10

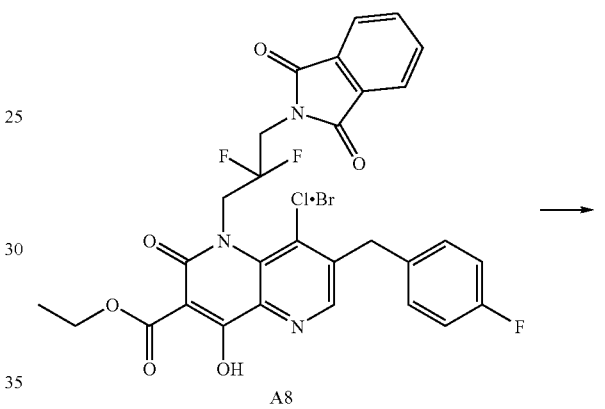

A8

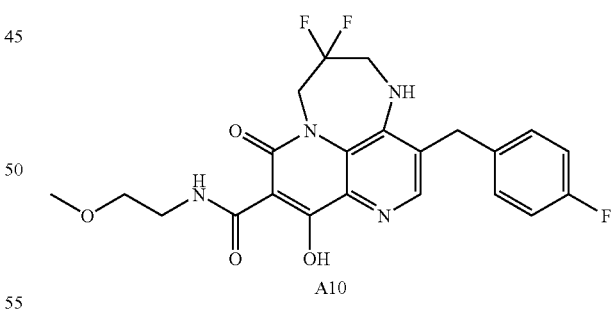

A10

Microwave treatment (120° C., 2×1200 sec) of A8 (302 mg, 0.5 mmol) and 2-methoxyethylamine (150 µL, 86.4 mg, 1.15 mmol) in 2.5 mL of DMF was followed by the addition of hydrazine (0.1 mL, 102 mg, 3.2 mmol) and additional microwave treatment (120° C., 1200 sec) afforded crude A10. Isolation and purification were accomplished via preparative HPLC to afford 139.7 mg of A10 (as a TFA salt).

$^1$H NMR (400 MHz, CH$_3$OH d$_4$) d 7.85 (s, 1H), 7.28 (m, 2H), 7.10 (m, 2H), 4.71 (t, J=12 Hz, 2H), 4.06 (s, 2H), 3.93 (t, J=12.4 Hz, 2H), 3.68 (t, J=5 Hz, 2H), 3.59 (t, J=5.1 Hz, 2H), 3.23 (s, 3H).

EXAMPLE 31

Preparation of Compound A11

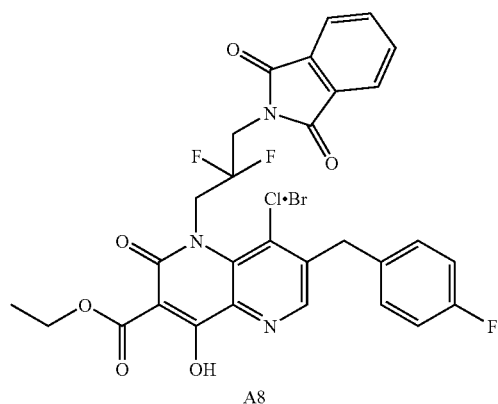

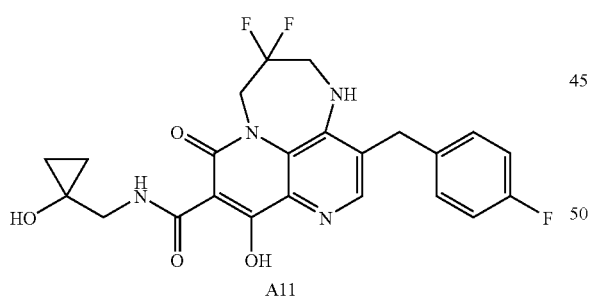

A solution of A8 (354.9 mg, 0.59 mmol) and 1-aminomethyl-cyclopropanol (112 mg, 1.11 mmol) in 2.5 mL of DMF was treated in a microwave reactor (120° C., 1200 sec, followed by 150° C., 1200 sec). Additional 1-aminomethyl-cyclopropanol was added before the reaction was subjected to further microwave treatment (150° C., 1200 sec), followed by the addition of hydrazine (0.1 mL, 102 mg, 3.2 mmol) and another microwave treatment (120° C., 1200 sec) to afforded crude A11. Isolation and purification were accomplished via preparative HPLC to afford 64.6 mg of A11 (as a TFA salt).
$^1$H NMR (400 MHz, CH$_3$OH d$_4$) d 7.84 (s, 1H), 7.28 (m, 2H), 7.10 (m, 2H), 4.73 (t, J=11.8 Hz, 2H), 4.07 (s, 2H), 3.94 (t, J=12.5 Hz, 2H), 3.62 (s, 2H), 0.78 (m, 2H), 0.69 (m, 2H).
$^{19}$F NMR (376 MHz, CH$_3$OH d$_4$) d −77.26 (s, TFA), −107.757 (m), −117.3226 (m) MS [M+1]=475.08.

EXAMPLE 32

Preparation of Compound A12

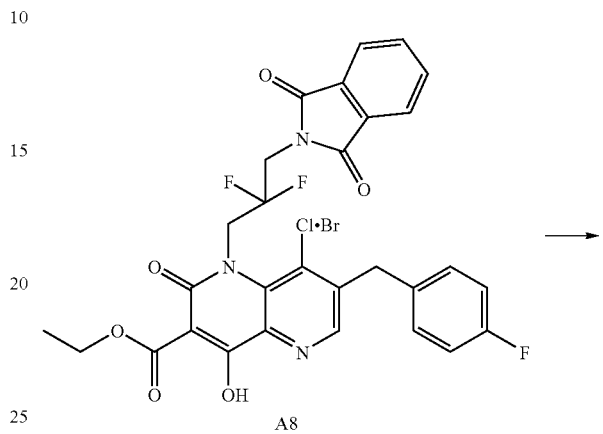

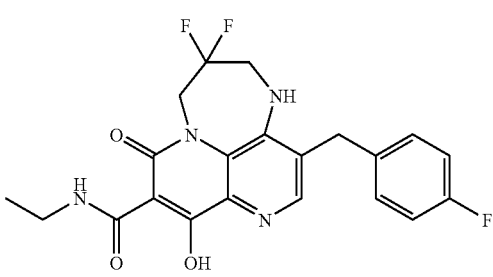

Microwave treatment (130° C., 900 sec) of A8 (115.5 mg, 0.186 mmol) and ethylamine (0.5 mL, 2M/THF, 1 mmol in 1 mL was followed by the addition of hydrazine (0.05 mL, 51 mg, 1.6 mmol) and additional microwave treatment (150° C., 900 sec) afforded crude A12. Isolation and purification were accomplished via preparative HPLC to afford 7.2 mg of A12 (as a TFA salt).
$^1$H NMR (400 MHz, CH$_3$OH$_4$) d 7.76 (s, 1H), 7.20 (m, 2H), 7.02 (m, 2H), 4.63 (t, J=11.9 Hz, 2H), 3.98 (s, 2H), 3.85 (t, J=12.4 Hz, 2H), 3.45 (q, J=7.31 Hz, 2H), 1.20 (t, J=7.3 Hz, 3H)

$^{19}$F NMR (376 MHz, CH$_3$OH d$_4$) d –77.134 (s, TFA), –107.792 (m), –117.369 (m) MS [M+1]=433.08.

EXAMPLE 33

Preparation of Compound A13

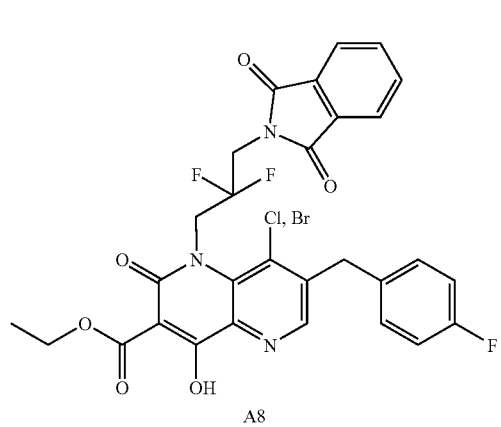

$^{19}$F NMR (376 MHz, CH$_3$OH d$_4$) d –77.001 (S, TFA), –108.359 (m), –118.166 (m) MS [M+1]=463.07.

EXAMPLE 34

Preparation of Compound A14

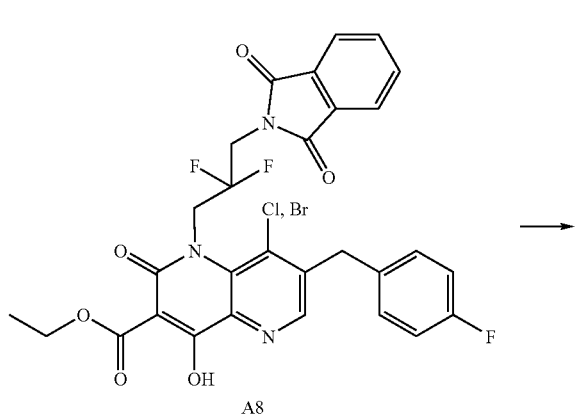

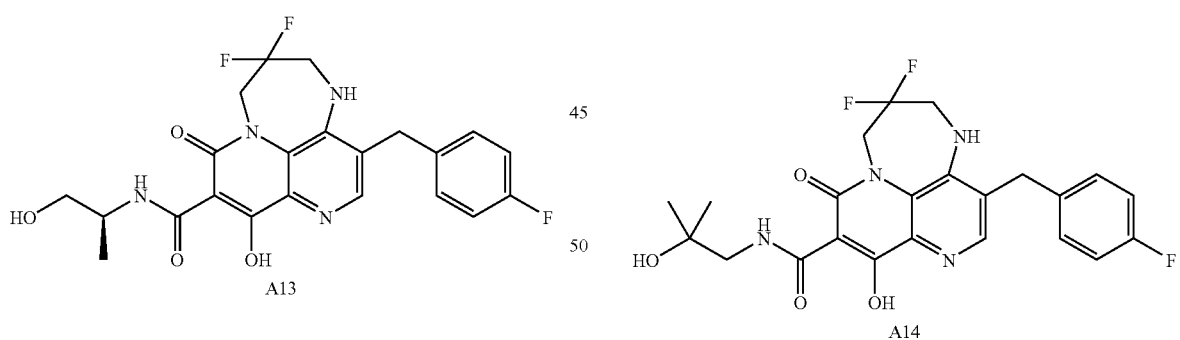

Microwave treatment (130° C., 600 sec, followed by 160° C., 900 sec) of A8 (111.7 mg, 0.186 mmol) and S(+)-2-amino-1-propanol (72 mg, 0.96 mmol) in 1 mL was followed by the addition of hydrazine (0.05 mL, 51 mg, 1.6 mmol) and additional microwave treatment (150° C., 900 sec) afforded crude A13. Isolation and purification were accomplished via preparative HPLC to afford 60.4 mg of A13 (as a TFA salt).

$^1$H NMR (400 MHz, CH$_3$OH d$_4$) d 7.98 (s, 1H), 7.24 (m, 2H), 7.05 (m, 2H), 4.71 (m, 2H), 4.19 (m, 1H), 4.04 (s, 2H) 3.74 (t, J=12.5 Hz, 2H), 3.61 (m, 2H), 1.27 (d, J=6.9 Hz, 3H).

Microwave treatment (130° C., 600 sec followed by 150° C., 900 sec) of A8 (116.7 mg, 0.19 mmol) and 1-amino-2-methyl-propan-2-ol (85.7 mg, 0.96 mmol) in 1 mL afforded crude A14. Isolation and purification were accomplished via preparative HPLC to afford 56.2 mg of A14 (as a TFA salt).

$^1$H NMR (400 MHz, CH$_3$OH d$_4$) d 8.03 (s, 1H), 7.23 (m, 2H), 7.03 (m, 2H), 4.72 (t, J=11.7 Hz, 2H), 4.03 (s, 2H), 3.68 (t, J=12.7 Hz, 2H), 3.43 (s, 2H), 1.24 (s, 6H).

$^{19}$F NMR (376 MHz, CH$_3$OH d$_4$) d –77.296 (s, TFA), –107.771.746 (m), –117.391 (m)

MS [M+1]=477.15.

EXAMPLE 35

Preparation of Compound A15

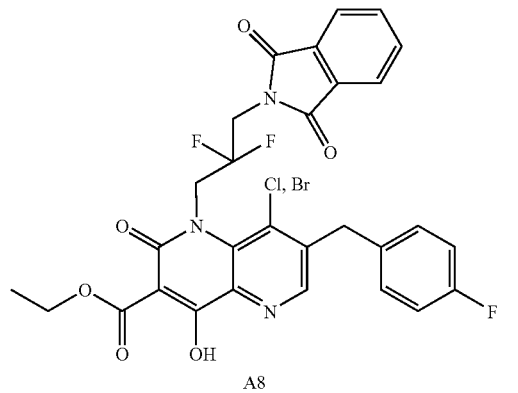

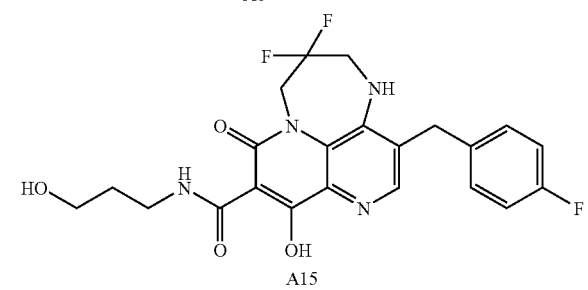

Microwave treatment (130° C., 900 sec followed by 150° C., 1200 sec) of A8 (113.3 mg, 0.19 mmol) and 3-amino-1-propanol (73 mg, 0.98 mmol) in 1 mL of DMF afforded crude GS-431735. Isolation and purification were accomplished via preparative HPLC to afford 33.3 mg of A15 (as a TFA salt).

$^1$H NMR (400 MHz, CH$_3$OH d$_4$) d 7.83 (s, 1H), 7.28 (m, 2H), 7.10 (m, 2H), 4.71 (t, J=12 Hz, 2H), 4.06 (s, 2H), 3.94 (t, J=12.5 Hz, 2H), 3.67 (t, J=6.1 Hz, 2H), 3.62 (t, J=6.75 Hz, 2H), 1.87 (qt, J=6.35, 2H)

$^{19}$F NMR (376 MHz, CH$_3$OH d$_4$) d −77.289 (s, TFA), 10.746 (m), −117.317 (m) MS [M+1]=463.08.

EXAMPLE 36

Preparation of Compound A17

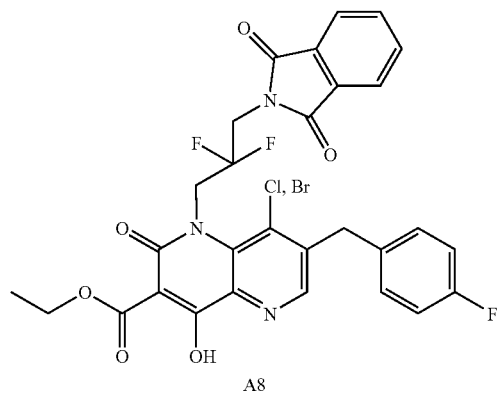

Microwave treatment (130° C., 1200 sec.) of A8 (127 mg, 0.212 mmol) and 3-aminobutylnitril hydrochloride salt (77 mg, 0.626 mmol), diisopropylethylamine (0.18 mL) in 1.5 mL of DMF was followed by the addition of hydrazine (31 mg, 1 mmol) and additional microwave treatment (120° C., 1800 sec) afforded crude A17. Isolation and purification were accomplished via preparative HPLC to afford 25.4 mg of A17 (as a TFA salt).

$^1$H NMR (400 MHz, CH$_3$OH d$_4$) d 7.783 (s, 1H), 7.2 (m, 2H), 7.02 (m, 2H), 4.65 (t, 2H), 3.99 (s, 2H), 3.84 (t, 2H), 3.54 (t, 2H), 2.47 (t, 2H), 1.92 (t, 2H).

$^{19}$F NMR (376 MHz, CH$_3$OH d$_4$) d −77.17 (s, TFA), −107.79 (m), −117.39 (m)

MS [M+1]=472.08.

EXAMPLE 37

Preparation of Compound A18

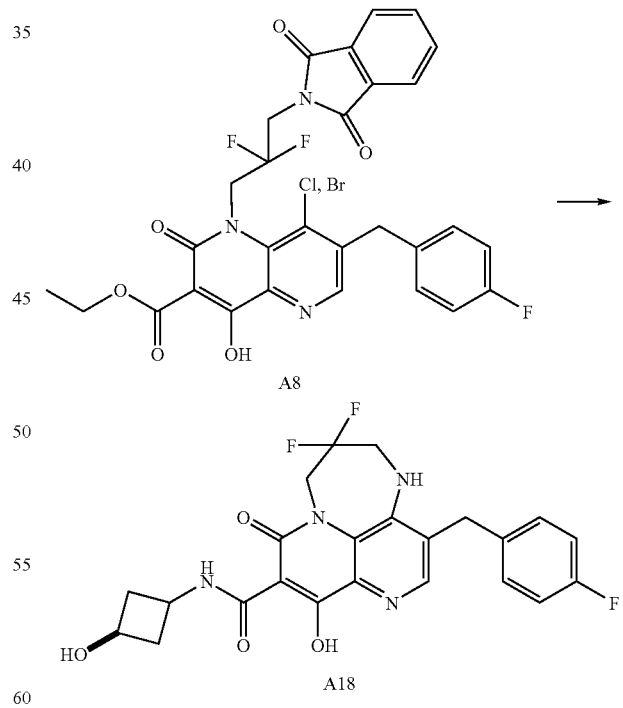

Microwave treatment (140° C., 1200 sec. followed by 145° C., 900 sec) of A8 (165 mg, 0.28 mmol) and trans-3-aminobutanol hydrochloride salt (104 mg, 0.84 mmol), diisopropylethylamine (0.25 ml) in 2 mL of DMF was followed by the addition of hydrazine (58 mg, 1.8 mmol) and additional microwave treatment (110° C., 1200 sec) afforded crude A18.

Isolation and purification were accomplished via preparative HPLC to afford 61.8 mg of A18 (as a TFA salt) (trans-isomer).

$^1$H NMR (400 MHz, CH$_3$OH d$_4$) d 7.774 (s, 1H), 7.21 (m, 2H), 7.03 (m, 2H), 4.65 (t, 2H), 4.53 (t, 1H), 4.4 (t, 1H), 3.99 (s, 2H), 3.86 (t, 2H), 2.34 (m, 4H).

$^{19}$F NMR (376 MHz, CH$_3$OH d$_4$) d −77.147 (s, TFA), −107.755 (m), −117.34 (m)

MS [M+1]=475.09.

EXAMPLE 38

Preparation of Compound A25

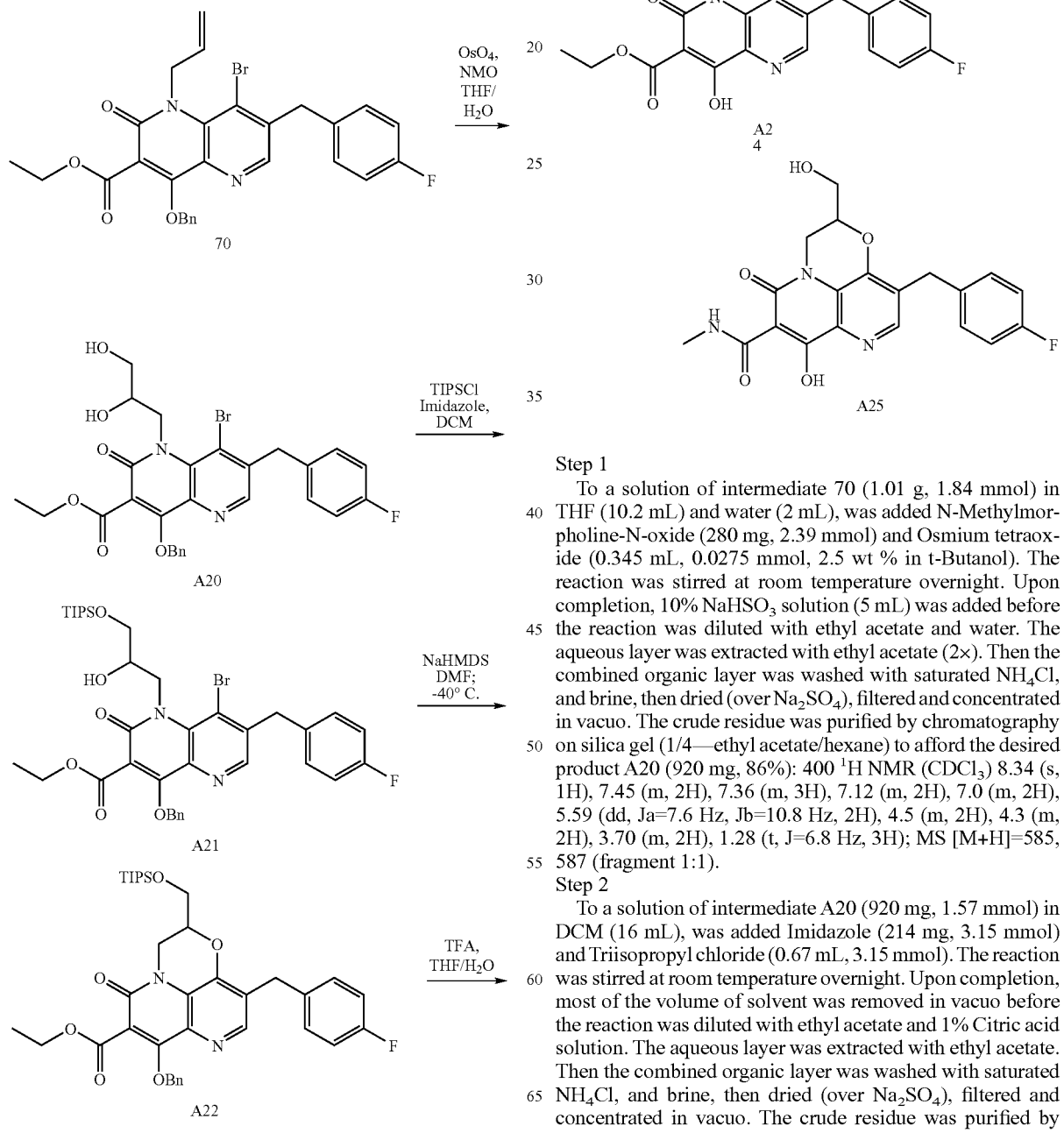

Step 1

To a solution of intermediate 70 (1.01 g, 1.84 mmol) in THF (10.2 mL) and water (2 mL), was added N-Methylmorpholine-N-oxide (280 mg, 2.39 mmol) and Osmium tetraoxide (0.345 mL, 0.0275 mmol, 2.5 wt % in t-Butanol). The reaction was stirred at room temperature overnight. Upon completion, 10% NaHSO$_3$ solution (5 mL) was added before the reaction was diluted with ethyl acetate and water. The aqueous layer was extracted with ethyl acetate (2×). Then the combined organic layer was washed with saturated NH$_4$Cl, and brine, then dried (over Na$_2$SO$_4$), filtered and concentrated in vacuo. The crude residue was purified by chromatography on silica gel (1/4—ethyl acetate/hexane) to afford the desired product A20 (920 mg, 86%): 400 $^1$H NMR (CDCl$_3$) 8.34 (s, 1H), 7.45 (m, 2H), 7.36 (m, 3H), 7.12 (m, 2H), 7.0 (m, 2H), 5.59 (dd, Ja=7.6 Hz, Jb=10.8 Hz, 2H), 4.5 (m, 2H), 4.3 (m, 2H), 3.70 (m, 2H), 1.28 (t, J=6.8 Hz, 3H); MS [M+H]=585, 587 (fragment 1:1).

Step 2

To a solution of intermediate A20 (920 mg, 1.57 mmol) in DCM (16 mL), was added Imidazole (214 mg, 3.15 mmol) and Triisopropyl chloride (0.67 mL, 3.15 mmol). The reaction was stirred at room temperature overnight. Upon completion, most of the volume of solvent was removed in vacuo before the reaction was diluted with ethyl acetate and 1% Citric acid solution. The aqueous layer was extracted with ethyl acetate. Then the combined organic layer was washed with saturated NH$_4$Cl, and brine, then dried (over Na$_2$SO$_4$), filtered and concentrated in vacuo. The crude residue was purified by chromatography on silica gel (1/4—ethyl acetate/hexane) to afford the desired product A21 (1.25 g, 95%): 300 ¹H NMR (CDCl₃) 8.32 (s, 1H), 7.46 (m, 2H), 7.36 (m, 3H), 7.15 (m, 2H), 7.02 (m, 2H), 5.58 (s, 2H), 4.84 (m, 2H), 4.35 (q, J=7.8 Hz, 2H), 4.26 (s, 2H), 4.13 (m, 1H), 3.74 (m, 2H), 1.57 (m, 3H), 1.30 (t, J=7.2 Hz, 3H), 1.05 (s, 18H); MS [M+H]=741, 743 (fragment 1:1).

Step 3

To a solution of intermediate A21 (1.05 g, 1.42 mmol) in DMF (71 mL), cooled to −40° C. was added Sodium bis (trimethylsilyl)amide (NaHMDS) (1.56 mL, 1.56 mmol, 1M THF) dropwise then stirred for an additional 15 minutes. The reaction was immediately diluted with ethyl acetate and saturated NH₄Cl. The aqueous layer was extracted with ethyl acetate. Then the combined organic layer was washed with aqueous LiCl (2×), and brine, then dried (over Na₂SO₄), filtered and concentrated in vacuo. The desired product A22 crashed out of solution during concentration to yield 500 mg of solid. The mother liquor was purified by chromatography on silica gel (1/4—ethyl acetate/hexane) to afford additional desired product A22 (300 mg, total 800 mg; 71%): 400 ¹H NMR (CDCl₃) 8.30 (s, 1H), 7.44 (m, 2H), 7.32 (m, 3H), 7.17 (m, 2H), 6.95 (m, 2H), 5.66 (s, 2H), 4.7 (m, 1H), 4.32 (q, J=7.2 Hz, 2H), 4.21 (m, 1H), 4.02 (m, 4H), 3.75 (m, 2H), 1.6 (m, 7H), 1.27 (t, J=6.8 Hz, 3H), 1.05 (m, 18H); MS [M+H]=661.

Step 4

To a solution of intermediate A22 (800 mg, 1.21 mmol) in THF (12 mL) and water (4 mL), was added Trifluoroacetic acid (1 mL). The reaction was stirred at 50° C. overnight. Upon completion, the reaction was diluted with ethyl acetate and 10% sodium citrate solution. The aqueous layer was extracted with ethyl acetate. Then the combined organic layer was washed with brine (2×), then dried (over Na₂SO₄), filtered and concentrated in vacuo. The solid was triturated in hexanes to afford desired product A23 (600 mg, quant): 300 ¹H NMR (CDCl₃) 8.35 (s, 1H), 7.47 (m, 2H), 7.36 (m, 3H), 7.20 (m, 2H), 7.01 (m, 2H), 5.71 (s, 2H), 4.7 (m, 1H), 4.35 (q, J=7.2 Hz, 2H), 4.28 (m, 1H), 4.07 (s, 2H), 3.95 (m, 2H), 3.75 (m, 1H), 1.30 (t, J=6.9 Hz, 3H); MS [M+H]=505.

Step 5

To a solution of intermediate A23 (300 mg, 0.595 mmol) dissolved in EtOH:EtOAc (6 mL:6 mL) was added Palladium (10 wt % on carbon) [Pd/C] (60 mg). The reaction was run under hydrogen gas (using a balloon), purging several times with vacuum, at room temperature for 2 hours. At which point the reaction was degassed, and filtered to remove Palladium (DMF was used to completely solubilize the desired product), and concentrated in vacuo to afford the desired product A24 (250 mg): 300 ¹H NMR (CDCl₃) 8.33 (s, 1H), 7.32 (m, 2H), 7.07 (m, 2H), 4.41 (m, 1H), 4.3 (m, 1H), 4.20 (q, J=7.2 Hz, 2H), 4.03 (dd, J=3.2 Hz, Jb=14.4 Hz, 2H), 3.70 (m, 2H), 3.57 (m, 1H), 1.22 (t, J=7.2 Hz, 3H); MS [M+H]=415.

Step 6

To a solution of intermediate A24 (50 mg) in DMF (1.5 mL) was added methylamine (0.300 mL, 2M THF solution). The reaction was heated at 120° C. for 15 minutes. Upon completion, the reaction was quenched with TFA (0.050 mL) then purified directly by reversed phase HPLC [Phenomenex Gemini Axia packed column] (eluting with 0.1% TFA) to afford the desired product A25 (26 mg, 60%) as the TFA salt: 400 ¹H NMR (DMSO) 10.05 (m, 1H), 8.41 (s, 1H), 7.3 (m, 2H), 7.07 (m, 2H), 4.5 (m, 1H), 4.34 (m, 1H), 4.015 (dd, J=2.8 Hz, Jb=14.4 Hz, 2H), 3.71 (m, 2H), 3.64 (m, 1H), 2.88 (d, J=4.8 Hz, 3H); 400 ¹⁹F NMR (DMSO) −74.215, −116.79; MS [M+H]=400.

EXAMPLE 39

Preparation of Compound A26

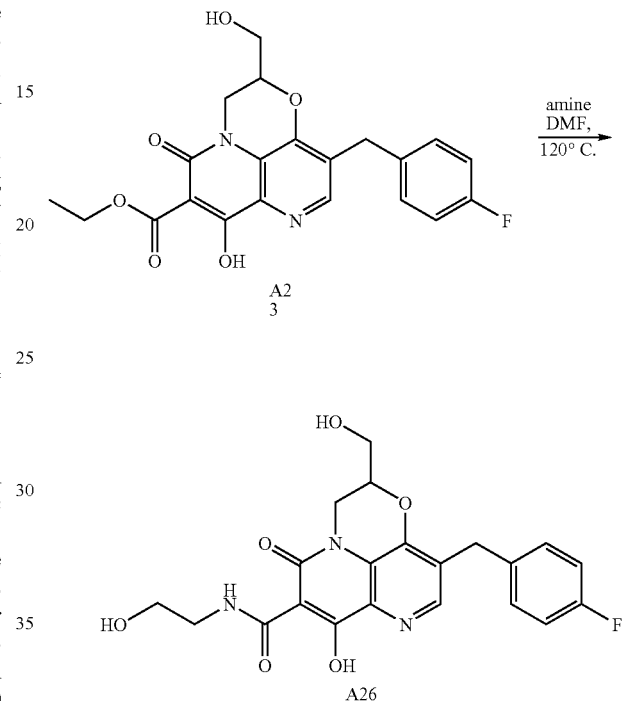

The compound was made in a similar fashion as compound A25 to afford the desired product A26 (28 mg, 60%) as the TFA salt: 400 ¹H NMR (DMSO) 10.3 (m 1H), 8.38 (s, 1H), 7.3 (m, 2H), 7.04 (m, 2H), 4.45 (m, 1H), 4.34 (m, 1H), 3.99 (dd, J=3.2 Hz, Jb=14.4 Hz, 2H), 3.70-3.5 (m, 7H); 400 ¹⁹F NMR (DMSO) −74.26, −116.78; MS [M+H]=430.

EXAMPLE 40

Preparation of Compound A27

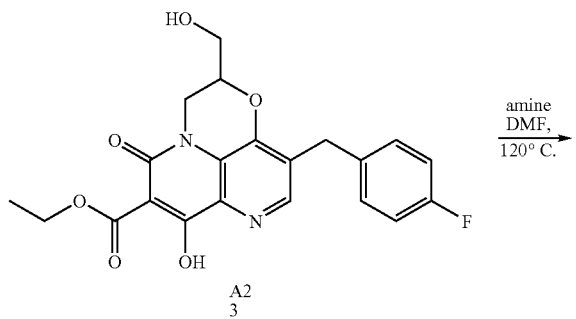

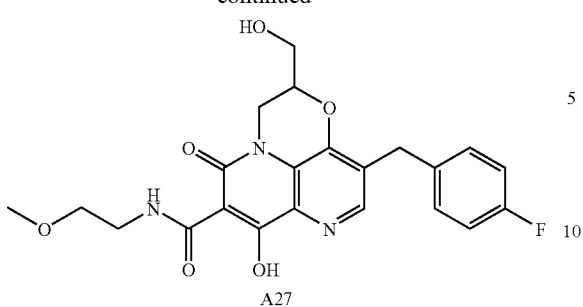

A27

The compound was made in a similar fashion as compound A25 to afford the desired product A27 (55 mg, from 70 mg of SM) as the TFA salt: 400 ¹H NMR (DMSO) 10.3 (m, 1H), 8.41 (s, 1H), 7.3 (m, 2H), 7.07 (m, 2H), 4.49 (m, 1H), 4.35 (m, 1H), 4.02 (dd, J=3.2 Hz, Jb=14.4 Hz, 2H), 3.80-3.4 (m, 7H), 3.26 (s, 3H); 400 ¹⁹F NMR (DMSO) −74.51, −116.77; MS [M+H]=444.

EXAMPLE 41

Preparation of Compound A28

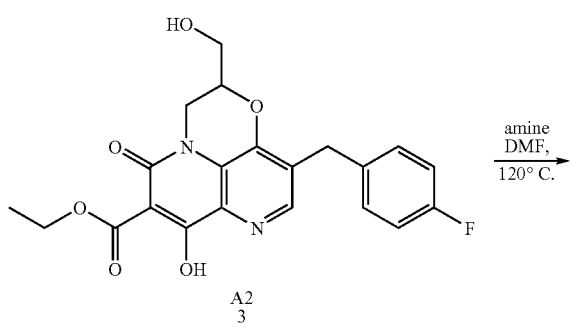

A23

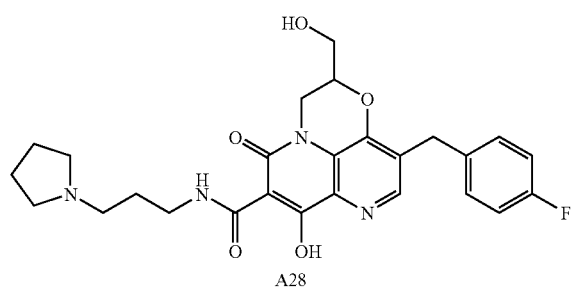

A28

The compound was made in a similar fashion as compound A25 to afford the desired product A28 (41 mg, from 70 mg of SM) as the TFA salt: 400 ¹H NMR (DMSO) 10.25 (m, 1H), 9.4 (m, 1H), 8.42 (s, 1H), 7.3 (m, 2H), 7.082 (t, 2H), 4.48 (m, 1H), 4.36 (m, 1H), 4.02 (dd, J=2.4 Hz, Jb=14.8 Hz, 2H), 3.73 (m, 2H), 3.66 (m, 1H), 3.52 (m, 2H), 3.45 (m, 2H), 3.15 (m, 2H), 2.97 (m, 2H), 1.98 (m, 2H), 1.91 (m, 2H), 1.81 (m, 2H); 400 ¹⁹F NMR (DMSO) −74.02, −116.75; MS [M+H]=497.

EXAMPLE 42

Preparation of Compound A31

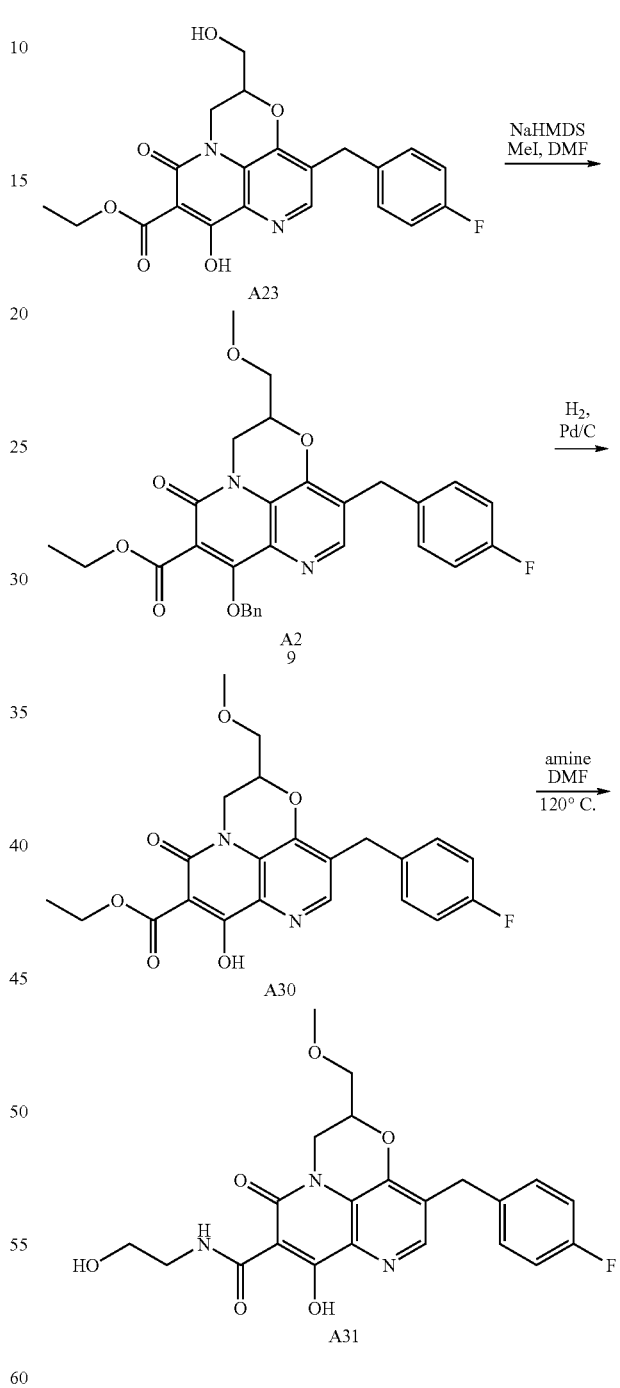

Step 1

To a solution of intermediate A23 (75 mg, 0.149 mmol) in DMF (1.5 mL), cooled to 0° C. was added Sodium bis(trimethylsilyl)amide (NaHMDS) (0.156 mL, 0.156 mmol, 1M THF) dropwise then Iodomethane (0.010 mL, 0.156 mmol). The reaction was stirred for an additional 30 minutes. The reaction was immediately diluted with ethyl acetate and saturated NH₄Cl. The aqueous layer was extracted with ethyl acetate. Then the combined organic layer was washed with aqueous LiCl (2×), and brine, then dried (over Na₂SO₄), filtered and concentrated in vacuo. The crude residue was purified by chromatography on silica gel (3/2—ethyl acetate/hexane) to afford the desired product A29 (22 mg, 29%): 400 ¹H NMR (CDCl₃) 8.30 (s, 1H), 7.44 (m, 2H), 7.33 (m, 3H), 7.19 (m, 2H), 6.97 (m, 2H), 5.67 (s, 2H), 4.65 (m, 1H), 4.33 (m, 3H), 4.03 (s, 2H), 3.7 (m, 3H), 3.75 (m, 1H), 3.42 (s, 2H), 1.27 (t, J=7.2 Hz, 3H); MS [M+H]=519.

Step 2

The compound was made in a similar fashion as compound A24 to afford the desired product A30 (40 mg, from 44 mg of SM): 400 ¹H NMR (CD₃OD) 8.36 (s, 1H), 7.31 (m, 2H), 7.08 (m, 2H), 4.53 (m, 1H), 4.38 (m, 1H), 4.19 (q, J=7.2 Hz, 2H), 4.00 (s, 2H), 3.66 (d, J=4.8 Hz, 2H), 3.56 (m, 1H), 3.29 (s, 2H), 1.2 (t, 3H); MS [M+H]=429.

Step 3

The compound was made in a similar fashion as compound A25 to afford the desired product A31 (25 mg, from 40 mg of SM) as the TFA salt: 400 ¹H NMR (DMSO) 10.3 (m, 1H), 8.43 (s, 1H), 7.3 (m, 2H), 7.08 (m, 2H), 4.57 (m, 1H), 4.44 (m, 1H), 4.00 (s, 2H), 3.8-3.4 (m, 7H), 3.31 (s, 3H); 400 ¹⁹F NMR (DMSO) −76.37, −118.74; MS [M+H]=444.29.

EXAMPLE 43

Preparation of Compound A34

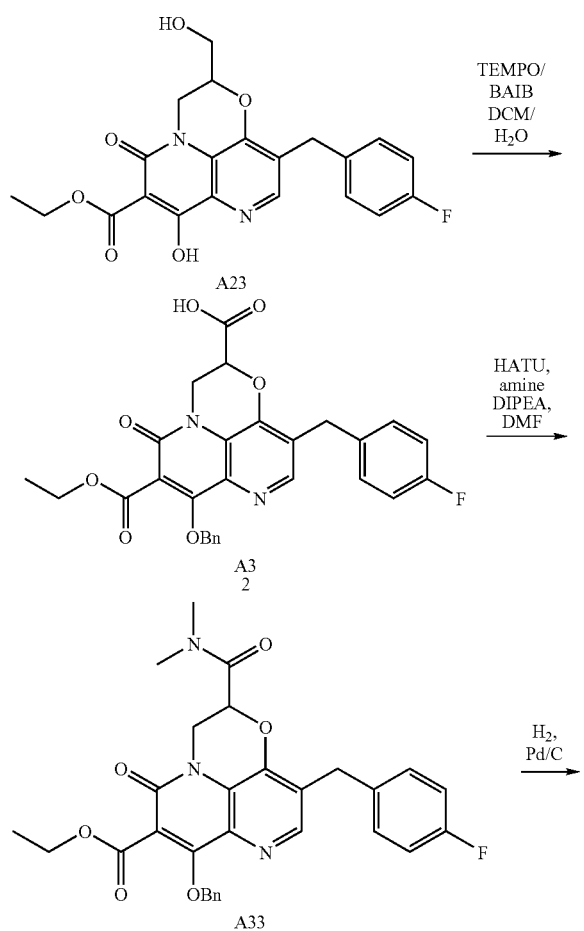

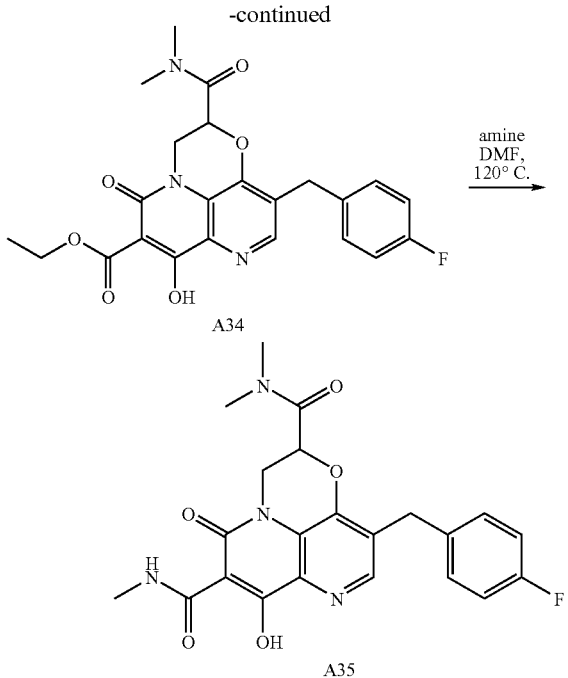

Step 1

To a solution of intermediate A23 (447 mg, 0.887 mmol) in DCM (3 mL) and water (1.5 mL), was added 2,2,6,6-Tetramethylpiperidine-1-oxyl or TEMPO (28 mg, 0.177 mmol) and [bis(acetoxy)]iodobenzene (0.571 mg, 1.77 mmol). The reaction was stirred at room temperature overnight. Upon completion, methanol (5 mL) was added to the reaction before being concentrated in vacuo. The crude residue was triturated with DCM. Desired product A32 (200 mg) was filtered off as a solid. The mother liquor was diluted with ethyl acetate and a buffered citrate solution (pH=5). The organic layer was washed with brine, then dried (over Na₂SO₄), filtered and concentrated in vacuo to afford an additional, but impure, batch of desired product A32 (200 mg, crude): 400 ¹H NMR (DMSO) 8.40 (s, 1H), 7.4-7.3 (m, 7H), 7.07 (m, 2H), 5.58 (dd, Ja=15.2 Hz, Jb=11.2 Hz, 2H), 5.34 (bs, 1H), 4.52 (m, 1H), 4.14 (q, J=6.8 Hz, 1H), 4.07 (m, 1H), 4.04 (s, 2H), 1.13 (t, J=6.8 Hz, 3H); MS [M+H]=519.

Step 2

A solution of an impure batch of carboxylic acid A32 (200 mg, 0.386 mmol) in DMF (3 mL) that had been stirred with HATU (220 mg, 0.579 mmol) was treated with Dimethylamine (1.0 mL, 1.93 mmol, 2M THF solution). The reaction mixture was stirred for 1 hour at room temperature, under nitrogen atmosphere. The reaction was proceeding very slowly. So, an additional portion of HATU (220 mg), Dimethylamine (1.0 mL) and N,N-Diiisopropylethylamine (200 mL) was added. The reaction was stirred at room temperature and was monitored to completion (1 hour). At which point, the reaction was diluted with ethyl acetate and quenched with saturated NH₄Cl. The organic layer was washed with aqueous LiCl, and brine, then dried (NaSO₄), filtered and concentrated. The residue was purified by chromatography on silica gel ((3/2—ethyl acetate/hexane) to afford the desired product A33 (38.9 mg, quant): 400 ¹H NMR (CDCl₃) 8.28 (s, 1H), 7.44 (m, 2H), 7.33 (m, 3H), 7.14 (m, 2H), 6.97 (m, 2H), 5.67 (dd, Ja=29.2 Hz, Jb=11.2 Hz, 2H), 5.07 (m, 4H), 4.55 (m, 3H), 4.32 (q, J=7.2 Hz, 2H), 4.23 (m, 1H), 4.06 (s, 2H), 3.0 (s, 3H), 2.98 (s, 3H), 1.27 (t, J=7.2 Hz, 3H); MS [M+H]=546.

Step 3

The compound was made in a similar fashion as compound A24 to afford the desired product A34 (40 mg, from 44 mg of SM): 400 $^1$H NMR (DMSO) 8.27 (s, 1H), 7.24 (m, 2H), 6.99 (m, 2H), 5.62 (m, 1H), 4.40 (q, J=6.8 Hz, 2H), 4.35 (m, 2H), 4.12 (dd, Ja=4.8 Hz, 2H), 3.09 (s, 3H), 2.90 (s, 3H), 1.37 (t, J=7.2 Hz, 3H); MS [M+H]=456.

Step 4

The compound was made in a similar fashion as compound A25 to afford the desired product A35 (15 mg, from 35 mg of SM): 400 $^1$H NMR (DMSO) 10.02 (m, 1H), 8.38 (s, 1H), 7.24 (m, 2H), 7.08 (m, 2H), 5.72 (s, 2H), 5.59 (m, 1H), 4.2 (m, 2H), 4.04 (s, 2H), 3.0 (s, 3H), 2.89 (d, 3H), 2.79 (s, 3H); 400 $^{19}$F NMR (DMSO) −116.74; MS [M+H]=441.

EXAMPLE 44

Preparation of Compound A50

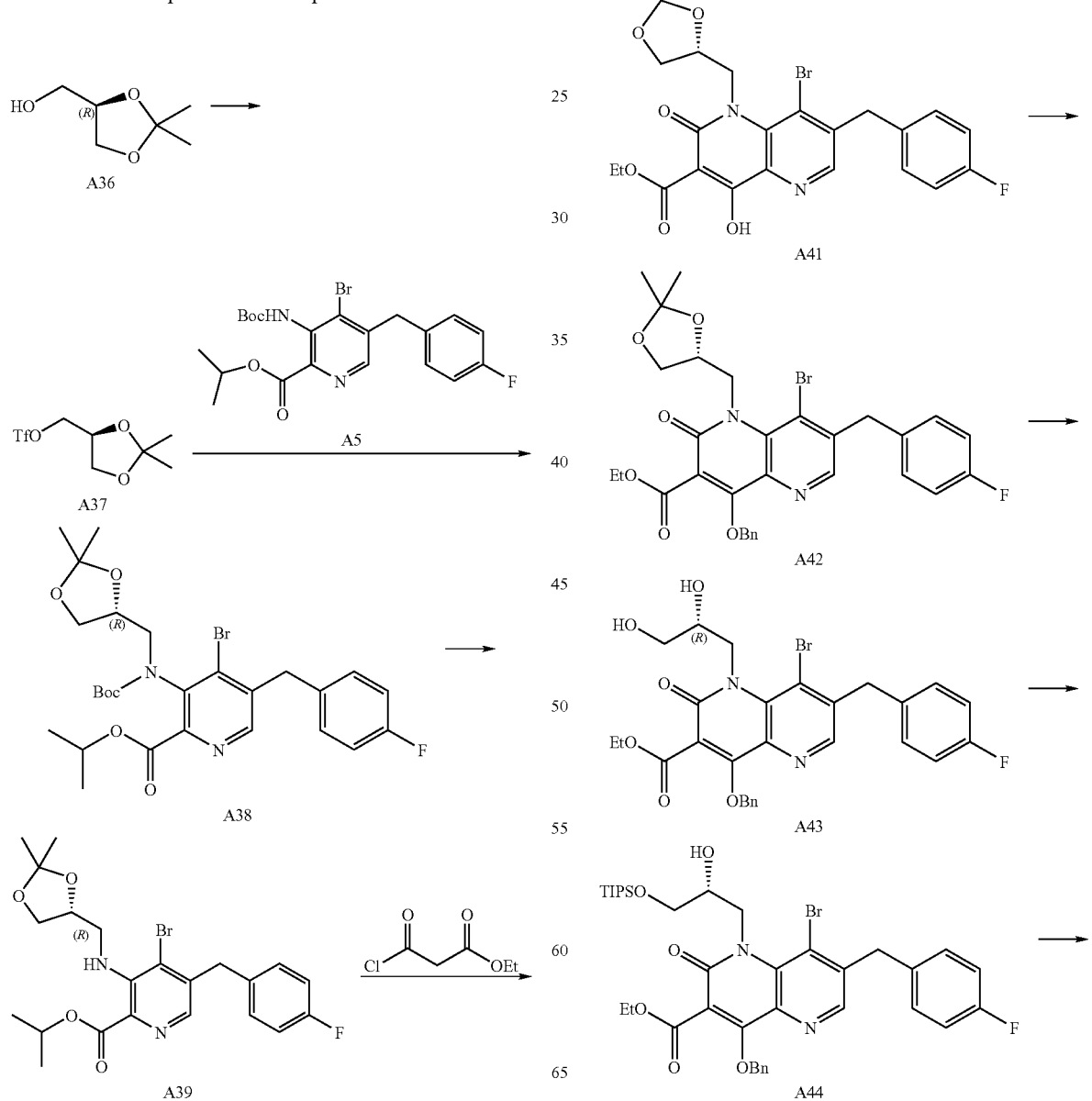

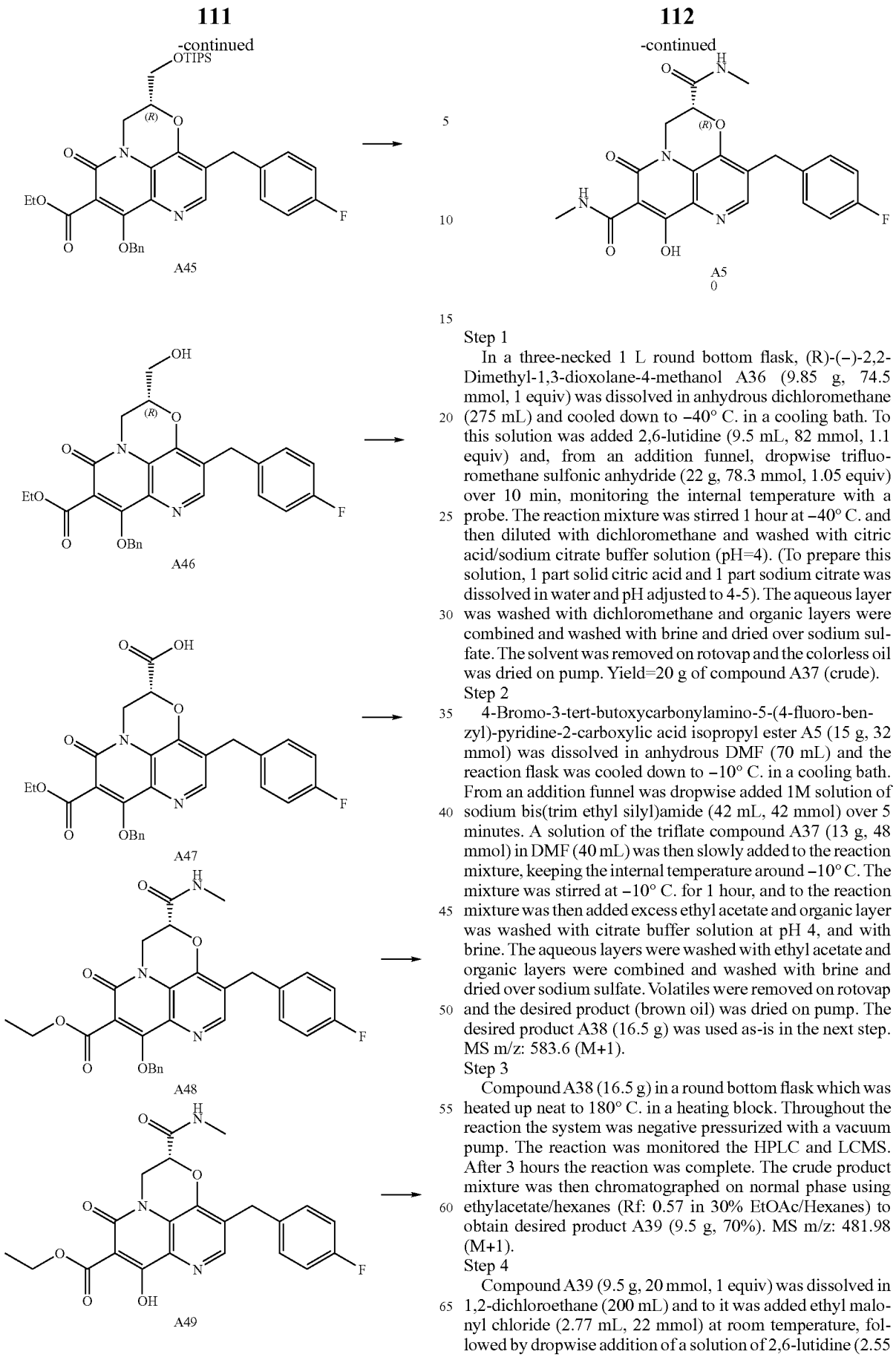

Step 1

In a three-necked 1 L round bottom flask, (R)-(−)-2,2-Dimethyl-1,3-dioxolane-4-methanol A36 (9.85 g, 74.5 mmol, 1 equiv) was dissolved in anhydrous dichloromethane (275 mL) and cooled down to −40° C. in a cooling bath. To this solution was added 2,6-lutidine (9.5 mL, 82 mmol, 1.1 equiv) and, from an addition funnel, dropwise trifluoromethane sulfonic anhydride (22 g, 78.3 mmol, 1.05 equiv) over 10 min, monitoring the internal temperature with a probe. The reaction mixture was stirred 1 hour at −40° C. and then diluted with dichloromethane and washed with citric acid/sodium citrate buffer solution (pH=4). (To prepare this solution, 1 part solid citric acid and 1 part sodium citrate was dissolved in water and pH adjusted to 4-5). The aqueous layer was washed with dichloromethane and organic layers were combined and washed with brine and dried over sodium sulfate. The solvent was removed on rotovap and the colorless oil was dried on pump. Yield=20 g of compound A37 (crude).

Step 2

4-Bromo-3-tert-butoxycarbonylamino-5-(4-fluoro-benzyl)-pyridine-2-carboxylic acid isopropyl ester A5 (15 g, 32 mmol) was dissolved in anhydrous DMF (70 mL) and the reaction flask was cooled down to −10° C. in a cooling bath. From an addition funnel was dropwise added 1M solution of sodium bis(trim ethyl silyl)amide (42 mL, 42 mmol) over 5 minutes. A solution of the triflate compound A37 (13 g, 48 mmol) in DMF (40 mL) was then slowly added to the reaction mixture, keeping the internal temperature around −10° C. The mixture was stirred at −10° C. for 1 hour, and to the reaction mixture was then added excess ethyl acetate and organic layer was washed with citrate buffer solution at pH 4, and with brine. The aqueous layers were washed with ethyl acetate and organic layers were combined and washed with brine and dried over sodium sulfate. Volatiles were removed on rotovap and the desired product (brown oil) was dried on pump. The desired product A38 (16.5 g) was used as-is in the next step. MS m/z: 583.6 (M+1).

Step 3

Compound A38 (16.5 g) in a round bottom flask which was heated up neat to 180° C. in a heating block. Throughout the reaction the system was negative pressurized with a vacuum pump. The reaction was monitored the HPLC and LCMS. After 3 hours the reaction was complete. The crude product mixture was then chromatographed on normal phase using ethylacetate/hexanes (Rf: 0.57 in 30% EtOAc/Hexanes) to obtain desired product A39 (9.5 g, 70%). MS m/z: 481.98 (M+1).

Step 4

Compound A39 (9.5 g, 20 mmol, 1 equiv) was dissolved in 1,2-dichloroethane (200 mL) and to it was added ethyl malonyl chloride (2.77 mL, 22 mmol) at room temperature, followed by dropwise addition of a solution of 2,6-lutidine (2.55 mL, 22 mmol) in 1,2-dichloroethane over 10 min. The mixture was stirred about 1 hour at room temperature. LCMS confirmed the completion of the reaction. The reaction content was diluted with dichloromethane and washed with the Citric acid buffer solution at pH 4, and with brine. The organic layers were combined and dried over sodium sulfate and concentrated down on rotovap and further dried on pump. The crude residue was then purified on a normal phase column (from 30% EtOAc/Hexanes to 65% EtOAc/Hexane in 1 hour). Purified Yield=10 g of compound A40 (85%). MS m/z: 596.26 (M+1).

Step 5

Compound A40 (10 g, 16.8 mmol) was taken up in ethanol (160 mL) and to it was added 21% sodium ethoxide in ethanol (8 mL, 20.2 mmol). The mixture was stirred at room temperature for 1 hour. LCMS indicated a complete reaction. The ethanol was removed on rotovap and the residue was taken up in ethyl acetate and washed with citric acid solution buffered with sodium citrate at pH 4, twice. The organic layer was then washed with brine. The aqueous layers were combined and extracted with more ethyl acetate and the organic layers were combined and dried over sodium sulfate, and concentrated down on rotovap. The resulting residue was then further dried on pump. Yield=8 g of compound A41 (crude). The desired product was not attempted to purify and used as-is in the next step. MS m/z: 536.68 (M+1).

Step 6

Compound A41 (7.5 g, 12 mmol) was dissolved in anhydrous dichloromethane and silver(I) oxide (5.57 g, 24 mmol) was added. The mixture was stirred for 20 minutes at room temperature. A solution of benzyl bromide (1.57 mL, 13.2 mmol,) in dichloromethane was dropwise added over 5 min and the reaction mixture was stirred overnight at room temperature. In the beginning of the reaction, some of the benzyl group will react with the 2-C carbonyl oxygen to give the unwanted regioisomer in addition to the 4C oxygen isomer, which is the desired isomer. Overnight reaction at room temperature will equilibrate the reaction towards the thermodynamic desired regioisomer as almost at a hundred percent rate. After overnight reaction the LCMS showed a complete conversion with single isomer. The wrong isomer was less than 2%. The crude mixture was then passed through a Celite plug and the filtrate was concentrated down on rotovap and taken up in ethyl acetate. The organic layer was then washed with brine a couple of times and dried over sodium sulfate. The volatiles were then removed and the residue was purified on normal phase column. (Rf=0.22 in 30% EtOAc/Hexanes). Purified Yield=7.8 g of compound A42 (90%). MS m/z: 626.73 (M+1).

Step 7

Compound A42 (6.5 g, 10.4 mmol, 1 equiv) was treated with 60% acetic acid in water (260 mL), overnight at room temperature. After overnight reaction the HPLC data showed 96% completion. The reaction content was then slightly warmed to 45° C. in an oil bath and stirred for 3 more hours. HPLC then indicated a complete reaction. The crude reaction mixture was then reduced on rotovap as much as possible and then transferred into a separatory funnel and washed (1V:1V) mixture of (brine:water) to remove most of excess acetic acid. Then the aqueous layer was checked by HPLC to make sure product did not escape there. The organic layer was then washed with sodium bicarbonate adjusting the pH to 8. Basic aqueous layer was extracted with ethyl acetate and the organic layers were combined and washed with brine and dried over sodium sulfate. Yield=5.4 g of compound A43 (90%). $^1$H NMR (300 MHz, CDCl$_3$) 8.34 (s, 1H), 7.45 (m, 2H), 7.36 (m, 3H), 7.12 (m, 2H), 7.0 (m, 2H), 5.59 (dd, Ja=7.6 Hz, Jb=10.8 Hz, 2H), 4.5 (m, 2H), 4.3 (m, 2H), 3.70 (m, 2H), 1.28 (t, J=6.8 Hz, 3H); MS m/z: 586.84 (M+1).

Step 8

Compound A43 (5.4 g, 9.2 mmol) was dissolved in anhydrous dichloromethane (92 mL). To this solution was added triisopropyl silyl chloride (3.9 mL, 18.4 mmol, 2 equiv) and imidazole (1.25 g, 18.4 mmol), followed by DMAP (112 mg, 0.92 mmol). The mixture was stirred overnight at room temperature. After overnight reaction the HPLC showed the reaction went to completion. The volatiles were removed on rotovap and the residue was taken up in ethyl acetate and washed with citric acid solution buffered with sodium citrate at pH 4, once, and the aqueous layer was extracted with ethyl acetate. The combined organic layers were washed with brine and dried over sodium sulfate. The volatiles were removed and the residue dried on pump. The crude material was then purified on normal phase column with ethyl acetate/hexanes. (30% EtOAc/Hexanes, Rf=0.46). Purified Yield=4.4 g of compound A44 (65%). $^1$H NMR ((400 MHz, CDCl$_3$) 8.32 (s, 1H), 7.46 (m, 2H), 7.36 (m, 3H), 7.15 (m, 2H), 7.02 (m, 2H), 5.58 (s, 2H), 4.84 (m, 2H), 4.35 (q, J=7.8 Hz, 2H), 4.26 (s, 2H), 4.13 (m, 1H), 3.74 (m, 2H), 1.57 (m, 3H), 1.30 (t, J=7.2 Hz, 3H), 1.05 (s, 18H); MS m/z: 741.21 (M+1).

Step 9

Compound A44 (4 g, 5.4 mmol) was dissolved in anhydrous N,N-dimethylformamide (100 mL) and cooled down to −40° C. in a cooling bath. 1M Solution of sodium bis(trimethyl silyl)amide (5.9 mL, 5.9 mmol) was then dropwise added. The reaction was maintained at −40° C. for about 15 min and confirmed by LCMS to be complete. In addition to the desired product peak, LCMS also showed a smaller peak with the same molecular weight as the desired product. This byproduct peak might be the corresponding 7-member cyclized byproduct. This byproduct was easily separated from the desired product by normal phase column chromatography. Yield=350 mg (10%)]

The crude mixture was diluted with ethyl acetate and washed with citric acid solution buffered with sodium citrate at pH 4, once, and the aqueous layer was extracted with ethyl acetate. The combined organic layers were washed with brine and dried over sodium sulfate. The crude product was then purified on normal phase column (30% EtOAc/Hexanes, Rf=0.4). Purified Yield=2.16 g of compound A45 (61%). $^1$H NMR (400 MHz, CDCl$_3$) 8.30 (s, 1H), 7.44 (m, 2H), 7.32 (m, 3H), 7.17 (m, 2H), 6.95 (m, 2H), 5.66 (s, 2H), 4.7 (m, 1H), 4.32 (q, J=7.2 Hz, 2H), 4.21 (m, 1H), 4.02 (m, 4H), 3.75 (m, 2H), 1.6 (m, 7H), 1.27 (t, J=6.8 Hz, 3H), 1.05 (m, 18H); MS m/z: 661.35 (M+1).

Step 10

Compound A45 (2 g, 3 mmol) was dissolved in THF/DI-water (1 v:1 v, 12 mL, 12 mL) and to it was added trifluoroacetic acid (4 mL). The mixture was stirred overnight at room temperature. LCMS showed a complete reaction. HPLC showed spot-to-spot conversion. Excess TFA and THF was reduced on rotovap as much as possible and the remaining slurry was extracted into ethyl acetate and the aqueous layers was extracted with ethylacetate until no desired peak was detected on HPLC of aqueous layer. The organic layers were combined and washed with saturated solution of sodium bicarbonate twice and with brine one time. The organic layer was then dried over sodium sulfate and further dried on pump. Yield=1.3 g of compound A46 (86%). $^1$H NMR (300 MHz, CDCl$_3$) 8.35 (s, 1H), 7.47 (m, 2H), 7.36 (m, 3H), 7.20 (m, 2H), 7.01 (m, 2H), 5.71 (s, 2H), 4.7 (m, 1H), 4.35 (q, J=7.2 Hz, 2H), 4.28 (m, 1H), 4.07 (s, 2H), 3.95 (m, 2H), 3.75 (m, 1H), 1.30 (t, J=6.9 Hz, 3H); MS m/z: 505.19 (M+1).

Step 11

To a solution of intermediate A46 (1.3 g, 2.6 mmol) in 1,2-dichloroethane (13 mL) and water (5 mL), was added iodobenzene diacetate (1.7 g, 5.2 mmo) and 2,2,6,6-tetramethylpiperidine-1-oxyl or TEMPO (81 mg, 0.52 mmol). The reaction was stirred at room temperature overnight. Upon completion, methanol (50 mL) was added to the reaction before being concentrated in vacuo. The crude residue was then trituration with EtOAc and Hexane. After filtration to give the white solid product A47 (1.1 g, 83%). $^1$H NMR (400 MHz, DMSO-D6) δ 8.40 (s, 1H), 7.4-7.3 (m, 7H), 7.07 (m, 2H), 5.58 (dd, Ja=15.2 Hz, Jb=11.2 Hz, 2H), 5.34 (bs, 1H), 4.52 (m, 1H), 4.14 (q, J=6.8 Hz, 1H), 4.07 (m, 1H), 4.04 (s, 2H), 1.13 (t, J=6.8 Hz, 3H); MS m/z: 519.16 (M+1).

Step 12

To a solution of an impure batch of carboxylic acid A47 (800 mg, 1.54 mmol) in DMF (15 mL) that had been stirred with HATU (1.1 g, 3 mmol) was treated with Methylamine (1.5 mL, 3 mmol, 2M THF solution) and N,N-Diiisopropylethylamine (1 mL, 6 mmol). The reaction mixture was stirred for 1 hour at room temperature, under nitrogen atmosphere. At which point, the reaction was diluted with ethyl acetate and quenched with saturated NH$_4$Cl. The organic layer was washed with brine, then dried (NaSO$_4$), filtered and concentrated. The residue was purified by chromatography on silica gel ((9/1—DCM/MeOH) to afford the desired product A48 (664 mg, 81%): 400 MHz $^1$H NMR (CDCl$_3$) 8.39 (s, 1H), 7.44 (m, 2H), 7.34 (m, 3H), 7.20 (m, 2H), 7.03 (m, 2H), 5.67 (d, 2H), 4.74 (m, 2H), 4.32 (q, J=7.2 Hz, 2H), 4.09 (s, 2H), 3.92 (m, 1H), 2.70 (d, 3H), 1.28 (t, J=7.2 Hz, 3H); MS [M+H]=532.

Step 13

To a solution of intermediate A48 (664 mg, 1.25 mmol) dissolved in EtOH:EtOAc (18 mL:9 mL) was added Palladium (10 wt % on carbon) [Pd/C] (100 mg). The reaction was run under hydrogen gas (using a balloon), purging several times with vacuum, at room temperature for 2 hours. At which point the reaction was degassed, and filtered to remove Palladium (MeOH was used to completely solubilize the desired product), and concentrated in vacuo to afford the desired product A49 (523 mg, 95%); 400 MHz $^1$H NMR (CD$_3$OD) 8.18 (s, 1H), 7.21 (m, 2H), 6.94 (m, 2H), 4.91 (m, 1H), 4.50 (m, 1H), 4.32 (q, J=7.2 Hz, 2H), 4.11 (m, 2H), 3.92 (m, 1H), 2.70 (s, 3H), 1.27 (t, J=7.2 Hz, 3H); MS [M+H]=442

Step 14

To a solution of intermediate A49 (300 mg, 0.68 mmol) in DMF 6.8 mL) was added Methylamine (2 m, 4 mmol). The reaction was heated in a microwave reactor at 125° C. for 20 minutes. Upon completion, after trituration to afford the desired product A50 (218 mg, 75%): 400 MHz $^1$H NMR (DMSO) 10.05 (m, 1H), 8.29 (s, 1H), 8.11 (m, 1H), 7.31 (m, 2H), 7.08 (m, 2H), 5.02 (m, 1H), 4.42 (m, 1H), 4.19-4.05 (m, 1H), 3.98 (m, 2H), 2.83 (d, 3H), 2.62 (d, 3H); MS[M+H]=427

Chiral HPLC: Chiralcel OD-H, MeOH/EtOH=50/50, Retention time: 26.7 min.

EXAMPLE 45

Preparation of Compound A65

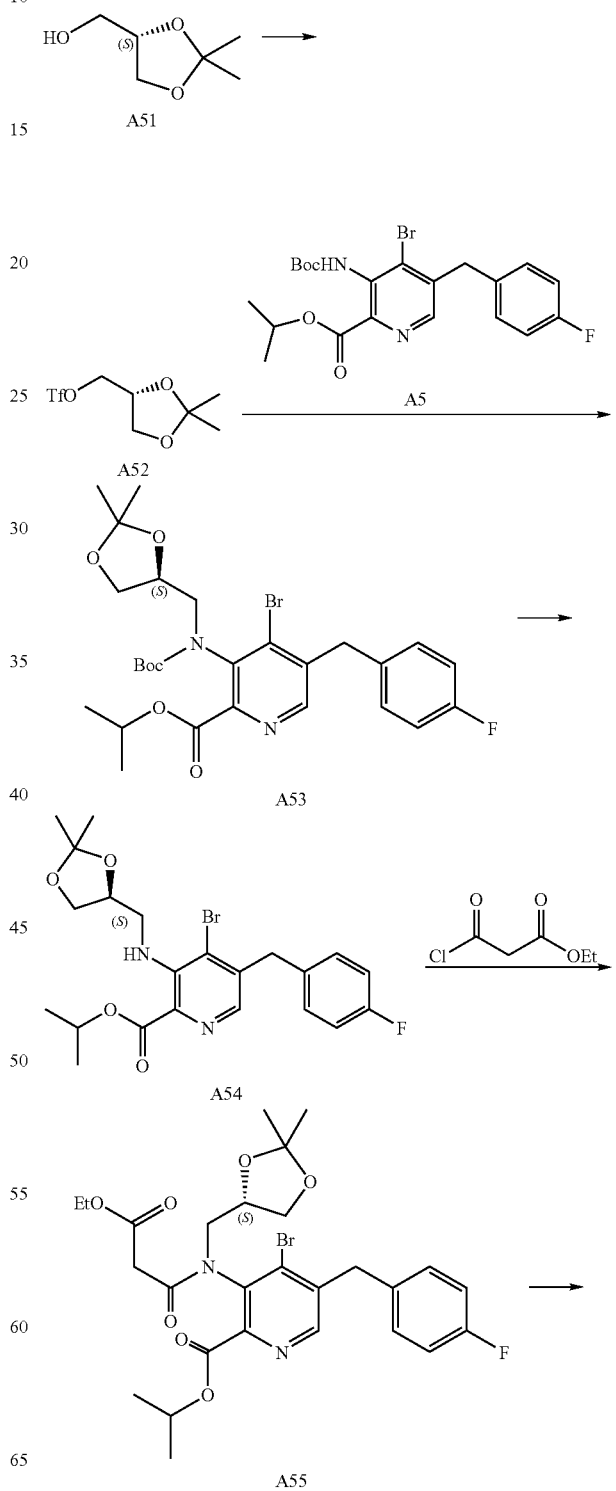

-continued
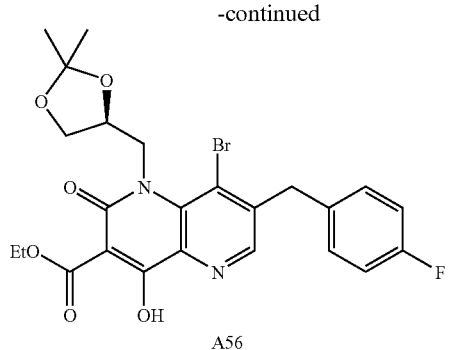
A56
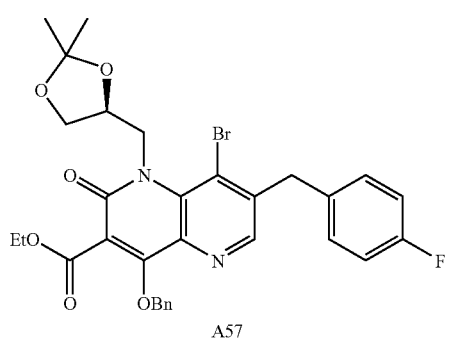
A57
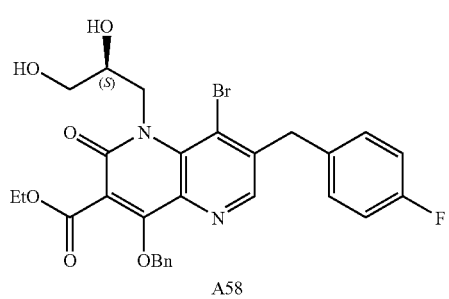
A58
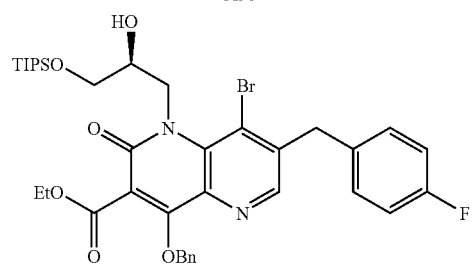
A59
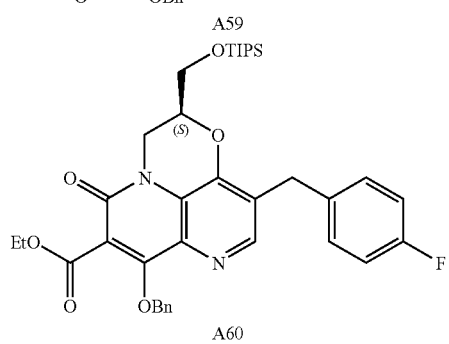
A60
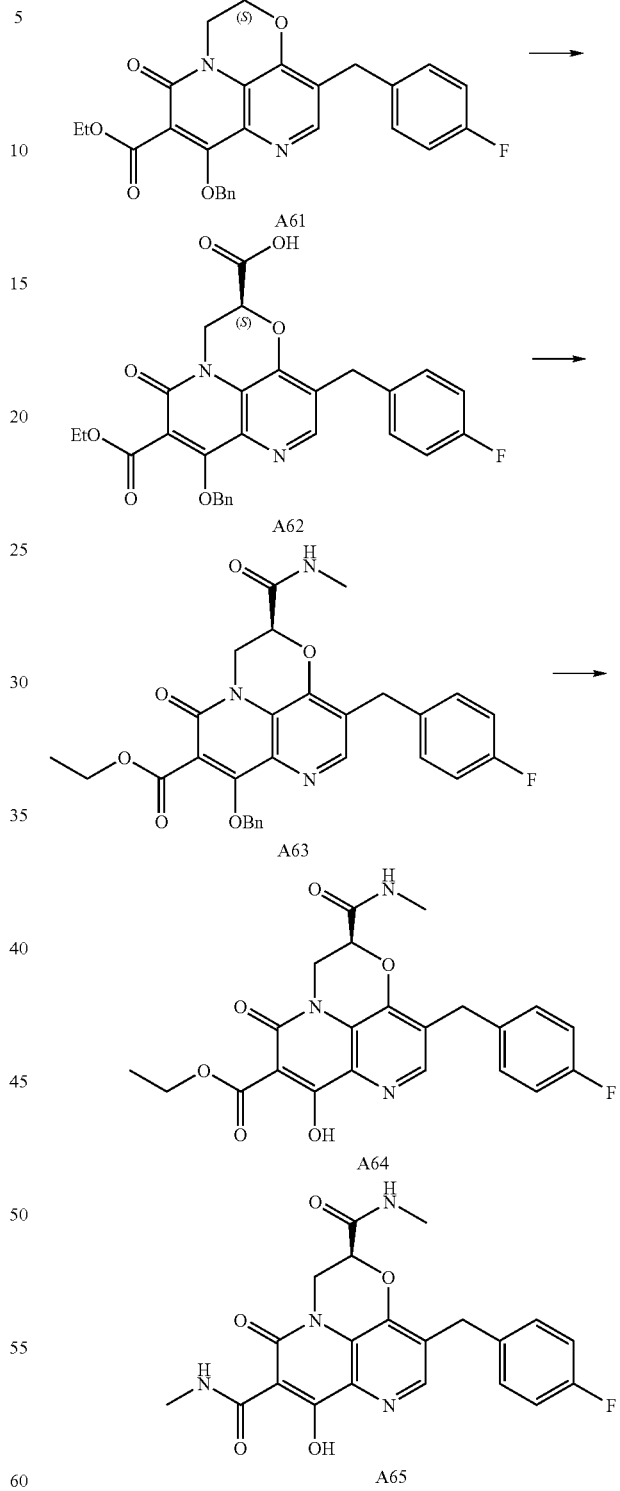
Step 1
In a three-necked 1 L round bottom flask, (S)-(+)-1,2-isoploplidene glycerol A51 (10 g, 75.7 mmol, 1 equiv) was dissolved in anhydrous dichloromethane (250 mL, 0.3M) and cooled down to −40° C. in a cooling bath. To this solution was added 2,6-lutidine (8.93 g, 9.7 mL, 83.3 mmol, 1.1 equiv) and, from an addition funnel, dropwise trifluoromethane sulfonic anhydride (22.5 g, 13.4 mL, 79.5 mmol, 1.05 equiv) over 10 min, monitoring the internal temperature with a probe. The reaction mixture was stirred 1 hour at −40° C. and then diluted with dichloromethane and washed with citric acid/sodium citrate buffer solution (pH=4). (Note: To prepare this solution, 1 part solid citric acid and 1 part sodium citrate was dissolved in water and pH adjusted to 4-5). The aqueous layer was washed with dichloromethane and organic layers were combined and washed with brine and dried over sodium sulfate. The solvent was removed on rotovap and the colorless oil was dried on pump. Yield=20.43 g (crude compound A52). $^1$H NMR (400 MHz, CDCl$_3$) δ 4.46-4.42 (m, 2H), 4.39-4.35 (m, 1H), 4.11 (dd, J$_{1,2}$=6.4, 9.2 Hz, 1H), 3.84 (dd, J$_{1,2}$=4.8, 8.8 Hz, 1H), 1.41 (s, 3H), 1.33 (s, 3H).

Step 2

4-Bromo-3-tert-butoxycarbonylamino-5-(4-fluoro-benzyl)-pyridine-2-carboxylic acid isopropyl ester A5 (14.7 g, 31.4 mmol, 1 equiv) was dissolved in anhydrous DMF (66 mL) and the reaction flask was cooled down to −10° C. in a cooling bath. From an addition funnel was dropwise added 1M solution of sodium bis(trimethyl silyl)amide (41.7 mL, 1.3 equiv) over 5 minutes. A solution of the triflate compound A52 (12.7 g, 48.2 mmol, 1.5 equiv) in DMF (40 mL) was then slowly added to the reaction mixture, keeping the internal temperature around −10° C. The mixture was stirred at −10° C. for 1 hour, and to the reaction mixture was then added excess ethyl acetate and organic layer was washed with citrate buffer solution at pH 4, and with brine. The aqueous layers were washed with ethyl acetate and organic layers were combined and washed with brine and dried over sodium sulfate. Volatiles were removed on rotovap and the desired product A53 (brown oil) was dried on pump. The desired product was used as-is in the next step. MS m/z: 583.6 (M+1).

Step 3

Compound A53 (31.4 mmol, 1 equiv) in a round bottom flask which was equipped with a Dean-Stark apparatus and a condenser was heated up neat to 175° C. in a heating block (silicone oil as a heating source might be a better choice to prevent unequal heating). Throughout the reaction the system was negative pressurized with a high vacuum pump at about 500 mbar. The reaction was monitored by amount of liquid collected in Dean Stark apparatus, as well as by observing the gas evolution through the bubbler, in addition to the HPLC and LCMS. After 2 hours the reaction was complete. The crude product mixture was then chromatographed on normal phase using ethylacetate/hexanes (Rf: 0.57 in 30% EtOAc/Hexanes). Purified Yield=5 g (desired product A54, 33%).

Step 4

Compound A54 (5.0 g, 10.39 mmol, 1 equiv) was dissolved in 1,2-dichloroethane and to it was added ethyl malonyl chloride (1.72 g, 1.44 mL, 11.43 mmol, 1.1 equiv) at room temperature, followed by dropwise addition of a solution of 2,6-lutidine (1.67 g, 1.8 mL, 15.6 mmol, 1.5 equiv) in 1,2-dichloroethane over 10 min. the mixture was stirred about 1 hour at room temperature. LCMS confirmed the completion of the reaction. The reaction content was diluted with dichloromethane and washed with the Citric acid buffer solution at pH 4, and with brine. The organic layers were combined and dried over sodium sulfate and concentrated down on rotovap and further dried on pump. The crude residue was then purified on a normal phase column (from 30% EtOAc/Hexanes to 65% EtOAc/Hexane in 1 hour). Purified Yield=5.3 g of compound A55 (86%). MS m/z: 596.26 (M+1).

Step 5

Compound A55 (5.3 g, 8.9 mmol, 1 equiv) was taken up in 200 proof ethanol (90 mL) and, to it was added 21% sodium ethoxide in ethanol (6.65 mL, 17.8 mmol, 2 equiv). The mixture was stirred at room temperature for 1 hour. LCMS indicated a complete reaction. The ethanol was removed on rotovap and the residue was taken up in ethyl acetate and washed with citric acid solution buffered with sodium citrate at pH 4, twice. The organic layer was then washed with brine. The aqueous layers were combined and extracted with more ethyl acetate and the organic layers were combined and dried over sodium sulfate, and concentrated down on rotovap. The resulting residue was then further dried on pump. Yield=4.8 g (crude). The desired product A56 was not attempted to purify and used as-is in the next step. MS m/z: 536.68 (M+1).

Step 6

Compound A56 (4.76 g, 8.9 mmol, 1 equiv) was dissolved in anhydrous dichloromethane and silver (I) oxide (4.1 g, 17.8, 2 equiv) was added. The mixture was stirred for 20 minutes at room temperature. A solution of benzyl bromide (1.67 g, 1.16 mL, 9.79 mmol, 1.1 equiv) in dichloromethane was dropwise added over 5 min and the reaction mixture was stirred overnight at room temperature. In the beginning of the reaction, some of the benzyl group will react with the 2-C carbonyl oxygen to give the unwanted regioisomer in addition to the 4C oxygen isomer, which is the desired isomer. Overnight reaction at room temperature will equilibrate the reaction towards the thermodynamic desired regioisomer as almost at a hundred percent rate. After overnight reaction the LCMS showed a complete conversion with single isomer. The wrong isomer was less than 2%. The crude mixture was then passed through a Celite plug and the filtrate was concentrated down on rotovap and taken up in ethyl acetate. The organic layer was then washed with brine a couple of times and dried over sodium sulfate. The volatiles were then removed and the residue was purified on normal phase column. (Rf=0.22 in 30% EtOAc/Hexanes). Purified Yield=3.76 g of compound A57 (68%). MS m/z: 626.73 (M+3).

Step 7

Compound A57 (3.7 g, 5.9 mmol, 1 equiv) was treated with 60% acetic acid in water, overnight at root temperature. After overnight reaction the HPLC data showed 96% completion. The reaction content was then slightly warmed to 45° C. in an oil bath and stirred for 3 more hours. HPLC then indicated a complete reaction. The crude reaction mixture was then reduced on rotovap as much as possible and then transferred into a separatory funnel and washed (1V:1V) mixture of (brine:water) to remove most of excess acetic acid. Then the aqueous layer was checked by HPLC to make sure product did not escape there. The organic layer was then washed with sodium bicarbonate adjusting the pH to 8. Basic aqueous layer was extracted with ethyl acetate and the organic layers were combined and washed with brine and dried over sodium sulfate. Yield=3.24 g of compound A58 (94%). $^1$H NMR (300 MHz, CDCl$_3$) 8.34 (s, 1H), 7.45 (m, 2H), 7.36 (m, 3H), 7.12 (m, 2H), 7.0 (m, 2H), 5.59 (dd, Ja=7.6 Hz, Jb=10.8 Hz, 2H), 4.5 (m, 2H), 4.3 (m, 2H), 3.70 (m, 2H), 1.28 (t, J=6.8 Hz, 3H); MS m/z: 586.84 (M+1).

Step 8

Compound A58 (3.24 g, 5.53 mmol, 1, equiv) was dissolved in anhydrous dichloromethane (55 mL). To this solution was added triisopropyl silyl chloride (2.13 g, 2.35 ml, 11.07 mmol, 2 equiv) and imidazole (754 mg, 11.07 mmol, 2 equiv), followed by DMAP (68 mg, 0.553 mmol, 0.1 equiv). The mixture was stirred overnight at room temperature. After overnight reaction the HPLC showed 95% completion.

Therefore, 320 mg of TIPSCl and 113 mg of imidazole were added. The mixture was stirred another 3 hours. The reaction went to completion. The volatiles were removed on rotovap and the residue was taken up in ethyl acetate and washed with citric acid solution buffered with sodium citrate at pH 4, once, and the aqueous layer was extracted with ethyl acetate. The combined organic layers were washed with brine and dried over sodium sulfate. The volatiles were removed and the residue dried on pump. The crude material was then purified on normal phase column with ethyl acetate/hexanes. (30% EtOAc/Hexanes, Rf=0.46). Purified Yield=2.66 g of compound A59 (66%). $^1$H NMR ((400 MHz, CDCl$_3$) 8.32 (s, 1H), 7.46 (m, 2H), 7.36 (m, 3H), 7.15 (m, 2H), 7.02 (m, 2H), 5.58 (s, 2H), 4.84 (m, 2H), 4.35 (q, J=7.8 Hz, 2H), 4.26 (s, 2H), 4.13 (m, 1H), 3.74 (m, 2H), 1.57 (m, 3H), 1.30 (t, J=7.2 Hz, 3H), 1.05 (s, 18H); MS m/z: 741.21 (M+1).

Step 9

Compound A59 (2.52 g, 3.4 mmol, 1 equiv) was dissolved in anhydrous N,N-dimethylformamide (34 mL) and cooled down to −40° C. in a cooling bath. 1M Solution of sodium bis(trimethyl silyl)amide (3.57 mL, 3.57 mmol, 1.05 equiv) was then dropwise added. The reaction was maintained at −40° C. for about 15 min and confirmed by LCMS to be complete. The crude mixture was diluted with ethyl acetate and washed with citric acid solution buffered with sodium citrate at pH 4, once, and the aqueous layer was extracted with ethyl acetate. The combined organic layers were washed with brine and dried over sodium sulfate. The crude product was then purified on normal phase column (30% EtOAc/Hexanes, Rf=0.4). Purified Yield=1.68 g of compound A60 (75%). $^1$H NMR (400 MHz, CDCl$_3$) 8.30 (s, 1H), 7.44 (m, 2H), 7.32 (m, 3H), 7.17 (m, 2H), 6.95 (m, 214), 5.66 (s, 2H), 4.7 (m, 1H), 4.32 (q, J=7.2 Hz, 2H), 4.21 (m, 1H), 4.02 (m, 4H), 3.75 (m, 2H), 1.6 (m, 7H), 1.27 (t, J=6.8 Hz, 3H), 1.05 (m, 18H); MS m/z: 661.35 (M+1).

Step 10

Starting material A60 (1.66 g, 2.51 mmol, 1 equiv) was dissolved in THF/DI-water (1 v:1 v, 11.25 mL, 11.25 mL) and to it was added trifluoroacetic acid (3.75 mL). The mixture was stirred overnight at room temperature. LCMS showed a complete reaction. HPLC showed spot-to-spot conversion. Excess TFA and THF was reduced on rotovap as much as possible and the remaining slurry was extracted into ethyl acetate and the aqueous layers was extracted with ethylacetate until no desired peak was detected on HPLC of aqueous layer. The organic layers were combined and washed with saturated solution of sodium bicarbonate twice and with brine one time. The organic layer was then dried over sodium sulfate and further dried on pump. Yield=1.16 g of compound A61 (crude) (92%). $^1$H NMR (300 MHz, CDCl$_3$) 8.35 (s, 1H), 7.47 (m, 2H), 7.36 (m, 3H), 7.20 (m, 2H), 7.01 (m, 2H), 5.71 (s, 2H), 4.7 (m, 1H), 4.35 (q, J=7.2 Hz, 2H), 4.28 (m, 1H), 4.07 (s, 2H), 3.95 (m, 2H), 3.75 (m, 1H), 1.30 (t, J=6.9 Hz, 3H); MS m/z: 505.19 (M+1).

Step 11

Compound A61 (1.16 g, 2.3 mmol, 1 equiv) in 1,2-dichloroethane (16 mL) and water (8 mL), was added iodobenzene diacetate (1.48 g, 4.6 mmol, 2 equiv) and 2,2,6,6-tetramethylpiperidine-1-oxyl or TEMPO (28 mg, 0.177 mmol). The reaction was stirred at room temperature overnight. Upon completion, methanol (50 mL) was added to the reaction before being concentrated in vacuo. The crude residue was then dissolved in DMSO and purified on reverse phase HPLC. Yield=870 mg of compound A62 (73%). $^1$H NMR (400 MHz, DMSO-D6) δ 8.40 (s, 1H), 7.4-7.3 (m, 7H), 7.07 (m, 2H), 5.58 (dd, Ja=15.2 Hz, Jb=11.2 Hz, 2H), 5.34 (bs, 1H), 4.52 (m, 1H), 4.14 (q, J=6.8 Hz, 1H), 4.07 (m, 1H), 4.04 (s, 2H), 1.13 (t, J=6.8 Hz, 3H); MS m/z: 519.16 (M+1).

Step 12

Compound A63 was made from compound A62 in a similar fashion as compound A48 to afford the desired product A63 (20 mg, 67%), 400 MHz $^1$H NMR (CDCl$_3$) 8.42 (s, 1H), 7.47 (m, 2H), 7.37 (m, 3H), 7.20 (m, 2H), 7.05 (m, 2H), 5.69 (d, 2H), 4.74 (m, 2H), 4.34 (q, J=7.2 Hz, 2H), 4.09 (s, 2H), 3.92 (m, 1H), 2.70 (d, 3H), 1.28 (t, J=7.2 Hz, 3H); MS [M+H]=532.

Step 13

Compound A64 was made in a similar fashion as compound A49 to afford the desired product (15 mg, 95%), MS [M+H]=442.

Step 14

Compound A65 was made in a similar fashion as compound A50 to afford the desired product (10.2 mg, 70%), 400 MHz $^1$H NMR (DMSO) 10.0 (m, 1H), 8.36 (s, 1H), 8.16 (m, 1H), 7.31 (m, 2H), 7.09 (m, 2H), 5.07 (m, 1H) 4.43 (m, 2H), 4.21-4.11 (m, 1H), 4.03 (m, 2H), 2.85 (d, 3H), 2.62 (d, 3H); MS[M+H]=427

Chiral HPLC: Chiralcel OD-H, MeOH/EtOH=50/50, Retention time: 30.3 min

EXAMPLE 46

Preparation of Compound A67

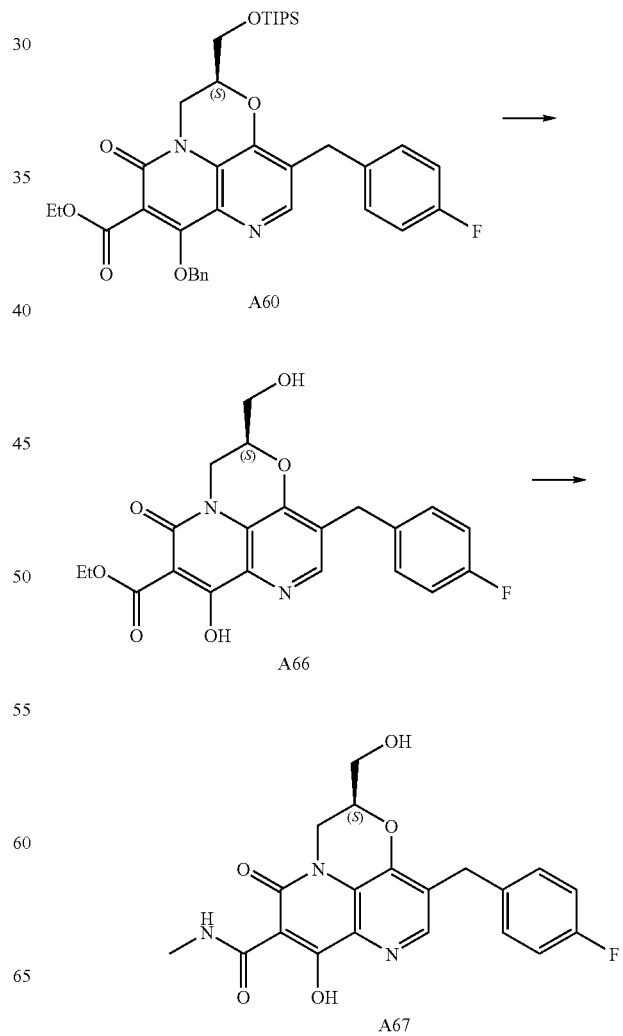

Step 1

Compound A60 (100 mg, 0.2 equiv, 1 equiv) was treated with 50% trifluoroacetic acid in dichloromethane (2 mL) for about 30 minutes at room temperature. The crude mixture was diluted with dichloromethane and washed with (1 v:1 v) mixture of (brine:water) and brine. The organic layer was dried over sodium sulfate and used as-is in the next step.

Step 2

The crude intermediate A66 (82 mg, 0.2 mmol, 1 equiv) was dissolved in N,N-dimethylformamide (2 mL) in a microwave tube and 2M methyl amine solution in tetrahydrofuran was added. The tube was sealed and heated in microwave at 130° C. for 20 minutes. The resulting crude product was then purified on prep. HPLC. Yield=44 mg of compound A67 (55%) (from last three steps). %). $^1$H NMR (400 MHz, CD3OD) δ 8.22 (s, 1H), 7.24 (dd, J=8.4, 5.6 Hz, 2H), 6.91 (t, J=8.8 Hz, 2H), 4.61 (d, J=14.0 Hz, 1H), 4.48 (s, 1H), 4.27-4.26 (m, 1H), 4.03 (d, J=4.0 Hz, 2H), 3.83 (d, J=4.8 Hz, 2H), 3.64-3.59 (m, 1H), 2.88 (s, 1H); MS m/z: 400.06 (M+1).

Chiral HPLC: Chiralcel OD-H, MeOH/EtOH=50/50, Retention time: 18.7 min

EXAMPLE 47

Preparation of Compound A69

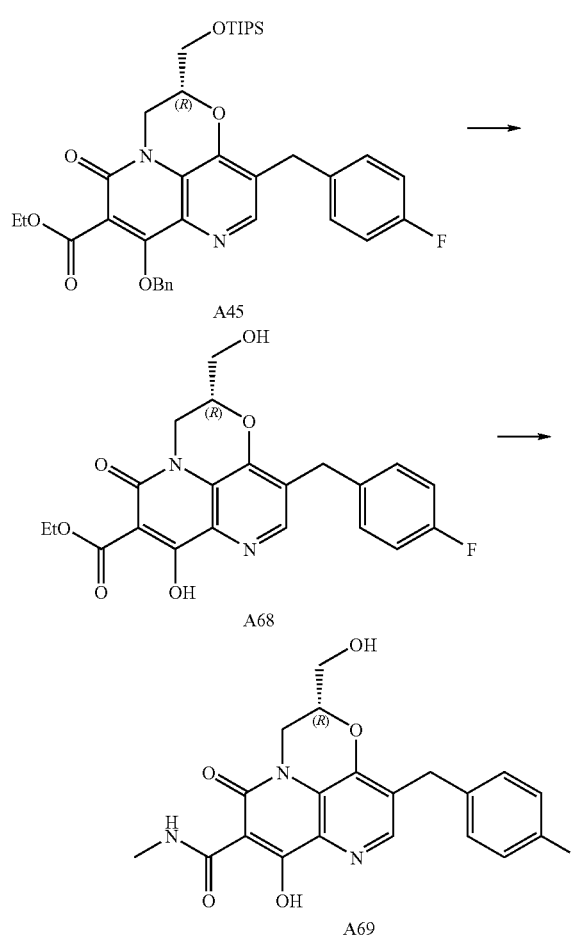

Step 1

Compound A45 (100 mg, 0.2 equiv, 1 equiv) was treated with 50% trifluoroacetic acid in dichloromethane (2 mL) for about 30 minutes at room temperature. The crude mixture was diluted with dichloromethane and washed with (1 v:1 v) mixture of (brine:water) and brine. The organic layer was dried over sodium sulfate and obtained the desired product A68 (74 mg, 90%). MS[M+H]=415

Step 2

The crude intermediate A68 (20 mg, 0.05 mmol) was dissolved in N,N-dimethylformamide (0.5 mL) in a microwave tube and 2M methyl amine solution in tetrahydrofuran (0.15 mL, 0.3 mmol) was added. The tube was sealed and heated in microwave at 130° C. for 20 minutes. The resulting crude product was then purified on prep. HPLC. Yield=13 mg of compound A69 (68%) $^1$H NMR (400 MHz, CD3OD) δ 8.29 (s, 1H), 7.29 (m 2H), 6.98 (m 2H), 4.61 (d, 1H), 4.48 (m, 1H), 4.27-4.26 (m, 1H), 4.03 (d, 2H), 3.83 (d, 2H), 3.64-3.59 (m, 1H), 2.96 (s, 3H); MS m/z: 400.06 (M+1).

Chiral HPLC: Chiralcel OD-H, MeOH/EtOH=50/50, Retention time: 21.1 min

EXAMPLE 48

Preparation of Compounds A70, A71 and A72

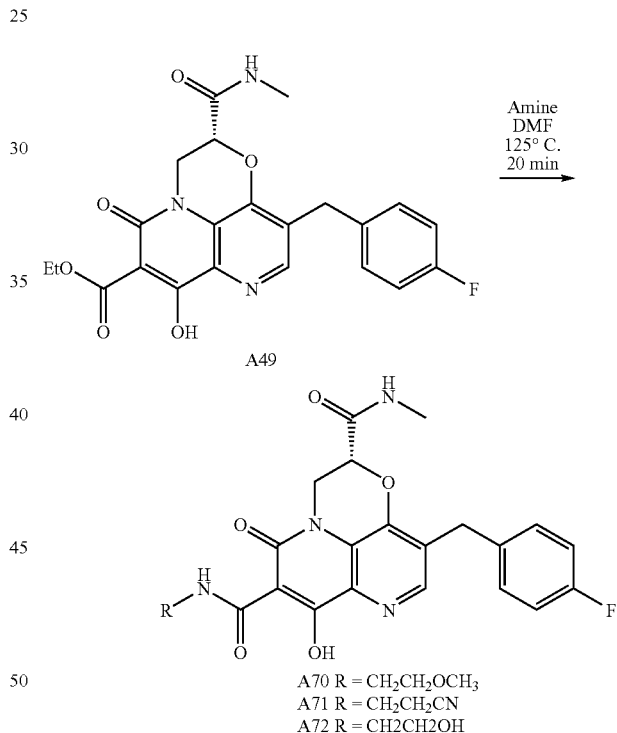

Compound A70 was made using 2-methoxyethylamine in a similar fashion as compound A50 to afford the desired product (38 mg, 82%), 400 MHz $^1$H NMR (DMSO) 10.3 (m, 1H), 8.30 (s, 1H), 8.12 (m, 1H), 7.31 (m, 2H), 7.08 (m, 2H), 5.03 (m, 1H), 4.40 (m, 1H), 4.19-4.09 (m, 1H), 3.99 (m, 2H), 3.46 (m, 2H), 3.25 (s, 3H), 3.21 (m, 2H), 2.62 (d, 3H); MS[M+H]=471

Compound A71 was made using 2-cyanoethyl amine in a similar fashion as compound A50 to afford the desired product A71 (25 mg, 72%), 400 MHz $^1$H NMR (DMSO) 10.39 (m, 1H), 8.36 (s, 1H), 8.15 (m, 1H), 7.32 (m, 2H), 7.08 (m, 2H), 5.07 (m, 1H), 4.43 (m, 1H), 4.18-4.02 (m, 3H), 3.60 (m, 2H), 2.81 (m, 2H), 2.62 (d, 3H); MS[M+H]=466.

Compound A72 was made using 2-hydroxyethylamine in a similar fashion as compound A50 to afford the desired product A72 (25 mg, 90%), 400 MHz $^1$H NMR (DMSO) 10.29 (m, 1H), 8.27 (s, 1H), 8.10 (m, 1H), 7.30 (m, 2H), 7.08 (m, 2H), 5.00 (m, 1H), 4.39 (m, 1H), 4.13-3.95 (m, 3H), 3.48 (m, 2H), 3.38 (m, 2H), 2.61 (m, 3H); MS[M+H]=457

EXAMPLE 49

Synthetic Procedures for Examples 50-64

General Procedures

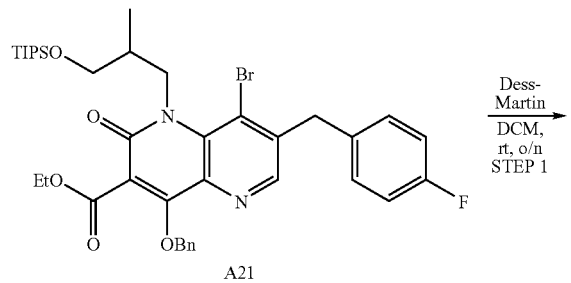

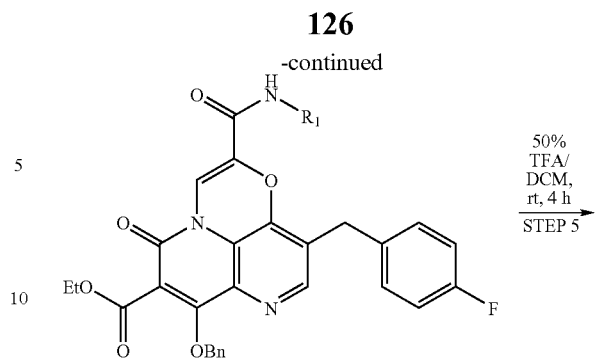

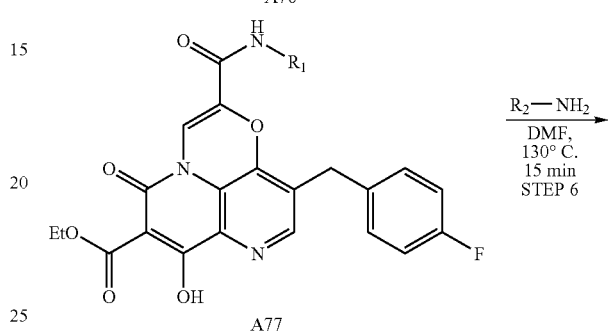

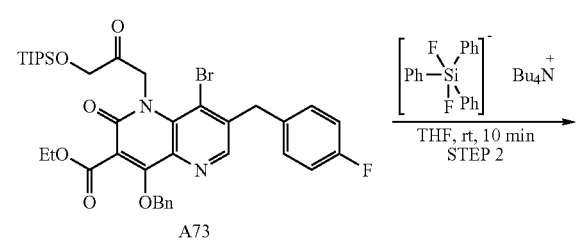

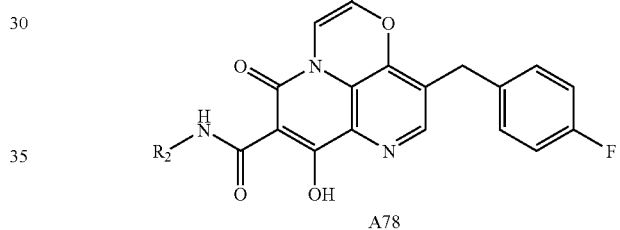

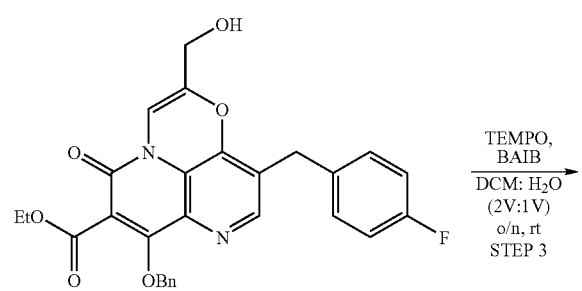

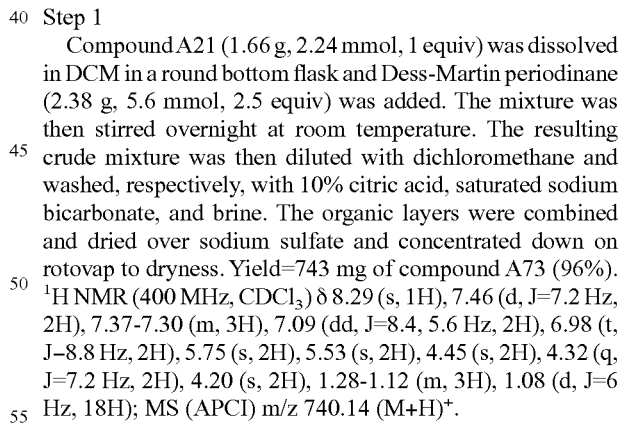

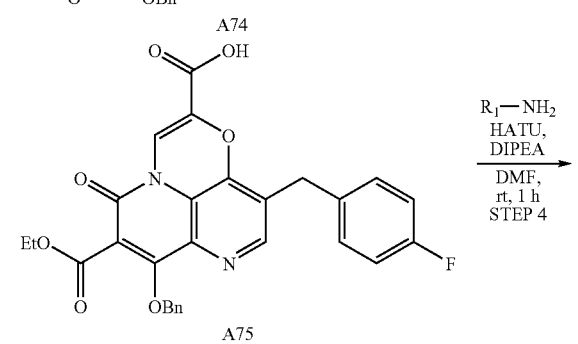

Step 1

Compound A21 (1.66 g, 2.24 mmol, 1 equiv) was dissolved in DCM in a round bottom flask and Dess-Martin periodinane (2.38 g, 5.6 mmol, 2.5 equiv) was added. The mixture was then stirred overnight at room temperature. The resulting crude mixture was then diluted with dichloromethane and washed, respectively, with 10% citric acid, saturated sodium bicarbonate, and brine. The organic layers were combined and dried over sodium sulfate and concentrated down on rotovap to dryness. Yield=743 mg of compound A73 (96%). $^1$H NMR (400 MHz, CDCl$_3$) δ 8.29 (s, 1H), 7.46 (d, J=7.2 Hz, 2H), 7.37-7.30 (m, 3H), 7.09 (dd, J=8.4, 5.6 Hz, 2H), 6.98 (t, J=8.8 Hz, 2H), 5.75 (s, 2H), 5.53 (s, 2H), 4.45 (s, 2H), 4.32 (q, J=7.2 Hz, 2H), 4.20 (s, 2H), 1.28-1.12 (m, 3H), 1.08 (d, J=6 Hz, 18H); MS (APCI) m/z 740.14 (M+H)$^+$.

Step 2

Intermediate A73 (4.64 g, 6.3 mmol) was taken up 100 mL of THF and treated with tetrabutylammonium difluorotriphenylsilicate (4.06 g, 7.5 mmol) and the mixture allowed to stir for 24 h. After removal of the THF in vacuo, the residue was partitioned between EtOAc and sat. bicarbonate solution. The organic layer was separated, dried with sodium sulfate and filtered thru a silica plug. The filtrate was concentrated in vacuo, and the residue triturated with ether and hexanes to provided the desire product A74 (2.23 g, 71% yield) as a bright, yellow solid. The mother liquor was purified by silica gel chromatography (ISCO) to provide an additional batch of the desired product A74 (461 mg, 14.5% yield). MS [M+H]+= 503.0 LCMS RT=2.58 min Step 3

A solution of Intermediate A74 (500 mg, 1.0 mmol), TEMPO (31 mg, 0.2 mmol) and bis-acetoxyiodobenzene (580 mg, 1.8 mmol) in 10 mL DCM and 2.5 mL water was allowed to stir at rt for 8 h. The reaction was then diluted with EtOAc and water. The organic layer was washed with brine, dried with sodium sulfate and concentrated in vacuo to provide a yellow solid. This material was slurried in ether and sonicated for 5 min. Filtration provided the desired acid A75 (441 mg, 85% yield) as a bright yellow solid. The mother liquor was extracted with 0.5N NaHCO$_3$ (3×). The aqueous layers were combined, acidified with pH 2.0 buffer (bisulfate) and extracted with EtOAc (3×). The organic layers were combined, dried with sodium sulfate and concentrated in vacuo to provide an additional batch of the desired product A75 (38 mg, 8% yield). $^1$H-NMR (CDCl$_3$-d$_6$) d 8.63 (s, 1H), 7.92 (dd, 2H, J=8, 6 Hz), 7.38-7.30 (m, 6H), 7.28 (s, 1H), 5.52 (s, 1H), 4.14 (q, 2H, J=7 Hz), 3.89 (s, 1H), 1.12 (t, 3H, J=7 Hz); MS [M+H]+=517.0

LCMS RT=2.60 min.

Step 4

The intermediates A75 (200 mg, 0.387 mmol, 1.0 equiv) was weighed out in a 2 dram scintillation vial and HATU (309 mg, 0.813 mmol, 2.1 equiv) was added and the mixture was dissolved in DMF (4 mL). To this mixture was then added DIPEA (200 mg, 1.548 mmol, 4.0 equiv) and the choice of amine (2 equiv). The mixture was stirred for 1 hour at room temperature. The crude reaction mixture was then diluted with EtOAc and washed, respectively, with (1 v:1 v) mixture of (brine:water), saturated sodium bicarbonate, and brine. Dried on sodium sulfate and the volatiles evaporated on rotovap. The residue was then purified on normal phase column chromatography.

Step 5

The intermediates of formula A76 (0.14 mmol, 1 equiv) were dissolved in a 50% mixture of trifluoroacetic acid: dichloromethane (0.03M). The mixture was stirred at room temperature for 2 hours. Upon completion of the reaction the mixture was diluted with dichloromethane and washed with a (1 v:1 v) mixture of (brine:water) and brine to remove the excess of TFA. The organic layer was dried over sodium sulfate and concentrated down on rotovap and dried on pump to complete dryness.

Step 6

The intermediates of formula A77 (0.14 mmol, 1 equiv) were treated with an amine of choice in a microwave reactor and the products of formula A78 was purified by preparative HPLC.

EXAMPLE 50

Preparation of Compound A81

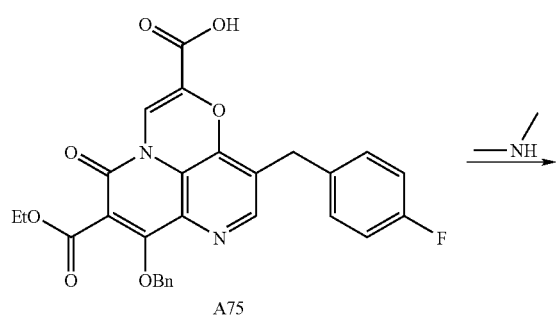

A75

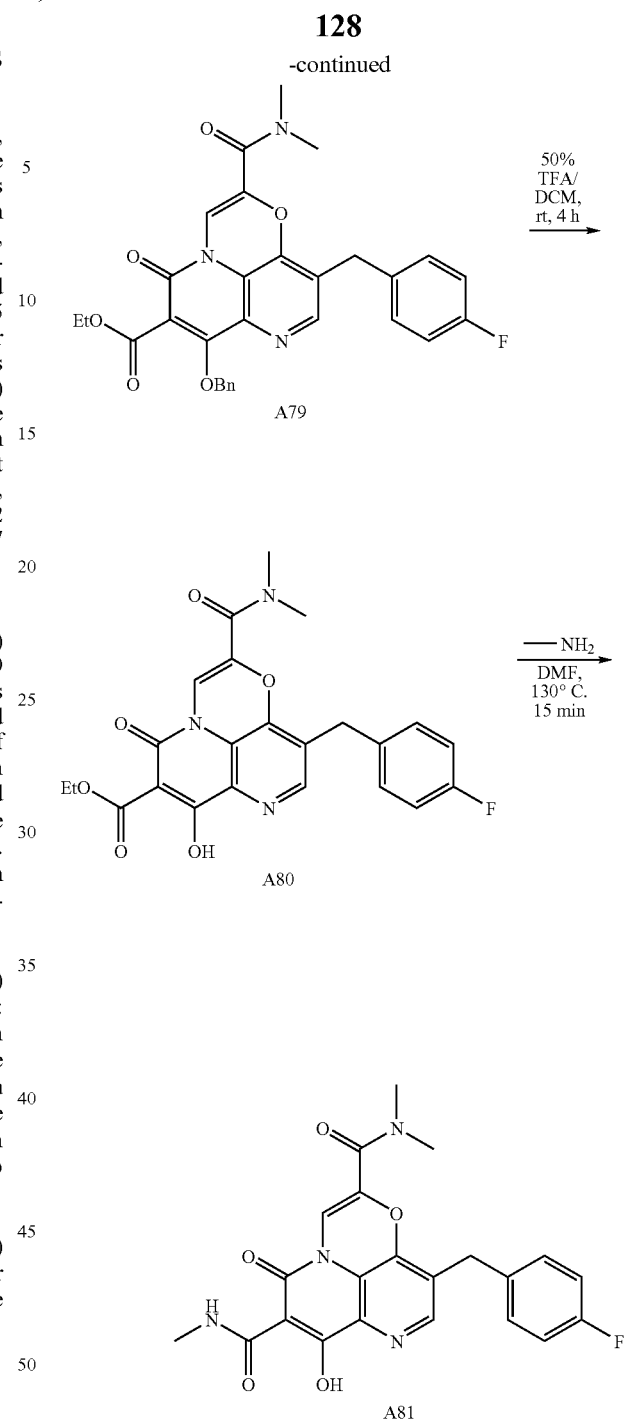

Step 1

The general procedures in step 4 from Example 49 were used. Yield=68%

MS (APCI) m/z 544.35 (M+H)$^+$.

Step 2

The general procedures in step 5 of Example 49 were used. A quantitative yield was obtained.

Step 3

The general procedures in step 6 of Example 49 were used. Yield=40% for compound 81 after three steps. $^1$H NMR (400 MHz, CD$_3$OD) δ 8.14 (s, 1H), 7.35 (s, 1H), 7.19 (dd, J=8.8, 5.6 Hz, 2H), 6.94 (t, J=8.8, 2H), 3.88 (s, 2H), 2.95 (brs, 6H), 2.87 (s, 3H); MS (APCI) m/z 439.44 (M+H)$^+$.

EXAMPLE 51

Preparation of Compound A82

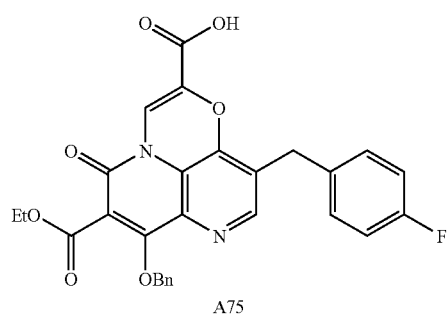
A75

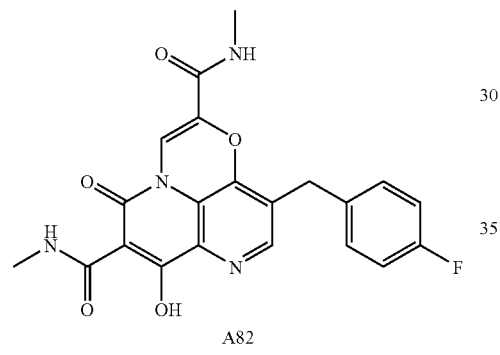
A82

The general procedures in steps 4-6 of Example 49 were used. Yield=40% for compound A82 after three steps. $^1$H NMR (400 MHz, CD3OD) δ 8.12 (s, 1H), 7.70 (s, 1H), 7.25 (dd, J=8.8, 5.6 Hz, 2H), 6.99 (t, J=8.8, 2H), 4.02 (s, 2H), 2.88 (s, 3H), 2.79 (s, 3H); MS (APCI) m/z 425.55 (M+H)$^+$.

EXAMPLE 52

Preparation of Compound A83

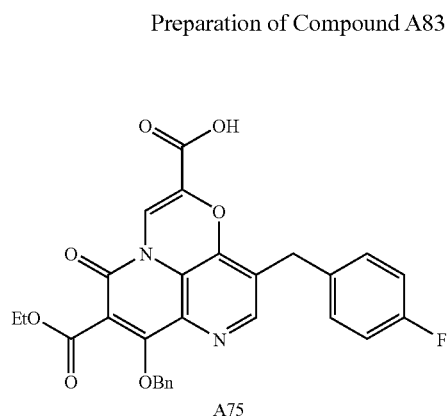
A75

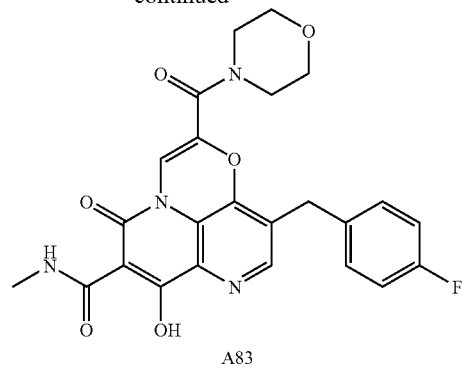
A83

The general procedures in steps 4-6 of Example 49 were used. Yield=40% for compound A83 after three steps. $^1$H NMR (400 MHz, DMSO-D6) δ 10.15 (brs, 1H), 8.12 (brs, 1H), 7.38 (s, 1H), 7.27 (dd, J=8.8, 5.6 Hz, 2H), 7.14 (t, J=8.8, 2H), 3.85 (s, 2H), 3.50 (s, 8H), 2.73 (s, 3H); MS (APCI) m/z 481.24 (M+H)$^+$

EXAMPLE 53

Preparation of Compound A84

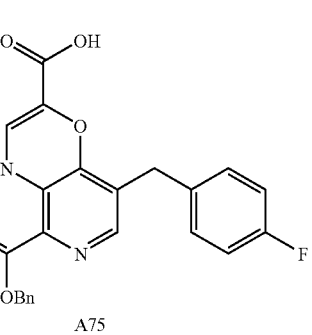
A75

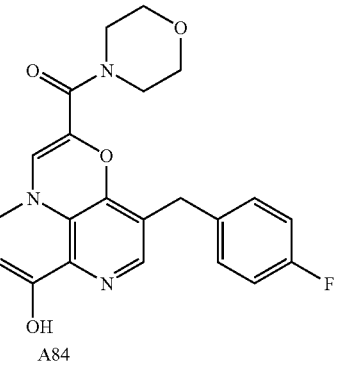
A84

The general procedures in steps 4-6 of Example 49 were used. Yield=72% after three steps. $^1$H NMR (400 MHz, DMSO-D6) δ 10.50 (brs, 1H), 8.08 (brs, 1H), 7.40 (s, 1H), 7.25 (dd, J=8.8, 5.6 Hz, 2H), 7.14 (t, J=8.8, 2H), 3.83 (s, 2H), 3.50 (s, 8H), 3.40 (m, 4H), 3.27 (s, 3H), 3.16 (s, 1H); MS (APCI) m/z 525.07 (M+H)⁺.

EXAMPLE 54

Preparation of Compound A85

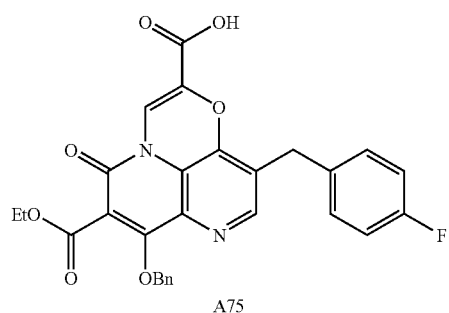
A75

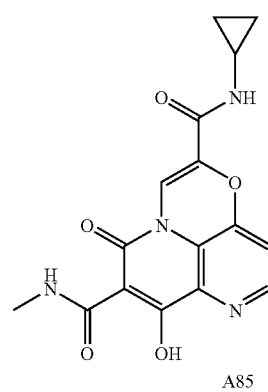
A85

The general procedures in steps 4-6 of Examples 49 were used. Yield=30% after three steps. ¹H NMR (400 MHz, DMSO-D6) δ 9.86 (brs, 1H), 8.18 (s, 1H), 7.88 (brs, 1H), 7.58 (s, 1H), 7.35 (dd, J=8.8, 5.6 Hz, 2H), 7.12 (t, J=8.8, 2H), 4.02 (s, 2H), 2.74 (d, J=3.6 Hz, 3H), 0.72-0.70 (m, 2H), 0.57-0.55 (m, 2H); MS (APCI) m/z 451.15 (M+H)⁺.

EXAMPLE 55

Preparation of Compound A86

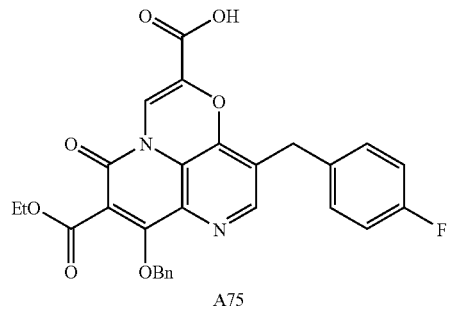
A75

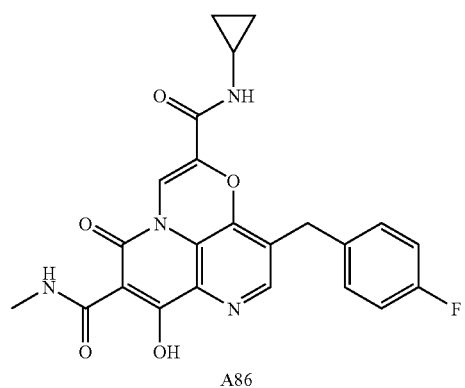
A86

The general procedures in steps 4-6 of Example 49 were used. Yield=30% after three steps. ¹H NMR (400 MHz, DMSO-D6) δ 9.86 (brs, 1H), 8.18 (s, 1H), 7.88 (brs, 1H), 7.58 (s, 1H), 7.35 (dd, J=8.8, 5.6 Hz, 2H), 7.12 (t, J=8.8, 2H), 4.02 (s, 2H), 2.74 (d, J=3.6 Hz, 3H), 0.72-0.70 (m, 2H), 0.57-0.55 (m, 2H); MS (APCI) m/z 451.15 (M+H)⁺.

EXAMPLE 56

Preparation of Compound A87

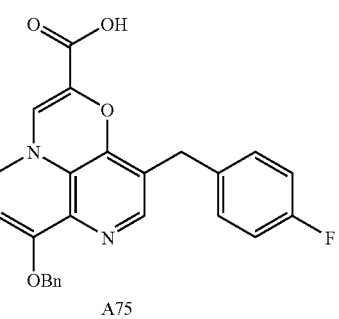
A75

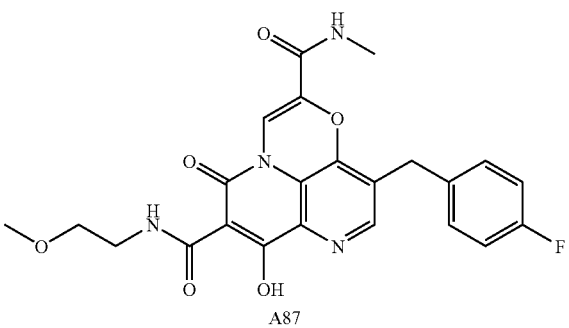
A87

The general procedures in steps 4-6 of Example 49 were used. Yield=35% after three steps. ¹H NMR (400 MHz, DMSO-D6) δ 10.05 (brs, 1H), 8.37 (s, 1H), 8.23 (brs, 1H), 7.59 (s, 1H), 7.40 (dd, J=8.8, 5.6 Hz, 2H), 7.15 (t, J=8.8, 2H), 4.13 (s, 2H), 3.56-3.50 (m, 4H), 3.30 (s, 3H), 2.78 (d, J=4.8 Hz, 3H); MS (APCI) m/z 469.16 (M+H)+.

EXAMPLE 57

Preparation of Compound A88

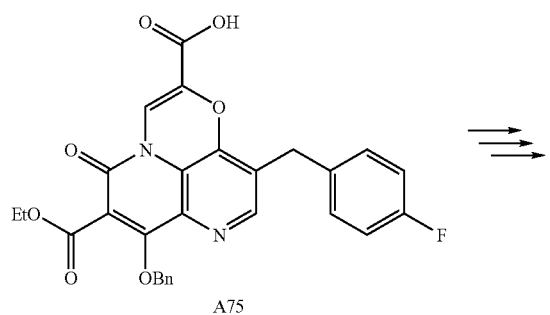

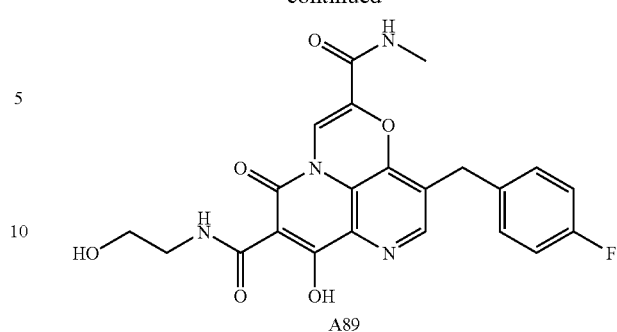

The general procedures in steps 4-6 of Example 49 were used. Yield=31% after three steps. $^1$H NMR (400 MHz, DMSO-D6) δ 10.10 (brs, 1H), 8.35 (s, 1H), 8.19 (brs, 1H), 7.57 (s, 1H), 7.40 (dd, J=8.8, 5.6 Hz, 2H), 7.15 (t, J=8.8, 2H), 4.34 (t, J=4.8 Hz, 1H), 4.12 (s, 2H), 3.56-3.54 (m, 2H), 3.44-3.43 (m, 2H), 2.78 (d, J=4.8 Hz, 3H); MS (APCI) m/z 454.99 (M+H)+.

EXAMPLE 59

Preparation of Compound A90

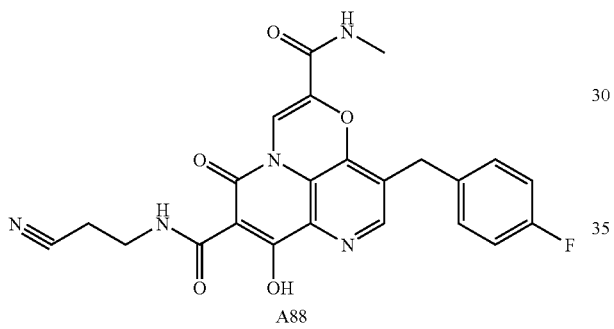

The general procedures in steps 4-6 of Example 49 were used. Yield=36% after three steps. $^1$H NMR (400 MHz, DMSO-D6) δ 10.13 (brs, 1H), 8.37 (s, 1H), 8.22 (brs, 1H), 7.57 (s, 1H), 7.40 (dd, J=8.8, 5.6 Hz, 2H), 7.15 (t, J=8.8, 2H), 4.13 (s, 2H), 3.7-3.64 (m, 2H), 2.86 (t, J=6.4 Hz, 2H), 2.78 (d, J=4.4 Hz, 3H); MS (APCI) m/z 464.41 (M+H)+.

EXAMPLE 58

Preparation of Compound A89

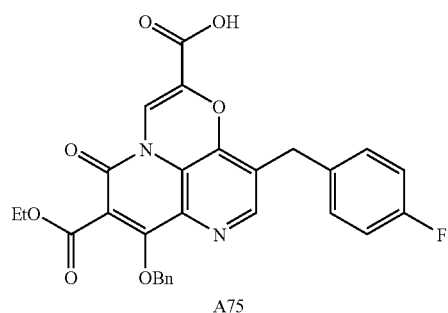

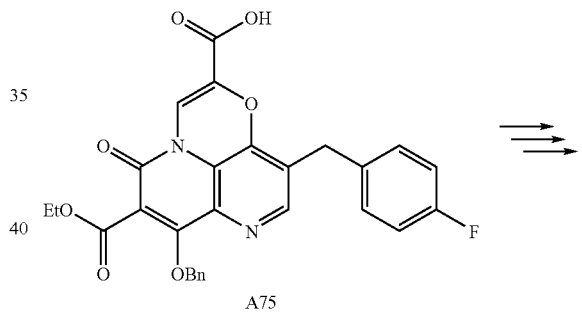

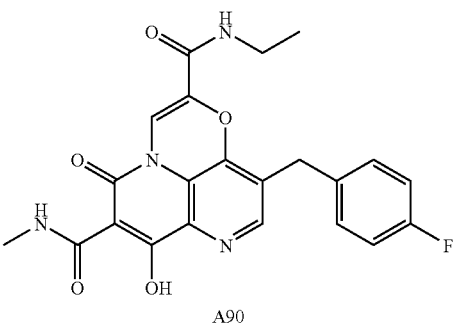

The general procedures in steps 4-6 of Example 49 were used. Yield=29% after three steps. $^1$H NMR (400 MHz, DMSO-D6) δ 9.82 (brs, 1H), 8.38 (s, 1H), 8.22 (brs, 1H), 7.55

(s, 1H), 7.40 (dd, J=8.8, 5.6 Hz, 2H), 4.12 (s, 2H), 3.29-3.24 (m, 2H), 2.91 (d, J=4.4 Hz, 3H), 1.11 (t, J=7.2 Hz, 3H); MS (APCI) m/s 439.35 (M+H)⁺.

EXAMPLE 60

Preparation of Compound A91

A75

A91

The general procedures in steps 4-6 of Example 49 were used. Yield=45% after three steps. ¹H NMR (400 MHz, DMSO-D6) δ 9.82 (brs, 1H), 8.33 (s, 1H), 7.26-7.22 (m, 3H), 7.10 (t, J=8.8 Hz, 2H), 3.90 (s, 2H), 3.37-3.31 (m, 4H), 2.88 (d, J=4.4 Hz, 3H), 1.03 (t, J=7.2 Hz, 6H); MS (APCI) m/z 467.27 (M+H)⁺.

EXAMPLE 61

Preparation of Compound A92

A75

A92

The general procedures in steps 4-6 of Example 49 were used. Yield=17% after three steps, ¹H NMR (400 MHz, CD₃OD) δ 8.15 (s, 1H), 7.78 (s, 1H), 7.23 (t, J=8.4 Hz, 2H), 7.06 (t, J=8.8, 2H), 4.48 (brs, 4H), 4.02 (s, 2H), 2.96 (s, 3H); MS (APCI) m/z 487.06 (M+H)⁺.

EXAMPLE 62

Preparation of Compound A94

A75

A93

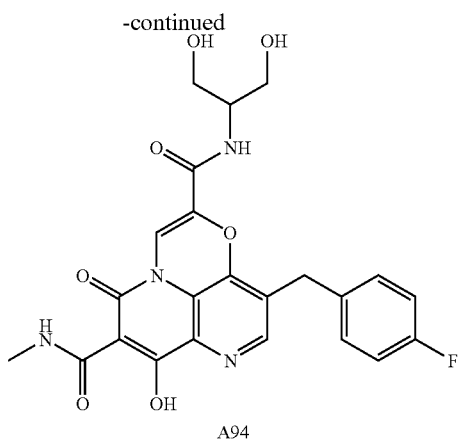

A94

The general procedures in steps 4-6 of Example 49 were used. However the oxetane ring opened up with water to give A94. Yield=21% after the last two steps. $^1$H NMR (400 MHz, DMSO-D6) δ 9.82 (brs, 1H), 8.48 (s, 1H), 7.57 (s, 1H), 7.46 (d, J=7.6 Hz, 1H), 7.40 (dd, J=8.8, 5.6 Hz, 2H), 7.12 (t, J=8.8 Hz, 2H), 4.84 (t, J=5.2 Hz, 2H), 4.05 (s, 2H), 3.93-3.88 (m, 1H), 3.53 (t, J=5.6 Hz, 4H), 2.91 (d, J=4.8 Hz, 3H); MS (APCI) m/z 485.08 (M+H)$^+$.

EXAMPLE 63

Preparation of Compound A95

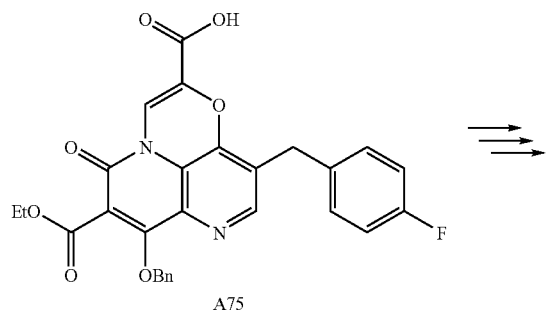

A75

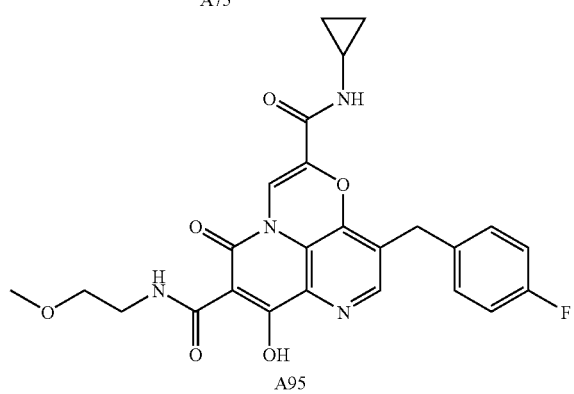

A95

The general procedures in steps 4-6 of Example 49 were used. Yield=34% after three steps. $^1$H NMR (400 MHz, CD$_3$OD) δ 8.14 (s, 1H), 7.64 (s, 1H), 7.24 (dd, J=8.4, 5.6 Hz, 2H), 6.96 (t, J=8.8, 2H), 4.49 (s, 1H), 3.99 (s, 2H), 3.53-3.47 (m, 4H), 3.30 (s, 3H), 2.68-2.64 (m, 1H), 0.74 (d, J=6.4 Hz, 2H), 0.53 (brs, 2H); MS (APCI) m/z 495.07 (M+H)$^+$.

EXAMPLE 64

Preparation of Compound A96

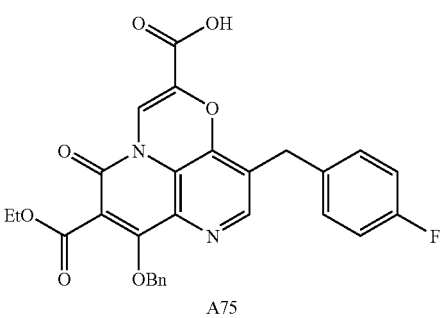

A75

A96

The general procedures in steps 4-6 of Example 49 were used. Yield=34% after three steps. $^1$H NMR (400 MHz, CD$_3$OD) δ 8.14 (s, 1H), 7.64 (s, 1H), 7.24 (dd, J=8.4, 5.6 Hz, 2H), 6.96 (t, J=8.8, 2H), 4.49 (s, 1H), 3.99 (s, 2H), 3.53-3.47 (m, 4H), 3.30 (s, 3H), 2.68-2.64 (m, 1H), 0.74 (d, J=6.4 Hz, 2H), 0.53 (brs, 2H); MS (APCI) m/z 495.07 (M+H)$^+$.

EXAMPLE 65

Preparation of Compounds A108 and A109

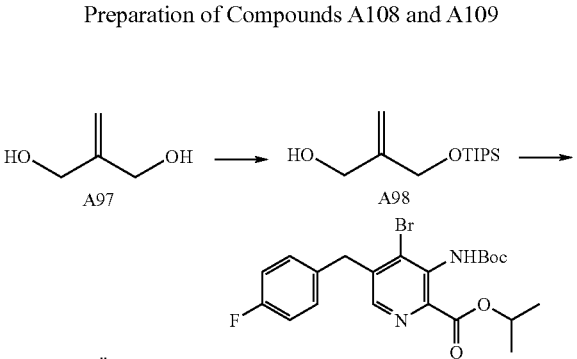

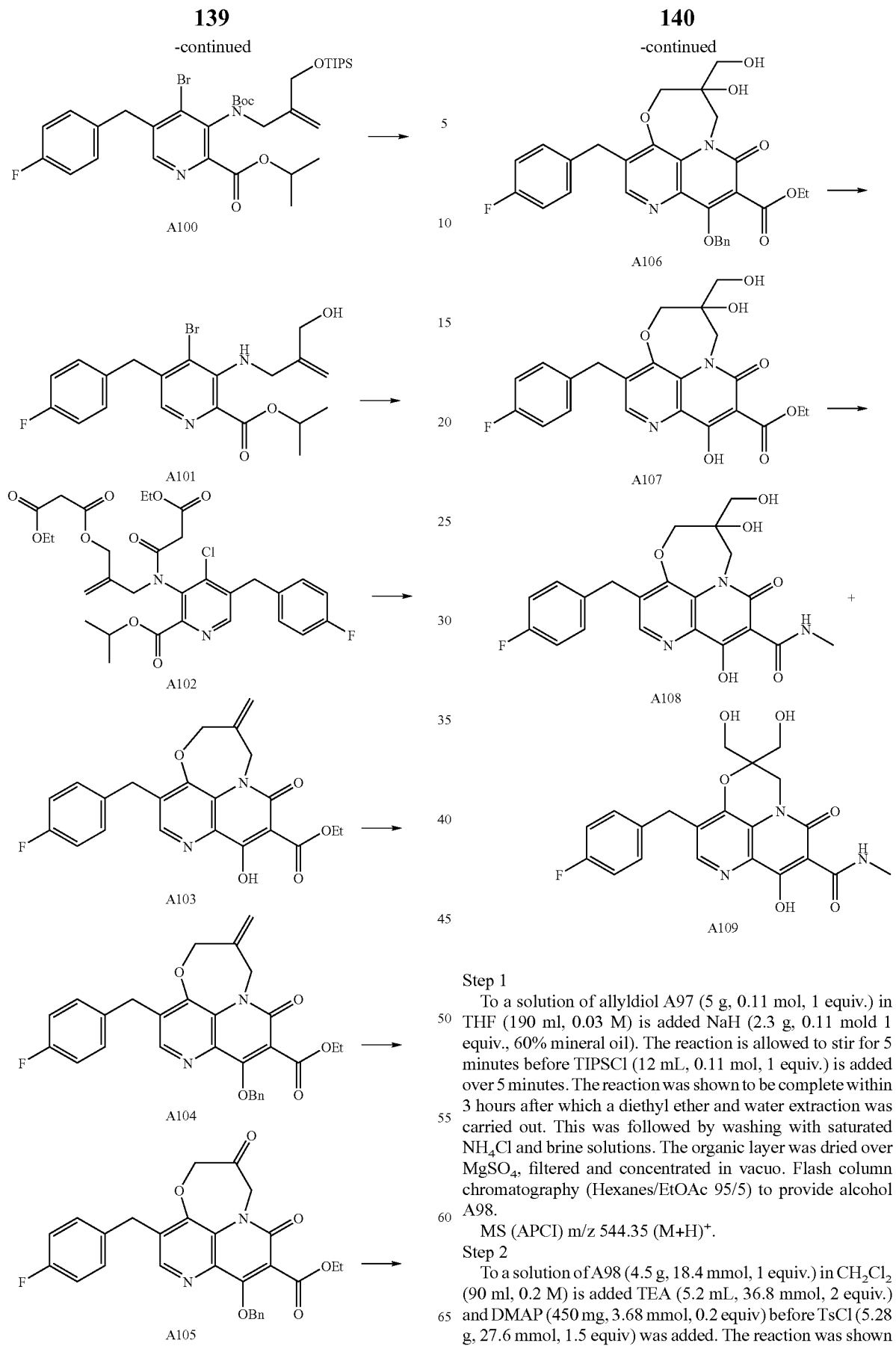

Step 1

To a solution of allyldiol A97 (5 g, 0.11 mol, 1 equiv.) in THF (190 ml, 0.03 M) is added NaH (2.3 g, 0.11 mold 1 equiv., 60% mineral oil). The reaction is allowed to stir for 5 minutes before TIPSCl (12 mL, 0.11 mol, 1 equiv.) is added over 5 minutes. The reaction was shown to be complete within 3 hours after which a diethyl ether and water extraction was carried out. This was followed by washing with saturated $NH_4Cl$ and brine solutions. The organic layer was dried over $MgSO_4$, filtered and concentrated in vacuo. Flash column chromatography (Hexanes/EtOAc 95/5) to provide alcohol A98.

MS (APCI) m/z 544.35 $(M+H)^+$.

Step 2

To a solution of A98 (4.5 g, 18.4 mmol, 1 equiv.) in $CH_2Cl_2$ (90 ml, 0.2 M) is added TEA (5.2 mL, 36.8 mmol, 2 equiv.) and DMAP (450 mg, 3.68 mmol, 0.2 equiv) before TsCl (5.28 g, 27.6 mmol, 1.5 equiv) was added. The reaction was shown to be complete within an hour. It was quenched and washed with water. This was followed by washing with saturated NH₄Cl and brine solution. The organic layer was dried over MgSO₄, filtered and concentrated in vacuo. Flash column chromatography (Hexanes/EtOAc 95/5) to provide A99.

Step 3

Into a flask containing compound A5 (5.90 g, 12.7 mmol, 1 equiv.) is added DMF (65 mL, 0.2 M). To this was added NaHMDS (16.5 mL, 16.45 mmol, 1.3 equiv.) and tosylate A99 (5.1 g, 12.65 mmol, 1) and the reaction allowed to stir overnight. After completion, the reaction was diluted with EtOAc and washed with water, saturated NH₄Cl and brine solutions. The organic layer was dried over MgSO₄, filtered and concentrated in vacuo. Flash column chromatography (Hexanes/EtOAc 4/1) to furnish bromide A100.

400 MHz $^1$H NMR (CDCl₃) δ (ppm): 8.19 (s, 1H), 8.00 (s, 1H), 6.93-6.90 (m, 2H), 6.85-6.80 (m, 2H), 6.45-6.44 (m, 2H), 5.13 (sp, 1H), 5.02 (d, J=2.0 Hz, 1H), 4.60 (s, 1H), 4.17-4.02 (m, 3H), 3.90-3.95 (m, 3H), 1.54 (s, 9H), 1.54-1.53 (sp, J=7.6 Hz, 3H), 0.87 (s, 3H), 0.89 (s, 3H).

400 MHz $^{19}$H NMR (CDCl₃) δ (ppm): −116.03

MS: 694.80 (M+1)

Step 4

To a solution of A100 (4.85 g, 7 mmol, 1 equiv.) in 1,2-Dichloroethane (5 mL) and water (3 mL) was added TFA (15 mL) and warmed to 60° C. After the reaction was complete, it was concentrated in vacuo to about half the volume. It was diluted with EtOAc and washed with water (2×), saturated NaHCO₃ (2×) and brine solution. The organic layer was dried over MgSO₄, filtered and concentrated in vacuo. Flash column chromatography (Hexanes/EtOAc 4/1) to furnish amine A101.

400 MHz $^1$H NMR (CDCl₃) δ (ppm): 7.96 (s, 1H), 7.10-7.25 (m, 2H), 6.93-6.98 (m, 2H), 5.28 (sp, 1H), 5.15 (s, 1H), 5.13 (s, 1H), 4.16 (m, 2H), 4.08 (m, 2H), 3.97 (s, 2H), 1.40 (d, J=7.6 Hz, 6H).

400 MHz $^{19}$F NMR (CDCl₃) δ (ppm): −116.05, −74.92.

MS: 438.93 (M+1)

Step 5

To a solution of A101 (200 mg, 0.46 mmol, 1 equiv.) in 1,2-dichloroethane (5 mL, 0.1 M) was added ethyl malonyl chloride (175 μL, 1.4 mmol, 3 equiv.) and heated to 80° C. After the reaction was complete, it was quenched and washed with water, saturated NaHCO₃ and brine. The organic layer was dried over MgSO₄, filtered and concentrated in vacuo. A light yellow oil of A102 was obtained and used without further purification.

MS: 507.12 (M+1), 4-Cl; 621.12 (M+1), 4-Br. Ratio ~3:1 respectively.

Step 6

To a solution of A102 (1.82 g, 2.90 mmol, 1 equiv.) in EtOH (30 mL, 0.1 M) was added NaOEt (4.4 mL, 11.7 mmol, 4 equiv., 28% EtOH). After 10 min of stirring at ambient temperature, the reaction was heated onto a 90° C. heating mantle. After 10 min, the reaction was shown to be complete. It was concentrated in vacuo and diluted with EtOAc and HCl (10 mL, 2 N) before being washed with water (2×) and brine. The organic layer was dried over MgSO₄, filtered and concentrated in vacuo. Hexanes were added to the brown oil, sonicated and washed before being allowed to air dry to leave behind a brown powder of A103 (1.1 g).

400 MHz $^1$H NMR (CDCl₃) δ (ppm) 8.42 (s, 1H), 7.10-7.25 (m, 2H), 6.93-6.98 (m, 2H), 5.34 (s, 1H), 5.06 (s, 2H), 5.00 (s, 1H), 4.59 (m, 2H), 4.50 (q, J=6.8 Hz, 2H), 4.02 (s, 2H), 1.45 (t, J=6.8 Hz, 3H).

400 MHz $^{19}$F NMR (CDCl₃) δ (ppm) −116.04

MS: 410.88 (M+1)

Step 7

To a solution of A103 (750 mg, 1.83 mmol, 1 equiv.) in CH₂Cl₂ (20 mL, 0.1 M) was added silver (I) oxide (850 mg, 3.66 mmol, 2 equiv.) followed by benzyl bromide (435 μL, 3.66 mmol, 2 equiv.). After the reaction was shown to be complete, the solid was filtered off and rinsed with CH₂Cl₂. It was concentrated in vacuo and flash column chromatography (7/3 Hex/EtOAc) carried out to yield olefin A104.

400 MHz $^1$H NMR (CDCl₃) δ (ppm) 8.38 (s, 1H), 7.48-7.40 (m, 2H), 7.10-7.25 (m, 5H), 6.93-6.98 (m, 2H), 5.57 (s, 2H), 5.32 (s, 1H), 5.07 (s, 2H), 5.00 (s, 1H), 4.68 (s, 2H), 4.35 (q, J=5.4 Hz, 2H), 4.02 (s, 2H), 1.45 (t, J=5.4 Hz, 3H).

400 MHz $^{19}$F NMR (CDCl₃) δ (ppm) −116.01

MS: 501.13 (M+1)

Step 8

To a solution of A104 (202 mg, 0.40 mmol, 1 equiv.) in CH₂Cl₂ (8 mL) and MeOH (2 mL) was subjected to standard ozonolysis conditions. Following standard workup conditions, the organic layer was dried over MgSO₄, filtered and concentrated in vacuo before flash column chromatography (7/3 Hex/EtOAc) was carried out to furnish ketone A105.

400 MHz $^1$H NMR (CDCl₃) δ (ppm) 8.45 (s, 1H), 7.48-7.40 (m, 2H), 7.10-7.25 (m, 5H), 6.93-6.98 (m, 2H), 5.60 (s, 2H), 5.25 (s, 2H), 4.37 (s, 2H), 4.35 (q, J=6.8 Hz, 2H), 4.06 (s, 2H), 1.45 (t, J=5.4 Hz, 3H).

400 MHz $^{19}$F NMR (CDCl₃) δ (ppm) −116.64

MS: 501.13 (M+1)

Step 9

To a solution of olefin A105 (230 mg, 0.46 mmol, 1 equiv.) in acetone (5 mL, 0.1 M) and water (5 mL, 0.1 M) was added N-methylmorpholine-N-oxide (108 mg, 0.91 mmol, 2 equiv.) and potassium osmate dihydrate (17 mg, 0.05 mmol, 0.1 equiv.) and stirred until the starting material was consumed. It was concentrated in vacuo and diluted with EtOAc and water before being washed with water (2×), saturated NH₄Cl solution and brine. The organic layer was dried over MgSO₄, filtered and concentrated in vacuo to furnish diol 106 which was used without further purification.

MS: 534.18 (M+1)

Step 10

To a solution of A106 (155 mg, 0.29 mmol, 1 equiv.) in EtOH/EtOAc (10 mL, 1/1 v/v) was added Pd (30 mg, 0.02 mmol, 0.1 equiv, 10% C) and hydrogenolysis carried out via a balloon. After the reaction was shown to be complete, the solid was filtered off and rinsed with ethanol. It was concentrated in vacuo to provide A107 as a light yellow solid that was used without further purification.

MS: 444.87 (M+1)

Step 11

Into a vial containing A107 (52 mg, 0.097 mmol, 1 equiv) was added DMF (2 mL) and N-methylamine (400 μL, 0.38 mmol, 4 equiv). It was capped and heated at 120° C. until the starting material was consumed. It was then purified by HPLC to furnish A108 as its TFA salt. Variable amounts of A109 were also obtained that seem to be dependent on the duration of the reaction.

A108: 400 MHz $^1$H NMR (DMSO-d₆) δ (ppm) 10.07 (bs, 1H), 8.43 (1, 1H), 7.10-7.35 (m, 2H), 7.05-7.12 (m, 2H), 4.33 (d, J=14 Hz, 2H), 4.09-3.97 (m, 2H), 4.02 (s, 2H), 3.35 (s, 2H), 2.87 (d, J=4.8 Hz, 3H).

400 MHz $^{19}$F NMR (DMSO-d₆) δ (ppm) −116.87, −74.30

MS: 430.09 (M+1)

A109: 400 MHz $^1$H NMR (DMSO-d₆) δ (ppm) 10.03 (bs, 1H), 8.38 (1, 1H), 7.10-7.35 (m, 2H), 7.05-7.12 (m, 2H), 4.03 (s, 2H), 4.00 (s, 2H), 3.44 (d, J=11.6 Hz, 2H), 3.37 (d, J=11.6 Hz, 2H), 2.87 (d, J=4.8 Hz, 3H).

400 MHz $^{19}$F NMR (DMSO-d₆) δ (ppm) −116.86, −74.08

MS: 430.09 (M+1)

EXAMPLE 66

Preparation of Compound A110

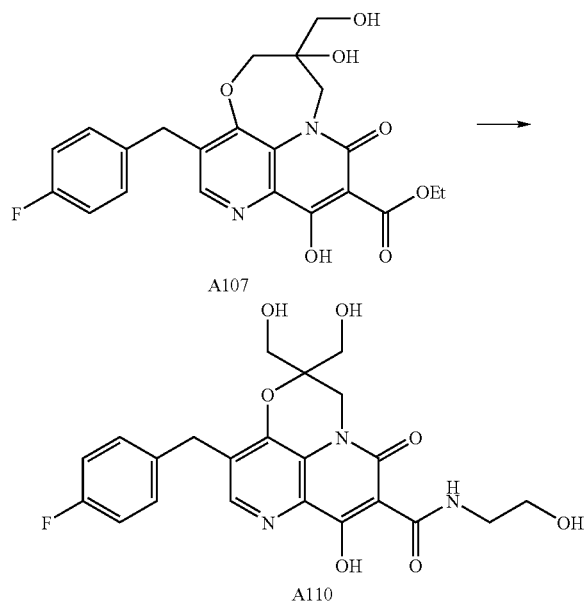

Procedure was carried out as in step 11 of Example 65.

A110: 400 MHz $^1$H NMR (DMSO-$d_6$) δ (ppm): 10.34 (bs, 1H), 8.42 (1, 1H), 7.10-7.35 (m, 2H), 7.05-7.12 (m, 2H), 4.14 (s, 2H), 4.00 (s, 2H), 3.41-3.54 (m, 8H).

400 MHz $^{19}$F NMR (DMSO-$d_6$) δ (ppm) −116.80, −74.75

MS: 460.07 (M+1)

EXAMPLE 67

Preparation of Compound A112

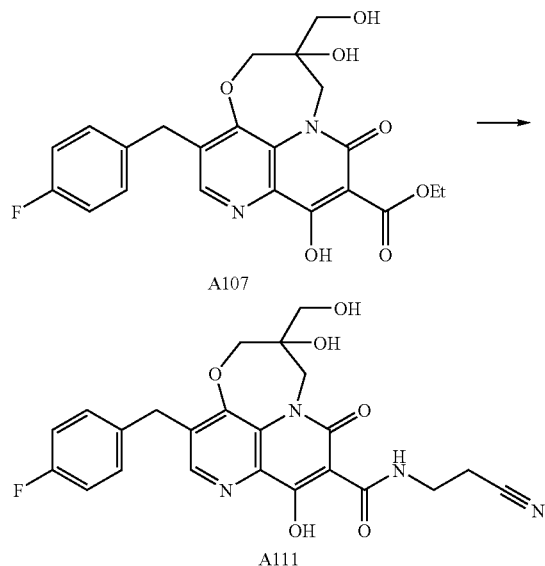

Procedure was carried out as in step 11 of Example 65.

A111: 400 MHz $^1$H NMR (DMSO-$d_6$) δ (ppm) 10.43 (bs, 1H), 8.45 (1, 1H), 7.10-7.35 (m, 2H), 7.05-7.12 (m, 2H), 4.33 (d, J=14 Hz, 2H), 4.09-3.97 (m, 4H), 4.02 (s, 2H), 3.68 (t, J=4.8 Hz, 2H), 3.35 (s, 2H), 2.83 (d, J=4.8 Hz, 3H).

400 MHz $^{19}$F NMR (DMSO-$d_6$) δ (ppm) −116.87, −74.30

MS: 430.09 (M+1)

A112: 400 MHz $^1$H NMR (DMSO-$d_6$) δ (ppm): 10.39 (bs, 1H), 8.41 (1, 1H), 7.10-7.35 (m, 2H), 7.05-7.12 (m, 2H), 4.08 (s, 2H), 4.00 (s, 2H), 3.54-3.41 (m, 6H), 2.81 (t, J=6.4 Hz, 2H).

400 MHz $^{19}$F NMR (DMSO-$d_6$) δ (ppm) −116.83, −74.04

MS: 469.03 (M+1).

EXAMPLE 68

Preparation of Compound A120

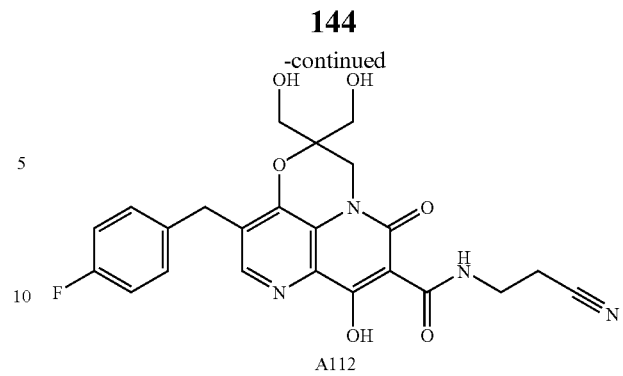

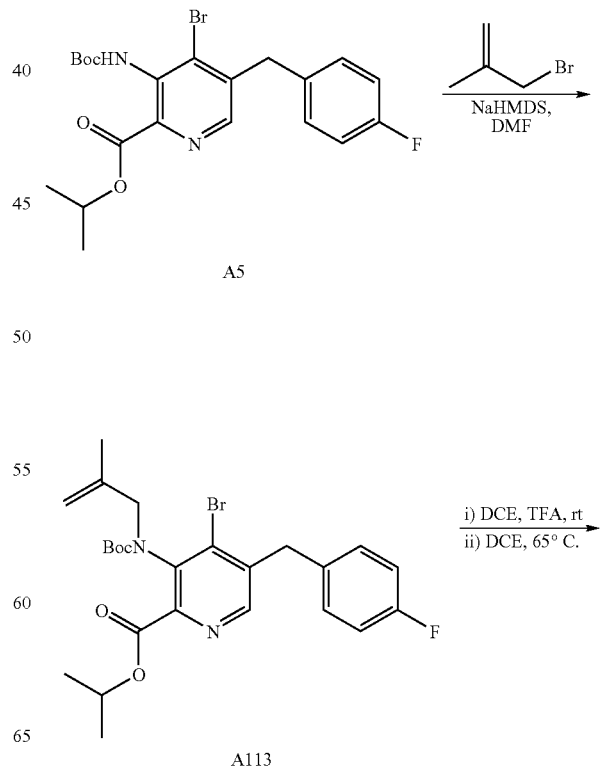

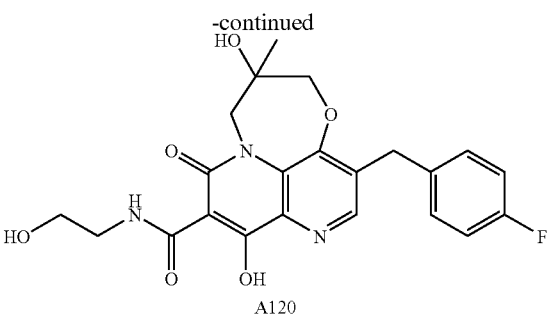

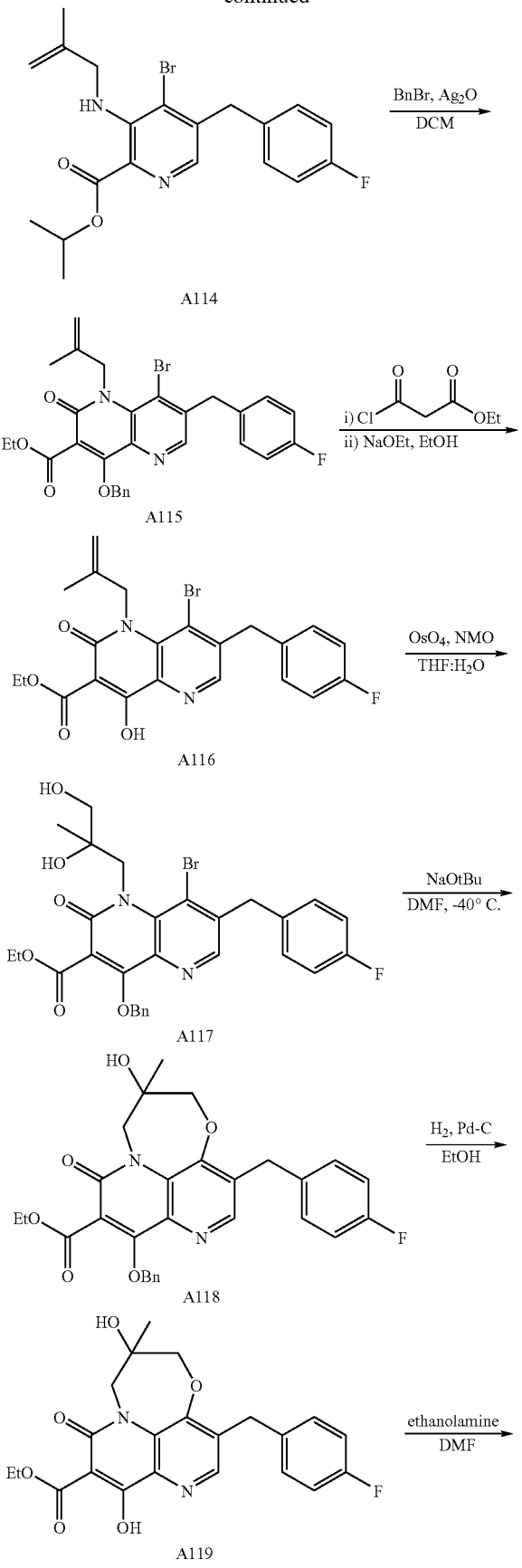

Step 1

Intermediate A5 (3.37 g, 7.28 mmol) was taken up 20 mL of dry DMF and cooled to −10° C. in an ice-acetone bath. A solution of NaHMDS in THF (7.95 mL, 7.95 mmol, 1N) was added dropwise, followed by 3-bromo-2-methylpropene (876 μL, 6.44 mmol). The cooling bath was then removed and the reaction allowed to warm towards ambient temperature. After 30 min, the reaction was quenched with 50 mL pH 4 citrate buffer and 200 mL EtOAc. The layers were separated and the organic was washed with 5% LiCl solution (2×) and brine. The organic was then dried ($Na_2SO_4$) and filtered through a plug of silica. Concentration in vacuo provided the desired product A113 (3.75 g, 98% yield) as a yellow oil. MS [M+H]+=520.0, 522.8. LCMS RT=2.63 min.

Step 2

Intermediate A113 (3.75 g, 7.2 mmol) was taken up 16 mL of DCE and 8 mL TFA. After 1 h stirring at room temperature the reaction mixture was concentrated in vacuo. The residue was taken up in 50 mL DCE and heated to 80° C. for 15 min. After cooling to room temperature this solution was washed with 10% sodium citrate and brine. The organic layer was separated, dried ($Na_2SO_4$), and concentrated in vacuo to provide 3.74 g of crude product as an orange oil. This material was used in the next step without purification. MS [M+H]+= 421.0 LCMS RT=2.73 min.

Step 3

Intermediate A114 (3.74 g, 7.2 mmol, 81% pure) was taken up 50 mL of dry DCM and treated with ethyl malonyl chloride (1.35 mL, 10.7 mL), followed by dropwise addition of 2,6-lutidine (1.14 mL, 10.7 mL) over a 5 min period. After 30 minutes stirring the reaction was diluted with EtOAc (100 mL) and pH 4 citrate buffer. The organic was washed with water (2×) and brine, dried and filtered thru a silica plug. Concentration in vacuo provided the desired intermediate as a dark yellow oil. This material was taken up in 100 mL EtOH and cooled to 0° C. After treatment with NaOEt in EtOH (6.52 mL, 17.84 mmol, 22% by wt) the reaction mixture was allowed to warm to room temperature and stir for 1 h. The reaction mixture was concentrate in vacuo and the residue portioned between EtOAc and 1N KH2PO4. The organic layer was washed with 0.1N KH2PO4, water (2×) and brine. The organics were dried with sodium sulfate and concentrated to provide the desired product A115 (2.79 g, 82% yield) as a brown semi-solid. MS [M+H]+=535.0, 536.9 LCMS RT=2.63 min.

Step 4

Intermediate A115 (2.79 g, 5.9 mmol) was taken up 50 mL of DCM and treated with benzyl bromide (1.16 mL, 9.81 mmol) and silver(I) oxide (7.23 g, 31.22 mmol). After 3 h vigorous stirring the reaction was filtered thru celite and concentrated in vacuo. Purification by silica gel chromatography (ISCO, 120 g cartridge, 0 to 100% EtOAc) provided the desired product A116 (2.43 g, 73% yield). MS [M+H]+= 565.2, 567.1 LCMS RT=2.73 min.

Step 5

To a solution of Intermediate A116 (670 mg, 1.19 mmol) in 10 mL of THF and 2 mL water was added potassium osmate (0.5 mg, 0.1 mol %) and NMO (208 mg, 1.78 mmol) and the reaction mixture allowed to stir at 40° C. for 12 h. The reaction was diluted with EtOAc and 50 mL of 5% sodium sulfite. After stirring for 30 min at room temperature, the organic was washed with water and brine, dried with sodium sulfate and filtered through a silica plug. Concentration in vacuo provided the desired product A117 (640 mg, 90% yield) as a yellow oil. MS [M+H]+=599.1, 600.8 LCMS RT=2.61 min.

Step 6

Intermediate A117 (640 mg, 1.07 mmol) was taken up 20 mL of DMF and cooled to −40° C. A solution of sodium tert-butoxide (103 mg, 1.07 mmol) in 10 mL THF was added dropwise, and the reaction allowed to stir for 5 min. The reaction was then quenched with 1 mL AcOH and diluted with EtOAc and 10% sodium citrate. The organic layer was washed with 5% LiCl (2×) and brine. After drying with sodium sulfate, the organics were concentrated in vacuo to provide an orange oil. Purification by silica gel chromatography (ISCO) provided the desired product A118 (340 mg, 61% yield) as a yellow semi-solid. MS [M+H]+=519.1 LCMS RT=2.53 min.

Step 7

A mixture of Intermediate A118 (340 mg, 0.656 mmol) and 25 mg 5% Pd—C in 5 mL EtOH was stirred under an atmosphere of $H_2$ for 5 min. The reaction was diluted with EtOAc and filtered thru a plug of celite. Concentration of the filtrate provided the desired product A119 (251 mg, 91% yield) as a yellow semi-solid.

MS [M+H]+=428.9 LCMS RT=2.00 min.

Step 8

Intermediate A119 (112 mg g, 0.262 mmol) was taken up in 2 mL DMF and treated with 350 μL ethanolamine. The mixture was heated for 5 min at 120° C. in a microwave reactor. Purification of the reaction mixture by RP HPLC (30 to 100% MeCN) provided the desired product A120 (11.4 mg, 10% yield) as a yellow solid.

$^1$H-NMR (MeOD-$d_4$) d 10.19 (s, 1H), 8.47 (s, 1H), 7.30 (t, 2H, J=6 Hz), 7.07 (t, 2H, J=6 Hz), 4.06 to 3.94 (m, hH), 3.54 (t, J=6 Hz, 2H), 3.46 to 3.38 (m, 4H), 1.16 (s, 3H). MS [M+H]+=444.1 LCMS RT=2.00 min.

Scheme 10

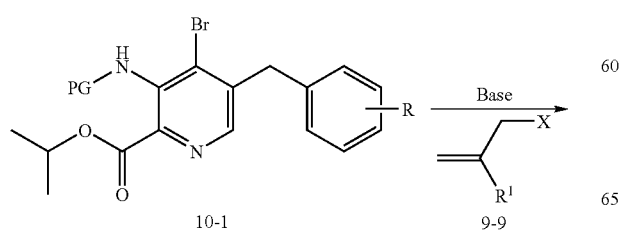

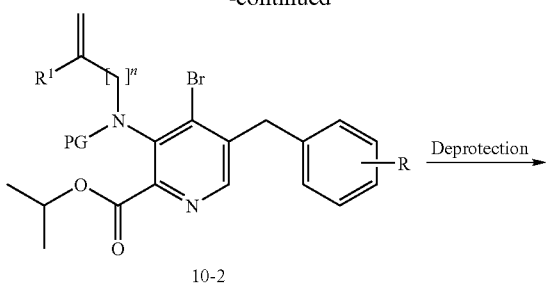

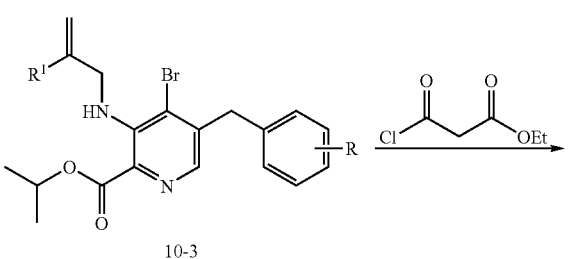

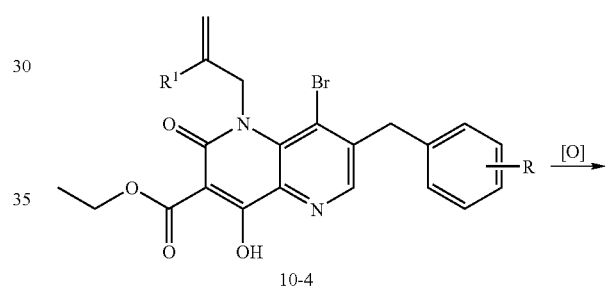

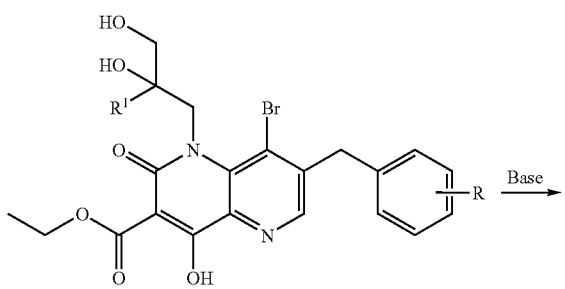

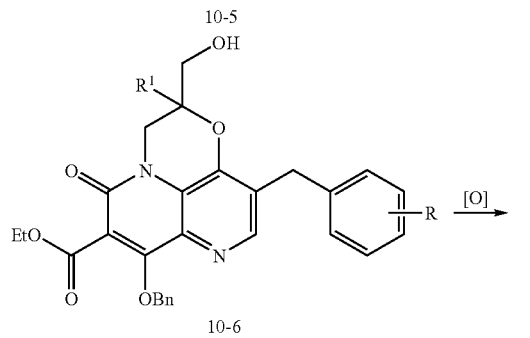

-continued

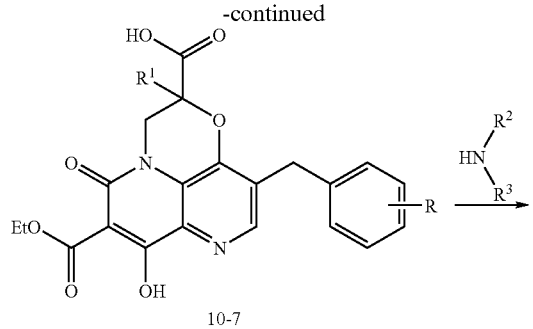
10-7

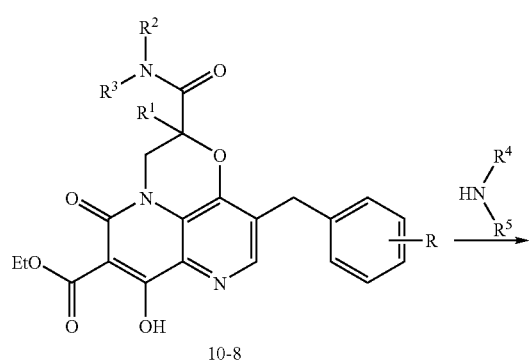
10-8

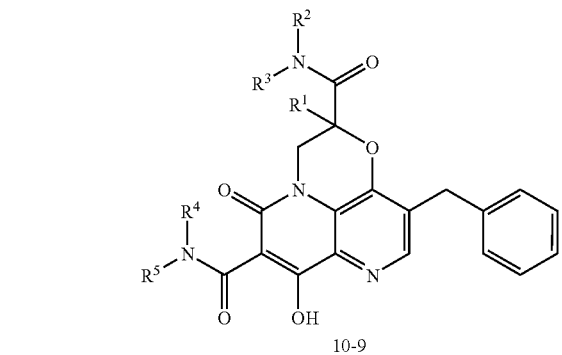
10-9

The compounds of formula 10-9 can be prepared by the methods described in Scheme 10. Treatment of suitably protected compounds of formula 10-1, where PC is a carbamate protecting group such as Boc or the like, with an alkyl halide of formula 10-9, where $R^1$=alkyl, in the presence of a suitable base provides compounds of formula 10-2. Removal of the nitrogen protecting group provides compounds of formula 10-3. Acylation with ethyl malonyl chloride, followed by treatment with a suitable base, such as sodium ethoxide or the like, provides bicyclic heterocycles of formula 10-4. Oxidation of the alkene functionality with a suitable reagent, preferably osmium tetroxide, provides compounds of formula 10-5. Subsequent treatment with a suitable base, such as DBU or the like, provides tricyclic heterocycles of formula 10-6. Oxidation of the alcohol functionality with a suitable oxidizing agent, such as TEMPO, provides compounds of formula 10-7. Treatment with an appropriate 1° or 2°-amine in the presence of a suitable coupling reagent such as py-BOP or the like provides compounds of formula 10-8. Exposure to an appropriate 1° or 2°-amine in the presence of heat provides Compounds of Formula I-G. The substituents $R^2$, $R^3$, $R^4$, and $R^5$ in Scheme 9 can be independently H or substituted alkyl.

Intermediate G
Preparation of Intermediate G

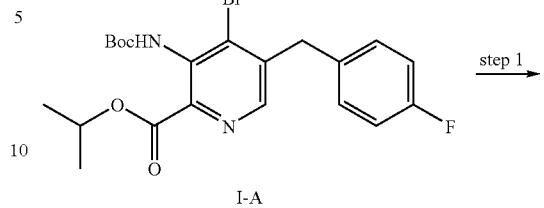
I-A

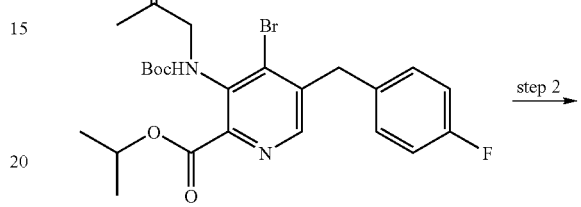
I-B

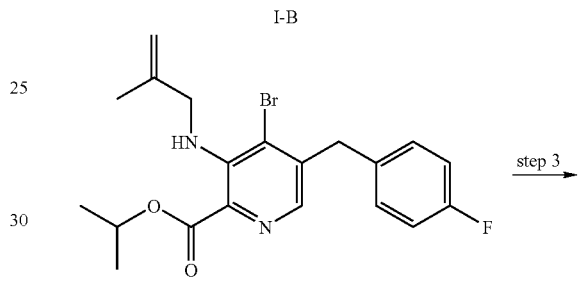
I-C

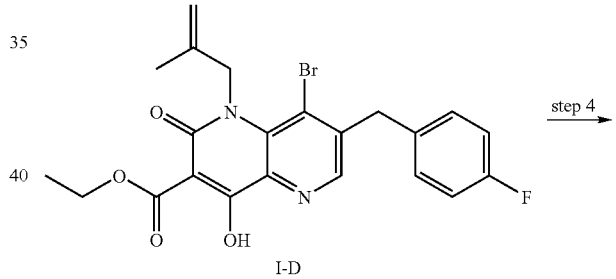
I-D

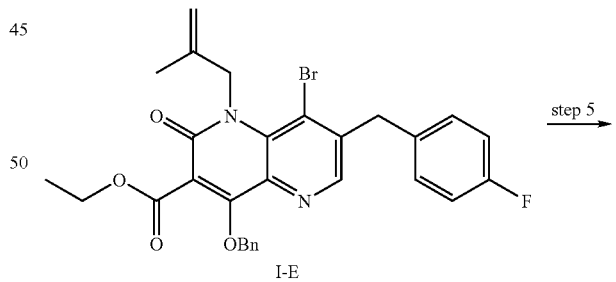
I-E

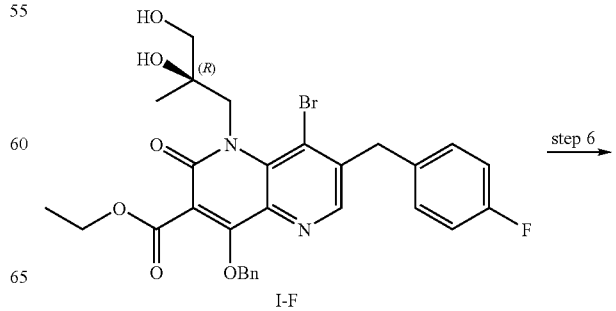
I-F

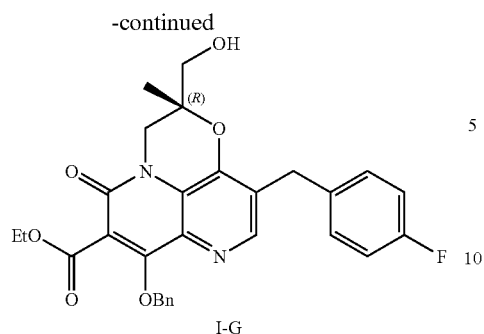

I-G

Step 1

Intermediate B was prepared using the same procedure as for Compound 66, substituting 2-methyl-3-bromopropene for benzyl bromide. $^1$H NMR (CDCl$_3$) δ 8.66 (s, 1H), 8.03 (s, 1H), 7.13 to 7.10 (m, 2H), 7.02 to 6.97 (m, 2H), 5.31 (heptet, J=6 Hz, 1H), 4.03 (s, 3H), 1.35 (d, J=6 Hz, 6H); MS [M−H]= 522.7.

Step 2

Intermediate C was prepared using the same procedure used for preparation of Compound 67. $^1$H NMR (CDCl$_3$) δ 8.99 (s, 1H), 7.10-7.00 (m, 2H), 6.96 (m, 2H), 5.28 (heptet, J=6 Hz, 1H), 4.95 (s, 1H), 4.86 (s, 1H), 4.10 (s, 2H), 3.89 (s, 1H), 3.71 (s, 1H), 1.71 (s, 3H), 1.42 (d, J=6 Hz, 6H); MS [M+H]=423.0.

Step 3

Intermediate D was prepared using the same procedure used for the preparation of Compound 69. MS [M+H]=474.9.

Step 4

Intermediate E was prepared using the same procedure used to prepare Compound 70. $^1$H-NMR (DMSO-d$_6$) d 8.53 (s, 1H) 7.42-7.23 (m, 5H), 7.23-7.17 (m, 2H), 7.17-7.04 (m, 2H), 5.51 (s, 2H), 5.05 (s, 2H), 4.42 (d, 1H) 4.27 (s, 2H), 4.19 (q, J=7 Hz, 2H), 4.02 (m, 1H), 1.59 (s, 3H), 1.15 (t, J=7 Hz, 3H); MS [M+H]=566.9.

Step 5

A solution of 80 mL water and 65 mL t-BuOH was treated with 18.34 g of AD-mix-B and stirred vigorously for 5 min. The mixture was then cooled to 0° C. in an ice bath treated with (DHQD)$_2$-PHAL (1.28 g, 1.63 mmol) and potassium osmate dihydrate (120 mg, 0.32 mmol). After 30 min of stirring, a solution of Intermediate E (7.42 g, 13.1 mmol) in 8 mL Acetone and 24 mL t-BuOH was added dropwise over 3 h. The reaction was then allowed to warm to room temperature and diluted with 500 mL EtOAc and 500 mL of a 5% NaHSO$_3$ solution. This mixture was stirred vigorously for 30 min and the layers were separated. The organic layer was washed with 10% citric acid solution, sat. sodium bicarbonate and brine. After drying with sodium sulfate, the organics were concentrated in vacuo. The crude product was purified by silica chromatography (ISCO 220 g Cartridge, 0 to 100% EtOAc) to provide Intermediate F (7.49 g, 95%) as a light brown oil. Mosher analysis indicated 81% ee. $^1$H-NMR (DMSO) d 8.45 (s, 1H), 7.41-7.30 (s, 5H), 7.22 to 7.17 (m, 2H), 7.11 to 7.06 (m, 2H), 5.52 (s, 2H), 5.04-4.93 (m, 2H), 4.26 (s, 2H), 4.17 (apparent q, J=6 Hz, 2H), 3.99 (apparent q, J=7 Hz, 2H), 3.04 to 2.96 (m, 2H), 1.45 (d, J=6 Hz, 6H), 0.69 (s, 3H), 1.14 (t, J=6 Hz, 3H); MS [M+H]=600.9

Step 6

A solution of Intermediate F (5.46 g, 9.11 mmol) in 500 mL DMSO was degassed by bubbling Ar through the solution for 30 min. DBU was then added (10.3 g, 68.3 mmol) and the reaction heated in an 80° C. reaction block for 1 h. The reaction was quenched with 5 mL AcOH and connected to a short path distillation apparatus. The DMSO was removed under vacuum (temp 60° C.) and the residue partitioned between EtOAc and 10% citric acid. The organic was washed with water, 10% sodium citrate and brine, then dried with sodium sulfate and concentrated in vacuo. The residue was purified by column chromatography (ISCO, 125 g cartridge, 0% to 100% EtOAc) to provide Intermediate G (3.38 g, 72% Yield). MS [M+H]=519.1.

Intermediate I

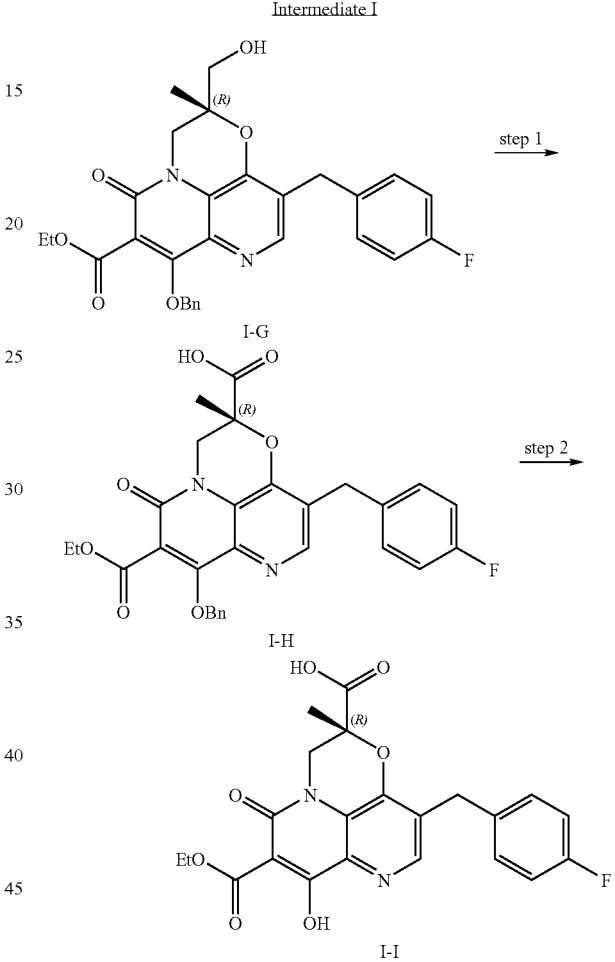

Step 1

A solution of Intermediate G (3.38 g, 6.55 mmol), TEMPO (204 mg, 1.31 mmol) and BAIB (2.53 g, 7.86 mmol) in 20 mL DCM was diluted with 4 mL water and left to stir for 16 h at room temperature. The volatiles were removed under a hard vacuum to provide an off-white solid. This was triturated with DCM:hexanes to provide compound GG (2.96 g, 85% Yield). This material was recrystallized from IPA to provide Intermediate H (2.35 g, 67% Yield) as white, needle-like crystals. Analysis by Chiral HPLC indicated the sample was >95% ee. $^1$H-NMR (DMSO) d 13.62 (bs, 1H), 8.43 (s, 1H), 7.41-7.30 (m, 7H), 7.11-7.05 (m, 2H), 5.60 (app q, J=14 Hz, 2H), 4.88 (d, J=14 Hz, 1H), 4.16 (q, J=7 Hz, 2H), 4.06-4.04 (m, 2H), 3.67 (d, J=14 hz, 1H), 1.76 (s, 3H), 1.14 (t, J=7 Hz, 3H); MS [M+H]=533.1.

Step 2

A mixture of Intermediate H (862 mg g, 1.61 mmol) and 50 mg 10% Pd—C in 5 mL DMF was stirred vigorously under H₂ for 15 min. The mixture was then filtered thru celite, rinsing with DMF to provide a 0.1 M solution of the desired product in DMF. This stock solution of Intermediate I was used in subsequent steps. MS [M+H]=442.9.

Intermediate J

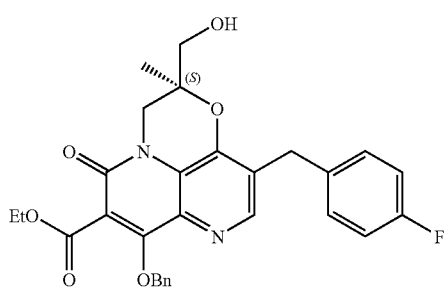

I-J

Step 1

Intermediate J was prepared using the same method used to prepare I-G, by substituting AD-mix-® and (DHQ)₂PHAL. MS [M+H]=519.0.

Intermediate K

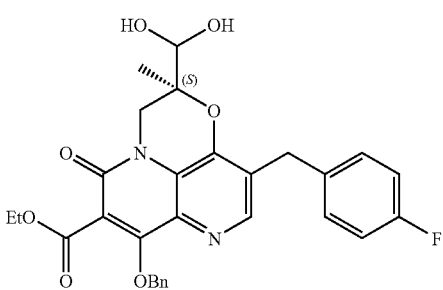

I-K

Step 1

Intermediate K was prepared using the same procedure used to prepare Intermediate H. ¹H-NMR (DMSO) 8.43 (s, 1H), 7.43-7.31 (m, 7H), 7.12-7.06 (m, 2H), 5.64 (app q, J=14 Hz, 2H), 4.88 (d, J=14 Hz, 1H), 4.16 (q, J=7 Hz, 2H), 4.06-4.02 (m, 2H), 3.66 (d, J=14 hz, 1H), 1.76 (s, 3H), 1.14 (t, J=7 Hz, 3H); MS [M+H]=442.9.

EXAMPLE 69

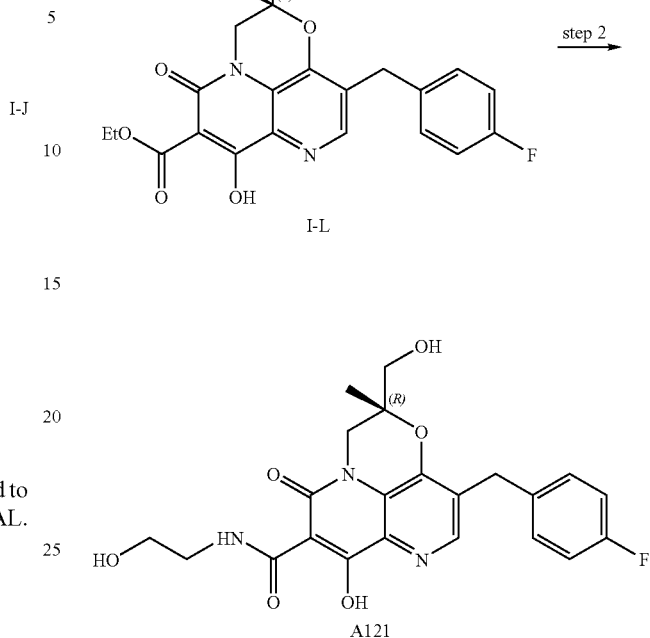

Step 1

Intermediate L was prepared using the same hydrogenation conditions as Intermediate 1. MS [M+H]⁺=429.2.

Step 2

A solution of Intermediate L (96 mg, 0.22 mmol) and 0.5 mL ethanolamine in 5 mL DMF was heated to 120 C for 20 min. The reaction was cooled to room temperature and diluted with 100 mL EtOAc. The solution was washed with 10% citric acid, 10% citrate buffer (pH 6.0) and sat. LiCl solution. The organic layer was dried with sodium sulfate and concentrated in vacuo. The residue was triturated with ether to provide the desired product (57 mg, 58% yield) as an off-white powder. ¹H-NMR (DMSO) 10.31 (t, J=6 Hz, 1H), 8.43 (s, 1H), 7.32-7.28 (m, 2H), 7.09-7.04 (m, 2H), 5.27 (t, J=6 Hz, 1H), 4.89 (t, J=5 Hz, 1H), 4.02-3.93 (m, 4H), 3.55-3.51 (m, 2H), 3.45-3.36 (m 4H), 1.15 (s, 3H); MS [M+H]⁺=444.1.

EXAMPLE 70

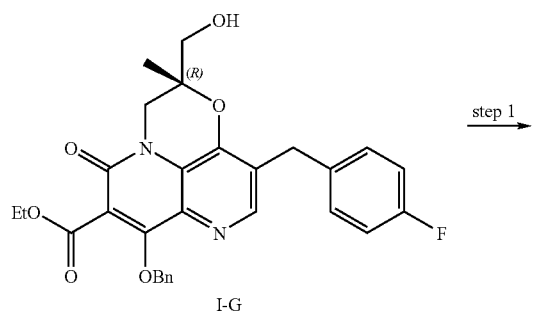

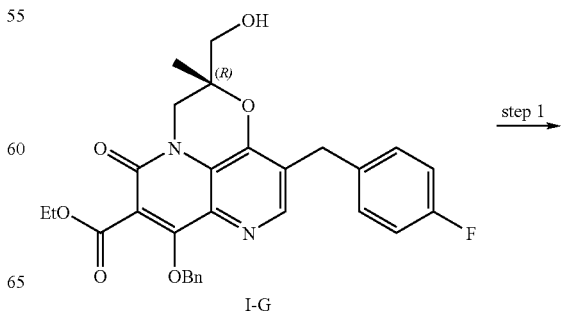

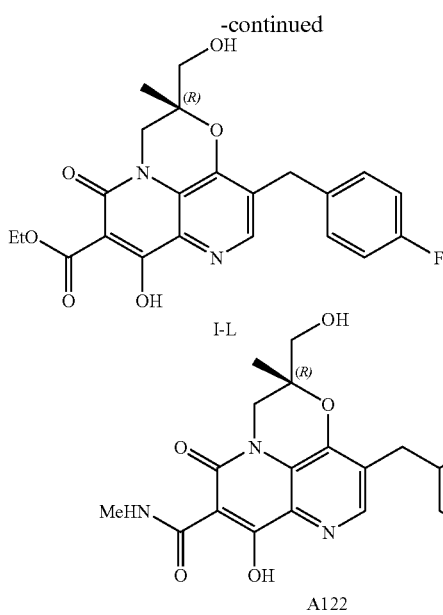

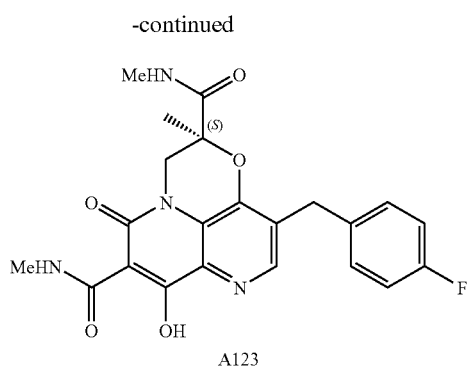

Example 70 was prepared in the same manner as Example 69, by substituting methylamine for ethanolamine in step 2. $^1$H-NMR (DMSO) 10.02 (bs, 1H), 8.43 (s, 1H), 7.32-7.28 (m, 2H), 7.09-7.04 (m, 2H), 5.27 (t, J=6 Hz, 1H), 4.01-3.96 (m, 4H), 3.42-3.39 (m, 2H), 2.88 (d, J=5 Hz, 1H), 1.14 (s, 3H); $^{19}$F NMR (376 MHz, DMSO-$d_6$) d −116.10 (m); MS [M+H]$^+$= 487.12.

EXAMPLE 71

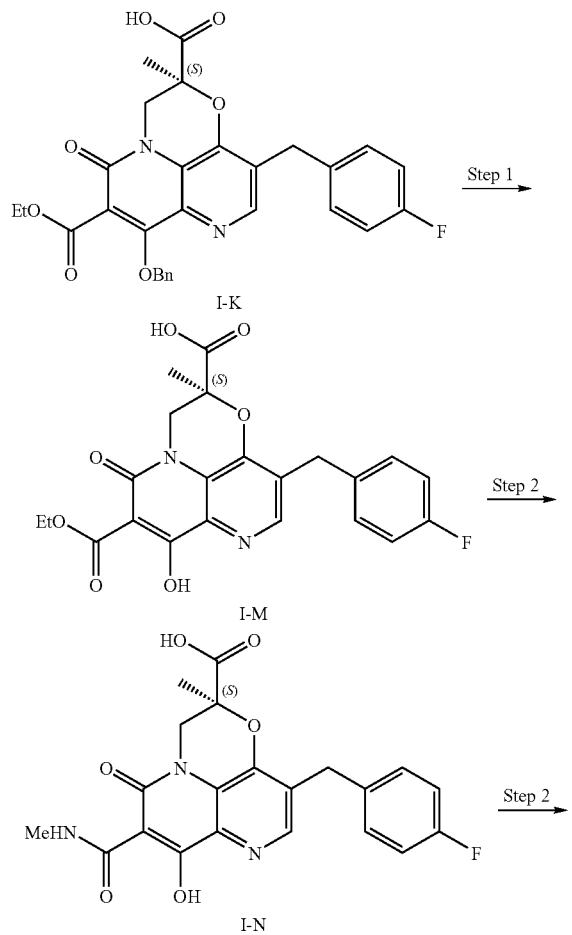

Step 1
Intermediate M was prepared using the same hydrogenation conditions as Intermediate I. MS [M+H]=442.9.

Step 2
Intermediate N was prepared using the same procedure used for example 1, substituting methylamine for ethanolamine. MS [M+H]$^+$=428.1.

Step 3
A solution of Intermediate N (315 mg, 0.74 mmol) in 15 mL DMF was treated with DIEA (122 μL, 0.7 mmol), providing a homogeneous solution. A solution of methylamine in THF (700 μL, 1.4 mmol, 2M) was added, followed by BOP reagent (300 mg, 0.71 mmol). After 5 min stirring, the reaction was diluted with 100 mL EtOAc. The solution was then washed with 10% citric acid, 10% citrate buffer (pH 6.0), water (2 times) and sat. LiCl solution. The organic layer was dried with sodium sulfate and concentrated in vacuo. The residue was stirred with ether:water (3:1) for 1 hr and then filtered to provide the desired product (269 mg, 84% yield) as an off-white powder. $^1$H-NMR (DMSO-$d_4$) d 9.96 (s, 1H), 8.42 (s, 1H), 7.83 (s, 1H), 7.26-7.20 (m, 2H), 7.12-7.06 (m, 2H), 4.53 (d, J=14 Hz, 1H), 4.30 (d, J=14 Hz), 4.05 (d, J=14 Hz, 1H), 3.87 (d, J=15 Hz, 1H), 2.88 (d, J=4 Hz, 3H), 2.52 (d, J=4 Hz, 3H), 1.46 (s, 3H); MS [M+H]$^+$=441.1, rt=2.24 min.

EXAMPLE 72

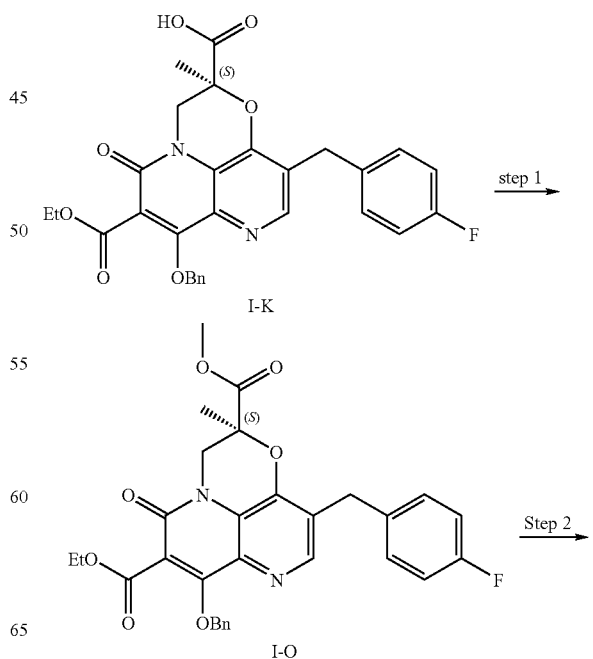

157

-continued

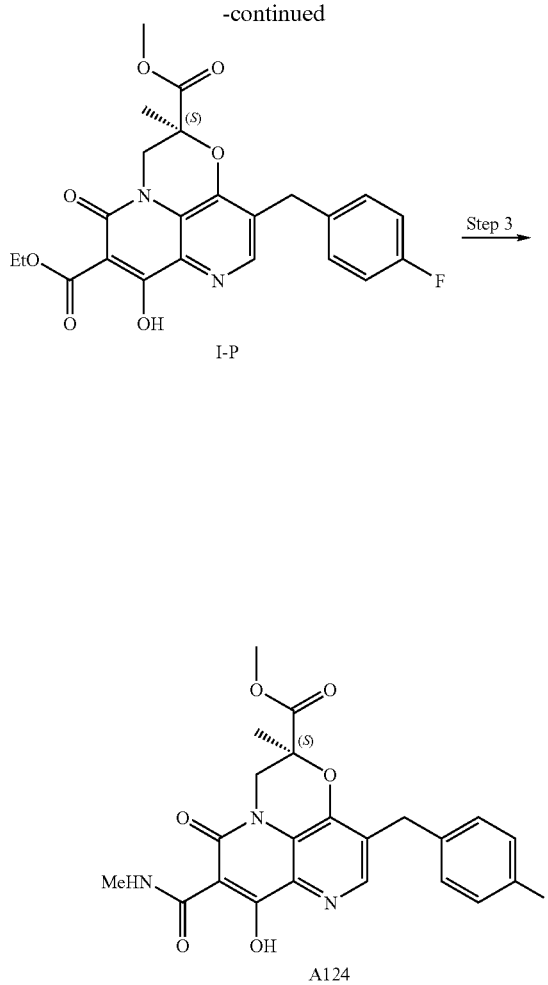

I-P

A124

Step 1

Intermediate D (150 mg, 0.28 mmol) was taken up in 5 mL MeOH and 5 mL Toluene and cooled to 0° C. TMS-diazomethane (1.0 mL, 2 mmol, 2 M in ether) was added dropwise and the reaction allowed to stir for 15 min. Excess diazomethane was quenched with 250 µL AcOH and the Reaction mixture was concentrated in vacuo to provide the desired product (135 mg, 85 mg) as a tan oil. $^{0.1}$H-NMR (DMSO-$d_6$) d 8.46 (s, 1H), 7.40-7.31 (m, 7H), 7.13-7.08 (m, 2H), 5.60 (app t, J=11 Hz, 2H), 4.84 (d, J=14 Hz, 1H), 4.18 (t, J=7 Hz, 2H), 4.05 (app q, J=12 Hz, 2H), 3.53 (s, 3H), 1.71 (s, 3H), 1.14 (t, J=7 Hz, 3H); MS [M+H]$^+$=547.1.

Step 2 & 3

The crude product from step 1 was taken up in 2.5 mL DMF and stirred with 25 mg 10% Pd—C under H$_2$ for 10 min. The solution was filtered thru celite and a solution of methylamine in THF (1 mL, 2 M, 2 mmol) was added. The mixture was heated to 120° C. for 10 min, then cooled to room temperature and partitioned between EtOAc and citrate buffer (pH 5.0). The organic layer was dried with sodium sulfate and concentrated in vacuo to provide an off-white solid. Trituration with ethyl acetate provided the desired product (51.3 mg, 38% Yield).

$^{0.1}$H-NMR (DMSO-$d_6$) d 9.92 (bs, 1H), 8.45 (s, 1H), 7.36-7.31 (m, 2H), 7.12-7.05 (m, 2H), 4.92 (d, J=14 Hz, 1H), 4.06 (app q, J=14 Hz, 2H), 3.71 (d, J=14 Hz, 1H), 3.51 (s, 3H), 2.87 (d, J=5 Hz, 3H), 1.71 (s, 3H); $^{19}$F NMR (376 MHz, DMSO-$d_6$) d 116.8 (m); MS [M+H]$^+$=442.1.

EXAMPLE 73

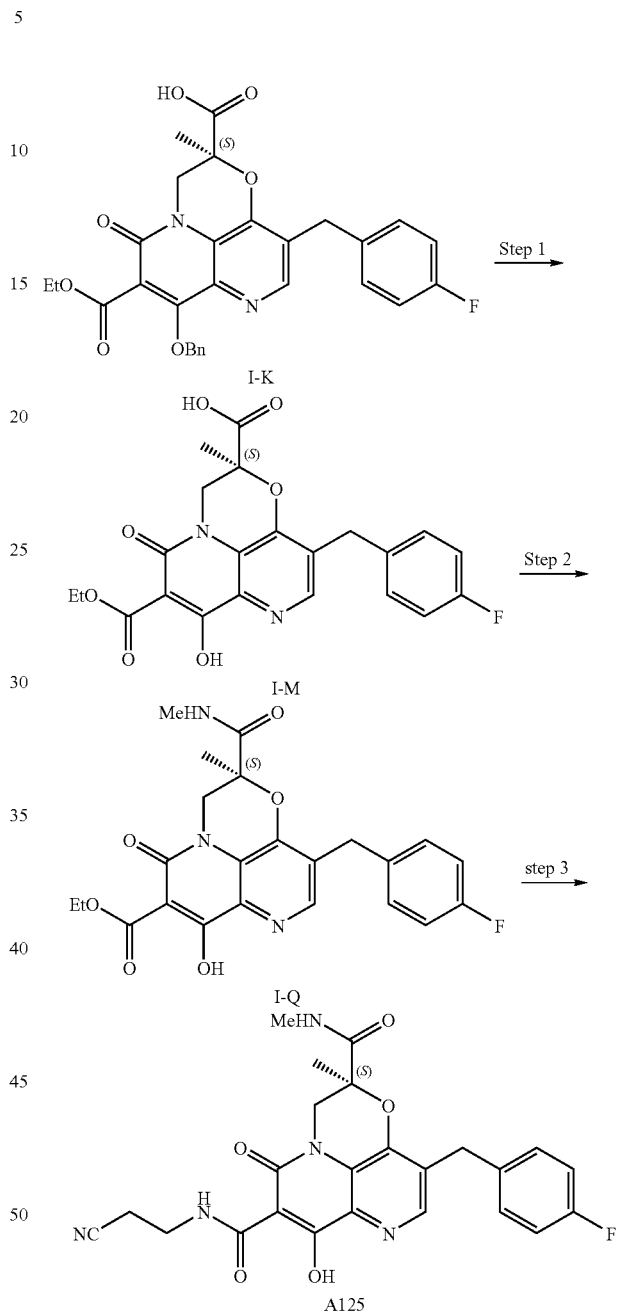

Step 1

Intermediate M was prepared using the same hydrogenation conditions as Intermediate I. MS [M+H]=442.9.

Step 2

Intermediate M was prepared using the same amide coupling conditions used for Example 3. MS [M+H]$^+$=456.2.

Step 3

Example 73 was prepared using the same procedure used for Example 1, by substituting methylamine for ethanolamine. $^{0.1}$H-NMR (DMSO-$d_6$) d 10.31 (bs, 1H), 8.44 (s, 1H), 7.83 (d, J=5 Hz, 1H), 7.36-7.32 (m, 2H), 7.12-7.07 (m, 2H), 4.54 (d, J=14 Hz, 1H), 4.30 (d, J=14 Hz, 1H), 4.05 (d, J=14

Hz, 1H), 3.89 (d, J=14 Hz, 1H), 3.65-3.60 (m, 2H), 3.34-3.28 (m, 2H), 2.88 (t, J=6 Hz, 1H), 2.63 (d, J=5 Hz, 1H), 1.47 (s, 3H); $^{19}$F NMR (376 MHz, DMSO-$d_6$) δ 116.8 (m); MS [M+H]$^+$=480.2.

EXAMPLE 74

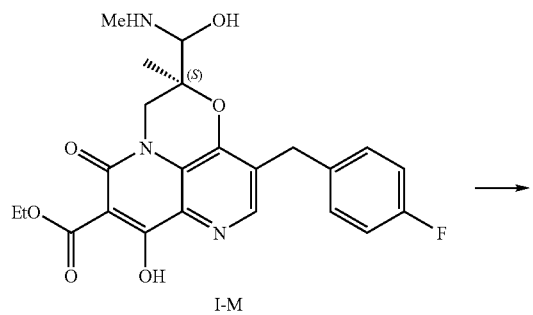

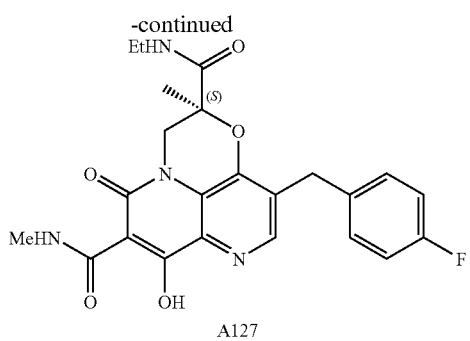

Example 75 was prepared using the same procedure used for Example 3, substituting ethylamine for methylamine in step 2. $^1$H-NMR (DMSO-$d_6$) d 9.97 (s, 1H), 8.43 (s, 1H), 7.81 (bs, 1H), 7.37-7.33 (m, 2H), 7.12-7.07 (m, 2H), 4.56 (d, J=14 Hz, 1H), 4.27 (d, J=14 Hz, 1H), 4.05 (d, J=14 Hz, 1H), 3.84 (d, J=14 Hz, 1H), 3.34 (q, J=7 Hz, 2H), 32.88 (d, J=4 Hz, 3H), 1.47 (s, 3H), 1.06 (t, J=7 Hz, 3H); MS [M+H]$^+$=455.2.

EXAMPLE 76

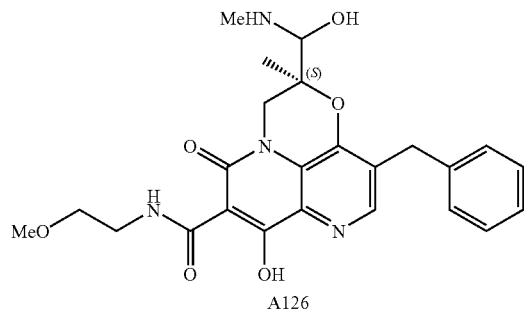

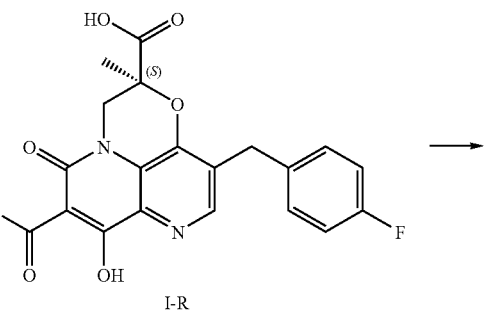

Example 74 was prepared in the same manner as Example 1, by substituting methoxyethylamine for ethanolamine in step 2. $^{0.1}$H-NMR (DMSO-$d_6$) d 10.24 (s, 1H), 8.43 (s, 1H), 7.84 (s, 1H), 7.36-7.28 (m, 2H), 7.21-7.07 (m, 2H), 4.56 (d, J=14 Hz, 1H), 4.30 (d, J=14 Hz, 1H), 4.05 (d, J=14 Hz, 1H), 3.86 (d, J=14 Hz, 1H), 3.57-3.48 (m, 4H), 3.26 (s, 3H), 2.52 (d, J=4 Hz, 3H), 1.47 (s, 3H); $^{19}$F NMR (376 MHz, DMSO-$d_6$) d −71.1 (s, TFA), −116.7 (m); MS [M+H]$^+$=485.2.

EXAMPLE 75

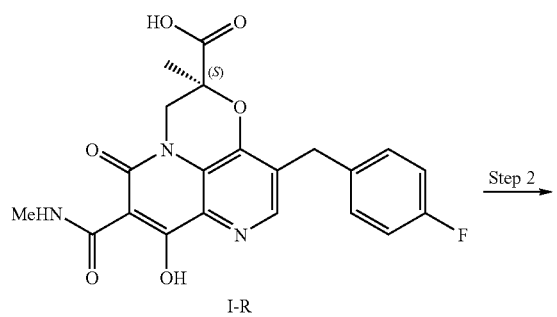

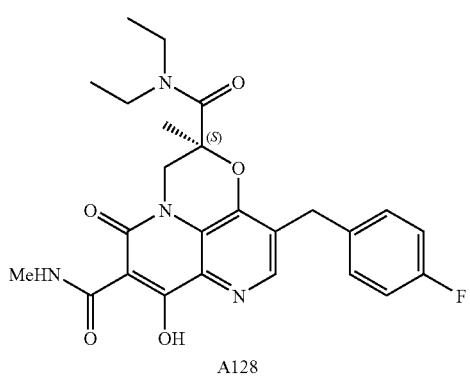

Example 76 was prepared using the same procedure used for Example 71, substituting diethylamine for methylamine in step 2. $^1$H-NMR (DMSO-$d_6$) d 10.03 (s, 1H), 8.37 (s, 1H), 7.26-7.22 (m, 2H), 7.12-7.07 (m, 2H), 4.60 (d, J=14 Hz, 1H), 4.17 (d, J=14 Hz, 1H), 4.05 (d, J=14 Hz, 1H), 3.91 (d, J=14 Hz, 1H), 3.75-3.61 (m, 1H), 3.54-3.40 (m, 1H), 3.25-3.18 (m, 1H), 3.18-3.03 (m, 1H), 2.90 (d, J=5 Hz, 3H), 1.60 (s, 3H), 1.03 (m, 3H), 0.78 (m, 3H); MS [M+H]⁺=483.2.

EXAMPLE 77

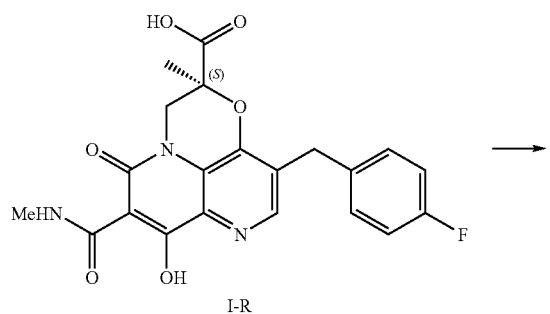

I-R

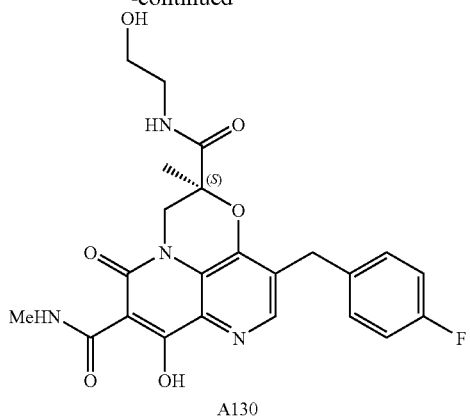

A130

Example 78 was prepared in the same manner as Example 71 using ethanolamine in place of methylamine. $^{0.1}$H-NMR (DMSO-d₆) d 9.98 (s, 1H), 8.43 (s, 1H), 7.85-7.78 (m, 1H), 7.37-7.32 (m, 2H), 7.12-7.05 (m, 2H), 4.51 (d, J=14 Hz, 1H), 4.26 (d, J=14 Hz, 1H), 4.05 (d, J=14 Hz, 1H), 3.89 (d, J=14 Hz, 1H), 3.26 to 3.20 (m, 2H), 3.12-3.03 (m, 2H), 2.88 (d, J=5 Hz, 2H), 1.45 (s, 3H); $^{19}$F NMR (376 MHz, DMSO-d₆) –116.7 (m); MS [M+H]⁺=471.1.

EXAMPLE 79

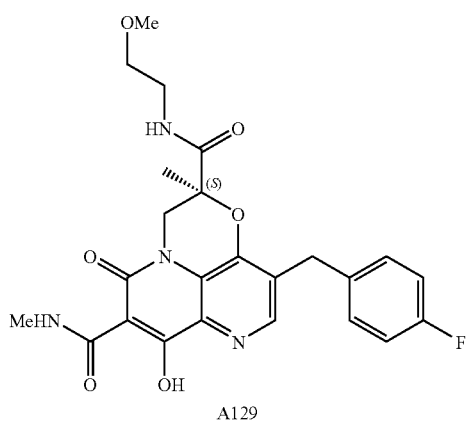

A129

Example 77 was prepared in the same manner as Example 71 using 2-methoxyethylamine in place of methylamine. $^{0.1}$H-NMR (DMSO-d₆) d 9.99 (s, 1H), 7.85 to 7.83 (m 1H), 7.37-7.33 (m, 2H), 7.09 (t, H=9 Hz, 2H), 4.63 (d, J=14 Hz, 1H), 4.27 (d, J=14 Hz, 1H) 4.04 (d, J=15 Hz, 1H), 3.80 (d, J=14 Hz, 1H), 3.20 to 3.04 (m, 4H), 3.03 (s, 3H), 2.88 (d, J=5 Hz, 3H), 1.49 (s, 3H). $^{19}$F NMR (376 MHz, CH₃OH-d₄) –116.7 (m); MS [M+H]⁺=485.2.

EXAMPLE 78

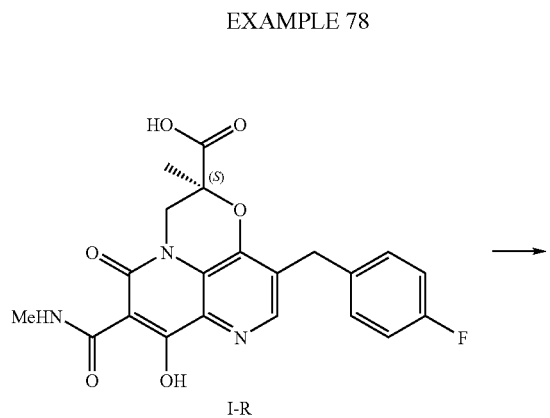

I-R

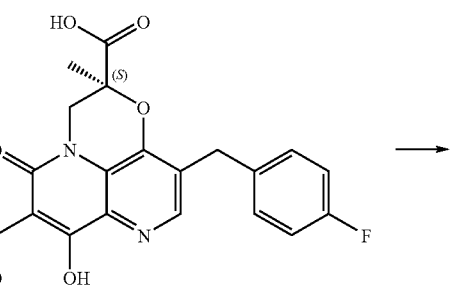

I-R

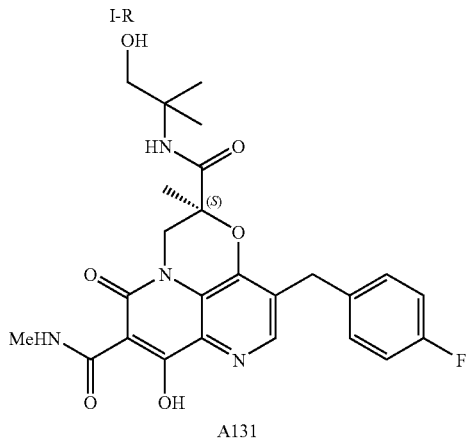

A131

Example 79 was prepared in the same manner as Example 71 by using 2-amino-2-methylpropane-1-ol in place of methylamine. $^{0.1}$H-NMR (DMSO-d₆) d 10.03 (s, 1H), 8.37 (s, 1H), 7.26-7.22 (m, 2H), 7.12-7.07 (m, 2H), 4.62 (d, J=14 Hz, 1H), 4.16 (d, J=16 Hz, 1H), 4.05 (d, J=16 Hz, 1H), 3.91 (d, J=14 Hz, 1H), 3.71-3.62 (m, 1H), 3.40-3.49 (m, 1H), 3.21-

3.10 (m, 1H), 3.10-3.12 (m, 1H), 2.89 (d, J=5 Hz, 3H), 2.77 (d, J=10 Hz, 1H), 1.60 (s, 3H), 1.03 (s, 1H), 0.78 (s, 3H); MS [M+H]+=499.2.

EXAMPLE 80

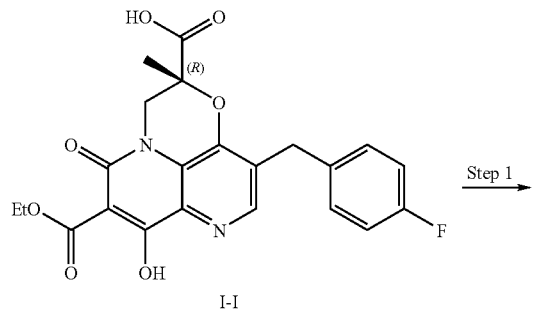
I-I

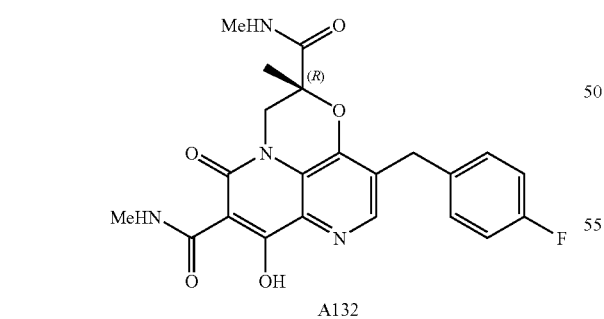

Example 80 was prepared in the same manner as Example 71 by substituting Intermediate I for Intermediate M. ¹H-NMR (DMSO-d₄) d 9.97 (s, 1H), 8.42 (s, 1H), 7.83 (s, 1H), 7.33 (t, J=8 Hz, 2H), 7.10 (t, J=8 Hz, 2H), 4.53 (d, J=14 Hz, 1H), 4.30 (d, J=14 Hz), 4.05 (d, J=14 Hz, 1H), 3.87 (d, J=15 Hz, 1H), 2.88 (d, J=4 Hz, 3H), 2.52 (d, J=4 Hz, 3H), 1.46 (s, 3H); $^{19}$F NMR (376 MHz, CH₃OH-d₄) d −116.7 (m); MS [M+H]+=441.1, rt=2.24 min.

EXAMPLE 81

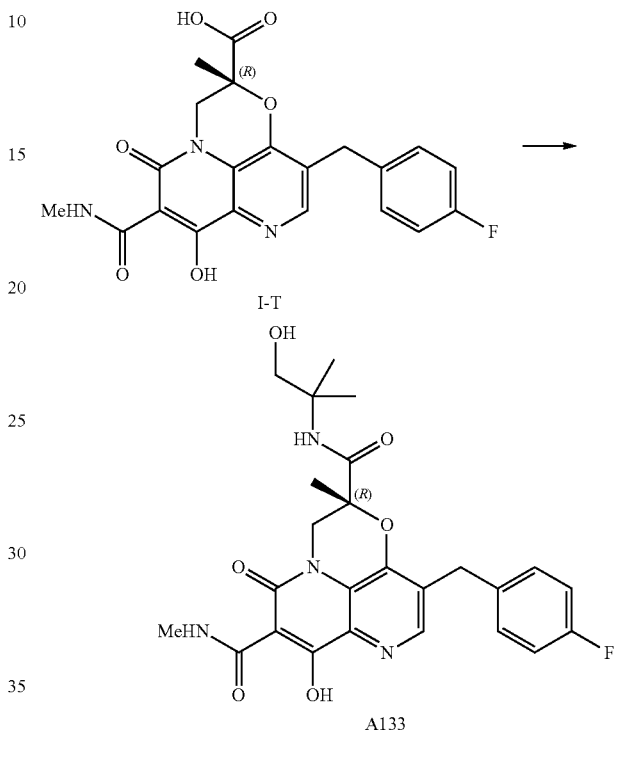

Example 81 was prepared from Intermediate T in the same manner as Example 80 by substituting 1,1-dimethyl-ethanolamine for methylamine. $^{0.1}$H-NMR (DMSO-d₆) d 9.98 (s, 1H), 8.44 (s, 1H), 7.37-7.33 (m, 2H), 7.77-7.08 (m, 2H), 4.93, (t, 1H), 4.52 (d, J=14 Hz, 1H), 4.16 (d, J=14 Hz, 1H), 4.05 (d, J=14 Hz, 1H), 3.86 (d, J=14 Hz, 1H), 3.28 to 3.20 (m, 2H), 2.88 (d, J=5 Hz, 3H), 1.45 (s, 3H), 1.08 (s, 3H), 0.99 (s, 3H); $^{19}$F NMR (376 MHz, DMSO-d₆) d −116.7 (m); MS [M+H]+= 499.1, rt=2.24 min.

EXAMPLE 82

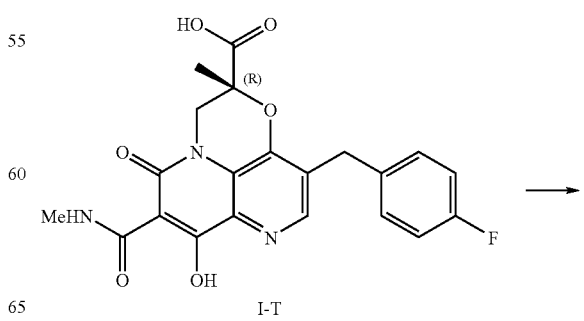
I-T

-continued

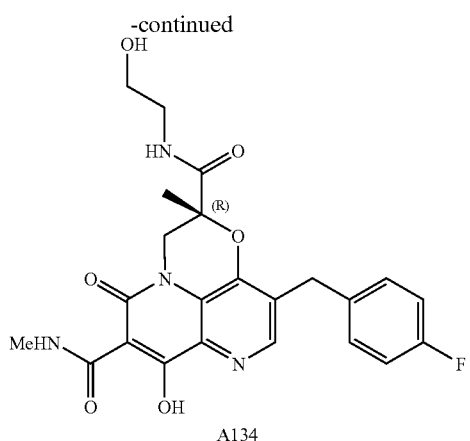

A134

Example 82 was prepared from Intermediate T in the same manner as Example 80 by substituting ethanolamine for methylamine. [0.1]H-NMR (DMSO-$d_6$) d 9.97 (d, J=4 Hz, 1H), 8.43 (s, 1H), 7.83 (t, J=4 Hz, 1H), 7.37-7.32 (m, 2H), 7.11-7.05 (m, 2H), 4.62 (t, J=5 Hz, 1H), 4.50 (6, J=14 Hz, 1H), 4.26 (d, J=14 Hz, 1H), 4.05 (d, J=14 Hz, 1H), 3.90 (4, J=14 Hz, 1H), 3.29-3.21 (m, 2H), 3.08-3.05 (m, 2H), 2.88 (d, J=4 Hz, 3H), 1.45 (s, 3H); $^{19}$F NMR (376 MHz, DMSO-$d_6$) d −116.7 (m); MS [M+H]$^+$=471.1, rt=2.05 min.

EXAMPLE 83

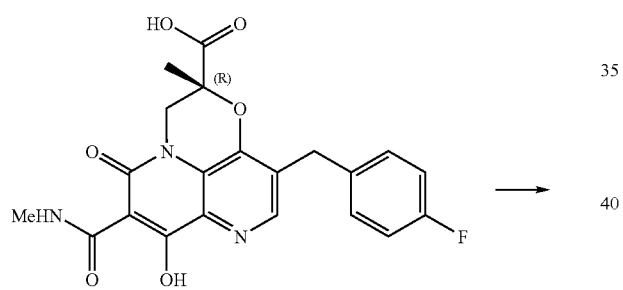

A135

Example 83 was prepared from Intermediate T in the same manner as Example 80 by substituting cyano-ethanolamine for methylamine. [0.1]H-NMR (DMSO-$d_6$) d 9.96 (d, J=5 Hz, 1H), 8.43 (s, 1H), 8.36 (t, J=5 Hz, 1H), 7.38-7.34 (m, 2H), 7.11-7.06 (m, 2H), 4.54 (d, J=13 Hz, 1H), 4.32 (d, J=14 Hz, 1H), 4.03 (d, J=14 Hz, 1H), 3.90 (d, J=13 Hz, 1H), 3.29-3.23 (m, 2H, 2.88 (d, J=5 Hz, 1H), 2.56 (t, J=6 Hz, 2H), 1.46 (s, 3H); $^{19}$F NMR (376 MHz, DMSO-$d_6$) d −116.7 (m); MS [M+H]$^+$=480.1, rt=2.20 min.

EXAMPLE 84

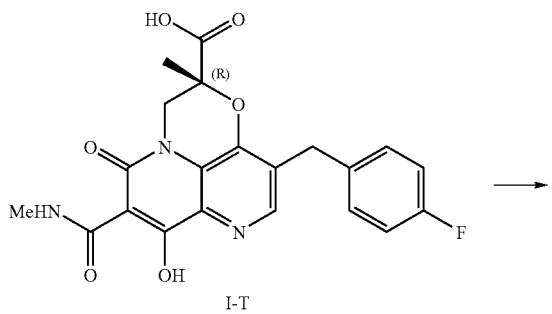

I-T

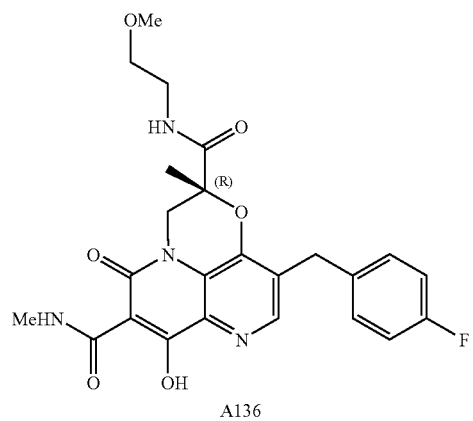

A136

Example 84 was prepared from Intermediate T in the same manner as Example 80 by substituting 2-methoxyethylamine for methylamine. [0.1]H-NMR (DMSO-$d_6$) d 9.98 (s, 1H), 8.43 (s, 1H), 7.83 (1s, 1H), 7.38-7.33 (m, 2H), 7.12-7.06 (m, 2H), 4.63 (d, J=14 Hz, 1H), 4.28 (d, J=14 Hz, 1H), 4.05, (d, J=14 Hz, 1H), 3.80 (d, J=14 Hz, 1N), 3.21-3.03 (m, 4H), 3.03 (s, 3H), 2.88 (d, J=5 Hz, 3H), 1.49 (s, 3H); $^{19}$F NMR (376 MHz, DMSO-$d_6$) d −116.7; MS [M+H]$^+$=485.1, rt=2.24 min.

EXAMPLE 85

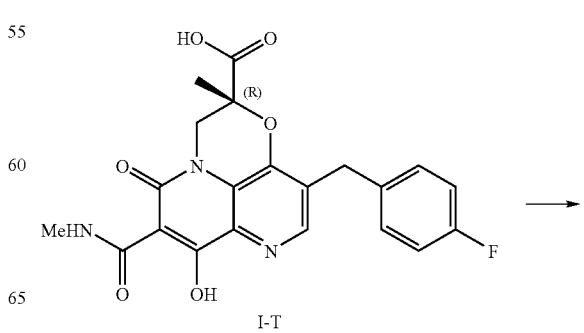

I-T

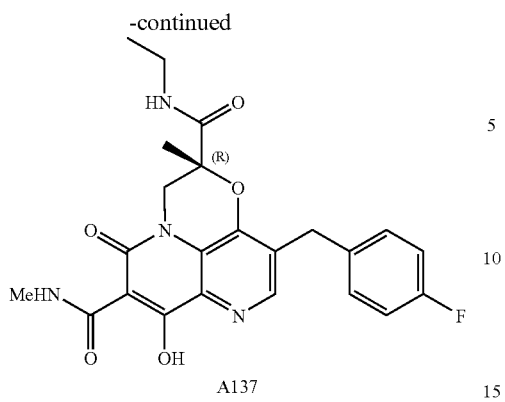

A137

Example 85 was prepared from Intermediate T in the same manner as Example 80 by substituting ethylamine for methylamine. [0.1]H-NMR (DMSO-$d_6$) d 9.97 (bs, 1H), 8.44 (s, 1H), 7.98 (d, J=6 Hz, 1H), 7.37-7.33 (m, 2H), 7.12-7.06 (m, 2H), 4.57 (d, J=13 Hz, 1H), 4.28 (d, J=14 Hz, 1H), 4.05 (d, J=14 Hz, 1H), 3.84 (d, J=13 Hz, 1H), 2.98 (dq, J=7, 6 Hz, 2H), 2.88 (d, J=5 Hz, 3H), 1.47 (s, 3H), 0.85 (t, J=7 Hz, 3H); $^{19}$F NMR (376 MHz, DMSO-$d_6$) d −116.7 (m); MS [M+H]$^+$=455.1, rt=2.29 min.

EXAMPLE 86

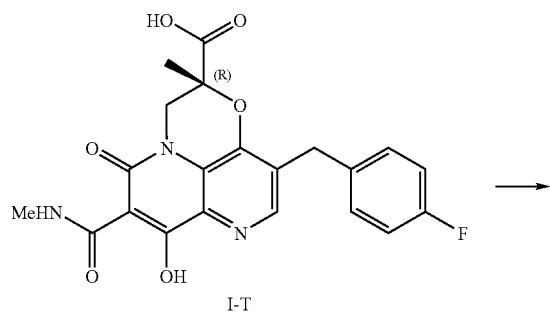

I-T

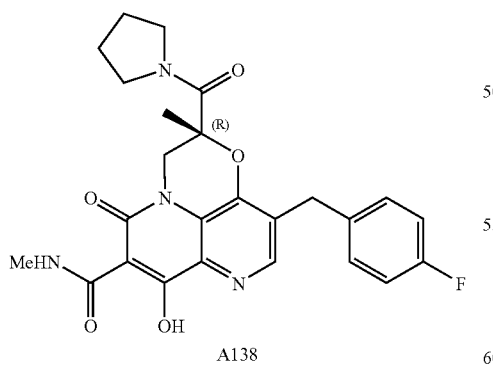

A138

Example 86 was prepared from Intermediate T in the same manner as Example 80 by substituting pyrollidine for methylamine. [0.1]H-NMR (DMSO-$d_6$) d 10.01 (d, J=5 Hz, 1H), 8.39 (s, 1H), 7.26-7.20 (m, 2H), 7.12-7.07 (m, 2H), 4.61 (d, J=14 Hz, 1H), 4.16 (d, J=14 Hz, 1H), 4.06 (d, J=14 Hz, 1H), 3.89 (d, J=14 Hz, 1H), 3.69-3.60 (m, 1H), 3.40-3.13 (m, 3H), 2.89 (d, J=4 Hz, 3H), 1.79-1.59 (m, 4H), 1.55 (s, 3H; MS [M+H]$^+$= 481.1, rt=2.29 min.

EXAMPLE 87

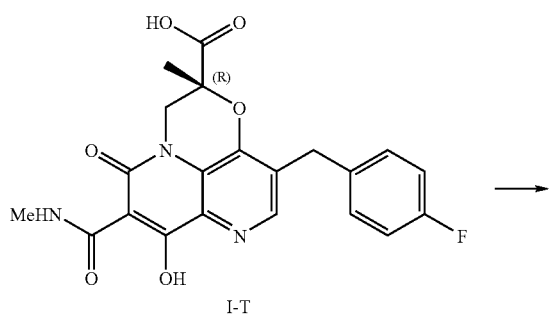

I-T

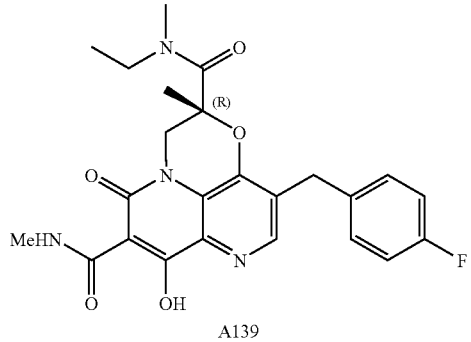

A139

Example 87 was prepared from Intermediate T in the same manner as Example 80 by substituting N-methyl-N-ethylamine for methylamine [0.1]H-NMR (DMSO-$d_6$) d 10.02 (s, 1H), 8.34 (s, 1H), 7.25-7.22 (m, 2H), 7.12-7.07 (m, 2H), 4.80-4.71 (m, 1H), 4.19 (d, J=14 Hz, 1H), 4.07 (d, J=14 Hz, 1H), 3.25-3.04 (m, 2H), 2.88 (d, J=5 Hz, 3H), 1.63 (s, 3H), 0.080 (m, 3H); $^{19}$F NMR (376 MHz, DMSO-$d_6$) d 116.6 (s); MS [M+H]$^+$=469.1.

EXAMPLE 88

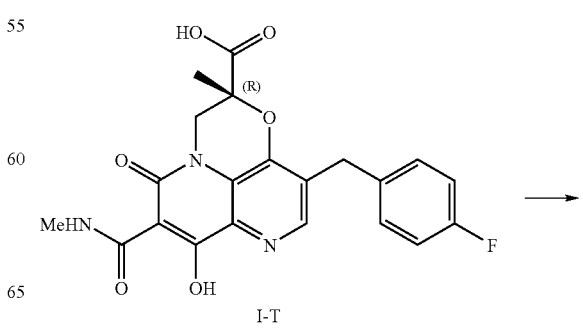

I-T

-continued

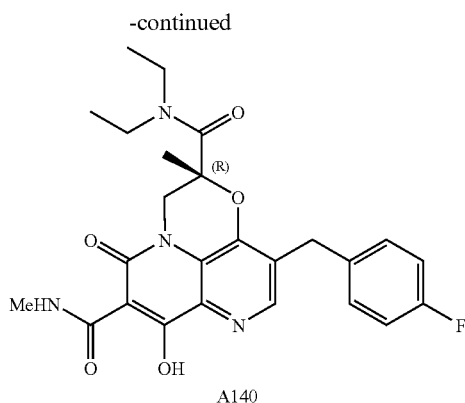

A140

Example 88 was prepared from Intermediate T in the same manner as Example 80 by substituting N,N-diethylamine for methylamine. $^{0.1}$H-NMR (DMSO-d$_6$) d 9.99 (s, 1H), 8.34 (s, 1H), 7.23-7.19 (m, 2H), 7.09-7.04 (m, 2H), 4.57 (d, J=14 Hz, 1H), 4.14 (d, J=14 Hz, 1H), 4.02 (d, J=14 Hz, 1H), 3.87 (d, J=14 Hz, 1H), 3.75-3.61 (m, 1H), 3.54-3.40 (m, 1H), 3.25-3.18 (m, 1H), 3.18-3.03 (m, 1H), 2.86 (d, J=5 Hz, 3H), 1.60 (s, 3H), 1.00 (m, 3H), 0.75 (m, 3H); $^{19}$F NMR (376 MHz, DMSO-d$_6$) d −116.7 (m); MS [M+H]$^+$=483.2.

EXAMPLE 89

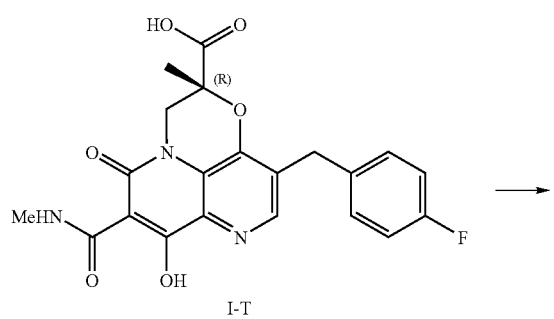

I-T

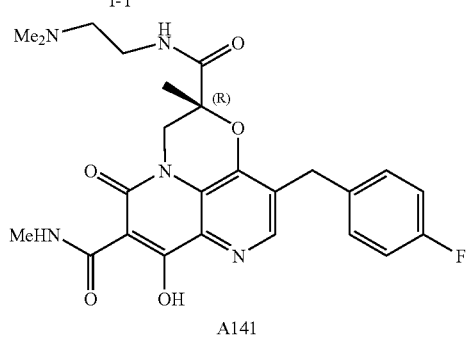

A141

Example 89 was prepared from Intermediate T in the same manner as Example 80 by substituting N,N-dimethyl-ethylenediamine for methylamine. $^{0.1}$H-NMR (DMSO-d$_6$) d 9.96 (d, J=4 Hz, 1H), 8.43 (s, 1H), 8.33 (t, 1H), 7.36-7.30 (m, 2H), 7.13-7.06 (m, 2H), 4.54 (d, J=14 Hz, 1H), 4.30 (d, J=15 Hz, 1H), 4.05 (d, J=15 Hz, 1H), 3.93 (d, J=14 Hz, 1H), 3.40-3.35 (m, 2H) 3.07-3.04 (m, 2H), 2.89 (d, J=4 Hz, 3H), 2.72 (s, 6H), 1.49 (s, 3H) $^{19}$F NMR (376 MHz, CH$_3$OH-d$_4$) d −74.7 (s, TFA), −116.6 (m); $^{19}$F NMR (376 MHz, DMSO-d$_6$) d −74.7 (s, TFA), −116.6 (m); MS [M+H]$^+$=498.2.

EXAMPLE 90

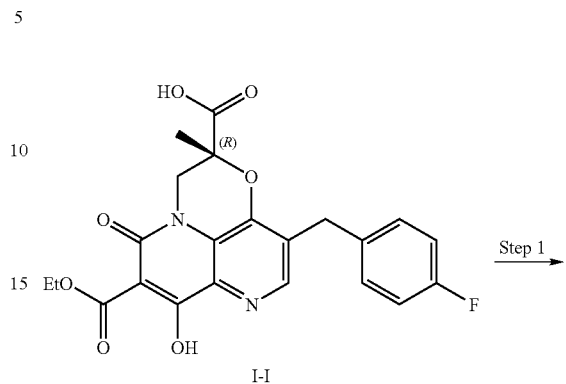

I-I

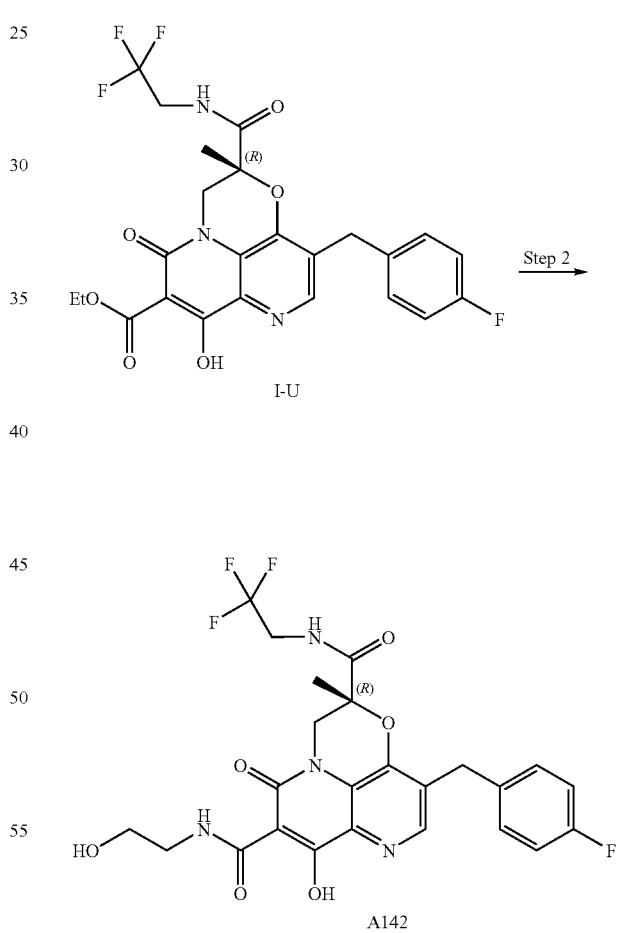

Example 90 was prepared for Intermediate I using the procedure for Example 73, but substituting 2,2,2-trifluoroethylamine for methylamine in Step 2, and ethanolamine for cyanoethylamine in Step 3. $^{0.1}$H-NMR (DMSO-d$_6$) d 10.25 (bs, 1H), 8.79 (t, J=6 Hz, 1H), 7.38-7.32 (m, 2H), 7.11-7.04 (m, 2H), 4.70 (6, J=14 Hz, 1H), 4.05 (d, J=14 Hz, 1H), 3.97-3.73 (m, 2H), 3.87 (d, J=14 Hz, 1H), 3.55-3.50 (m, 2H), 3.45-3.40 (m, 2H), 1.55 (s, 3H); $^{19}$F NMR (376 MHz, DMSO-d$_6$) d −71.0 (m, CF3) −74.2 (s, TFA), −116.7 (m); MS [M+H]$^+$=539.1, rt=2.22 min.

EXAMPLE 91

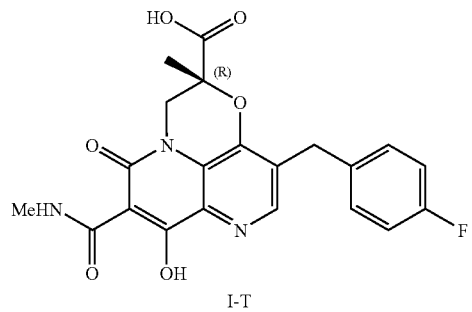

I-T

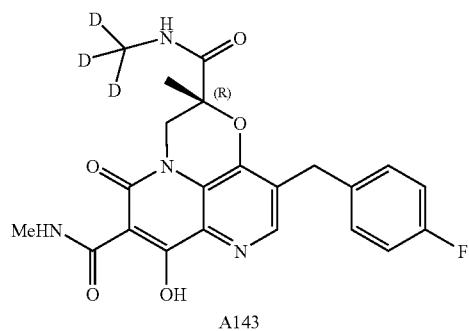

A143

Example 91 was prepared from Intermediate T in the same manner as Example 80 by substituting and d$_3$-methylamine for methylamine. $^1$H-NMR (DMSO-d$_4$) d 9.97 (bs, 1H), 8.42 (s, 1H), 7.78 (s, 1H), 7.36 (m, 2H), 7.10 (m, 2H), 4.53 (d, J=14 Hz, 1H), 4.30 (d, J=14 Hz), 4.05 (d, J=14 Hz, 1H), 3.87 (d, J=15 Hz, 1H), 2.88 (d, J=4 Hz, 3H), 1.46 (s, 3H); $^{19}$F NMR (376 MHz, DMSO-d$_6$) d −116.7 (m); MS [M+H]$^+$=444.1, rt=2.23 min.

EXAMPLE 92

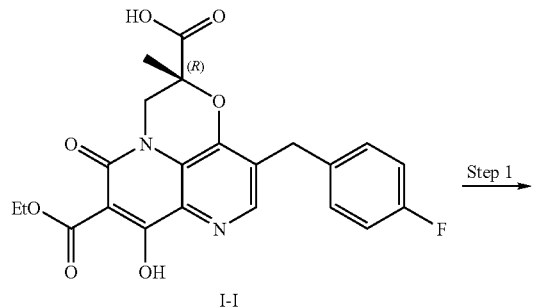

I-I

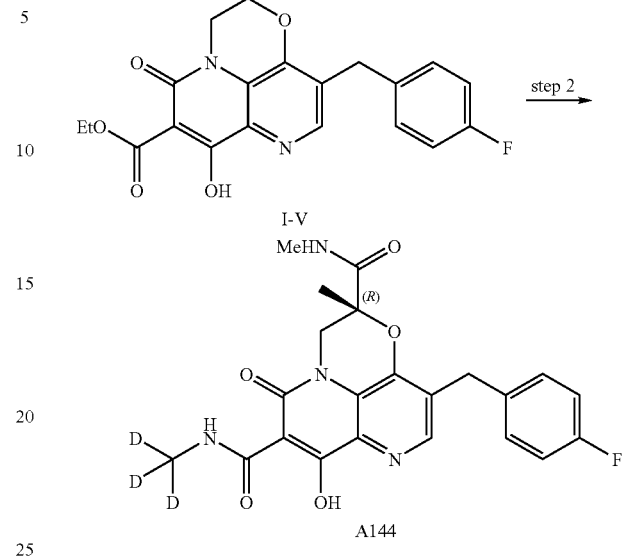

Example 92 was prepared from Intermediate I in the same manner used for Example 73, by substituting d$_3$-methylamine for cyanoethylamine in the final step in the same manner as step 11 in Example 1. $^1$H-NMR (DMSO-d$_4$) d 9.95 (s, 1H), 8.43 (s, 1H), 7.79 (s, 1H), 7.33 (t, J=8 Hz, 2H), 7.10 (t, J=8 Hz, 2H), 4.53 (d, J=14 Hz, 1H), 4.30 (d, J=14 Hz), 4.05 (d, J=14 Hz, 1H), 3.87 (d, J=15 Hz, 1H), 2.52 (d, J=4 Hz, 3H), 1.46 (s, 3H); $^{19}$F NMR (376 MHz, CH$_3$OH-d$_4$) d −116.7 (m); MS [M+H]$^+$=444.1.

EXAMPLE 93

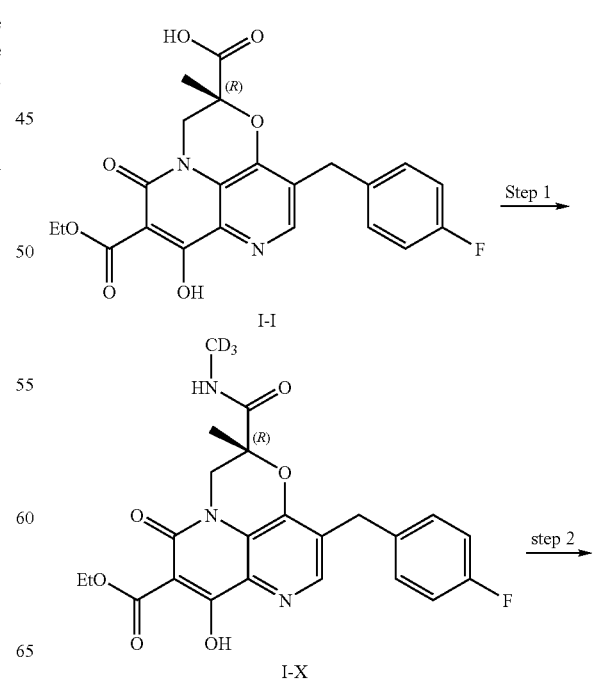

-continued

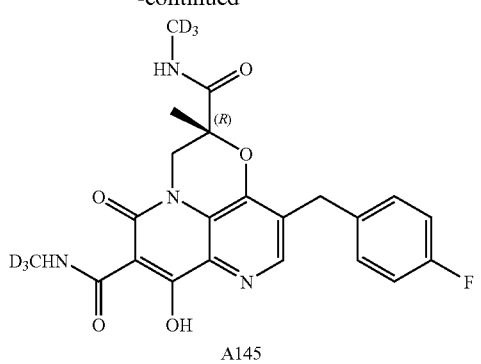
A145

Example 93 was prepared from Intermediate I in the same manner used for Example 73, by substituting d₃-methylamine both for methylamine in the first amide coupling, and for cyanoethylamine in the second amide coupling. [0.1]H-NMR (DMSO-d₆) δ 9.95 (s, 1H), 8.43 (s, 1H), 7.88 (s, 1H), 7.36-7.31 (m, 2H), 7.12-7.06 (m, 2H), 4.53 (6, J=14 Hz, 1H), 4.30 (d, J=14 Hz, 1H), 4.05 (d, J=14 Hz, 1H), 3.87 (d, J=14 Hz, 1H), 1.46 (s, 3H); MS [M+H]⁺=446.1.

EXAMPLE 94

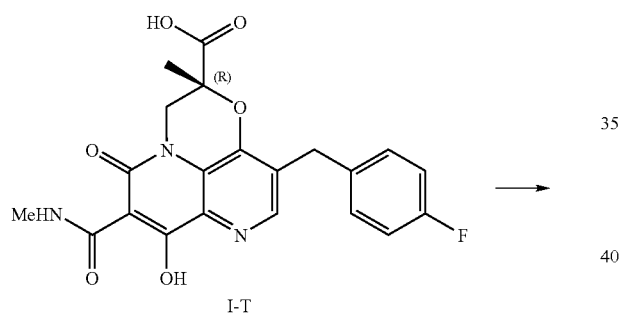
I-T

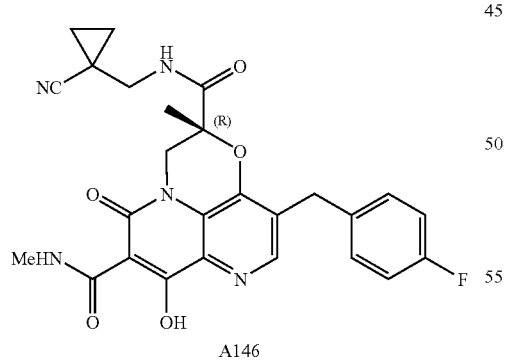
A146

Example 94 was prepared from Intermediate T in the same manner as Example 80, by substituting 1-aminomethyl-cyclopropanecarbonitrile for methylamine. ¹H-NMR (DMSO-d₆) δ 9.97 (bs, 1H), 8.41 (t, J=6 Hz, 1H), 8.40 (m, 1H), 7.36-7.32 (m, 2H), 7.08-7.03 (m, 2H), 4.64 (d, J=14 Hz, 1H), 4.31 (d, J=14 Hz, 1H), 4.01 (d, J=14 Hz, 1H), 3.80 (d, J=14 Hz, 1H), 3.21 (dd, J=14, 6 Hz, 1H), 3.09 (dd, J=14, 6 Hz, 1H), 2.84 (d, J=5 Hz, 3H), 1.49 (s, 3H), 0.98-0.94 (m, 2H), 0.80-0.77 (m, 2H); MS [M+H]⁺=506.1.

EXAMPLE 95

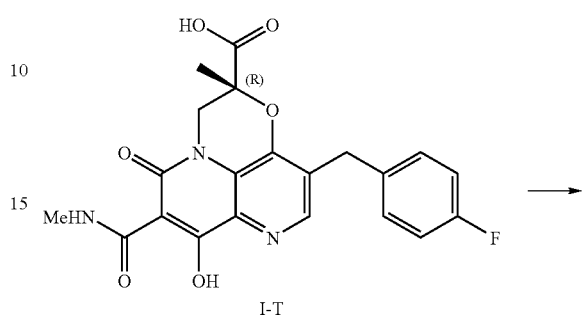
I-T

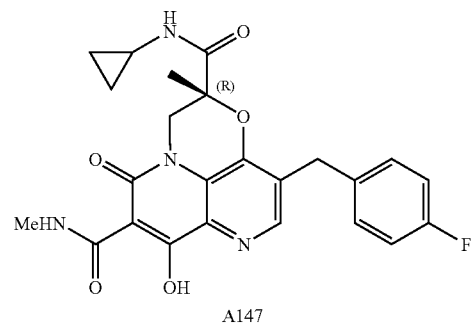
A147

Example 95 was prepared from Intermediate T in the same manner as Example 80, by substituting cyclopropylamine for methylamine. [0.1]H-NMR (DMSO-d₆) δ 9.77 (s, 1H), 8.19 (s, 1H), 7.12 (d, J=4 Hz, 7.14-7.10 (m, 2H), 6.90-6.85 (m, 2H), 4.43 (6, J=14 Hz, 1H), 4.01 (d, J=14 Hz, 1H), 3.83 (d, J=14 Hz, 1H), 3.55 (d, J=14 Hz, 1H), 2.67 (d, J=4 Hz, 3H), 2.27-2.50 (m, 1H), 1.30 (s, 3H), 0.35-0.30 (m, 2H), 0.07-0.00 (m, 2H); MS [M+H]⁺=467.1

EXAMPLE 96

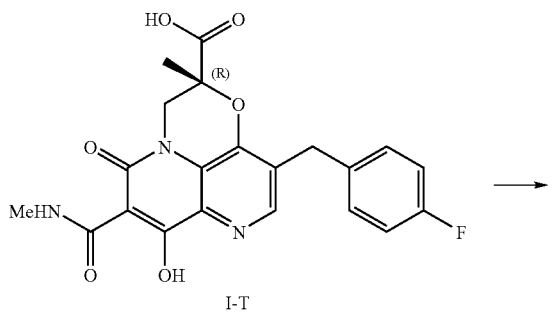
I-T

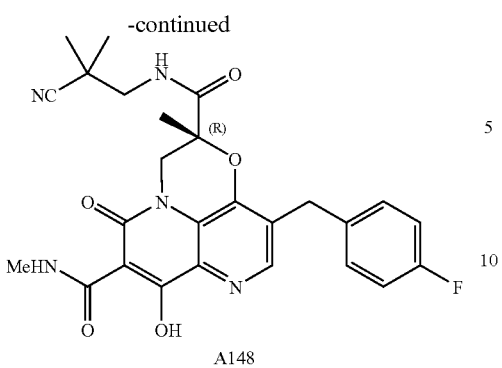

A148

Example 96 was prepared from Intermediate T in the same manner as Example 80, by substituting 3-amino-2,2-dimethyl-propionitrile for methylamine. $^{0.1}$H-NMR (DMSO-d$_6$) d 9.99 (s, 1H), 8.42 (s, 1H), 8.37 (m, 1H), 7.40-7.36 (m, 2H), 7.11-7.07 (m, 2H), 4.88 (6, J=14 Hz, 1H), 4.37 (d, J=14 Hz, 1H), 4.02 (6, J=14 Hz, 1H), 3.69 (d, J=14 Hz, 1H), 3.31-3.27 (m, 1H), 3.07-3.01 (m, 1H), 2.88 (d, J=5 Hz, 3H), 1.61 (s, 3H), 1.01 (s, 3H), 0.91 (s, 3H); MS [M+H]$^+$=508.1

EXAMPLE 97

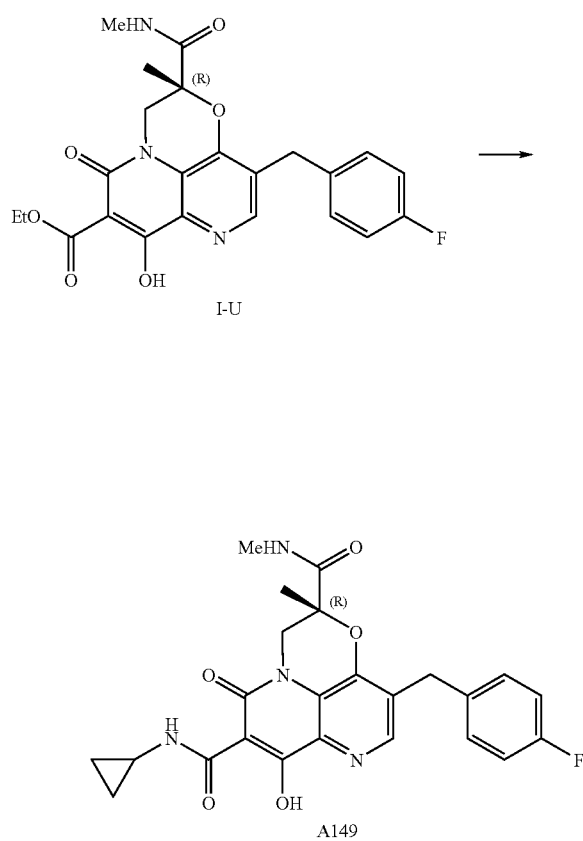

Example 97 was prepared from Intermediate V using the same procedure as for Example 73, by substituting cyclopropylamine for methylamine. $^{0.1}$H-NMR (DMSO-d$_6$) d 10.04 (s, 1H), 8.40 (s, 1H), 7.78 (m, 1H), 7.32-7.28 (m, 2H), 7.09-7.04 (m, 2H), 4.49 (6, J=14 Hz, 1H), 4.27 (d, J=14 Hz, 1H), 4.02 (6, J=14 Hz, 1H), 3.82 (d, J=14 Hz, 1H), 2.87-2.85 (m, 1H), 2.49 (d, J=4 Hz, 3H), 1.42 (s, 3H), 0.76-0.74 (m, 2H), 0.59-0.57 (m, 2H); $^{19}$F NMR (376 MHz, DMSO-d$_6$) d −116.7 (m); MS [M+H]$^+$=467.1.

EXAMPLE 98

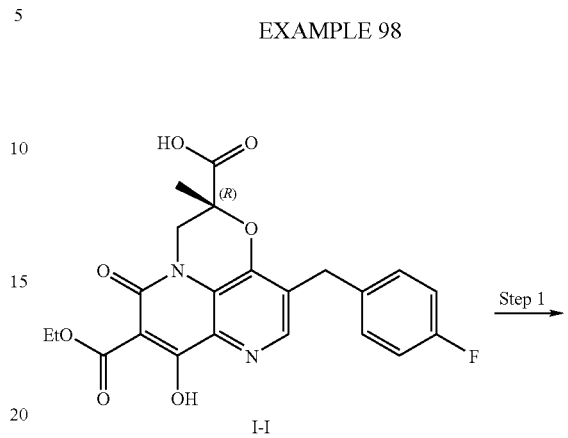

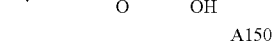

A150

Example 98 was prepared from Intermediate I in the same manner used for Example 73, by substituting 3-amino-2,2-dimethyl-propionitrile for methylamine in the first amide coupling, and cyclopropylamine for cyanoethylamine in the second amide coupling. $^1$d 10.10 (s, 1H), 8.43 (s, 1H), 8.38 (m, 1H), 7.40-7.36 (m, 2H), 7.11-7.06 (m, 2H), 4.86 (6, J=14 Hz, 1H), 4.38 (d, J=14 Hz, 1H), 4.02 (6, J=14 Hz, 1H), 3.67 (d, J=14 Hz, 1H), 3.30-3.28 (m, 1H), 3.05-3.01 (m, 1H) 2.90-2.88 (m, 1H), 1.60 (s, 3H), 1.00 (s, 3H), 0.91 (s, 3H), 0.80-0.77 (m, 2H), 0.61-0.59 (m, 2H); $^{19}$F NMR (376 MHz, DMSO-d$_6$) d −74.2 (s, TFA), −116.7 (m); MS [M+H]$^+$= 534.2.

EXAMPLE 99

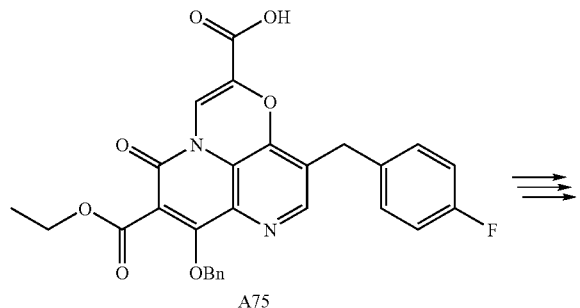
A75

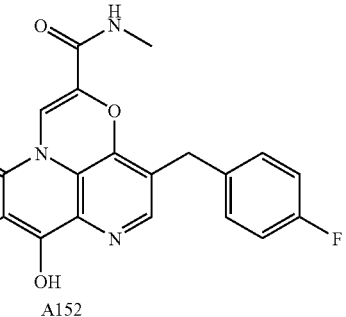
A152

The general procedures in steps 4-6 of Example 49 were used. Yield=57%. $^1$H NMR (400 MHz, DMSO-D6) d 10.05 (brs, 1H), 8.37 (s, 1H), 8.23 (d, J=5.2 Hz, 1H), 7.59 (s, 1H), 7.40 (dd, J=8.8, 5.6 Hz, 2H), 7.17 (t, J=8.8, 2H), 4.13 (s, 2H), 3.56-3.50 (m, 4H), 3.30 (s, 3H), 2.78 (d, J=4.8 Hz, 3H); MS (APCI) m/z 469.16 (M+H)$^+$.

EXAMPLE 101

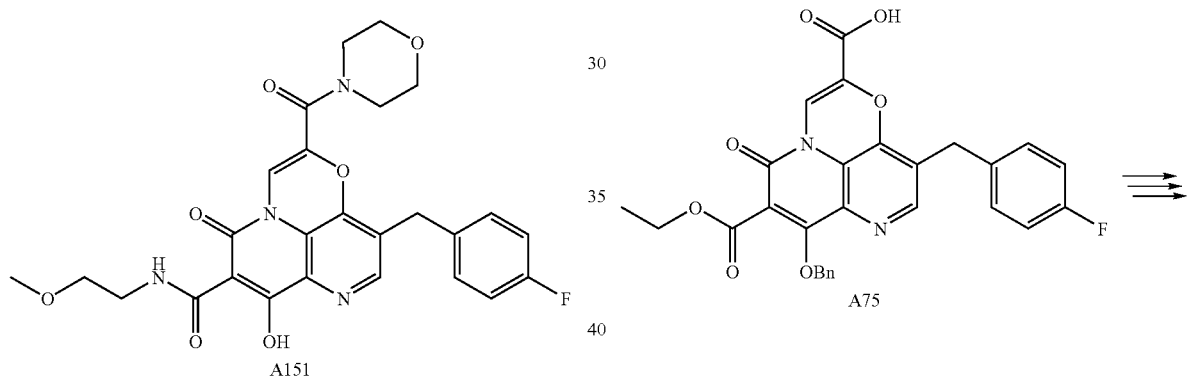
A151
A75

The general procedures in steps 4-6 of Example 49 were used. Yield=72.5%. $^1$H NMR (400 MHz, DMSO-D6) d 10.49 (brs, 1H), 8.08 (brs, 1H), 7.4 (s, 1H), 7.25 (dd, J=8.8, 5.6 Hz, 2H), 7.16 (t, J=8.8, 21H), 3.83 (s, 2H), 3.5-3.27 (m, 15H); MS (APCI) m/z 525.07 (M+H)$^+$.

EXAMPLE 100

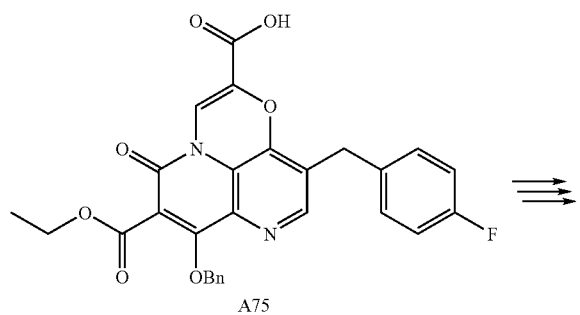
A75

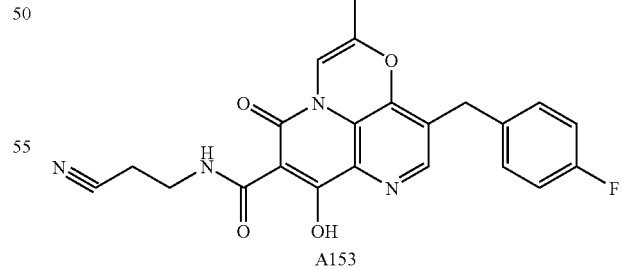
A153

The general procedures in steps 4-6 of Example 49 were used. Yield=40%. $^1$H NMR (400 MHz, DMSO-D6) d 10.13 (brs, 1H), 8.37 (s, 1H), 8.23 (d, J=5.2 Hz, 1H), 7.57 (s, 1H), 7.40 (dd, J=8.8, 5.6 Hz, 2H), 7.17 (t, J=8.8, 2H), 4.13 (s, 2H), 3.75-3.25 (m, 2H), 3.86 (t, J=6.4 Hz, 2H), 2.78 (d, J=4.4 Hz, 3H); MS (APCI) m/z 464.41 (M+H)+.

EXAMPLE 102

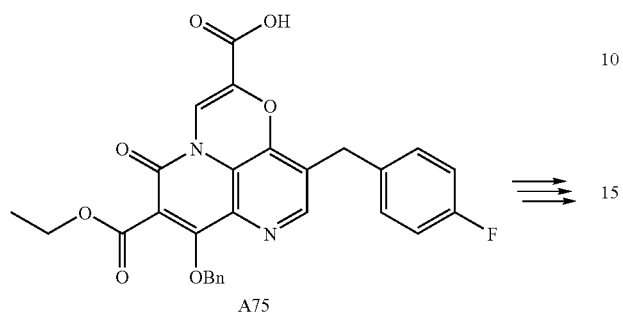
A75

⇛

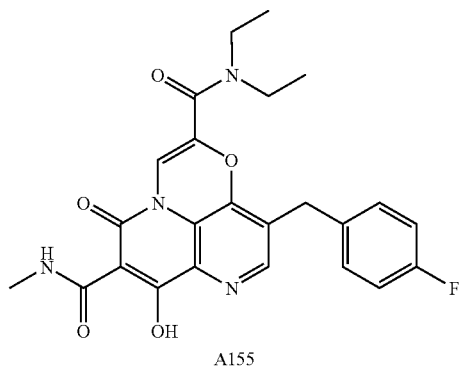
A155

The general procedures in steps 4-6 of Example 49 were used. Yield=45%. ¹H NMR (400 MHz, DMSO-D6) d 9.82 (brs, 1H), 8.33 (s, 1H), 7.26-7.22 (m, 3H), 7.12 (t, J=8.8, 2H), 3.90 (s, 2H), 3.37-3.35 (m, 4H), 2.88 (d, J=4.4 Hz, 3H), 1.05 (t, J=7.2 Hz, 6H); MS (APCI) m/z 467.27 (M+H)+.

EXAMPLE 104

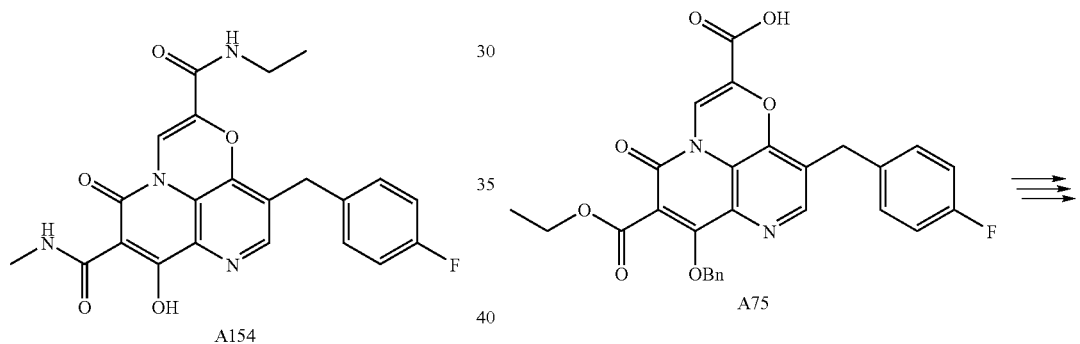
A154        A75

The general procedures in steps 4-6 of Example 49 were used. Yield=40%. ¹H NMR (400 MHz, DMSO-D6) d 9.82 (brs, 1H), 8.38 (s, 1H), 8.23 (m, 1H), 7.55 (s, 1H), 7.40 (dd, J=8.8, 5.6 Hz, 2H), 7.17 (t, J=8.8, 2H), 4.12 (s, 2H), 3.29-3.24 (m, 2H), 2.91 (d, J=4.4 Hz, 3H), 1.13 (t, J=7.2 Hz, 3H); MS (APCI) m/z 439.35 (M+H)+.

EXAMPLE 103

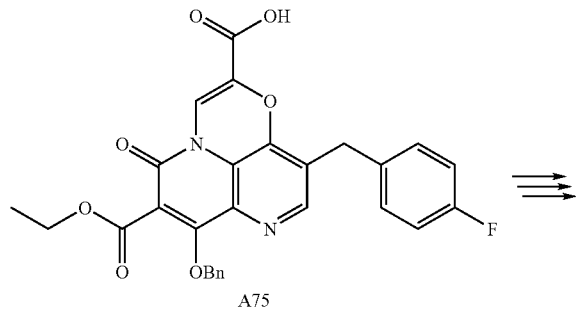
A75

⇛

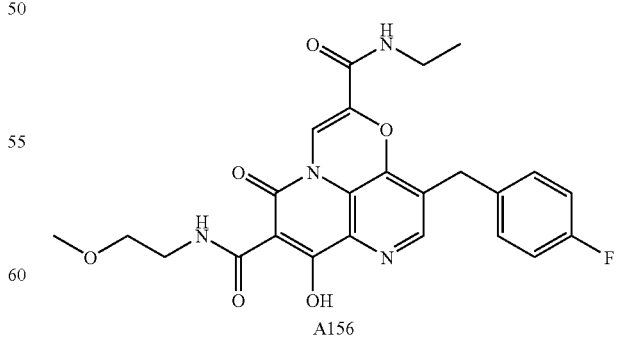
A156

The general procedures in steps 4-6 of Example 49 were used. Yield=53%. ¹H NMR (400 MHz, CD₃OD) d 8.23 (s, 1H), 7.76 (s, 1H), 7.34 (dd, J=8.8, 5.4 Hz, 2H), 7.06 (t, J=8.8, 2H), 4.11 (s, 2H), 3.62-3.54 (m, 4H), 3.46-3.34 (m, 5H), 1.18 (t, J=7.2 Hz, 3H); MS (APCI) m/z 487.06 (M+H)+.

EXAMPLE 105

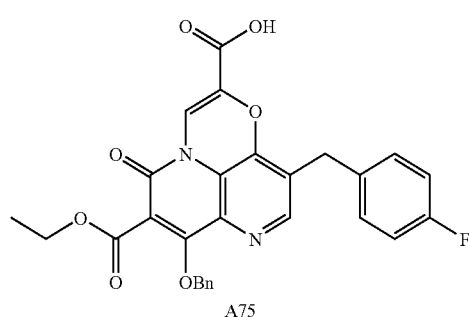
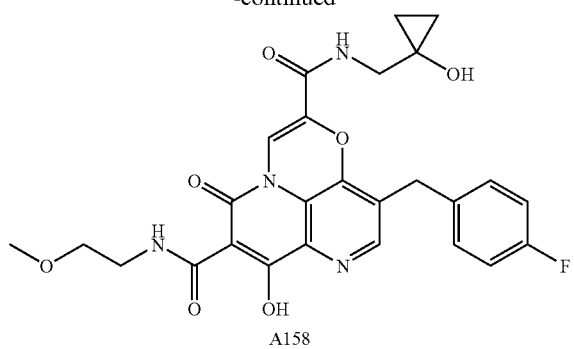

The general procedures in steps 4-6 of Example 49 were used. Yield=56%. ¹H NMR (400 MHz, CD₃OD) d 8.28 (s, 1H), 7.78 (s, 1H), 7.35 (dd, J=8.4, 5.6 Hz, 2H), 7.07 (t, J=8.8, 2H), 4.09 (s, 2H), 3.61-3.54 (m, 4H), 3.46 (s, 2H), 3.37 (s, 3H), 0.75 (m, 2H), 0.654 (m, 2H); MS (APCI) m/z 525.96 (M+H)+.

EXAMPLE 107

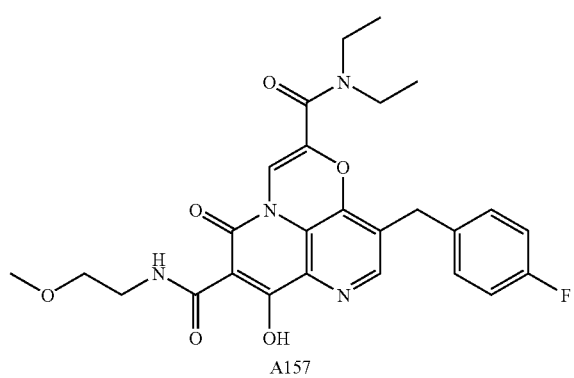
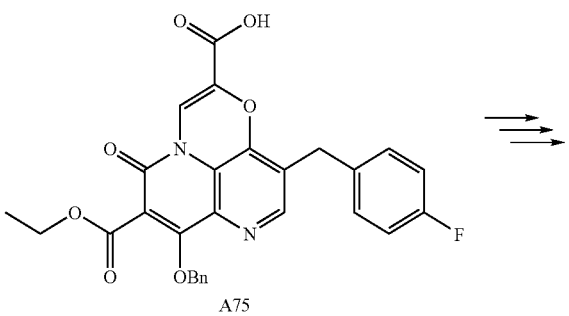

The general procedures in steps 4-6 of Example 49 were used. Yield=71%. ¹H NMR (400 MHz, CD₃OD) d 8.22 (s, 1H), 7.42 (s, 1H), 7.26 (dd, J=8.4, 5.6 Hz, 2H), 7.04 (t, J=8.8, 2H), 3.97 (s, 2H), 3.60-3.55 (m, 4H), 3.49 (q, J=6.8 Hz, 4H), 3.37 (s, 3H), 1.18 (t, J=7.2 Hz, 6H); MS (APCI) m/z 511.07 (M+H)+.

EXAMPLE 106

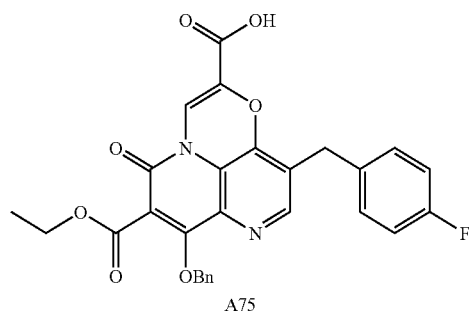
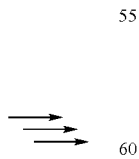
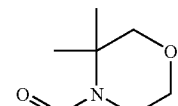
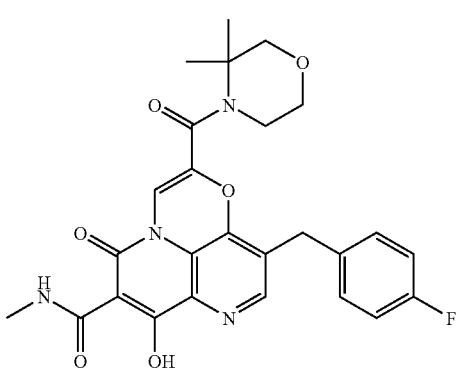

The general procedures in steps 4-6 of Example 49 were used. Yield=71%. ¹H NMR (400 MHz, DMSO-D6) d 9.92 (brs, 1H), 8.17 (brs, 1H), 7.32 (s, 1H), 7.29 (dd, J=8.4, 5.6 Hz, 2H), 7.16 (t, J=8.8, 2H), 3.84 (s, 2H), 3.47-3.46 (m, 4H), 2.74 (s, 2H), 2.37 (s, 3H), 1.30 (s, 6H); MS (APCI) m/z 509.08 (M+H)$^+$.

EXAMPLE 108

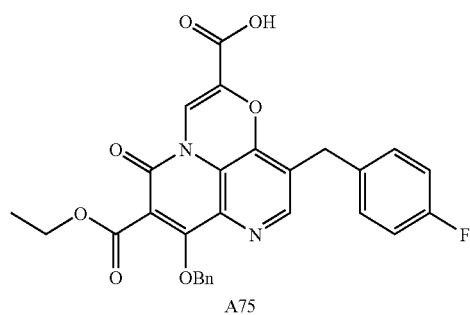
A75

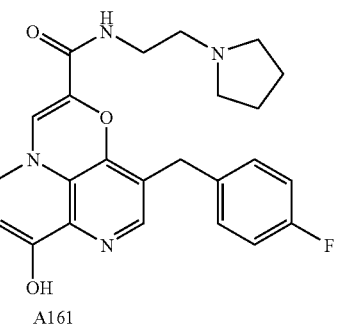
A161

The general procedures in steps 4-6 of Example 49 were used. Yield=40%. $^1$H NMR (400 MHz, CD$_3$OD) d 7.70 (s, 1H), 7.63 (s, 1H), 7.29 (dd, J=8.4, 5.6 Hz, 2H), 7.06 (t, J=8.8, 2H), 3.96-2.68 (m, 17H), 2.08 (brs, 4H); MS (APCI) m/z 552.31 (M+H)$^+$.

EXAMPLE 110

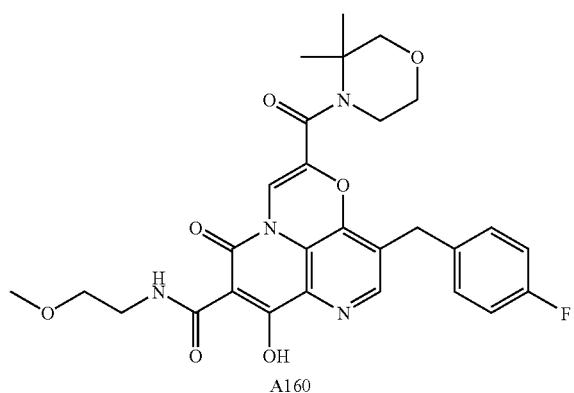
A160

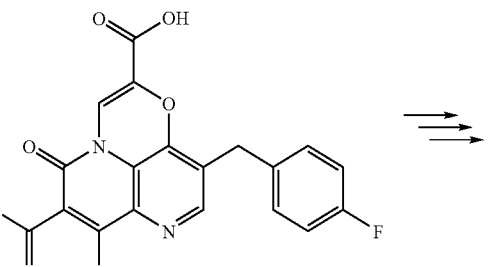
A75

The general procedures in steps 4-6 of Example 49 were used. Yield=60%. $^1$H NMR (400 MHz, DMSO-D6) d 10.06 (brs, 1H), 8.41 (brs, 1H), 7.32 (dd, J=8.4, 5.6 Hz, 2H), 7.27 (s, 1H), 7.17 (t, J=8.8, 2H), 3.92 (s, 2H), 3.56-3.50 (m, 8H), 3.35 (s, 2H), 3.29 (s, 3H), 1.32 (s, 6H); MS (APCI) m/z 553.07 (M+H)$^+$.

EXAMPLE 109

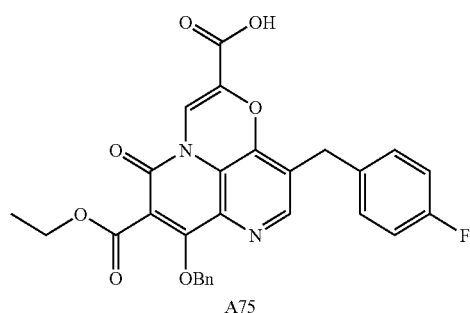
A75

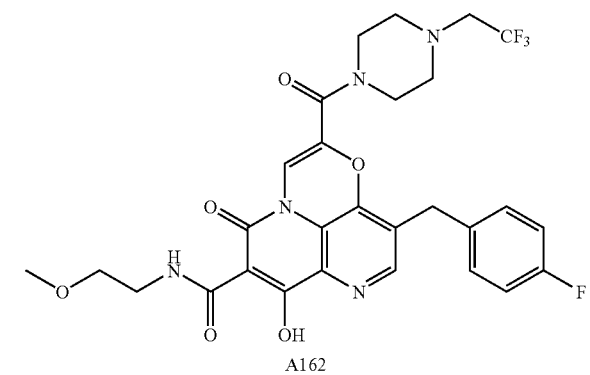
A162

The general procedures in steps 4-6 of Example 49 were used. Yield=71%. $^1$H NMR (400 MHz, CD$_3$OD) d 8.27 (s, 1H), 7.47 (s, 1H), 7.30 (dd, J=8.4, 5.6 Hz, 2H), 7.09 (t, J=8.8, 2H), 4.00 (s, 2H), 3.64-3.60 (m, 8H), 3.41 (s, 3H), 3.15 (q, J=9.6 Hz, 2H), 2.66 (brs, 4H); MS (APCI) m/z 606.34 (M+H)+.

EXAMPLE 111

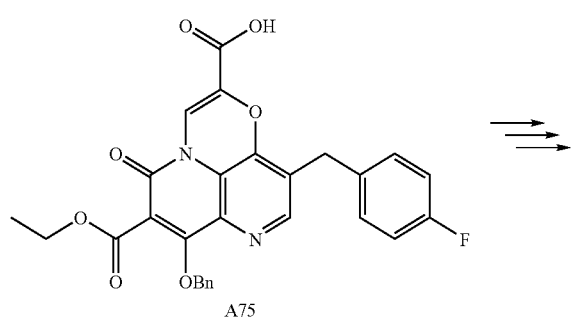
A75

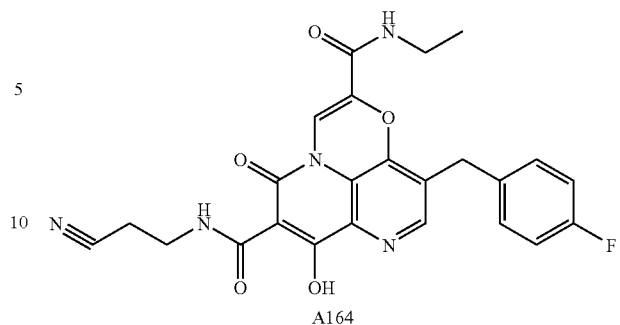
A164

The general procedures in steps 4-6 of Example 49 were used. Yield=45%. $^1$H NMR (400 MHz, DMSO-D6) d 10.64 (brs, 1H), 8.15 (s, 1H), 7.90 (t, J=5.2 Hz, 1H), 7.62 (s, 1H), 7.40 (dd, J=8.4, 5.6 Hz, 2H), 7.17 (t, J=8.8, 2H), 4.05 (s, 2H), 3.50-3.45 (m, 2H), 3.30-3.23 (m, 2H), 2.75-2.72 (m, 2H), 1.13 (t, J=6.8 Hz, 3H); MS (APCI) m/z 478.40 (M+H)+.

EXAMPLE 113

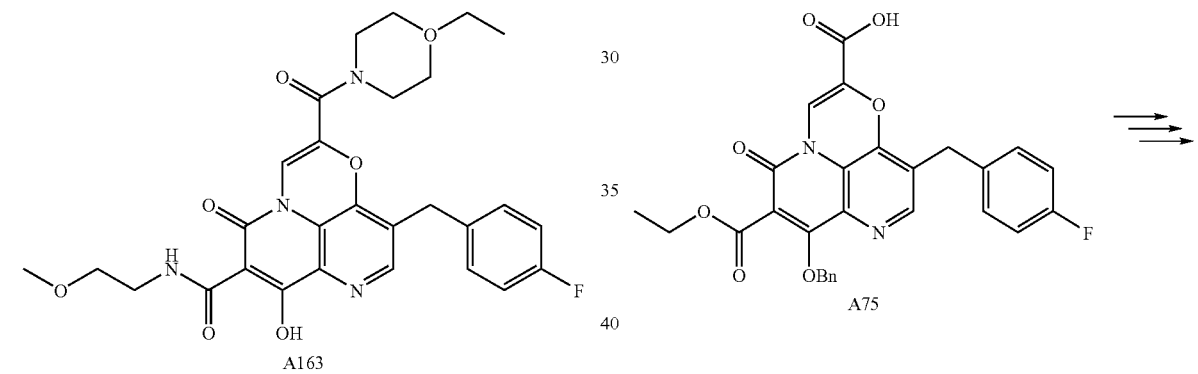
A163        A75

The general procedures in steps 4-6 of Example 49 were used. Yield=35%. $^1$H NMR (400 MHz, CD$_3$OD) d 8.24 (s, 1H), 7.43 (s, 1H), 7.26 (dd, J=8.4, 5.6 Hz, 2H), 7.05 (t, J=8.8, 2H), 3.96 (s, 2H), 3.80-3.75 (m, 2H), 3.60-3.54 (m, 4H), 3.52-3.43 (m, 1H), 3.42-3.35 (m, 4H), 3.33 (s, 3H), 1.81 (m, 2H), 1.53 (m, 2H); MS (APCI) m/z 553.38 (M+H)+.

EXAMPLE 112

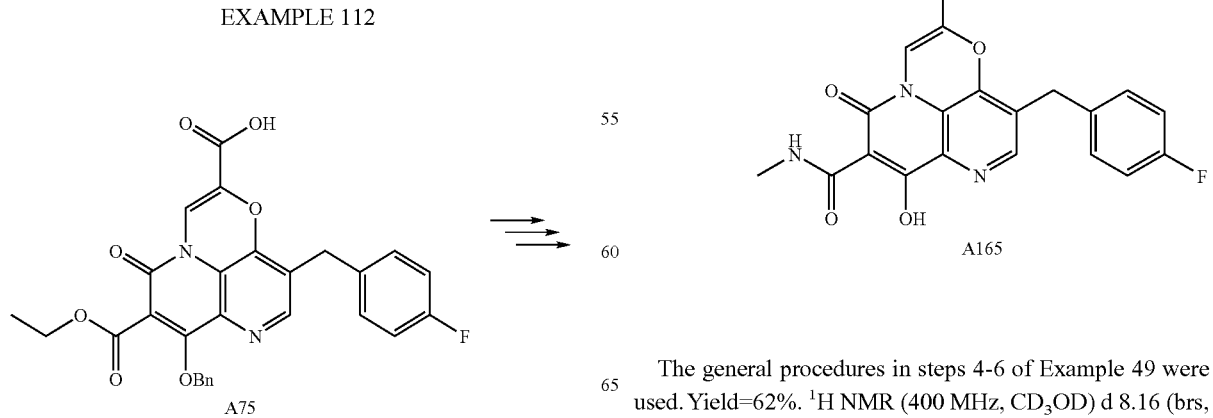
A75        A165

The general procedures in steps 4-6 of Example 49 were used. Yield=62%. $^1$H NMR (400 MHz, CD$_3$OD) d 8.16 (brs, 1H), 7.82 (s, 1H), 7.34 (dd, J=8.4, 5.6 Hz, 2H), 7.17 (t, J=8.8, 2H), 4.02 (s, 2H), 3.54-3.50 (m, 4H), 2.90 (s, 3H), 2.54 (s, 2H); MS (APCI) m/z 469.32 (M+H)+.

EXAMPLE 114

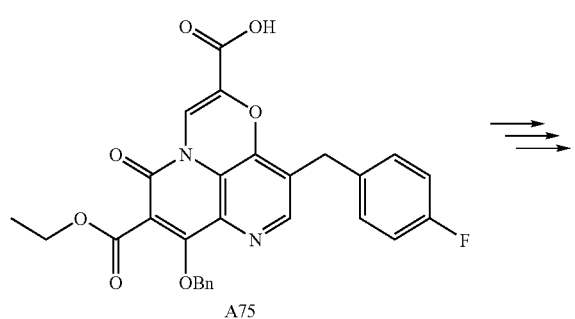
A75

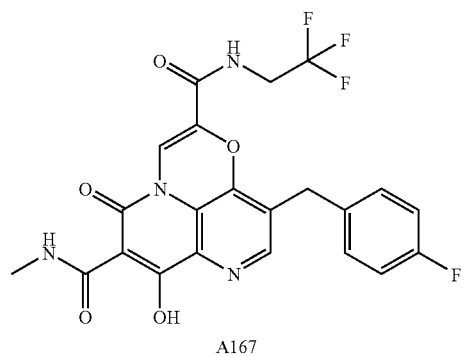
A167

The general procedures in steps 4-6 of Example 49 were used. Yield=50%. ¹H NMR (400 MHz, DMSO-D6) d 9.83 (brs, 1H), 8.51 (brs, 1H), 8.15 (s, 1H), 7.67 (s, 1H), 7.38 (dd, J=8.8, 5.6 Hz, 2H), 7.09 (t, J=8.8, 2H), 4.11-4.02 (m, 4H), 2.71 (d, J=4.4 Hz, 3H); MS (APCI) m/z. 492.94 (M+H)+.

EXAMPLE 116

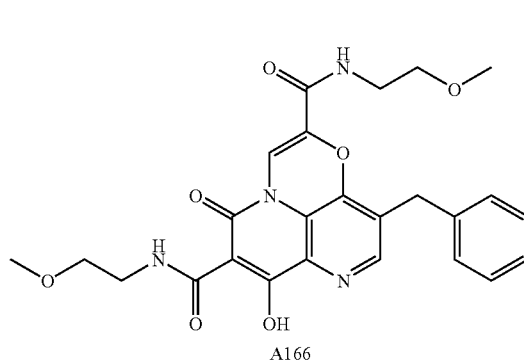
A166

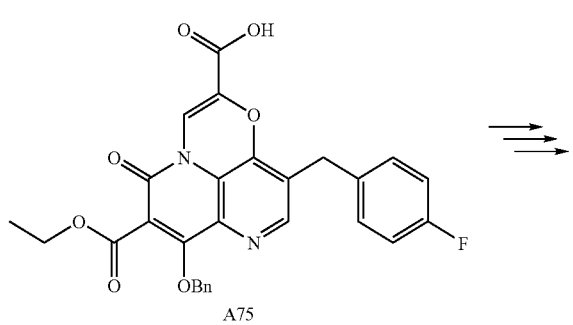
A75

The general procedures in steps 4-6 of Example 49 were used. Yield=51%. ¹H NMR (400 MHz, CD₃OD) d 8.23 (s, 1H), 7.83 (s, 1H), 7.36 (dd, J=8.4, 5.6 Hz, 2H), 7.09 (t, J=8.8, 2H), 4.07 (s, 2H), 3.58-3.53 (m, 9H), 3.33 (s, 6H), 3.04 (t, J=5.2 Hz, 1H); MS (APCI) m/z 513.44 (M+H)+.

EXAMPLE 115

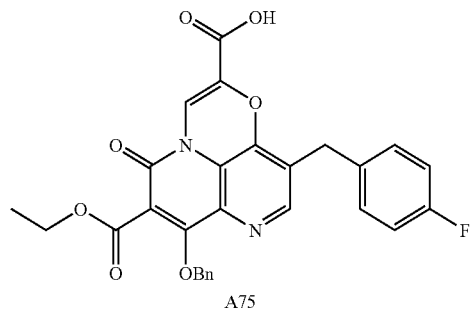
A75

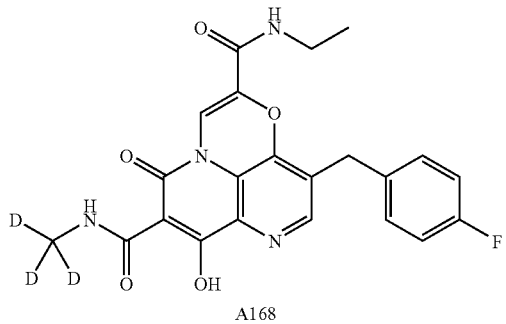
A168

The general procedures in steps 4-6 of Example 49 were used. Yield=54%. ¹H NMR (400 MHz, DMSO-D6) d 9.79 (brs, 1H), 8.36 (s, 1H), 8.21 (brs, 1H), 7.54 (s, 1H), 7.40 (dd, J=8.8, 5.6 Hz, 2H), 7.16 (t, J=8.8, 2H), 4.12 (s, 2H), 3.33-3.24 (m, 2H), 1.13 (t, J=6.8, 3H); MS (APCI) m/z. 442.04 (M+H)⁺.

EXAMPLE 117

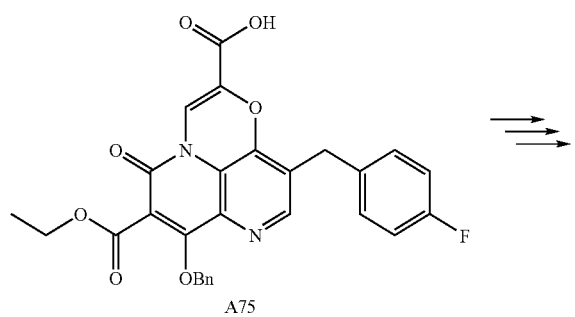
A75

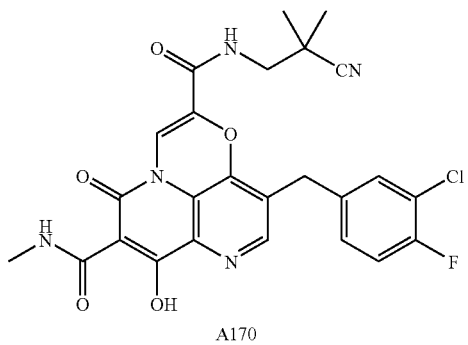
A170

The general procedures in steps 4-6 of Example 49 were used. Yield=61%. $^1$H NMR (400 MHz, DMSO-D6) d 9.83 (brs, 1H), 8.58 (brs, 1H), 8.47 (s, 1H), 7.63 (s, 1H), 7.58 (dd, J=7.2, 2.0 Hz, 1H), 7.43 (m, 1H), 7.33 (t, J=8.8, 1H), 4.14 (s, 2H), 3.46 (d, J=6.4 Hz, 2H), 2.91 (d, J=5.2 Hz, 3H), 1.31 (s, 6H); MS (APCI) m/z. 525.90 (M+H)⁺.

EXAMPLE 119

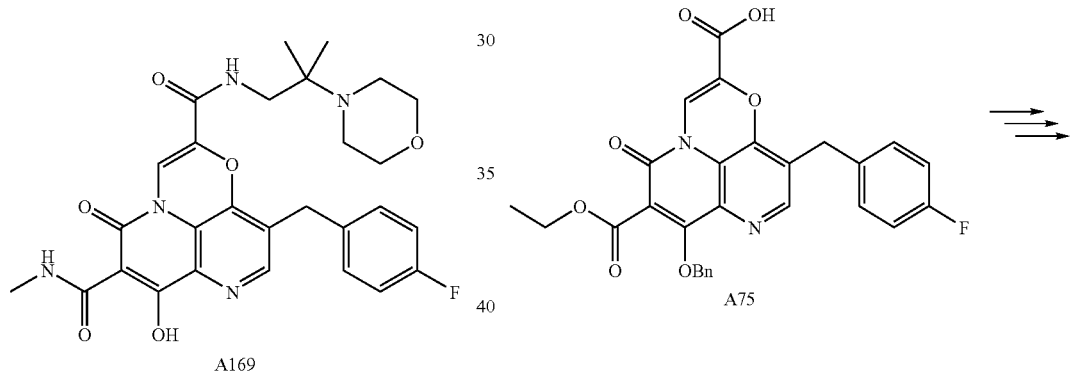
A169            A75

The general procedures in steps 4-6 of Example 49 were used. Yield=70%. $^1$H NMR (400 MHz, CD$_3$OD) d 8.25 (s, 1H), 7.84 (s, 1H), 7.38 (dd, J=8.8, 5.6 Hz, 2H), 7.12 (t, J=8.8, 2H), 4.15 (s, 2H), 3.37 (s, 2H), 3.01 (s, 3H), 2.62 (brs, 4H), 1.11 (s, 6H); MS (APCI) m/z. 551.96 (M+H)⁺.

EXAMPLE 118

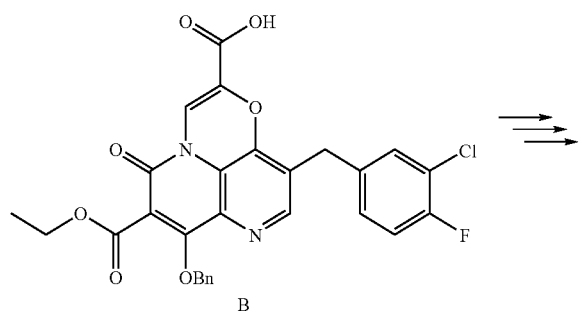
B

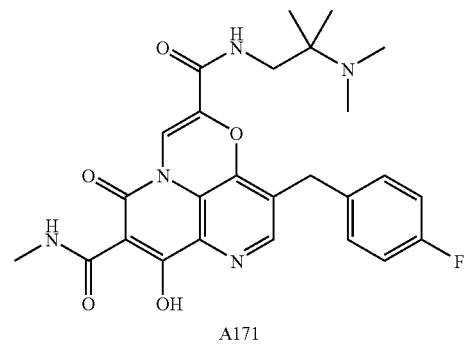
A171

The general procedures in steps 4-6 of Example 49 were used. Yield=61%. $^1$H NMR (400 MHz, CD3OD) d 7.79 (brs, 1H), 7.42 (s, 1H), 7.29 (dd, J=8.8, 5.6 Hz, 2H), 7.07 (t, J=8.8, 2H), 3.72 (brs, 4H), 2.92 (s, 3H), 2.88 (s, 6H); MS (APCI) m/z. 509.97 (M+H)+.

EXAMPLE 120

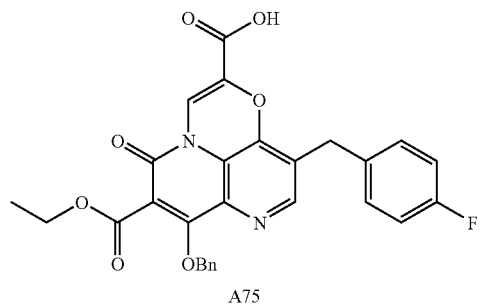
A75

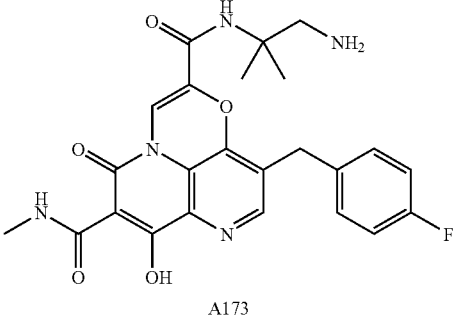
A173

The general procedures in steps 4-6 of Example 49 were used. Yield=86%. 1H NMR (400 MHz, D2O) d 8.37 (s, 1H), 8.36 (s, 1H), 7.64 (s, 1H), 7.34 (dd, J=8.8, 5.6 Hz, 2H), 7.19 (t, J=8.8, 2H), 4.08 (s, 2H), 3.41 (s, 2H), 2.99 (s, 3H), 2.76 (s, 1H), 1.48 (s, 6H); MS (APCI) m/z. 481.97 (M+H)+.

EXAMPLE 122

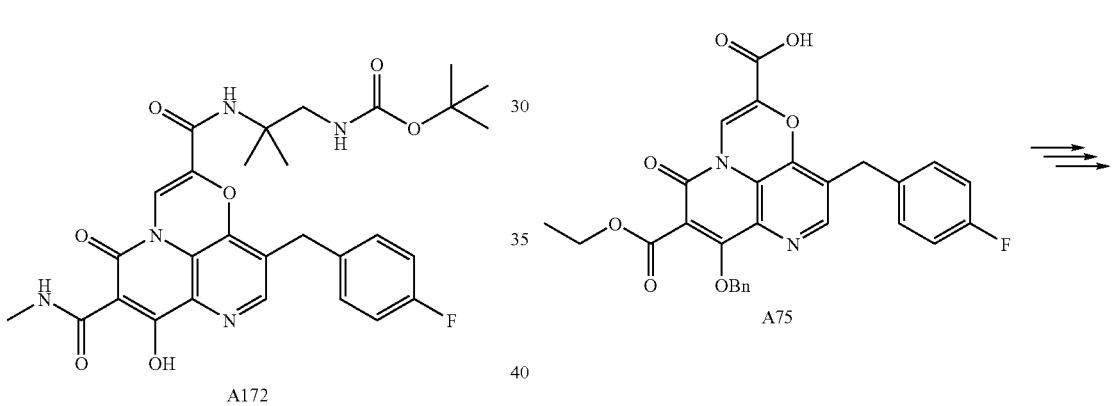
A172 / A75

The general procedures in steps 4-6 of Example 49 were used. Yield=61%. 1H NMR (400 MHz, CD3OD) d 8.21 (brs, 1H), 7.66 (s, 1H), 7.39 (dd, J=8.8, 5.6 Hz, 2H), 7.11 (t, J=8.8, 2H), 4.25 (s, 2H), 3.75-3.64 (m, 1H), 3.25 (s, 2H), 2.96 (s, 3H), 1.44 (s, 9H), 1.42 (s, 6H); MS (APCI) m/z. 583.11 (M+H)+.

EXAMPLE 121

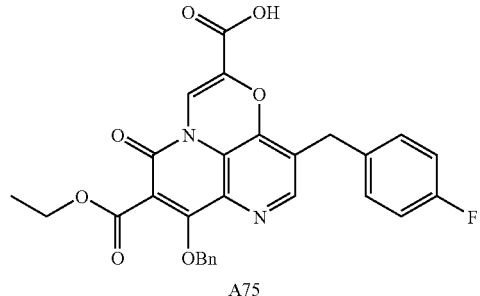
A75

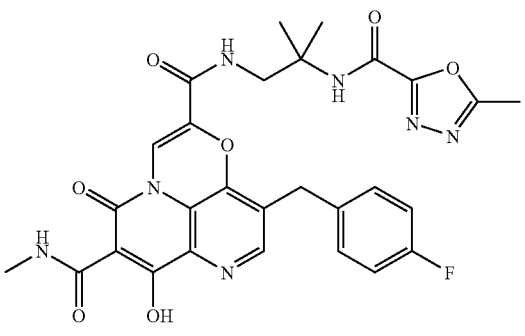
A174

The general procedures in steps 4-6 of Example 49 were used. Yield=50%. 1H NMR (400 MHz, CD3OD) d 8.21 (s, 1H), 7.79 (s, 1H), 7.35 (dd, J=8.8, 5.6 Hz, 2H), 7.07 (t, J=8.8, 2H), 4.13 (s, 2H), 3.68 (s, 2H), 2.99 (s, 3H), 2.55 (s, 3H), 1.49 (s, 6H); MS (APCI) m/z. 591.98 (M+H)+.

EXAMPLE 123

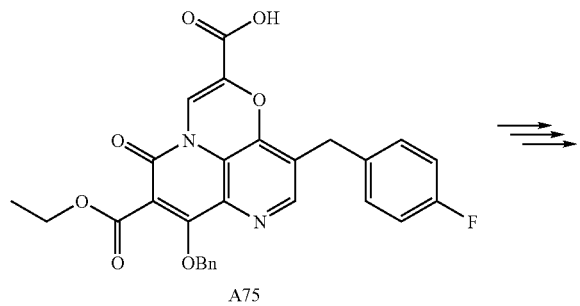
A75

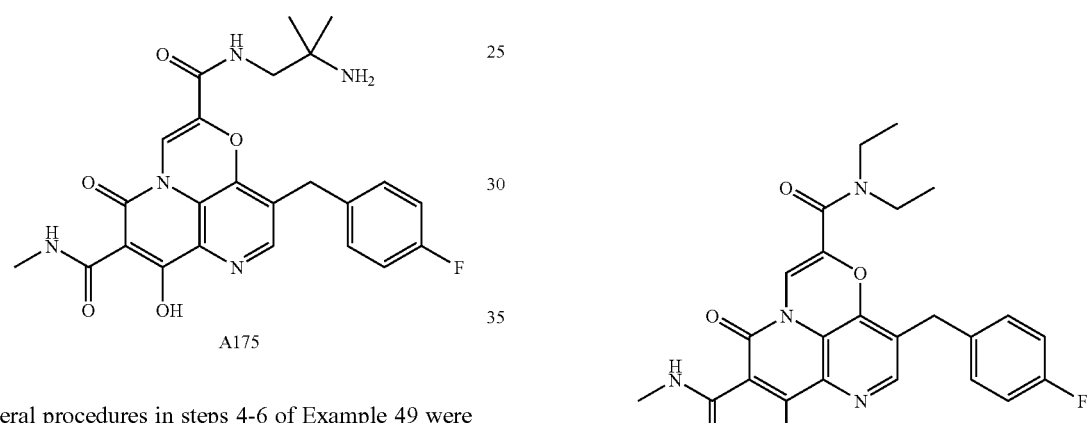
A175

The general procedures in steps 4-6 of Example 49 were used. Yield=57%. ¹H NMR (400 MHz, DMSO-D6) d 8.14 (s, 1H), 8.02 (brs, 1H), 7.81 (brs, 1H), 7.43 (s, 1H), 7.23 (dd, J=8.8, 5.6 Hz, 2H), 7.08 (t, J=8.8, 2H), 3.63 (s, 2H), 3.38 (brs, 4H), 2.79 (d, J=4.4, 3H), 1.29 (s, 6H); MS (APCI) m/z. 481.89 (M+H)+.

EXAMPLE 124

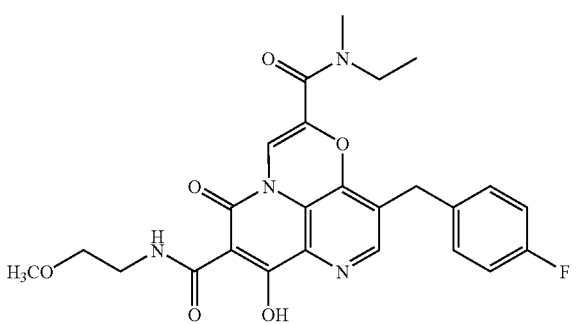
A176

The general procedures in steps 4-6 of Example 49 were used. Yield=70% for compound MM 7 after three steps. ¹H NMR (400 MHz, CDCl₃) d 9.85 (s, 1H), 8.28 (s, 1H), 7.45 (s, 1H), 7.15 (m, 2H), 6.95 (m, 2H), 3.94 (s, 2H), 3.45 (m, 4H), 2.99 (s, 3H); 2.94 (s, 3H), 1.2 (m, 3H). MS=513.55 [M+H].

EXAMPLE 125

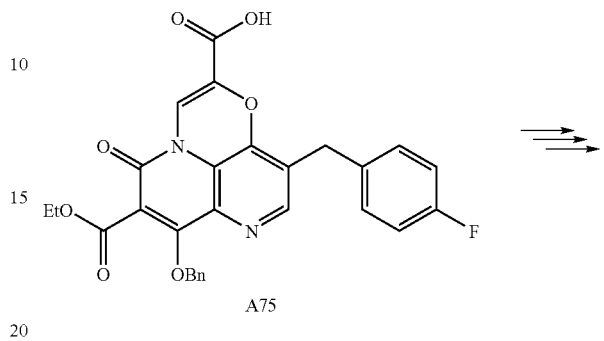
A75

A177

The general procedures in steps 4-6 of Example 49 were used. Yield=67% for compound Z1 after three steps. ¹H NMR (400 MHz, DMSO-d6) d 9.82 (s, 1H), 8.33 (s, 1H), 7.25 (dd, J=8.8, 6.0 Hz, 2H), 7.10 (t, J=8.8 Hz, 2H), 3.90 (s, 2H), 3.33 (m, 4H), 2.88 (s, 3H), 1.03 (m, 6H); MS [M+H]=467.09. LC/MS RT=2.46 min.

EXAMPLE 126

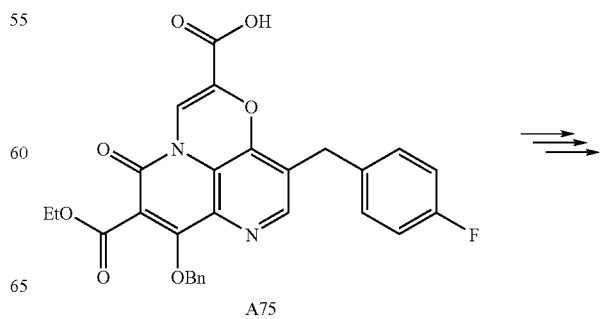
A75

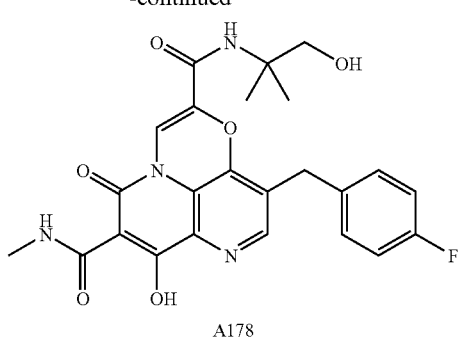

A178

The general procedures in steps 4-6 of Example 49 were used. Yield=32% for compound Z2 after three steps. ¹H NMR (400 MHz, DMSO-d6) d 9.78 (s, 1H), 8.47 (s, 1H), 7.48 (s, 1H), 7.34 (dd, J=8.8, 5.6 Hz, 2H), 7.09 (t, J=8.8 Hz, 2H), 6.96 (s, 1H), 3.98 (s, 2H), 3.45 (s, 2H), 2.89 (d, J=5.2 Hz, 3H), 1.27 (s, 3H), 1.25 (s, 3H); MS [M+H]=483.09. LC/MS RT=2.35 min.

EXAMPLE 127

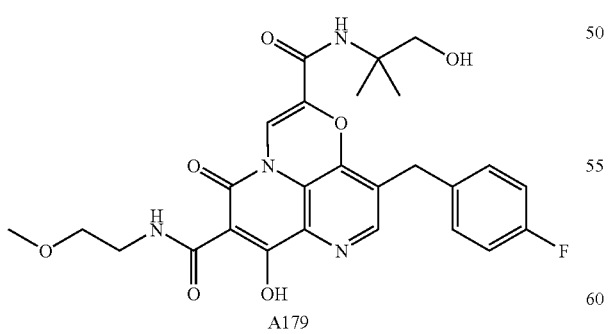

A75

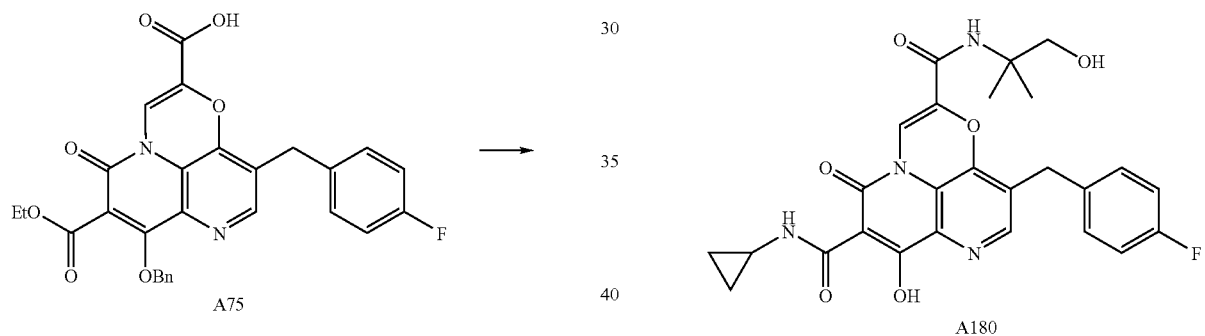

A179

The general procedures in steps 4-6 of Example 49 were used. Yield=10% for compound Z3 after three steps. ¹H NMR (400 MHz, DMSO-d6) d 10.01 (s, 1H), 8.48 (s, 1H), 7.51 (s, 1H), 7.34 (dd, J=8.8, 5.6 Hz, 2H), 7.09 (t, J=8.8 Hz, 2H), 7.01 (s, 1H), 3.98 (s, 2H), 3.53 (m, 2H), 3.48 (m, 2H), 3.41 (s, 2H), 3.26 (s, 3H), 1.26 (s, 6H); MS [M+H]=527.15. LC/MS RT=2.32 min.

EXAMPLE 128

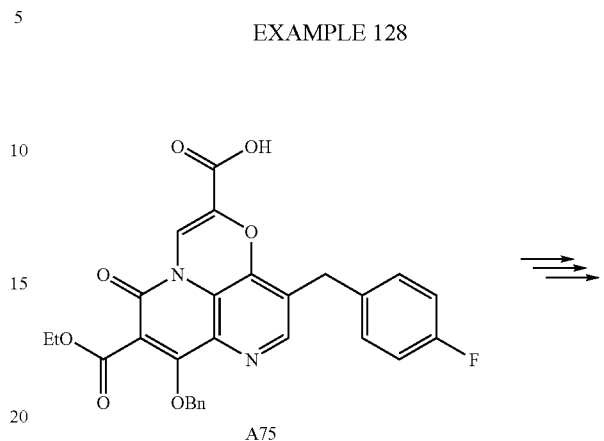

A75

A180

The general procedures in steps 4-6 of Example 49 were used. Yield=10% for compound Z4 after three steps. ¹H NMR (400 MHz, DMSO-d6) d 9.84 (s, 1H), 8.48 (s, 1H), 7.47 (s, 1H), 7.33 (dd, J=8.4, 5.2 Hz, 2H), 7.09 (t, J=8.8 Hz, 2H), 7.01 (s, 1H), 3.98 (s, 2H), 3.41 (s, 2H), 2.91 (m, 1H), 0.79 (m, 2H), 0.64 (m, 2H); MS [M+H]=509.08. LC/MS RT=2.46 min.

EXAMPLE 129

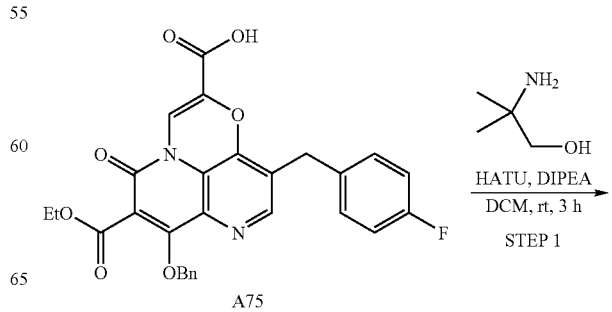

A75

STEP 1
HATU, DIPEA
DCM, rt, 3 h

Hz, 2H), 4.23 (s, 2H), 3.89 (m, 2H), 2.90 (d, J=5.2 Hz, 3H), 1.27 (s, 6H); MS [M+H]=465.08. LC/MS RT=2.60 min.

EXAMPLE 130

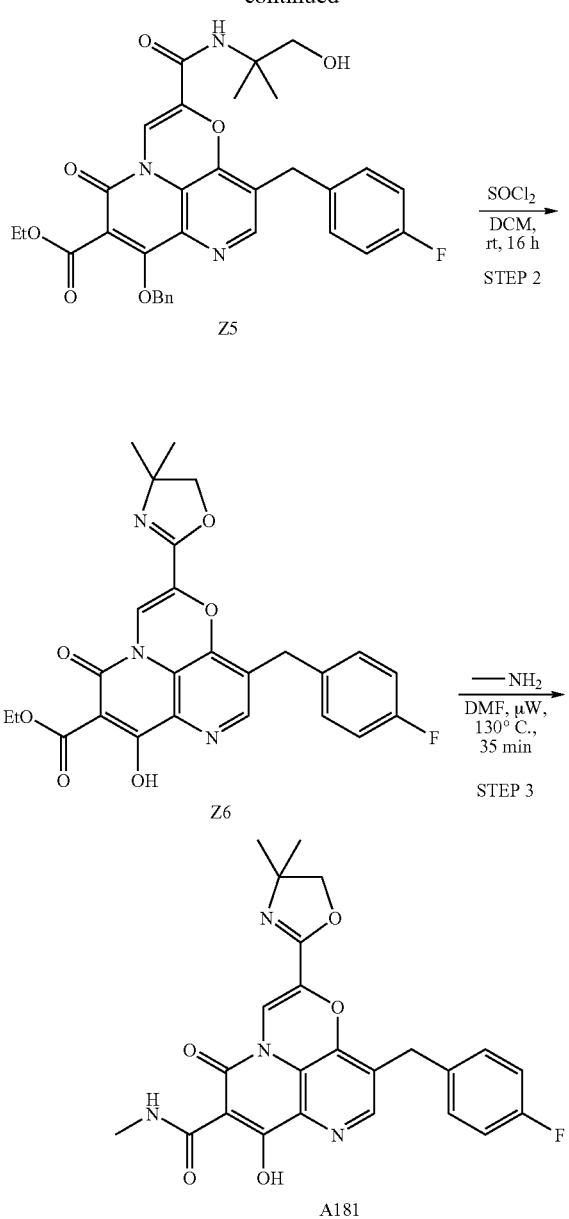

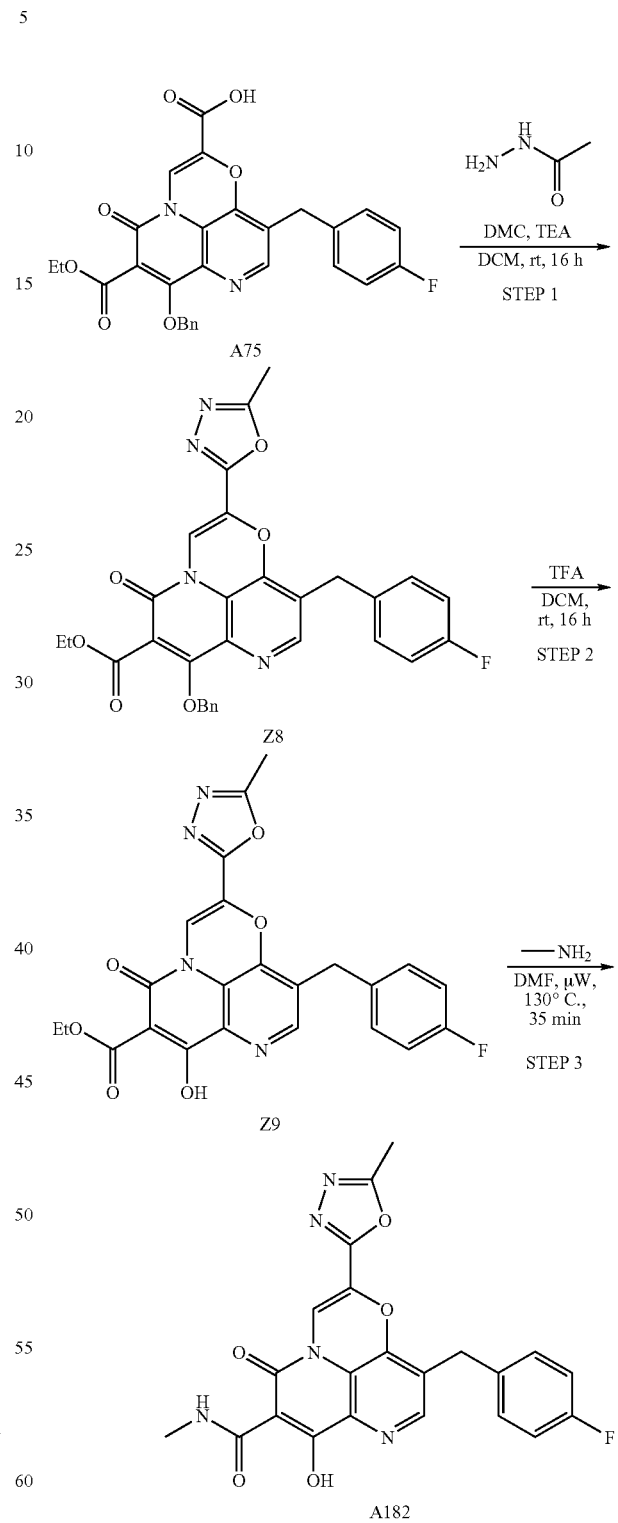

Step 1

The general procedures in step 4 of Example 49 were used. A quantitative yield was obtained.

Step 2

Compound Z5 (170 mg, 0.290 mmol) in DCM (5 mL) was treated with dropwise addition of thionyl chloride (200 µL, 2.896 mmol) at room temperature. Reaction was stirred at room temperature for 16 h. Reaction mixture was diluted with EtOAc, and washed with sodium citrate solution and brine. The organic layer was dried over sodium sulphate and concentrate in vacuo. A quantitative yield was obtained.

Step 3

The general procedures in steps 6 of Example 49 were used. Yield=11% for the product of this example after three steps. $^1$H NMR (400 MHz, DMSO-d6) d 9.75 (s, 1H), 8.49 (s, 1H), 7.95 (s, 1H), 7.36 (dd, J=8.8, 5.6 Hz, 2H), 7.09 (t, J=8.8

Step 1

To acetic hydrazide (8 mg, 0.0969 mmol) in DCM (1 mL) was added compound A75 (50 mg, 0.0969 mmol), followed by 2-chloro-1,3-dimethylimidazolinium chloride (33 mg, 0.194 mmol) and triethylamine (55 μL, 0.388 mmol). Reaction was stirred at room temperature overnight. The reaction mixture was treated with 3N HCl and the layers were separated. The organic layer was washed with water, dried, and concentrated to give 50 mg (93%) of compound Z8 as a reddish-brown oil.

Step 2

The general procedures in step 2 of Example 1 were used. Yield=55%; MS [M+H]=464.93. LC/MS RT=2.24 min.

Step 3

The general procedures in steps 6 of Example 49 were used. Yield=5% for the product of this example after three steps. $^1$H NMR (400 MHz, DMSO-d6) d 9.75 (s, 1H), 8.52 (s, 1H), 7.58 (s, 1H), 7.41 (m, 2H), 7.11 (m, 2H), 3.93 (s, 2H), 2.90 (d, J=4.0 Hz, 3H), 2.57 (s, 3H); MS [M+H]=450.06. LC/MS RT=2.55 min.

EXAMPLE 131

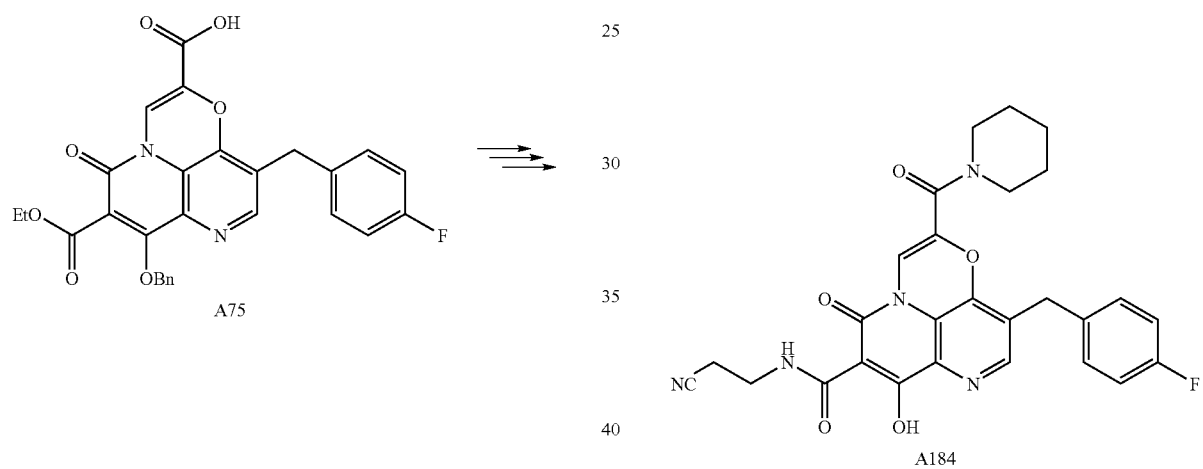

A75

The general procedures in steps 4-6 of Example 49 were used. Yield=22% for the product of this example after three steps. $^1$H NMR (400 MHz, DMSO-d6) d 9.89 (s, 1H), 8.06 (s, 1H), 7.27 (s, 1H), 7.22 (dd, J=8.4, 5.6 Hz, 2H), 7.09 (t, J=8.8 Hz, 2H), 3.80 (s, 2H), 3.41 (m, 2H), 2.70 (m, 2H), 2.68 (s, 3H), 1.53 (m, 2H), 1.39 (m, 4H); MS [M+H]=479.13. LC/MS RT=2.51 min.

EXAMPLE 132

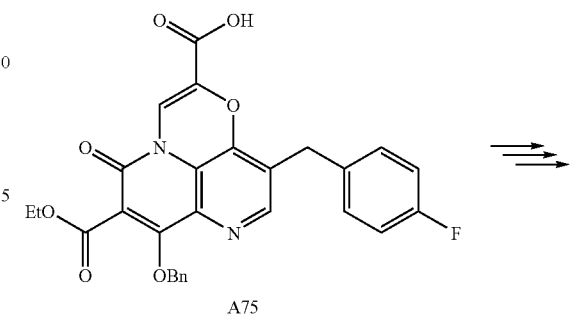

A75

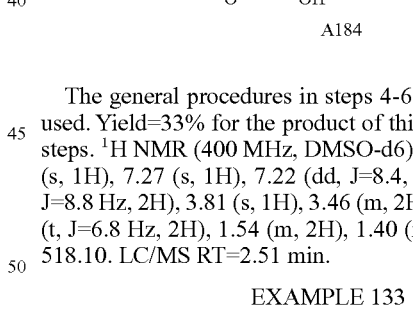

A184

The general procedures in steps 4-6 of Example 49 were used. Yield=33% for the product of this example after three steps. $^1$H NMR (400 MHz, DMSO-d6) d 10.48 (s, 1H), 8.13 (s, 1H), 7.27 (s, 1H), 7.22 (dd, J=8.4, 5.6 Hz, 2H), 7.09 (t, J=8.8 Hz, 2H), 3.81 (s, 1H), 3.46 (m, 2H), 3.41 (m, 4H), 2.70 (t, J=6.8 Hz, 2H), 1.54 (m, 2H), 1.40 (m, 4H); MS [M+H]= 518.10. LC/MS RT=2.51 min.

EXAMPLE 133

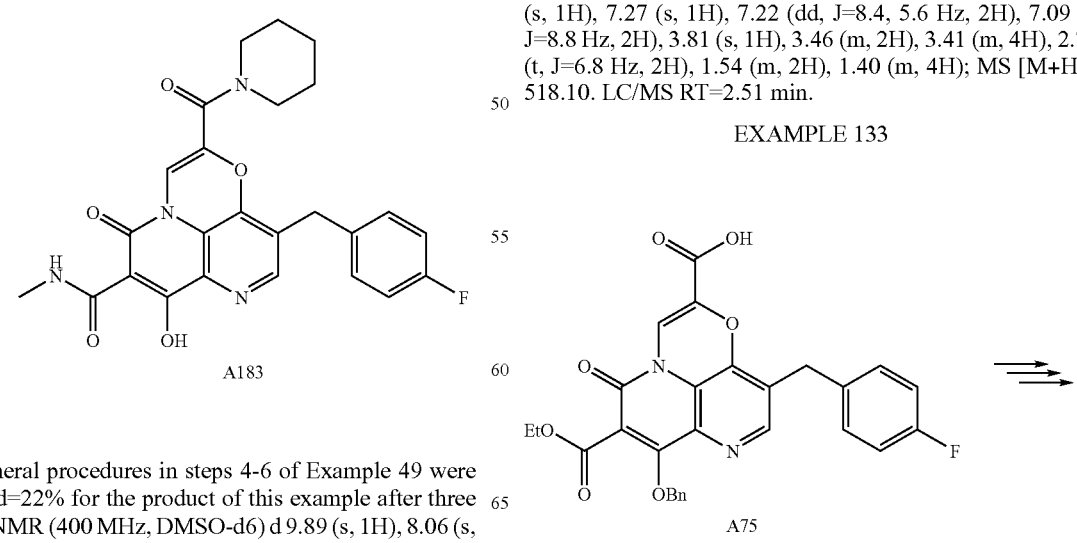

A75

-continued

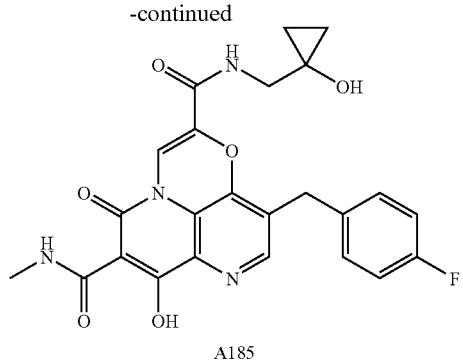

A185

The general procedures in steps 4-6 of Example 49 were used. Yield=6% for compound Z13 after three steps. ¹H NMR (400 MHz, DMSO-d6) d 9.80 (s, 1H), 8.41 (s, 1H), 8.03 (m, 1H), 7.54 (s, 1H), 7.36 (dd, J=8.4, 5.6 Hz, 2H), 7.11 (t, J=8.8 Hz, 2H), 4.08 (s, 2H), 3.38 (d, J=5.6 Hz, 2H), 2.89 (d, J=5.2 Hz, 3H), 0.55 (m, 4H); MS [M+H]=481.09. LC/MS RT=2.31 min.

EXAMPLE 134

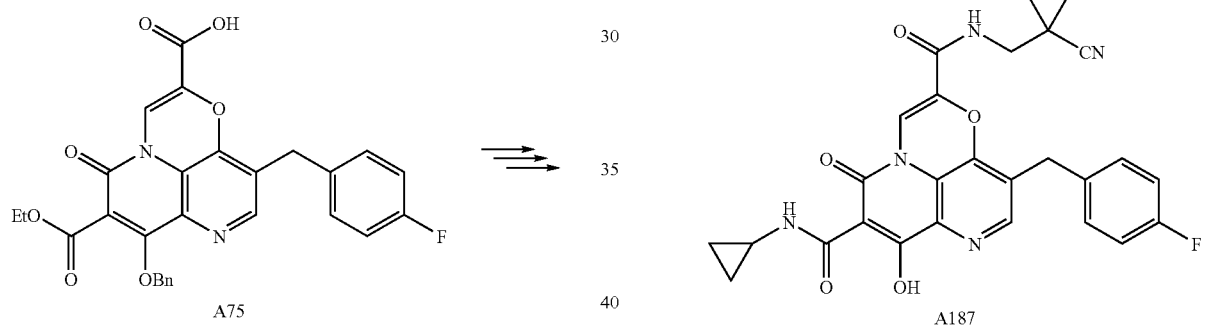

A75

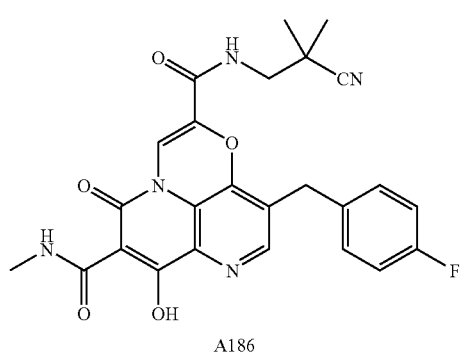

A186

The general procedures in steps 4-6 of Example 49 were used. Yield=26% for the product of this example after three steps. ¹H NMR (400 MHz, DMSO-d6) d 9.79 (s, 1H), 8.56 (t, J=5.6 Hz, 1H), 7.58 (s, 1H), 7.39 (dd, J=8.4, 5.6 Hz, 2H), 7.09 (t, J=8.8 Hz, 2H), 4.10 (s, 2H), 3.42 (d, J=6.8 Hz, 2H), 2.88 (d, J=4.8 Hz, 3H), 1.29 (s, 6H); MS [M+H]=492.10. LC/MS RT=2.43 min.

EXAMPLE 135

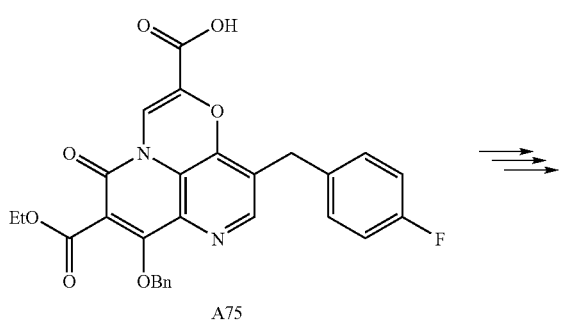

A75

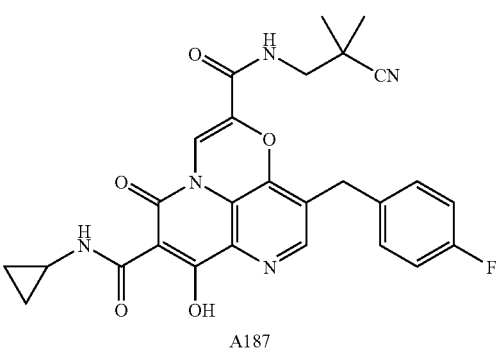

A187

The general procedures in steps 4-6 of Example 49 were used. Yield=26% for the product of this example after three steps. ¹H NMR (400 MHz, DMSO-d6) d 9.84 (d, J=4 Hz, 1H), 8.57 (t, J=6.4 Hz, 1H), 8.45 (s, 1H), 7.57 (s, 1H), 7.39 (dd, J=8.4, 5.6 Hz, 2H), 7.09 (t, J=8.8 Hz, 2N), 4.10 (s, 2H), 3.43 (d, J=6.8 Hz, 2H), 2.90 (m, 1H), 1.29 (s, 6H), 0.80 (m, 2H), 0.64 (m, 2H); MS [M+H]=518.13. LC/MS RT=2.58 min.

EXAMPLE 136

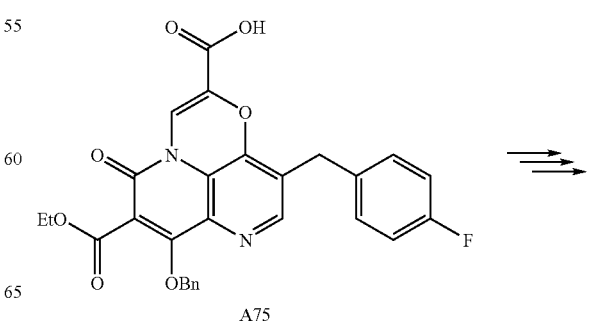

A75

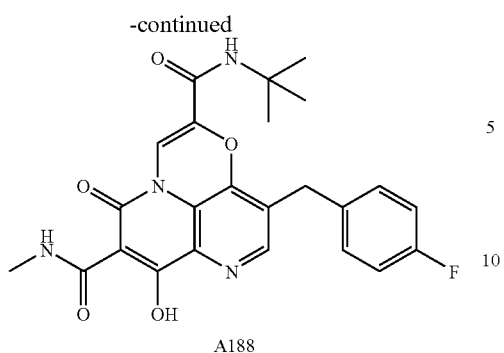

A188

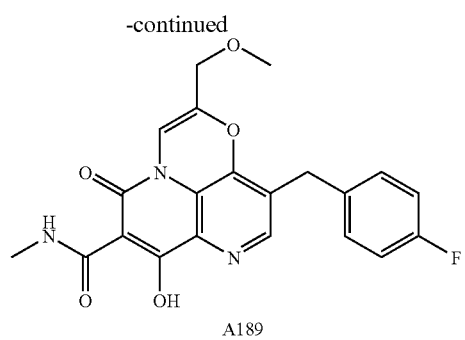

A189

The general procedures in steps 4-6 of Example 49 were used. Yield=40% for compound Z16 after three steps. $^1$H NMR (400 MHz, DMSO-d6) d 9.80 (s, 1H), 8.45 (s, 1H), 7.49 (s, 1H), 7.32 (dd, J=8.4, 5.6 Hz, 2H), 7.09 (t, J=8.8 Hz, 2H), 7.08 (s, 1H), 4.06 (s, 2H), 2.89 (d, J=4.8 Hz, 3H), 1.31 (s, 9H); MS [M+H]=467.07. LC/MS RT=2.55 min.

EXAMPLE 137

Step 1
Compound A74 (200 mg, 0.398 mmol) was suspended in DCM (4 mL) and treated with iodomethane (600 μL, 9.96 mmol) followed by silver (I) oxide (150 mg, 0.638 mmol). Reaction was stirred at room temperature overnight. An additional 600 μL of iodomethane and 150 mg of silver (I) oxide were added. Reaction was stirred at room temperature for an additional day and then filtered through a syringe filter. The filtrate was concentrated to give the crude product as yellow foam (200 mg, 97%).

Step 2 & 3
The general procedures in steps 5-6 of Example 49 were used. Yield=42% for compound Z19 after three steps. $^1$H NMR (400 MHz, DMSO-d6) d 9.80 (s, 1H), 8.45 (s, 1H), 7.49 (s, 1H), 7.32 (dd, J=8.4, 5.6 Hz, 2H), 7.09 (t, J=8.8 Hz, 2H), 7.08 (s, 1H), 3.86 (s, 2H), 2.89 (d, J=4.8 Hz, 3H), 1.31 (s, 9H); MS [M+H]=412.02. LC/MS RT=2.45 min.

EXAMPLE 138

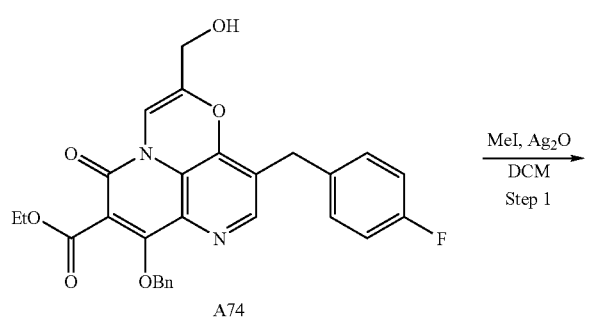

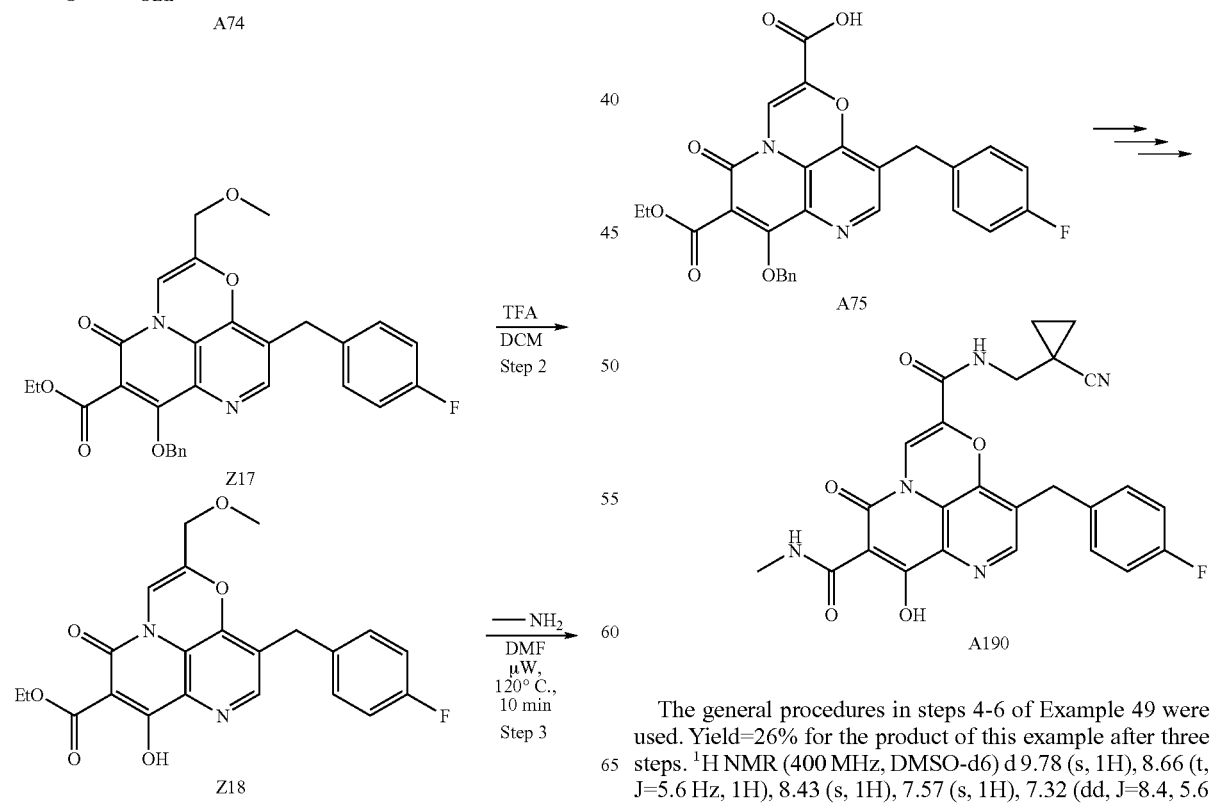

The general procedures in steps 4-6 of Example 49 were used. Yield=26% for the product of this example after three steps. $^1$H NMR (400 MHz, DMSO-d6) d 9.78 (s, 1H), 8.66 (t, J=5.6 Hz, 1H), 8.43 (s, 1H), 7.57 (s, 1H), 7.32 (dd, J=8.4, 5.6 Hz, 2H), 7.09 (t, J=8.8 Hz, 2H), 4.11 (s, 2H), 3.39 (d, J=6.0

Hz, 2H), 2.89 (d, J=4.8 Hz, 3H), 1.24 (m, 2H), 1.14 (m, 2H); MS [M+H]=490.09. LC/MS RT=2.45 min.

EXAMPLE 139

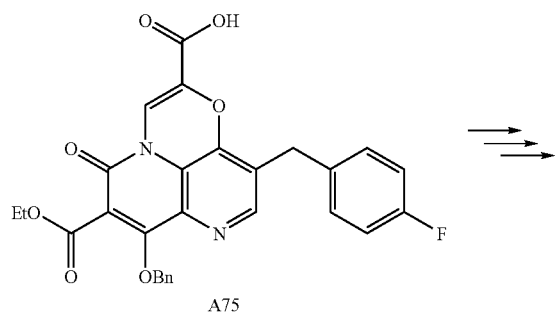
A75

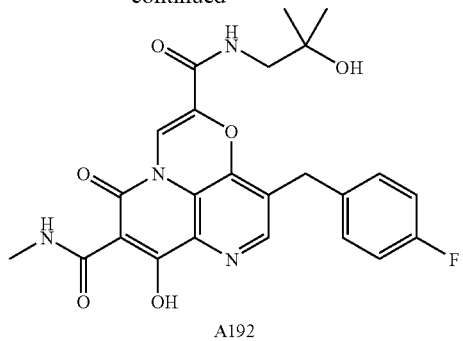
A192

The general procedures in steps 4-6 of Example 49 were used. Yield=26% for the product of this example after three steps. $^1$H NMR (400 MHz, DMSO-d6) d 9.78 (s, 1H), 8.42 (s, 1H), 7.75 (t, J=5.6 Hz, 1H), 7.51 (s, 1H), 7.36 (dd, J=8.4, 5.6 Hz, 2H), 7.10 (t, J=8.8 Hz, 2H), 4.04 (s, 2H), 3.19 (d, J=6 Hz, 2H), 2.86 (d, J=4.8 Hz, 2H), 1.07 (s, 6H); MS [M+H]=483.10. LC/MS RT=2.23 min.

EXAMPLE 141

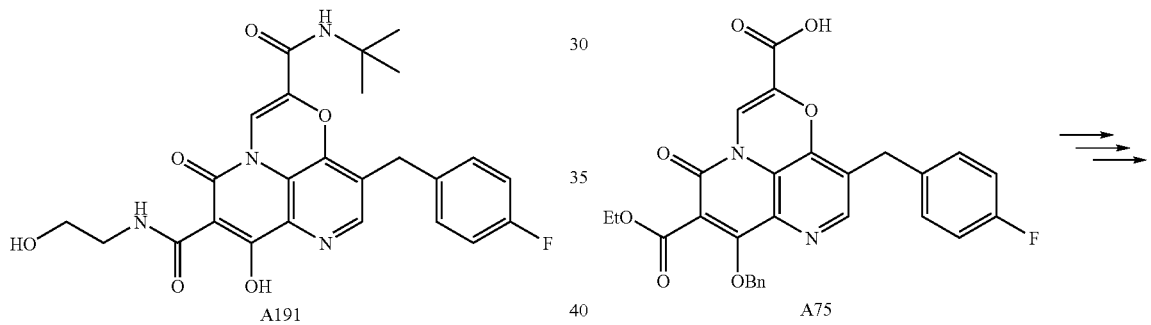
A191                                      A75

The general procedures in steps 4-6 of Example 49 were used. Yield=48% for A191 after three steps. $^1$H NMR (400 MHz, DMSO-d6) d 10.05 (s, 1H), 8.45 (s, 1H), 7.53 (s, 1H), 7.32 (dd, J=8.4, 5.6 Hz, 2H), 7.11 (t, J=8.8 Hz, 2H), 7.08 (s, 1H), 4.06 (s, 2H), 3.53 (m, 2H), 3.42 (m, 2H), 1.31 (s, 9H); MS [M+H]=497.12. LC/MS RT=2.45 min.

EXAMPLE 140

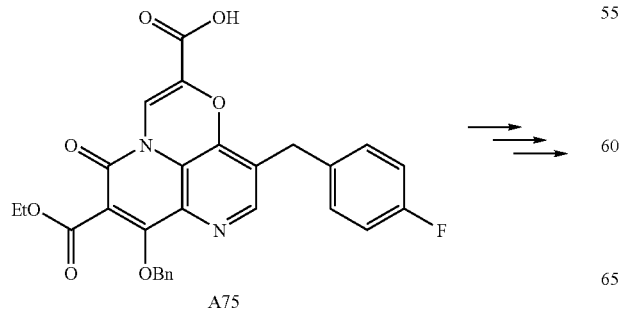
A75

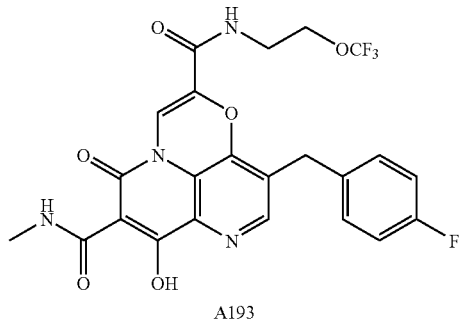
A193

The general procedures in steps 4-6 of Example 49 were used. Yield=2% for the product of this example after three steps. $^1$H NMR (400 MHz, DMSO-d6) d 9.79 (s, 1H), 8.45 (t, J=5.2 Hz, 1H), 8.37 (s, 1H), 7.55 (s, 1H), 7.38 (dd, J=8.4, 5.6 Hz, 2H), 7.09 (t, J=8.8 Hz, 2H), 4.18 (t, J=5.2 Hz, 2H), 4.09

(s, 2H), 3.55 (m, 2H), 2.89 (d, J=4.8 Hz, 2H); MS [M+H]= 523.07. LC/MS RT=2.23 min.

EXAMPLE 142

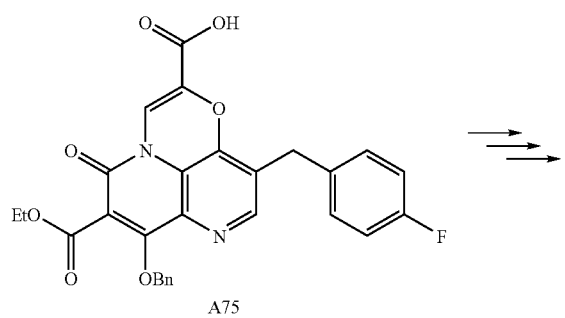

A75

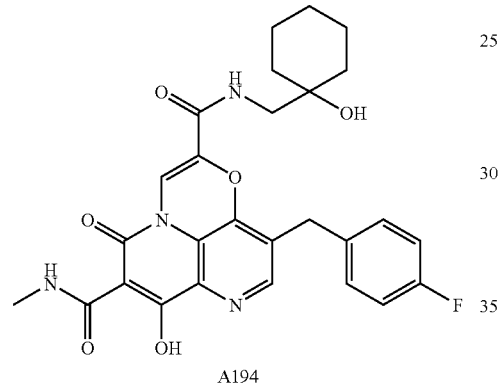

A194

The general procedures in steps 4-6 of Example 49 were used. Yield=4% for the product of this example after three steps. ¹H NMR (400 MHz, DMSO-d6) d 9.80 (s, 1H), 8.46 (s, 1H), 7.67 (m, 1H), 7.52 (s, 1H), 7.38 (dd, J=8.4, 5.6 Hz, 2H), 7.09 (t, J=8.8 Hz, 2H), 4.04 (s, 2H), 3.20 (m, 2H), 2.87 (d, J=4.8 Hz, 2H), 1.52-1.15 (m, 10H); MS [M+H]=523.16. LC/MS RT=2.48 min.

EXAMPLE 143

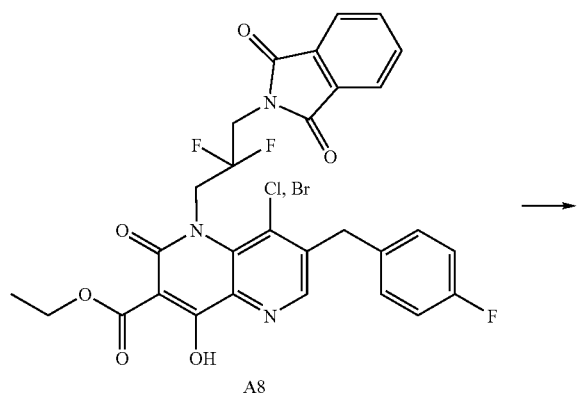

A8

-continued

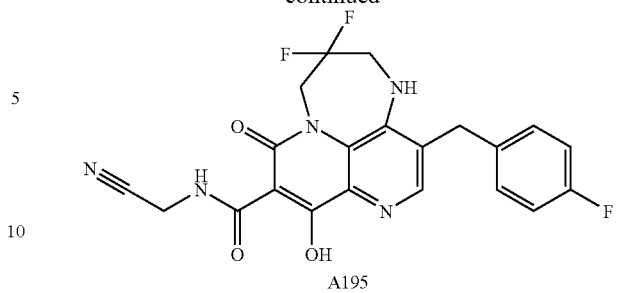

A195

The product of this example was made similarly to Example 30. ¹H NMR (400 MHz, CH₃OH d₄) d 10.31 (1H, t), 8.1 (1H, s), 7.2 (2H, m) 7.1 (2H, m), 4.9 (2H, t), 4.37 (2H, d), 4 (2H, s), 3.73 (2H, m)

¹⁹F NMR (376 MHz, CH₃OH d₄) d −74.6 (s, TFA), −105.2 (m) −116.4 (m)

MS [M+1]=444

EXAMPLE 144

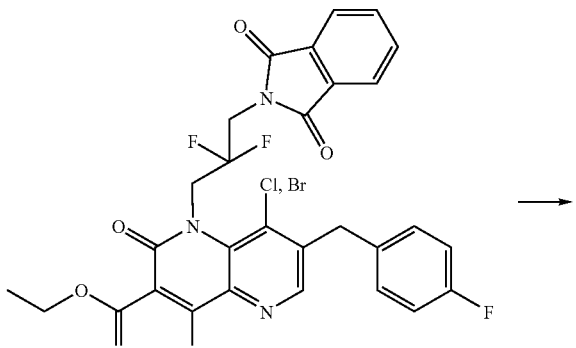

A8

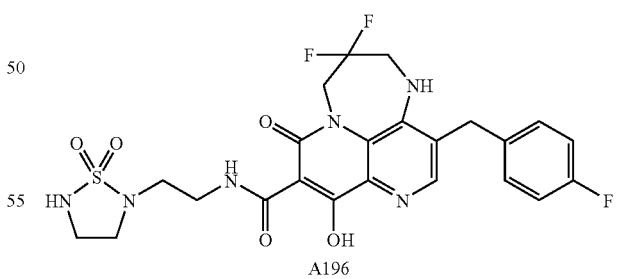

A196

The product of this example was made similarly to Example 30. ¹H NMR (400 MHz, DMSO-d) d 7.78 (1H, s), 7.2 (2H, m), 7.03 (2H, m), 4.6 (2H, t) 3.99 (2H, s), 3.85 (2H, t), 3.66 (2H, t), 3.41 (2H, m), 3.34 (2H, m), 3.2 (2H, m)

¹⁹F NMR (376 MHz, CH₃OH d₄) d −77.1 (s, TFA), −107.7 (m), −117.38 (m)

MS [M+1]=553.07

EXAMPLE 145

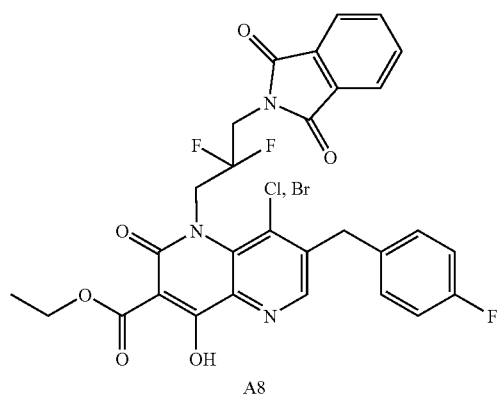

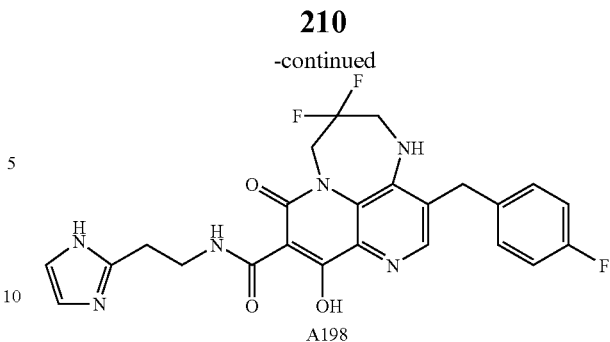

The product of this example was made similarly to Example 30.

$^{1}$H NMR (400 MHz, DMSO-d) d 8.93 (1H, s), 7.84 (1H, s), 7.61 (1H, m), 7.47 (1H, m), 7.19 (2H, m), 7 (2H, m), 4.64 (2H, t), 4.44 (2H, t), 3.97 (2H, s), 3.87 (2H, t), 3.76 (2H, t) 7.83 (1H, s), 7.28 (2H, m), 7.12 (2H, m), 4.72 (2H, t), 4.07 (2H, s), 3.94 (2H, t), 3.43 (2H, s), 3.36 (2H, s), 0.96 (6H, s)

$^{19}$F NMR (376 MHz, CH$_3$OH d$_4$) d −77.04 (s, TFA), −108 (s), −117.7 (m)

MS [M+1]=499.1

EXAMPLE 147

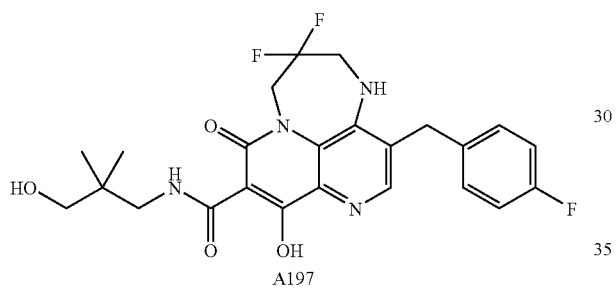

The product of this example was made similarly to Example 30.

$^{1}$H NMR (400 MHz, DMSO-d) d 7.83 (1H, s), 7.28 (2H, m), 7.12 (2H, m), 4.72 (2H, t), 4.07 (2H, s), 3.94 (2H, t), 3.43 (2H, s), 3.36 (2H, s), 0.96 (6H, s)

$^{19}$F NMR (376 MHz, CH$_3$OH d$_4$) d −77.1 (s, TFA), −107.7 (s), −117.33 (m)

MS [M+1]=491.13

EXAMPLE 146

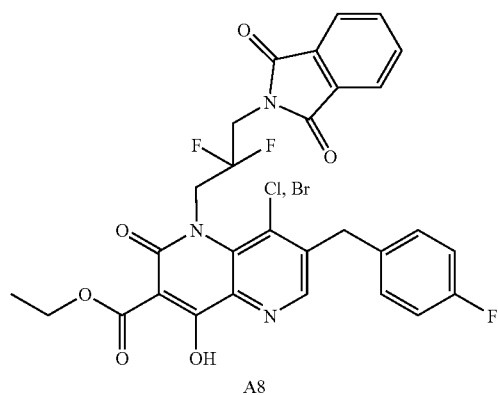

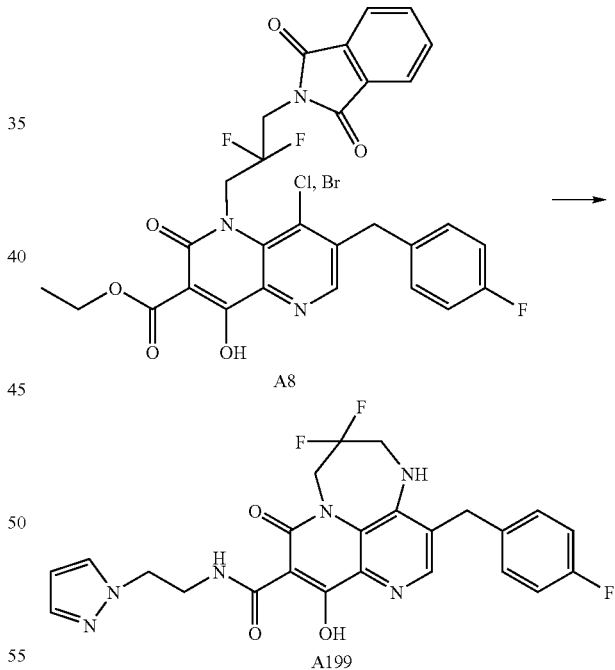

The product of this example was made similarly to Example 30.

$^{1}$H NMR (400 MHz, DMSO-d) d 7.75 (1H, s), 7.58 (1H, d), 7.41 (1H, d), 7.21 (2H, m), 7.03 (2H, m), 6.19 (1H, m), 4.64 (2H, t), 4.18 (2H, t), 3.99 (2H, s), 3.87 (2H, t), 3.4 (2H, m), 2.12 (2H, m)

$^{19}$F NMR (376 MHz, CH$_3$OH d$_4$) δ −77.3 (s, TFA), −107.71 (s), −117.27 (m)

MS [M+1]=513.09

EXAMPLE 148

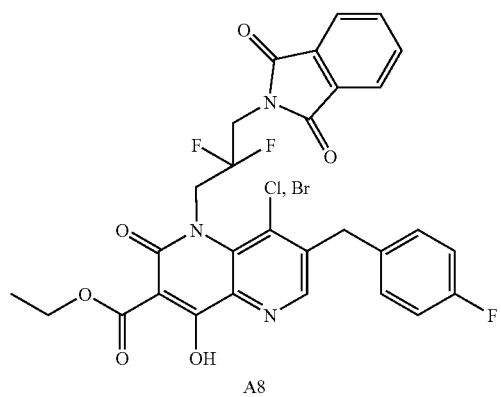
A8

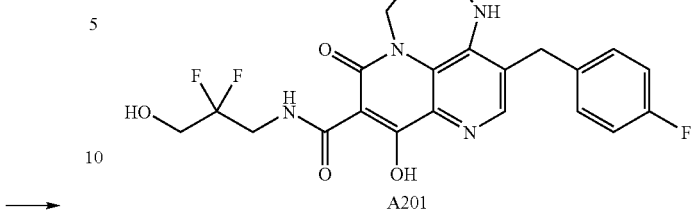
A201

The product of this example was made similarly to Example 30.

$^1$H NMR (400 MHz, DMSO-d) d 7.81 (1H, s), 7.21 (2H, m), 7.02 (2H, m), 4.6 (2H, t), 3.99 (2H, s), 3.95 (2H, t), 3.84 (2H, t), 3.69 (2H, t)

$^{19}$F NMR (376 MHz, CH$_3$OH d$_4$) d −77.14 (s, TFA), −107.8 (s), −114.6 (m), −117.4 (m) MS [M+1]=499.07

EXAMPLE 150

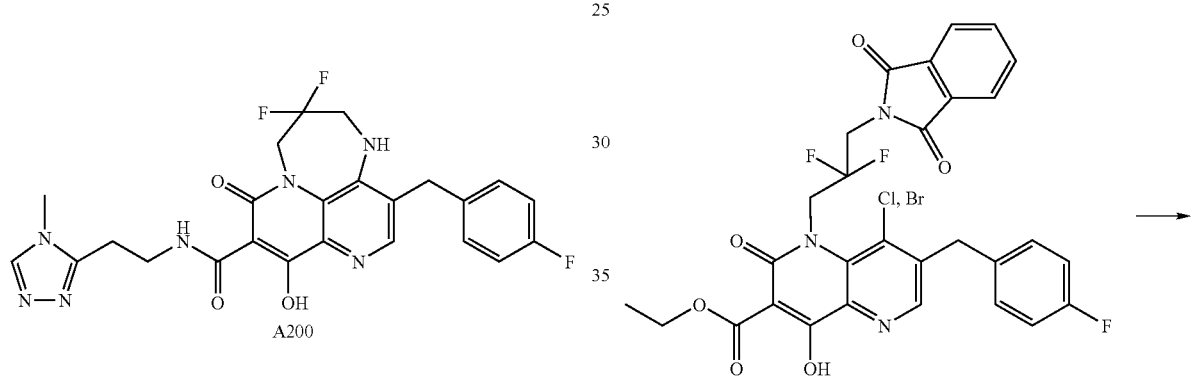
A8

A202

Microwave treatment (150° C., 900 sec followed by 180° C., 900 sec) of A8 (153.6 mg, 0.256 mmol) and (1-aminomethyl-cyclobutyl)-methanol (119.8 mg, 1.04 mmol) in 1.66 mL of DMF. As the reaction did not appear to be complete an additional portion of amine (0.05 mL) was added to the reaction before a third microwave treatment (180° C., 900 sec). Hydrazine (0.1 mL, 102 mg, 3.2 mmol) was added to the reaction before a fourth microwave treatment (150° C., 900 sec) afforded crude A202. Isolation and purification were accomplished via preparative HPLC to afford 28.9 mg of the product (as a TFA salt).

$^1$H NMR (400 MHz, CH$_3$OH d$_4$) d 7.83 (s, 1H), 7.28 (m, 2H), 7.10 (m, 2H), 4.71 (t, J=11.8 Hz, 2H), 4.06 (s, 2H), 3.94 (t, J=12.3 Hz, 2H), 3.65 (s, 2H), 3.60 (s, 2H), 2.94 (m, 2H), 1.87 (m. 2H).

The product of this example was made similarly to Example 30.

$^1$H NMR (400 MHz, DMSO-d) d 8.3 (1H, s), 7.93 (1H, s), 7.15 (2H, m), 6.99 (2H, m), 4.62 (2H, t), 3.95 (2H, s), 3.79 (2H, t), 3.66 (3H, s), 3.62 (2H, t), 3.1 (2H, t)

MS [M+1]=514.08

EXAMPLE 149

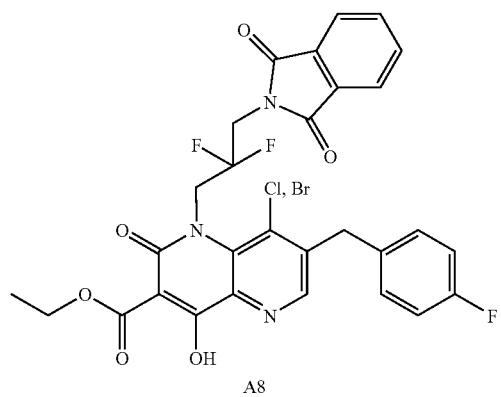
A8

$^{19}$F NMR (376 MHz, CH$_3$OH d$_4$) d −77.2 (s, TFA), −107.715 (m), −117.326 (m)
MS [M+1]=503.11.

EXAMPLE 151

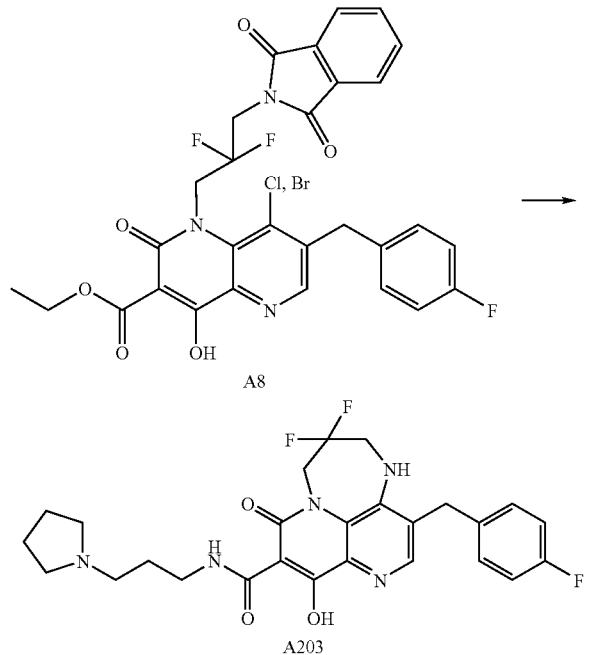

Microwave treatment (120° C., 900 sec) of A8 (143 mg, 0.238 mmol) and 3-pyrrolidin-1-yl-propylamine (154.9 mg, 1.21 mmol) in 1.5 mL of DMF was followed by the addition of hydrazine (0.1 mL, 102 mg, 3.2 mmol) and additional microwave treatment (120° C., 600 sec; 120° C. 1800 sec) afforded crude product. Isolation and purification were accomplished via preparative HPLC to afford 67.2 mg of the product of this example (as a TFA salt).

$^1$H NMR (400 MHz, CH$_3$OH d$_4$) d 7.93 (s, 1H), 7.26 (m, 2H), 7.08 (m, 2H), 4.73 (t, J=11.7 Hz, 2H), 4.06 (s, 2H), 3.84 (t, J=12.3 Hz, 2H), 3.67 (m, 2H), 3.59 (t, J=6.1 Hz, 2H), 3.09 (m, 2H), 2.68 (m, 6H).

$^{19}$F NMR (376 MHz, CH$_3$OH d$_4$) d −77.085 (s, TFA), −108.056 (m), −117.708 (m) MS [M+1]=516.17.

EXAMPLE 152

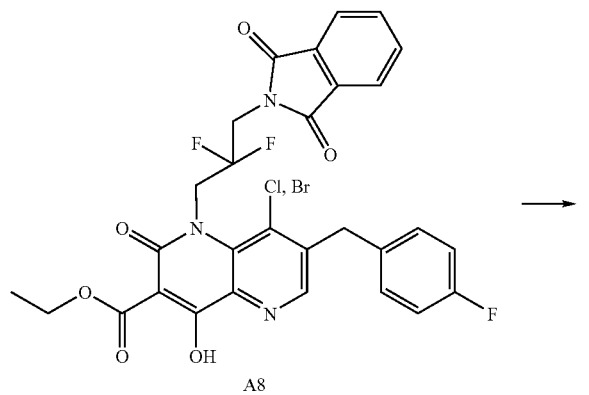

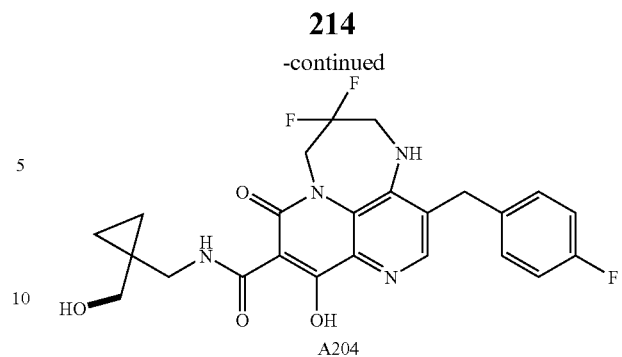

Microwave treatment (150° C., 1200 sec) of A8 (154.5 mg, 0.258 mmol) and (1-aminomethyl-cyclopropyl)-methanol (132.6.4 mg, 1.311 mmol) in 2.5 mL of DMF was followed by the addition of hydrazine (0.1 mL, 102 mg, 3.2 mmol) and additional microwave treatment (150° C., 1200 sec) afforded crude product. Isolation and purification were accomplished via preparative HPLC to afford 41.8 mg of the product of this example (as a TFA salt).

$^1$H NMR (400 MHz, CH$_3$OH d$_4$) d 7.90 (s, 1H), 7.33 (m, 2H), 7.15 (m, 2H), 4.77 (t, J=11.7 Hz, 2H), 4.11 (s, 2H), 3.97 (t, J=12.3 Hz, 2H), 3.60 (s, 2H), 3.52 (s, 2H), 0.66 (m, 2H), 0.61 (m, 2H).

$^{19}$F NMR (376 MHz, CH$_3$OH d$_4$) d −73.115 (s, TFA), −103.897 (m), −113.543 (m)
MS [M+1]=489.08.

EXAMPLE 153

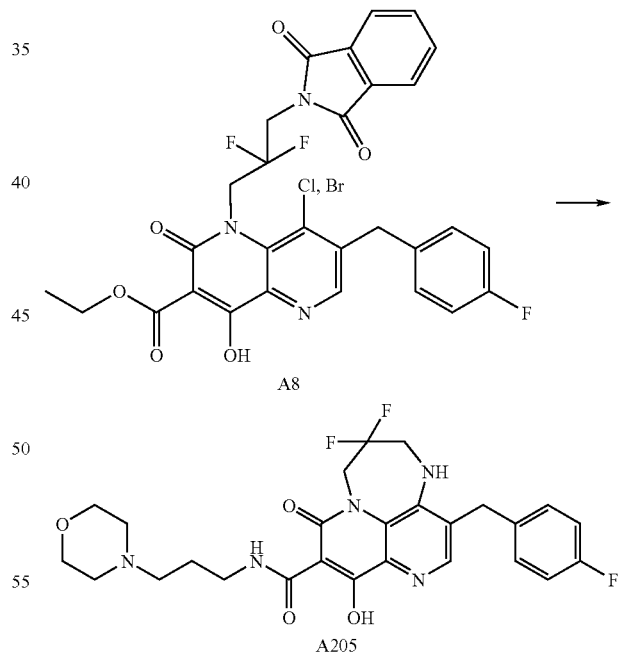

Microwave treatment (120° C., 1200 sec) of A8 (154.7 mg, 0.25 mmol) and 3-morpholin-yl-propylamine (150 μL, 148 mg, 1.15 mmol) in 1.5 mL of DMF was followed by the addition of hydrazine (0.1 mL, 102 mg, 1.026 mmol) and additional microwave treatment (120° C., 1800 sec) afforded crude product. Isolation and purification were accomplished via preparative HPLC to afford 60.6 mg of the product of this example (as a TFA salt).

215

$^1$H NMR (400 MHz, CH$_3$OH d$_4$) d 7.87 (s, 1H), 7.28 (m, 2H), 7.10 (m, 2H), 4.73 (t, J=11.7 Hz, 2H), 4.07 (s, 2H), 4.05, (m, 2H), 3.88 (t, J=12.5 Hz, 2H), 3.74 (m, 2H), 3.59 (t, J=9.9 Hz, 2H), 3.49 (m, 2H), 3.31 (m, under methanol), 3.14 (m, 2H), 2.11 (m, 2H).

$^{19}$F NMR (376 MHz, CH$_3$OH d$_4$) d −77.221 (s, TFA), −107.825.746 (m), −117.404 (m) MS [M+1]=532.23

EXAMPLE 154

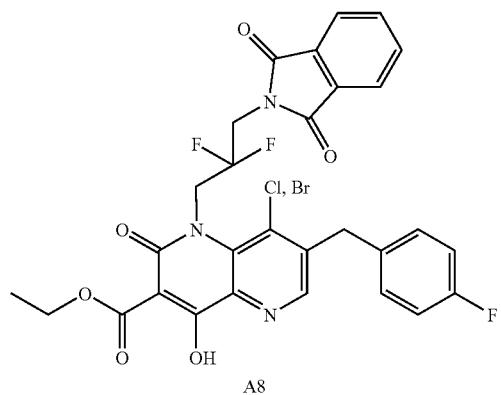

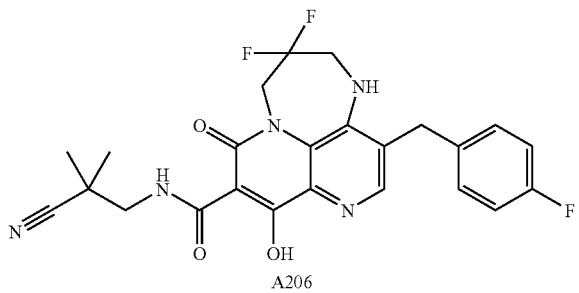

Microwave treatment (120° C., 2×900 sec) of A8 (151.6 mg, 0.25 mmol), 3-amino-2,2-dimethylpropionitrile hydrochloride [synthesis well precedented in the literature from commercially available corresponding carboxylic acid] (163.6 mg, 1.22 mmol) and TEA (245 μL, 178 mg, 1.76 mmol) in 1.5 mL of DMF was followed by the addition of hydrazine (25 μL, 25.5 mg, 0.796 mmol) and additional microwave treatment (100° C., 600 sec, and 120° C., 1800 sec), followed by heating at 120° C. for 4.25 h afforded crude product. Isolation and purification were accomplished via preparative HPLC to afford 49.6 mg of the product of this example (as a TFA salt).

$^1$H NMR (400 MHz, CH$_3$OH d$_4$) d 7.88 (s, 1H), 7.28 (m, 2H), 7.10 (m, 2H), 4.74 (t, J=11.9 Hz, 2H), 4.07 (s, 2H), 3.93 (t, J=12.3 Hz, 2H), 3.70 (s, 2H), 1.43 (s, 6H).

216

$^{19}$F NMR (376 MHz, CH$_3$OH d$_4$) d −77.248 (s, TFA), −107.747 (m), −117.392 (m) MS [M+]=486.07.

EXAMPLE 155

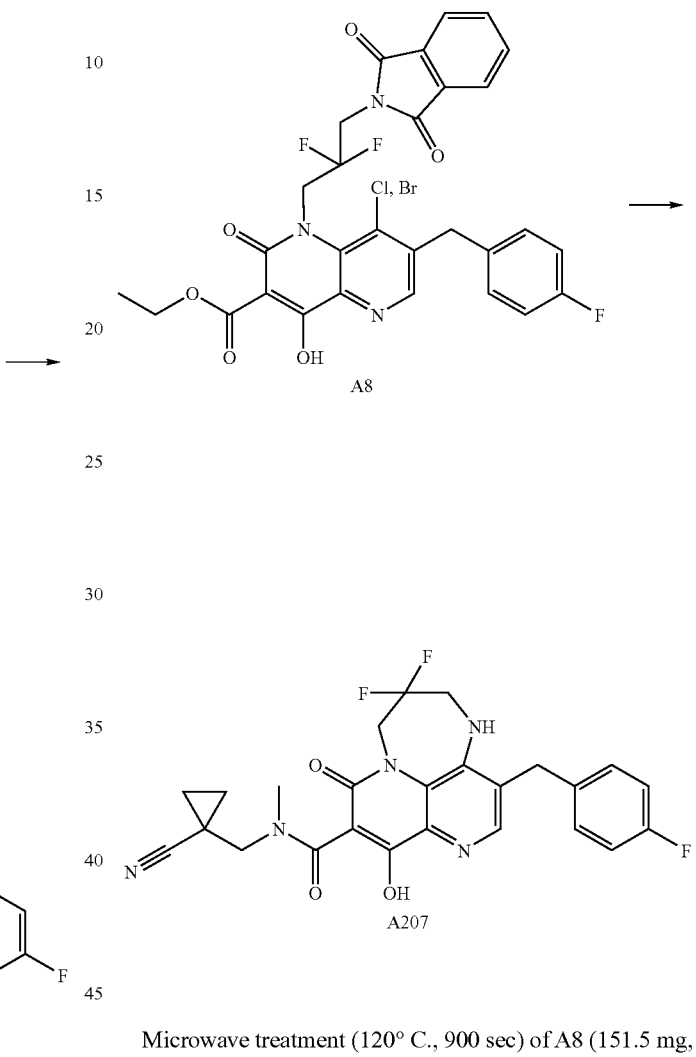

Microwave treatment (120° C., 900 sec) of A8 (151.5 mg, 0.25 mmol), 1-aminomethyl-cyclopropanecarbonitrile hydrochloride [synthesis well precedented in the literature from commercially available corresponding carboxylic acid] (164 mg, 1.24 mmol) and TEA (245 μL, 178 mg, 1.76 mmol) in 1.5 mL of DMF was followed by the addition of hydrazine 25 μL, 25.5 mg, 0.796 mmol) and additional microwave treatment (100° C., 600 sec), followed by 110° C., 1800 sec and heating (120° C., 1.25 h) afforded crude product. Isolation and purification were accomplished via preparative HPLC to afford 80.8 mg of the product of this example (as a TFA salt).

$^1$H NMR (400 MHz, CH$_3$OH d$_4$) d 7.79 (s, 1H), 7.22 (m, 2H), 7.03 (m, 2H), 4.67 (t, J=11.9 Hz, 2H), 4.00 (s, 2H), 3.87 (t, J=12.3 Hz, 2H), 3.58 (s, 2H), 1.23 (m, 2H), 1.13 (m, 2H).

$^{19}$F NMR (376 MHz, CH$_3$OH d$_4$) d −77.320 (s, TFA), −107.695 (m), −117.314 (m)

MS [M+1]=484.05.

EXAMPLE 156

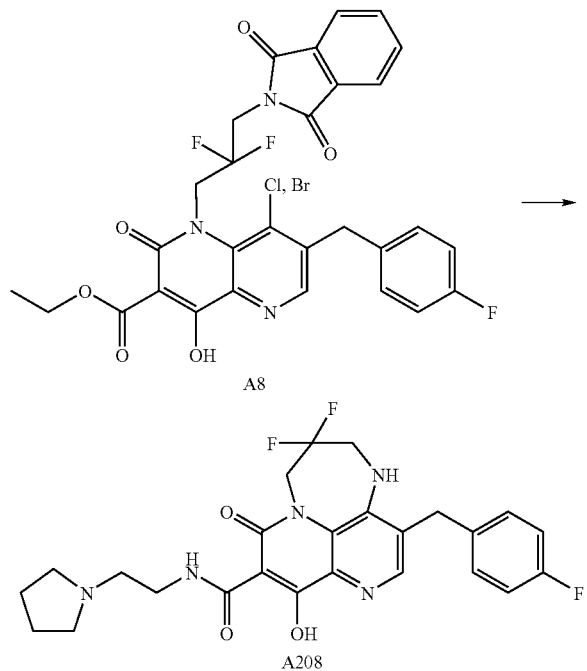

Microwave treatment (120° C., 900 sec) of A8 (225.2 mg, 0.375 mmol) and 2-pyrrolidin-1-yl-ethylamine (100 μL, 90.2 mg, 0.794 mmol) in 2 mL of DMF was followed by the addition of hydrazine (0.1 mL, 102 mg, 3.2 mmol) and additional microwave treatment (120° C., 1800 sec) afforded crude product. Isolation and purification were accomplished via preparative HPLC to afford 143 mg of the product of this example. (as a TFA salt).

$^1$H NMR (400 MHz, CH$_3$OH d$_4$) d 7.90 (s, 1H), 7.27 (m, 2H), 7.09 (m, 2H), 4.74 (t, J=11.7 Hz, 2H), 4.05 (s, 2H), 3.85 (m, 3H), 3.78 (bs, 2H), 3.48 (t, J=5.68 Hz, 2H), 3.15 (bs, 2H), 2.15 (bs, 2H), 2.03 (bs, 2H).

$^{19}$F NMR (376 MHz, CH$_3$OH d$_4$) d −77.209 (s, TFA), −107.952 (m), −117.593 (m)

MS [M+1]=502.14.

EXAMPLE 157

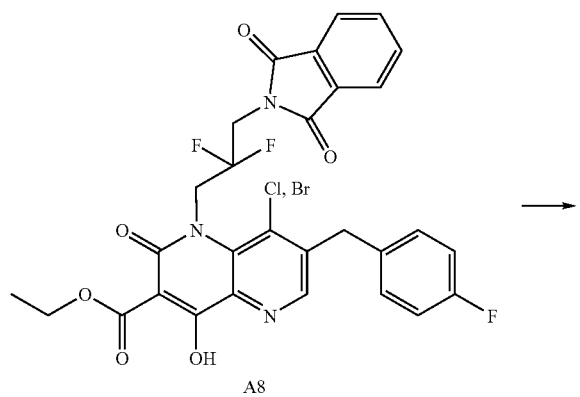

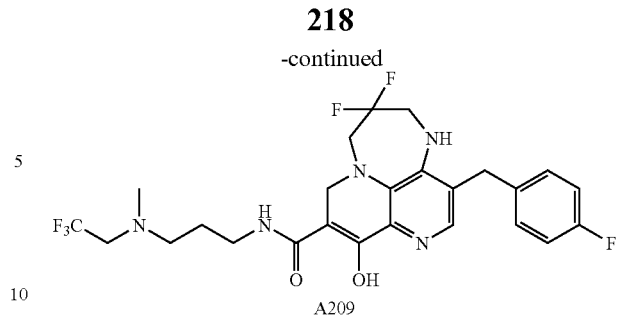

Microwave treatment (120° C., 1200 sec; 120° C., 2×900 sec after the addition of 53.5 mg of 2-methoxyethylamine) of A8 (224.5 mg, 0.374 mmol) and 2-methoxyethylamine (123.7 mg, 0.727 mmol) in 2 mL of DMF was followed by the addition of hydrazine (0.1 mL, 102 mg, 3.2 mmol) and additional microwave treatment (120° C., 2×1800 sec) afforded crude product. Isolation and purification were accomplished via preparative HPLC to afford 96 mg of the product of this example (as a TFA salt).

$^1$H NMR (400 MHz, CH$_3$OH d$_4$) d 7.83 (s, 1H), 7.28 (m, 2H), 7.10 (m, 2H), 4.72 (t, J=12.5 Hz, 2H), 4.06 (s, 2H), 3.93 (t, J=12.5 Hz, 2H), 3.57 (t, J=6.7 Hz, 2H), 3.24 (q, J=9.8 Hz, 2H), 2.76 (t, J=6.7 Hz, 2H), 2.51 (s, 3H), 1.86 (quint, J=7.1 Hz, 2H).

$^{19}$F NMR (376 MHz, CH$_3$OH d$_4$) −70.507 (m), d −77.258 (s, TFA), −107.507 (m), −117.339 (m)

MS [M+1]=558.13.

EXAMPLE 158

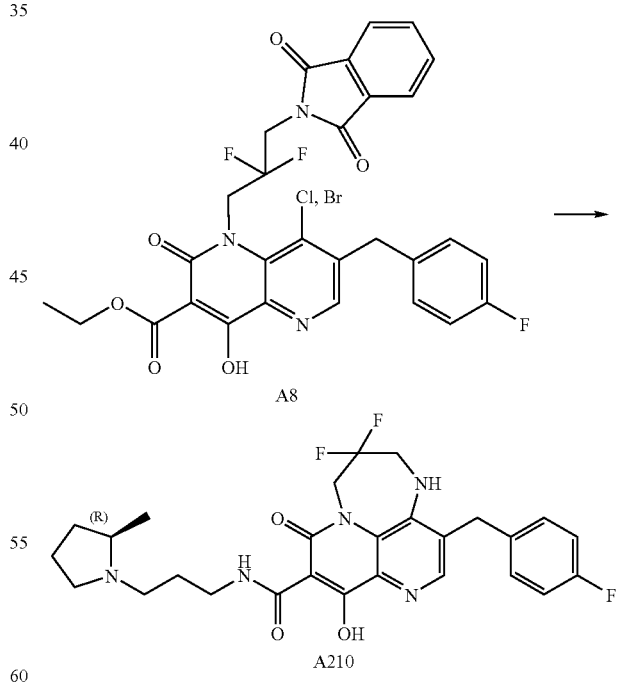

Microwave treatment (120° C./900 sec, 135° C./900 see, 150° C./900 sec) of A8 (228.4 mg, 0.38 mmol), (R)-3-(2-methyl-pyrrolidin-1-yl)-propylamine (HCl)$_2$ [synthesis well precedented in the literature from commercially available N-(3-bromopropyl)-phthalimide] (337.5 mg, 1.56 mmol) and TEA (0.25 mL, 181.5 mg, 1.79 mmol) in 2.5 mL of DMF was followed by the addition of amine dihydrochloride (68 mg, 0.26 mmol), TEA (0.25 mL, 181.5 mg, 1.79 mmol) and 0.5 mL of DMF and additional microwave treatment (150° C./900 sec). Subsequently, addition of hydrazine (0.1 mL, 102 mg, 3.2 mmol) and additional microwave treatment (120° C., 1800 sec) afforded crude product. Isolation and purification were accomplished via preparative HPLC to afford 34.3 mg of the product of this example (as a TFA salt).

$^1$H NMR (400 MHz, CH$_3$OH d$_4$) d 794 (s, 1H), 7.26 (m, 2H), 7.08 (m, 2H), 4.73 (t, J=11.9 Hz, 2H), 4.05 (s, 2H), 3.83 (t, J=14.9 Hz, 2H), 3.68 (m, 1H), 3.57 (t, J=6.84 Hz, 2H), 3.44 (m, 2H), 3.18 (m, 1), 3.06 (m, 1H), 2.33 (m, 1H), 2.08 (4H), 1.73 (m, 1H) 1.43 (d, J=6.5, 3H).

$^{19}$F NMR (376 MHz, CH$_3$OH d$_4$) d −77.087 (s, TFA), −108.067 (m), −117.745 (m) MS [M+1]=530.23.

EXAMPLE 159

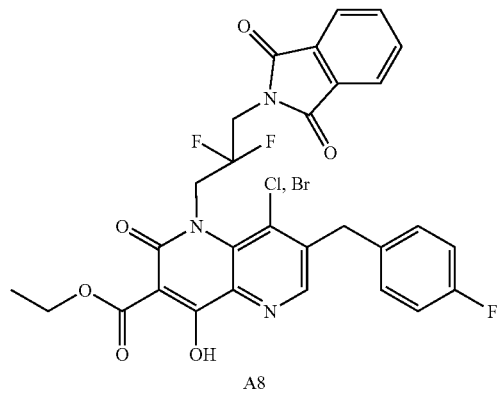

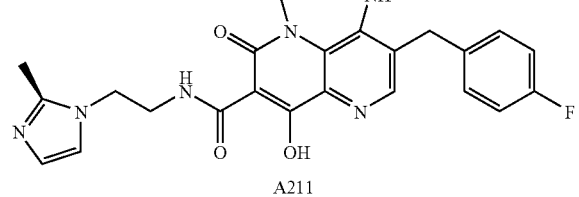

Microwave treatment (120° C., 2×1200 sec, 120° C., 1200 sec after the addition of 20 µL additional amine) of A8 (22.7 mg, 0.038 mmol) and 3-(2-methylimidazol-1-yl)-propylamine [synthesis well precedented in the literature from commercially available N-(3-bromopropyl)-phthalimide] (20 µL, neat) in 1 mL of DMF was followed by the addition of A8 (234.3 mg, 0.39 mmol), amine (300 µL, neat), 1 ml of DMF microwave treatment (120° C., 1800 sec). Hydrazine (0.1 mL, 102 mg, 3.2 mmol) was added to the reaction and additional microwave treatment (120° C., 1800 sec) afforded crude product. Isolation and purification were accomplished via preparative HPLC to afford 153.3 mg of the product of this example (as a TFA salt).

$^1$H NMR (400 MHz, CH$_3$OH d$_4$) d 7.91 (s, 1H), 7.57 (d, J=2 Hz, 1H), 7.42 (d, J=2 Hz, 1H), 7.27 (m, 2H), 7.09 (m, 2H), 4.76 (t, J=11.9 Hz, 2H), 4.24 (t, J=7.2, 2H), 4.06 (s, 2H), 3.87 (t, J=12.3 Hz, 2H), 3.57 (t, J=6.7 Hz, 2H) 2.64 (s, 3H), 2.22 (quint, J=6.7 Hz, 2H).

$^{19}$F NMR (376 MHz, CH$_3$OH d$_4$) d −77.207 (s, TFA), −107.978 (m), −117.608 (m) MS [M+1]=527.14.

EXAMPLE 160

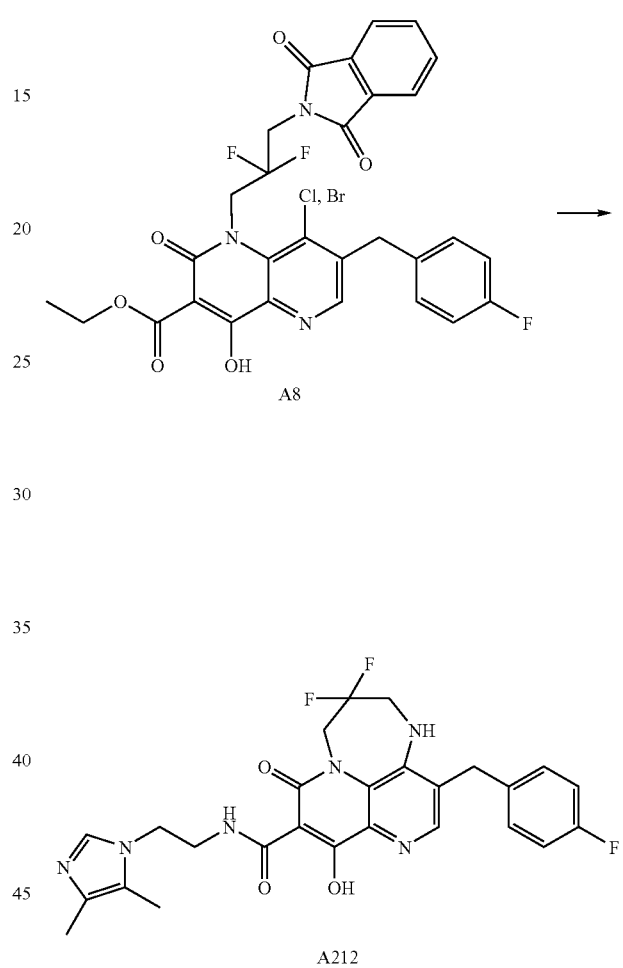

Microwave treatment (120° C., 1×1800 sec, 1×1200 sec, and 120° C. after the addition of 75 µL additional amine) of A8 (22.7 mg, 0.038 mmol) and 3-(3,4-dimethylimidazol-1-yl)-propylamine [synthesis well precedented in the literature from commercially available N-(3-bromopropyl)-phthalimide] (150 µL, 233.1 mg (total) 1.52 mmol) in 2 mL of DMF was followed by the addition of hydrazine (0.1 mL, 102 mg, 3.2 mmol) and additional microwave treatment (120° C., 1800 sec) afforded crude product. Isolation and purification were accomplished via preparative HPLC to afford 108.6 mg of the product of this example (as a TFA salt).

$^1$H NMR (400 MHz, CH$_3$OH d$_4$) d 8.79 (s, 1H), 7.93 (s, 1H), 7.27 (m, 2H), 7.08 (m, 2H), 4.76 (t, J=11.9 Hz, 2H), 4.23 (t, J=7.0 Hz, 2H), 4.06 (s, 2H), 3.85 (t, J=12.3 Hz, 2H), 3.57 (t, J=6.7 Hz, 2H), 2.28 (s, 3H), 2.47 (s, 3H), (quint., J=7.0 Hz, 2H).

$^{19}$F NMR (376 MHz, CH$_3$OH d$_4$) d −77.164 (s, TFA), −107.974 (m), −117.656 (m) MS [M+1]=541.16.

EXAMPLE 161

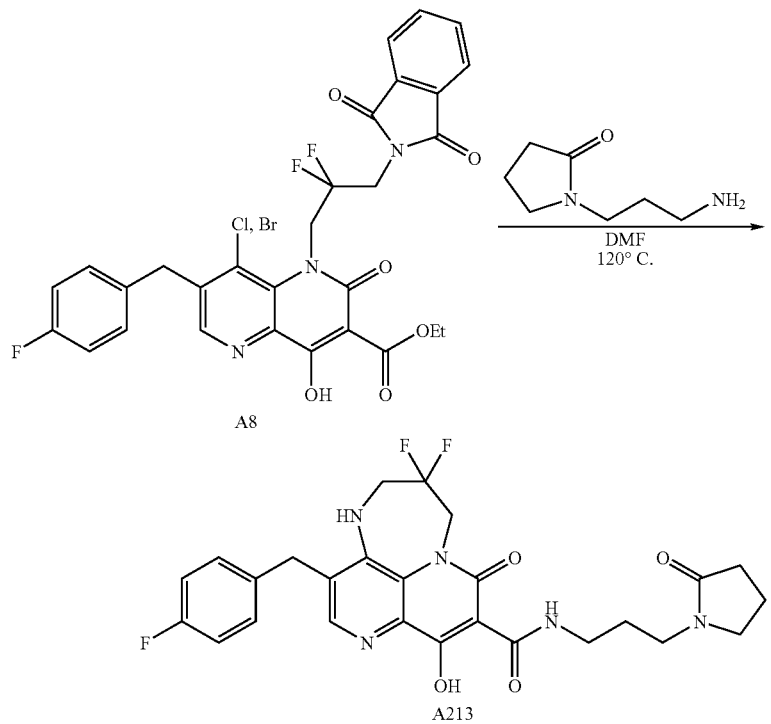

150 mg of A8 (0.254 mmol) were dissolved in 1.5 ml of DMF in a 5 mL microwave vial. To this solution, 300 mg of the amine (2.11 mmol) were added using a syringe. The mixture was subjected to microwave treatment for 15 min at 120° C. LCMS analysis revealed partial conversion to the desired product. The reaction was re-sealed and subjected to heating overnight on a heating block at 120° C. The crude solution was purified via preparative HPLC to afford 45 mg of the product of this example (as a TFA salt).

400 MHz $^1$H NMR (DMSO): d 10.24 (s, 1H), 8.08 (s, 1H), 7.85-7.79 (t, 1H), 7.54-7.30 (t, 2H), 7.16-7.11 (t, 2H), 4.65-4.59 (t, 2H), 4.05 (s, 2H), 4.00-3.97 (m, 2H), 3.85-3.80 (m, 2H), 3.21 (m, 2H), 3.13 (s, 2H), 2.20-2.12 (m, 2H), 1.95-1.85 (m, 2H), 1.77-1.70 (m, 2H), 1.14 (m, 2H).

MS[M+H]=540

LCMS RT=2.16 min

EXAMPLE 162

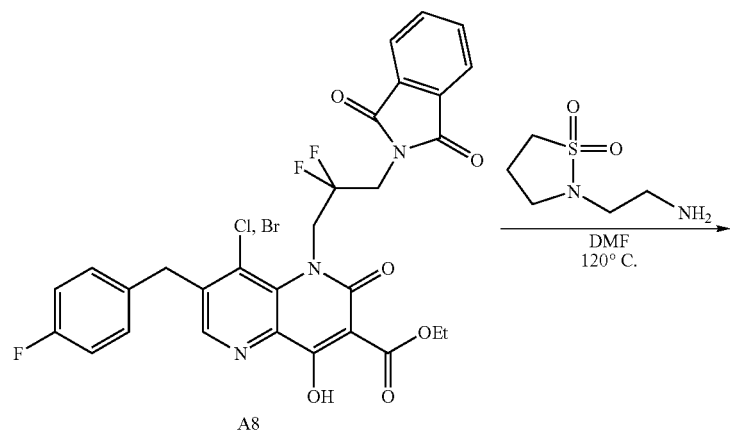

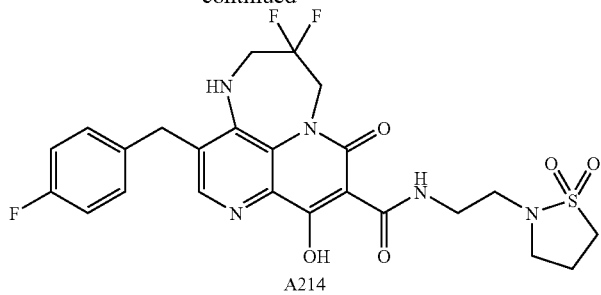

A214

150 mg of A8 (0.254 mmol) were dissolved in 1.3 mL of DMF in a 5 mL microwave vial. To this solution, 300 mg of the amine (1.83 mmol) were added using a syringe. The mixture was subjected to microwave treatment for 15 min at 120° C. LCMS analysis revealed partial conversion to the desired product. The reaction was re-sealed and subjected to heating 1 h on a heating block at 120° C. The crude solution was purified via preparative HPLC to afford 2.5 mg of the product of this example (as a TFA salt).

400 MHz $^1$H NMR (DMSO): d 10.14 (s, 1H), 8.08 (s, 1H), 7.27-7.22 (t, 2H), 7.21-7.07 (t, 2H), 6.83 (s, 1H), 4.59 (t, 2H), 4.05 (s, 2H), 3.97 (s, 2H), 3.63-3.60 (m, 2H), 3.21 (m, 2H), 3.13 (s, 2H), 2.20-2.12 (m, 4H).

MS[M+H]=552
LCMS RT=4.25 min

EXAMPLE 163

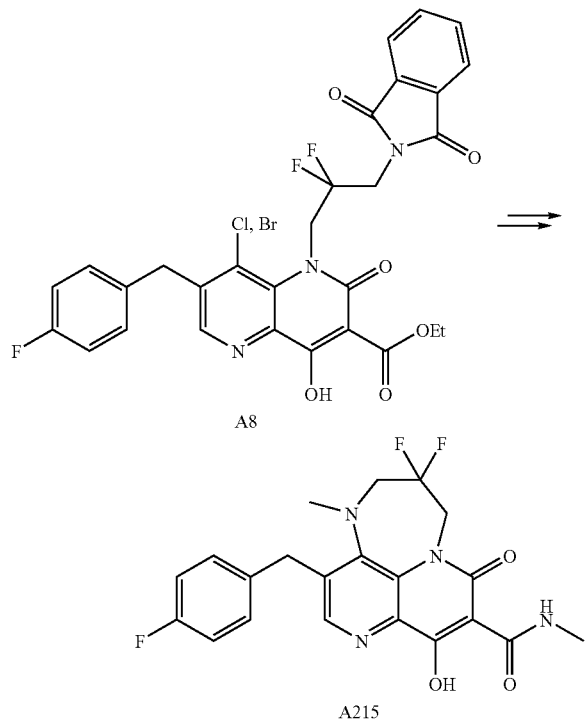

Step 1

200 mg of Intermediate A8 was treated at 100° C. with excess methylamine in DMF such that in addition to amide formation, imide cleavage is affected.

Step 2

The resulting intermediate, 80 mg, was subjected to reductive amination utilizing excess aq. formaldehyde and sodium triacetoxyborohydride to give 70 mg of the N-methylated product.

Step 3

The intermediate from above, 70 mg in 2 mL DMF, was heated to 120° C. in the presence of excess triethylamine. HPLC purification furnished 4 mg of final product.

$^1$H NMR (d$_6$-DMSO) d 8.18 (s, 1H) 7.22 (m, 2H), 7.04 (m, 2H), 4.76 (m, 2H), 4.27 (s, 3H), 3.68 (m, 2H), 3.20 (s, 3H), 3.05 (s, 3H); MS [M+H]=433.

EXAMPLE 164

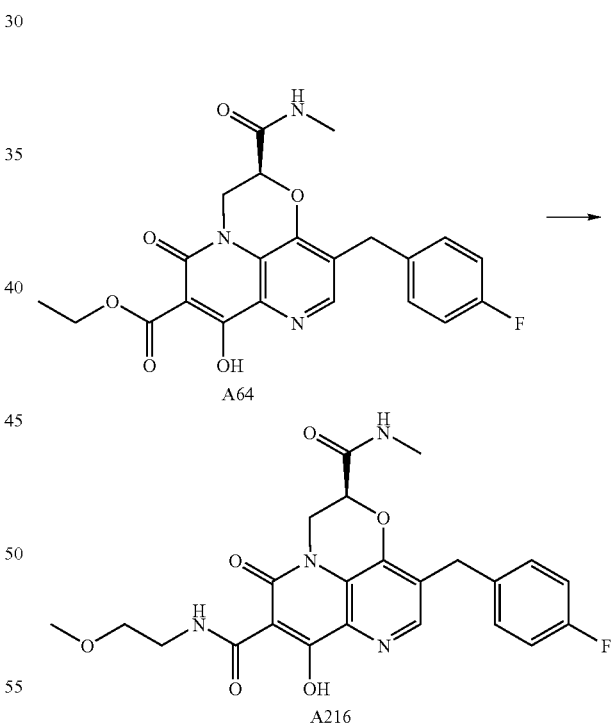

To a solution of intermediate A64 (40 mg, 0.093 mmol, 1 equiv.) in DMF (0.5 mL, 0.2 M) was added 2-Methoxyethylamine (16 µL, 2 equiv.). The reaction was heated in a microwave reactor at 120° C. for 20 minutes. Upon completion, the material was purified by RP-HPLC (MeCN—H$_2$O gradient) to furnish the desired product.

400 MHz $^1$H NMR (DMSO-d$_6$): d 10.37 (bs, 1H), 8.27 (s, 1H), 8.32 (d, J=4.4 Hz, 1H), 7.33-7.30 (m, 2H), 7.11-7.06 (m, 2H), 5.00-5.04 (m, 1H), 4.39 (d, J=11.2 Hz, 1H), 4.15 (d,

J=14.4 Hz, 1H), 3.90-4.05 (m, 2H), 3.44 (s, 3H), 3.10-3.17 (m, 2H), 2.83 (d, 3H), 2.70-2.75 (m, 2H), 2.62 (d, J=4.4 Hz, 3H).

400 MHz $^{19}$F NMR (DMSO-d$_6$): −116.85

LCMS (m/z+1): 471.03.

EXAMPLE 165

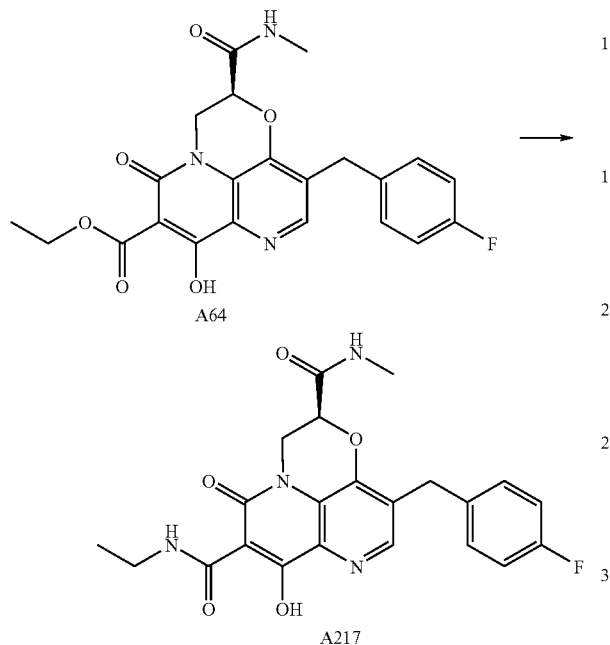

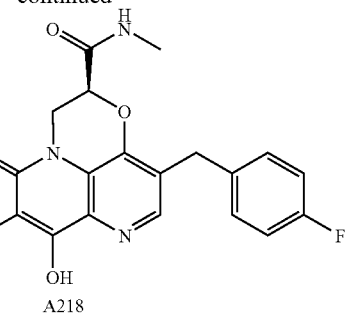

To a solution of intermediate A64 (43 mg, 0.097 mmol, 1 equiv.) in DMF (0.5 mL, 0.2 M) was added 3-amino-propanol (22 μL, 3 equiv). The reaction was heated in a microwave reactor at 120° C. for 40 minutes. Upon completion, the material was purified by RP-HPLC (MeCN—H$_2$O gradient) to furnish the desired product.

400 MHz $^1$H NMR (DMSO-d$_6$): d 10.37 (bs, 1H), 8.27 (s, 1H), 8.32 (d, J=4.4 Hz, 1H), 7.33-7.30 (m, 2H), 7.11-7.06 (m, 2H), 5.00-5.04 (m, 1H), 4.39 (d, J=11.2 Hz, 1H), 4.15 (d, J=14.4 Hz, 1H), 3.90-4.05 (m, 2H), 3.10-3.17 (m, 2H), 2.83 (d, 3H), 2.70-2.75 (m, 2H), 2.64 (d, J=4.2 Hz, 3H).

400 MHz $^{19}$F NMR (DMSO-d$_6$): −116.85

LCMS (m/z+1): 471.03.

To a solution of intermediate A64 (43 mg, 0.097 mmol, 1 equiv.) in DMF (0.5 mL, 0.2 M) was added ethylamine (150 μL, 3 equiv, 2 M THF). The reaction was heated in a microwave reactor at 120° C. for 40 minutes. Upon completion, the material was purified by RP-HPLC (MeCN—H$_2$O gradient) to furnish the desired product.

400 MHz $^1$H NMR (DMSO-d$_6$): d 10.12 (bs, 1H), 8.39 (s, 1H), 8.38 (d, J=4.4 Hz, 1H), 7.33-7.30 (m, 2H), 7.11-7.06 (m, 2H), 5.00-5.04 (m, 1H), 4.39 (d, J$_{1,2}$=3.6, 14.0 Hz, 1H), 4.25 (d, J=14.8 Hz, 1H), 3.90-4.05 (m, 2H), 3.38-3.42 (m, 2H), 2.63 (d, J=48 Hz, 3H), 1.15-1.20 (m, 3H).

400 MHz $^{19}$F NMR (DMSO-d$_6$): −116.72, −74.10 (TFA salt).

LCMS (m/z+1): 441.04

EXAMPLE 166

EXAMPLE 167

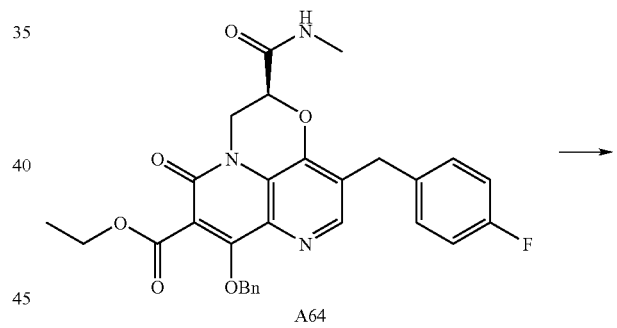

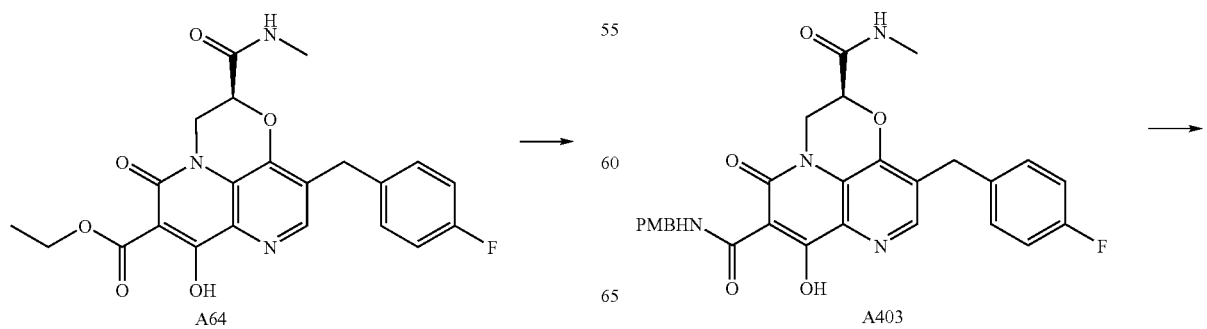

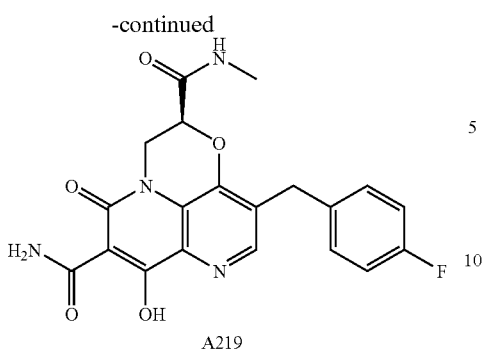

A219

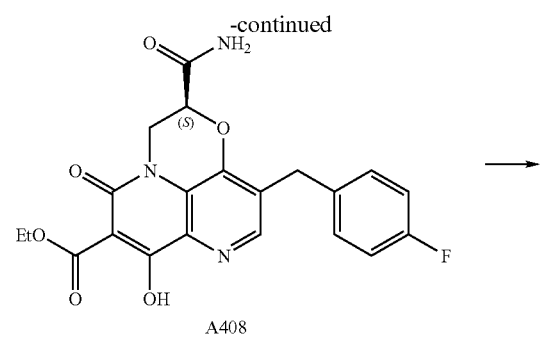

A408

To a solution of intermediate A64 (50 mg, 0.11 mmol, 1 equiv.) in THF/CH₃CN (1 mL/1 mL) was added para-methoxybenzylamine (50 μL, 4 equiv). The reaction was heated in a microwave reactor at 120° C. for 20 minutes to form A403. Upon completion, the material was concentrated in vacuo and dissolved in CH₃CN/water (3 mL/1 mL) before cerium ammonium nitrate (90 mg, 1.5 equiv.) was added. The flask was warmed to 45° C. and carried out until the starting material was consumed. The material was purified by RP-HPLC (MeCN—H$_2$O gradient) to furnish the desired product.

400 MHz $^1$H NMR (DMSO-d$_6$): d 9.48 (bs, 1H), 8.76 (bs, 1H), 8.38 (s, 1H), 8.20 (d, J=5.2 Hz, 1H), 7.32-7.30 (m, 2H), 7.11-7.06 (m, 2H), 5.07-5.12 (m, 1H), 4.40 (dd, J=3.6, 14.0 Hz, 1H), 4.15 (d, J=14.4 Hz, 1H, 3.98-4.10 (m, 2H), 2.62 (d, J=4.8 Hz, 3H).

400 MHz $^{19}$F NMR (DMSO-d$_6$): −116.72, −74.44 (TFA salt).

LCMS (m/z+1): 413.01.

EXAMPLE 168

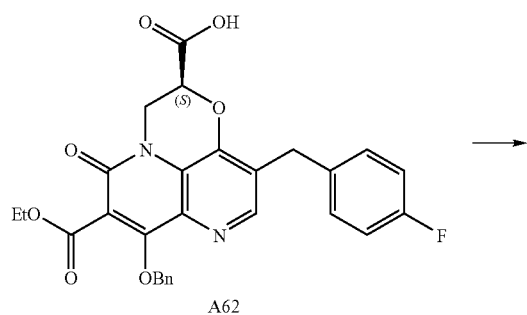

A62

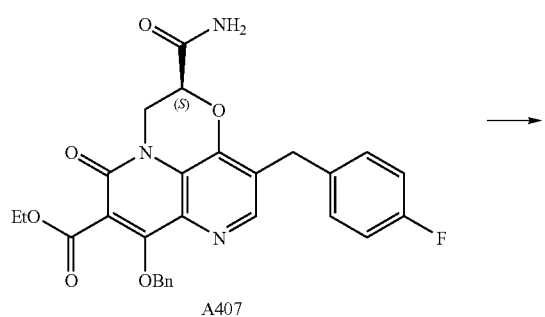

A407

To the carboxylic acid A62 (190 mg, 0.36 mmol, 1.0 equiv) was added DMF (4.4 mL, 0.15 M) and to it added HATU (245 mg, 1.5 equiv.). After stirring for 1 minute NH$_3$ (2.6 mL, 1.29 mmol, 3 equiv, 0.5 M THF) was added. The mixture was stirred for 1 hour at room temperature. The crude reaction mixture was then diluted with EtOAc and washed with water and brine. The organic layer was dried over sodium sulfate and concentrated in vacuo to form A407 which was used without farther purification.

The crude A407 was dissolved in EtOH/EtOAc (5 mL/5 mL) and Pd (70 mg, 0.07 mmol, 0.2 equiv, 10% in carbon) and stirred under an atmosphere of hydrogen via a balloon. After the reaction was complete, the solid was filtered and the filtrate concentrated down before being purified by RP-HPLC (MeCN—H$_2$O gradient) to furnish A408.

A408 was placed in a microwave vial in DMF (0.5 mL, 0.2 M) was added methylamine (170 μL, 3 equiv, 2 M in THF). The reaction was heated in a microwave reactor at 120° C. for 40 minutes. Upon completion, the material was purified by RP-HPLC (MeCN—H$_2$O gradient) to furnish the desired product. 400 MHz $^1$H NMR (DMSO-d$_6$): d 10.14 (bs, 1H), 8.19 (s, 1H), 7.59 (bs, 2H), 7.32-7.30 (m, 2H), 7.11-7.06 (m, 2H), 4.93-4.97 (m, 1H), 4.32 (d, J=13.2 Hz, 1H), 4.15 (d, J=16.6 Hz, 1H), 3.90-4.05 (m, 2H), 2.75 (d, J=3.6 Hz, 3H).

400 MHz $^{19}$F NMR (DMSO-d$_6$): −116.99

LCMS (m/z+1): 413.01.

EXAMPLES 169-175

Compounds were prepared from A62 in a manner similar to A50 steps 12-14 by substituting the appropriate amines. Final compounds were purified by HPLC and isolated as TFA salts (3-step yields 50-70%).

EXAMPLES 169-171

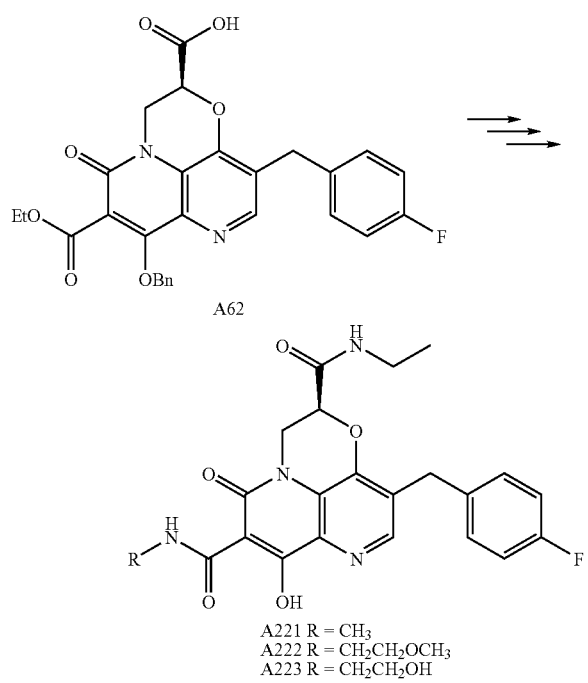

EXAMPLE 169
400 MHz $^1$H NMR (DMSO) d 10.13 (s, 1H), 8.24 (s, 1H), 8.13 (s, 1H), 7.31 (q, 2H), 7.07 (t, 2H), 4.94 (m, 1H), 4.38 (dd, 1H), 4.09 (d, 1H), 3.98 (d, 1H), 3.93-3.88 (m, 1H), 3.93-3.88 (m, 1H), 3.12-3.07 (m, 2H), 2.78 (d, 2H), 2.28 (s, 3H), 0.99 (t, 3H); $^{19}$F NMR (DMSO); 69, 71, 117; MS[M+H]=441

EXAMPLE 170
400 MHz $^1$H NMR (DMSO) d 10.35 (s, 1H), 8.32 (s, 1H), 8.19 (s, 1H), 7.32 (q, 2H), 7.08 (t, 2H), 5.01 (m, 1H), 4.38 (dd, 1H), 4.14-4.02 (m, 3H), 3.46-3.33 (m, 3H), 3.30-3.10 (m, 6H), 2.74 (s, 1H), 0.99 (t, 3H); $^{19}$F NMR (DMSO); 69, 71, 117; MS[M+H]=485

EXAMPLE 171
400 MHz $^1$H NMR (DMSO) d 10.32 (s, 1H), 8.28 (s, 1H), 8.11 (s, 1H), 7.31 (q, 2H), 7.10 (t, 2H), 4.98 (m, 1H), 4.37 (dd, 1H), 4.16-3.96 (m, 3H), 3.38-3.29 (m, 2H), 3.14-3.07 (m, 2H), 2.70-2.61 (m, 4H) 0.99 (t, 3H); $^{19}$F NMR (DMSO); 69, 71, 117; MS[M+H]=471

EXAMPLES 172-173

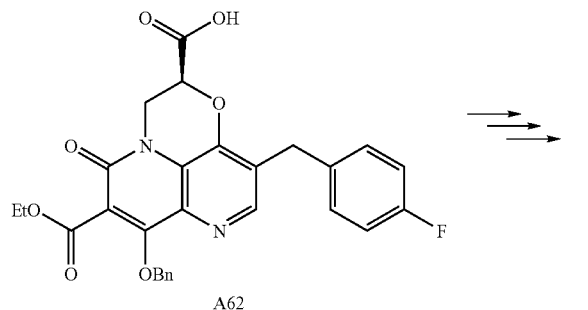

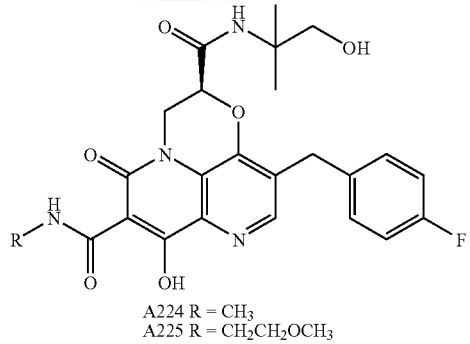

EXAMPLE 172
400 MHz $^1$H NMR (DMSO) d 10.18 (s, 1H), 8.21 (s, 1H), 7.92 (s, 1H), 7.48 (s, 1H), 7.31 (t, 2H), 7.06 (t, 2H), 4.87 (m, 1H), 4.32 (dd, 1H), 4.05-3.95 (m, 3H), 2.85 (s, 1H), 2.75 (d, 2H), 2.69 (s, 1H) 2.34 (s, 3H), 1.19-1.15 (m, 6H); $^{19}$F NMR (DMSO); 69, 71, 117; MS[M+H]=485

EXAMPLE 173
400 MHz $^1$H NMR (DMSO) d 10.41 (s, 1H), 8.32 (s, 1H), 7.53 (s, 1H), 7.30 (q, 2H), 7.07 (t, 2H), 4.94 (s, 2H), 4.32 (dd, 1H), 4.05-3.97 (m, 3H), 3.45-3.35 (m, 4H), 3.30-3.19 (m, 4H), 0.99 (m, 6H); $^{19}$F NMR (DMSO); 69, 71, 117; MS[M+H]=529

EXAMPLE 174

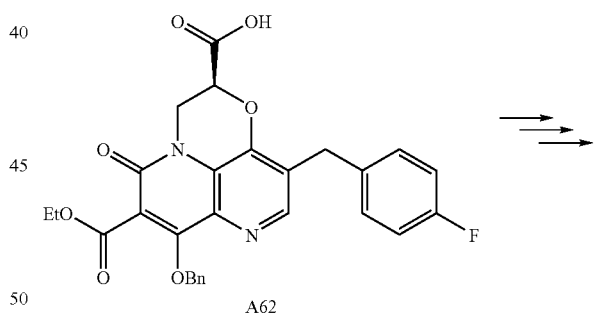

400 MHz $^1$H NMR (DMSO) d 10.00 (s, 1H), 8.43 (s, 1H), 8.05 (t, 1H), 7.33 (q, 2H), 7.06 (t, 2H), 5.22 (t, 1H), 4.28 (d,

2H), 4.09 (d, 2H), 3.03 (d, 2H), 2.89-2.85 (m, 4H), 0.99 (m, 6H); 19F NMR (DMSO); 75, 117; MS[M+H]=485

EXAMPLE 175

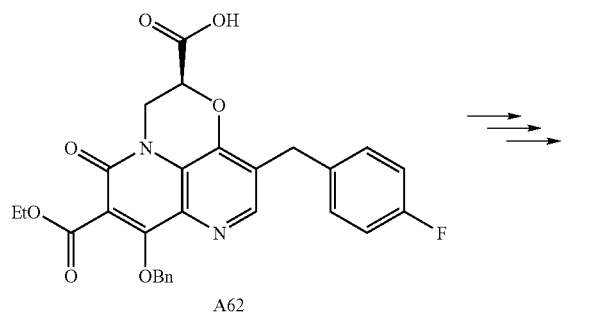

A62

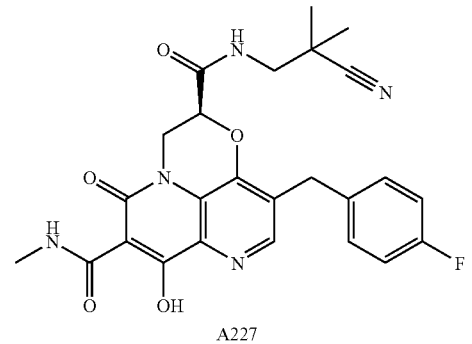

A227

400 MHz ¹H NMR (DMSO) d 9.99 (d, 1H), 8.68 (t, 1H), 8.42 (s, 1H), 7.34 (q, 2H), 7.06 (t, 2H), 5.27 (t, 1H), 4.39-4.06 (m, 3H) 3.28 (t, 2H), 2.87 (s, 3H), 1.16 (d, 6H); ¹⁹F NMR (DMSO); 75, 117; MS[M+H]=494

EXAMPLE 176

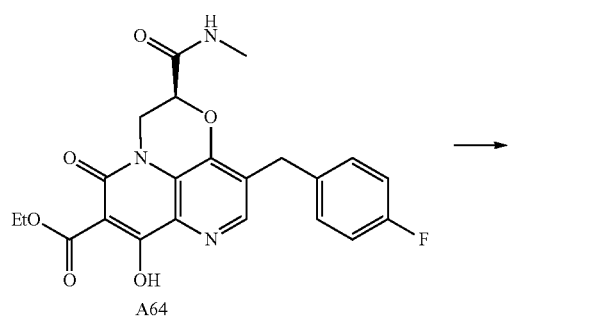

A64

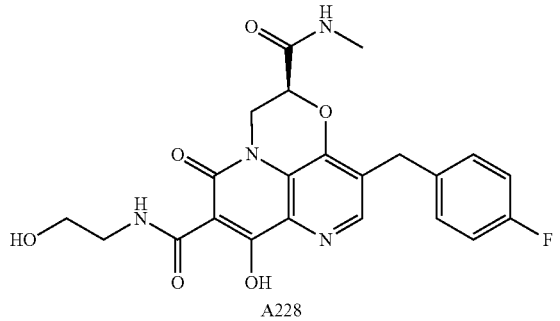

A228

400 MHz ¹H NMR (DMSO) d 10.26 (s, 1H), 8.38 (s, 1H), 8.16 (d, 1H), 7.63 (br, 1H), 7.32 (q, 2H), 7.08 (t, 2H), 5.10 (q, 2H), 4.40 (dd, 1H), 4.15 (d, 1H), 4.12-4.08 (m, 2H), 3.53-3.43 (m, 4H), 3.40 (t, 2H), 2.63 (t, 2H); ¹⁹F NMR (DMSO); 73, 117; MS[M+H]=457

EXAMPLE 177

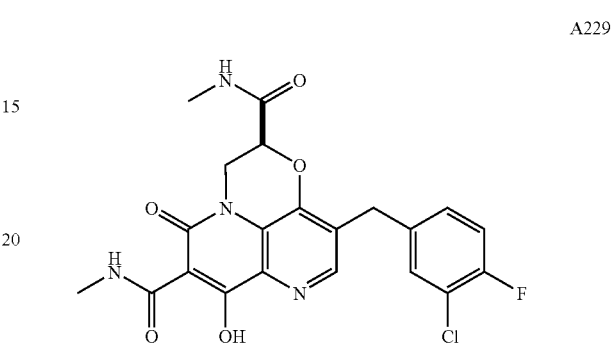

A229

Compound was prepared in a synthetic sequence identical to that previously described for the preparation of compound A65. In a procedure identical to that described in Schemes 1 and 3, 100 g of the beginning 2-Chloro, 4-fluoro-1-Iodobenzene was advanced to the dihalobenzyl intermediate that is analogous to compound A53. Following the procedure of Scheme 45 with the analogous intermediate, the chloro, fluorobenzyl compound of this example, 11 mg, was obtained.

¹H NMR (400 MHz, d₆-DMSO) d 10.03 (m, 1H), 8.42 (s, 1H), 8.25 (m, 1H), 7.55 (m, 1H), 7.30 (m, 2H), 5.09 (m, 1H), 4.42 (d, J=7.2 Hz, 1H), 4.2-4.04 (m, 3H), 2.86 (s, 3H), 2.59 (s, 3H); MS=461 [M+H].

EXAMPLE 178-179

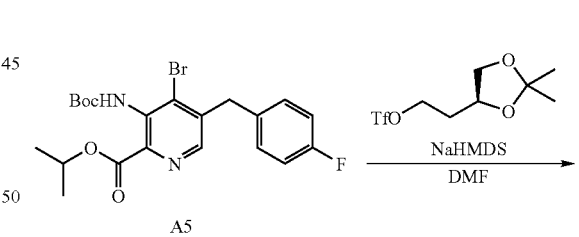

A5

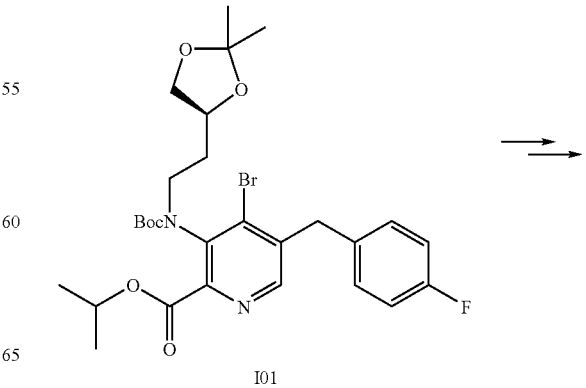

I01

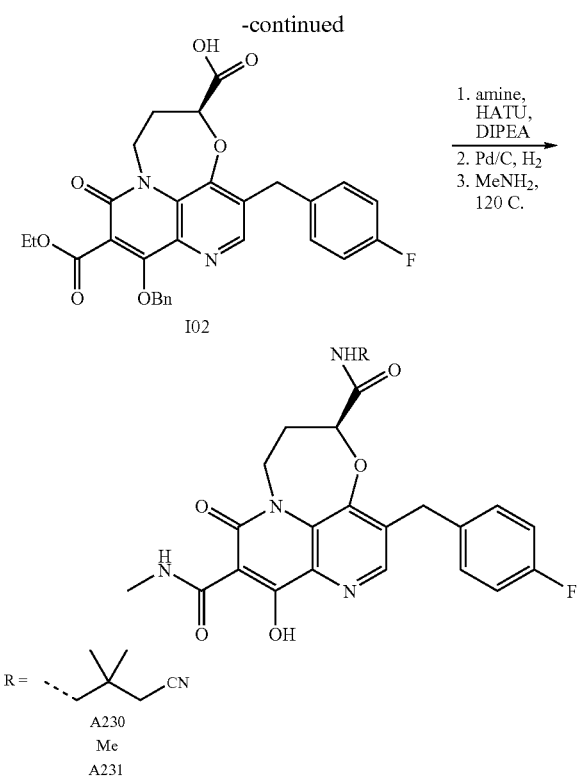

Compound I 01 was prepared from A5 in a similar manner as the synthesis of A 53. I 01 was converted to I 02 in a similar manner as the preparation of A 62 from A53. Compounds S 01 and S02 were prepared from I 01 in a similar manner as the conversion of A 62 to A 65 substituting the appropriate amines (3-step yield 50-70%).

I01
MS[M+H]=541
LCMS RT=2.67 min
I02
MS[M+H]=533
LCMS RT=3.68 min

EXAMPLE 178

400 MHz $^1$H NMR (DMSO): d 10.11 (s, 1H), 8.33 (t, 1H), 8.25 (s, 1H), 7.25 (t, 2H), 7.05 (t, 2H), 4.86-4.82 (d, 1H), 4.72-4.68 (m, 1H), 4.06-4.01 (m, 2H), 3.76-3.69 (m, 1H), 2.76 (d, 3H), 2.29 (d, 4H), 1.21 (s, 6H).

MS[M+H]=508
LCMS RT=2.20 min

EXAMPLE 179

400 MHz $^1$H NMR (DMSO): d 10.05 (s, 1H), 8.42 (s, 1H), 7.82 (s, 1H), 7.21 (t, 2H), 7.05 (t, 2H), 4.83-4.80 (d, 1H), 4.60-4.30 (m, 1H), 4.18-4.00 (dd, 2H), 3.92-3.28 (m, 1H), 2.88-2.85 (d, 3H), 2.57 (d, 3H), 2.34-2.24 (m, 2H).

MS [M+H]=441
LCMS RT=2.08 min

EXAMPLE 180

Compound was produced in a preparative sequence identical to that described for its enantiomer of example 111, having started from the corresponding enantiomeric triflate as alkylating agent. 22 mg final product was obtained. $^1$H NMR (d$_6$-DMSO) d 10.04 (d, 1H), 8.45 (s, 1H) 7.82 (m, 1H), 7.25 (m, 2H), 7.06 (m, 2H), 4.85 (dd, 1H), 4.54 (m, 1H), 4.2-3.9 (m, 2H), 3.92 (m, 1H), 2.95 (d, 3H), 2.54 (d, 3H), 2.35 (m, 2H); MS [M+H]=441.

EXAMPLES 181-183

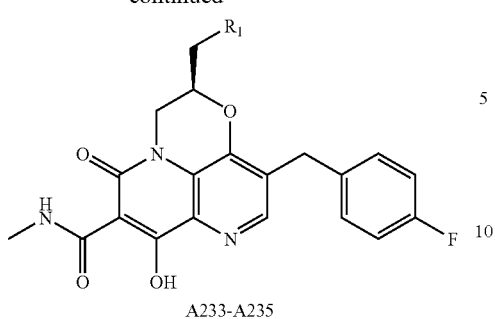

A233-A235

IntA was prepared by dissolving 1 Eq of A61 in DCM to prepare a 0.01M solution in a flame dried argon purged round bottom flask. To this was added 2 Eq lutidine and the reaction stirred for 1 minute before adding 1.2 Eq of triflic anhydride. The reaction was stirred under argon and reaction completion was confirmed by LCMS after 15 minutes. MS[M+H]=637. At this point 3 Eq of amine is added to the reaction vessel. In the case of a stalled or heterogeneous reaction a small amount of DMSO was added to the reaction. Reaction progress was monitored by LCMS. Upon completion reaction was diluted with DCM and washed with aqueous ammonium chloride. Aqueous layer was washed with DCM 3× and the organic layer washed with ammonium chloride, water, brine then dried over sodium sulfate. Solvent was removed in vacuo and compound was purified by normal phase silica to afford IntA.

Compounds of examples 111-113 were prepared from IntA following the established procedures for the preparation A50 steps 12-14 by substituting the appropriate amines. Final compounds were purified by HPLC and isolated as TFA salts (yields from A61, 30-70%).

EXAMPLE 181

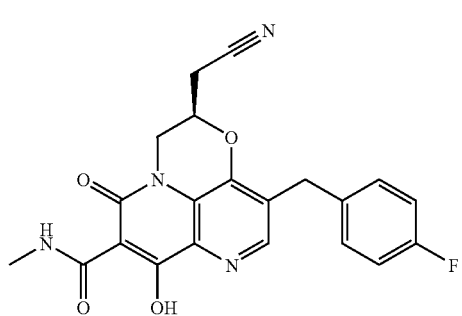

A233

400 MHz $^1$H NMR (DMSO) d 10.00 (d, 1H), 8.48 (s, 1H), 7.35 (q, 1H), 7.07 (t, 2H), 4.75 (m, 1H), 4.61-4.58 (dd, 1H), 4.03 (s, 4.03), 3.64-3.58 (m, 1H), 3.35 (dd, 1H), 3.23-3.17 (m, 1H) 2.89 (d, 3H); $^{19}$F NMR (DMSO); 75, 117; MS[M+H]=409

EXAMPLE 182

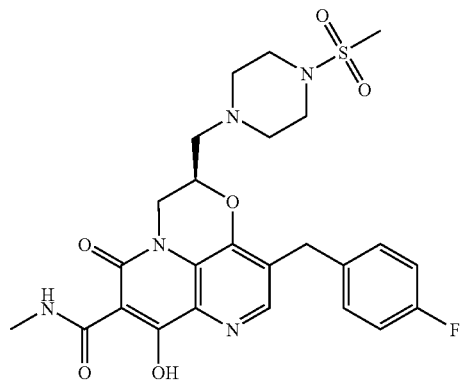

A234

400 MHz $^1$H NMR (DMSO) d 10.00 (d, 1H), 8.42 (s, 1H), 7.29 (q, 2H), 7.09 (t, 2H), 4.81 (m, 1H), 4.58 (dd, 1H), 4.06 (s, 2H) 3.66-3.61 (m, 1H), 3.40-3.05 (m, 8H), 2.95 (s, 3H), 2.90 (d, 3H); $^{19}$F NMR (DMSO); 75, 117; MS[M+H]=546

EXAMPLE 183

A235

400 MHz $^1$H NMR (DMSO) d 9.99 (2, 1H), 9.14 (s, 1H), 8.14 (s, 1H), 7.72 (d, 2H), 7.11-7.00 (m, 4H), 4.84-4.79 (m, 2H), 4.73-4.62 (m, 2H), 3.96 (d, 1H), 3.88 (d, 1H), 3.61-3.56 (m, 1H), 2.90 (d, 3H); $^{19}$F NMR (DMSO); 74, 78, 117; MS[M+H]=450

EXAMPLES 184-198

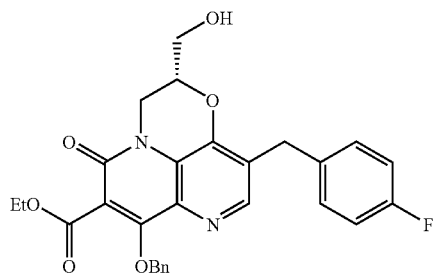

A46

-continued

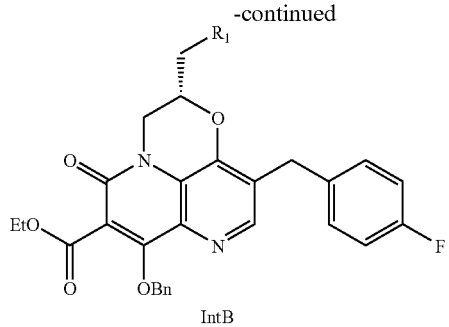
IntB

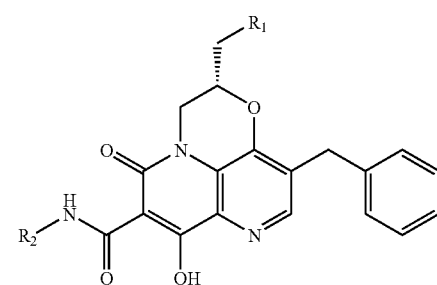

IntB was prepared by dissolving 1 Eq of A46 in DCM to prepare a 0.01M solution in a flame dried argon purged round bottom flask. To this was added 2 Eq lutidine and the reaction stirred for 1 minute before adding 1.2 Eq of triflic anhydride. The reaction was stirred under argon and reaction completion was confirmed by LCMS after 15 minutes, MS[M+H]=637. At this point 3 Eq of amine is added to the reaction vessel. In the case of a stalled or heterogeneous reaction a small amount of DMSO was added to the reaction. Reaction progress was monitored by LCMS. Upon completion reaction was diluted with DCM and washed with aqueous ammonium chloride. Aqueous layer was washed with DCM 3× and the organic layer washed with ammonium chloride, water, brine then dried over sodium sulfate. Solvent was removed in vacuo and compound was purified by normal phase silica to afford IntB.

Compounds of examples 114-128 were prepared from IntB following the established procedures for the preparation A50 steps 12-14 by substituting the appropriate amines. Final compounds were purified by HPLC (yields from A50, 30-70%).

EXAMPLES 184-186

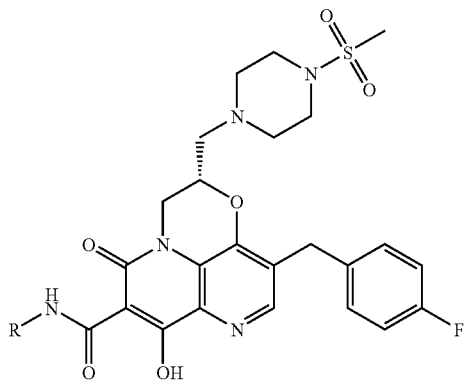
A236 R = CH₃
A237 R = CD₃
A238 R = CH₂CH₂OCH₃

EXAMPLE 184

400 MHz ¹H NMR (DMSO) d 10.00 (d, 1H), 8.42 (s, 1H), 7.29 (q, 2H), 7.09 (t, 2H), 4.81 (m, 1H), 4.58 (dd, 1H), 4.06 (s, 2H) 3.66-3.61 (m, 1H), 3.40-3.05 (m, 8H), 2.95 (s, 3H), 2.90 (d, 3H); ¹⁹F NMR (DMSO); 75, 117; MS[M+H]=546

EXAMPLE 185

400 MHz ¹H NMR (DMSO) d 10.00 (d, 1H), 8.42 (s, 1H), 7.29 (q, 2H), 7.09 (t, 2H), 4.81 (m, 1H), 4.58 (dd, 1H), 4.06 (s, 2H) 3.66-3.61 (m, 1H), 3.40-3.05 (m, 8H), 2.96 (s, 3H); ¹⁹F NMR (DMSO); 75, 317; MS[M+H]=549

EXAMPLE 186

400 MHz ¹H NMR (DMSO) d 10.30 (s, 1H), 8.44 (s, 1H), 7.29 (q, 2H), 7.09 (t, 2H), 4.57 (dd, 1H), 4.58 (dd, 1H), 4.04 (s, 2H) 3.66-3.61 (m, 1H), 3.65-3.47 (m, 14H), 3.07 (m, 3H), 2.90 (s, 3H); ¹⁹F NMR (DMSO); 75, 117; MS[M+H]=590

EXAMPLES 187-188

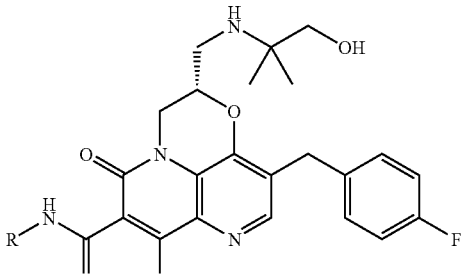
A239 R = CH₃
A240 R = CH₂CH₂OCH₃

EXAMPLE 187

400 MHz ¹H NMR (DMSO) d 9.99 (s, 1H), 8.65 (br, 1H), 8.55 (br, 1H), 8.40 (s, 1H), 7.33 (q, 2H), 7.10 (t, 2H), 5.67 (s, 1H), 4.69-4.66 (m, 2H), 4.19 (d, 1H), 4.08 (d, 1H), 3.68 (q, 1H), 3.60-3.25 (m, 2H), 2.90 (d, 3H), 1.24 (s, 6H); ¹⁹F NMR (DMSO); 74, 117; MS[M+H]=471

EXAMPLE 188

400 MHz ¹H NMR (DMSO) d 10.23 (s, 1H), 8.66 (br, 1H), 8.52 (r, 1H), 8.41 (s, 1H), 7.34 (q, 2H), 7.09 (t, 2H), 5.67 (s, 1H), 4.69-4.66 (m, 2H), 4.19 (d, 1H), 4.09 (d, 1H), 3.68 (q,

1H), 3.75-3.46 (m, 6H), 3.27 (d, 3H), 1.23 (s, 6H); $^{19}$F NMR (DMSO); 74, 117; MS[M+H]=515

EXAMPLES 189-190

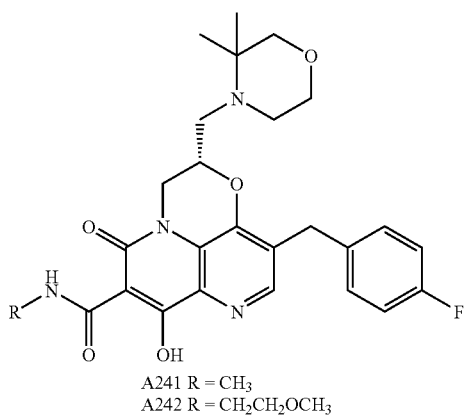

A241 R = CH$_3$
A242 R = CH$_2$CH$_2$OCH$_3$

EXAMPLE 189

400 MHz $^1$H NMR (DMSO) d 10.01 (s, 1H), 8.43 (s, 1H), 7.26 (br, 2H), 7.10 (br, 2H), 4.92-4.61 (br, 2H), 4.06-3.27 (m, 8H), 2.90 (d, 3H), 1.32 (s, 3H), 1.24 (s, 3H); $^{19}$F NMR (DMSO); 74, 117; MS[M+H]=497

EXAMPLE 190

400 MHz $^1$H NMR (DMSO) d 10.30 (s, 1H), 8.44 (br, 1H), 7.28 (br, 1H), 7.09 (s, 1H), 4.92-4.40 (m, 2H), 4.06-3.27 (m, 15H), 1.32 (s, 3H), 1.24 (s, 3H); $^{19}$F NMR (DMSO); 74, 117; MS[M+H]=541

EXAMPLES 191-192

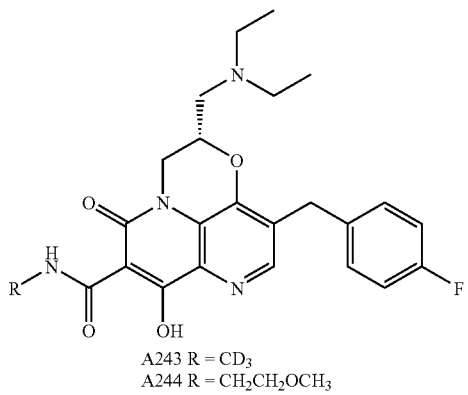

A243 R = CD$_3$
A244 R = CH$_2$CH$_2$OCH$_3$

EXAMPLE 191

400 MHz $^1$H NMR (DMSO) d 9.74 (s, 1H), 9.59 (br, 1H), 8.39 (s, 1H), 7.25 (t, 2H), 7.10 (t, 2H), 4.87 (t, 1H), 4.72 (d, 1H), 4.11 (s, 2H), 3.72-3.61 (m, 1H), 3.61-3.55 (m, 2H), 3.19 (m, 4H), 1.18 (t, 6H); $^{19}$F NMR (DMSO); 75, 117; MS[M+H]=458

EXAMPLE 192

400 MHz $^1$H NMR (DMSO) d 10.28 (t, 1H), 9.55 (br, 1H), 8.40 (s, 1H), 7.26 (1, 2H), 7.10 (t, 2H), 4.88 (t, 1H), 4.73 (d, 1H), 4.11 (s, 1H), 3.71-3.47 (m, 9H), 3.20 (m, 4H), 1.18 (t, 6H); $^{19}$F NMR (DMSO); 74, 117; MS[M+H]=499

EXAMPLE 193-194

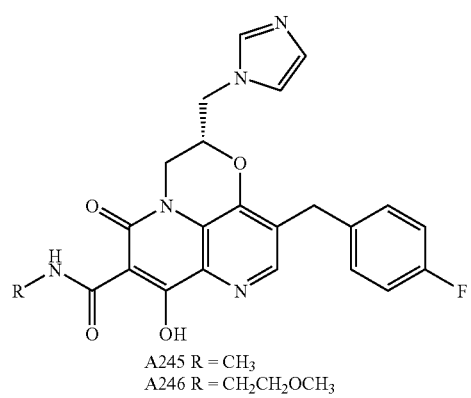

A245 R = CH$_3$
A246 R = CH$_2$CH$_2$OCH$_3$

EXAMPLE 193

400 MHz $^1$H NMR (DMSO) d 9.99 (d, 1H), 9.14 (s, 1H), 8.14 (s, 1H), 7.72 (d, 2H), 7.11-7.00 (m, 4H), 4.84-4.79 (m, 2H), 4.73-4.62 (m, 2H), 3.96 (d, 1H), 3.88 (d, 1H), 3.61-3.56 (m, 1H), 2.90 (d, 3H); $^{19}$F NMR (DMSO); 74, 78, 117; MS[M+H]=450

EXAMPLE 194

400 MHz $^1$H NMR (DMSO) d 10.27 (s, 1H), 9.12 (s, 1H), 8.44 (s, 1H), 7.71 (d, 2H), 7.13-7.01 (m, 4H), 4.84-4.79 (m, 2H), 4.73-4.63 (m, 2H), 3.96 (d, 1H), 3.89 (d, 1H), 3.61-3.47 (m, 5H), 3.27 (s, 3H); $^{19}$F NMR (DMSO); 74, 117; MS[M+H]=494

EXAMPLES 195-196

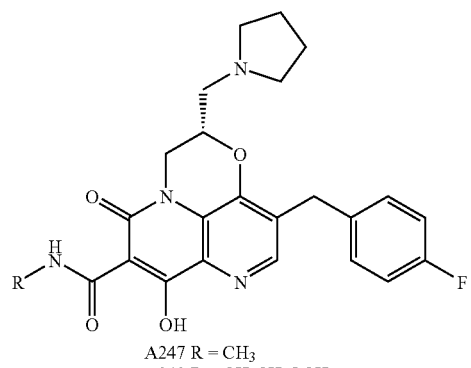

A247 R = CH$_3$
A248 R = CH$_2$CH$_2$OCH$_3$

EXAMPLE 195

400 MHz $^1$H NMR (DMSO) d 9.98 (s, 1H), 9.84 (br, 1H), 8.14 (s, 1H), 7.27 (q, 2H), 7.10 (t, 2H), 4.82 (t, 1H), 4.60 (dd,

1H), 4.12 (s, 2H), 3.80-3.73 (m, 1H), 3.66-3.48 (m, 4H), 3.08 (m, 2H), 2.90 (s, 3H), 1.99 (m, 2H), 1.84 (m, 2H); $^{19}$F NMR (DMSO); 74, 117; MS[M+H]=453

EXAMPLE 196

400 MHz $^1$H NMR (DMSO) d 10.26 (s, 1H), 9.84 (br, 1H), 8.42 (s, 1H), 7.27 (q, 2H), 7.10 (t, 2H), 4.82 (t, 1H), 4.62 (dd, 1H), 4.12 (s, 2H), 3.76-3.45 (m, 9H), 3.27 (s, 3H), 3.12-3.02 (m, 2H), 2.90 (s, 3H), 1.99 (m, 2H), 1.84 (m, 2H); $^{19}$F NMR (DMSO); 74, 117; MS[M+H]=497

EXAMPLE 197

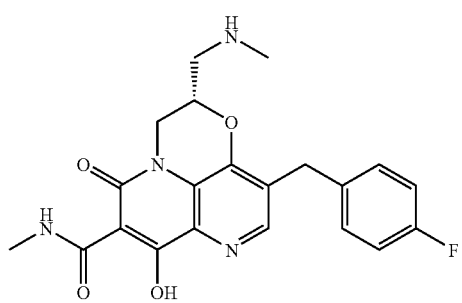

A249

400 MHz $^1$H NMR (DMSO) d 10.00 (s, 1H), 8.85 (br, 1H), 8.39 (s, 1H), 7.32 (1, 2H), 7.09 (t, 2H), 4.72 (t, 1H), 4.63 (dd, 1H), 4.13 (s, 2H), 3.70-3.27 (m, 3H), 2.89 (d, 3H), 2.66 (t, 3H); $^{19}$F NMR (DMSO); 74, 117; MS[M+H]=413

EXAMPLE 198

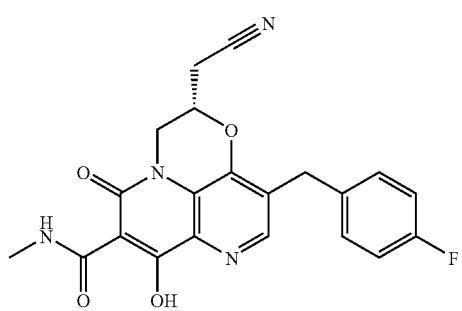

A250

400 MHz $^1$H NMR (DMSO) d 10.00 (d, 1H), 8.47 (s, 1H), 7.35 (q, 2H), 7.07 (t, 2H), 4.37 (m, 1H), 4.58 (dd, 1H), 4.24 (s, 2H), 3.64-3.59 (m, 1H), 3.33 (dd, 1H), 2.89 (d, 3H); $^{19}$F NMR (DMSO); 75, 117; MS[M+H]=409

EXAMPLE 199

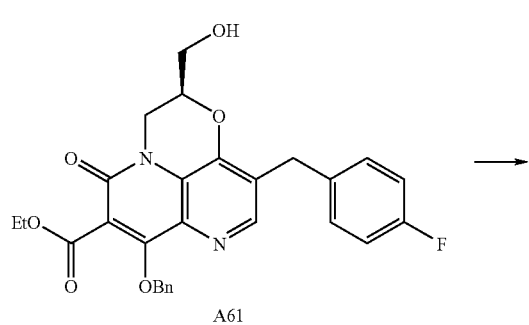

A61

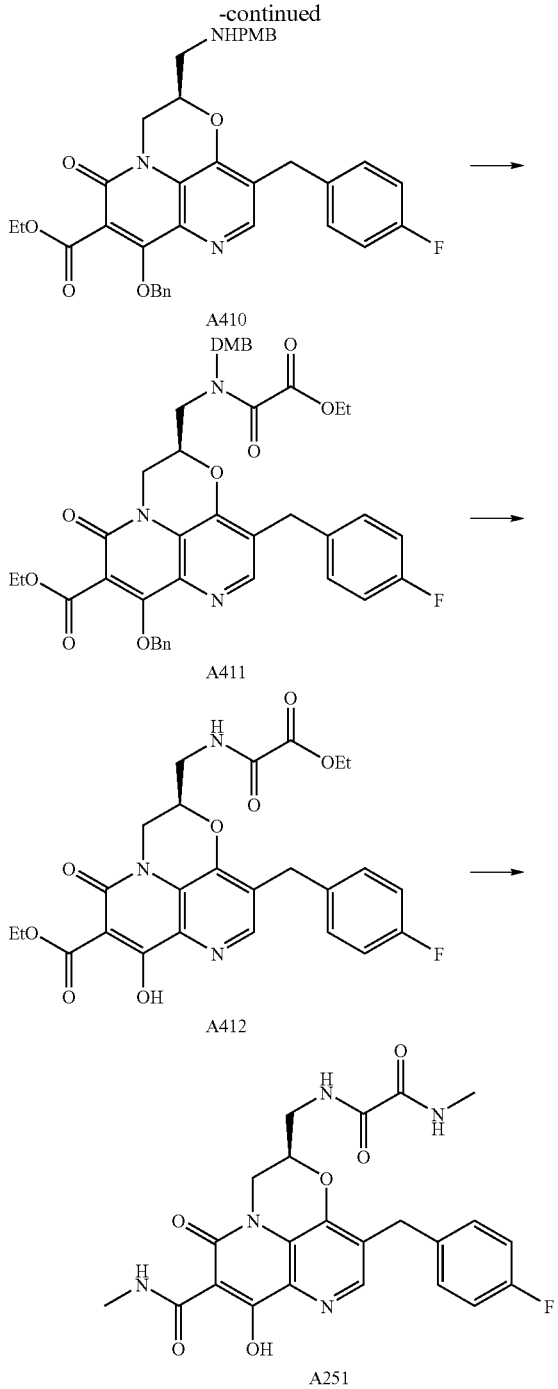

To a flask containing A61 (250 mg, 0.50 mmol, 1 equiv.) is added CH$_2$Cl$_2$ (3 mL, 0.2 M). This is followed by addition of 2,6-lutidine (170 µL, 1.49 mmol, 3 equiv.), MS 4 Å (200 mg) and lastly triflic anhydride (90 µL, 0.54 mmol, 1.1 equiv). After 15 minutes, the reaction was shown to be complete by LCMS. To the flask was added para-methoxybenzylamine (225 µL, 1.49 mmol, 3 equiv). After consumption of the starting material, the reaction mixture was washed with water, saturated NH4Cl and brine. The organic layer was dried over MgSO4, filtered and concentrated in vacuo. The material was purified by flash column chromatography (EtOAc) was carried out to furnish amine A410.

To a solution of A410 (100 mg, 0.15 mmol, 1 equiv.) in CH$_2$Cl$_2$ (3 mL, 0.05 M) is added TEA (65 μL, 0.42 mmol, 3 equiv.) and DMAP (10 mg, 0.08 mmol, 0.5 equiv) before ethyl chlorooxoacetate (35 μL, 0.31 mmol, 2 equiv) was added. The reaction was shown to be complete within an hour. It was quenched and washed with water. This was followed by washing with saturated NH$_4$Cl and brine solution. The organic layer was dried over MgSO$_4$, filtered and concentrated in vacuo. A light yellow solid was realized and used in the next step without further purification.

A solution of A411 (140 mg, 0.11 mmol, 1 equiv.) and TFA (15 mL) was heated to 120° C. overnight. The reaction was then concentrated in vacuo and azeotroped with toluene (3×). The material was then washed with Ethyl ether/Hexanes to furnish a yellow solid of A412.

A412 (70 mg, 0.14 mmol, 1 equiv) was placed in a microwave vial in DMF (2 mL, 0.2 M) and to it added methylamine (410 μL, 6 equiv, 2 M in THF). The reaction was heated in a microwave reactor at 130° C. for 3 hr. Upon completion, the material was purified by RP-HPLC (MeCN—H$_2$O gradient) to furnish the desired product.

400 MHz $^1$H NMR (DMSO-d$_6$: d 10.02 (bs, 1H), 9.11 (bs, 1H), 8.77 (bs, 1H), 8.45 (s, 1H), 7.43-7.30 (m, 2H), 7.06-7.15 (m, 2H), 4.44-4.58 (m, 2H), 3.95-4.15 (m, 3), 3.45-3.60 (m, 2H), 3.00 (d, J=4.8 Hz, 3H), 2.89 (d, J=3.6 Hz, 3H).

400 MHz $^{19}$F NMR (DMSO-d$_6$): −117.03, −73.87 (TFA salt).

LCMS (m/z+1): 484.09

EXAMPLE 200

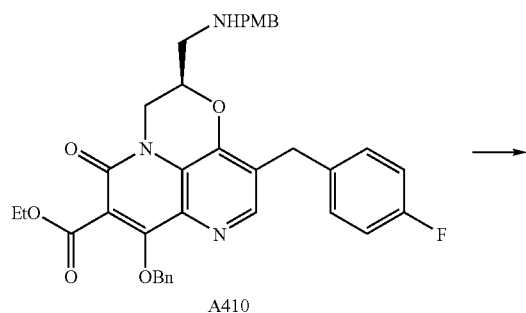
A410

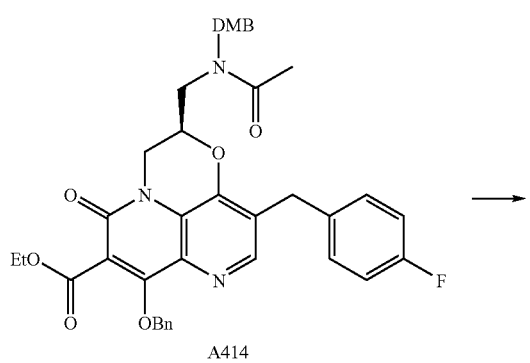
A414

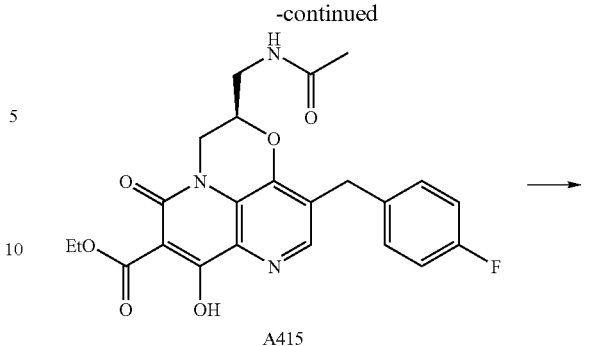
A415

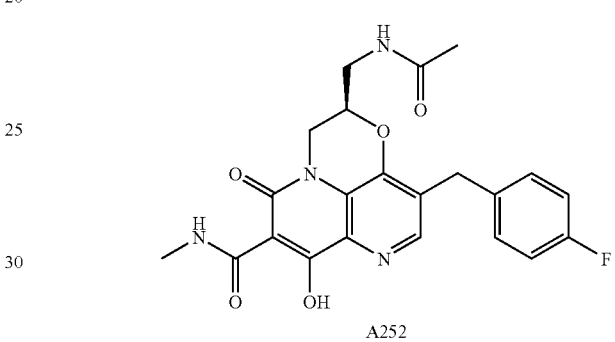
A252

To a solution of A410 (130 mg, 0.20 mmol, 1 equiv.) in CH$_2$CO$_2$ (3 mL, 0.05 M) is added TEA (85 μL, 0.60 mmol, 3 equiv.) and DMAP (15 mg, 0.10 mmol, 0.5 equiv) before acetyl chloride (30 μL, 0.40 mmol, 2 equiv) was added. The reaction was shown to be complete within an hour. It was quenched and washed with water. This was followed by washing with saturated NH$_4$Cl and brine solution. The organic layer was dried over MgSO$_4$, filtered and concentrated in vacuo. A light yellow solid was realized and used in the next step without further purification. A solution of A414 (70 mg, 0.22 mmol, 1 equiv.) and TFA (15 mL) was heated to 120° C. overnight. The reaction was then concentrated in vacuo and azeotroped with toluene (3×). The material was then washed with Ethyl ether/Hexanes to furnish a yellow solid of A415.

A415 (70 mg, 0.14 mmol, 1 equiv) was placed in a microwave vial in DMF (2 mL, 0.2 M) and to it added methylamine (410 μL, 6 equiv, 2 M in THF). The reaction was heated in a microwave reactor at 130° C. for 30 min. Upon completion, the material was purified by RP-HPLC (MeCN—H$_2$O gradient) to furnish the desired product.

400 MHz $^1$H NMR (DMSO-d$_6$): d 10.04 (bs, 1H), 8.42 (s, 1H), 8.20 (t, J=6 Hz, 1H), 7.30-7.36 (m, 2H), 7.04-7.10 (m, 2H), 4.51 (dd, J=2.8, 14.0 Hz, 1H), 4.48-4.34 (m, 1H), 4.05 (d, J=14.4 Hz, 2H), 3.57-3.72 (m, 1H), 3.50 (t, J=11.2 Hz, 2H), 2.89 (d, J=5.2 Hz, 3H), 1.83 (s, 3H).

400 MHz $^{19}$F NMR (DMSO-d$_6$): −116.77, −73.69 (TFA salt).

LCMS (m/z+1): 441.07

EXAMPLE 201

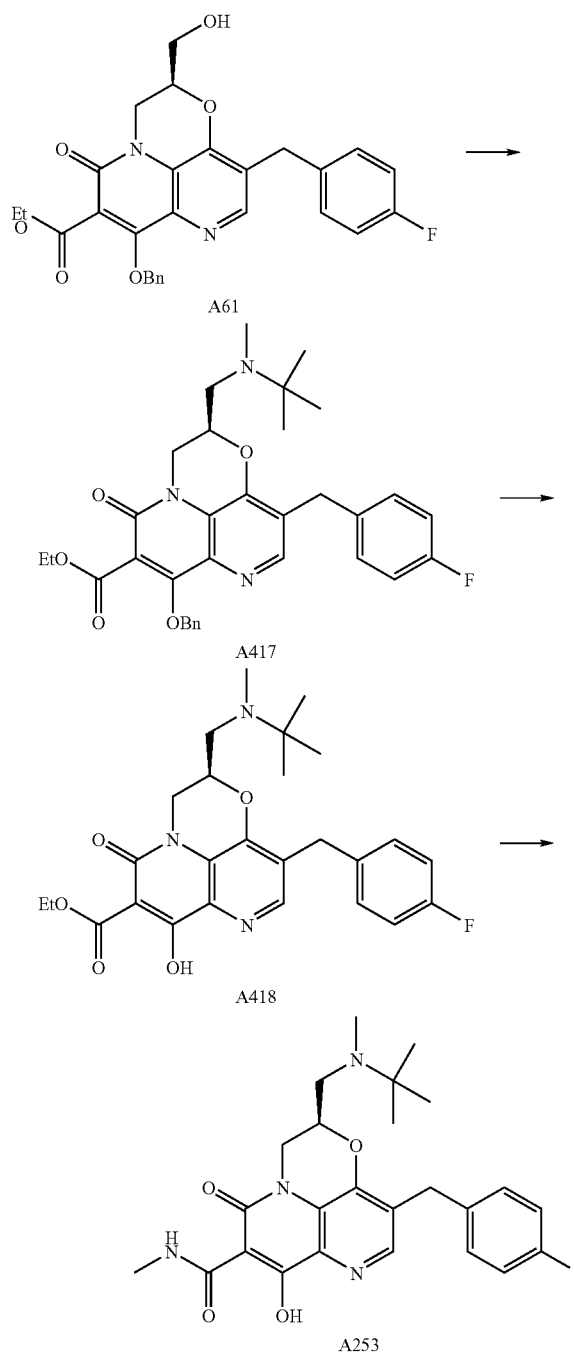

To a flask containing A61 (250 mg, 0.50 mmol, 1 equiv.) is added $CH_2Cl_2$ (3 mL, 0.2 M). This is followed by addition of 2,6-lutidine (170 µL, 1.49 mmol, 3 equiv.), MS 4 Å (200 mg) and lastly triflic anhydride (90 µL, 0.54 mmol, 1.1 equiv). After 15 minutes, the reaction was shown to be complete by LCMS. To the flask was added N-methyl-tert-butylamine (240 µL, 0.64 mmol, 3 equiv). After consumption of the starting material, the reaction mixture was washed with water, saturated $NH_4Cl$ and brine. The organic layer was dried over $MgSO_4$, filtered and concentrated in vacuo. The material was purified by flash column chromatography (EtOAc) was carried out to furnish amine A417.

A solution of A417 (60 mg, 0.18 mmol, 1 equiv.) and TFA (15 mL) was heated to 120° C. overnight. The reaction was then concentrated in vacuo and azeotroped with toluene (3×). The material was then washed with Ethyl ether/Hexanes to furnish a yellow solid of A418.

A418 (80 mg, 0.17 mmol, 1 equiv) was placed in a microwave vial in DMF (2 mL, 0.2 M) and to it added methylamine (410 µL, 5 equiv, 2 M in THF). The reaction was heated in a microwave reactor at 130° C. for 30 min. Upon completion, the material was purified by RP-HPLC (MeCN—$H_2O$ gradient) to furnish the desired product.

400 MHz $^1$H NMR (DMSO-$d_6$): d 9.93 (bs, 1H), 8.41 (s, 1H), 7.15-7.28 (m, 2H), 7.04-7.10 (m, 2H), 4.51 (dd, J=2.8, 14.0 Hz, 1H), 4.48-4.34 (m, 1H), 4.05 (d, J=14.4 Hz, 2H), 3.57-3.72 (m, 1H), 2.85 (d, J=7.2 Hz, 3H), 2.65 (s, 3H), 1.31 (s, 9H).

400 MHz $^{19}$F NMR (DMSO-$d_6$): −116.56, −74.17 (TFA salt).

LCMS (m/z+1): 469.15

EXAMPLE 202

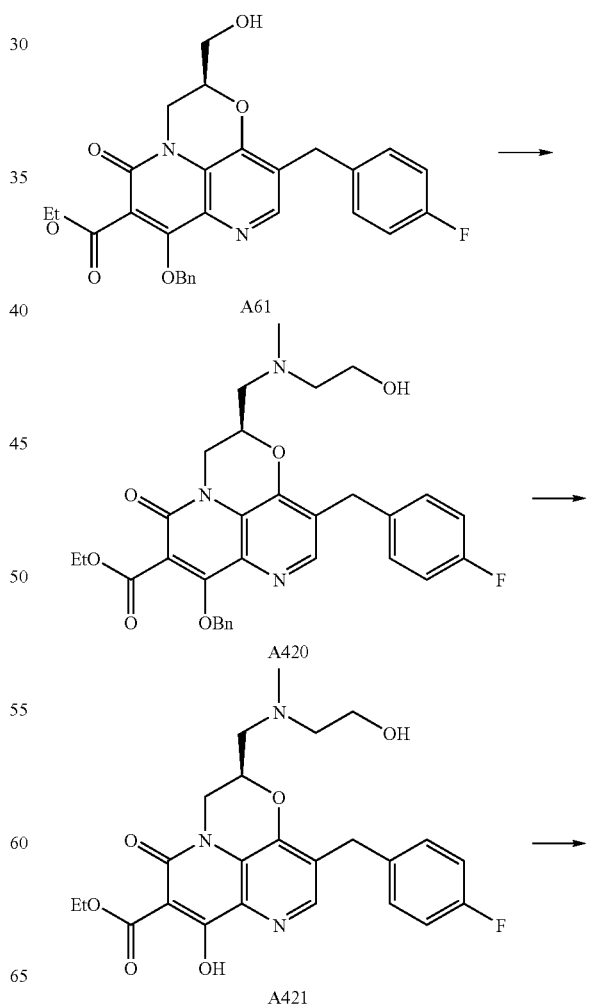

-continued

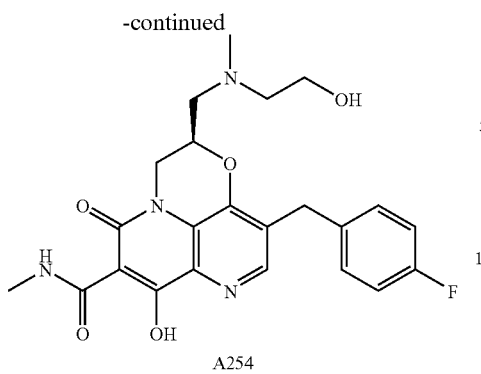

A254

To a flask containing A61 (250 mg, 0.50 mmol, 1 equiv.) is added CH$_2$Cl$_2$ (3 mL, 0.2 M). This is followed by addition of 2,6-lutidine (170 µL, 1.49 mmol, 3 equiv.), MS 4 Å (200 mg) and lastly triflic anhydride (90 µL, 0.54 mmol, 1.1 equiv). After 15 minutes, the reaction was shown to be complete by LCMS. To the flask was added 2-methylaminoethanol (135 µL, 1.65 mmol, 3 equiv). After consumption of the starting material, the reaction mixture was washed with water, saturated NH$_4$Cl and brine. The organic layer was dried over MgSO$_4$, filtered and concentrated in vacuo. The material was purified by flash column chromatography (EtOAc) was carried out to furnish amine A420.

To a solution of A420 (60 mg, 0.18 mmol, 1 equiv.) and EtOH (10 mL) was added Pd (60 mg, 0.055 mmol, 0.2 equiv, 10% in carbon) and stirred under an atmosphere of hydrogen via a balloon. After the reaction was complete, the solid was filtered and the filtrate concentrated down to a light yellow oil of A421.

A421 (106 mg, 0.22 mmol, 1 equiv.) was placed in a microwave vial in DMF (2 mL, 0.1 M) and to it added methylamine (550 µL, 5 equiv, 2 M in THF). The reaction was heated in a microwave reactor at 130° C. for 30 min. Upon completion, the material was purified by RP-HPLC (MeCN—H$_2$O gradient) to furnish the desired product A254.

400 MHz $^1$H NMR (DMSO-d$_6$): d9.98 (bs, 1H), 9.69 (bs, 1H), 8.41 (s, 1H), 7.15-7.28 (m, 2H), 7.04-7.10 (m, 2H), 5.43 (bs, 1H), 4.90-4.85 (m, 1H), 4.64 (d, J=13.6 Hz, 1H), 4.05 (s, 2H), 3.95-4.05 (m, 2H), 3.57-3.72 (m, 4H), 3.10-3.28 (m, 3H), 2.85 (d, J=7.2 Hz, 3H), 2.82 (s, 3H).

400 MHz $^{19}$F NMR (DMSO-d$_6$): −116.65, −73.99 (TFA salt).

LCMS (m/z+1): 457.12

EXAMPLE 203

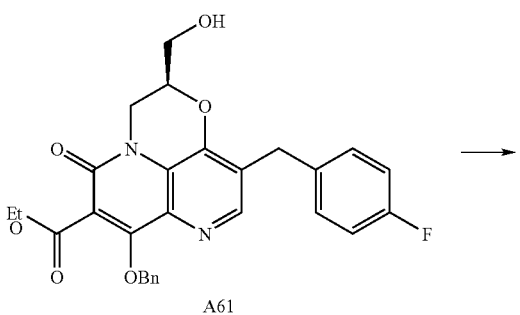

A61

-continued

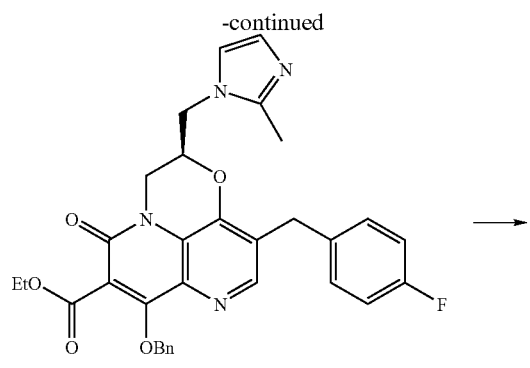

A423

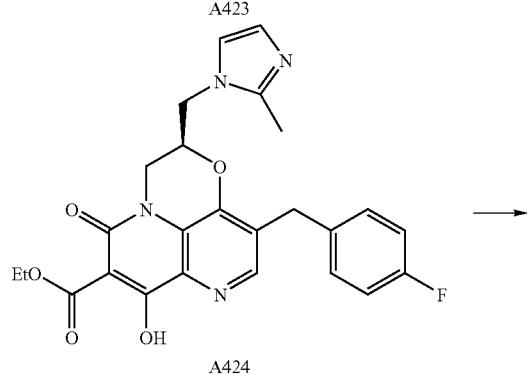

A424

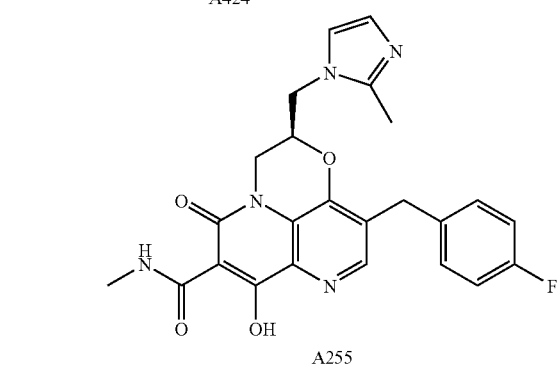

A255

To a flask containing A61 (125 mg, 0.25 mmol, 1 equiv.) is added CH$_2$Cl$_2$ (5 mL, 0.05 M). This is followed by addition of 2,6-lutidine (85 µL, 0.74 mmol, 3 equiv.), MS 4 Å (200 mg) and lastly triflic anhydride (50 µL, 0.30 mmol, 1.2 equiv). After 15 minutes, the reaction was shown to be complete by LCMS. To the flask was added 2-methylamidazole (61 mg, 10.74 mmol, 3 equiv). After consumption of the starting material, the reaction mixture was washed with water, saturated NH$_4$Cl and brine. The organic layer was dried over MgSO$_4$, filtered and concentrated in vacuo. The material was purified by flash column chromatography (EtOAc) was carried out to furnish amine A423 which was used without further purification. A solution of A423 (180 mg) and TFA (15 mL) was heated to 120° C. overnight. The reaction was then concentrated in vacuo and azeotroped with toluene (3×). The material was then washed with Ethyl ether/Hexanes to furnish a yellow solid of A424.

A424 (225 mg, 0.47 mmol, 1 equiv.) was placed in a microwave vial in DMF (2 mL, 0.1 M) and to it added methylamine (1.2 mL, 5 equiv, 2 M in THF). The reaction was heated in a microwave reactor at 130° C. for 30 min. Upon completion, the material was purified by RP-HPLC (MeCN—H$_2$O gradient) to furnish the desired product.

400 MHz $^1$H NMR (DMSO-d$_6$): d 10.00 (bs, 1H), 8.41 (s, 1H), 7.58 (s, 1H), 6.95-7.10 (m, 5H), 4.71-4.70 (m, 5H), 4.55-4.59 (m, 2H), 3.95-4.05 (m, 2H), 3.62-3.70 (m, 2H), 2.91 (d, J=4.8 Hz, 3H), 2.55 (s, 3H).

400 MHz $^{19}$F NMR (DMSO-d$_6$): −116.63, −74.11 (TFA salt).

LCMS (m/z+1): 464.11

EXAMPLE 204

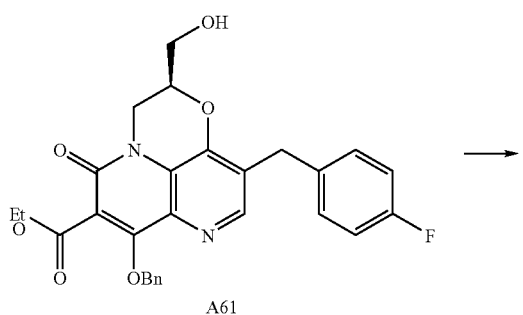
A61

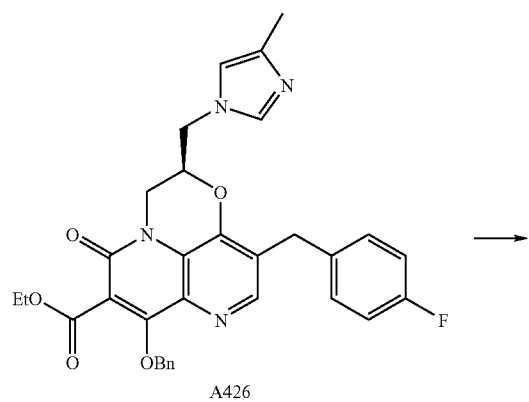
A426

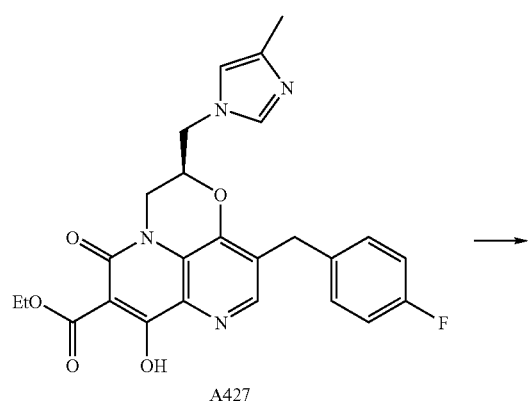
A427

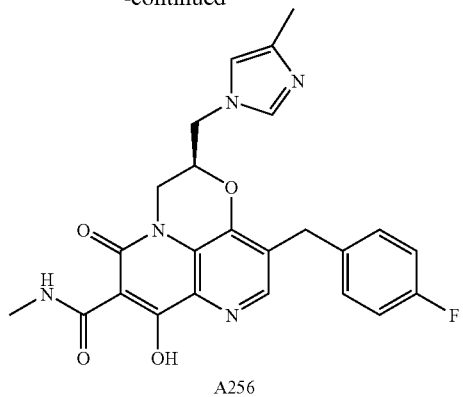
A256

To a flask containing A61 (125 mg, 0.25 mmol, 1 equiv.) is added CH$_2$Cl$_2$ (5 mL, 0.05 M). This is followed by addition of 2,6-lutidine (85 μL, 0.74 mmol, 3 equiv.), MS 4 Å (200 mg) and lastly triflic anhydride (50 μL, 0.30 mmol, 1.2 equiv). After 15 minutes, the reaction was shown to be complete by LCMS. To the flask was added 2-methylamidazole (61 mg, 0.74 mmol, 3 equiv). After consumption of the starting material, the reaction mixture was washed with water, saturated NH$_4$Cl and brine. The organic layer was dried over MgSO$_4$, filtered and concentrated in vacuo, A426 was obtained and used without further purification.

A solution of A426 (180 mg) and TFA (15 mL) was heated to 120° C. overnight. The reaction was then concentrated in vacuo and azeotroped with toluene (3×). The material was then washed with Ethyl ether/Hexanes to furnish a yellow solid of A427.

A427 (185 mg, 0.39 mmol, 1 equiv.) was placed in a microwave vial in DMF (2 mL, 0.1 M) and to it added methylamine (1.2 mL, 5 equiv, 2 M in THF). The reaction was heated in a microwave reactor at 130° C. for 30 min. Upon completion, the material was purified by RP-HPLC (MeCN—H$_2$O gradient) to furnish the desired product.

Major isomer: 400 MHz $^1$H NMR (DMSO-d$_6$): d 9.99 (bs, 1H), 8.44 (s, 1H), 7.36 (s, 1H), 6.95-7.20 (m, 5H), 4.71-4.70 (m, 5H), 4.55-4.59 (m, 2H), 3.95-4.05 (m, 2H), 3.62-3.70 (m, 2H), 2.91 (d, J=4.8 Hz, 3H), 2.21 (s, 3H).

Minor isomer: 400 MHz $^1$H NMR (DMSO-d$_6$) partial: 9.99 (bs, 1H), 9.05 (s, 1H), 8.41 (s, 1H), 7.45 (s, 1H), 2.29 (s, 3H).

400 MHz $^{19}$F NMR (DMSO-d$_6$): −116.68, −73.94 (TFA salt).

LCMS (m/z+1): 464.11

EXAMPLE 205

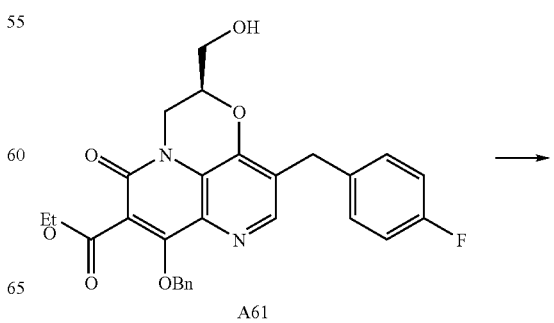
A61

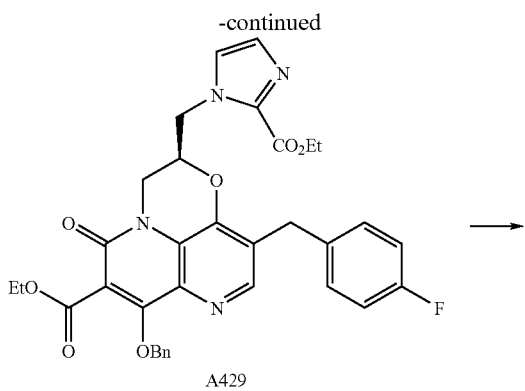

A429

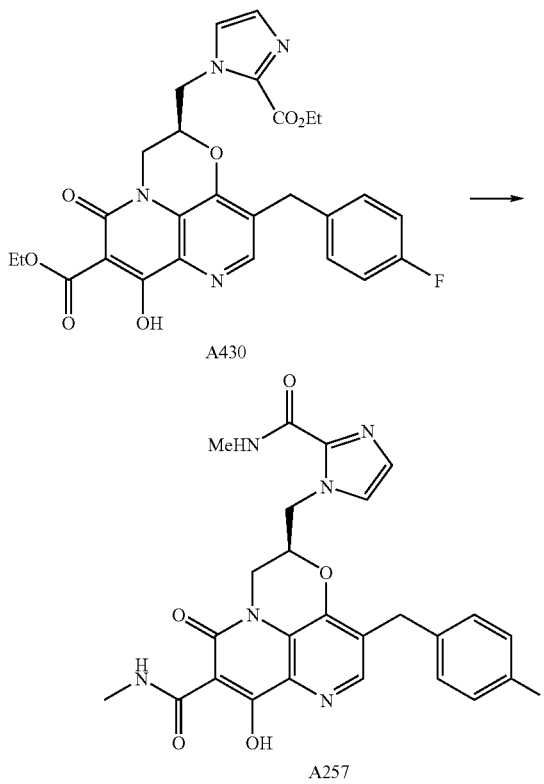

A430

A257

To a flask containing A61 (150 mg, 0.29 mmol, 1 equiv.) is added $CH_2Cl_2$ (3 mL, 0.1 M). This is followed by addition of 2,6-lutidine (105 µL, 0.87 mmol, 3 equiv.), MS 4 Å (200 mg) and lastly triflic anhydride (60 µL, 0.35 mmol, 1.2 equiv). After 15 minutes, the reaction was shown to be complete by LCMS. To the flask was added ethyl-imidazole-2-caroboxylate (125 mg, 0.89 mmol, 3 equiv). After consumption of the starting material, the reaction mixture was washed with water, saturated $NH_4Cl$ and brine. The organic layer was dried over $MgSO_4$, filtered and concentrated in vacuo. The material was purified by flash column chromatography (EtOAc) was carried out to furnish amine A429 which was used without further purification.

A solution of A429 (275 mg) and TFA (15 mL) was heated to 120° C. overnight. The reaction was then concentrated in vacuo and azeotroped with toluene (3×). The material was then washed with Ethyl ether/Hexanes to furnish a yellow solid of A430.

A430 (60 mg, 0.11 mmol, 1 equiv.) was placed in a microwave vial in DMF (2 mL, 0.1 M) and to it added methylamine (220 µL, 4 equiv, 2 M in THF). The reaction was heated in a microwave reactor at 130° C. for 4 hr. Upon completion, the material was purified by RP-HPLC (MeCN—$H_2O$ gradient) to furnish the desired product.

400 MHz $^1$H NMR (DMSO-$d_6$): d 9.99 (bs, 1H), 8.46 (bs, 1H), 8.38 (s, 1H), 7.34 (s, 1H), 7.19-7.10 (m, 2H), 6.96-7.00 (m, 3H), 4.86-4.91 (m, 2H), 4.71-4.70 (m, 1H), 4.49 (d, J=11.6 Hz, 2H), 3.75-3.90 (m, 4H), 3.12-3.58 (m, 2H), 2.84 (d, J=4.4 Hz, 3H), 2.64 (d, J=4.8 Hz, 3H).

400 MHz $^{19}$F NMR (DMSO-$d_6$): −116.73, −74.58 (TFA salt).

LCMS (m/z+1): 507.14

EXAMPLE 206

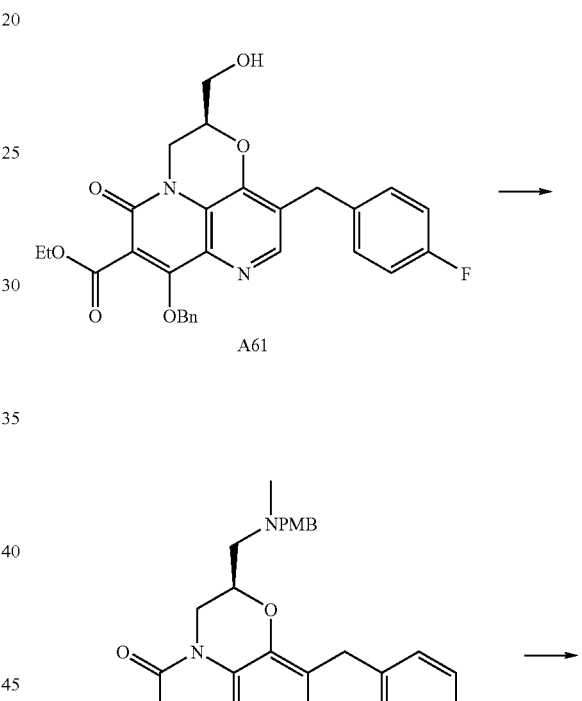

A61

A432

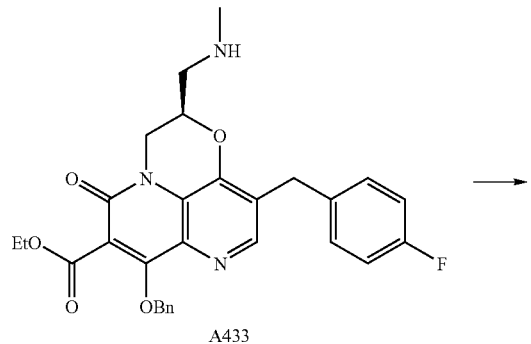

A433

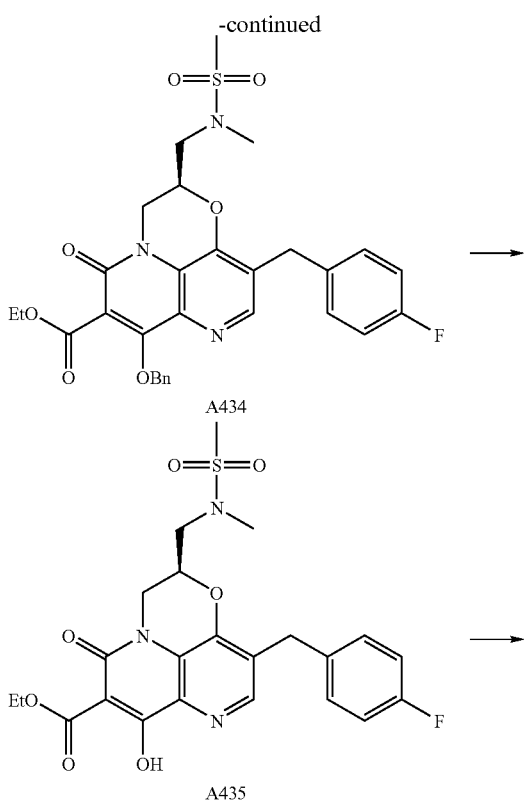

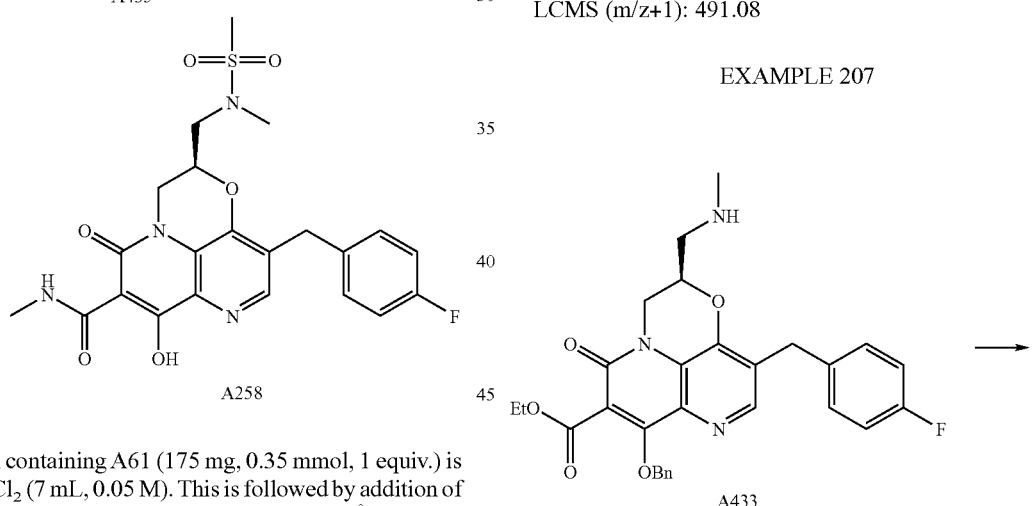

To a flask containing A61 (175 mg, 0.35 mmol, 1 equiv.) is added CH$_2$Cl$_2$ (7 mL, 0.05 M). This is followed by addition of 2,6-lutidine (115 µL, 1.04 mmol, 3 equiv.), MS 4 Å (200 mg) and lastly triflic anhydride (70 µL, 0.41 mmol, 1.2 equiv). After 15 minutes, the reaction was shown to be complete by LCMS. To the flask was added N-para-methoxybenzyl-N-methylamine (250 mg, 1.38 mmol, 4 equiv). After consumption of the starting material, the reaction mixture was washed with water, saturated NH$_4$Cl and brine. The organic layer was dried over MgSO$_4$, filtered and concentrated in vacuo. The material was purified by flash column chromatography (EtOAc) was carried out to furnish amine A432 (180 mg).

To a solution of A432 (120 mg, 0.18 mmol, 1 equiv.) with acetonitrile-water (4 mL/4 mL) wad added cerric ammonium nitrate (200 mg, 0.36 mmol, 4 equiv.). After the reaction was complete, the mixture was dissolved in EtOAc and washed with water (3×). The organics were then washed with brine solution before being dried over MgSO$_4$, filtered and concentrated in vacuo. A tan brown oil was obtained of A433 which was used without further purification.

To a solution of A433 (60 mg, 0.12 mmol, 1 equiv.) in CH$_2$Cl$_2$ (4 mL, 0.05 M) is added N—N'-diisopropylethylamine (100 µL, 0.58 mmol, 5 equiv.) before methanesulfonyl chloride (28 mmol µL, 0.35 mmol, 3 equiv) was added. The reaction was shown to be complete within an hour. It was quenched and washed with water. This was followed by washing with saturated NH$_4$Cl and brine solution. The organic layer was dried over MgSO$_4$, filtered and concentrated in vacuo. A light yellow solid was realized and used in the next step without further purification.

A solution of A434 (75 mg) and TFA (15 mL) was heated to 120° C. overnight. The reaction was then concentrated in vacuo and azeotroped with toluene (3×). The material was then washed with Ethyl ether/Hexanes to furnish a yellow solid of A435.

A435 (55 mg, 0.11 mmol, 1 equiv.) was placed in a microwave vial in DMF (2 mL, 0.1 M) and to it added methylamine (200 µL, 4 equiv, 2 M in THF). The reaction was heated in a microwave reactor at 130° C. for 30 min. Upon completion, the material was purified by RP-HPLC (MeCN—H$_2$O gradient) to furnish the desired product.

400 MHz $^1$H NMR (DMSO-d$_6$); d 10.03 (bs, 1H), 8.44 (s, 1H), 7.31-7.35 (m, 2H), 7.06-7.09 (m, 2H), 4.51-4.60 (m, 2H), 4.47 (d, J=14.0 Hz, 1H), 4.02 (s, 2H), 3.783-3.65 (m, 6H), 2.91 (s, 3H), 2.80 (s, 3H), 2.83 (d, J=5.2 Hz, 3H).

400 MHz $^{19}$F NMR (DMSO-d$_6$): −116.78, −74.07 (TFA salt).

LCMS (m/z+1): 491.08

EXAMPLE 207

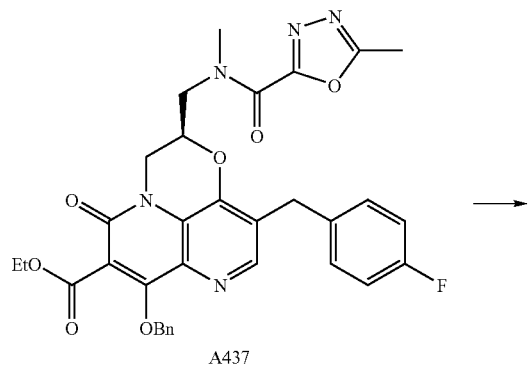

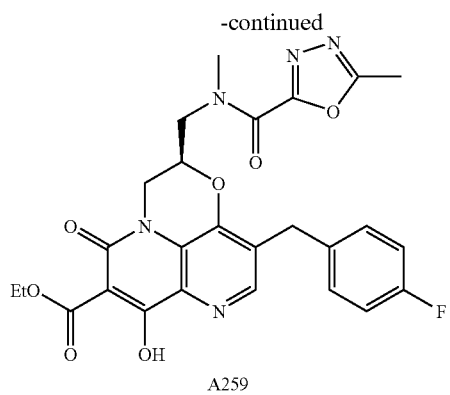

A259

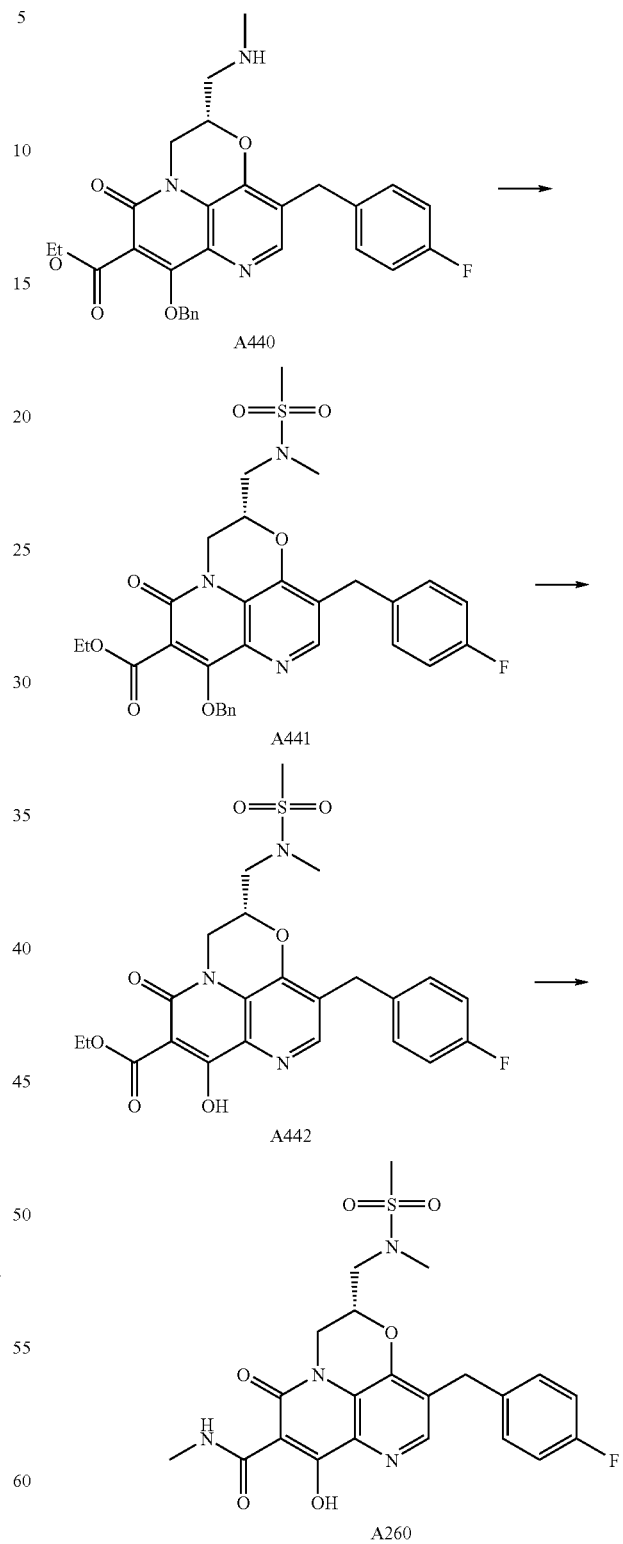

EXAMPLE 208

Into a flask containing amine A433 (70 mg, 0.14 mmol, 1 equiv.) is added DMF (3 mL, 0.05 M) followed by HATU (129 mg, 0.34 mmol, 2.5 equiv) and DIPEA (95 μL, 0.54 mmol, 4 equiv.) and 5-Methyl-[1,3,4]oxadiazole-2-carboxylic acid (35 mg, 0.27 mmol, 2 equiv.). After the substrate was consumed it was diluted with EtOA and quenched and washed with water. This was followed by washing with saturated $NH_4Cl$ and brine solution. The organic layer was dried over $MgSO_4$, filtered and concentrated in vacuo. A light yellow oil was realized and used in the next step without further purification.

To the crude A437 was added TFA (15 mL) was heated to 90° C. overnight. The reaction was then concentrated in vacuo and azeotroped with toluene (3×). The material was then washed with Ethyl ether/Hexanes to furnish a yellow solid of A438.

A438 (75 mg, 0.14 mmol, 1 equiv.) was placed in a microwave vial in DMF (2 mL, 0.1 M) and to it added methylamine (200 μL, 4 equiv, 2 M in THF). The reaction was heated in a microwave reactor at 130° C. for 30 min. Upon completion, the material was purified by RP-HPLC (MeCN—$H_2O$ gradient) to furnish the desired product.

400 MHz $^1$H NMR (DMSO-$d_6$): d 10.11 (bs, 1H), 8.38 (s, 1H), 7.19-7.10 (m, 2H), 6.96-7.00 (m, 3H), 4.86-4.91 (m, 2H), 4.71-4.70 (m, 1H), 4.49 (d, J=11.6 Hz, 2H), 3.75-3.90 (m, 4H), 3.12-3.58 (m, 2H), 3.08 (s, 3H), 2.84 (d, J=4.4

400 MHz $^{19}$F NMR (DMSO-$d_6$): −116.80, −73.91 (TFA salt).

LCMS (m/z+1): 523.12

To a solution of A440 (390 mg, 0.75 mmol, 1 equiv., previously reported) in $CH_2Cl_2$ (15 mL, 0.05 M) is added N—N'-diisopropylethylamine (655 μL, 3.77 mmol, 5 equiv.)

before methanesulfonyl chloride (175 mmol µL, 2.26 mmol, 3 equiv) was added. The reaction was shown to be complete within an hour. It was quenched and washed with water. This was followed by washing with saturated NH₄Cl and brine solution. The organic layer was dried over MgSO₄, filtered and concentrated in vacuo. A light yellow solid was realized and used in the next step without farther purification.

A solution of A441 (395 mg) and TFA (15 mL) was heated to 120° C. overnight. The reaction was then concentrated in vacuo and azeotroped with toluene (3×). The material was then washed with Ethyl ether/Hexanes to furnish a yellow solid of A442.

A442 (360 mg, 0.71 mmol, 1 equiv.) was placed in a microwave vial in DMF (3 mL, 0.2 M) and to it added methylamine (1.4 mL, 4 equiv, 2 M in THF). The reaction was heated in a microwave reactor at 130° C. for 30 min. Upon completion, the material was purified by RP-HPLC (MeCN—H₂O gradient) to furnish the desired product.

400 MHz $^1$H NMR (DMSO-$d_6$): d 10.05 (bs, 1H), 8.44 (s, 1H), 7.29-7.35 (m, 2H), 7.04-7.10 (m, 2H), 4.51-4.60 (m, 2H), 4.47 (dd, J=2.8, 14.0 Hz, 1H), 4.02 (s, 2H), 3.783-3.65 (m, 6H), 2.91 (s, 3H), 2.80 (s, 3H), 2.83 (d, J=5.2 Hz, 3H).

400 MHz $^{19}$F NMR (DMSO-$d_6$): −116.77, −74.53 (TFA salt).

LCMS (m/z+1): 491.08

EXAMPLE 209

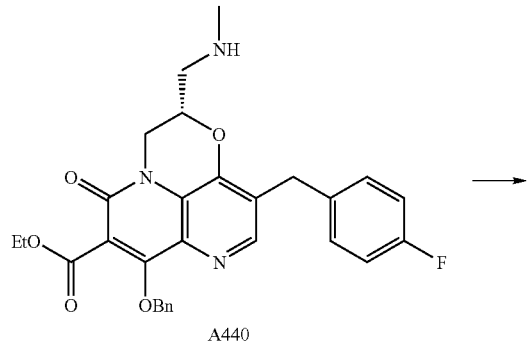

A440

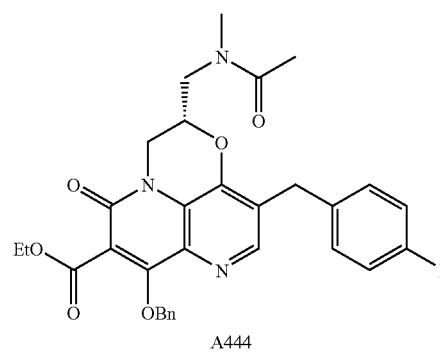

A444

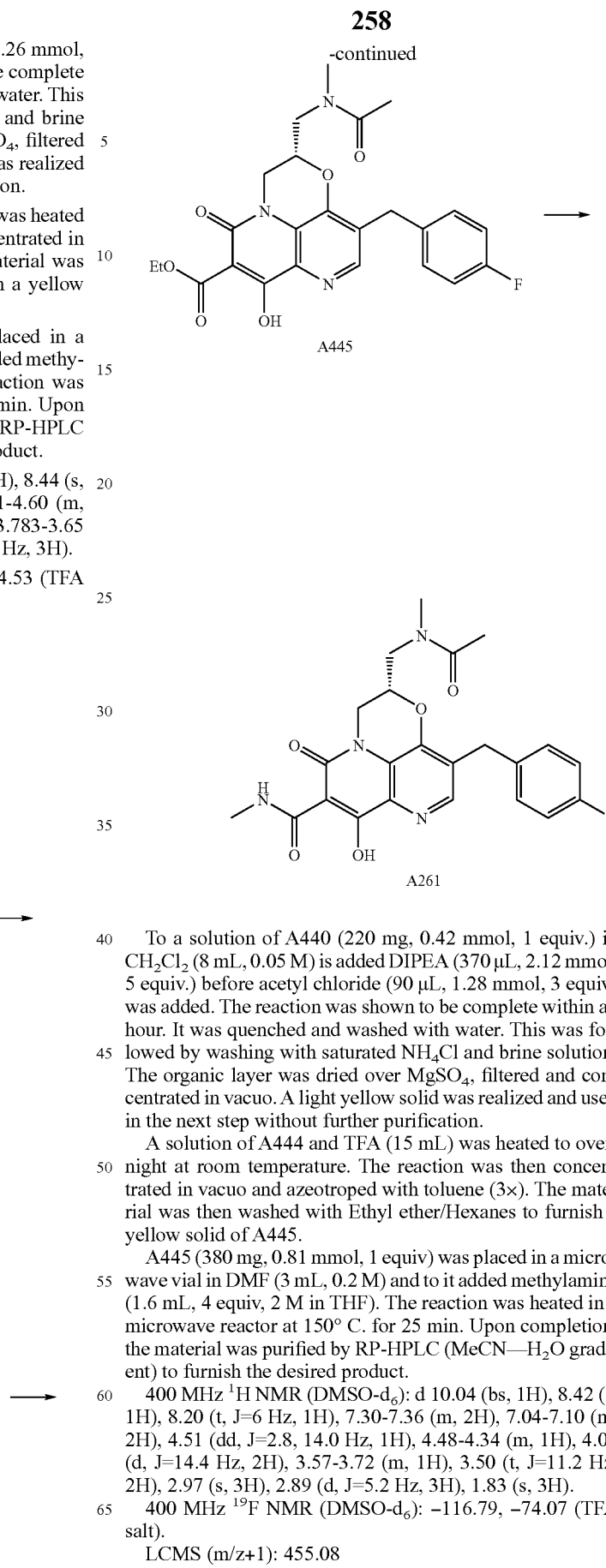

To a solution of A440 (220 mg, 0.42 mmol, 1 equiv.) in CH₂Cl₂ (8 mL, 0.05 M) is added DIPEA (370 µL, 2.12 mmol, 5 equiv.) before acetyl chloride (90 µL, 1.28 mmol, 3 equiv) was added. The reaction was shown to be complete within an hour. It was quenched and washed with water. This was followed by washing with saturated NH₄Cl and brine solution. The organic layer was dried over MgSO₄, filtered and concentrated in vacuo. A light yellow solid was realized and used in the next step without further purification.

A solution of A444 and TFA (15 mL) was heated to overnight at room temperature. The reaction was then concentrated in vacuo and azeotroped with toluene (3×). The material was then washed with Ethyl ether/Hexanes to furnish a yellow solid of A445.

A445 (380 mg, 0.81 mmol, 1 equiv) was placed in a microwave vial in DMF (3 mL, 0.2 M) and to it added methylamine (1.6 mL, 4 equiv, 2 M in THF). The reaction was heated in a microwave reactor at 150° C. for 25 min. Upon completion, the material was purified by RP-HPLC (MeCN—H₂O gradient) to furnish the desired product.

400 MHz $^1$H NMR (DMSO-$d_6$): d 10.04 (bs, 1H), 8.42 (s, 1H), 8.20 (t, J=6 Hz, 1H), 7.30-7.36 (m, 2H), 7.04-7.10 (m, 2H), 4.51 (dd, J=2.8, 14.0 Hz, 1H), 4.48-4.34 (m, 1H), 4.05 (d, J=14.4 Hz, 2H), 3.57-3.72 (m, 1H), 3.50 (t, J=11.2 Hz, 2H), 2.97 (s, 3H), 2.89 (d, J=5.2 Hz, 3H), 1.83 (s, 3H).

400 MHz $^{19}$F NMR (DMSO-$d_6$): −116.79, −74.07 (TFA salt).

LCMS (m/z+1): 455.08

EXAMPLE 210

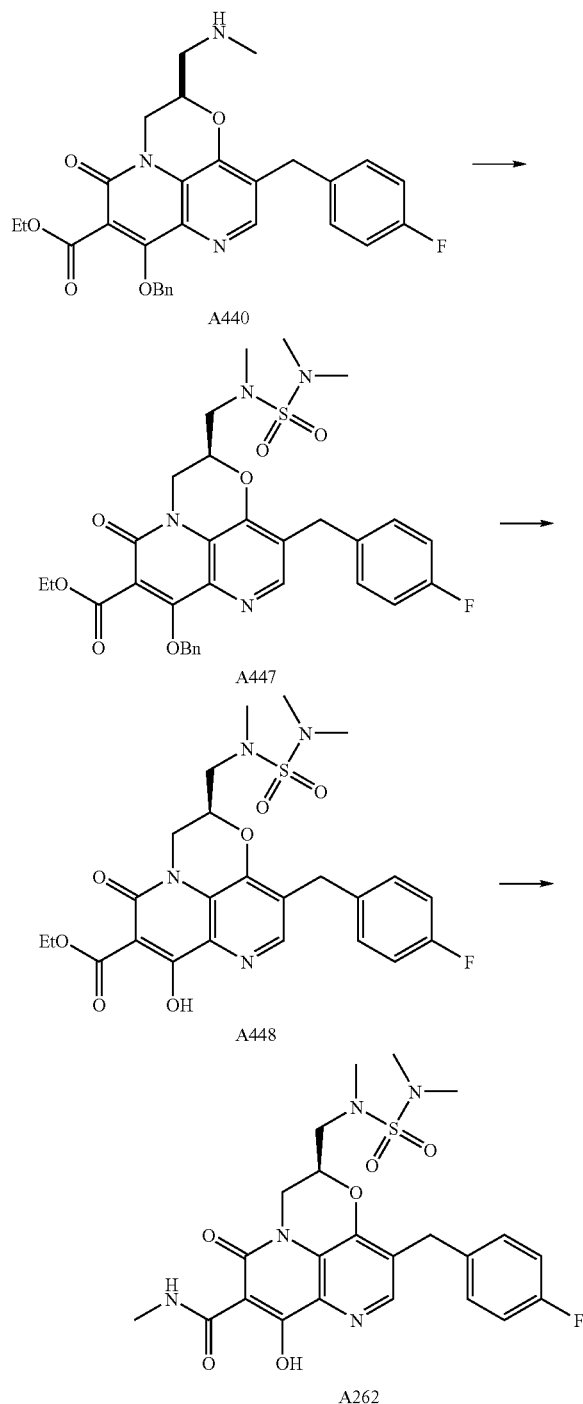

To a solution of A440 (260 mg, 0.51 mmol, 1 equiv., previously reported by Vangelis) in $CH_2Cl_2$ (10 mL, 0.05 M) is added N—N'-diisopropylethylamine (438 μL, 2.51 mmol, 5 equiv.) before sulfamoyl chloride (160 mmol μL, 1.58 mmol, 3 equiv) was added. The reaction was allowed to stir overnight at room temperature. It was quenched and washed with water. This was followed by washing with saturated $NH_4Cl$ and brine solution. The organic layer was dried over $MgSO_4$, filtered and concentrated in vacuo. A light yellow solid was realized and used in the next step without further purification.

A solution of A447 (395 mg) and TFA (15 mL) was heated to 120° C. overnight. The reaction was then concentrated in vacuo and azeotroped with toluene (3×). The material was then washed with Ethyl ether/Hexanes to furnish a yellow solid of A448.

A448 (175 mg, 0.33 mmol, 1 equiv.) was placed in a microwave vial in DMF (3 mL, 0.2 M) and to it added methylamine (0.5 mL, 3 equiv, 2 M in THF). The reaction was heated in a microwave reactor at 130° C. for 30 min. Upon completion, the material was purified by RP-HPLC (MeCN—$H_2O$ gradient) to furnish the desired product.

400 MHz $^1H$ NMR (DMSO-$d_6$): d 10.05 (s, 1H), 8.43 (s, 1H), 7.29-7.35 (m, 2H), 7.04-7.10 (m, 2H), 4.51-4.60 (m, 2H), 4.47 (d, J=14.0 Hz, 2H), 4.02 (s, 2H), 3.78-3.65 (m, 6H), 2.83 (d, J=5.2 Hz, 3H), 2.81 (s, 3H), 2.63 (s, 6H).

400 MHz $^{19}F$ NMR (DMSO-$d_6$): −116.78, −74.16 (TFA salt).

LCMS (m/z+1): 491.12

EXAMPLE 211

Antiviral Assays in MT2 and MT4 Cells

For the antiviral assay utilizing MT-2 cells, 50 μL of 2× test concentration of 5-fold serially diluted compound in culture medium with 10% FBS was added to each well of a 96-well plate (9 concentrations) in triplicate. MT-2 cells were infected with HIV-IIIb at a multiplicity of infection (m.o.i) of 0.01 for 3 hours. Fifty microliters of infected cell suspension in culture medium with 10% FBS (~1.5×10$^4$ cells) was then added to each well containing 50 μL of diluted compound. The plates were then incubated at 37° C. for 5 days. For the antiviral assay utilizing MT-4 cells, 20 μL of 2× test concentration of 5-fold serially diluted compound in culture medium with 10% FBS was added to each well of a 384-well plate (7 concentrations) in triplicate. MT-4 cells were next mixed with HIV-IIIb at an m.o.i. of 0.1 and 20 μL of virus/cell mixture (~2000 cells) was immediately added to each well containing 20 μL of diluted compound. The plates were then incubated at 37° C. for 5 days. After 5 days of incubation, 100 μL of CellTiter-Glo™ Reagent (catalog # G7571, Promega Biosciences, Inc., Madison, Wis.) was added to each well containing MT-2 cells and 40 μl to each well containing MT-4 cells. Cell lysis was carried out by incubating at room temperature for 10 min and then chemiluminescence was read.

$EC_{50}$ values for compounds of the present invention are shown in Table 1.

TABLE 1

| Example | Compound No. | $EC_{50}$ in MT-2 cells (nM) |
| --- | --- | --- |
| 1 | 12 | 3.2 |
| 2 | 13 | 7.0 |
| 3 | 14 | 5.5 |
| 4 | 15 | 13 |
| 5 | 16 | 12 |
| 6 | 17 | |
| 7 | 18 | 20 |
| 8 | 24 | 4.6 |
| 9 | 30 | 7.0 |
| 10 | 32 | 6.0 |
| 11 | 33 | 3.3 |
| 12 | 34 | 9.5 |
| 13 | 35 | 5.5 |

TABLE 1-continued

| Example | Compound No. | EC$_{50}$ in MT-2 cells (nM) |
|---|---|---|
| 14 | 36 | 3.5 |
| 15 | 37 | 5.8 |
| 16 | 38 | 8.5 |
| 17 | 39 | 9.5 |
| 18 | 43 | 982 |
| 19 | 45 | 2.0 |
| 20 | 49 | 8.0 |
| 21 | 50 | 17.0 |
| 22 | 51 | 4.0 |
| 23 | 52 | 8.0 |
| 24 | 59 | 85 |
| 25 | 60 | 400 |
| 26 | 65 | 1.5 |
| 27 | 72 | 20 |
| 28 | 79 | 7.0 |
| 29 | A-9 | 4.0 |
| 30 | A-10 | 4.0 |
| 31 | A-11 | 3.5 |
| 32 | A-12 | 3.0 |
| 33 | A-13 | 6.5 |
| 34 | A-14 | 7.0 |
| 35 | A-15 | 4.0 |
| 36 | A-17 | 2.5 |
| 37 | A-18 | 7.0 |
| 38 | A-25 | 5.5 |
| 39 | A-26 | 16 |
| 40 | A-27 | 4.0 |
| 41 | A-28 | 51 |
| 42 | A-31 | 1.5 |
| 43 | A-35 | 5.7 |
| 44 | A-50 | 6.8 |
| 45 | A-65 | 6.3 |
| 46 | A-67 | 1.7 |
| 47 | A-69 | 4.0 |
| 48 | A-70 | 12 |
| 48 | A-71 | 41 |
| 48 | A-72 | 39 |
| 49 | A-78 | |
| 50 | A-81 | 10.5 |
| 51 | A-82 | 8.0 |
| 52 | A-83 | 37 |
| 53 | A-84 | |
| 54 | A-85 | 4.0 |
| 56 | A-87 | 3.6 |
| 57 | A-88 | 18 |
| 58 | A-89 | 23 |
| 59 | A-90 | 2.9 |
| 60 | A-91 | 10 |
| 61 | A-92 | 21 |
| 62 | A-94 | 49 |
| 65 | A-108 | 4.0 |
| 65 | A-109 | 7.1 |
| 66 | A-110 | 32 |
| 67 | A-111 | 11 |
| 67 | A-112 | 7.0 |
| 68 | A-120 | 2.0 |
| 69 | A-121 | 7.0 |
| 70 | A-122 | 5.0 |
| 71 | A-123 | 7.8 |
| 72 | A-124 | 22.7 |
| 73 | A-125 | 31.4 |
| 74 | A-126 | 14.7 |
| 75 | A-127 | 14.5 |
| 76 | A-128 | 13.2 |
| 77 | A-129 | 5.1 |
| 78 | A-130 | 30.5 |
| 79 | A-131 | 26.5 |
| 80 | A-132 | 9.4 |
| 81 | A-133 | 8.5 |
| 82 | A-134 | 14 |
| 83 | A-135 | 14 |
| 84 | A-136 | 19 |
| 85 | A-137 | 12 |
| 86 | A-138 | 22 |
| 87 | A-139 | 2.5 |
| 88 | A-140 | 7.9 |
| 89 | A-141 | 225 |
| 90 | A-142 | 24 |
| 91 | A-143 | 17 |
| 92 | A-144 | 19 |
| 93 | A-145 | 12 |
| 94 | A-146 | 14 |
| 95 | A-147 | 15 |
| 96 | A-148 | 29 |
| 97 | A-149 | 16 |
| 98 | A-150 | 29 |
| 99 | A-151 | 14.3 |
| 100 | A-152 | 3.5 |
| 101 | A-153 | 78 |
| 102 | A-154 | 2.9 |
| 103 | A-155 | 10 |
| 104 | A-156 | 3.0 |
| 105 | A-157 | 71 |
| 106 | A-158 | 6.0 |
| 107 | A-159 | 25 |
| 108 | A-160 | 7.5 |
| 109 | A-161 | 37.5 |
| 110 | A-162 | 27.4 |
| 111 | A-163 | 19.2 |
| 112 | A-164 | 11.7 |
| 113 | A-165 | 5.3 |
| 114 | A-166 | 6.4 |
| 115 | A-167 | 3.9 |
| 116 | A-168 | 2.5 |
| 117 | A-169 | 14 |
| 118 | A-170 | 0.7 |
| 119 | A-171 | 2.4 |
| 120 | A-172 | 19 |
| 121 | A-173 | 5.8 |
| 122 | A-174 | 64 |
| 123 | A-175 | 35 |
| 124 | A-176 | 6.1 |
| 125 | A-177 | 5.5 |
| 126 | A-178 | 3.3 |
| 127 | A-179 | 5.0 |
| 128 | A-180 | 7.1 |
| 129 | A-181 | 2.2 |
| 130 | A-182 | 4.6 |
| 131 | A-183 | 13.9 |
| 132 | A-184 | 37.4 |
| 133 | A-185 | 7.0 |
| 134 | A-186 | 2.5 |
| 135 | A-187 | 2.7 |
| 136 | A-188 | 7.2 |
| 137 | A-189 | 5.0 |
| 138 | A-190 | 1.5 |
| 139 | A-191 | 2.4 |
| 140 | A-192 | 3.5 |
| 141 | A-193 | 3.7 |
| 142 | A-194 | 1.9 |
| 143 | A-195 | 4.0 |
| 144 | A-196 | 20 |
| 145 | A-197 | 9.0 |
| 146 | A-198 | 5.5 |
| 147 | A-199 | 3.0 |
| 148 | A-200 | 45.6 |
| 149 | A-201 | 5.0 |
| 150 | A-202 | 6.0 |
| 151 | A-203 | 23 |
| 152 | A-204 | 7.0 |
| 153 | A-205 | 12.0 |
| 154 | A-206 | 6.0 |
| 155 | A-207 | 4.3 |
| 156 | A-208 | 34 |
| 157 | A-209 | 18 |
| 158 | A-210 | 8.2 |
| 159 | A-211 | 14 |
| 160 | A-212 | 15 |
| 161 | A-213 | 4.2 |
| 162 | A-214 | 4.6 |
| 163 | A-215 | 18.5 |
| 164 | A-216 | 37 |
| 165 | A-217 | 8.0 |
| 166 | A-218 | 9.0 |

TABLE 1-continued

| Example | Compound No. | EC$_{50}$ in MT-2 cells (nM) |
|---|---|---|
| 167 | A-219 | 25.6 |
| 168 | A-220 | 12 |
| 169 | A-221 | 4.1 |
|  | A-222 | 8.0 |
|  | A-223 | 9.7 |
| 172 | A-224 | 12 |
|  | A-225 | 12 |
| 174 | A-226 | 2.6 |
| 175 | A-227 | 2.4 |
| 176 | A-228 | 23.2 |
| 177 | A-229 | 1.2 |
| 178 | A-230 | 18 |
|  | A-231 | 17.4 |
| 180 | A-232 | 43 |
| 181 | A-233 | 1.2 |
| 182 | A-234 | 0.3 |
| 183 | A-235 | 1.8 |
| 184 | A-236 | 0.4 |
|  | A-237 | 5.3 |
|  | A-238 | 9.7 |
| 187 | A-239 | 12 |
|  | A-240 | 15 |
| 189 | A-241 | 7.6 |
|  | A-242 | 8.9 |
| 191 | A-243 | 21 |
|  | A-244 | 19 |
| 193 | A-245 | 1.2 |
|  | A-246 | 6.6 |
| 195 | A-247 | 22 |
|  | A-248 | 21 |
| 197 | A-249 | 32 |
| 198 | A-250 | 3.0 |
| 199 | A-251 | 6.7 |
| 200 | A-252 | 1.1 |
| 201 | A-253 | 2.8 |
| 202 | A-254 | 12 |
| 203 | A-255 | 12 |
| 204 | A-256 | 8.3 |
| 205 | A-257 | 1.0 |
| 206 | A-258 | 0.1 |
| 207 | A-259 | 4.6 |
| 208 | A-260 | 0.6 |
| 209 | A-261 | 5.1 |
| 210 | A-262 | 5.0 |

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

The invention has been described with reference to various specific and preferred embodiments and techniques. However, it should be understood that many variations and modifications may be made while remaining within the spirit and scope of the invention.

What is claimed:
1. A compound of formula I:

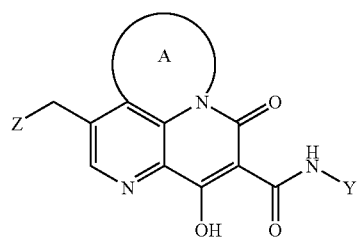

or a pharmaceutically acceptable salt thereof, wherein:
A is a 5 membered to 8 membered, optionally substituted, heterocyclic ring;
Z is a substituted phenyl; and
Y is selected from the group consisting of optionally substituted alkoxycarbonyl, carboxy, optionally substituted alkyl, optionally substituted heteroalkyl, optionally substituted alkoxy, alkoxyalkyl, nitro, hydroxy, hydroxyalkyl, optionally substituted alkenyl, optionally substituted alkynyl, alkylsulfonyl, alkyloxysulfonyl, optionally substituted amino, optionally substituted aminosulfonyl, alkylthio, alkylthioalkyl, haloalkyl, haloalkoxy, haloalkoxyalkyl, cycloalkyl, cycloalkenyl, oxo, thioxo, alkylenedioxy, alkylene, alkenylene, nitroso, amidino, guanidine, cyano, optionally substituted carbamoyl, optionally substituted carbamoylalkyl, optionally substituted sulfamoyl, sulfoamino, sulfo, formyl, alkylcarbonyl, alkylcarbonyloxy, hydrazino, morpholino, phosphono, phosphinico, optionally substituted aryl, optionally substituted heteroaryl, optionally substituted heterocycle, optionally substituted aralkyl, optionally substituted heteroaralkyl, optionally substituted aryloxy, optionally substituted heteroaryloxy, optionally substituted heterocycleoxy, optionally substituted arylthio, optionally substituted heteroarylthio, optionally substituted aralkyloxy, optionally substituted heteroaralkyloxy, optionally substituted aralkylthio, optionally substituted heteroaralkylthio, optionally substituted aryloxyalkyl, optionally substituted heteroaryloxyalkyl, optionally substituted arylthioalkyl, optionally substituted heteroarylthioalkyl, optionally substituted arylsulfonyl, optionally substituted heteroarylsulfonyl, optionally substituted aralkylsulfonyl, optionally substituted heteroaralkylsulfonyl, optionally substituted alkylcarbonyl alkyl, optionally substituted arylcarbonyl alkyl, alkylsulfonyloxy, sulfamoyloxy and optionally substituted arylcarbonyl.

2. The compound of claim 1 wherein the A ring is selected from the group consisting of:

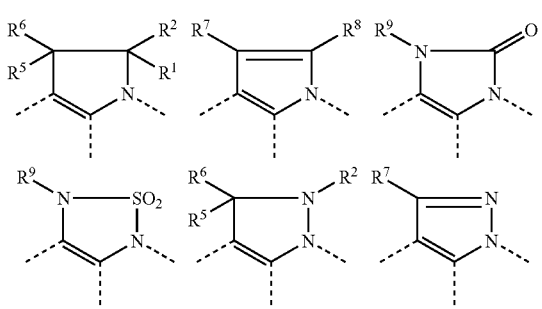

-continued

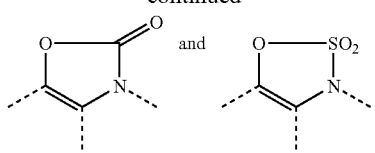
and wherein, $R^1$, $R^2$, $R^5$, $R^6$, $R^7$, $R^8$ and $R^9$ are each independently selected from the group consisting of X, R, —O⁻, =O, —OR, —SR, —S⁻, —NR$_2$, —N⁺R$_3$, =NR, —CX$_3$, —CN, —OCN, —SCN, —N=C=O, —NCS, —NO, —NO$_2$, =N$_2$, —N$_3$, —NHC(=O)R, —C(=O)R, —C(=O)NRR—S(=O)$_2$—, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —P(=O)(O⁻)$_2$, —P(=O)(OH)$_2$, —P(O)(OR)(O⁻), —C(=O)R, —C(=O)X, —C(S)R, —C(O)OR, —C(O)O⁻, —C(S)OR, —C(O)SR, —C(S)SR, —C(O)NRR, —C(S)NRR, and —C(=NR)NRR, where (a) each X is independently selected from the group consisting of F, Cl, Br, and I;

(b) each R is independently selected from the group consisting of H, alkyl, heteroalkyl, aryl, and arylalkyl;

(c) any two members of the group consisting of $R^1$, $R^2$, $R^5$, $R^6$, $R^7$, $R^8$ and $R^9$ can together form a spiro ring, provided that said two members are attached to the same carbon atom in the A ring; and (d) any two members of the group consisting of $R^1$, $R^2$, $R^5$, $R^6$, $R^7$, $R^8$ and $R^9$ can together form a fused ring, provided that said two members are attached to adjacent carbon or nitrogen atoms in the A ring.

3. The compound of claim 1 wherein the A ring is selected from the group consisting of:

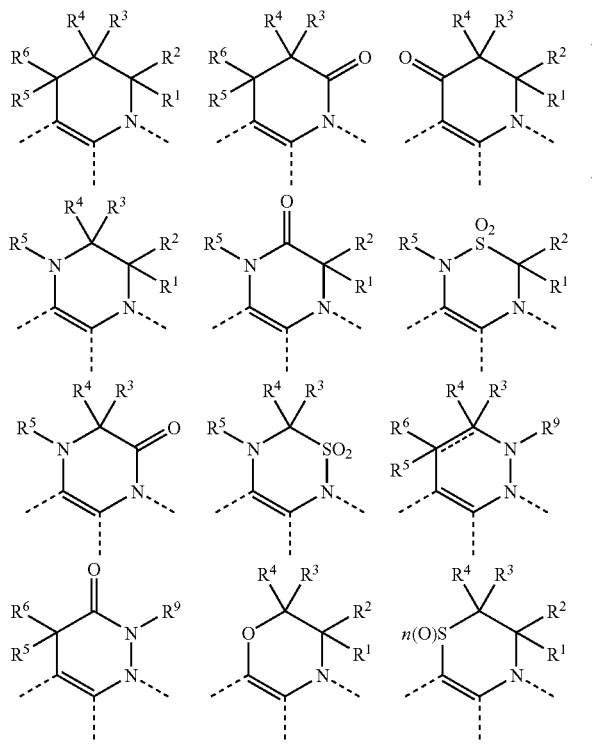

-continued

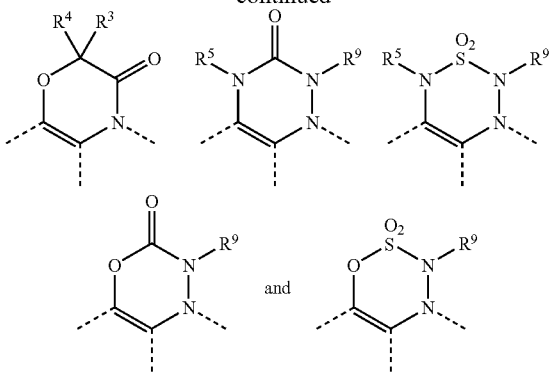

and wherein, n is 0, 1, or 2; and $R^1$, $R^2$, $R^3$, $R^4$, $R^5$, $R^6$, and $R^9$ are each independently selected from the group consisting of X, R, —O⁻, =O, —OR, —SR, —S⁻, —NR$_2$, —N⁺R$_3$, =NR, —CX$_3$, —CN, —OCN, —SCN, —N=C=O, —NCS, —NO, —NO$_2$, =N$_2$, —N$_3$, —NHC(=O)R, —C(=O)R, —C(=O)NRR—S(=O)$_2$—, —S(=O)$_2$OH, —S(=O)$_2$ R, —OS(=O)$_2$OR, —S(=O)$_2$NR, —S(=O)R, —OP(=O)(OR)$_2$, —P(=O)(OR)$_2$, —P(=O)(O⁻)$_2$, —P(=O)(OH)$_2$, —P(O)(OR)(O⁻), —C(=O)R, —C(=O)X, —C(S)R, —C(O)OR, —C(O)O⁻, —C(S)OR, —C(O)SR, —C(S)SR, —C(O)NRR, —C(S)NRR, and —C(=NR)NRR, where (a) each X is independently selected from the group consisting of F, Cl, Br, and I;

(b) each R is independently selected from the group consisting of H, alkyl, heteroalkyl, aryl, and arylalkyl;

(c) any two members of the group consisting of $R^1$, $R^2$, $R^3$, $R^5$, $R^6$, and $R^9$ can together form a spiro ring, provided that said two members are attached to the same carbon atom in the A ring; and (d) any two members of the group consisting of $R^1$, $R^2$, $R^3$, $R^4$, $R^5$, $R^6$, and $R^9$ can together form a fused ring, provided that said two members are attached to adjacent carbon or nitrogen atoms in the A ring.

4. The compound of claim 1 wherein the A ring is selected from the group consisting of:

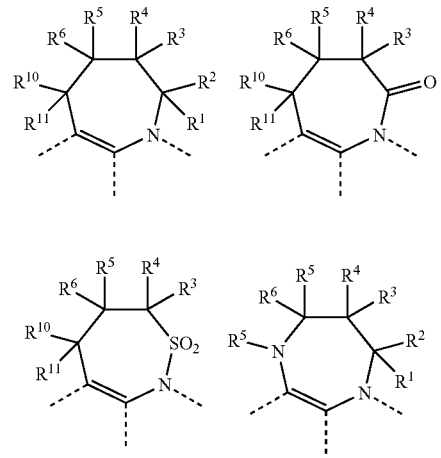

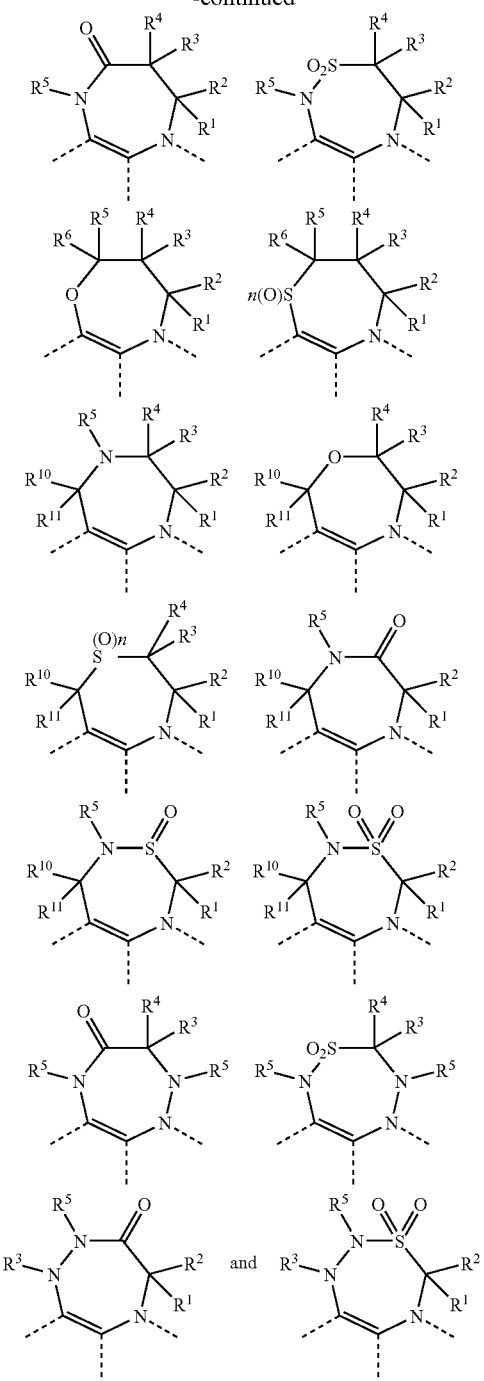

wherein, n is 0, 1, or 2; and
$R^1, R^2, R^3, R^4, R^5, R^6, R^{10}$, and $R^{11}$ are each independently selected from the group consisting of X, R, —O⁻, =O, —OR, —SR, —S⁻, —NR₂, —N⁺R₃, =NR, —CX₃, —CN, —OCN, —SCN, —N=C=O, —NCS, —NO, —NO₂, =N₂, —N₃, —NHC(=O)R, —C(=O)R, —C(=O)NRR—S(=O)₂—, —S(=O)₂OH, —S(=O)₂ R, —OS(=O)₂OR, —S(=O)₂NR, —S(=O)R, —OP(=O)(OR)₂, —P(=O)(OR)₂, —P(=O)(O⁻)₂, —P(=O)(OH)₂, —P(O)(OR)(O⁻), —C(=O)R, —C(=O)X, —C(S)R, —C(O)OR, —C(O)O⁻, —C(S)OR, —C(O)SR, —C(S)SR, —C(O)NRR, —C(S)NRR, and —C(=NR)NRR, where (a) each X is independently selected from the group consisting of F, Cl, Br, and I;

(b) each R is independently selected from the group consisting of H, alkyl, heteroalkyl, aryl, and arylalkyl;

(c) any two members of the group consisting of $R^1, R^2, R^3, R^4, R^5, R^6, R^{10}$, and $R^{11}$ can together form a spiro ring, provided that said two members are attached to the same carbon atom in the A ring; and (d) any two members of the group consisting of $R^1, R^2, R^3, R^4, R^5, R^6, R^{10}$, and $R^{11}$ can together form a fused ring, provided that said two members are attached to adjacent carbon or nitrogen atoms in the A ring.

5. The compound of claim 1 wherein the A ring is selected from the group consisting of:

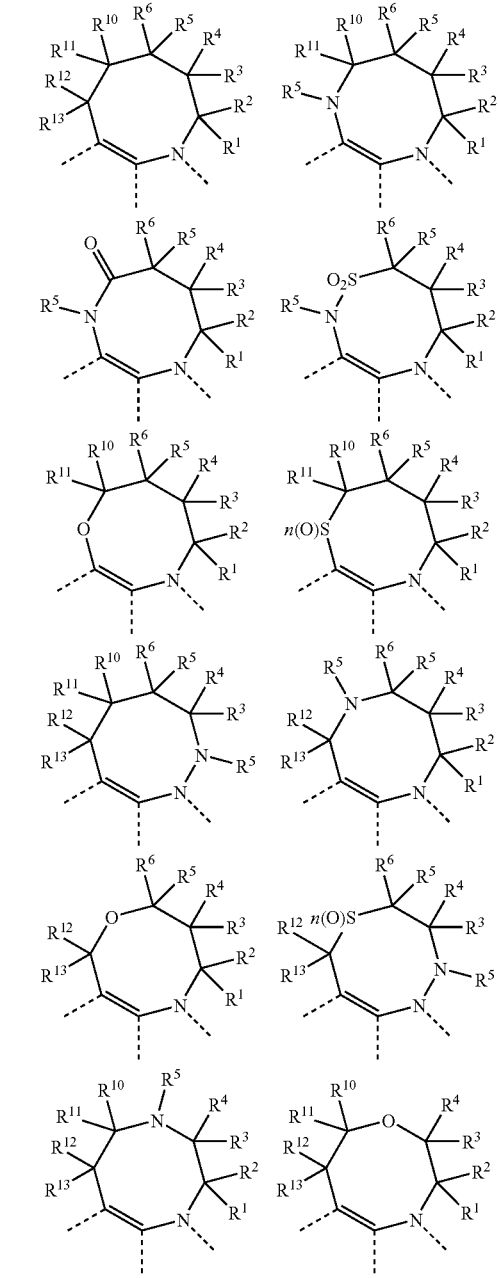

-continued

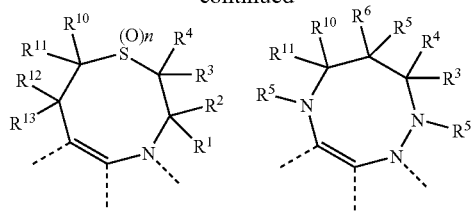

wherein, n is 0, 1, or 2; and
R$^1$, R$^2$, R$^3$, R$^4$, R$^5$, R$^6$, R$^{10}$, R$^{11}$, R$^{12}$ and R$^{13}$ are each independently selected from the group consisting of X, R, —O$^-$, =O, —OR, —SR, —S$^-$, —NR$_2$, —N$^+$R$_3$, =NR, —CX$_3$, —CN, —OCN, —SCN, —N=C=O, —NCS, —NO, —NO$_2$, =N$_2$, —N$_3$, —NHC(=O)R, —C(=O)R, —C(=O)NRR—S(=O)$_2$—, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —P(=O)(O$^-$)$_2$, —P(=O)(OH)$_2$, —P(O)(OR)(O$^-$), —C(=O)R, —C(=O)X, —C(S)R, —C(O)OR, —C(O)O$^-$, —C(S)OR, —C(O)SR, —C(S)SR, —C(O)NRR, —C(S)NRR, and —C(=NR)NRR, where
(a) each X is independently selected from the group consisting of F, Cl, Br, and I;
(b) each R is independently selected from the group consisting of H, alkyl, heteroalkyl, aryl, and arylalkyl;
(c) any two members of the group consisting of R$^1$, R$^2$, R$^3$, R$^4$, R$^5$, R$^6$, R$^{10}$, R$^{11}$, R$^{12}$ and R$^{13}$ can together form a spiro ring, provided that said two members are attached to the same carbon atom in the A ring; and
(d) any two members of the group consisting of R$^1$, R$^2$, R$^3$, R$^4$, R$^5$, R$^6$, R$^{10}$, R$^{11}$, R$^{12}$ and R$^{13}$ can together form a fused ring, provided that said two members are attached to adjacent carbon atoms in the A ring.

6. The compound of claim 1 wherein the phenyl is substituted with a substituent selected from the group consisting of X, R, —O$^-$, =O, —OR, —SR, —S$^-$, —NR$_2$, —N$^+$R$_3$, =NR, —CX$_3$, —CN, —OCN, —SCN, —N=C=O, —NCS, —NO, —NO$_2$, =N$_2$, —N$_3$, —NHC(=O)R, —C(=O)R, —C(=O)NRR—S(=O)$_2$—, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —P(=O)(O$^-$)$_2$, —P(=O)(OH)$_2$, —P(O)(OR)(O$^-$), —C(=O)R, —C(=O)X, —C(S)R, —C(O)OR, —C(O)O$^-$, —C(S)OR, —C(O)SR, —C(S)SR, —C(O)NRR, —C(S)NRR, —C(=NR)NRR, where each X is independently selected from the group consisting of F, Cl, Br, and I, and each R is independently selected from the group consisting of H, alkyl, heteroalkyl, aryl, and arylalkyl.

7. A compound of claim 1 having the structure set forth in Formula II

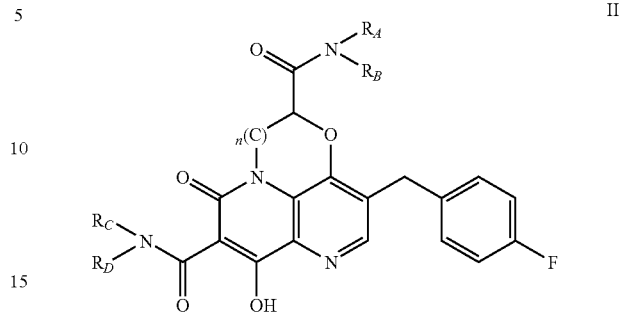

wherein,
n is selected from 0, 1, 2 and 3;
R$_A$ and R$_B$ are each independently selected from H and optionally substituted C$_1$-C$_8$ alkyl, and R$_A$ and R$_B$ can be linked, together with the N to which they are each attached, to form a heterocycle; and
R$_C$ and R$_D$ are each independently selected from H, optionally substituted C$_1$-C$_8$ alkyl, optionally substituted heterocyclyl alkyl, optionally substituted amine, optionally substituted aryloxy, and optionally substituted alkoxy.

8. A compound of claim 1 having the structure set forth in Formula III

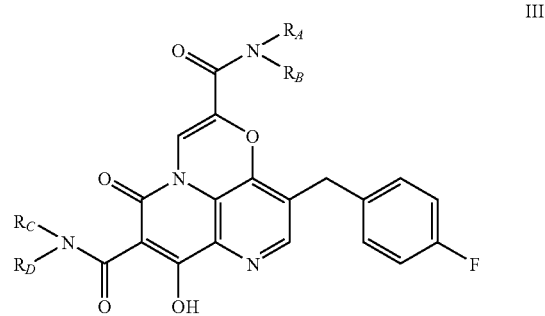

wherein,
n is selected from 0, 1, 2 and 3;
R$_A$ and R$_B$ are each independently selected from H and optionally substituted C$_1$-C$_8$ alkyl, and R$_A$ and R$_B$ can be linked, together with the N to which they are each attached, to form a heterocycle; and
R$_C$ and R$_D$ are each independently selected from H, optionally substituted C$_1$-C$_8$ alkyl, optionally substituted heterocyclyl alkyl, optionally substituted amine, optionally substituted aryloxy, and optionally substituted alkoxy.

9. A compound of claim 1 having the structure set forth in Formula IV

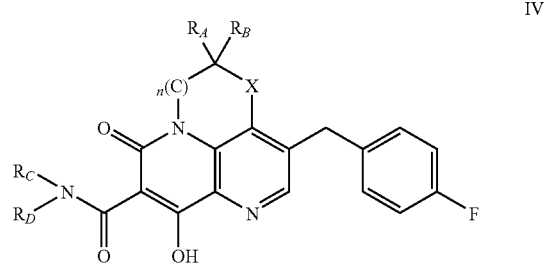

wherein:
n is selected from 0, 1, 2 and 3;
X is selected from C, O and NR$_E$, wherein R$_E$ is selected from H, optionally substituted alkoxy and optionally substituted C$_1$-C$_8$ alkyl;
R$_A$ and R$_B$ are each independently selected from H and optionally substituted C$_1$-C$_8$ alkyl; and
R$_C$ and R$_D$ are each independently selected from H, optionally substituted C$_1$-C$_8$ alkyl, optionally substituted heterocyclyl alkyl, optionally substituted amine, optionally substituted aryloxy, and optionally substituted alkoxy.

10. A compound of claim 1 having the structure set forth in Formula V

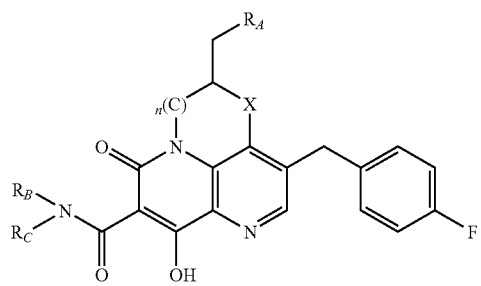

wherein:
n is selected from 0, 1, 2 and 3;
X is selected from C, O and NR$_E$, wherein R$_E$ is selected from H, optionally substituted alkoxy and optionally substituted C$_1$-C$_8$ alkyl;
R$_A$ is independently selected from H, optionally substituted alkoxy and optionally substituted C$_1$-C$_8$ alkyl; and
R$_B$ and R$_C$ are each independently selected from H, optionally substituted C$_1$-C$_8$ alkyl, optionally substituted heterocyclyl alkyl, optionally substituted amine, optionally substituted aryloxy, and optionally substituted alkoxy.

11. A compound of claim 1 having the structure set forth in Formula VI:

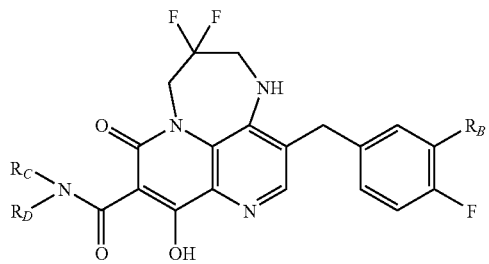

wherein:
R$_B$ is independently selected from H, alkoxy and optionally substituted C$_1$-C$_8$ alkyl; and
R$_C$ and R$_D$ are each independently selected from H, optionally substituted C$_1$-C$_8$ alkyl, optionally substituted heterocyclyl alkyl, optionally substituted amine, optionally substituted aryloxy, and optionally substituted alkoxy.

12. The compound of claim 1 which is a pharmaceutically acceptable salt thereof.

13. A pharmaceutical composition comprising the compound of claim 1 and at least one pharmaceutically acceptable carrier.

14. The pharmaceutical composition of claim 13, further comprising a therapeutic agent.

15. The pharmaceutical composition of claim 14, wherein said therapeutic agent is selected from the group consisting of 1) HIV protease inhibitors, 2) a HIV non-nucleoside inhibitor of reverse transcriptase, 3) a HIV nucleoside inhibitor of reverse transcriptase, 4) a HIV nucleotide inhibitor of reverse transcriptase, 5) a HIV integrase inhibitor, 6) a gp41 inhibitor, 7) a CXCR4 inhibitor, 8) an entry inhibitor, 9) a gp120 inhibitor, 10) a G6PD and NADH-oxidase inhibitor, 10) a CCR5 inhibitor, 11) an interferon, 12) ribavirin analogs, 13) NS5a inhibitors, 14) NS5b polymerase inhibitors, 15) NS3 protease inhibitors, 16) alpha-glucosidase 1 inhibitors, 17) hepatoprotectants, 18) non-nucleoside inhibitors of HIV, and 19) a pharmacokinetic enhancer.

16. A method of inhibiting HIV infection, said method comprising administering to an individual in need thereof a pharmaceutical composition which comprises a therapeutically effective amount of the compound of claim 1.

17. A compound selected from the group consisting of

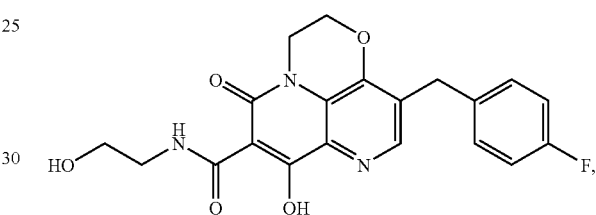

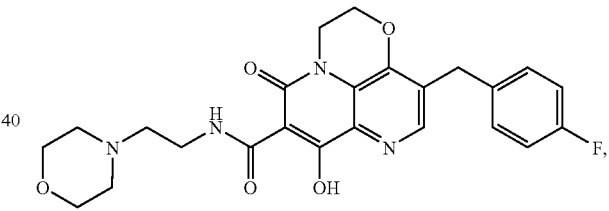

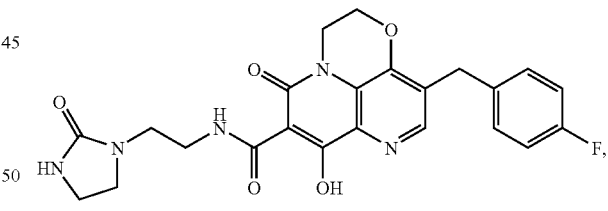

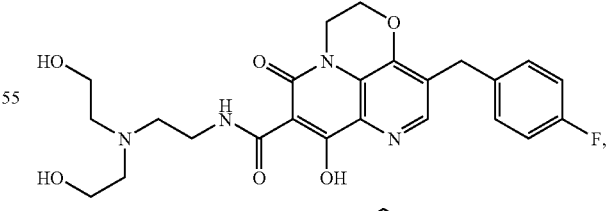

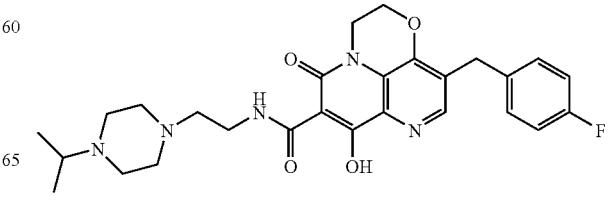

273
-continued
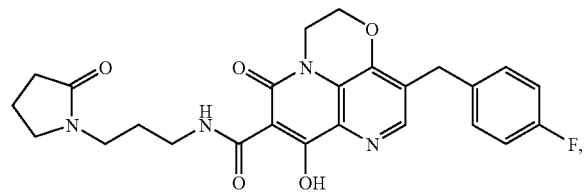
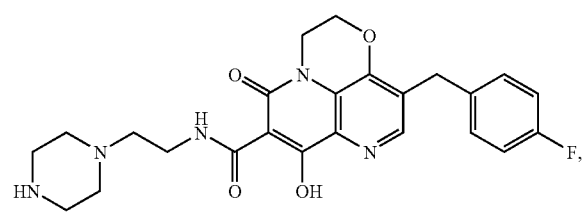
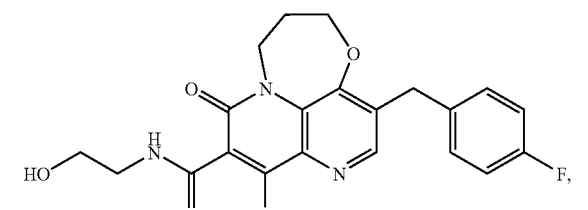
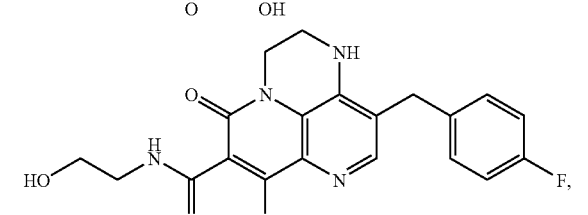
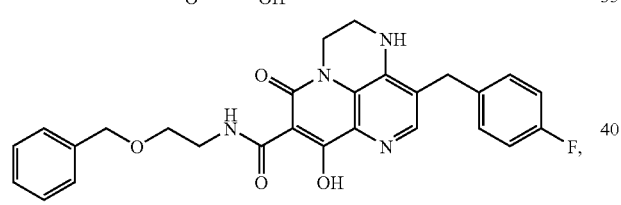
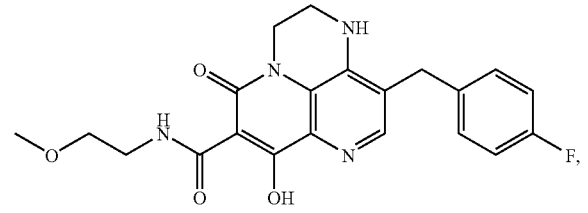
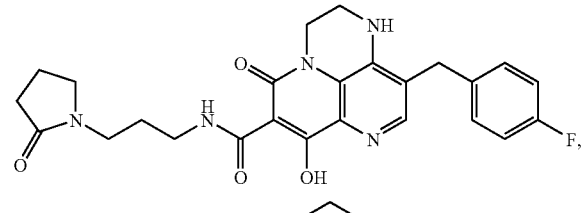
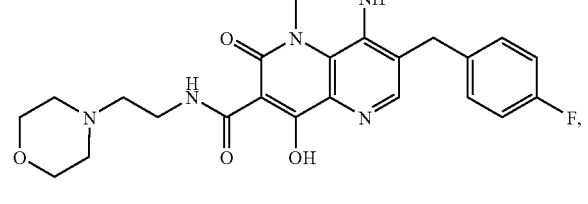
274
-continued
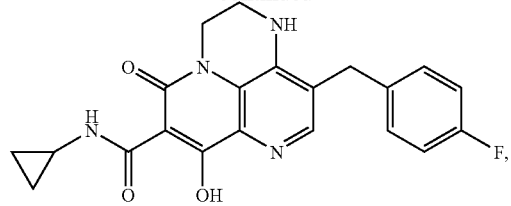
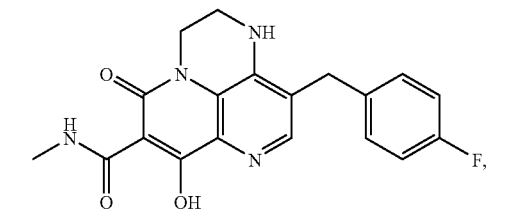
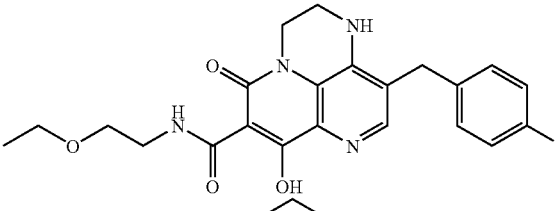
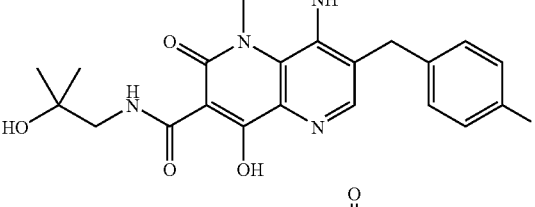
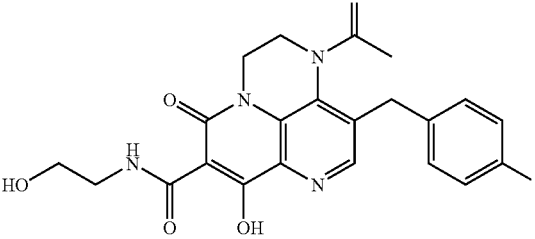
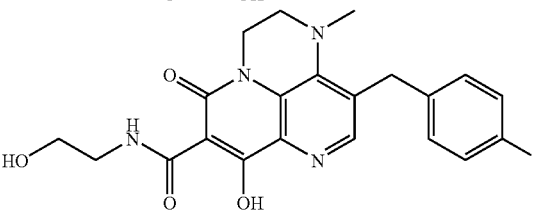
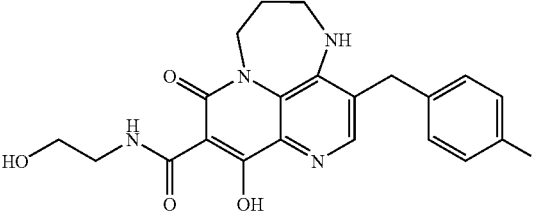
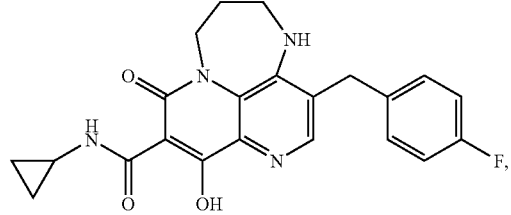

275
-continued
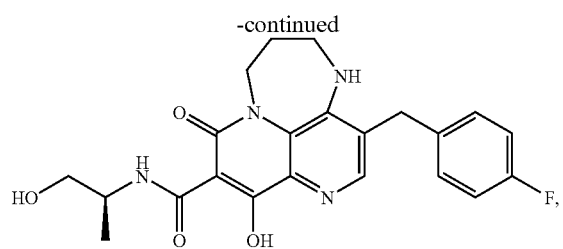
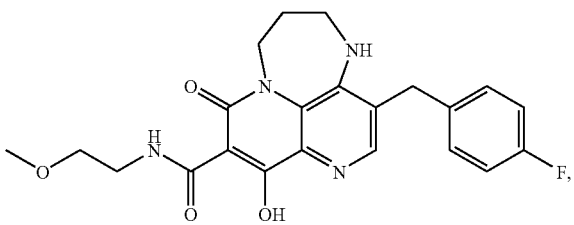
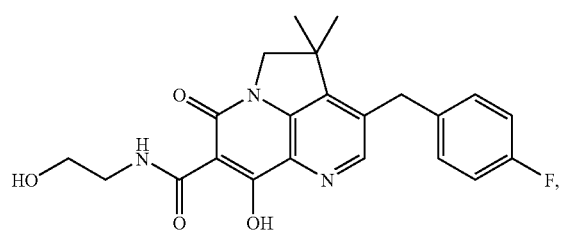
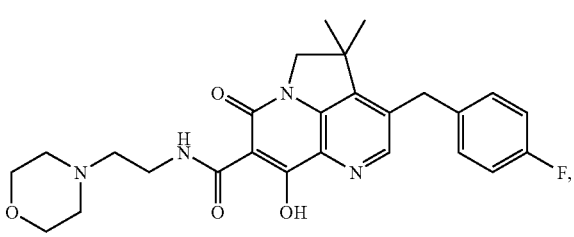
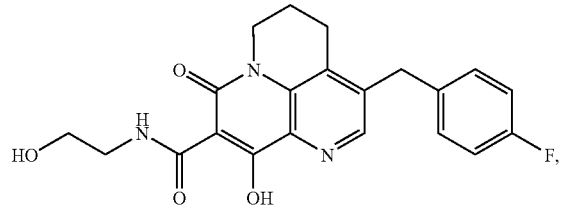
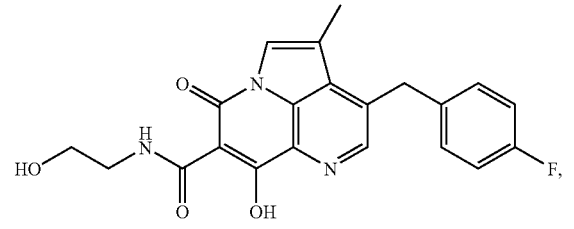
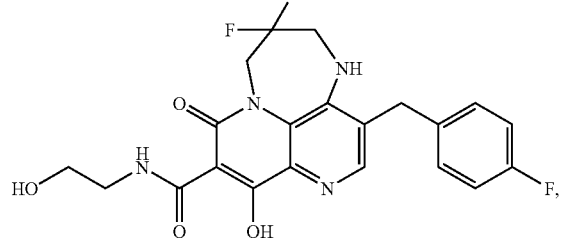
276
-continued
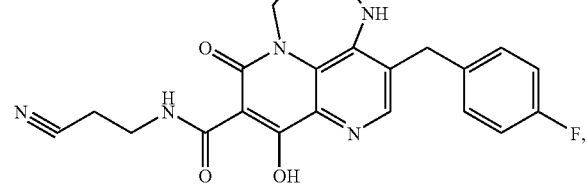
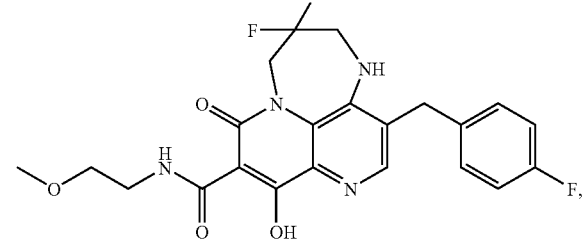
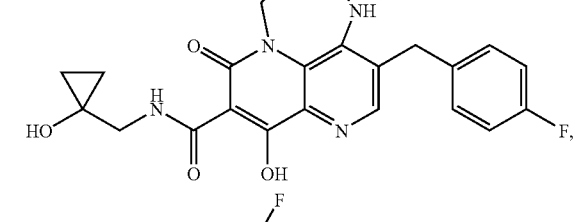
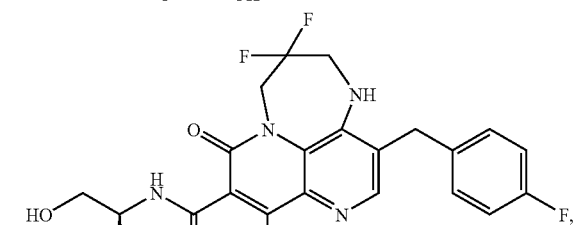
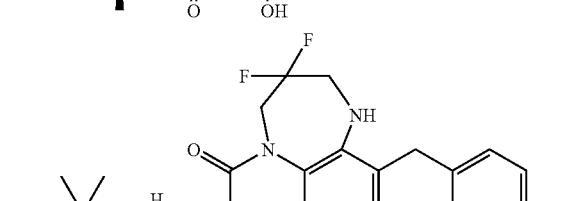
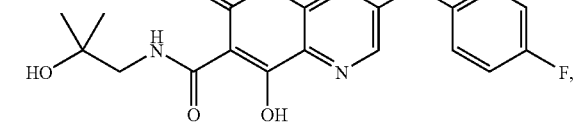

277
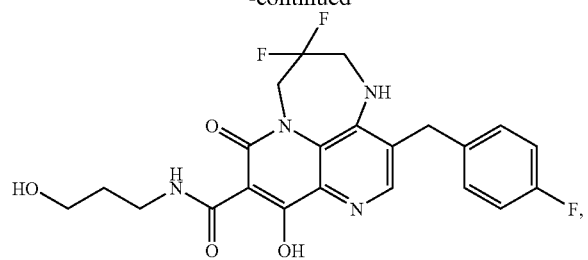
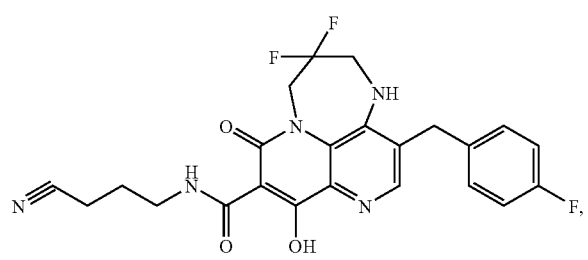
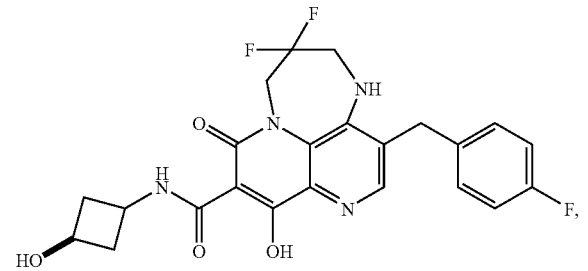
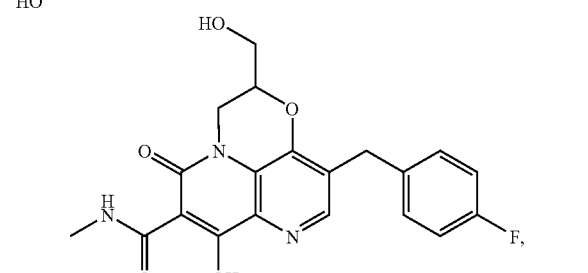
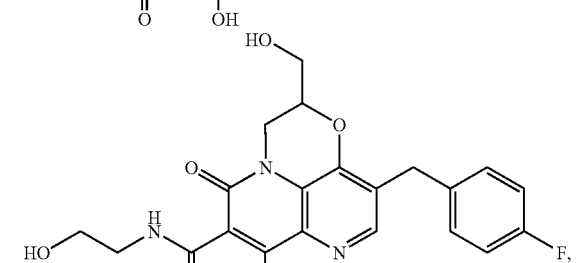
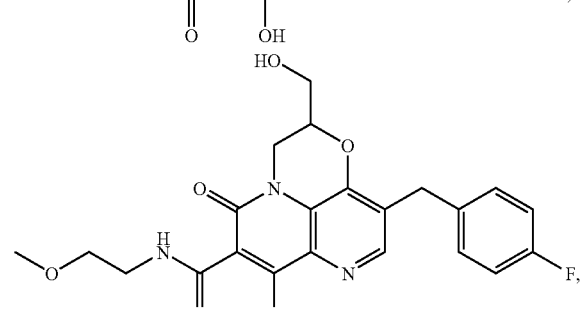
278
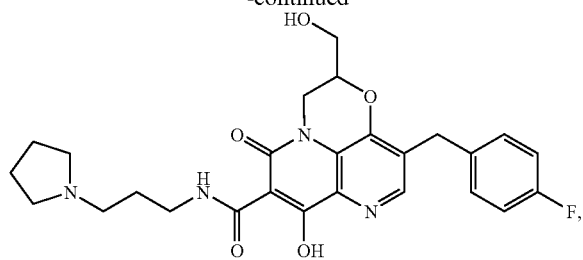
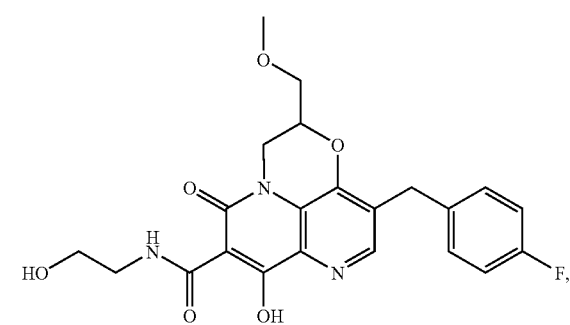
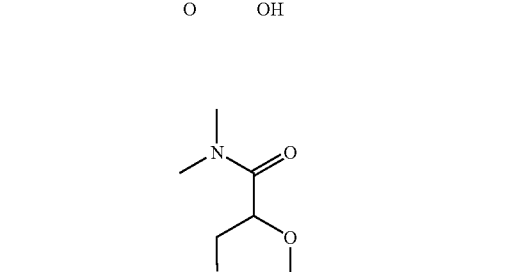
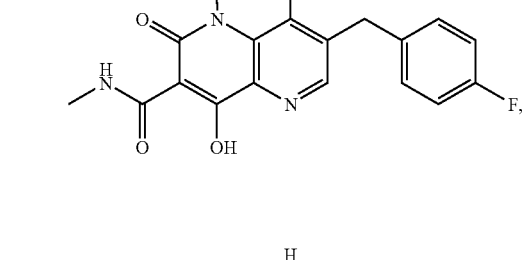
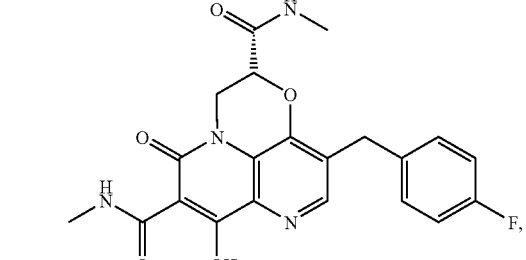
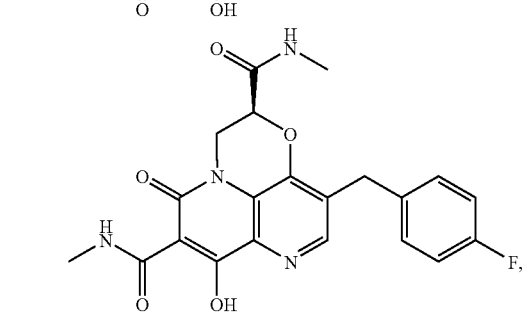

| 279 -continued | 280 -continued |
|---|---|
| 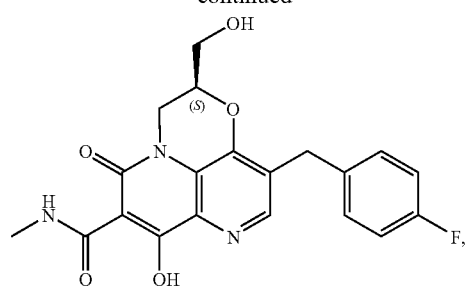 | 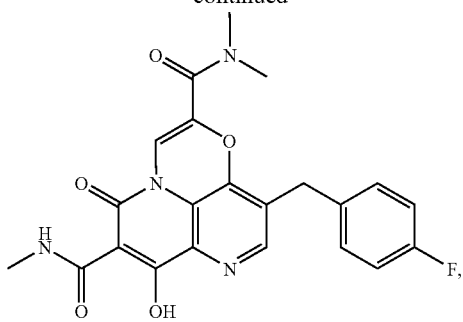 |
| 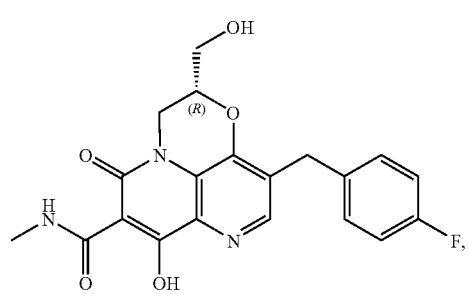 | 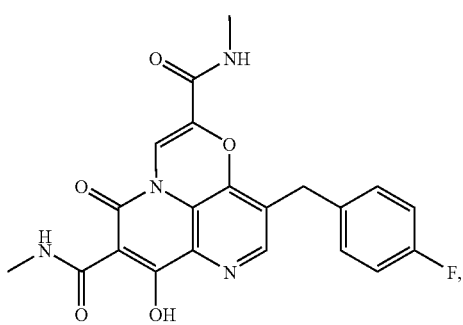 |
| 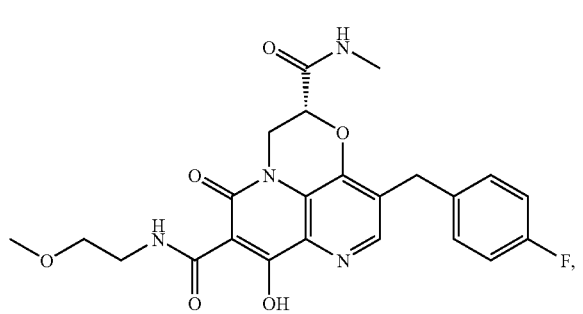 | 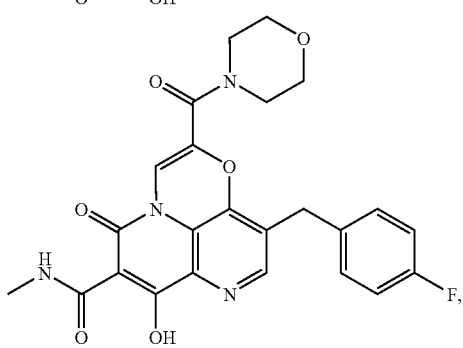 |
| 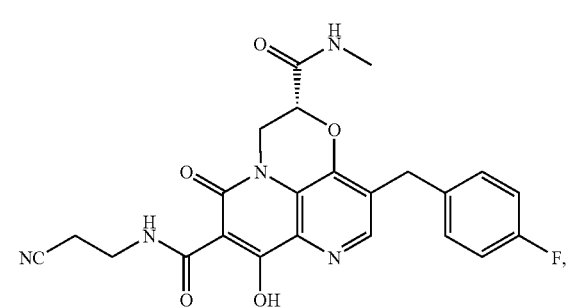 | 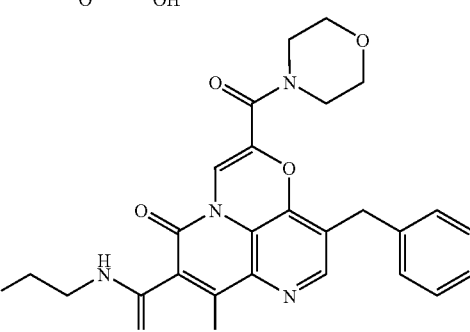 |
| 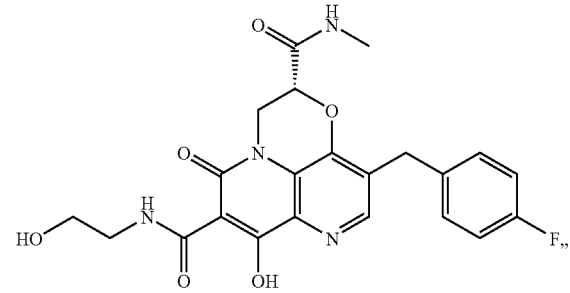 | 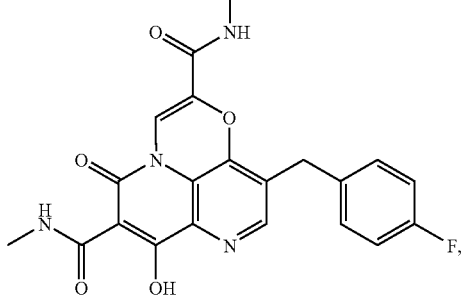 |

281
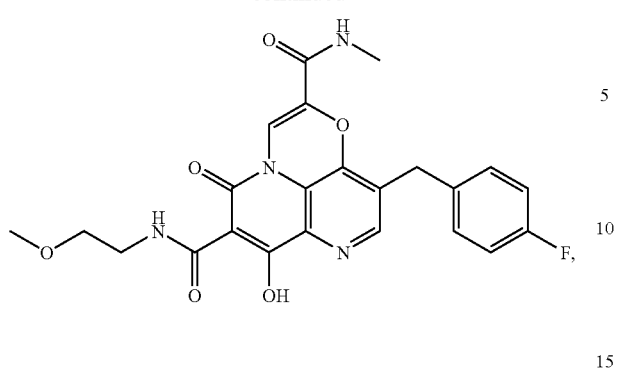
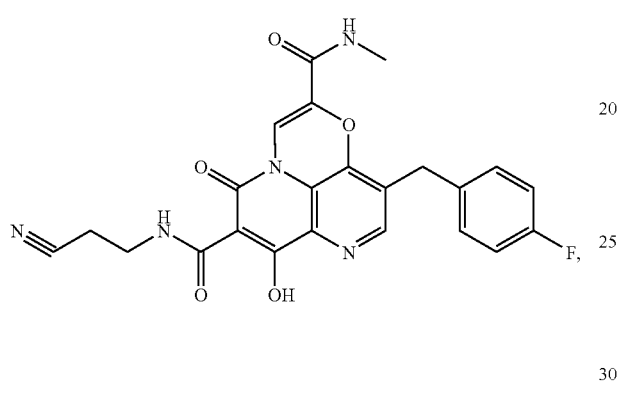
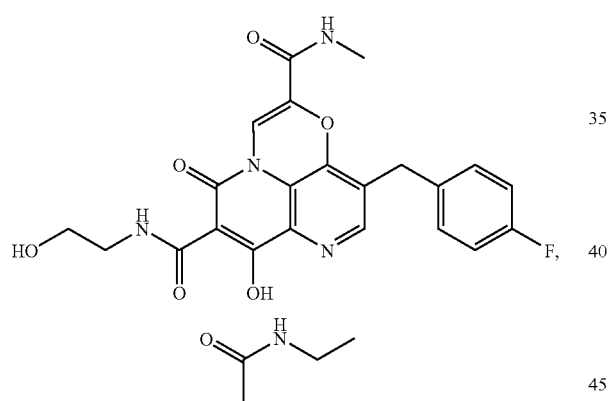
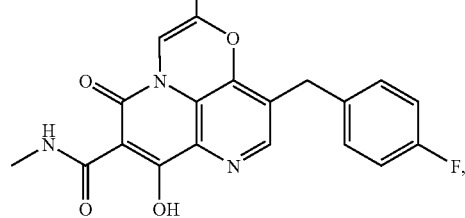
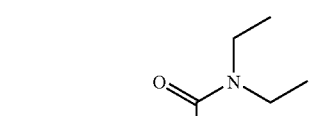
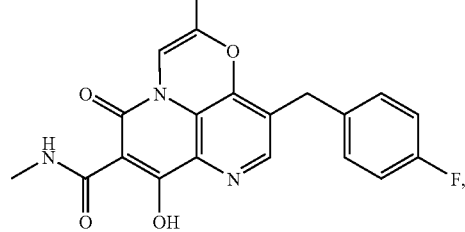
282
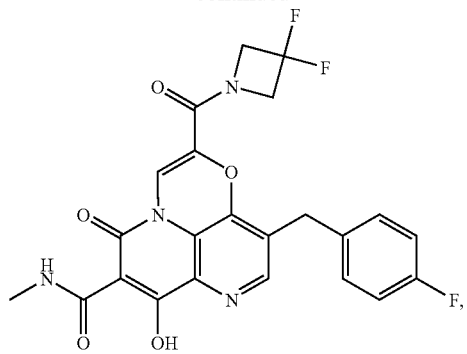
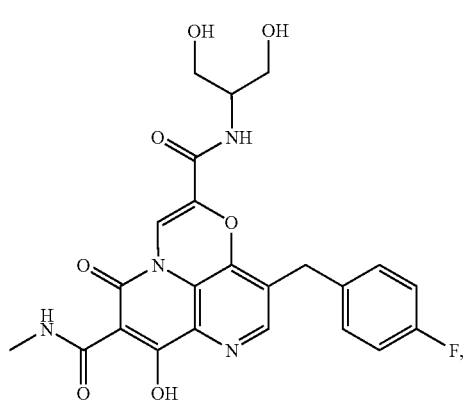
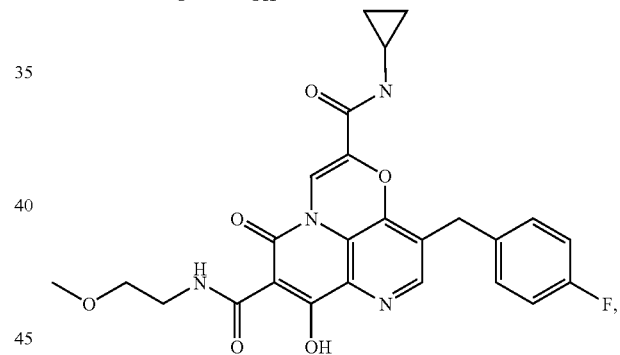
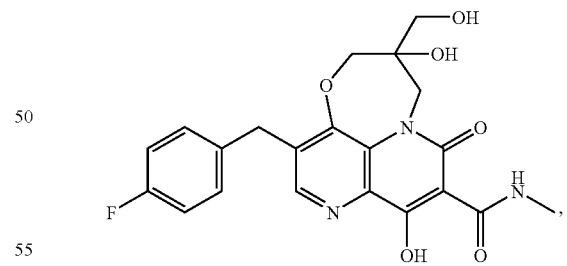
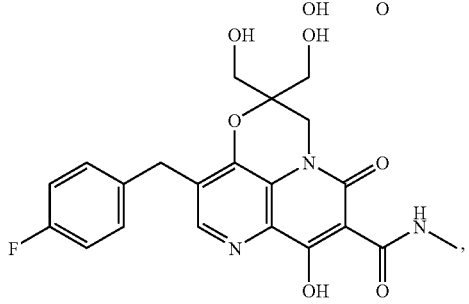

283
-continued
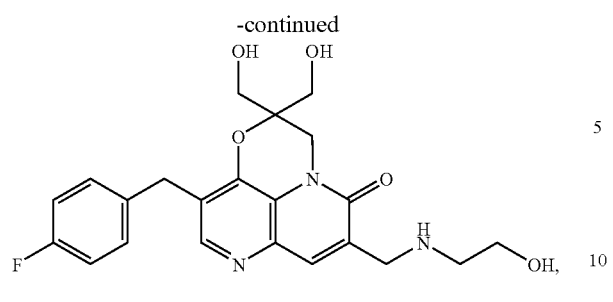
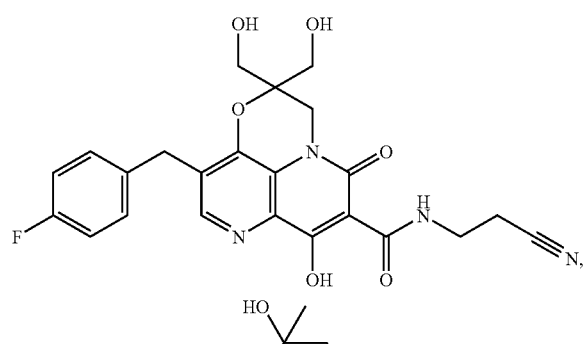
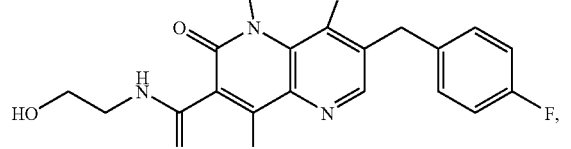
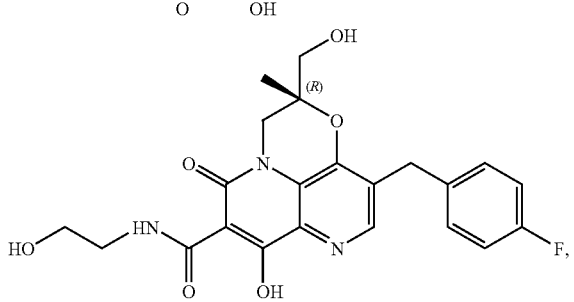
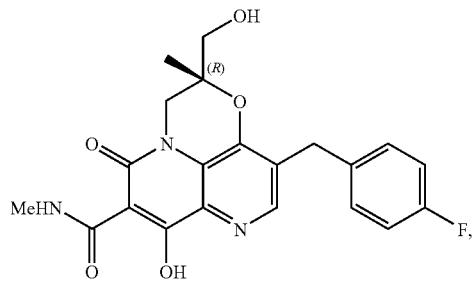
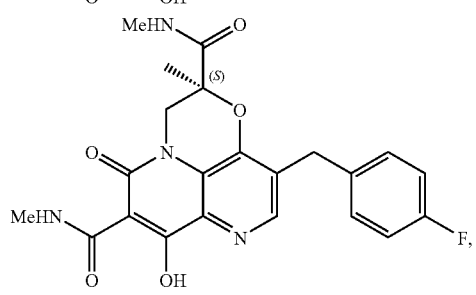
284
-continued
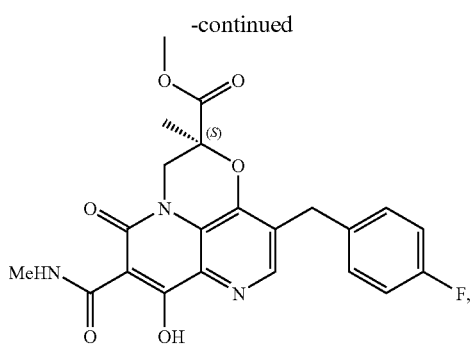
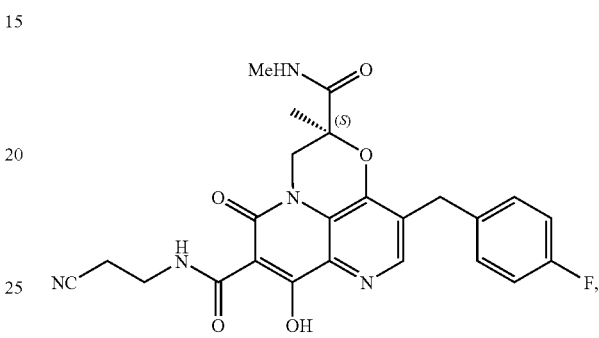
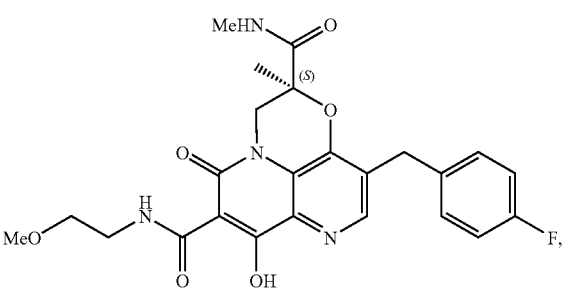
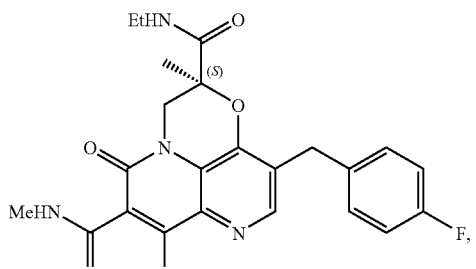
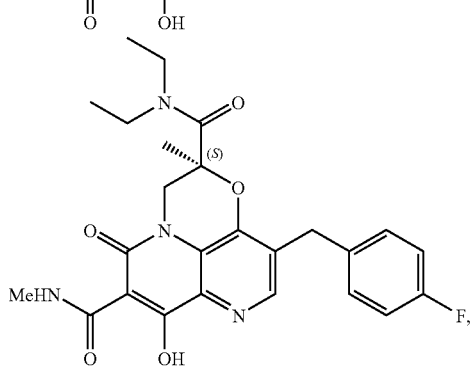

285
-continued
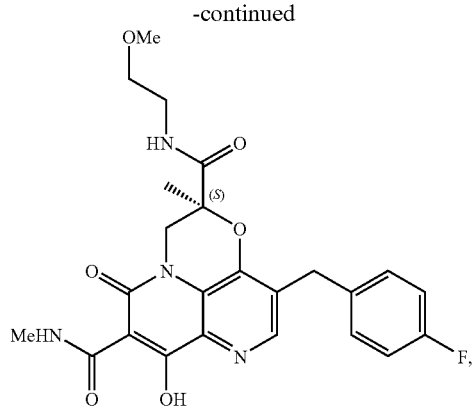
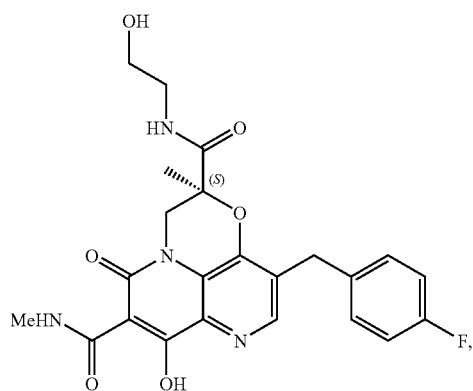
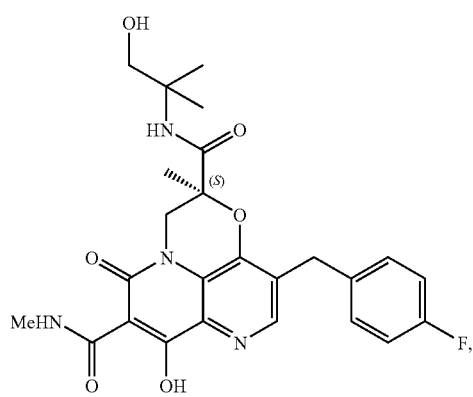
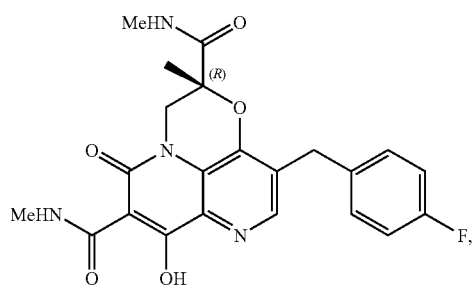
286
-continued
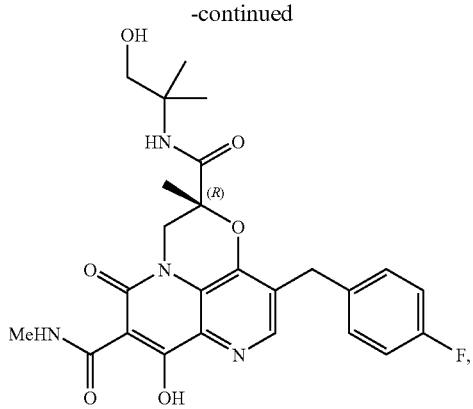
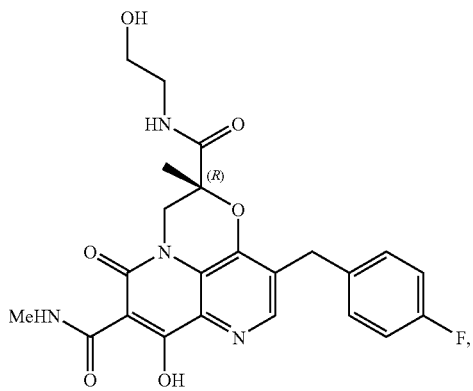
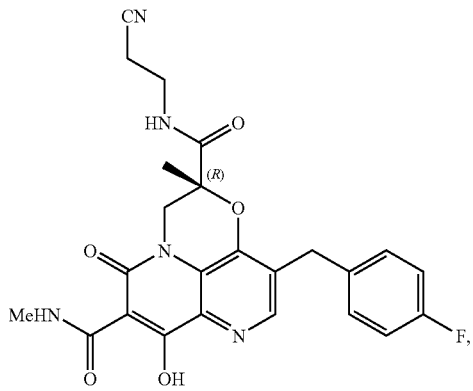
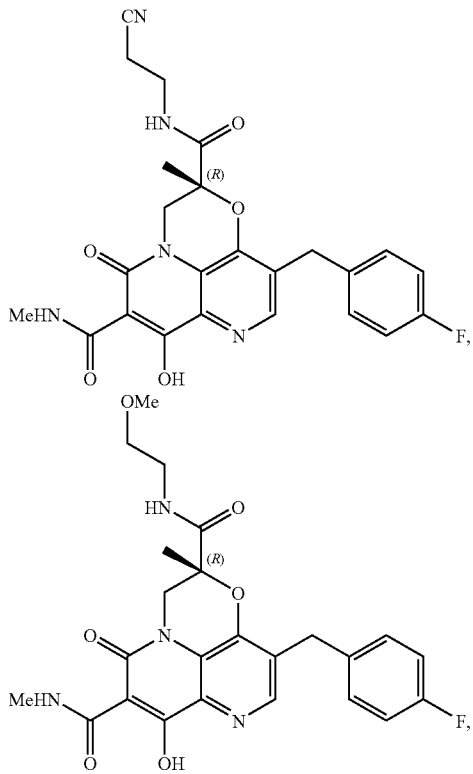

287
-continued
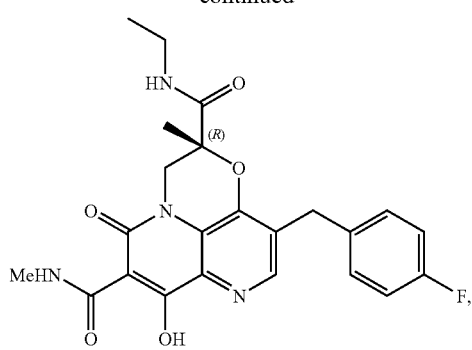
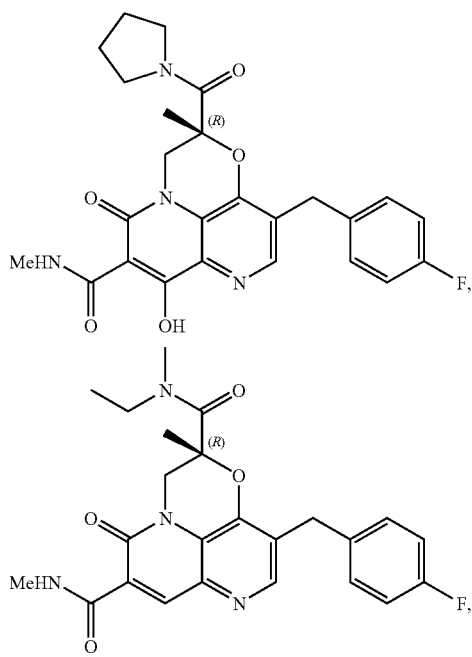
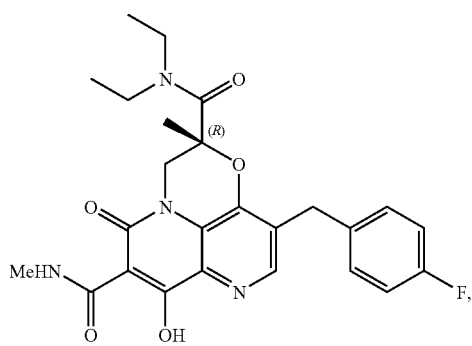
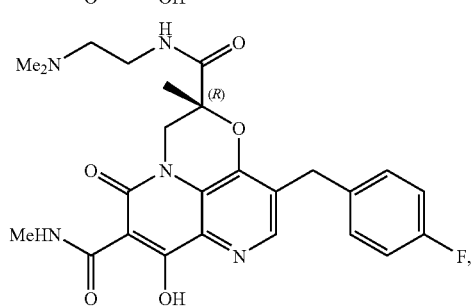
288
-continued
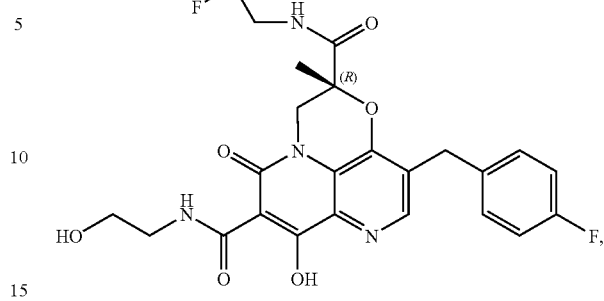
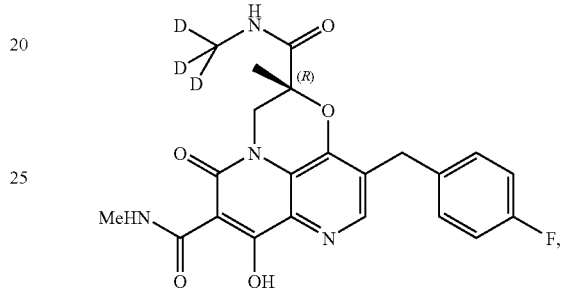
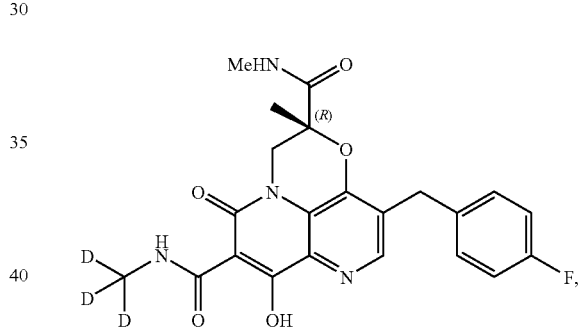
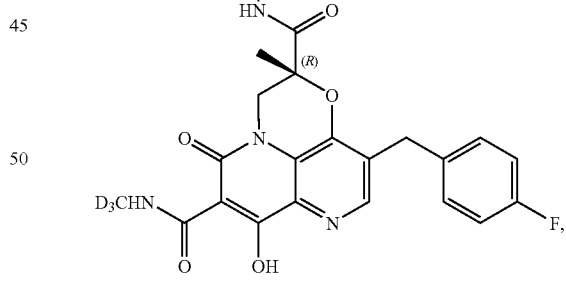
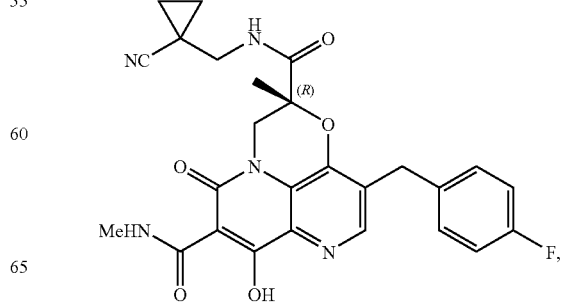

289
-continued
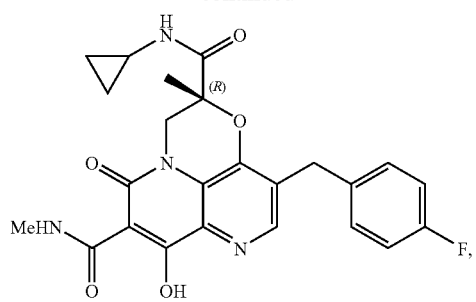
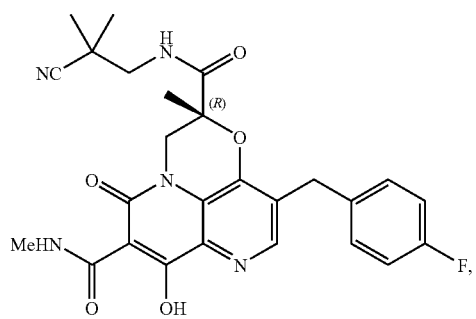
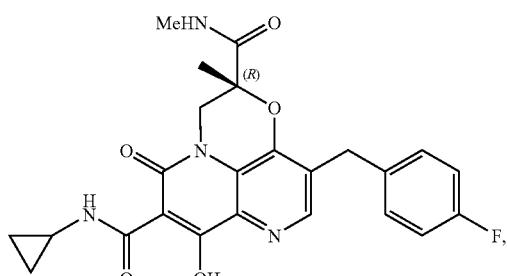
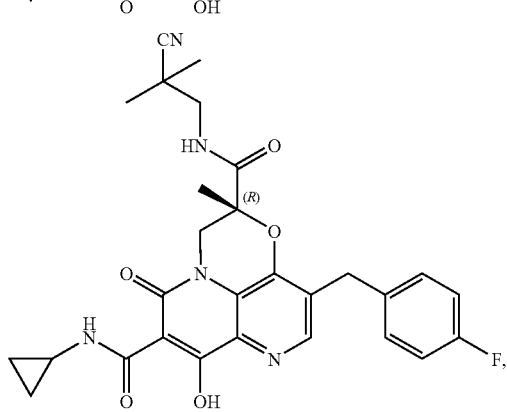
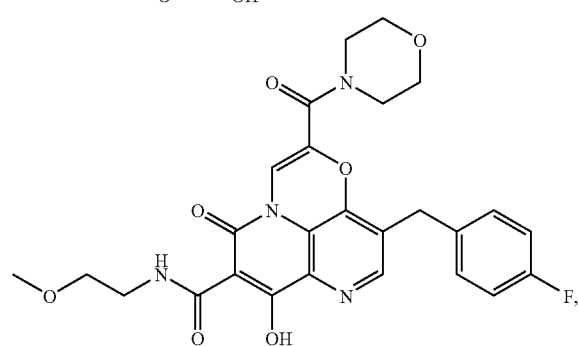
290
-continued
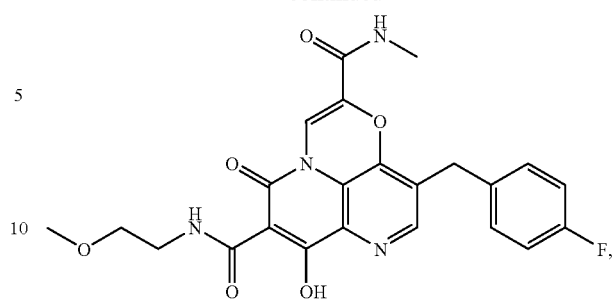
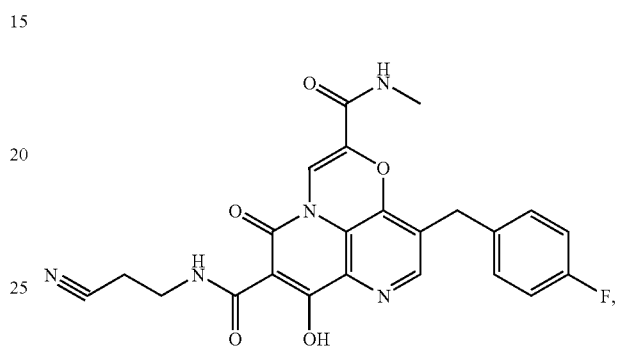
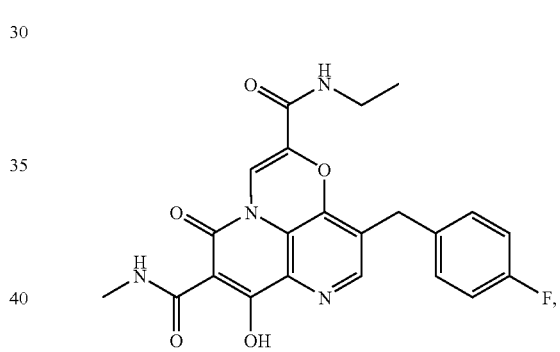
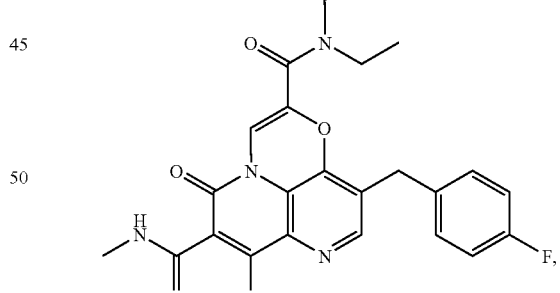
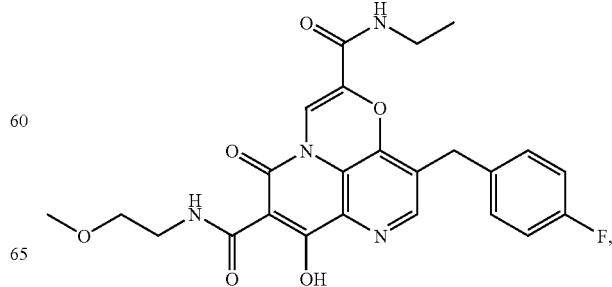

291
-continued
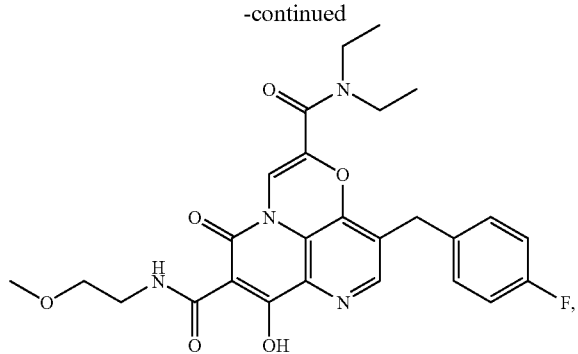
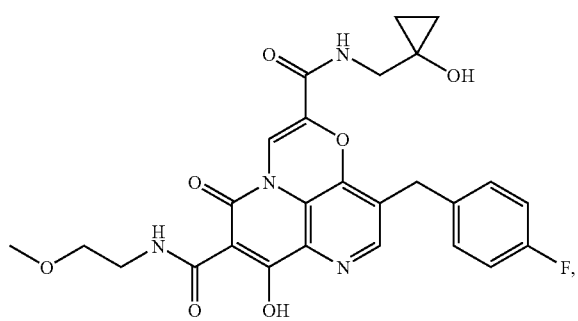
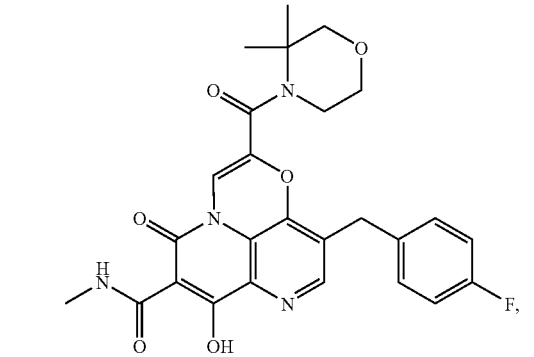
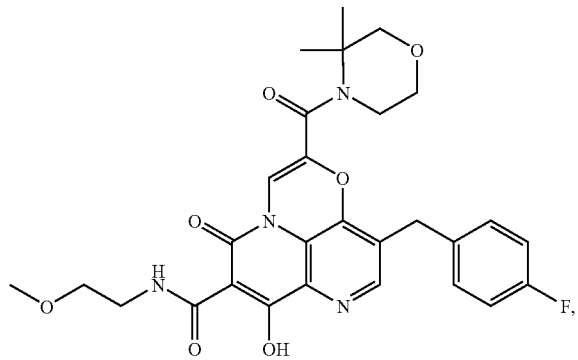
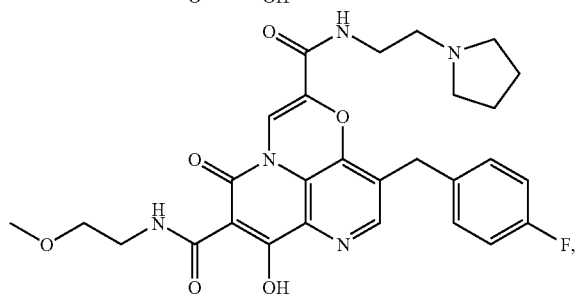
292
-continued
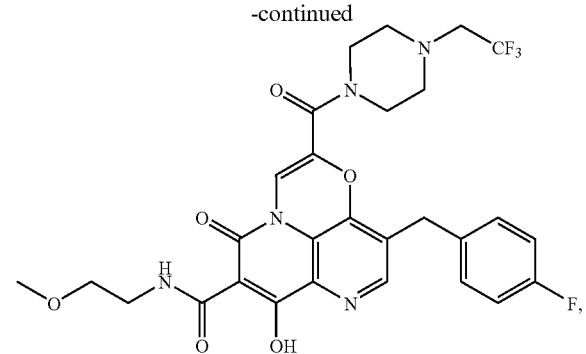
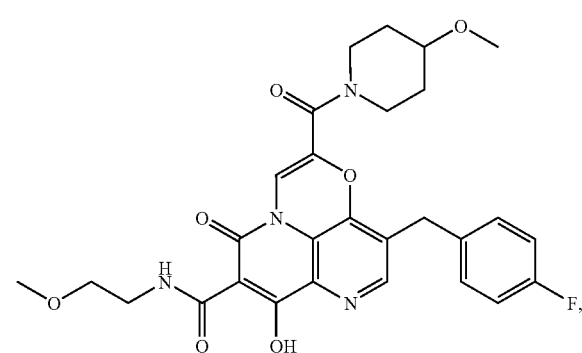
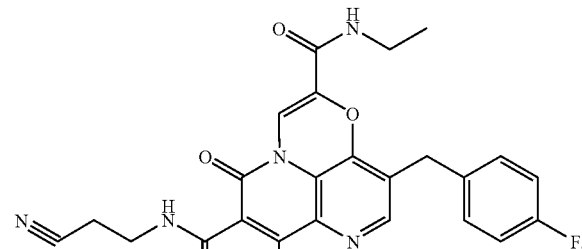
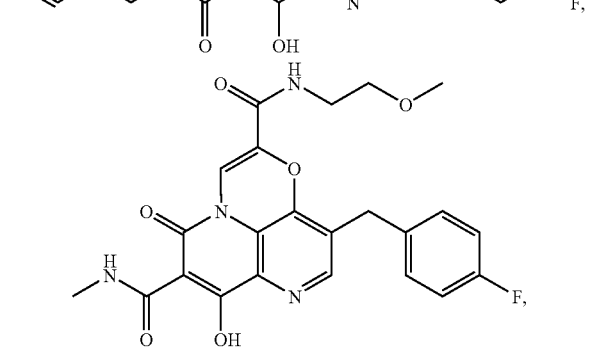
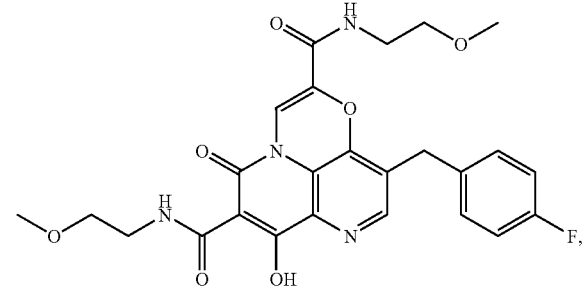

293
-continued
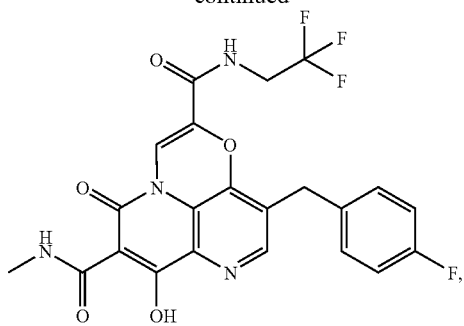
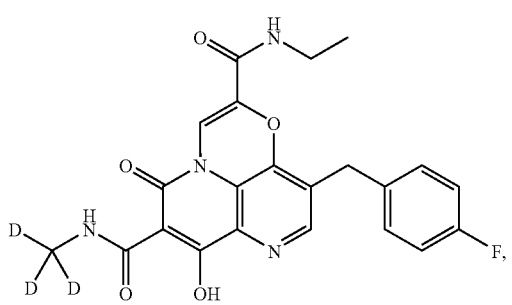
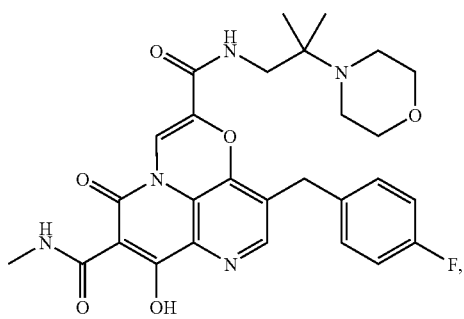
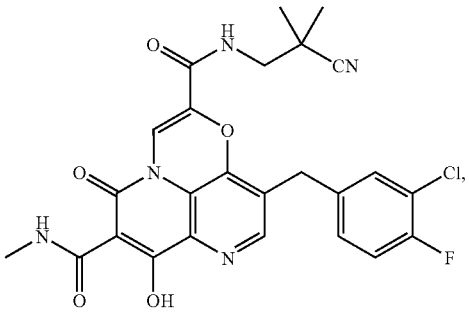
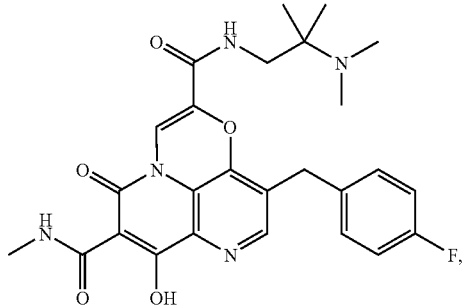
294
-continued
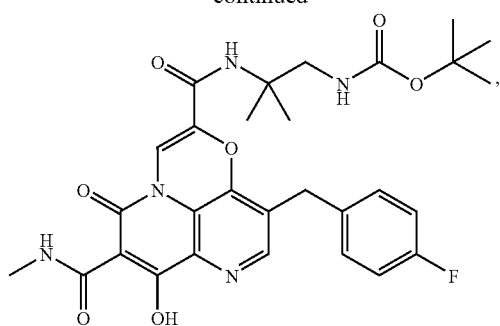
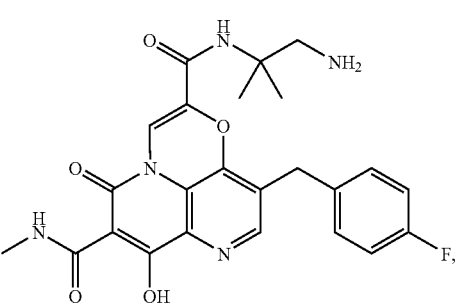
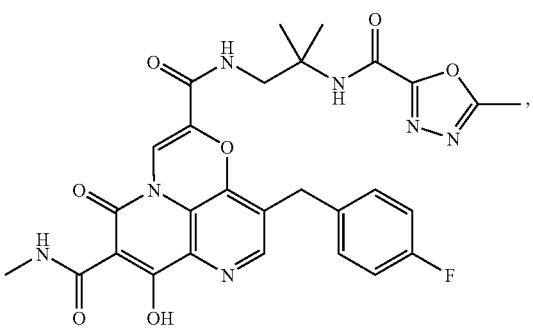
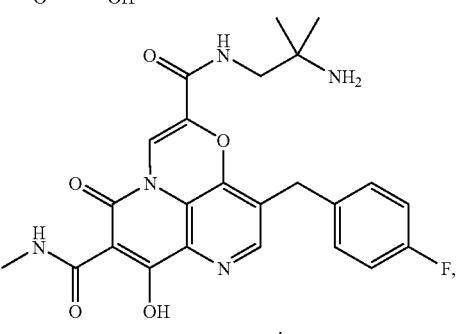
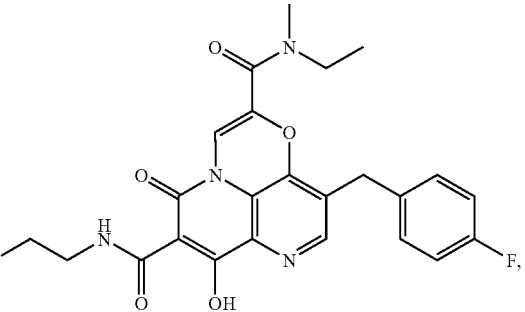

295
-continued
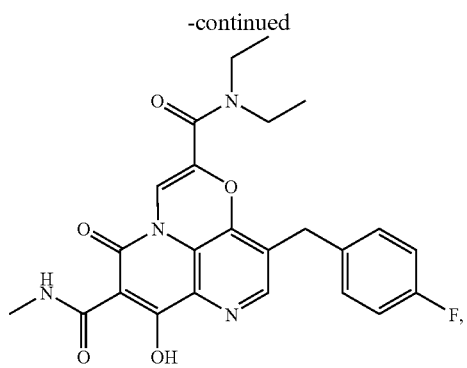
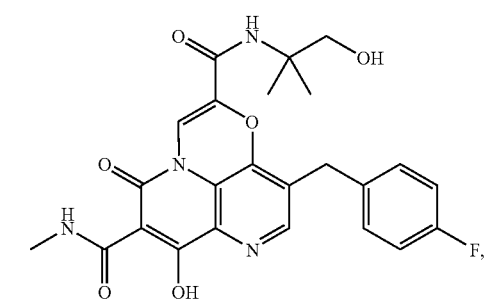
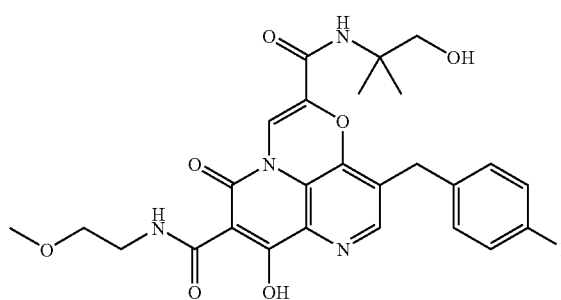
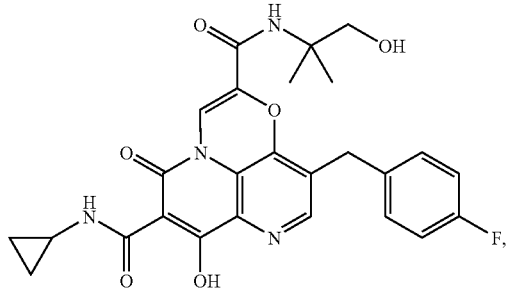
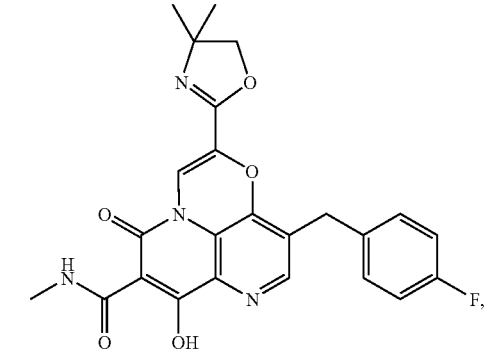
296
-continued
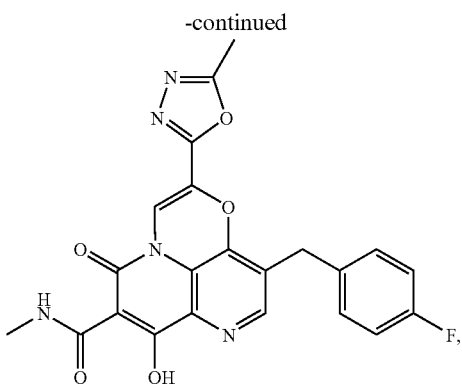
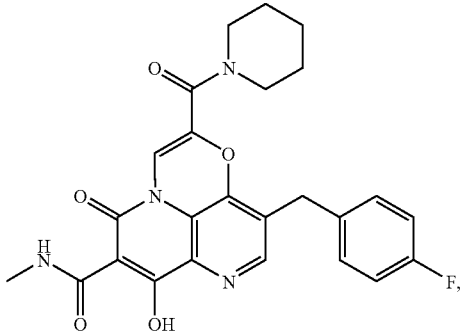
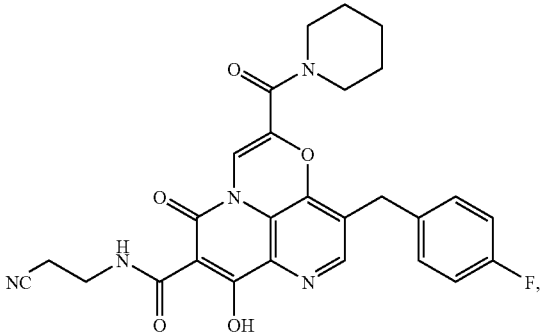
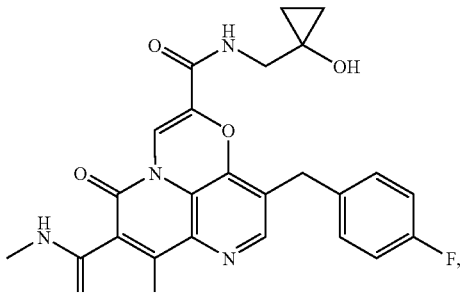
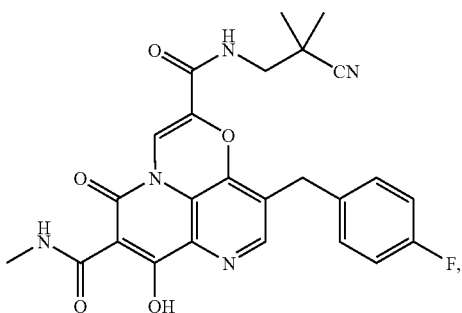

297
-continued
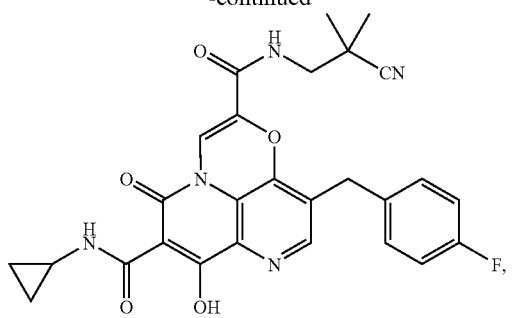
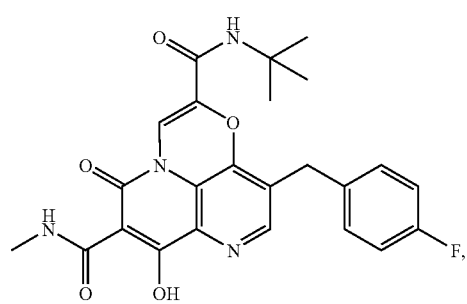
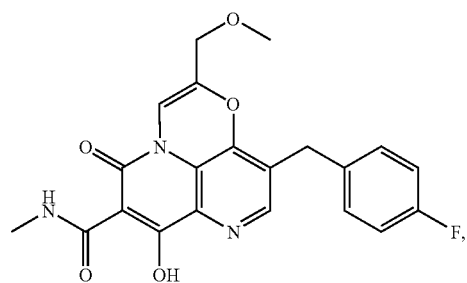
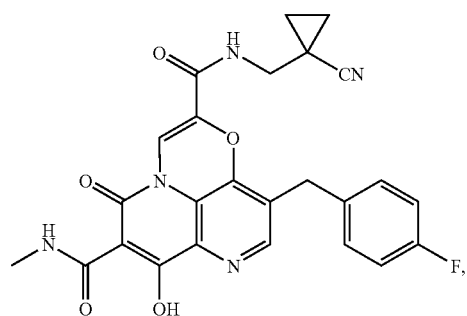
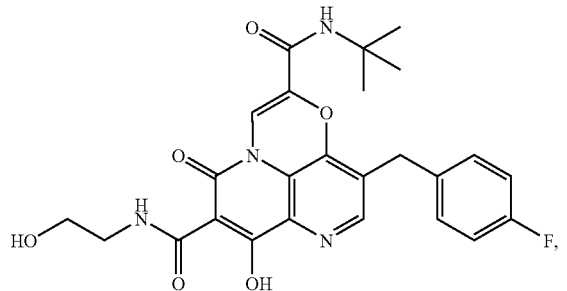
298
-continued
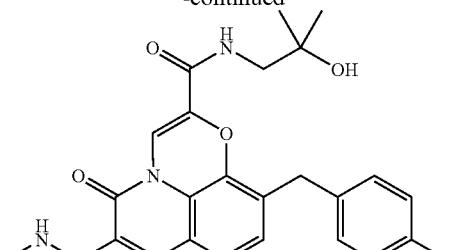
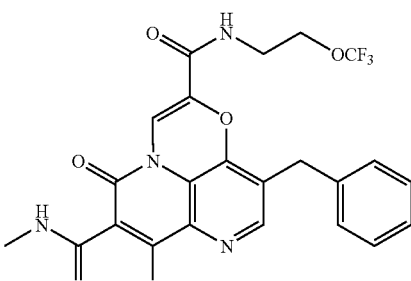
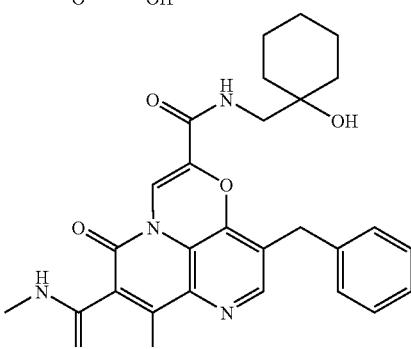
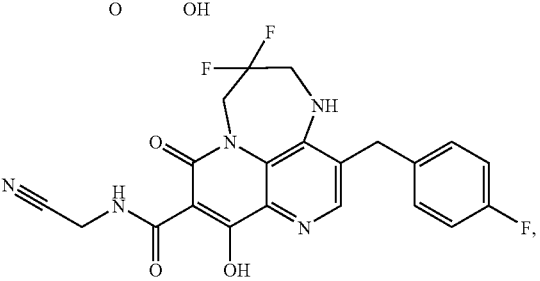
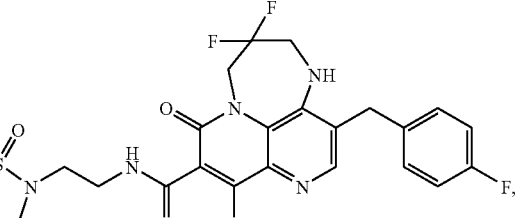
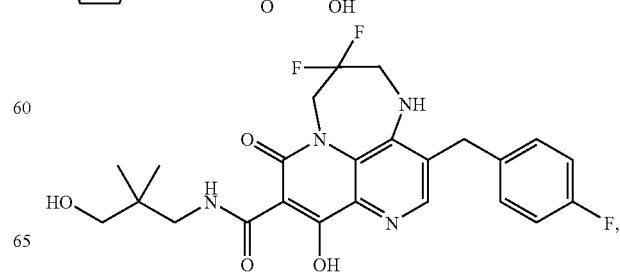

299
-continued
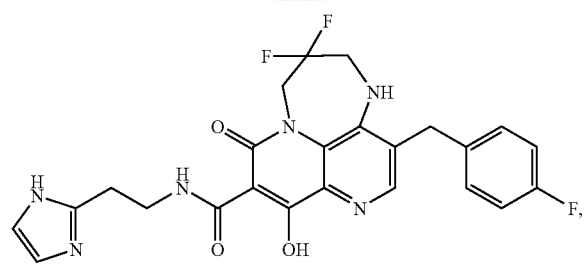
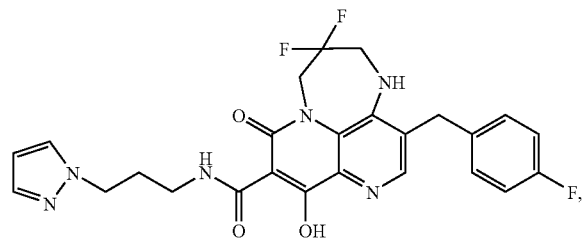
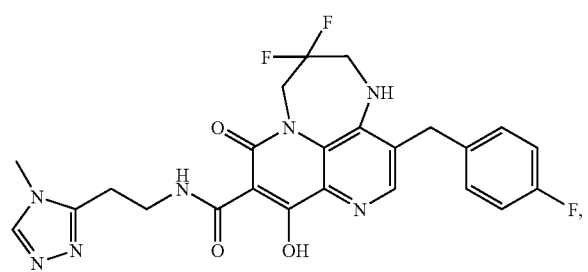
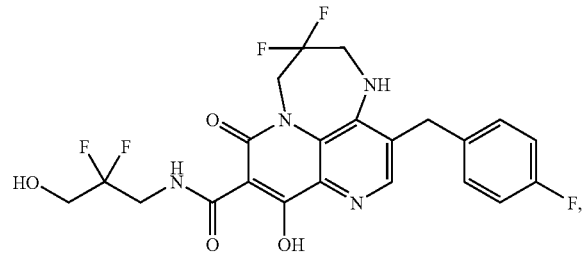
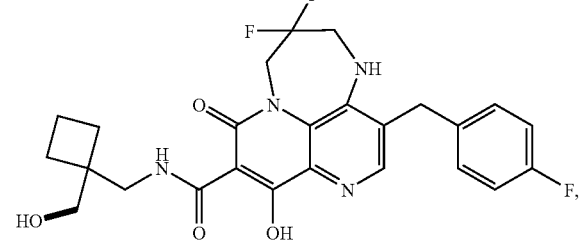
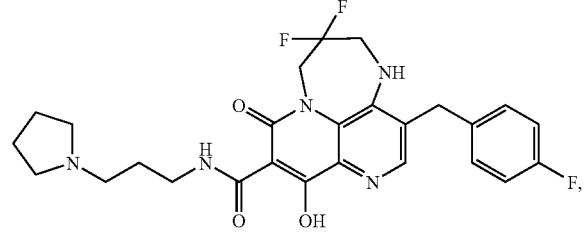
300
-continued
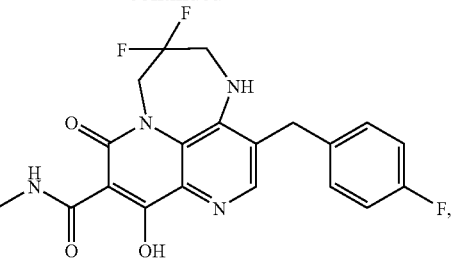
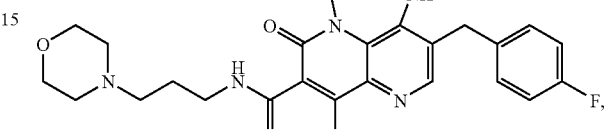
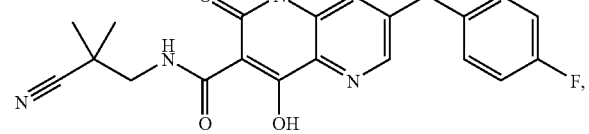
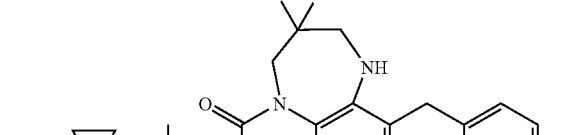
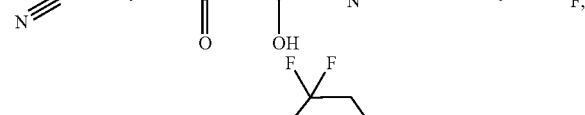
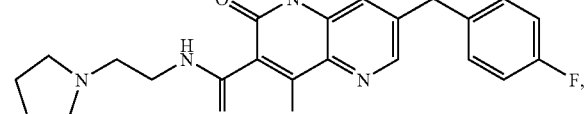
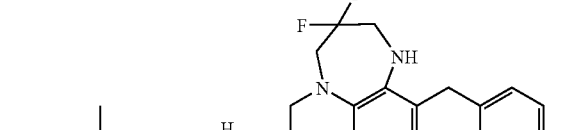
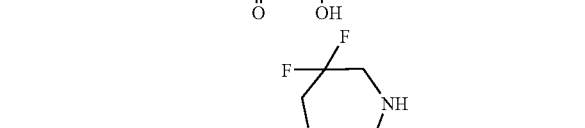

301
-continued
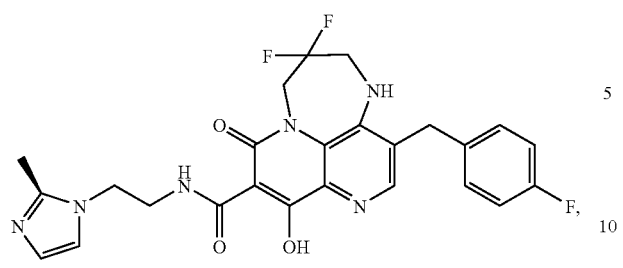
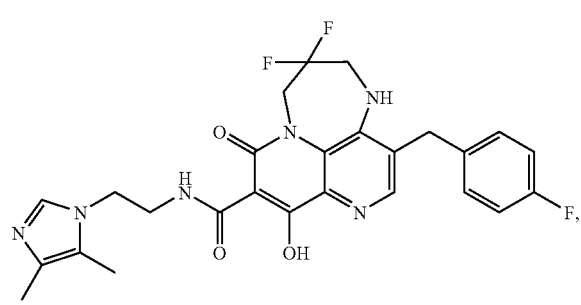
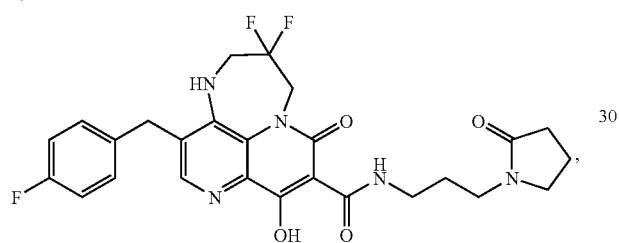
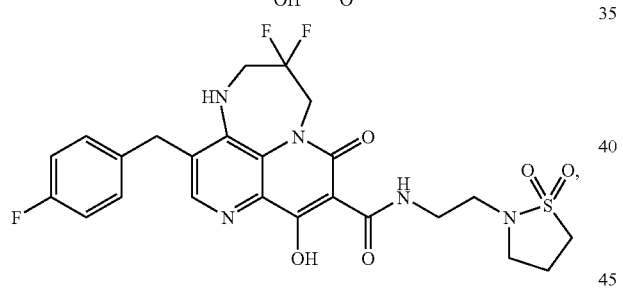
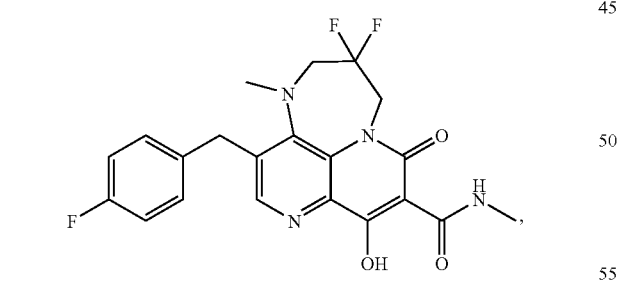
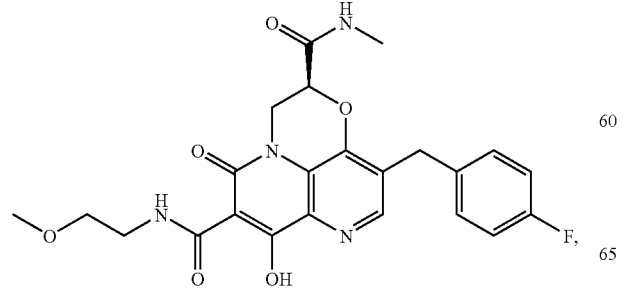
302
-continued
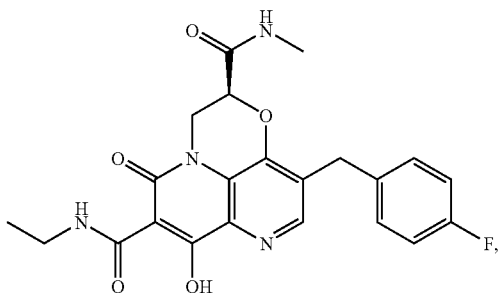
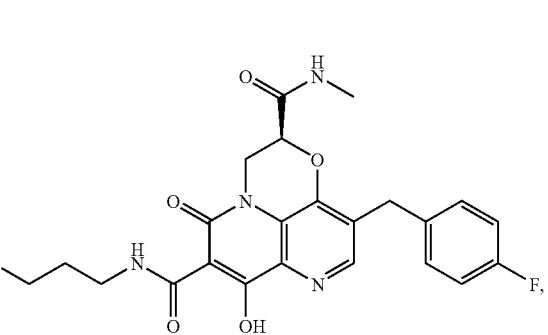
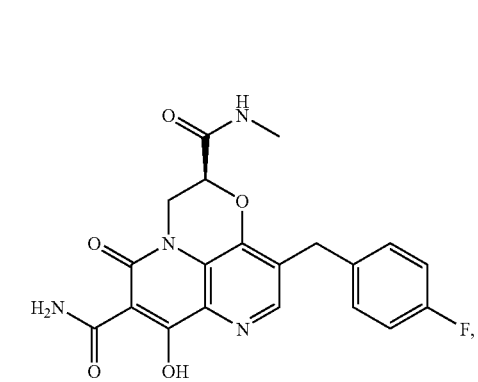
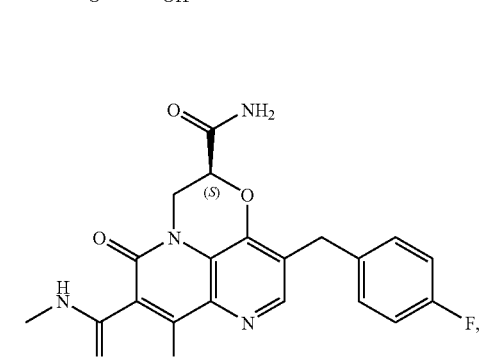
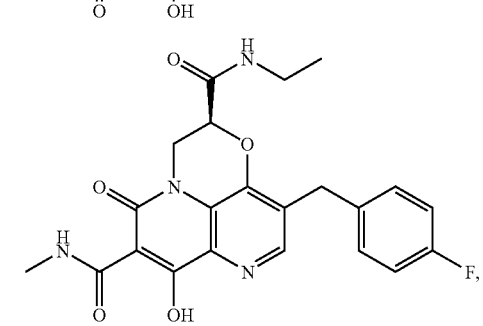

303
-continued
304
-continued
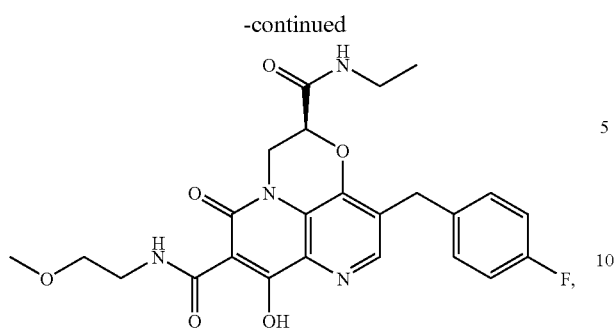
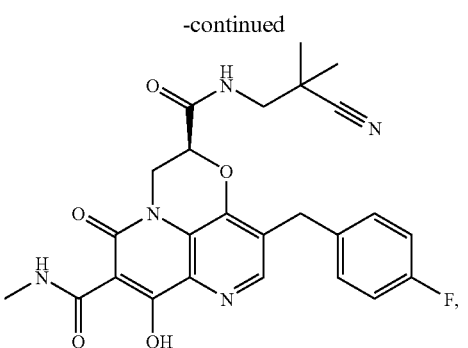

305
-continued
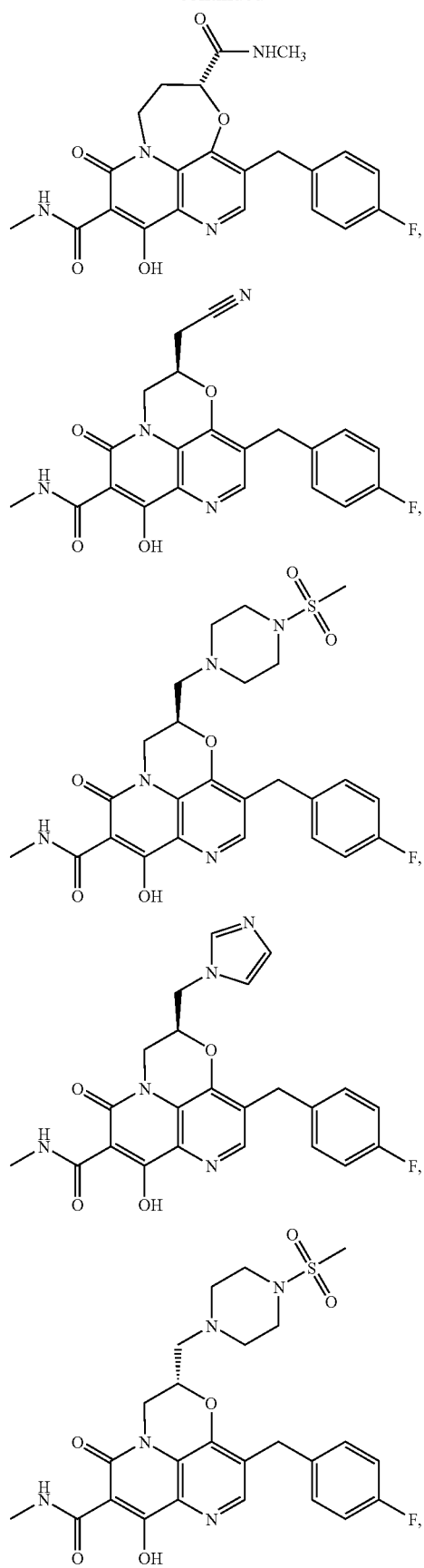
306
-continued
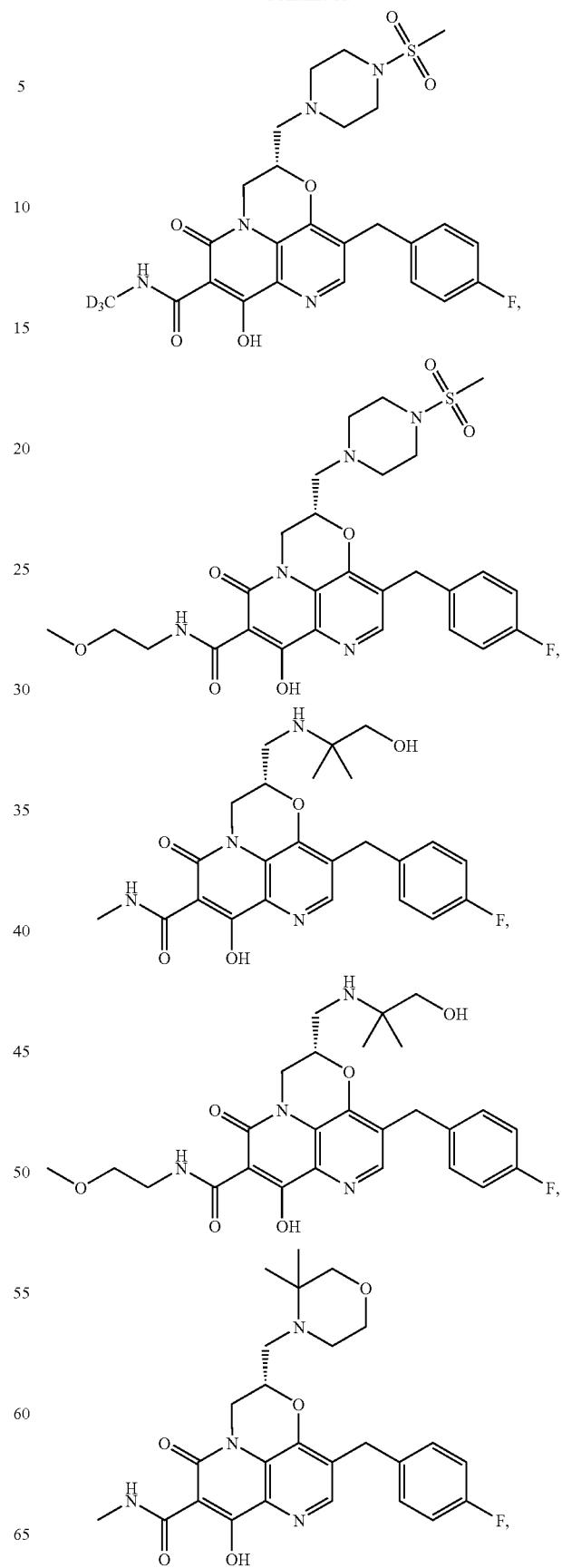

307
-continued
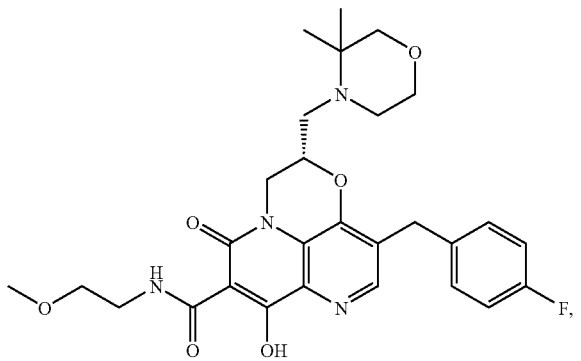
308
-continued
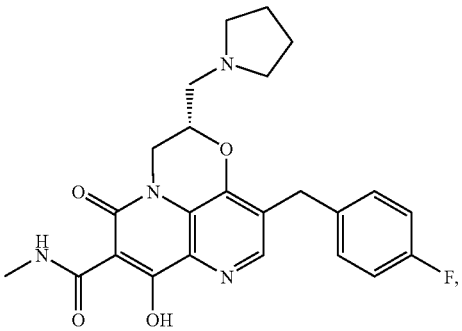
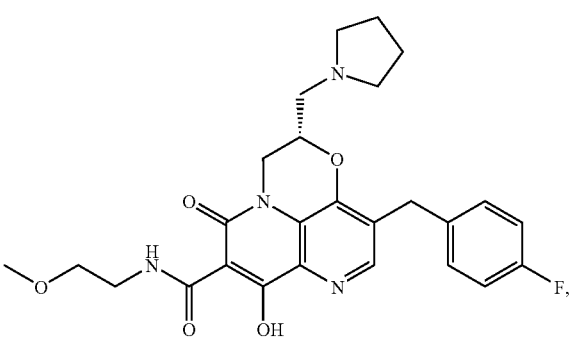
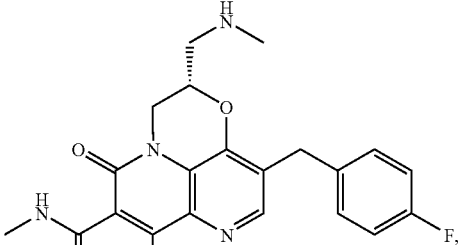
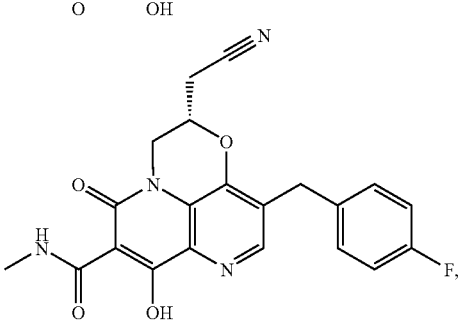
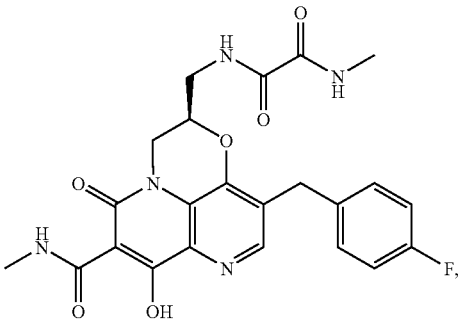

309
-continued
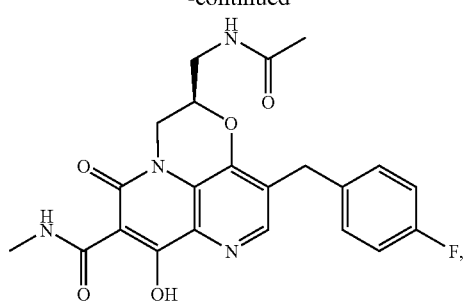
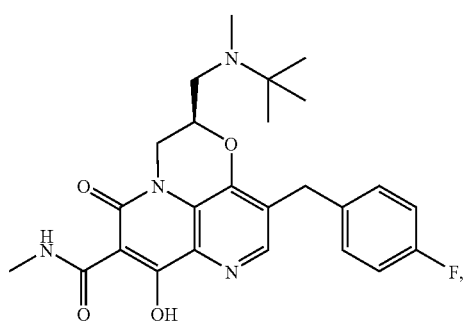
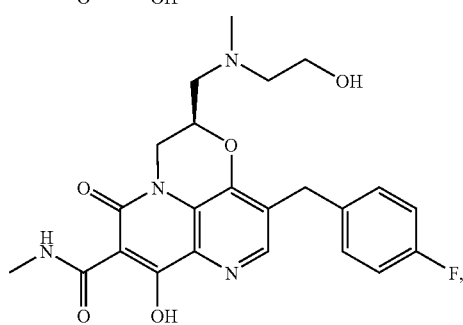
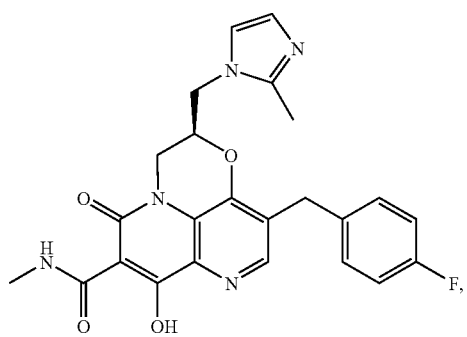
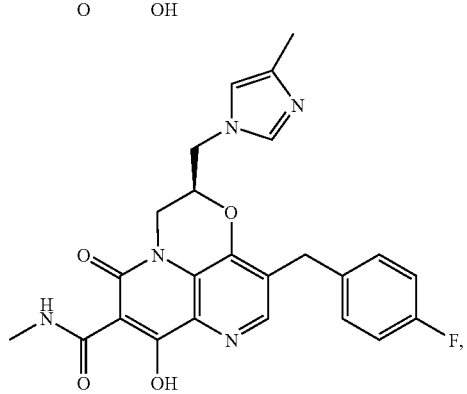
310
-continued
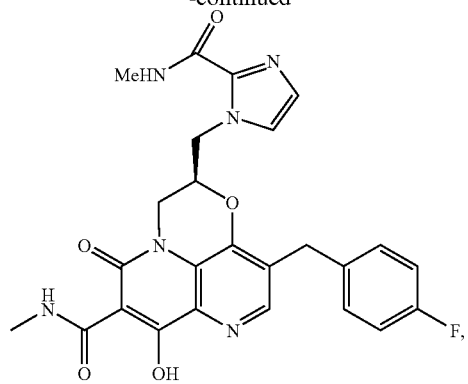
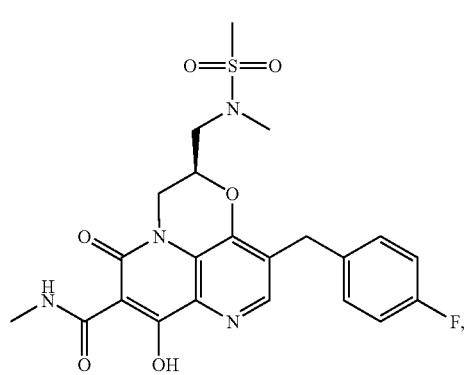
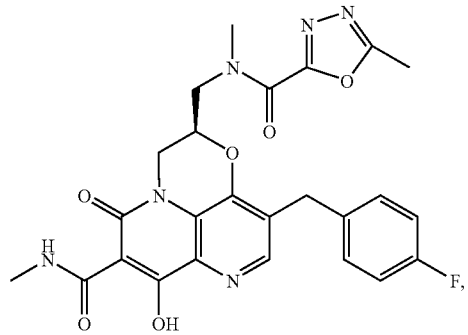
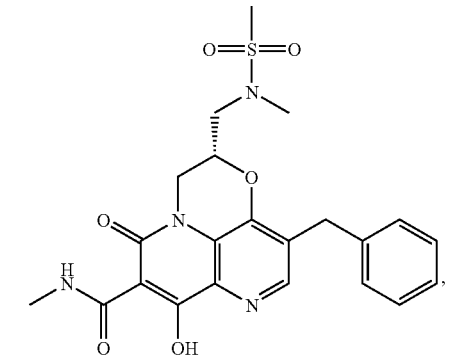

311
-continued
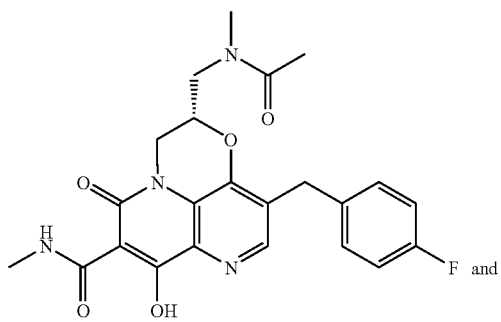
and
312
-continued
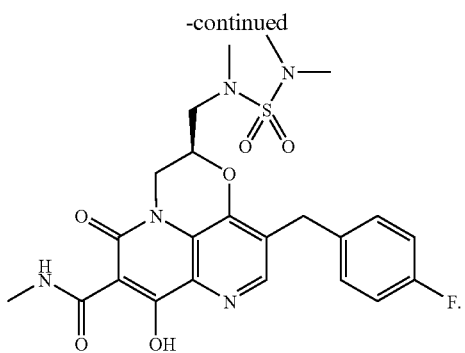
* * * * *